(12) United States Patent
Corte et al.

(10) Patent No.: US 9,777,001 B2
(45) Date of Patent: Oct. 3, 2017

(54) MACROCYCLES WITH AROMATIC P2' GROUPS AS FACTOR XIA INHIBITORS

(71) Applicant: BRISTOL-MYERS SQUIBB COMPANY, Princeton, NJ (US)

(72) Inventors: James R. Corte, Lawrenceville, NJ (US); Indawati De Lucca, Pennington, NJ (US); Tianan Fang, Levittown, PA (US); Wu Yang, Princeton Junction, NJ (US); Yufeng Wang, North Brunswick, NJ (US); Andrew K. Dilger, Ewing, NJ (US); Kumar Balashanmuga Pabbisetty, Piscataway, NJ (US); William R. Ewing, Yardley, PA (US); Yeheng Zhu, Stockton, NJ (US); Ruth R. Wexler, Belle Mead, NJ (US); Donald J. P. Pinto, Churchville, PA (US); Michael J. Orwat, New Hope, PA (US); Leon M. Smith, II, Somerset, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/115,314

(22) PCT Filed: Jan. 30, 2015

(86) PCT No.: PCT/US2015/013652
§ 371 (c)(1),
(2) Date: Jul. 29, 2016

(87) PCT Pub. No.: WO2015/116885
PCT Pub. Date: Aug. 6, 2015

(65) Prior Publication Data
US 2017/0096429 A1    Apr. 6, 2017

Related U.S. Application Data

(60) Provisional application No. 61/933,942, filed on Jan. 31, 2014, provisional application No. 62/058,293, filed on Oct. 1, 2014.

(51) Int. Cl.
| | | |
|---|---|---|
| *A61K 31/506* | (2006.01) | |
| *C07D 471/08* | (2006.01) | |
| *C07D 487/08* | (2006.01) | |
| *C07D 403/14* | (2006.01) | |
| *C07D 471/18* | (2006.01) | |
| *C07D 403/06* | (2006.01) | |

(52) U.S. Cl.
CPC ......... *C07D 471/08* (2013.01); *C07D 403/14* (2013.01); *C07D 471/18* (2013.01); *C07D 487/08* (2013.01); *C07D 403/06* (2013.01)

(58) Field of Classification Search
CPC .. C07D 401/06; C07D 403/06; C07D 405/06; C07D 407/06; C07D 408/06; C07D 409/06; C07D 411/06; C07D 413/06; C07D 417/06; C07D 419/06
See application file for complete search history.

(56) References Cited

U.S. PATENT DOCUMENTS

| | | | |
|---|---|---|---|
| 5,624,936 A | 4/1997 | deSolms | |
| 5,869,682 A | 2/1999 | deSolms | |
| 6,951,840 B2 | 10/2005 | Belvo et al. | |
| 7,544,699 B2 | 6/2009 | Mjalli et al. | |
| 8,901,115 B2 | 12/2014 | Lam et al. | |
| 8,940,720 B2 | 1/2015 | Corte et al. | |
| 8,952,024 B2* | 2/2015 | Patel | A01N 43/54 514/269 |
| 9,409,908 B2 | 8/2016 | Yang et al. | |
| 9,453,018 B2* | 9/2016 | Dilger | C07D 471/18 |
| 2012/0041190 A1* | 2/2012 | Corte | C07D 487/08 540/456 |
| 2014/0038969 A1* | 2/2014 | Yang | C07D 401/04 514/248 |
| 2014/0163002 A1* | 6/2014 | Lam | C07D 471/06 514/210.18 |
| 2015/0203492 A1* | 7/2015 | Yang | C07D 401/04 514/43 |
| 2016/0096839 A1* | 4/2016 | Dilger | C07D 471/18 514/248 |

(Continued)

FOREIGN PATENT DOCUMENTS

| | | |
|---|---|---|
| DE | 40 34 829 A1 | 5/1992 |
| EP | 0 525 420 B1 | 5/1999 |
| EP | 1 016 663 A1 | 7/2000 |

(Continued)

OTHER PUBLICATIONS

W.A. Schumacher et al., 30 Arteriosclerosis, Thrombosis, and Vascular Biology, 388-392 (2010).*

(Continued)

*Primary Examiner* — Alexander R Pagano
(74) *Attorney, Agent, or Firm* — Hong Liu

(57) ABSTRACT

The present invention provides compounds of Formula (I): or stereoisomers, tautomers, or pharmaceutically acceptable salts thereof, wherein all the variables are as defined herein. These compounds are selective factor XIa inhibitors or dual inhibitors of FXIa and plasma kallikrein. This invention also relates to pharmaceutical compositions comprising these compounds and methods of treating thromboembolic and/or inflammatory disorders using the same.

11 Claims, No Drawings

(56) References Cited

U.S. PATENT DOCUMENTS

2016/0368923 A1* 12/2016 Dilger .................. C07D 471/18
2017/0002006 A1* 1/2017 Corte .................. C07D 471/08

FOREIGN PATENT DOCUMENTS

| | | |
|---|---|---|
| EP | 1 125 925 A1 | 8/2001 |
| FR | 1525186 | 5/1968 |
| FR | 7155 M | 2/1970 |
| GB | 2497806 A | 6/2013 |
| JP | 2015-120685 A | 7/2015 |
| KR | 2015-0136294 A | 12/2015 |
| WO | WO 93/20099 A2 | 10/1993 |
| WO | WO 96/34010 A2 | 10/1996 |
| WO | WO 97/36891 A1 | 10/1997 |
| WO | WO 99/15530 A1 | 4/1999 |
| WO | WO 99/47545 A2 | 9/1999 |
| WO | WO 99/61444 A2 | 12/1999 |
| WO | WO 00/18733 A1 | 4/2000 |
| WO | WO 00/40571 A1 | 7/2000 |
| WO | WO 00/61608 A2 | 10/2000 |
| WO | WO 01/85695 A1 | 11/2001 |
| WO | WO 02/18369 A2 | 3/2002 |
| WO | WO 03/011222 A2 | 2/2003 |
| WO | WO 03/041641 A2 | 5/2003 |
| WO | WO 03/106438 A1 | 12/2003 |
| WO | WO 2004/080971 A1 | 9/2004 |
| WO | WO 2004/094372 A2 | 11/2004 |
| WO | WO 2005/014533 A2 | 2/2005 |
| WO | WO 2005/099709 A2 | 10/2005 |
| WO | WO 2005/123050 A2 | 12/2005 |
| WO | WO 2005/123680 A1 | 12/2005 |
| WO | WO 2006/017295 A2 | 2/2006 |
| WO | WO 2006/076575 A2 | 7/2006 |
| WO | WO 2006/089005 A2 | 8/2006 |
| WO | WO 2007/047608 A2 | 4/2007 |
| WO | WO 2007/054453 A2 | 5/2007 |
| WO | WO 2007/070816 A2 | 6/2007 |
| WO | WO 2007/070818 A1 | 6/2007 |
| WO | WO 2007/070826 A1 | 6/2007 |
| WO | WO 2007/076431 A1 | 7/2007 |
| WO | WO 2008/076805 A2 | 6/2008 |
| WO | WO 2008/079836 A2 | 7/2008 |
| WO | WO 2008/157162 A1 | 12/2008 |
| WO | WO 2009/114677 A1 | 9/2009 |
| WO | WO 2010/151317 A1 | 12/2010 |
| WO | WO 2011/002520 A2 | 1/2011 |
| WO | WO 2011/017296 A1 | 2/2011 |
| WO | WO 2011/100401 A1 | 8/2011 |
| WO | WO 2011/100402 A1 | 8/2011 |
| WO | WO 2013/009527 A2 | 1/2013 |
| WO | WO 2013/022814 A1 | 2/2013 |
| WO | WO 2013/022818 A1 | 2/2013 |
| WO | WO 2013/055984 A1 | 4/2013 |
| WO | WO 2013/056034 A1 | 4/2013 |
| WO | WO 2013/056060 A1 | 4/2013 |
| WO | WO 2013/093484 A1 | 6/2013 |
| WO | WO 2013/111107 A1 | 8/2013 |
| WO | WO 2013/111108 A1 | 8/2013 |
| WO | WO 2013/118805 A1 | 8/2013 |
| WO | WO 2013/167669 A1 | 11/2013 |
| WO | WO 2013/174937 A1 | 11/2013 |
| WO | WO 2014/014050 A1 | 1/2014 |
| WO | WO 2014/022766 A1 | 2/2014 |
| WO | WO 2014/022767 A1 | 2/2014 |
| WO | WO 2014/059202 A1 | 4/2014 |
| WO | WO 2014/059203 A1 | 4/2014 |
| WO | WO 2014/059214 A1 | 4/2014 |
| WO | WO 2014/108679 A1 | 7/2014 |
| WO | WO 2014/108685 A1 | 7/2014 |
| WO | WO 2014/120346 A1 | 8/2014 |
| WO | WO 2014/154794 A1 | 10/2014 |
| WO | WO 2014/160668 A1 | 10/2014 |
| WO | WO 2015/011087 A1 | 1/2015 |
| WO | WO 2015/044163 A1 | 4/2015 |
| WO | WO 2015/044165 A1 | 4/2015 |
| WO | WO 2015/044167 A1 | 4/2015 |
| WO | WO 2015/044169 A1 | 4/2015 |
| WO | WO 2015/044170 A1 | 4/2015 |
| WO | WO 2015/044172 A1 | 4/2015 |
| WO | WO 2015/044173 A1 | 4/2015 |
| WO | WO 2015/044174 A1 | 4/2015 |
| WO | WO 2015/047973 A1 | 4/2015 |
| WO | WO 2015/054087 A1 | 4/2015 |
| WO | WO 2015/107724 A1 | 7/2015 |
| WO | WO 2015/116882 A1 | 8/2015 |
| WO | WO 2015/116885 A1 | 8/2015 |
| WO | WO 2015/116886 A1 | 8/2015 |
| WO | WO 2015/120062 A2 | 8/2015 |
| WO | WO 2015/120777 A1 | 8/2015 |
| WO | WO 2015/123090 A1 | 8/2015 |
| WO | WO 2015/123091 A1 | 8/2015 |
| WO | WO 2015/123093 A1 | 8/2015 |
| WO | WO 2015116886 A1 * 8/2015 ........... C07D 471/08 |
| WO | WO 2015/134998 A1 | 9/2015 |
| WO | WO 2015/160634 A1 | 10/2015 |
| WO | WO 2015/160636 A1 | 10/2015 |
| WO | WO 2015/183709 A1 | 12/2015 |
| WO | WO 2016/046157 A1 | 3/2016 |
| WO | WO 2016/053455 A1 | 4/2016 |
| WO | WO 2016053455 A1 * 4/2016 ........... C07D 471/18 |
| WO | WO 2016/093285 A1 | 6/2016 |
| WO | WO 2016/205482 A1 | 12/2016 |

OTHER PUBLICATIONS

P.C. Wong et al., 32 Journal of Thrombosis and Thrombolysis, 129-137 (2011).*
R.A. Al-Horani et al., Journal of Medicinal Chemistry, 867-878 (2013).*
A.T. Cohen et al., The Lancet, 387-394 (2008).*
U.S. Appl. No. 15/115,314, dated Jul. 29, 2016, James R. Corte.
U.S. Appl. No. 15/115,319, dated Jul. 29, 2016, Andrew K. Dilger.
U.S. Appl. No. 15/115,327, dated Jul. 29, 2016, James R. Corte.
Approaches of Classic Medicinal Chemistry, Optimizing Drug Binding Affinity: (Semi) Empirical Studies, http://www.chem.uzh.ch/zerbe/MedChem/MedChem4_MedChem.pdf (Mar. 18, 2012).
Boger, D.L. et al., "Thermal Atropisomerism of Aglucovancomycin Derivatives: Preparation of (M,M,M)- and (P,M,M)-Aglucovancomycins", J. Am. Chem. Soc., vol. 120, No. 35, pp. 8920-8926 (1998).
Caballero, J. et al., "Quantitative Structure-Activity Relationship Modeling of Growth Hormone Secretagogues Agonist Activity of Some Tetrahydroisoquinoline 1-Carboxamides", Chem. Biol. Drug. Des., vol. 69, pp. 48-55 (2007).
Chan, J.C.Y. et al., "The Characterization of Mice with a Targeted Combined Deficiency of Protein C and Factor XI", American Journal of Pathology, vol. 158, No. 2, pp. 469-479 (2001).
Chen, X. et al., Chapter 32: "The use of bioisosteric groups in lead optimization", Annual Reports in Medicinal Chemistry, vol. 38, pp. 333-346, Elsevier Inc., publ. (2003).
Cho, J.E. et al., "Characterization of Binding Mode for Human Coagulation Factor XI (FXI) Inhibitors", Bull. Korean Chem. Soc., vol. 34, No. 4, pp. 1212-1220 (2013).
Crosby, J.R. et al., "Antithrombotic Effect of Antisense Factor XI Oligonucleotide Treatment in Primates", Arterioscler. Thromb. Vasc. Biol., vol. 33, pp. 1670-1678 (2013), and vol. 33, pp. e127 and e130 (errata) (2013).
Evans, D.A. et al., "Total Syntheses of Vancomycin and Eremomycin Aglycons", Angew. Chem. Int. Ed., vol. 37, No. 19, pp. 2700-2704 (1998).
Gailani, D., "Gene Targeting in Hemostasis, Factor XI", Frontiers in Bioscience, vol. 6, pp. 201-207 (2001).
Gailani, D. et al., "A murine model of factor XI deficiency", Blood Coagulation and Fibrinolysis, vol. 8, pp. 134-144 (1997).
Gruber, a. et al., "Factor XI-dependence of surface- and tissue factor- initiated thrombus propagation in primates", Blood, vol. 102, No. 3, pp. 953-955 (2003).
Hoffman, M., "A cell-based model of coagulation and the role of factor VIIa", Blood Reviews, vol. 17, pp. S1-S5 (2003).

(56) References Cited

OTHER PUBLICATIONS

Jiang, G. et al., "Highly Efficient Oxidation of Amines to Imines by Singlet Oxygen and Its Application in Ugi-Type Reactions", Organic Letters, vol. 11, No. 20, pp. 4568-4571 (2009).

Li, J.J. et al., "Tetrahydroisoquinoline 1-carboxamides as growth hormone secretagogues", Bioorganic & Medicinal Chemistry Letters, vol. 15, pp. 1799-1802 (2005).

Matafonov, A. et al., "Evidence for factor IX-independent roles for factor XIa in blood coagulation", Journal of Thrombosis and Haemostasis, vol. 11, pp. 2118-2127 (2013).

MayoClinic.com, "Pulmonary Embolism: Prevention", http://www.mayoclinic.com/health/pulmonary-embolism/DS00429/DSECTION=prevention, accessed May 20, 2013.

Meijers, J.C.M. et al., "High Levels of Coagulation Factor XI as a Risk Factor for Venous Thrombosis", The New England Journal of Medicine, vol. 342, pp. 696-701 (2000).

Meng, D. et al., "Development of a novel tricyclic class of potent and selective FIXa inhibitors", Bioorganic & Medicinal Chemistry Letters (2015), doi: http://dx.doi.org/10.1016/j.bmcl.2015.07.078.

Minnema, M.O. et al., "Activation of Clotting Factors XI and IX in Patients with Acute Myocardial Infarction", Arterioscler. Thromb. Vasc. Biol., vol. 20, pp. 2489-2493 (2000).

Murakami, T. et al., "Evaluation of Factor XIa-$\alpha_1$-Antitrypsin in Plasma, a Contact Phase-Activated Coagulation Factor-Inhibitor Complex, in Patients with Coronary Artery Disease", Arteriosclerosis, Thrombosis, and Vascular Biology, vol. 15, No. 8, pp. 1107-1113 (1995).

Ngouansavanh, T. et al., "IBX-Mediated Oxidative Ugi-Type Multicomponent Reactions: Application to the N And C1 Functionalization of Tetrahydroisoquinoline", Angew. Chem. Int. Ed., vol. 46, pp. 5775-5778 (2007).

Rosen, E.D. et al., "FXI is Essential for Thrombus Formation Following FeCI$_3$-Induced Injury of the Carotid Artery in the Mouse", Thromb. Haemost., vol. 87, pp. 774-776 (2002).

Schumacher, W.A. et al., "Inhibition of Factor XIa as a New Approach to Anticoagulation", Arterioscler. Thromb. Vasc. Biol., vol. 30, pp. 388-392 (2010).

Schuster, I. et al., "Convenient Synthesis of 1,2,3,4-Tetrahydroisoquinoline-1-Carboxylic Acid Derivatives via Isocyanide-Based Three-Component Reactions", Synthetic Communications, vol. 40, pp. 2488-2498 (2010).

Schuster, I. et al., "Synthesis of 1,2,3,4-Tetrahydroisoquinoline-1-Carboxylic Acid Derivatives Via Ugi Reactions", Letters in Organic Chemistry, vol. 4, No. 2, pp. 102-108 (2007).

Schuster, I. et al., "Synthesis of 1,2,3,4-Tetrahydroisoquinoline-1-carboxylic Acid Derivatives via Ugi Reactions", Magyar Kémiai Folyóirat (Hungarian Journal of Chemistry), vol. 116, No. 3, pp. 126-130 (2010).

Walsh, P.N., "Platelets and Factor XI Bypass the Contact System of Blood Coagulation", Thrombosis and Haemostasis, vol. 82, No. 2, pp. 234-242 (1999).

Wang, X. et al., "Effects of factor IX or factor XI deficiency on ferric chloride-induced carotid artery occlusion in mice", Journal of Thrombosis and Haemostasis, vol. 3, pp. 695-702 (2005).

Wu, Y.-J. et al., "Discovery of (S,E)-3-(2-fluorophenyl)-N-(1-(3-(pyridin-3-yloxy)phenypethyl)-acrylamide as a potent and efficacious KCNQ2 (Kv7.2) opener for the treatment of neuropathic pain", Bioorganic & Medicinal Chemistry Letters, vol. 23, pp. 6188-6191 (2013).

Al-Horani, R. et al., "Sulfated Pentagalloylglucoside Is a Potent, Allosteric, and Selective Inhibitor of Factor Xia" Journal of Medicinal Chemistry, vol. 56, pp. 867-878 (2013).

Cohen, A. et al., "Venous thromboembolism risk and prophylaxis in the acute hospital care setting (ENDORSE study): a multinational cross-sectional study", The Lancet vol. 371, pp. 387-394 (2008).

Wong, P.C. et al., "A small-molecule factor XIa inhibitor produces antithrombotic efficacy with minimal bleeding time prolongation in rabbits", J. Thromb Thrombolysis, vol. 32, pp. 129-137 (2011).

\* cited by examiner

```
                      SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: synthetic substrate S-2222
<220> FEATURE:
<221> NAME/KEY: MOD_RES
<222> LOCATION: (1)..(1)
<223> OTHER INFORMATION: benzine
<220> FEATURE:
<221> NAME/KEY: MOD_RES
<222> LOCATION: (2)..(3)
<223> OTHER INFORMATION: gamma-OMe
<220> FEATURE:
<221> NAME/KEY: MOD_RES
<222> LOCATION: (4)..(4)
<223> OTHER INFORMATION: para nitroaniline

<400> SEQUENCE: 1

Ile Glu Gly Arg
1
```

MACROCYCLES WITH AROMATIC P2' GROUPS AS FACTOR XIA INHIBITORS

CROSS REFERENCE TO RELATED APPLICATIONS

This application is a 371 application of PCT/US2015/013652, filed on Jan. 30, 2015, which is entitled to priority pursuant to 35 U.S.C. §119(e) to U.S. provisional patent application Ser. Nos. 61/933,942, filed on Jan. 31, 2014 and 62/058,293, filed on Oct. 1, 2014, which are incorporated herein in their entireties.

FIELD OF THE INVENTION

The present invention relates generally to novel macrocyclic compounds, and their analogues thereof, which are factor XIa inhibitors or dual inhibitors of factor XIa and plasma kallikrein, compositions containing them, and methods of using them, for example, for the treatment or prophylaxis of thromboembolic disorders, or for the treatment of retinal vascular permeability associated with diabetic retinopathy and diabetic macular edema.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

An alternative way of initiation of coagulation is operative when blood is exposed to artificial surfaces. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI.

Plasma prekallikrein is a zymogen of a trypsin-like serine protease and is present in plasma at 35 to 50 μg/mL. The gene structure is similar to that of factor XI. Overall, the amino acid sequence of plasma kallikrein has 58% homology to factor XI. Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastrointestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (Lehmann, A., "Ecallantide (DX-88), a plasma kallikrein inhibitor for the treatment of hereditary angioedema and the prevention of blood loss in on-pump cardiothoracic surgery", *Expert Opin. Biol. Ther.*, 8:1187-1199 (2008)).

The plasma kallikrein-kinin system is abnormally abundant in patients with advanced diabetic macular edema. It has been recently published that plasma kallikrein contributes to retinal vascular dysfunctions in diabetic rats (Clermont, A. et al., "Plasma kallikrein mediates retinal vascular dysfunction and induces retinal thickening in diabetic rats", *Diabetes*, 60:1590-1598 (2011)). Furthermore, administration of the plasma kallikrein inhibitor ASP-440 ameliorated both retinal vascular permeability and retinal blood flow abnormalities in diabetic rats. Therefore, a plasma kallikrein inhibitor should have utility as a treatment to reduce retinal vascular permeability associated with diabetic retinopathy and diabetic macular edema. Other complications of diabetes such as cerebral hemorrhage, nephropathy, cardiomyopathy and neuropathy, all of which have associations with plasma kallikrein may also be considered as targets for a plasma kallikrein inhibitor.

To date, no small molecule synthetic plasma kallikrein inhibitor has been approved for medical use. The large protein plasma kallikrein inhibitors present risks of anaphylactic reactions, as has been reported for Ecallantide. Thus there remains a need for compounds that inhibit plasma kallikrein, that do not induce anaphylaxis and that are orally available. Furthermore, the molecules in the known art feature a highly polar and ionizable guanidine or amidine functionality. It is well known that such functionalities may be limiting to gut permeability and therefore to oral availability.

SUMMARY OF THE INVENTION

The present invention provides novel macrocyclic compounds, their analogues, including stereoisomers, tautomers, pharmaceutically acceptable salts, or solvates thereof, which are useful as selective factor XIa inhibitors or dual inhibitors of factor XIa and plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof The compounds of the invention may be used in the treatment and/or prophylaxis of thromboembolic disorders.

The compounds of the invention may be used in the treatment of retinal vascular permeability associated with diabetic retinopathy and diabetic macular edema.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

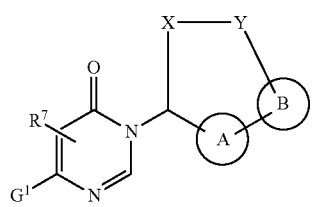

(1)

or stereoisomers, tautomers, pharmaceutically acceptable salts, solvates, or prodrugs thereof, wherein:

ring A is independently selected from 6-membered aryl and 5- to 6-membered heterocyclyl, wherein said aryl and heterocyclyl are optionally substituted with, where valence allows, one or more $R^4$;

ring B is 6-membered aryl optionally substituted with, where valence allows, one or more $R^3$;

$G^1$ is independently selected from $C_{3-10}$ carbocyclyl and 5- to 10-membered heterocyclyl, wherein said carbocyclyl and heterocyclyl are optionally substituted with, where valence allows, one or more $R^8$;

X is independently selected from $C_{4-8}$ alkylene and $C_{4-8}$ alkenylene, wherein said alkylene and alkenylene are substituted with $R^1$ and $R^2$; alternatively one or more of the carbon atoms of said alkylene and alkenylene may be replaced by O, C=O, $S(=O)_p$, $S(=O)_p NH$, and $NR^{15}$;

Y is independently selected from —$CR^{13}NH$—, —NHC(=O)—, —C(=O)NH—, —$S(=O)_p NH$—, —NHS(=O)$_p$—, and $C_{1-2}$ alkylene;

$R^1$ and $R^2$ are independently selected from H, halogen, haloalkyl, $C_{1-6}$ alkyl (optionally substituted with $R^6$), hydroxyl, and alkoxy (optionally substituted with $R^6$), and $C_{3-6}$ cycloalkyl optionally substituted with $R^6$; optionally, when $R^1$ and $R^2$ are attached to the same carbon atom, together they form an oxo group or $C_{3-6}$ cycloalkyl; optionally, when $R^1$ and $R^2$ are attached to carbon atoms adjacent to each other, together they form a bond or a carbocyclyl; optionally, $R^1$ and $R^{15}$ or $R^2$ and $R^{15}$ taken together form a ring;

$R^3$ is independently selected from H, $NO_2$, halogen, haloalkyl, $C_{1-4}$ alkyl (optionally substituted with $R^6$), $C_{2-4}$ alkenyl (optionally substituted with $R^6$), $C_{2-4}$ alkynyl (optionally substituted with $R^6$), CN, —(CH$_2$)$_n$—OR$^5$, —(CH$_2$)$_n$—NR$^5$R$^5$, —(CH$_2$)$_n$—C(=O)R$^5$, —(CH$_2$)$_n$—C(=O)OR$^5$, —(CH$_2$)$_n$—NR$^9$C(=O)OR$^5$, —(CH$_2$)$_n$—NR$^9$C(=O)R$^5$, —(CH$_2$)$_n$—NR$^9$C(N—CN)NHR$^5$, —(CH$_2$)$_n$—NR$^9$C(NH)NHR$^5$, —(CH$_2$)$_n$—N=CR$^9$NR$^5$R$^5$, —(CH$_2$)$_n$—NR$^9$C(=O)NR$^5$R$^5$, —(CH$_2$)$_n$—C(=O)NR$^5$R$^5$, —(CH$_2$)$_n$—NR$^9$C(=S)NR$^9$C(=O)R$^5$, —(CH$_2$)$_n$—S(=O)$_p$R$^5$, —(CH$_2$)$_n$—S(=O)$_p$NR$^5$R$^5$, —(CH$_2$)$_n$—NR$^9$S(=O)$_p$NR$^5$R$^5$, —(CH$_2$)$_n$—NR$^9$S(=O)$_p$R$^5$, —(CH$_2$)$_n$—C$_{3-10}$ carbocyclyl and —(CH$_2$)$_n$-4- to 10-membered heterocyclyl, wherein said carbocyclyl and heterocyclyl are optionally substituted with $R^6$; optionally, two adjacent $R^3$ groups on the carbocyclyl and heterocyclyl may form a ring optionally substituted with $R^6$;

$R^4$ is independently selected from H, OH, $NH_2$, halogen, CN, $C_{1-4}$ alkyl, $C_{1-4}$ haloalkyl, $C_{1-4}$ alkoxy, —CH$_2$OH, —C(=O)OH, —CH$_2$C(=O)OH, —CO$_2$(C$_{1-4}$ alkyl), —C(=O)NH$_2$, —C(=O)NH(C$_{1-4}$ alkyl), —C(=O)N(C$_{1-4}$ alkyl)$_2$, —S(=O)$_2$C$_{1-4}$ alkyl, —S(=O)$_2$NH$_2$, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H, $C_{1-4}$ alkyl (optionally substituted with halogen, hydroxyl, alkoxy, carboxy, hydroxycarbonyl, alkoxycarbonyl, amino, substituted amino), —(CH$_2$)$_n$—C$_{3-10}$ carbocyclyl and —(CH$_2$)$_n$-4- to 10-membered heterocyclyl, wherein said carbocyclyl and heterocyclyl are optionally substituted with $R^6$; alternatively, $R^5$ and $R^5$ together with the nitrogen atom to which they are both attached form a heterocyclic ring optionally substituted with $R^6$;

$R^6$ is independently selected from H, —(CH$_2$)$_n$—OH, =O, —(CH$_2$)$_n$NH$_2$, —(CH$_2$)$_n$CN, halogen, $C_{1-6}$ alkyl, —(CH$_2$)$_n$—C(=O)OH, —(CH$_2$)$_n$—C(=O)NH$_2$, —(CH$_2$)$_n$—C(=O)OC$_{1-4}$ alkyl, —(CH$_2$)$_n$—OC$_{1-4}$ alkyl, —(CH$_2$)$_n$—C$_{3-10}$ carbocyclyl, —(CH$_2$)$_n$-4- to 10-membered heterocyclyl, and —O-4- to 10-membered heterocyclyl, wherein said carbocyclyl and heterocyclyl are optionally substituted with $R^{10}$;

$R^7$ is independently selected from H, hydroxyl, alkoxy, halogen, amino, $C_{1-3}$haloalkyl, and $C_{1-3}$ alkyl;

$R^8$ is independently selected from H, halogen, —(CH$_2$)$_n$CN, $C_{1-6}$ alkyl, amino, aminoalkyl, haloalkyl, hydroxyl, alkoxy, haloalkoxy, alkylcarbonyl, carboxyl, carboxyl ester, amide, haloalkylaminocarbonyl, arylalkylaminocarbonyl, haloalkylaminocarbonyl, alkoxycarbonylamino, haloalkylcarbonylamino, arylamino, heteroarylamino, arylalkylcarbonyl, aryloxy, heteroaryloxy, alkylthio, alkylsulfonyl, arylsulfonyl, heteroarylsulfonyl, sulfonamide, —(CH$_2$)$_n$-aryl, —(CH$_2$)$_n$—C$_{3-6}$ cycloalkyl, and —(CH$_2$)$_n$-4- to 12-membered heterocyclyl, wherein said aryl, cycloalkyl, and heterocyclyl are optionally substituted with $R^{10}$; alternatively, two adjacent $R^8$ groups taken together form a heterocyclic ring optionally substituted with $R^{10}$;

$R^9$ is H or $C_{1-6}$ alkyl;

$R^{10}$ is independently selected from H, $C_{1-6}$ alkyl (optionally substituted with $R^{11}$), $C_{2-6}$ alkenyl, $C_{2-6}$ alkynyl, aryl (optionally substituted with $R^{11}$), —(CH$_2$)$_n$—C$_{3-6}$ cycloalkyl (optionally substituted with $R^{11}$), —(CH$_2$)$_n$—O-4- to 10-membered heterocyclyl (optionally substituted with $R^{11}$), halogen, —(CH$_2$)$_n$CN, $NO_2$, =O, C(=O)NR$^{12}$R$^{12}$, —(CH$_2$)$_n$—C(=O)OR$^{12}$, Si(C$_{1-4}$ alkyl)$_3$, —(CH$_2$)$_n$—OR$^{12}$, —(CH$_2$)$_n$—NR$^{12}$R$^{12}$, —S(=O)$_p$C$_{1-6}$ alkyl, NR$^{12}$S(=O)$_p$C$_{1-6}$ alkyl, S(=O)$_p$NR$^{12}$R$^{12}$, and C(=NOH)NH$_2$;

$R^{11}$, at each occurrence, is independently selected from H, halogen, $C_{1-5}$ alkyl, —$(CH_2)_n$—OH, $C_{3-6}$ cycloalkyl, phenyl, and heterocyclyl;

$R^{12}$, at each occurrence, is independently selected from H, $C_{1-5}$ alkyl optionally substituted with $R^{11}$, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$ alkyl;

$R^{13}$ is, independently at each occurrence, selected from H, $C_{1-4}$ haloalkyl, $C_{1-4}$ alkyl, C(=O)OH, C(=O)O($C_{1-4}$ alkyl), C(=O)O($CH_2)_2$O($C_{1-4}$ alkyl), C(=O)O($C_{1-4}$ haloalkyl), $CH_2$C(=O)OH, $CH_2$C(=O)O($C_{1-4}$ alkyl), C(=O)$NH_2$, C(=O)NH($C_{1-4}$ alkyl), C(=O)N($C_{1-4}$ alkyl)$_2$, and —C(=O)NH($C_{1-4}$ alkoxy);

$R^{15}$ is H or $C_{1-6}$ alkyl;

n, at each occurrence, is an integer independently selected from 0, 1, 2, 3, and 4; and p, at each occurrence, is an integer independently selected from 0, 1, and 2.

In another aspect, the present invention provides compounds of Formula (I) or stereoisomers, tautomers, pharmaceutically acceptable salts, solvates, or prodrugs thereof, wherein:

ring A is independently selected from a 6-membered aryl and a 5- to 6-membered heterocycle, wherein said aryl and heterocycle are optionally substituted with, where valence allows, one or more $R^4$;

ring B is a 6-membered aryl optionally substituted with, where valence allows, one or more $R^3$;

$G^1$ is independently selected from a $C_{3-10}$ carbocycle and a 5- to 10-membered heterocycle, wherein said carbocycle and heterocycle are optionally substituted with, where valence allows, one or more $R^8$;

X is independently selected from $C_{4-8}$ alkylene and $C_{4-8}$ alkenylene, wherein said alkylene and alkenylene are substituted with $R^1$ and $R^2$; alternatively one or more of the carbon atoms of said alkylene and alkenylene may be replaced by O, C=O, S(=O)$_p$, S(=O)$_p$NH, NH, and N($C_{1-4}$ alky);

Y is independently selected from —$CR^{13}$NH—, —NHC(=O)—, —C(=O)NH—, —S(=O)$_p$NH—, —NHS(=O)$_p$—, and $C_{1-2}$ alkylene;

$R^1$ and $R^2$ are independently selected from H, halogen, haloalkyl, $C_{1-6}$ alkyl (optionally substituted with $R^6$), hydroxyl, and alkoxy (optionally substituted with $R^6$), and $C_{3-6}$ cycloalkyl optionally substituted with $R^6$; optionally, when $R^1$ and $R^2$ are attached to the same carbon atom, together they form an oxo group or $C_{3-6}$ cycloalkyl; optionally, when $R^1$ and $R^2$ are attached to carbon atoms adjacent to each other, together they form a bond or a carbocycle;

$R^3$ is independently selected from H, $NO_2$, halogen, haloalkyl, $C_{1-4}$ alkyl (optionally substituted with $R^6$), $C_{2-4}$ alkenyl (optionally substituted with $R^6$), $C_{2-4}$ alkynyl (optionally substituted with $R^6$), CN, —$(CH_2)_n$—$OR^5$, —$(CH_2)_n$—$NR^5R^5$, —$(CH_2)_n$—C(=O)$R^5$, —$(CH_2)_n$—C(=O)$OR^5$, —$(CH_2)_n$—$NR^9$C(=O)$OR^5$, —$(CH_2)_n$—$NR^9$C(=O)$R^5$, —$(CH_2)_n$—$NR^9$C(N=CN)$NHR^5$, —$(CH_2)_n$—$NR^9$C(NH)$NHR^5$, —$(CH_2)_n$—N=$CR^9NR^5R^5$, —$(CH_2)_n$—$NR^9$C(=O)$NR^5R^5$, —$(CH_2)_n$—C(=O)$NR^5R^5$, —$(CH_2)_n$—$NR^9$C(=S)$NR^9$C(=O)$R^5$, —$(CH_2)_n$—S(=O)$_2$$C_{1-6}$ alkyl optionally substituted with $R^{11}$, —$(CH_2)_n$—S(=O)$_p$$NR^5R^5$, —$(CH_2)_n$—$NR^9$S(=O)$_p$$NR^5R^5$, —$(CH_2)_n$—$NR^9$S(=O)$_p$$C_{1-6}$ alkyl optionally substituted with $R^{11}$, —$(CH_2)_n$—$C_{3-10}$ carbocycle and —$(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$;

$R^4$ is independently selected from H, OH, $NH_2$, halogen, CN, $C_{1-4}$ alkyl, $C_{1-4}$ haloalkyl, $C_{1-4}$ alkoxy, —$CH_2$OH, —C(=O)OH, —$CH_2$C(=O)OH, —$CO_2$($C_{1-4}$ alkyl), —C(=O)$NH_2$, —C(=O)NH($C_{1-4}$ alkyl), —C(=O)N($C_{1-4}$ alkyl)$_2$, —S(=O)$_2$$C_{1-4}$ alkyl, S(=O)$_2$$NH_2$, $C_{3-6}$ cycloalkyl, aryl, and 5- to 6-membered heterocycle, wherein said cycloalkyl, aryl and heterocycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), —$(CH_2)_n$—$C_{3-10}$ carbocycle and —$(CH_2)_n$-4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from H, —$(CH_2)_n$—OH, =O, —$(CH_2)_n$$NH_2$, —$(CH_2)$CN, halogen, $C_{1-6}$ alkyl, —$(CH_2)_n$—C(=O)OH, —$(CH_2)_n$—C(=O)$OC_{1-4}$ alkyl, —$(CH_2)_n$—$OC_{1-4}$ alkyl, —$(CH_2)_n$—$C_{3-10}$ carbocycle, —$(CH_2)_n$4- to 10-membered heterocycle, and -0-4- to 10-membered heterocycle, wherein said carbocycle and heterocycle are optionally substituted with $R^{10}$;

$R^7$ is independently selected from H, hydroxyl, alkoxy, halogen, amino, and $C_{1-3}$ alkyl;

$R^8$ is independently selected from H, halogen, CN, $NH_2$, $C_{1-6}$ alkyl, haloalkyl, haloalkylcarbonylamine, alkylcarbonyl, hydroxyl, alkoxy, haloalkoxy, —$(CH_2)_n$-aryl, —$(CH_2)_n$—$C_{3-6}$ cycloalkyl, and —$(CH_2)_n$-4- to 6-membered heterocycle, wherein said aryl, cycloalkyl, and heterocycle are optionally substituted with $R^{10}$; alternatively, two adjacent $R^8$ groups form a heterocyclic ring optionally substituted with $R^{10}$;

$R^9$ is H or $C_{1-6}$ alkyl;

$R^{10}$ is independently selected from H, $C_{1-6}$ alkyl (optionally substituted with $R^{11}$), $C_{2-6}$ alkenyl, $C_{2-6}$ alkynyl, aryl, —$(CH_2)_n$—$C_{3-6}$ cycloalkyl (optionally substituted with $R^{11}$), —$(CH_2)_n$—O-4- to 10-membered heterocycle (optionally substituted with $R^{11}$), halogen, CN, $NO_2$, =O, C(=O)$NR^{12}R^{12}$, C(=O)OH, Si($C_{1-4}$ alkyl)$_3$, —$(CH_2)_n$—$OR^{12}$, —$(CH_2)_n$—$NR^{12}R^{12}$, and C(=NOH)$NH_2$;

$R^{11}$, at each occurrence, is independently selected from H, halogen, $C_{1-5}$ alkyl, —$(CH_2)_n$—OH, $C_{3-6}$ cycloalkyl, phenyl, and heterocycle, or $R^{11}$ and $R^{11}$ together with the nitrogen atom to which they are both attached form a heterocyclic ring optionally substituted with $C_{1-4}$ alkyl;

$R^{12}$, at each occurrence, is independently selected from H, $C_{1-5}$ alkyl, $C_{3-6}$ cycloalkyl, phenyl, and heterocycle, or $R^{12}$ and $R^{12}$ together with the nitrogen atom to which they are both attached form a heterocyclic ring optionally substituted with $C_{1-4}$ alkyl;

$R^{13}$ is, independently at each occurrence, selected from H, halogen, $C_{1-4}$ haloalkyl, $CO_2$H, $CO_2$($C_{1-4}$ alkyl), $CO_2$($CH_2$)$_2$O($C_{1-4}$ alkyl), $CO_2$($C_{1-4}$ haloalkyl), $CO_2$($CH_2$)$_2$$SO_2$($C_{1-4}$ alkyl), $CH_2CO_2$H, $CH_2CO_2$($C_{1-4}$ alkyl), $CONH_2$, CONH($C_{1-4}$ alkyl), CON($C_{1-4}$ alkyl)$_2$, —CONH($C_{1-4}$ alkoxy), —$CO_2$($CH_2$)$_2$O($C_{1-4}$ alkyl), —$CO_2$($CH_2$)$_2$N($C_{1-4}$ alkyl)$_2$, —CONH($CH_2$)$_2$O($C_{1-4}$ alkyl), —CONH($CH_2$)$_2$N($C_{1-4}$ alkyl)$_2$, —CON($C_{1-4}$ alkyl)($CH_2$)$_2$O($C_{1-4}$ alkyl), —CON($C_{1-4}$ alkyl)($CH_2$)$_2$N($C_{1-4}$ alkyl)$_2$, $C_{1-4}$ alkyl, —CONHBn, —CONH(OBn), —(CO)$_{0-1}$($CH_2$)$_{0-3}$—$C_{3-6}$ carbocycle, and —$(CH_2)_{0-1}$—(CO)$_{0-1}$—(V)$_{0-1}$—$(CH_2)_{0-2}$-(4- to 6-membered heterocycle comprising carbon atoms and 1-4 heteroatoms selected from N, NH, N($C_{1-4}$ alkyl), O, and S(O)$_p$); wherein said carbocycle and heterocycle are substituted with 0-2 $R^{14}$;

$R^{14}$ is, independently at each occurrence, selected from the group consisting of: halogen, OH, $CHF_2$, $CF_3$, $C_{1-4}$ alkoxy, $CH_2OH$, $CO_2H$, $CO_2(C_{1-4}$ alkyl), $CONH_2$, and $C_{1-4}$ alkyl;

V is independently selected from O, NH and N($C_{1-4}$ alkyl);

n, at each occurrence, is an integer independently selected from 0, 1, 2, 3, and 4; and p, at each occurrence, is an integer independently selected from 0, 1, and 2.

In another aspect, the present invention provides compounds of Formula (I) or stereoisomers, tautomers, pharmaceutically acceptable salts, solvates, or prodrugs thereof, wherein:

ring A is independently selected from a 6-membered aryl and a 5- to 6-membered heterocycle, wherein said aryl and heterocycle are optionally substituted with, where valence allows, one or more $R^4$;

ring B is a 6-membered aryl optionally substituted with, where valence allows, one or more $R^3$;

$G^1$ is independently selected from a $C_{3-10}$ carbocycle and a 5- to 10-membered heterocycle, wherein said carbocycle and heterocycle are optionally substituted with, where valence allows, one or more $R^8$;

X is independently selected from $C_{4-8}$ alkylene and $C_{4-8}$ alkenylene, wherein said alkylene and alkenylene are substituted with $R^1$ and $R^2$; alternatively one or more of the carbon atoms of said alkylene and alkenylene may be replaced by O, C=O, S(O)$_p$, S(O)$_p$NH, NH, and N($C_{1-4}$ alkyl);

Y is independently selected from —NH—C(O)— and —C(O)—NH—;

$R^1$ and $R^2$ are independently selected from H, halogen, haloalkyl, $C_{1-6}$ alkyl (optionally substituted with $R^6$), hydroxyl, and alkoxy (optionally substituted with $R^6$), and $C_{3-6}$ cycloalkyl optionally substituted with $R^6$; optionally, when $R^1$ and $R^2$ are attached to the same carbon atom, together they form an oxo group or $C_{3-6}$cycloalkyl; optionally, when $R^1$ and $R^2$ are attached to carbon atoms adjacent to each other, together they form a bond or a carbocycle;

$R^3$ is independently selected from H, $NO_2$, halogen, haloalkyl, $C_{1-4}$ alkyl (optionally substituted with $R^6$), $C_{2-4}$ alkenyl (optionally substituted with $R^6$), $C_{2-4}$ alkynyl (optionally substituted with $R^6$), CN, —$(CH_2)_n$—$OR^5$, —$(CH_2)_n$—$NR^5R^5$, —$(CH_2)_n$—C(O)$OR^5$, —$(CH_2)_n$—$NR^9C(O)OR^5$, —$(CH_2)_n$—$NR^9C(O)R^5$, —$(CH_2)_n$—$NR^9C(N═CN)NHR^5$, —$(CH_2)_n$—$NR^9C(NH)NHR^5$, —$(CH_2)_n$—N═$CR^9NR^5R^5$, —$(CH_2)_n$—$NR^9C(O)NR^5R^5$, —$(CH_2)_n$—C(O)$NR^5R^5$, —$(CH_2)_n$—$NR^9C(S)NR^9C(O)R^5$, —$(CH_2)_n$—S(O)$_pR^{12}$, —$(CH_2)_n$—S(O)$_pNR^5R^5$, —$(CH_2)_n$—$NR^9S(O)_pNR^5R^5$, —$(CH_2)_n$—$NR^9S(O)_pR^{12}$, —$(CH_2)_n$—$C_{3-10}$ carbocycle and —$(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$;

$R^4$ is independently selected from H, OH, $NH_2$, halogen, CN, $C_{1-4}$ alkyl, $C_{1-4}$ haloalkyl, $C_{1-4}$ alkoxy, —$CH_2OH$, —$CO_2H$, —$CH_2CO_2H$, —$CO_2(C_{1-4}$ alkyl), —C(O)$NH_2$, —C(O)NH($C_{1-4}$ alkyl), —C(O)N($C_{1-4}$ alkyl)$_2$, S(O)$_2NH_2$, $C_{3-6}$ cycloalkyl, aryl, and 5- to 6-membered heterocycle, wherein said cycloalkyl, aryl and heterocycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), —$(CH_2)_n$—$C_{3-10}$ carbocycle and —$(CH_2)_n$-4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from H, —$(CH_2)_n$—OH, =O, —$(CH_2)_n NH_2$, —$(CH_2)_n CN$, halogen, $C_{1-6}$ alkyl, —$(CH_2)_n$—C(=O)OH, —$(CH_2)_n$—C(=O)$OC_{1-4}$ alkyl, —$(CH_2)_n$—$OC_{1-4}$ alkyl, —$(CH_2)_n$—$C_{3-10}$ carbocycle, —$(CH_2)_n$-4- to 10-membered heterocycle, and —O-4- to 10-membered heterocycle, wherein said carbocycle and heterocycle are optionally substituted with $R^{10}$;

$R^7$ is independently selected from H, hydroxyl, alkoxy, halogen, amino, and $C_{1-3}$ alkyl;

$R^8$ is independently selected from H, halogen, CN, $NH_2$, $C_{1-6}$ alkyl, haloalkyl, haloalkylcarbonylamine, alkylcarbonyl, alkoxy, haloalkoxy, —$(CH_2)_n$-aryl, —$(CH_2)_n$—$C_{3-6}$ cycloalkyl, and —$(CH_2)_n$-4- to 6-membered heterocycle;

$R^9$ is H or $C_{1-6}$ alkyl;

$R^{10}$ is independently selected from H, $C_{1-6}$ alkyl (optionally substituted with $R^{11}$), $C_{2-6}$ alkenyl, $C_{2-6}$ alkynyl, —$(CH_2)_n$—$C_{3-6}$ cycloalkyl (optionally substituted with $R^{11}$), —O-4- to 10-membered heterocycle (optionally substituted with $R^{11}$), F, Cl, Br, CN, $NO_2$, =O, $CO_2H$, —$(CH_2)_n$—$OC_{1-5}$ alkyl, —$(CH_2)_n$—$OR^{11}$, and —$(CH_2)_n$—$NR^{11}R^{11}$;

$R^{11}$, at each occurrence, is independently selected from H, $C_{1-5}$ alkyl, —$(CH_2)_n$—OH' $C_{3-6}$ cycloalkyl, and phenyl, or $R^{11}$ and $R^{11}$ together with the nitrogen atom to which they are both attached form a heterocyclic ring optionally substituted with $C_{1-4}$ alkyl;

$R^{12}$ is $C_{1-6}$ alkyl optionally substituted with $R^{11}$;

n, at each occurrence, is an integer independently selected from 0, 1, 2, 3, and 4; and p, at each occurrence, is an integer independently selected from 0, 1, and 2.

In another aspect, the present invention provides compounds of Formula (II):

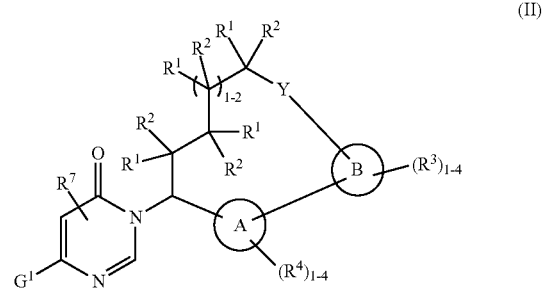

or stereoisomers, tautomers, pharmaceutically acceptable salts, solvates, or prodrugs thereof, wherein:

ring A is independently selected from a 6-membered aryl and a 5- to 6-membered heterocycle, wherein said aryl and heterocycle are substituted with 1-4 $R^4$;

ring B is a 6-membered aryl;

$G^1$ is independently selected from a $C_{3-10}$ carbocycle and a 5- to 10-membered heterocycle, wherein said carbocycle and heterocycle are substituted with 1-4 $R^8$;

Y is independently selected from —NH—C(O)— and —C(O)—NH—;

$R^1$ and $R^2$ are independently selected from H, halogen, haloalkyl, $C_{1-4}$ alkyl (optionally substituted with $R^6$), hydroxyl, and alkoxy (optionally substituted with $R^6$), and $C_{3-5}$ cycloalkyl optionally substituted with $R^6$;

$R^3$ is independently selected from H, halogen, haloalkyl, $C_{1-4}$ alkyl (optionally substituted with $R^6$), $C_{2-4}$ alkenyl (optionally substituted with $R^6$), $C_{2-4}$ alkynyl (optionally substituted with $R^6$), CN, $NO_2$, $-(CH_2)_n-OR^5$, $-(CH_2)_n-NR^5R^5$, $-(CH_2)_n-C(O)OR^5$, $-(CH_2)_n-NR^9C(O)OR^5$, $-(CH_2)_n-NR^9C(O)R^5$, $-(CH_2)_n-NR^9C(N-CN)NHR^5$, $-(CH_2)_n-NR^9C(NH)NHR^5$, $-(CH_2)_n-N=CR^9NR^5R^5$, $-(CH_2)_n-NR^9C(O)NR^5R^5$, $-(CH_2)_n-C(O)NR^5R^5$, $-(CH_2)_n-NR^9C(S)NR^9C(O)R^5$, $-(CH_2)_n-S(O)_pR^{12}$, $-(CH_2)_n-S(O)_pNR^5R^5$, $-(CH_2)_n-NR^9S(O)_pNR^5R^5$, $-(CH_2)_n-NR^9S(O)_pR^{12}$, $-(CH_2)_n-C_{3-10}$ carbocycle and $-(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$;

$R^4$ is independently selected from H, OH, halogen, CN, $C_{1-4}$ alkyl, $C_{1-4}$ haloalkyl, $C_{1-4}$ alkoxy, $-C(O)NH_2$, $-C(O)NH(C_{1-4}$ alkyl), $-C(O)N(C_{1-4}$ alkyl)$_2$, $C_{3-6}$ cycloalkyl, aryl, and 5- to 6-membered heterocycle, wherein said cycloalkyl, aryl and heterocycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), $C_{3-10}$ carbocycle and 4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from OH, =O, $-(CH_2)_n NH_2$, $-(CH_2)_nCN$, halogen, $C_{1-6}$ alkyl, $-(CH_2)_n-C(=O)OH$, $-(CH_2)_n-C(=O)OC_{1-4}$ alkyl, $-(CH_2)_n-OC_{1-4}$ alkyl, $-(CH_2)_n-C_{3-10}$ carbocycle, $-(CH_2)_n$-4- to 10-membered heterocycle, and $-(CH_2)_n$-4- to 10-membered heterocycle, wherein said carbocycle and heterocycle are optionally substituted with $R^{10}$;

$R^7$ is independently selected from H, hydroxyl, alkoxy, halogen, methyl, ethyl, and isopropyl;

$R^8$ is independently selected from H, halogen, CN, $NH_2$, $C_{1-6}$ alkyl, haloalkyl, alkylcarbonyl, alkoxy, haloalkoxy, $-(CH_2)_n$-aryl, $-(CH_2)_n-C_{3-6}$ cycloalkyl, and $-(CH_2)_n$-4- to 6-membered heterocycle;

$R^9$ is H or $C_{1-6}$ alkyl;

$R^{10}$ is independently selected from $C_{1-6}$ alkyl (optionally substituted with $R^{11}$), $C_{2-6}$ alkenyl, $C_{2-6}$ alkynyl, $-(CH_2)_n-C_{3-6}$ cycloalkyl, $-O$-4- to 10-membered heterocycle (optionally substituted with $R^{11}$), F, Cl, Br, CN, $NO_2$, =O, $CO_2H$, $-(CH_2)_n-OC_{1-5}$ alkyl, $-(CH_2)_n-OR^{11}$, and $-(CH_2)_n-NR^{11}R^{11}$;

$R^{11}$, at each occurrence, is independently selected from H, $C_{1-5}$ alkyl, $-(CH_2)_n-OH$, $C_{3-6}$ cycloalkyl, and phenyl, or $R^{11}$ and $R^{11}$ together with the nitrogen atom to which they are both attached form a heterocyclic ring optionally substituted with $C_{1-4}$ alkyl;

$R^{12}$ is $C_{1-6}$ alkyl optionally substituted with $R^{11}$;

n, at each occurrence, is an integer independently selected from 0, 1, 2, 3, and 4; and p, at each occurrence, is an integer independently selected from 0, 1, and 2.

In another aspect, the present invention provides compounds of Formula (IIa):

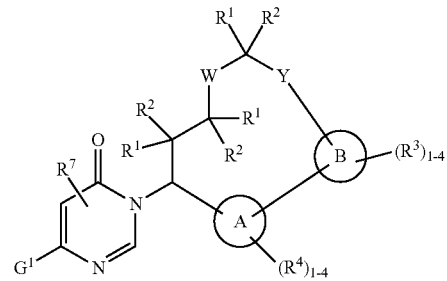

(IIa)

or stereoisomers, tautomers, pharmaceutically acceptable salts, solvates, or prodrugs thereof, wherein:

ring A is independently selected from 6-membered aryl and 5- to 6-membered heterocyclyl;

ring B is 6-membered aryl;

$G^1$ is independently selected from $C_{3-6}$ carbocyclyl and 5- to 10-membered heterocyclyl, wherein said carbocyclyl and heterocyclyl are substituted with 1-4 $R^8$;

W is independently selected from $(CR^1R^2)_{1-2}$, O, and $NR^{15}$;

Y is independently selected from $-CR^{13}NH-$, $-NHC(=O)-$ and $-C(=O)NH-$;

$R^1$ and $R^2$ are independently selected from H, halogen, haloalkyl, $C_{1-4}$ alkyl (optionally substituted with $R^6$), hydroxyl, and alkoxy (optionally substituted with $R^6$), and $C_{3-5}$ cycloalkyl optionally substituted with $R^6$; optionally, $R^1$ and $R^{15}$ or $R^2$ and $R^{15}$ taken together form a ring;

$R^3$ is independently selected from H, halogen, haloalkyl, $C_{1-4}$ alkyl (optionally substituted with $R^6$), $C_{2-4}$ alkenyl (optionally substituted with $R^6$), $C_{2-4}$ alkynyl (optionally substituted with $R^6$), CN, $NO_2$, $-(CH_2)_n-OR^5$, $-(CH_2)_n-NR^5R^5$, $-(CH_2)_n-C(=O)R^5$, $-(CH_2)_n-C(=O)OR^5$, $-(CH_2)_n-NR^9C(=O)OR^5$, $-(CH_2)_n-NR^9C(=O)R^5$, $-(CH_2)_n-NR^9C(N-CN)NHR^5$, $-(CH_2)_n-NR^9C(NH)NHR^5$, $-(CH_2)_n-N=CR^9NR^5R^5$, $-(CH_2)_n-NR^9C(=O)NR^5R^5$, $-(CH_2)_n-C(=O)NR^5R^5$, $-(CH_2)_n-NR^9C(S)NR^9C(=O)R^5$, $-(CH_2)_n-S(=O)_pC_{1-6}$ alkyl optionally substituted with $R^{11}$, $-(CH_2)_n-S(=O)_pNR^5R^5$, $-(CH_2)_n-NR^9S(=O)_pNR^5R^5$, $-(CH_2)_n-NR^9S(=O)_p C_{1-6}$ alkyl optionally substituted with $R^{11}$, $-(CH_2)_n-C_{3-10}$ carbocyclyl and $-(CH_2)_n$-4- to 10-membered heterocyclyl, wherein said carbocyclyl and heterocyclyl are optionally substituted with $R^6$; optionally, two adjacent $R^3$ groups on the carbocyclyl and heterocyclyl may form a ring optionally substituted with $R^6$;

$R^4$ is independently selected from H, OH, halogen, CN, $C_{1-4}$ alkyl, $C_{1-4}$ haloalkyl, $C_{1-4}$ alkoxy, $-C(=O)NH_2$, $-C(=O)NH(C_{1-4}$ alkyl), $-C(=O)N(C_{1-4}$ alkyl)$_2$, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), $C_{3-10}$ carbocyclyl and 4- to 10-membered heterocyclyl, wherein said carbocyclyl and heterocyclyl are optionally substituted with $R^6$;

$R^6$ is independently selected from OH, =O, $-(CH_2)_n NH_2$, $-(CH_2)_nCN$, halogen, $C_{1-6}$ alkyl, $-(CH_2)_n-C(=O)OH$, $-(CH_2)_n-C(=O)OC_{1-4}$ alkyl, $-(CH_2)_n-OC_{1-4}$ alkyl, $-(CH_2)_n-C(=O)NH_2$, $-(CH_2)_n-C_{3-10}$ carbocyclyl, $-(CH_2)_n$-4- to 10-membered heterocyclyl, and —(CH$_2$)$_n$-4- to 10-membered heterocyclyl, wherein said carbocyclyl and heterocyclyl are optionally substituted with R$^{10}$;

R$^7$ is independently selected from H, hydroxyl, halogen, and methyl;

R$^8$ is independently selected from H, halogen, CN, NH$_2$, C$_{1-6}$ alkyl, haloalkyl, haloalkylcarbonylamino, arylamino, heteroarylamino, hydroxycarbonyl, haloalkylaminocarbonyl, arylalkylcarbonyl, alkylcarbonyl, alkoxy, haloalkoxy, —(CH$_2$)$_n$-aryl, —(CH$_2$)$_n$—C$_{3-6}$ cycloalkyl, and —(CH$_2$)$_n$-4- to 12-membered heterocyclyl, wherein said aryl, cycloalkyl, and heterocyclyl are optionally substituted with R$^{10}$);

alternatively, two adjacent R$^8$ groups and G$_1$ form a fused heterocyclic group selected from

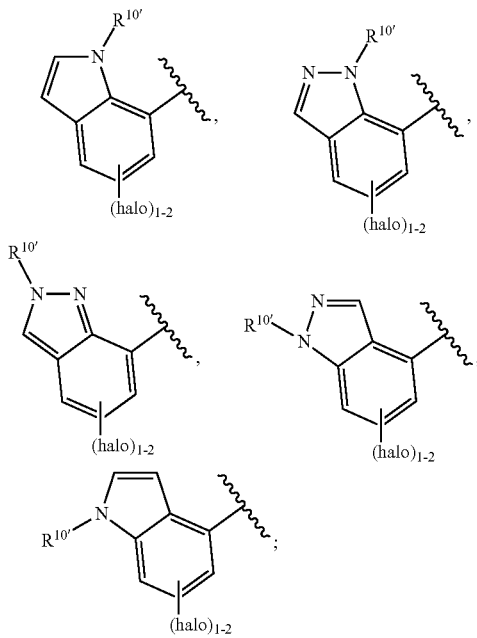

R$^9$ is H or C$_{1-6}$ alkyl;

R$^{10}$ is independently selected from H, C$_{1-6}$ alkyl (optionally substituted with R$^{11}$), C$_{2-6}$ alkenyl, C$_{2-6}$ alkynyl, aryl (optionally substituted with R$^{11}$), —(CH$_2$)$_n$—C$_{3-6}$ cycloalkyl (optionally substituted with R$^{11}$), —(CH$_2$)$_n$—O-4- to 10-membered heterocyclyl (optionally substituted with R$^{11}$), F, Cl, Br, —(CH$_2$)$_n$CN, NO$_2$, =O, C(=O)NR$^{12}$R$^{12}$, C(=O)OR$^{12}$, Si(C$_{1-4}$ alkyl)$_3$, —(CH$_2$)$_n$—OR$^{12}$, —(CH$_2$)$_n$—NR$^{12}$R$^{12}$, —S(=O)$_p$C$_{1-6}$ alkyl, NR$^{12}$S(=O)$_p$C$_{1-6}$ alkyl, S(=O)$_p$NR$^{12}$R$^{12}$, and C(=NOH)NH$_2$;

R$^{10'}$ is independently selected from H, C$_{1-6}$ alkyl (optionally substituted with R$^{11}$), aryl, —(CH$_2$)$_n$—C$_{3-6}$ cycloalkyl (optionally substituted with R$^{11}$), and —(CH$_2$)$_n$—O-4- to 10-membered heterocyclyl (optionally substituted with R$^{11}$);

R$^{11}$, at each occurrence, is independently selected from H, halogen, C$_{1-5}$ alkyl, —(CH$_2$)$_n$—OH, C$_{3-6}$ cycloalkyl, and phenyl;

R$^{12}$, at each occurrence, is independently selected from H, C$_{1-5}$ alkyl (optionally substituted with R$^{11}$), C$_{3-6}$ cycloalkyl, phenyl, and heterocyclyl, or R$^{12}$ and R$^{12}$ together with the nitrogen atom to which they are both attached form a heterocyclic ring optionally substituted with C$_{1-4}$alkyl;

R$^{13}$ is, independently at each occurrence, selected from H, CF$_3$, and CH$_3$;

n, at each occurrence, is an integer independently selected from 0, 1, 2, 3, and 4; and p, at each occurrence, is an integer independently selected from 0, 1, and 2.

In another aspect, the present invention provides compounds of Formula (III):

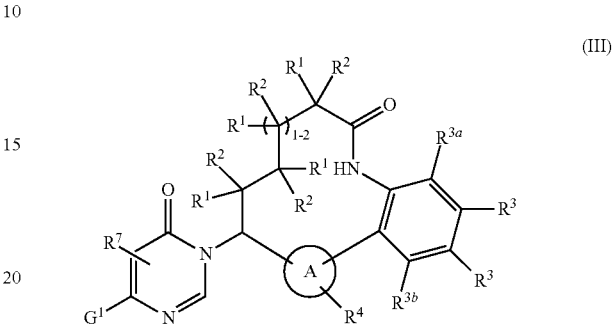

or stereoisomers, tautomers, pharmaceutically acceptable salts, solvates, or prodrugs thereof, wherein:

ring A is independently selected from phenyl and a 5- to 6-membered heterocycle;

G$^1$ is independently selected from aryl, C$_{3-6}$ cycloalkyl and a 5- to 6-membered heterocycle, wherein said aryl, cycloalkyl and heterocycle are substituted with 1-4 R$^8$;

R$^1$ and R$^2$ are independently selected from H, halogen, CF$_3$, C$_{1-6}$ alkyl, and hydroxyl;

R$^3$ is independently selected from H, halogen, haloalkyl, C$_{1-4}$ alkyl (optionally substituted with R$^6$), C$_{2-4}$ alkenyl (optionally substituted with R$^6$), CN, NO$_2$, —(CH$_2$)$_n$—OR$^5$, —(CH$_2$)$_n$—NR$^5$R$^5$, —(CH$_2$)$_n$—C(O)OR$^5$, —(CH$_2$)$_n$—NHC(O)OR$^5$, —(CH$_2$)$_n$—NHC(O)R$^5$, —(CH$_2$)$_n$—NHC(N=CN)NHR$^5$, —(CH$_2$)$_n$—NHC(NH)NHR$^5$, —(CH$_2$)$_n$—N=CHNR$^5$R$^5$, —(CH$_2$)$_n$—NHC(O)NR$^5$R$^5$, —(CH$_2$)$_n$—C(O)NR$^5$R$^5$, —(CH$_{2n}$—NHC(S)NR$^9$C(O)R$^5$, —(CH$_2$)$_n$—S(O)$_p$R$^{12}$, —(CH$_2$)$_n$—S(O)$_p$NR$^5$R$^5$, —(CH$_2$)$_n$—NHS(O)$_p$NR$^5$R$^5$, —(CH$_2$)$_n$—NHS(O)$_p$R$^{12}$, —(CH$_2$)$_n$—C$_{3-10}$ carbocycle and —(CH$_2$)$_n$-4- to 10-membered heterocycle, wherein said carbocycle and heterocycle are optionally substituted with R$^6$; optionally, two adjacent R$^3$ groups on the carbocycle and heterocycle may form a ring optionally substituted with R$^6$;

R$^{3a}$ is independently selected from H and halogen;

R$^{3b}$ is independently selected from H, halogen, and CN;

R$^4$ is independently selected from H, OH, F, Cl, Br, C$_{1-4}$ alkyl, C$_{1-4}$ alkoxy, CF$_3$, CN, C$_{3-6}$ cycloalkyl, aryl, and 5- to 6-membered heterocycle, wherein said cycloalkyl, aryl and heterocycle are optionally substituted with R$^6$;

R$^5$ is independently selected from H, C$_{1-4}$ alkyl (optionally substituted with halogen, hydroxyl, alkoxy, carboxy, alkoxycarbonyl, amino, substituted amino), —(CH$_2$)$_n$—C$_{3-10}$ carbocycle and —(CH$_2$)$_n$-4- to 10-membered heterocycle, wherein said carbocycle and heterocycle are optionally substituted with R$^6$;

R$^6$ is independently selected from —(CH$_2$)$_n$—OH, =O, NH$_2$, —(CH$_2$)$_n$—CN, halogen, C$_{1-6}$ alkyl, —(CH$_2$)$_n$—C(O)OH, —(CH$_2$)$_n$—C(O)OC$_{1-4}$ alkyl, —(CH$_2$)$_n$—OC$_{1-4}$ alkyl, —(CH$_2$)$_n$—C$_{3-6}$ cycloalkyl, —(CH$_2$)$_n$-4- to 10-membered heterocycle, and —O—(CH$_2$)$_n$-4- to 10-membered heterocycle, wherein said cycloalkyl and heterocycle are optionally substituted with R$^{10}$;

R⁷ is independently selected from H, F, methyl, and ethyl;

R⁸ is independently selected from H, halogen, CN, NH₂, C₁₋₆ alkyl, haloalkyl, alkylcarbonyl, alkoxy, haloalkoxy, aryl, C₃₋₆ cycloalkyl, and 4- to 6-membered heterocycle;

n, at each occurrence, is an integer independently selected from 0, 1, and 2; and p, at each occurrence, is an integer independently selected from 0, 1, and 2.

In another aspect, the present invention provides compounds of Formula (III), or stereoisomers, tautomers, pharmaceutically acceptable salts, solvates, or prodrugs thereof, wherein:

ring A is independently selected from phenyl and 5- to 6-membered heterocyclyl;

$G^1$ is independently selected from aryl, $C_{3-6}$ cycloalkyl and 5- to 6-membered heterocyclyl, wherein said aryl, cycloalkyl and heterocyclyl are substituted with 1-4 $R^8$;

$R^1$ and $R^2$ are independently selected from H, halogen, $CF_3$, $C_{1-6}$ alkyl, and hydroxyl;

$R^3$ is independently selected from H, halogen, haloalkyl, $C_{1-4}$alkyl (optionally substituted with $R^6$), $C_{2-4}$ alkenyl (optionally substituted with $R^6$), $C_{2-4}$ alkynyl (optionally substituted with $R^6$), CN, NO₂, —(CH₂)ₙ—OR⁵, —(CH₂)ₙ—NR⁵R⁵, —(CH₂)ₙ—C(=O)OR⁵, —(CH₂)ₙ—NHC(=O) OR⁵, —(CH₂)ₙ—NHC(=O)R⁵, —(CH₂)ₙ—NHC(N—CN) NHR⁵, —(CH₂)ₙ—NHC(NH)NHR⁵, —(CH₂)ₙ—N=CHNR⁵R⁵, —(CH₂)ₙ—NHC(=O)NR⁵R⁵, —(CH₂)ₙ—C(=O)NR⁵R⁵, —(CH₂)ₙ—NHC(S)NR⁹C(=O)R⁵, —(CH₂)ₙ—S(=O)ₚC₁₋₆ alkyl optionally substituted with $R^{11}$, —(CH₂)ₙ—S(=O)ₚNR⁵R⁵, —(CH₂)ₙ—NHS(=O)ₚNR⁵R⁵, —(CH₂)ₙ—NHS(=O)ₚC₁₋₆ alkyl optionally substituted with $R^{11}$, —(CH₂)ₙ—C₃₋₁₀ carbocyclyl and —(CH₂)ₙ-4- to 10-membered heterocyclyl, wherein said carbocyclyl and heterocyclyl are optionally substituted with $R^6$; optionally, two adjacent $R^3$ groups on the carbocyclyl and heterocyclyl may form a ring optionally substituted with $R^6$;

$R^{3a}$ is independently selected from H and halogen;

$R^{3b}$ is independently selected from H, halogen, methyl, and CN;

$R^4$ is independently selected from H, OH, F, Cl, Br, $C_{1-4}$ alkyl, $C_{1-4}$ alkoxy, $CF_3$, CN, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), —(CH₂)ₙ—C₃₋₁₀ carbocyclyl and —(CH₂)ₙ-4- to 10-membered heterocyclyl, wherein said carbocyclyl and heterocyclyl are optionally substituted with $R^6$;

$R^6$ is independently selected from —(CH₂)ₙ—OH, =O, NH₂, —(CH₂)ₙ—CN, halogen, C₁₋₆ alkyl, —(CH₂)ₙ—C(=O)OH, —(CH₂)ₙ—C(=O)OC₁₋₄ alkyl, —(CH₂)ₙ—C(=O)NH₂, —(CH₂)ₙ—OC₁₋₄ alkyl, —(CH₂)ₙ—C₃₋₆ cycloalkyl, —(CH₂)ₙ-4- to 10-membered heterocyclyl, and —O—(CH₂)ₙ-4- to 10-membered heterocyclyl, wherein said cycloalkyl and heterocyclyl are optionally substituted with $R^{10}$;

$R^7$ is independently selected from H, F, Cl, and methyl;

$R^8$ is independently selected from H, halogen, CN, NH₂, C₁₋₆ alkyl, haloalkyl, haloalkylcarbonylamino, arylamino, heteroarylamino, hydroxycarbonyl, haloalkylaminocarbonyl, alkylcarbonyl, alkoxy, haloalkoxy, aryl, $C_{3-6}$ cycloalkyl, and 4- to 12-membered heterocyclyl, wherein said aryl, cycloalkyl, and heterocyclyl are optionally substituted with $R^{10}$;

$R^{10}$ is independently selected from H, C₁₋₆ alkyl (optionally substituted with $R^{11}$), C₂₋₆ alkenyl, C₂₋₆ alkynyl, aryl (optionally substituted with $R^{11}$), —(CH₂)ₙ—C₃₋₆ cycloalkyl (optionally substituted with $R^{11}$), —(CH₂)ₙ—O-4- to 10-membered heterocyclyl (optionally substituted with $R^{11}$), F, Cl, Br, CN, NO₂, =O, C(=O)NR¹²R¹², C(=O) OR¹², Si(C₁₋₄ alkyl)₃, —(CH₂)ₙ—OR¹², —(CH₂)ₙ—NR¹²R¹², —S(=O)ₚC₁₋₆ alkyl, NR¹²S(=O)ₚC₁₋₆ alkyl, S(=O)ₚNR¹²R¹², and C(=NOH)NH₂;

$R^{11}$, at each occurrence, is independently selected from H, halogen, C₁₋₅ alkyl, —(CH₂)ₙOH, C₃₋₆ cycloalkyl, and phenyl;

$R^{12}$, at each occurrence, is independently selected from H, C₁₋₅ alkyl (optionally substituted with $R^{11}$), C₃₋₆ cycloalkyl, phenyl, and heterocyclyl, or $R^{12}$ and $R^{12}$ together with the nitrogen atom to which they are both attached form a heterocyclic ring optionally substituted with C₁₋₄ alkyl;

n, at each occurrence, is an integer independently selected from 0, 1, and 2; and p, at each occurrence, is an integer independently selected from 0, 1, and 2.

In another aspect, the present invention provides compounds of Formula (IV):

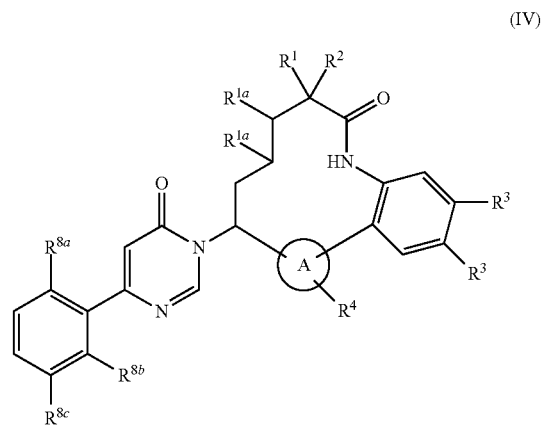

(IV)

or stereoisomers, tautomers, pharmaceutically acceptable salts, solvates, or prodrugs thereof, wherein:

ring A is independently selected from

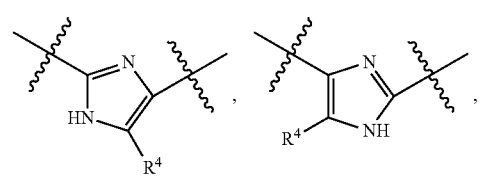

,

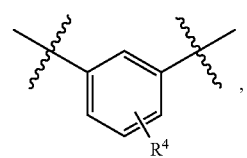

,

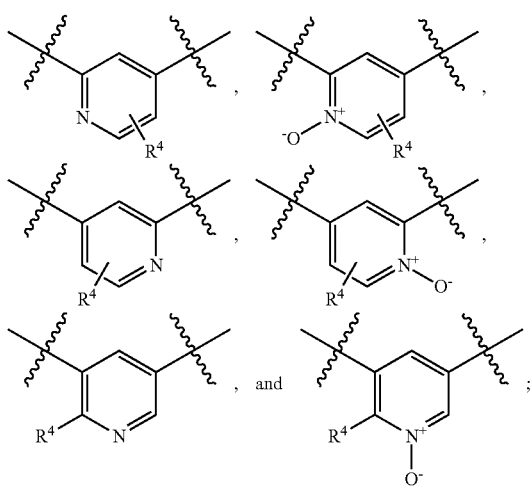

$R^1$ and $R^2$ are independently selected from H, F, $C_{1-4}$ alkyl, alkoxy, and hydroxyl;

$R^{1a}$, at each occurrence, is independently selected from H, F, and hydroxyl;

$R^3$ is independently selected from H, F, Cl, Br, I, $C_{2-4}$ alkenyl (optionally substituted C(O)OH), CN, —$(CH_2)_n$—$OR^5$, $NHR^5$, —$(CH_2)_n$—C(O)$OR^5$, —NHC(O)$OR^5$, —NHC(O)$R^5$, —NHC(O)$NR^5R^5$, —C(O)$NR^5R^5$, —NHC(S)NHC(O)$R^5$, —NHS(O)$_2C_{1-4}$ alkyl, and —$(CH_2)_n$-4- to 6-membered heterocycle selected from triazolyl and tetrazolyl, each optionally substituted with $R^6$;

$R^4$ is independently selected from H, OH, F, $OC_{1-4}$ alkyl, $C_{1-4}$ alkyl, CN, $C_{3-6}$ cycloalkyl, aryl, and 5- to 6-membered heterocycle, wherein said cycloalkyl, aryl and heterocycle are optionally substituted with $R^6$;

$R^5$ is independently selected from H, $C_{1-4}$ alkyl (optionally substituted with halogen, hydroxyl, alkoxy, carboxy, alkoxycarbonyl), —$(CH_2)_n$—$C_{3-10}$ carbocycle and —$(CH_2)_n$-4- to 10-membered heterocycle, wherein said carbocycle and heterocycle are optionally substituted with $R^6$;

$R^6$ is independently selected from OH, $NH_2$, halogen, $C_{1-6}$ alkyl, $C_{3-6}$ cycloalkyl, —$(CH_2)_n$—C(=O)OH, —$(CH_2)_n$—C(=O)$OC_{1-4}$ alkyl, —$(CH_2)_n$—$OC_{1-4}$ alkyl, =O, $C_{3-6}$ cycloalkyl, 4- to 10-membered heterocycle, and —O-4- to 10-membered heterocycle, wherein said cycloalkyl and heterocycle are optionally substituted with $R^{10}$;

$R^{8a}$ is independently selected from H, F, Cl, Br, CN, $OCH_3$, $CH_3$, C(O)$CH_3$, $CF_3$, $OCHF_2$, NHC(O)$C_{1-4}$ alkyl, aryl, $C_{3-6}$ cycloalkyl, and 4-6 membered heterocycle;

$R^{8b}$ is independently selected from H and F;

$R^{8c}$ is independently selected from H, F, Cl, and $OCH_3$; and n, at each occurrence, is an integer independently selected from 0, 1, and 2.

In another aspect, the present invention provides compounds of Formula (IV), or stereoisomers, tautomers, pharmaceutically acceptable salts, solvates, or prodrugs thereof, wherein:

ring A is independently selected from

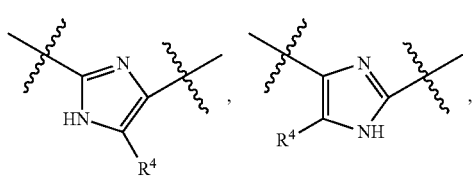

$R^1$ and $R^2$ are independently selected from H, F, $C_{1-4}$ alkyl, alkoxy, and hydroxyl;

$R^{1a}$, at each occurrence, is independently selected from H, F, and hydroxyl;

$R^3$ is independently selected from H, F, Cl, Br, I, $C_{2-4}$ alkenyl (optionally substituted C(=O)OH, CN, —$(CH_2)_n$—$OR^5$, $NHR^5$, —$(CH_2)_n$—C(=O)$OR^5$, —NHC(=O)$OR^5$, —NHC(=O)$R^5$, —NHC(=O)$NR^5R^5$, —C(=O)$NR^5R^5$, —NHC(=S)NHC(=O)$R^5$, —NHS(=O)$_2C_{1-4}$ alkyl, and —$(CH_2)_n$-4- to 6-membered heterocycle selected from triazolyl and tetrazolyl, each optionally substituted with $R^6$;

$R^4$ is independently selected from H, OH, F, $OC_{1-4}$ alkyl, $C_{1-4}$ alkyl, CN, $C_{3-6}$ cycloalkyl, aryl, and 5- to 6-membered heterocycle, wherein said cycloalkyl, aryl and heterocycle are optionally substituted with $R^6$;

$R^5$ is independently selected from H, $C_{1-4}$ alkyl (optionally substituted with halogen, hydroxyl, alkoxy, carboxy, alkoxycarbonyl), —$(CH_2)_n$—$C_{3-10}$ carbocycle and —$(CH_2)_n$-4- to 10-membered heterocycle, wherein said carbocycle and heterocycle are optionally substituted with $R^6$;

$R^6$ is independently selected from OH, $NH_2$, halogen, $C_{1-6}$ alkyl, $C_{3-6}$ cycloalkyl, —$(CH_2)_n$—C(=O)OH, —$(CH_2)_n$—C(=O)$OC_{1-4}$ alkyl, —$(CH_2)_n$—$OC_{1-4}$ alkyl, =O, $C_{3-6}$ cycloalkyl, 4- to 10-membered heterocycle, and —O-4- to 10-membered heterocycle, wherein said cycloalkyl and heterocycle are optionally substituted with $R^{10}$;

$R^{8a}$ is independently selected from H, F, Cl, Br, CN, $OCH_3$, $CH_3$, C(O)$CH_3$, $CF_3$, $OCHF_2$, NHC(O)$C_{1-4}$ alkyl, aryl, $C_{3-6}$ cycloalkyl, and 4-6 membered heterocycle optionally substituted with $R^{10}$;

$R^{8b}$ is independently selected from H and F;

$R^{8c}$ is independently selected from H, F, Cl, $CH_3$, and $OCH_3$;

$R^{10}$ is independently selected from H, $C_{1-6}$ alkyl (optionally substituted with $R^{11}$), $C_{2-6}$ alkenyl, $C_{2-6}$ alkynyl, aryl, —$(CH_2)_n$—$C_{3-6}$ cycloalkyl (optionally substituted with $R^{11}$), —$(CH_2)_n$O-4- to 10-membered heterocycle (optionally substituted with $R^{11}$), F, Cl, Br, CN, $NO_2$, =O, C(=O)$NR^{12}R^{12}$, C(=O)OH, Si($C_{1-4}$ alkyl)$_3$, —$(CH_2)_n$—$OR^{12}$, and —$(CH_2)_n$—$NR^{12}R^{12}$;

$R^{11}$, at each occurrence, is independently selected from H, halogen, $C_{1-5}$ alkyl, —$(CH_2)_n$—OH, $C_{3-6}$ cycloalkyl, and phenyl, or $R^{11}$ and $R^{11}$ together with the nitrogen atom to which they are both attached form a heterocyclic ring optionally substituted with $C_{1-4}$ alkyl;

$R^{12}$, at each occurrence, is independently selected from H, $C_{1-5}$ alkyl, $C_{3-6}$ cycloalkyl, phenyl, and heterocycle, or $R^{12}$ and $R^{12}$ together with the nitrogen atom to which they are both attached form a heterocyclic ring optionally substituted with $C_{1-4}$ alkyl; and n, at each occurrence, is an integer independently selected from 0, 1, and 2.

In another aspect, the present invention provides compounds of Formula (IV), or stereoisomers, tautomers, pharmaceutically acceptable salts, solvates, or prodrugs thereof, wherein:

ring A is independently selected from

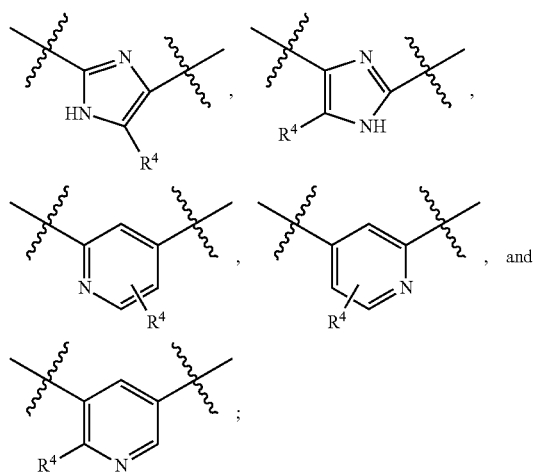

$R^1$ and $R^2$ are independently selected from H and $C_{1-4}$ alkyl;

$R^{1a}$, at each occurrence, is H;

$R^3$ is independently selected from H, F, and —NHC(O)OC$_{1-4}$ alkyl;

$R^4$ is independently selected from H and $C_{1-4}$ alkyl;

$R^{8a}$ is independently selected from H, F, Br, and triazole optionally substituted with $R^{10}$;

$R^{8b}$ is independently selected from H and F; and $R^{8c}$ is Cl; and other variables are as defined in Formula (IV) above.

In another aspect, the present invention provides compounds of Formula (IVa):

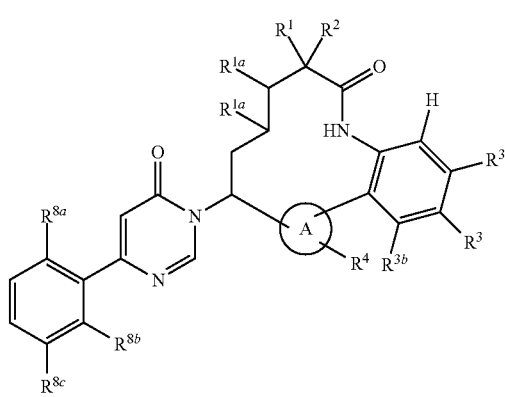

(IVa)

or stereoisomers, tautomers, pharmaceutically acceptable salts, solvates, or prodrugs thereof, wherein:

ring A is independently selected from

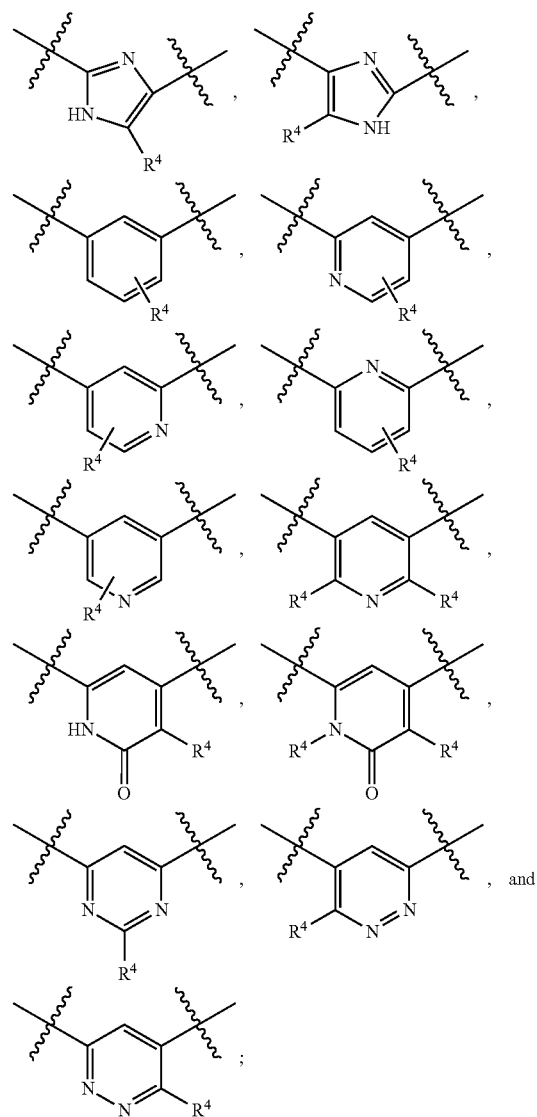

$R^1$ and $R^2$ are independently selected from H, F, $C_{1-4}$ alkyl, alkoxy, and hydroxyl;

$R^{1a}$, at each occurrence, is independently selected from H, F, CH$_3$, and hydroxyl;

$R^3$ is independently selected from H, F, Cl, Br, I, $C_{1-3}$ alkyl (optionally substituted with $R^6$), CN, —(CH$_2$)$_n$—OR$^5$, —(CH$_2$)$_n$—NHR$^5$, —(CH$_2$)$_n$—C(=O)OR$^5$, —NHC(=O)OR$^5$, —NHC(=O)R$^5$, —NHC(=O)NR$^5$R$^5$, —C(=O)NR$^5$R$^5$, and —S(=O)$_2$C$_{1-4}$ alkyl;

$R^4$ is independently selected from H, OH, F, OC$_{1-4}$ alkyl, $C_{1-4}$ alkyl, CN, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H, $C_{1-4}$ alkyl (optionally substituted with halogen, hydroxyl, alkoxy, carboxy, alkoxycarbonyl), —(CH$_2$)$_n$—C$_{3-10}$ carbocyclyl and —(CH$_2$)$_n$-4- to 10-membered heterocyclyl, wherein said carbocyclyl and heterocyclyl are optionally substituted with $R^6$;

$R^6$ is independently selected from OH, NH$_2$, halogen, $C_{1-6}$ alkyl, $C_{3-6}$ cycloalkyl, —(CH$_2$)$_n$—C(=O)OH, —(CH$_2$)$_n$—C(=O)OC$_{1-4}$ alkyl, —(CH$_2$)$_n$—C(=O)NH$_2$, —(CH$_2$)$_n$—

$OC_{1-4}$ alkyl, =O, $C_{3-6}$ cycloalkyl, 4- to 10-membered heterocyclyl, and —O-4- to 10-membered heterocyclyl, wherein said cycloalkyl and heterocyclyl are optionally substituted with $R^{10}$;

$R^{8a}$ is independently selected from H, F, Cl, Br, I, —$(CH_2)_nCN$, —$(CH_2)_nNH_2$, $CH_3CHF_2$, $CCH_3F_2$, $CF_3$, OH, $OCH_3$, $OCF_3$, $OCHF_2$, C(=O)$CH_3$, C(=O)OH, C(=O)$OCH_3$, C(=O)$NH_2$, C(=O)$NHCH_2CF_3$, C(=O)$NHCH_2Ph$, NHC(=O)$OCH_3$, NHC(=O)$CF_3$,

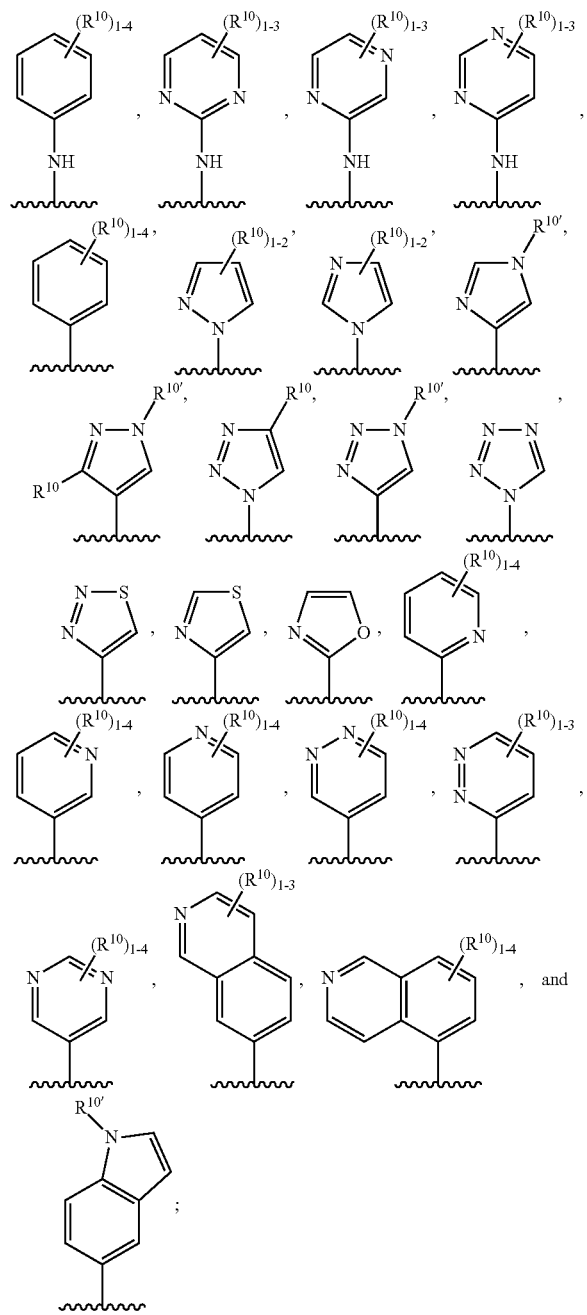

$R^{8b}$ is independently selected from H and F;
$R^{8c}$ is independently selected from H, F, Cl, $CH_3$, and $OCH_3$;
$R^{10}$ is independently selected from H, $C_{1-6}$ alkyl (optionally substituted with $R^{11}$), $C_{2-6}$ alkenyl, $C_{2-6}$ alkynyl, aryl, —$(CH_2)_n$—$C_{3-6}$ cycloalkyl (optionally substituted with $R^{11}$), —$(CH_2)_n$—O-4- to 10-membered heterocyclyl (optionally substituted with $R^{11}$), F, Cl, Br, CN, $CONR^{12}R^{12}$, C(=O)$OR^{12}$, —$(CH_2)_n$—$OR^{12}$, —$(CH_2)_n$—$NR^{12}R^{12}$, —S(=O)$_pC_{1-6}$ alkyl, $NR^{12}S$(=O)$_pC_{1-6}$ alkyl, S(=O)$_pNR^{12}R^{12}$ and C(=NOH)$NH_2$;

$R^{10'}$ is independently selected from H, $C_{1-6}$ alkyl (optionally substituted with $R^{11}$), aryl, —$(CH_2)_n$—$C_{3-6}$ cycloalkyl (optionally substituted with $R^{11}$), and —$(CH_2)_n$—O-4- to 10-membered heterocyclyl (optionally substituted with $R^{11}$);

$R^{11}$, at each occurrence, is independently selected from H, halogen, $C_{1-5}$ alkyl, —$(CH_2)_nOH$, $C_{3-6}$ cycloalkyl, and phenyl;

$R^{12}$, at each occurrence, is independently selected from H, $C_{1-5}$ alkyl optionally substituted with $R^{11}$, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$ alkyl;

n, at each occurrence, is an integer independently selected from 0, 1, and 2, and p, at each occurrence, is an integer independently selected from 0, 1, and 2.

In another aspect, the present invention provides compounds of Formula (IVa), or stereoisomers, tautomers, pharmaceutically acceptable salts, solvates, or prodrugs thereof, wherein:

ring A is independently selected from

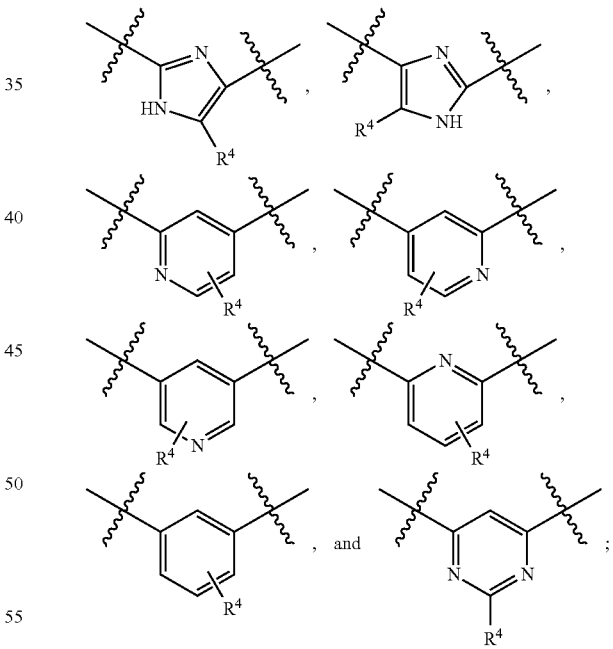

$R^1$ and $R^2$ are independently selected from H and $C_{1-4}$ alkyl;

$R^{1a}$, at each occurrence, is H;

$R^3$ is independently selected from H, F, Cl, $CH_3$, $CHF_2$, $C(CH_3)_2OH$, $CF_2CH_2OH$, $CF_2CONH_2$, $CH_2NHCOCF_3$, $CH_2NH_2$, CN, —NHC(=O)$OC_{1-4}$ alkyl, —$(CH_2)_{0-1}OH$, $OCHF_2$, $OCH_2COOCH_3$, $OCH_2COOH$, —C(=O)OH, —C(=O)$OC_{1-4}$ alkyl, —C(=O)$NH_2$, and S(=O)$_2C_{1-4}$ alkyl;

$R^4$ is independently selected from H and $C_{1-4}$ alkyl;

$R^{8a}$ is independently selected from H, F, Cl, Br, $OCH_3$, $OCF_3$, $C(=O)OCH_3$, $C(=O)OH$, $CF_3$,

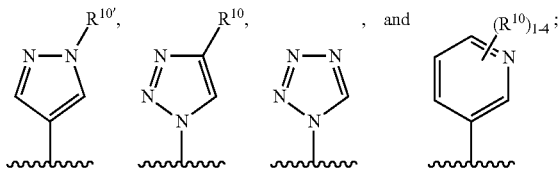

$R^{8b}$ is independently selected from H and F;

$R^{8c}$ is Cl and $OCHF_2$;

$R^{10}$ is independently selected from H, $CH_3$, $CF_3$, $CHF_2$, F, Cl, Br, CN, $C(=O)NR^{12}R^{12}$, $C(=O)OR^{12}$, $-OC_{1-4}$ alkyl, $-OH$, $-S(=O)_pC_{1-6}$ alkyl, and $C(=NOH)NH_2$; and $R^{10'}$ is independently selected from H, $CH_3$, $CF_3$, and $CHF_2$; and other variables are as defined in Formula (IVa) above.

In another aspect, the present invention provides compounds of Formula (IVb):

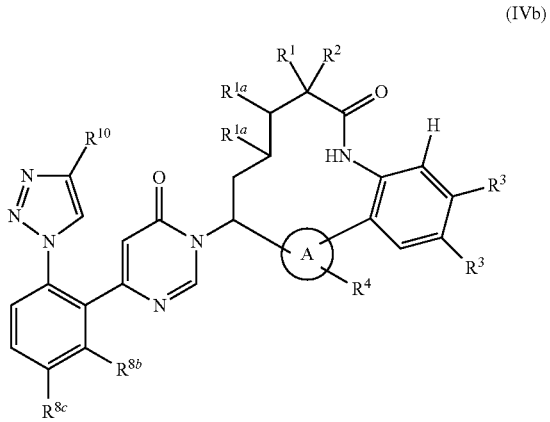

(IVb)

or stereoisomers, tautomers, pharmaceutically acceptable salts, solvates, or prodrugs thereof, wherein:

ring A is independently selected from

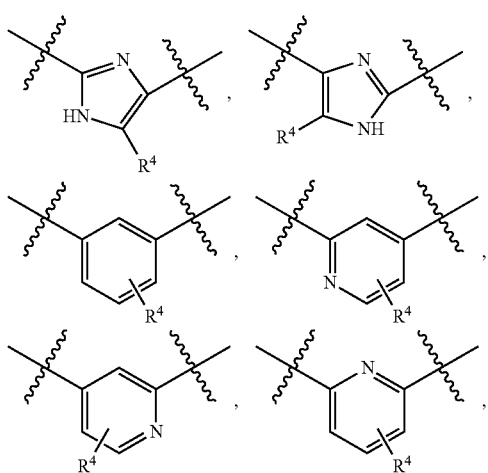

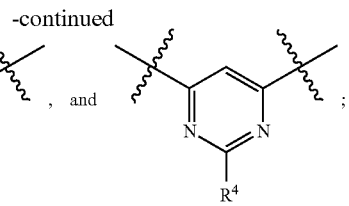

-continued

, and ;

$R^1$ and $R^2$ are independently selected from H, F, $C_{1-4}$ alkyl, alkoxy, and hydroxyl;

$R^{1a}$, at each occurrence, is independently selected from H, F, $CH_3$, and hydroxyl;

$R^3$ is independently selected from H, F, Cl, Br, I, $C_{1-3}$ alkyl (optionally substituted with $R^6$), CN, $-(CH_2)_n-OR^5$, $-(CH_2)_n-NHR^5$, $-(CH_2)_n-C(=O)OR^5$, $-NHC(=O)OR^5$, $-NHC(=O)R^5$, $-NHC(=O)NR^5R^5$, $-C(=O)NR^5R^5$, and $-S(=O)_2C_{1-4}$ alkyl;

$R^4$ is independently selected from H, OH, F, $OC_{1-4}$ alkyl, $C_{1-4}$ alkyl, CN, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H, $C_{1-4}$ alkyl (optionally substituted with halogen, hydroxyl, alkoxy, carboxy, alkoxycarbonyl), $-(CH_2)_n-C_{3-10}$ carbocyclyl and $-(CH_2)_n$-4- to 10-membered heterocyclyl, wherein said carbocyclyl and heterocyclyl are optionally substituted with $R^6$;

$R^6$ is independently selected from OH, $NH_2$, halogen, $C_{1-6}$ alkyl, $C_{3-6}$ cycloalkyl, $-(CH_2)_n-C(=O)OH$, $-(CH_2)_n-C(=O)OC_{1-4}$ alkyl, $-(CH_2)_n-C(=O)NH_2$, $-(CH_2)_n-OC_{1-4}$ alkyl, $=O$, $C_{3-6}$ cycloalkyl, 4- to 10-membered heterocyclyl, and $-O$-4- to 10-membered heterocyclyl, wherein said cycloalkyl and heterocyclyl are optionally substituted with $R^{10}$;

$R^{8b}$ is independently selected from H and F;

$R^{8c}$ is independently selected from H, F, Cl, $CH_3$, and $OCH_3$;

$R^{10}$ is independently selected from H, $C_{1-6}$ alkyl (optionally substituted with $R^{11}$), $C_{2-6}$ alkenyl, $C_{2-6}$ alkynyl, aryl, $-(CH_2)_n-C_{3-6}$ cycloalkyl (optionally substituted with $R^{11}$), $-(CH_2)_n-O$-4- to 10-membered heterocyclyl (optionally substituted with $R^{11}$), F, Cl, Br, CN, $CONR^{12}R^{12}$, $C(=O)OR^{12}$, $-(CH_2)_n-OR^{12}$, $-(CH_2)_n-NR^{12}R^{12}$, $-S(=O)_pC_{1-6}$ alkyl, $NR^{12}S(=O)_pC_{1-6}$ alkyl, $S(=O)_pNR^{12}R^{12}$ and $C(=NOH)NH_2$;

$R^{11}$, at each occurrence, is independently selected from H, halogen, $C_{1-5}$ alkyl, $-(CH_2)_n-OH$, $C_{3-6}$ cycloalkyl, and phenyl;

$R^{12}$, at each occurrence, is independently selected from H, $C_{1-5}$ alkyl optionally substituted with $R^{11}$, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$ alkyl;

n, at each occurrence, is an integer independently selected from 0, 1, and 2, and p, at each occurrence, is an integer independently selected from 0, 1, and 2.

In another aspect, the present invention provides compounds of Formula (IIa), or stereoisomers, tautomers, pharmaceutically acceptable salts, solvates, or prodrugs thereof, wherein:

ring A is independently selected from
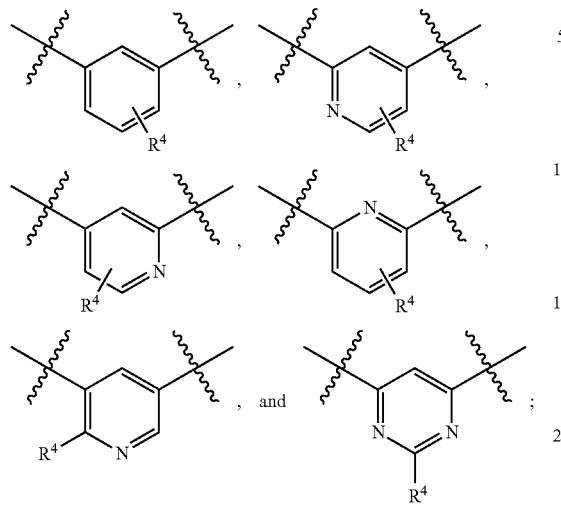
ring B is
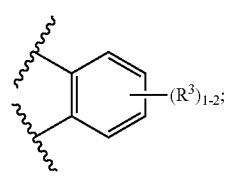
$G^1$ is independently selected from
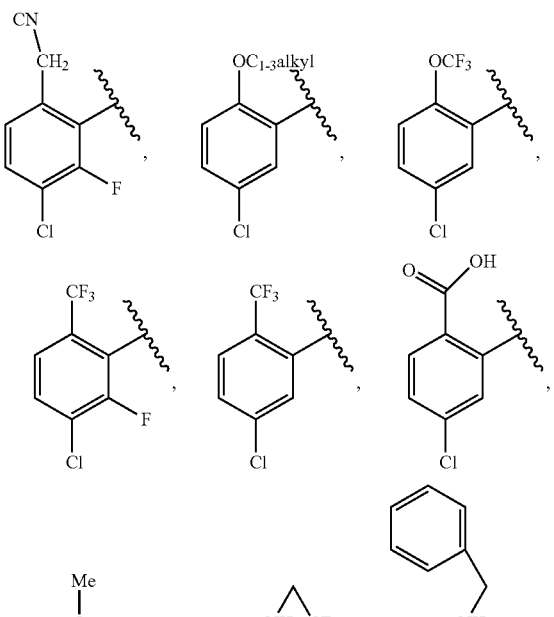

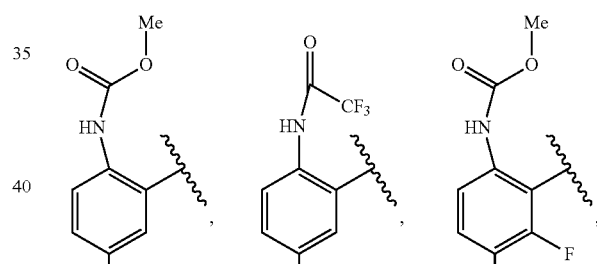
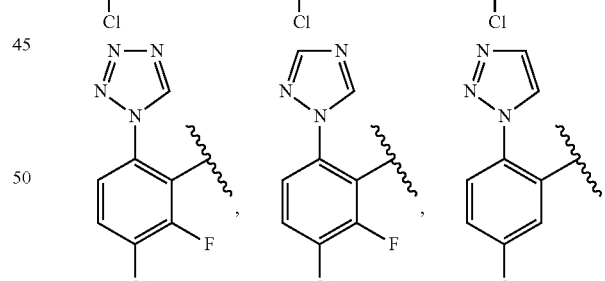
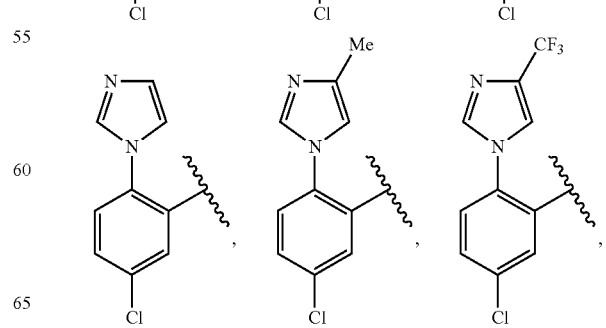

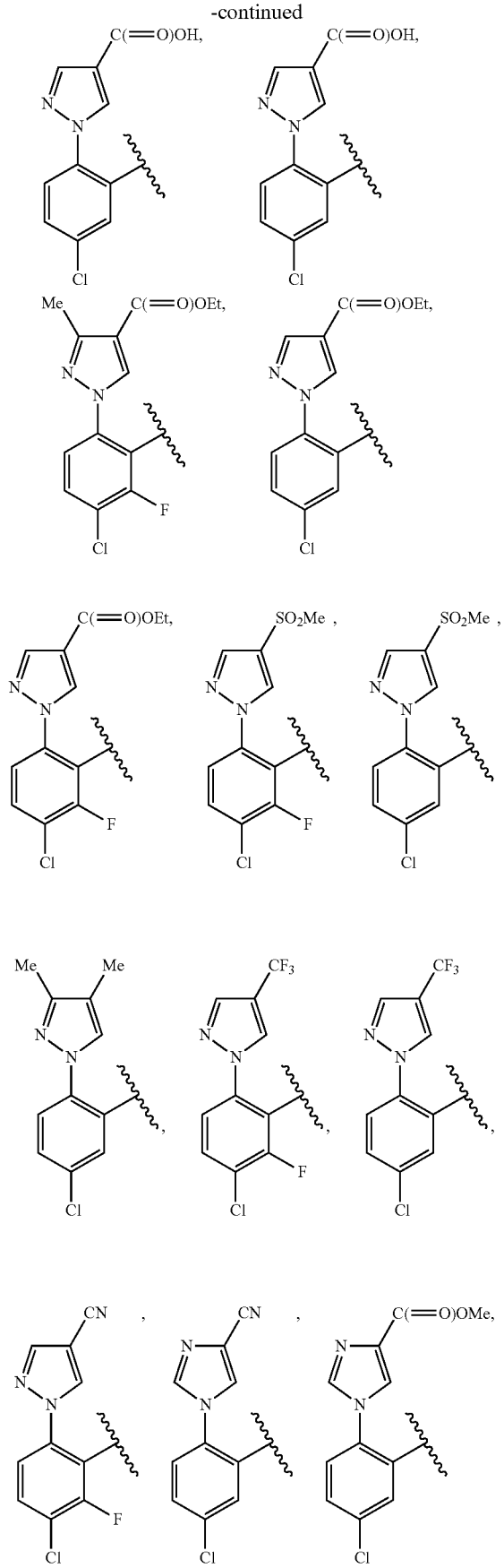
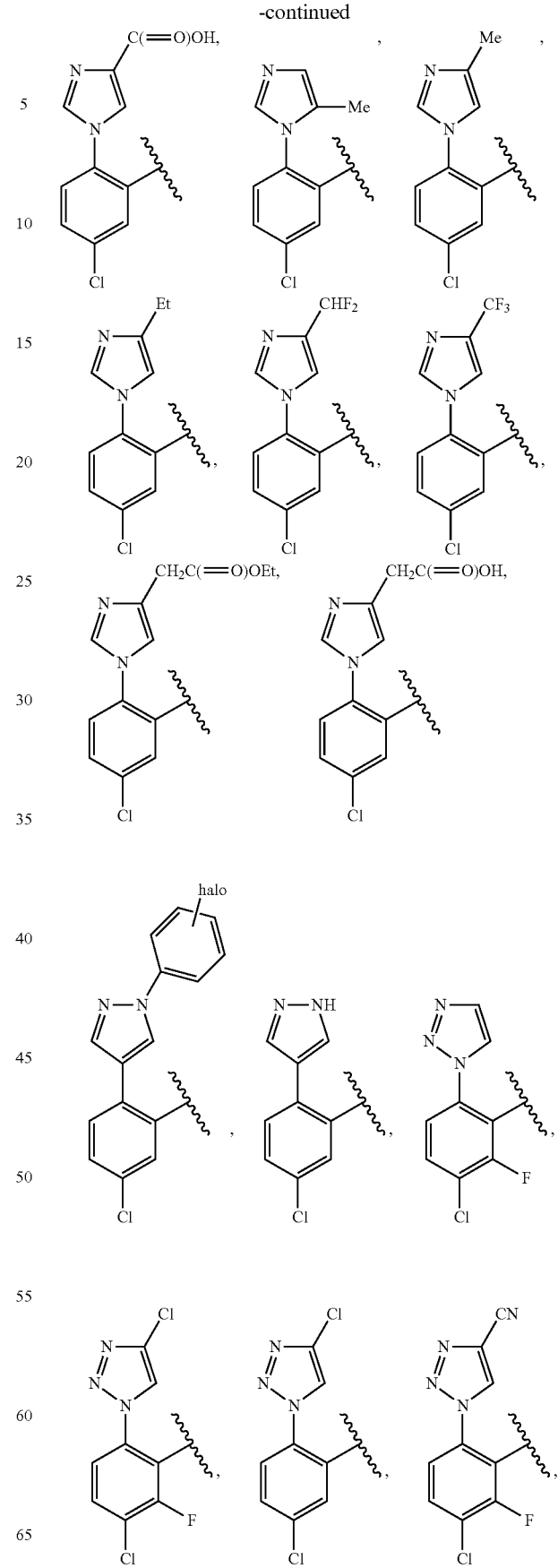

27
-continued
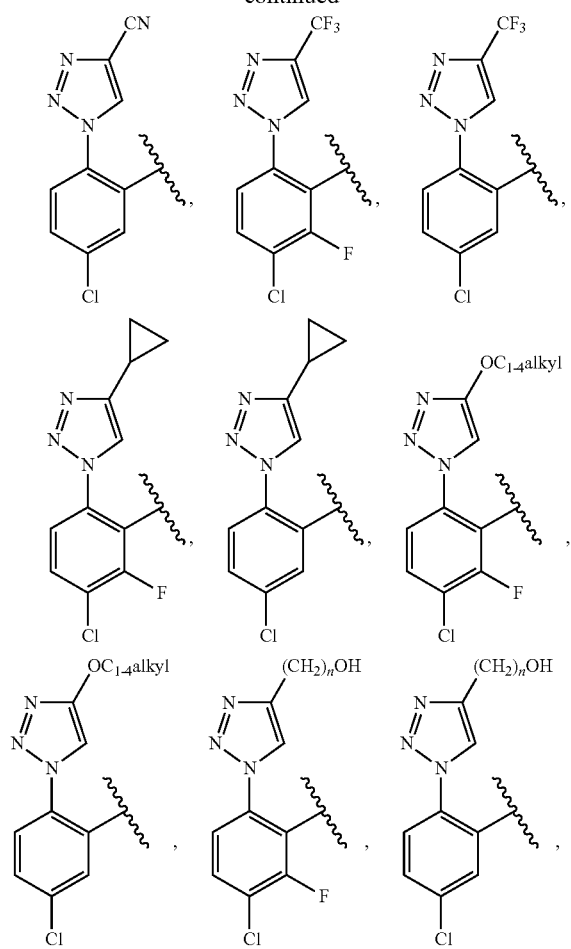
28
-continued
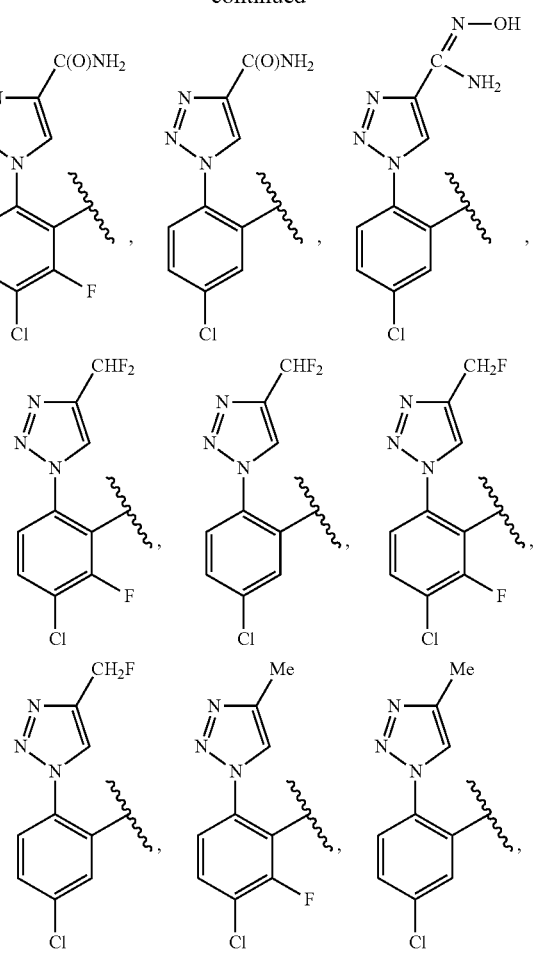
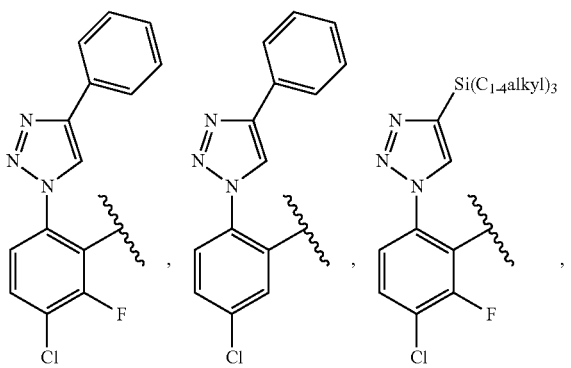
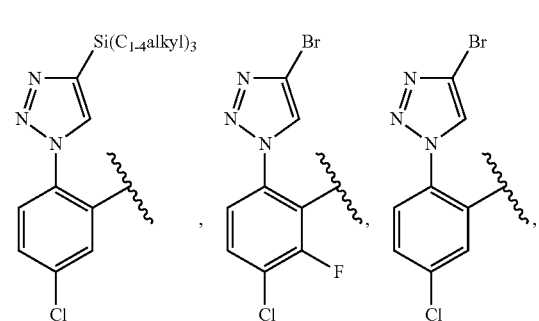

-continued
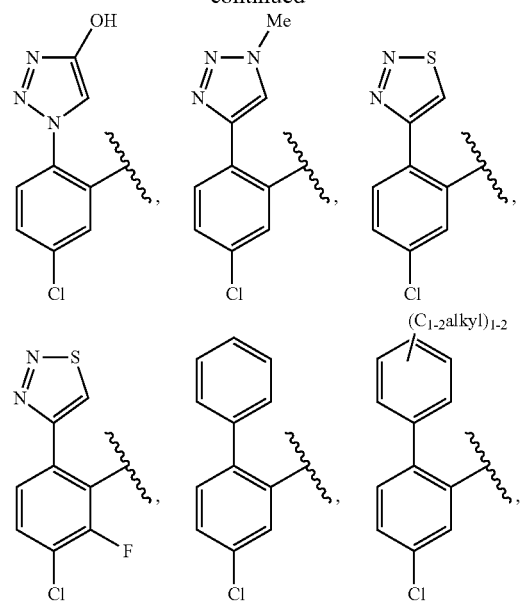
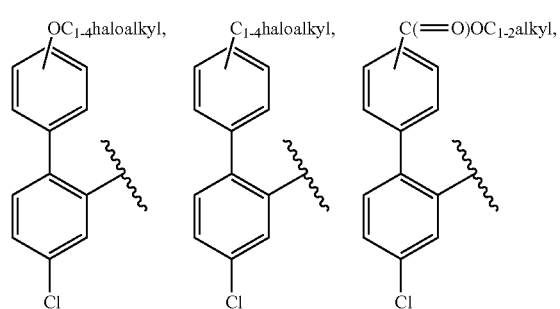
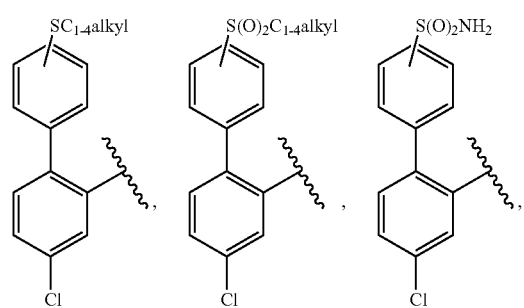
-continued
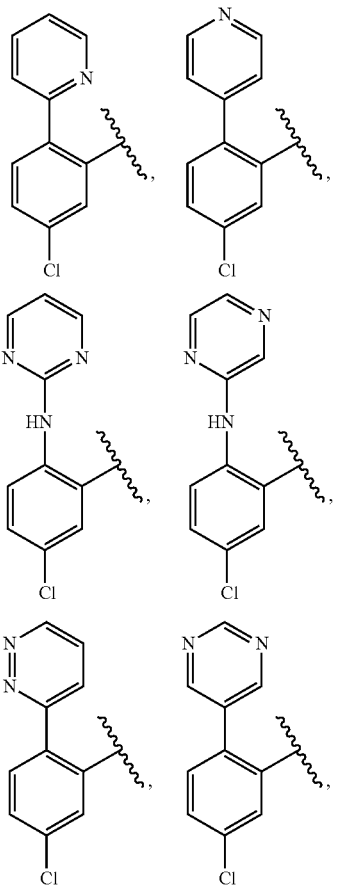
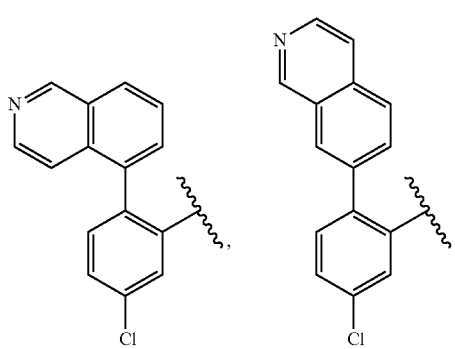
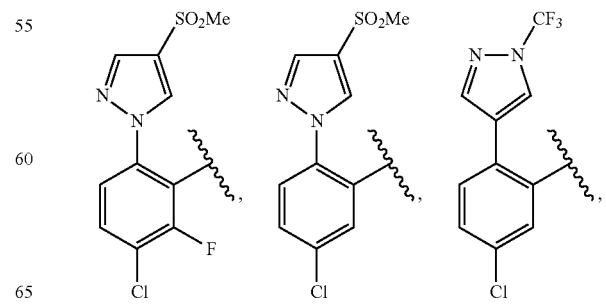

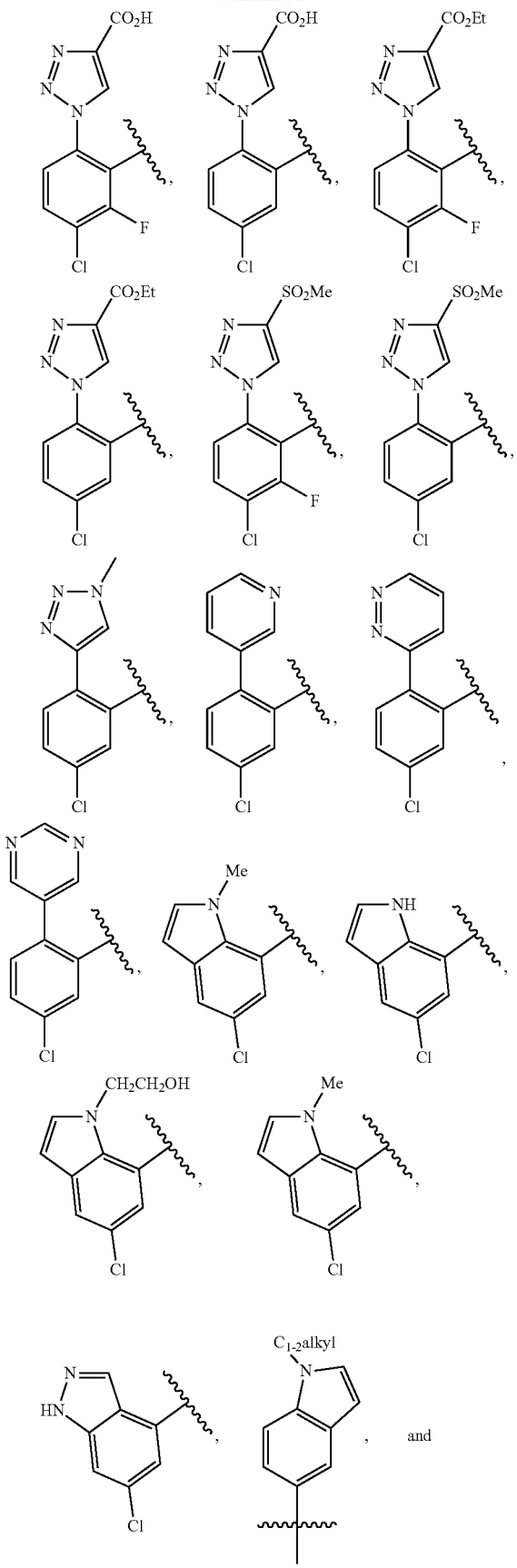

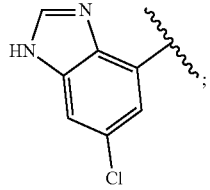

W is independently selected from CHR$^1$, O, NH, and N(C$_{1-4}$ alkyl);

Y is independently selected from —NH—, —NHC(=O)— and —C(=O)NH—;

R$^1$ and R$^2$ are independently selected from H, F, C$_{1-4}$ alkyl, and hydroxyl;

R$^3$ is independently selected from H, F, Cl, CHF$_2$, CF$_3$, OCF$_3$, OCHF$_2$, CH$_3$, CN, —(CH$_2$)$_{0-2}$—OH, OC$_{1-4}$ alkyl, C(=O)C$_{1-4}$ alkyl, —(CH$_2$)$_{0-1}$—C(=O)OH, —C(=O)OC$_{1-4}$ alkyl, —S(=O)$_2$C$_{1-4}$ alkyl, and —NHC(=O)OC$_{1-4}$ alkyl;

R$^4$ is independently selected from H, F, and C$_{1-4}$ alkyl; and

R$^7$ is H; and other variables are as defined in Formula (IIa) above.

In one embodiment, G$^1$ is independently selected from the group consisting of

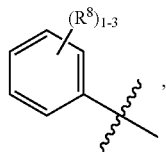

wherein R$^8$ is, independently at each occurrence, selected from the group consisting of H, halogen, CN, C$_{1-6}$ alkyl, haloalkyl, alkoxy, haloalkoxy, and 4-6 membered heterocyclyl.

In another embodiment, G$^1$ is

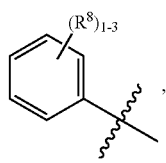

wherein R$^8$ is, independently at each occurrence, selected from the group consisting of H, halogen, CN, methyl, ethyl, CF$_3$, CHF$_2$, OMe, OEt, OCF$_3$, OCHF$_2$, aryl, C$_{3-6}$ cycloalkyl, and 4-6 membered heterocyclyl.

In another embodiment, G$^1$ is

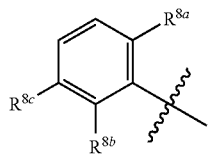

and selected from the group consisting of

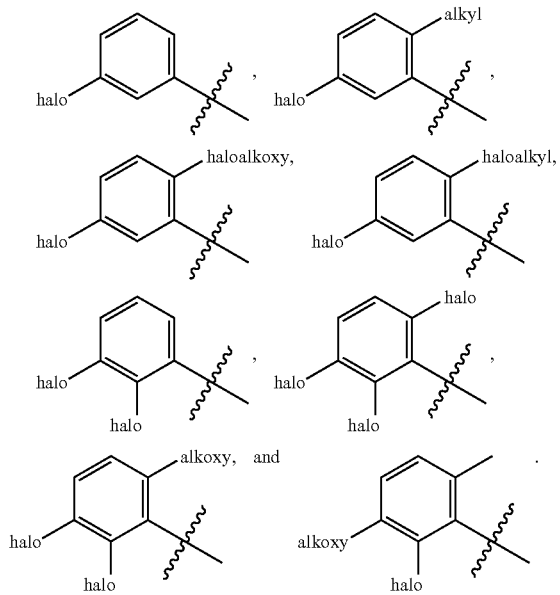

In another embodiment, $G^1$ is

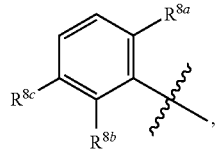

wherein $R^{8a}$ is independently selected from the group consisting of H, F, $OCH_3$, $OCHF_2$, and 4- to 6-membered heterocyclyl.

In another embodiment, $R^{8b}$ is independently selected from the group consisting of H, F and Cl.

In another embodiment, $R^{8b}$ is independently selected from the group consisting of H and F.

In another embodiment, $R^{8c}$ is Cl.

In another embodiment, $G^1$ is

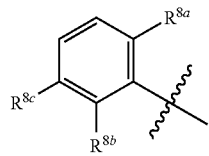

selected from the group consisting of

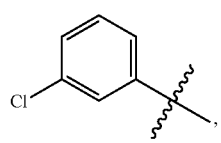 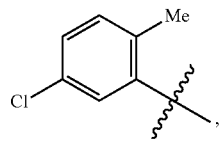

-continued

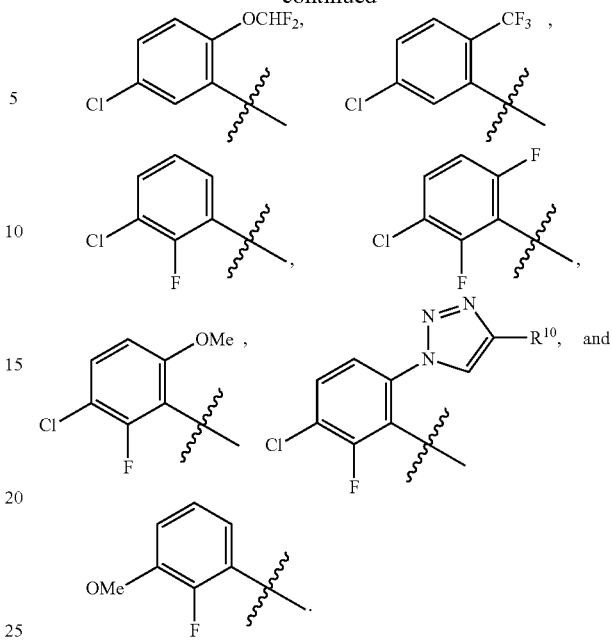

In another embodiment, $G^1$ is

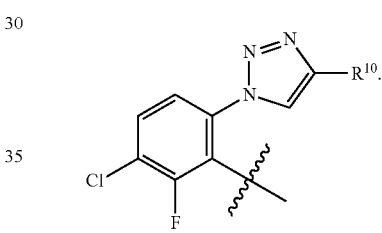

In one embodiment, the present invention provides compounds of Formulae (I), (II), (IIa), (III), (IV), (IVa), and (IVb) or stereoisomers, tautomers, pharmaceutically acceptable salts, solvates, or prodrugs thereof, wherein ring A is independently selected from the group consisting of imidazole, oxadiazole, pyridine, pyridinone, pyridazine, pyridazinone, and phenyl.

In another embodiment,

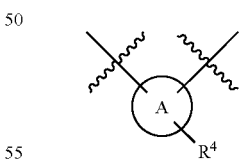

is independently selected from the group consisting of

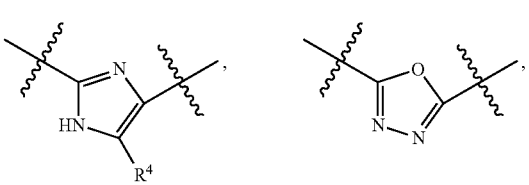

-continued
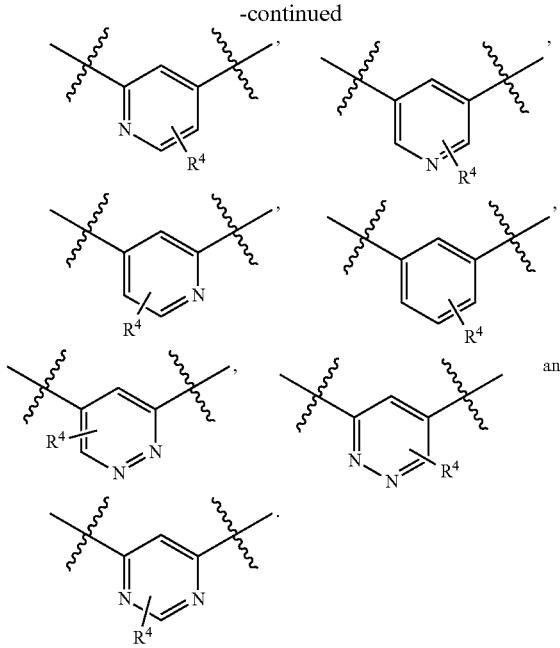
In another embodiment,
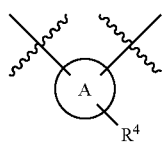
is independently selected from the group consisting of
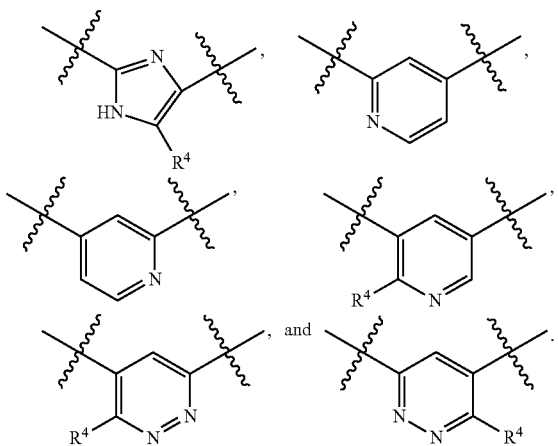
In another embodiment,
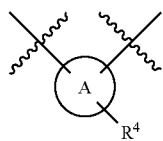
is independently selected from the group consisting of
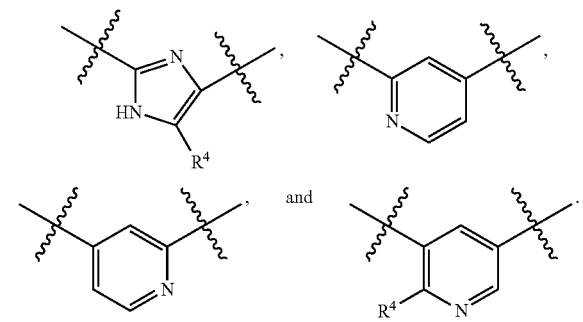
In still another embodiment,
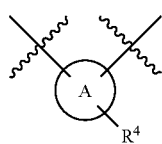
is independently selected from the group consisting of
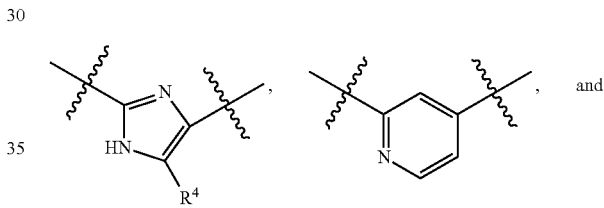
In another embodiment,
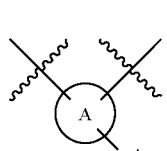 is 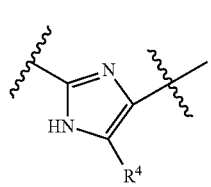.
In another embodiment,
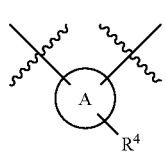 is 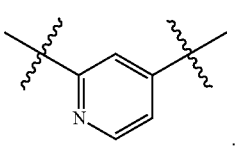

In another embodiment,

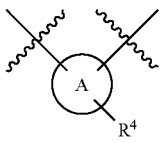 is 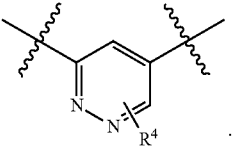.

In another embodiment,

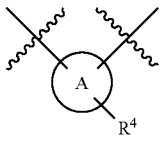 is 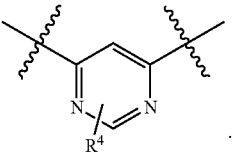.

In another embodiment,

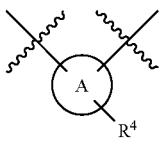 is 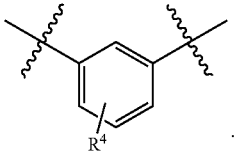.

In another embodiment,

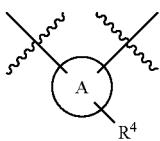 is 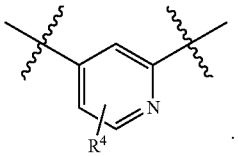.

In another embodiment,

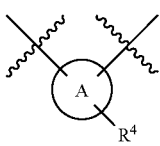 is 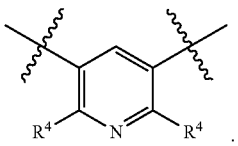.

In another embodiment, $R^1$ is independently selected from the group consisting of H, OH, F, and $C_{1-4}$ alkyl.

In another embodiment, $R^1$ is independently selected from the group consisting of H and methyl, ethyl, and isopropyl.

In one embodiment, $R^2$ is, independently at each occurrence, selected from the group consisting of H and $C_{1-4}$ alkyl.

In another embodiment, $R^2$ is, independently at each occurrence, selected from the group consisting of H and methyl.

In another embodiment, one of $R^1$ and $R^2$ is H and the other is methyl.

In another embodiment, $R^1$ and $R^2$ together are =O.

In one embodiment, ring B is phenyl, $R^3$ is independently selected from H, halogen, haloalkyl, $C_{1-4}$ alkyl (optionally substituted with $R^6$), $C_{2-4}$ alkenyl (optionally substituted with $R^6$), $C_{2-4}$ alkynyl (optionally substituted with $R^6$), CN, $NO_2$, $-(CH_2)_n-OR^5$, $-(CH_2)_n-NR^5R^5$, $-(CH_2)_n-C(O)OR^5$, $-(CH_2)_n-NR^9C(O)OR^5$, $-(CH_2)_n-NR^9C(O)R^5$, $-(CH_2)_n-NR^9C(O)C(O)R^5$, $-(CH_2)_n-NR^9C(N-CN)NHR^5$, $-(CH_2)_n-NR^9C(NH)NHR^5$, $-(CH_2)_n-N=CR^9NR^5R^5$, $-(CH_2)_n-NR^9C(O)NR^5R^5$, $-(CH_2)_n-NR^9C(O)NR^5R^5-$, $-(CH_2)_n-C(O)NR^5R^5$, $-(CH_2)_n-NR^9(S)NR^9C(O)R^5$, $-(CH_2)_n-S(O)_pC_{1-6}$ alkyl optionally substituted with $R^{11}$, $-(CH_2)_n-S(O)_pNR^5R^5$, $-(CH_2)_n-NR^9S(O)_pNR^5R^5$, $-(CH_2)_n-NR^9S(O)_pC_{1-6}$ alkyl optionally substituted with $R^{11}$, $-(CH_2)_n-C_{3-10}$ carbocycle and $-(CH_2)_n-4-$ to 10-membered heterocyclyl, wherein said carbocycle and heterocyclyl are optionally substituted with $R^6$; optionally, two adjacent $R^3$ groups on the carbocycle and heterocyclyl may form a ring optionally substituted with $R^6$; $R^5$ is independently selected from H, $C_{1-4}$ alkyl (optionally substituted with halogen, hydroxyl, alkoxy, carboxy, alkoxycarbonyl), $-(CH_2)_n-C_{3-10}$ carbocycle and $-(CH_2)_n-4-$ to 10-membered heterocyclyl, wherein said carbocycle and heterocyclyl are optionally substituted with $R^6$; alternatively, $R^5$ and $R^5$ together with the nitrogen atom to which they are both attached form a heterocyclic ring optionally substituted with $R^6$.

In another embodiment, $R^3$ is $NHR^5$; $R^5$ is independently selected from H, $C_{1-4}$ alkyl (optionally substituted with halogen, hydroxyl, alkoxy, carboxy, alkoxycarbonyl), $-(CH_2)_n-C_{3-10}$ carbocycle and $-(CH_2)_n-4-$ to 10-membered heterocyclyl, wherein said carbocycle and heterocyclyl are optionally substituted with $R^6$.

In another embodiment, ring B is phenyl, $R^3$ is $NHR^5$; $R^5$ is $C_{1-4}$ alkyl substituted with halogen, hydroxyl, alkoxy, carboxy, alkoxycarbonyl.

In another embodiment, ring B is phenyl, $R^3$ is independently selected from the group consisting of H, halogen, $NHC(O)O-C_{1-4}$ alkyl, CN, OH, $O-C_{1-4}$ alkyl; $CF_3$, $CO_2H$, $CO_2-C_{1-4}$ alkyl, $-CH_2CO_2H$, $-(CH_2)_2CO_2H$, $-CH_2CO_2(C_{1-4}$ alkyl), $-(CH_2)_2CO_2(C_{1-4}$ alkyl), $NH_2$, $-CH_2NH_2$, $-NHCO(C_{1-4}$ alkyl), $-NHCO_2(CH_2)_2O(C_{1-4}$ alkyl), $-NHCO_2(CH_2)_{1-3}O(C_{1-4}$ alkyl), $NHCO_2CH_2CH(C_{1-4}$ alkyl)$O(C_{1-4}$ alkyl), $-NHCO_2(CH_2)_{1-2}OH$, $-NHCO_2CH_2CO_2H$, $-CH_2NHCO_2(C_{1-4}$ alkyl), $-NHC(O)NH(C_{1-4}$ alkyl), $-NHC(O)N(C_{1-4}$ alkyl)$_2$, $NHC(O)NH(C_{1-4}$ alkyl)N[5- to 6-membered heterocyclyl)], $-NHSO_2(C_{1-4}$ alkyl), $-CONH_2$, $-CONH(C_{1-4}$ alkyl), $-CON(C_{1-4}$ alkyl)$_2$, and $-CH_2CONH_2$.

In another embodiment, ring B is phenyl, $R^3$ is independently selected from the group consisting of H, halogen, $NHC(O)O-C_{1-4}$ alkyl, $CONH_2$, $CO_2-C_{1-4}$ alkyl, COOH, CN, OH, and $O-C_{1-4}$ alkyl.

In another embodiment, ring B is phenyl, $R^3$ is $NHC(O)OR^5$, $R^5$ is $C_{1-4}$ alkyl optionally substituted with halogen, hydroxyl, alkoxy, carboxy, alkoxycarbonyl, amine, and substituted amine.

In another aspect, the present invention provides a compound selected from any subset list of compounds exemplified in the present application.

In another aspect, the present invention provides a compound selected from (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-4,5-dicarbonitrile trifluoroacetate;

(10R,14S)-14-{4-[5-chloro-2-(4-chloro-1H-1,2,3-triazol-1-yl)phenyl]-6-oxo-1,6-dihydropyrimidin-1-yl}-10-methyl-8,16-diazatricyclo[13.3.1.0$^{2,7}$]nonadeca-1(19),2,4,6,15,17-hexaen-9-one trifluoroacetate;

(10R,14S)-14-{4-[3-chloro-6-(4-chloro-1H-1,2,3-triazol-1-yl)-2-fluorophenyl]-6-oxo-1,6-dihydropyrimidin-1-yl}-5-(hydroxymethyl)-10-methyl-8,16-diazatricyclo [13.3.1.0$^{2,7}$] nonadeca-1(19),2(7),3,5,15,17-hexaen-9-one trifluoroacetate;

(10R,14S)-14-{4-[3-chloro-2-fluoro-6-(1H-1,2,3,4-tetrazol-1-yl)phenyl]-6-oxo -1,6-dihydropyrimidin-1-yl}-4-fluoro-10-methyl-8,16-diazatricyclo[13.3.1.0$^{2,7}$]nonadeca -1(19),2(7),3,5,15,17-hexaen-9-one trifluoroacetate;

(10R,14S)-14-{4-[5-chloro-2-(1H-1,2,3,4-tetrazol-1-yl) phenyl]-6-oxo-1,6-dihydropyrimidin-1-yl}-4-fluoro-10-methyl-8,16-diazatricyclo[13.3.1.0$^{2,7}$]nonadeca -1(19),2(7),3,5,15,17-hexaen-9-one trifluoroacetate;

(10R,14S)-14-(4-{5-chloro-2-[4-(trifluoromethyl)-1H-1,2,3-triazol-1-yl]phenyl}-6-oxo-1,6-dihydropyrimidin-1-yl)-5-(hydroxymethyl)-10-methyl-8,16-diazatricyclo [13.3.1.0$^{2,7}$]nonadeca-1(19),2(7),3,5,15,17-hexaen-9-one trifluoroacetate;

(10R,14S)-14-{4-[5-chloro-2-(4-cyano-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7),3,5,15,17-hexaene-5-carbonitrile trifluoroacetate;

(10R,14S)-14-{4-[5-chloro-2-(4-chloro-1H-1,2,3-triazol-1-yl)phenyl]-6-oxo-1,6-dihydropyrimidin-1-yl}-4-fluoro-12-hydroxy-10-methyl-8,16-diazatricyclo[13.3.1.0$^{2,7}$]nonadeca-1(19),2(7),3,5,15,17-hexaen-9-one trifluoroacetate;

(10R,14S)-14-{4-[3-chloro-6-(4-chloro-1H-1,2,3-triazol-1-yl)-2-fluorophenyl]-6-oxo-1,6-dihydropyrimidin-1-yl}-4-fluoro-12-hydroxy-10-methyl-8,16-diazatricyclo [13.3.1.0$^{2,7}$]nonadeca-1(19),2(7),3,5,15,17-hexaen-9-one trifluoroacetate;

methyl (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo [13.3.1.0$^{2,7}$]nonadeca-1(19),2(7),3,5,15,17-hexaene-5-carboxylate trifluoroacetate;

(10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-5-carbonitrile trifluoroacetate;

(10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-9-oxo-8,16-diazatricyclo[13.3.1.0$^{2,7}$]nonadeca-1(19),2(7),3,5,15,17-hexaene-5-carbonitrile trifluoroacetate;

(10R,14S)-14-(4-{5-chloro-2-[4-(difluoromethyl)-1H-1,2,3-triazol-1-yl]phenyl}-6-oxo-1,6-dihydropyrimidin-1-yl)-10-methyl-9-oxo-8,16-diazatricyclo[13.3.1.0$^{2,7}$]nonadeca-1(19),2(7),3,5,15,17-hexaene-5-carbonitrile trifluoroacetate;

methyl N-[(10R,14S)-14-[4-(3-chloro-2-fluorophenyl)-6-oxo-1,6-dihydropyrimidin-1-yl]-10-methyl-9-oxo-8,16-diazatricyclo[13.3.1.0$^{2,7}$]nonadeca -1(18),2,4,6,15(19),16-hexaen-5-yl]carbamate trifluoroacetate;

methyl N-[(10R,14S)-14-[4-(3-chloro-2,6-difluorophenyl)-6-oxo-1,6-dihydropyrimidin-1-yl]-10-methyl-9-oxo-8,16-diazatricyclo[13.3.1.0$^{2,7}$]nonadeca -1(18),2,4,6,15(19),16-hexaen-5-yl]carbamate trifluoroacetate;

methyl N-[(10R,14S)-14-[4-(3-chloro-2-fluorophenyl)-6-oxo-1,6-dihydropyrimidin-1-yl]-10,17-dimethyl-9-oxo-8,16,18-triazatricyclo[13.2.1.0$^{2,7}$]octadeca -1(17),2,4,6,15(18)-pentaen-5-yl]carbamate trifluoroacetate;

methyl N-[(10R,14S)-14-[4-(3-chloro-2,6-difluorophenyl)-6-oxo-1,6-dihydropyrimidin-1-yl]-10,17-dimethyl-9-oxo-8,16,18-triazatricyclo[13.2.1.0$^{2,7}$]octadeca -1(17),2,4,6,15(18)-pentaen-5-yl]carbamate trifluoroacetate;

methyl N-[(10R,14S)-14-[4-(5-chloro-2-fluorophenyl)-6-oxo-1,6-dihydropyrimidin-1-yl]-10-methyl-9-oxo-8,16-diazatricyclo[13.3.1.0$^{2,7}$]nonadeca -1(19),2(7),3,5,15,17-hexaen-5-yl]carbamate trifluoroacetate;

(10R,14S)-14-[4-(5-chloro-2-fluorophenyl)-6-oxo-1,6-dihydropyrimidin-1-yl]-4-fluoro-10-methyl-8,16-diazatricyclo[13.3.1.0$^{2,7}$]nonadeca-1(19),2(7),3,5,15,17-hexaen-9-one trifluoroacetate;

(10R,14S)-14-{4-[5-chloro-2-(1H-1,2,3-triazol-1-yl)phenyl]-6-oxo-1,6-dihydropyrimidin-1-yl}-4-fluoro-10-methyl-8,16-diazatricyclo[13.3.1.0$^{2,7}$]nonadeca -1(19),2(7),3,5,15,17-hexaen-9-one trifluoroacetate;

(10R,14S)-14-{4-[3-chloro-2-fluoro-6-(1H-1,2,3-triazol-1-yl)phenyl]-6-oxo-1,6-dihydropyrimidin-1-yl}-4-fluoro-10-methyl-8,16-diazatricyclo[13.3.1.0$^{2,7}$]nonadeca -1(19),2(7),3,5,15,17-hexaen-9-one trifluoroacetate;

(10R,14S)-14-[4-(2-bromo-5-chlorophenyl)-6-oxo-1,6-dihydropyrimidin-1-yl]-4-fluoro-10-methyl-8,16-diazatricyclo[13.3.1.0$^{2,7}$]nonadeca-1(19),2(7),3,5,15,17-hexaen-9-one trifluoroacetate;

(10R,14S)-14-{4-[3-chloro-2-fluoro-6-(1H-1,2,3-triazol-1-yl)phenyl]-6-oxo-1,6-dihydropyrimidin-1-yl}-3,4-difluoro-10-methyl-8,16-diazatricyclo[13.3.1.0$^{2,7}$]nonadeca -1(19),2(7),3,5,15,17-hexaen-9-one trifluoroacetate;

(10R,12R,14S)-14-{4-[3-chloro-6-(4-chloro-1H-1,2,3-triazol-1-yl)-2-fluorophenyl]-6-oxo-1,6-dihydropyrimidin-1-yl}-4,17-difluoro-12-hydroxy-10-methyl-8-azatricyclo [13.3.1.0$^{2,7}$]nonadeca-1(19),2(7),3,5,15,17-hexaen-9-one;

(10R,12R,14S)-14-{4-[5-chloro-2-(4-chloro-1H-1,2,3-triazol-1-yl)phenyl]-6-oxo -1,6-dihydropyrimidin-1-yl}-4,17-difluoro-12-hydroxy-10-methyl-8-azatricyclo[13.3.1.0$^{2,7}$]nonadeca-1(19),2(7),3,5,15,17-hexaen-9-one;

(10R,14S)-14-{4-[5-chloro-2-(4-chloro-1H-1,2,3-triazol-1-yl)phenyl]-6-oxo-1,6-dihydropyrimidin-1-yl}-10-methyl-8,16-diazatricyclo[13.3.1.0$^{2,7}$]nonadeca -1(19),2,4,6,15,17-hexaen-9-one;

(10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-8,16-diazatricyclo[13.3.1.0$^{2,7}$]nonadeca -1(19),2,4,6,15,17-hexaen-9-one;

(10S,14S)-14-{4-[5-chloro-2-(4-chloro-1H-1,2,3-triazol-1-yl)phenyl]-6-oxo-1,6-dihydropyrimidin-1-yl}-4-fluoro-10,11-dimethyl-8,11,16-triazatricyclo[13.3.1.0$^{2,7}$]nonadeca-1(19),2(7),3,5,15,17-hexaen-9-one;

(10S,14S)-14-{4-[3-chloro-6-(4-chloro-1H-1,2,3-triazol-1-yl)-2-fluorophenyl]-6-oxo-1,6-dihydropyrimidin-1-yl}-4-fluoro-10,11-dimethyl-8,11,16-triazatricyclo [13.3.1.0$^{2,7}$] nonadeca-1(19),2(7),3,5,15,17-hexaen-9-one;

6-[3-chloro-6-(4-chloro-1H-1,2,3-triazol-1-yl)-2-fluorophenyl]-3-[(10R,14S)-4-fluoro-10-methyl-8,16-diazatricyclo[13.3.1.0$^{2,7}$]nonadeca-1(19),2(7),3,5,15,17-hexaen -14-yl]-3,4-dihydropyrimidin-4-one;

(10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo[13.3.1.0$^{2,7}$]nonadeca-1 (19),2(7),3,5,15,17-hexaene-5-carbonitrile;

(10S,17S)-17-{4-[3-chloro-6-(4-chloro-1H-1,2,3-triazol-1-yl)-2-fluorophenyl]-6-oxo-1,6-dihydropyrimidin-1-yl}-4-fluoro-8,14,19-triazatetracyclo[16.3.1.0$^{2,7}$.0$^{10,14}$]docosa-1 (22),2(7),3,5,18,20-hexaen-9-one;

(10R,14S)-14-(4-{2,3-difluoro-6-[4-(trifluoromethyl)-1H-1,2,3-triazol-1-yl]phenyl}-6-oxo-1,6-dihydropyrimidin-1-yl)-4-fluoro-10-methyl-8,18-diazatricyclo [13.3.1.0$^{2,7}$] nonadeca-1(19),2(7),3,5,15,17-hexaen-9-one;

(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7),3,5,15,17-hexaene-5-carboxamide, hydrochloride;

(10R,14S)-14-{4-[5-chloro-2-(1-methyl-1H-pyrazol-4-yl)phenyl]-6-oxo-1,6-dihydropyrimidin-1-yl}-4-fluoro-10-methyl-8,16-diazatricyclo[13.3.1.0$^{2,7}$]nonadeca -1(19),2(7),3,5,15,17-hexaen-9-one;

(10R,14S)-14-{4-[5-chloro-2-(4-chloro-1H-1,2,3-triazol-1-yl)phenyl]-6-oxo-1,6-dihydropyrimidin-1-yl}-4-methanesulfonyl-10-methyl-8,16-diazatricyclo[13.3.1.0$^{2,7}$]nonadeca-1(19),2(7),3,5,15,17-hexaen-9-one;

methyl 4-chloro-2-{1-[(10R,14S)-4-fluoro-10-methyl-9-oxo-8,16-diazatricyclo [13.3.1.0$^{2,7}$]nonadeca-1(19),2(7),3,5,15,17-hexaen-14-yl]-6-oxo-1,6-dihydropyrimidin-4yl}benzoate;

(10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-8,16-diazatricyclo[13.3.1.0$^{2,7}$]nonadeca -1(19),2(7),3,5,15,17-hexaen-9-one;

1-(4-chloro-2-{1-[(10R,14S)-5-(difluoromethyl)-10-methyl-9-oxo-8,16-diazatricyclo[13.3.1.0$^{2,7}$]nonadeca-1(19),2(7),3,5,15,17-hexaen-14-yl]-6-oxo-1,6-dihydropyrimidin-4-yl}phenyl)-1H-1,2,3-triazole-4-carbonitrile;

(10R,14S)-14-[4-(5-chloro-1-methyl-1H-indazol-7-yl)-6-oxo-1,6-dihydropyrimidin-1-yl]-4-fluoro-10-methyl-8,16-diazatricyclo[13.3.1.0$^{2,7}$]nonadeca -1(19),2(7),3,5,15,17-hexaen-9-one;

(10R,14S)-14-(4-{5-chloro-2-[4-(trifluoromethyl)-1H-1,2,3-triazol-1-yl]phenyl}-6-oxo-1,6-dihydropyrimidin-1-yl)-3,10-dimethyl-8,16-diazatricyclo[13.3.1.0$^{2,7}$]nonadeca-1(19),2(7),3,5,15,17-hexaen-9-one;

(10R,14S)-14-{4-[5-chloro-2-(4-chloro-1H-1,2,3-triazol-1-yl)phenyl]-6-oxo-1,6- dihydropyrimidin-1-yl}-3,10-dimethyl-8,16-diazatricyclo[13.3.1.0$^{2,7}$]nonadeca -1(19),2(7),3,5,15,17-hexaen-9-one;

(10R,14S)-14-{4-[5-chloro-2-(4-chloro-1H-1,2,3-triazol-1-yl)phenyl]-6-oxo-1,6-dihydropyrimidin-1-yl}-5-(difluoromethyl)-10-methyl-8,16-diazatricyclo[13.3.1.0$^{2,7}$]nonadeca-1(19),2(7),3,5,15,17-hexaen-9-one;

(10R,14S)-5-chloro-14-{4-[5-chloro-2-(4-chloro-1H-1,2,3-triazol-1-yl)phenyl]-6-oxo-1,6-dihydropyrimidin-1-yl}-10-methyl-8,16-diazatricyclo[13.3.1.0$^{2,7}$]nonadeca -1(19),2(7),3,5,15,17-hexaen-9-one;

(10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-9-oxo-8,16-diazatricyclo[13.3.1.0$^{2,7}$]nonadeca-1(19),2(7),3,5,15,17-hexaene-5-carboxamide;

4-chloro-2-{1-[(10R,14S)-4-fluoro-10-methyl-9-oxo-8,16-diazatricyclo [13.3.1.0$^{2,7}$]nonadeca-1(19),2(7),3,5,15,17-hexaen-14-yl]-6-oxo-1,6-dihydropyrimidin-4-yl}benzoic acid;

(10R,14S)-14-(4-{5-chloro-2-[4-(trifluoromethyl)-1H-1,2,3-triazol-1-yl]phenyl}-6-oxo-1,6-dihydropyrimidin-1-yl)-5,10-dimethyl-8,16-diazatricyclo[13.3.1.0$^{2,7}$]nonadeca -1(19),2(7),3,5,15,17-hexaen-9-one;

(10R,14S)-14-{4-[5-chloro-2-(4-chloro-1H-1,2,3-triazol-1-yl)phenyl]-6-oxo-1,6-dihydropyrimidin-1-yl}-5,10-dimethyl-8,16-diazatricyclo[13.3.1.0$^{2,7}$]nonadeca -1(19),2(7),3,5,15,17-hexaen-9-one;

methyl N-[(10R,14S)-14-[4-(3-chloro-2-methylphenyl)-6-oxo-1,6-dihydropyrimidin-1-yl]-10-methyl-9-oxo-8,16-diazatricyclo[13.3.1.0$^{2,7}$]nonadeca -1(19),2(7),3,5,15,17-hexaen-5-yl]carbamate;

(10R,14S)-10-methyl-14-(4-{5-methyl-2-[4-(trifluoromethyl)-1H-1,2,3-triazol-1-yl]phenyl}-6-oxo-1,6-dihydropyrimidin-1-yl)-8,16-diazatricyclo[13.3.1.0$^{2,7}$]nonadeca-1(19),2(7),3,5,15,17-hexaen-9-one;

(10R,14S)-10-methyl-14-(4-{5-methyl-2-[4-(trifluoromethyl)-1H-1,2,3-triazol-1-yl]phenyl}-6-oxo-1,6-dihydropyrimidin-1-yl)-9-oxo-8,16-diazatricyclo[13.3.1.0$^{2,7}$]nonadeca-1(19),2(7),3,5,15,17-hexaene-5-carbonitrile;

(10R,14S)-14-{4-[3-chloro-2-fluoro-6-(1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7),3,5,15,17-hexaene-5-carbonitrile;

(10R,14S)-14-{4-[5-chloro-2-(4-chloro-1H-1,2,3-triazol-1-yl)phenyl]-6-oxo-1,6-dihydropyrimidin-1-yl}-5-methoxy-10-methyl-8,16-diazatricyclo[13.3.1.0$^{2,7}$]nonadeca -1(19),2(7),3,5,15,17-hexaen-9-one;

(10R,14S)-14-{4-[5-chloro-2-(4-chloro-1H-1,2,3-triazol-1-yl)phenyl]-6-oxo-1,6-dihydropyrimidin-1-yl}-5-hydroxy-10-methyl-8,16-diazatricyclo[13.3.1.0$^{2,7}$]nonadeca -1(19),2(7),3,5,15,17-hexaen-9-one trifluoroacetate;

(10R,14S)-14-(4-{5-chloro-2-[4-(trifluoromethyl)-1H-1,2,3-triazol-1-yl]phenyl}-6-oxo-1,6-dihydropyrimidin-1-yl)-5-(2-hydroxypropan-2-yl)-10-methyl-8,16-diazatricyclo[13.3.1.0$^{2,7}$]nonadeca-1(19),2(7),3,5,15,17-hexaen-9-one;

(10R,14S)-14-{4-[5-chloro-2-(5-fluoropyridin-3-yl)phenyl]-6-oxo-1,6-dihydropyrimidin-1-yl}-10-methyl-9-oxo-8,16-diazatricyclo[13.3.1.0$^{2,7}$]nonadeca -1(19),2(7),3,5,15,17-hexaene-5-carbonitrile;

(10R,14S)-14-{4-[5-chloro-2-(4-chloro-1H-1,2,3-triazol-1-yl)phenyl]-6-oxo-1,6-dihydropyrimidin-1-yl}-5-(1,1-difluoro-2-hydroxyethyl)-10-methyl-8,16-diazatricyclo[13.3.1.0$^{2,7}$]nonadeca-1(19),2(7),3,5,15,17-hexaen-9-one;

(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7),3,5,15,17-hexaene-5-carbonitrile trifluoroacetate;

2-[(10R,14S)-14-{4-[5-chloro-2-(4-chloro-1H-1,2,3-triazol-1-yl)phenyl]-6-oxo -1,6-dihydropyrimidin-1-yl}-10-methyl-9-oxo-8,16-diazatricyclo[13.3.1.0$^{2,7}$]nonadeca -1(19),2(7),3,5,15,17-hexaen-5-yl]-2,2-difluoroacetamide trifluoroacetate;

(10R,14S)-14-{4-[5-chloro-2-(4-chloro-1H-1,2,3-triazol-1-yl)phenyl]-6-oxo-1,6-dihydropyrimidin-1-yl}-5-ethynyl-10-methyl-8,16-diazatricyclo[13.3.1.0$^{2,7}$]nonadeca -1(19),2(7),3,5,15,17-hexaen-9-one;

(10R,14S)-14-(4-{5-chloro-2-[4-(trifluoromethyl)-1H-1,2,3-triazol-1-yl]phenyl}- -6-oxo-1,6-dihydropyrimidin-1-yl)-10-methyl-9-oxo-8,17-diazatricyclo[13.3.1.0$^{2,7}$]nonadeca-1(19),2(7),3,5,15,17-hexaene-5-carbonitrile trifluoroacetate;

(10R,14S)-14-{4-[5-chloro-2-(4-chloro-1H-1,2,3-triazol-1-yl)phenyl]-6-oxo-1,6-dihydropyrimidin-1-yl}-5-(difluoromethoxy)-10-methyl-8,16-diazatricyclo[13.3.1.0$^{2,7}$]nonadeca-1(19),2(7),3,5,15,17-hexaen-9-one trifluoroacetate;

(10R,14S)-14-(4-{5-chloro-2-[(4-(difluoromethyl)-1H-1,2,3-triazol-1-yl]phenyl}-6-oxo-1,6-dihydropyrimidin-1-yl)-10-methyl-8,16-diazatricyclo[13.3.1.0$^{2,7}$]nonadeca -1(19),2(7),3,5,15,17-hexaen-9-one;

(10R,14S)-14-(4-{3-chloro-6-[4-(difluoromethyl)-1H-1,2,3-triazol-1-yl]-2-fluorophenyl}-6-oxo-1,6-dihydropyrimidin-1-yl)-10-methyl-8,16-diazatricyclo [13.3.1.0$^{2,7}$]nonadeca-1(19),2(7),3,5,15,17-hexaen-9-one;

1-(4-chloro-2-{1-[(10R,14S)-10-methyl-9-oxo-8,16-diazatricyclo[13.3.1.0$^{2,7}$]nonadeca-1(19),2(7),3,5,15,17-hexaen-14-yl]-6-oxo-1,6-dihydropyrimidin-4-yl}phenyl)-1H-1,2,3-triazole-4-carbonitrile;

(10R,14S)-14-{5-chloro-4-[3-chloro-2-fluoro-6-(1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-5-carbonitrile;

(10R,14S)-14-{4-[3-chloro-6-(4-chloro-1H-1,2,3-triazol-1-yl)-2-fluorophenyl]-6-oxo-1,6-dihydropyrimidin-1-yl}-

10-methyl-9-oxo-8,16-diazatricyclo[13.3.1.0$^{2,7}$]nonadeca-1 (19),2(7),3,5,15,17-hexaene-4-carbonitrile trifluoroacetate;

2-{[(10R,14S)-14-{4-[5-chloro-2-(4-chloro-1H-1,2,3-triazol-1-yl)phenyl]-6-oxo -1,6-dihydropyrimidin-1-yl}-10-methyl-9-oxo-8,16-diazatricyclo[13.3.1.0$^{2,7}$]nonadeca -1(19),2(7),3,5,15,17-hexaen-5-yl]oxy}acetic acid;

N-{[(10R,14S)-14-{4-[5-chloro-2-(4-chloro-1H-1,2,3-triazol-1-yl)phenyl]-6-oxo -1,6-dihydropyrimidin-1-yl}-10-methyl-9-oxo-8,17-diazatricyclo[13.3.1.0$^{2,7}$]nonadeca -1(19),2(7),3,5,15,17-hexaen-5-yl]methyl}-2,2,2-trifluoroacetamide;

(10R,14S)-5-(aminomethyl)-14-{4-[5-chloro-2-(4-chloro-1H-1,2,3-triazol-1-yl)phenyl]-6-oxo-1,6-dihydropyrimidin-1-yl}-10-methyl-8,17-diazatricyclo[13.3.1.0$^{2,7}$]nonadeca-1(19),2(7),3,5,15,17-hexaen-9-one trifluoroacetate;

(10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-8,17-diazatricyclo[13.3.1.0$^{2,7}$]nonadeca -1(19),2 (7),3,5,15,17-hexaen-9-one;

(10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,17-diazatricyclo[13.3.1.0$^{2,7}$]nonadeca-1(19),2(7),3,5,15,17-hexaen-9-one;

(10R,14S)-3-chloro-14-{4-[5-chloro-2-(4-chloro-1H-1,2,3-triazol-1-yl)phenyl]-6-oxo-1,6-dihydropyrimidin-1-yl}-10-methyl-8,16-diazatricyclo[13.3.1.0$^{2,7}$]nonadeca 1(19),2 (7),3,5,15,17-hexaen-9-one;

(10R,14S)-3-chloro-14-(4-{5-chloro-2-[4-(trifluoromethyl)-1H-1,2,3-triazol-1-yl]phenyl}-6-oxo-1,6-dihydropyrimidin-1-yl)-10-methyl-8,16-diazatricyclo[13.3.1.0$^{2,7}$]nonadeca-1(19),2(7),3,5,15,17-hexaen-9-one;

methyl N-[(10R,14S)-14-[4-(3-chloro-2,6-difluorophenyl)-6-oxo-1,6-dihydropyrimidin-1-yl]-10-methyl-9-oxo-8,18-diazatricyclo[13.3.1.0$^{2,7}$]nonadeca -1(19),2(7),3,5,15,17-hexaen-5-yl]carbamate;

(10R,14S)-4-fluoro-14-(4-{5-methoxy-2-[4-(trifluoromethyl)-1H-1,2,3-triazol-1-yl]phenyl}-6-oxo-1,6-dihydropyrimidin-1-yl)-10-methyl-8,17-diazatricyclo[13.3.1.0$^{2,7}$]nonadeca-1(19),2(7),3,5,15,17-hexaen-9-one;

(10R,14S)-14- {4-[5-chloro-2-(4-chloro-1H-1,2,3-triazol-1-yl)phenyl]-6-oxo-1,6-dihydropyrimidin-1-yl}-4-fluoro-10-methyl-8,18-diazatricyclo[13.3.1.0$^{2,7}$]nonadeca -1(19),2(7),3,5,15,17-hexaen-9-one;

(10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,18-diazatricyclo[13.3.1.0$^{2,7}$]nonadeca-1(19),2(7),3,5,15,17-hexaen-9-one;

methyl N-[(10R,14S)-14-{4-[5-(difluoromethoxy)-2-[4-(trifluoromethyl)-1H -1,2,3-triazol-1-yl]phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaen-5-yl]carbamate;

(10R,14S)-14-(4-{5-chloro-2-[4-(trifluoromethyl)-1H-1, 2,3-triazol-1-yl]phenyl}-6-oxo-1,6-dihydropyrimidin-1-yl)-3-fluoro-10-methyl-8,16-diazatricyclo[13.3.1.0$^{2,7}$]nonadeca-1(19),2(7),3,5,15,17-hexaen-9-one;

(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,18-diazatricyclo[13.3.1.0$^{2,7}$]nonadeca -1(19),2(7), 3,5,15,17-hexaene-5-carbonitrile;

(10R,14S)-14-(4-{5-chloro-2-[4-(trifluoromethyl)-1H-1, 2,3-triazol-1-yl]phenyl}-6-oxo-1,6-dihydropyrimidin-1-yl)-10-methyl-9-oxo-8,18-diazatricyclo [ 13 .3 .1.0$^{2,17}$] -nonadeca-1(19),2(7),3,5,15,17-hexaene-5-carbonitrile;

(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7), 3,5,15,17-hexaene-4-carbonitrile trifluoroacetate;

methyl N-[(10R,14S)-14-(4-{5-methoxy-2-[4-(trifluoromethyl)-1H-1,2,3-triazol -1-yl]phenyl}-6-oxo-1,6-dihydropyrimidin-1-yl)-10-methyl-9-oxo-8,16-diazatricyclo [13.3.1.0$^{2,7}$]nonadeca-1(19),2(7),3,5,15,17-hexaen-5-yl] carbamate;

(10R,14S)-14-(4-{5-chloro-2-[4-(trifluoromethyl)-1H-1, 2,3-triazol-1-yl]phenyl}-6-oxo-1,6-dihydropyrimidin-1-yl)-4-fluoro-10-methyl-8,16,18-triazatricyclo[13.3.1.0$^{2,7}$]nonadeca-1(19),2(7),3,5,15,17-hexaen-9-one;

(10R,14S)-14-{4-[5-chloro-2-(1,2,3-thiadiazol-4-yl)phenyl]-6-oxo-1,6-dihydropyrimidin-1-yl}-4-fluoro-10-methyl-8,16-diazatricyclo[13.3.1.0$^{2,7}$]nonadeca -1(19),2(7), 3,5,15,17-hexaen-9-one;

(10R,14R)-14-(4-{5-chloro-2-[4-(trifluoromethyl)-1H-1, 2,3-triazol-1-yl]phenyl}-6-oxo-1,6-dihydropyrimidin-1-yl)-4-fluoro-10-methyl-8,16,18-triazatricyclo[13.3.1.0$^{2,7}$]nonadeca-1(19),2(7),3,5,15,17-hexaen-9-one;

(10R,14S)-14-[4-(5-chloro-1-methyl-1H-indazol-7-yl)-6-oxo-1,6-dihydropyrimidin-1-yl]-10-methyl-8,16-diazatricyclo[13.3.1.0$^{2,7}$]nonadeca -1(19),2(7),3,5,15,17-hexaen-9-one;

N-[(10R,14S)-14-[4-(5-chloro-1-methyl-1H-indazol-7-yl)-6-oxo-1,6-dihydropyrimidin-1-yl]-10-methyl-9-oxo-8, 16-diazatricyclo[13.3.1.0$^{2,7}$]nonadeca -1(19),2(7),3,5,15, 17-hexaen-5-yl]carbamate;

(10S,14S)-14-{4-[5-chloro-2-(4-chloro-1H-1,2,3-triazol-1-yl)phenyl]-6-oxo-1,6-dihydropyrimidin-1-yl}-4,11-difluoro-10-methyl-8,16-diazatricyclo[13.3.1.0$^{2,7}$]nonadeca -1(19),2(7),3,5,15,17-hexaen-9-one trifluoroacetate;

(10R,14S)-14-{4-[5-chloro-2-(4-chloro-1H-1,2,3-triazol-1-yl)phenyl]-6-oxo-1,6-dihydropyrimidin-1-yl}-N,10-dimethyl-9-oxo-8,16-diazatricyclo[13.3.1.0$^{2,7}$]nonadeca -1(19), 2(7),3,5,15,17-hexaene-4-carboxamide trifluoroacetate;

(10R,14S)-14-[4-(5-chloro-1-methyl-1H-indazol-7-yl)-6-oxo-1,6-dihydropyrimidin-1-yl]-10-methyl-9-oxo-8,16-diazatricyclo[13.3.1.0$^{2,7}$]nonadeca -1(19),2(7),3,5,15,17-hexaene-5-carbonitrile;

(10R,14S)-14-(4-{5-chloro-2-[1-(difluoromethyl)-1H-pyrazol-4-yl]phenyl}-6-oxo-1,6-dihydropyrimidin-1-yl)-4-fluoro-10-methyl-8,16-diazatricyclo[13.3.1.0$^{2,7}$]nonadeca-1 (19),2(7),3,5,15,17-hexaen-9-one trifluoroacetate;

(15S)-15-(4-{5-chloro-2-[4-(difluoromethyl)-1H-1,2,3-triazol-1-yl]phenyl}-6-oxo-1,6-dihydropyrimidin-1-yl)-4-fluoro-11-methyl-8,17-diazatricyclo[14.3.1.0$^{2,7}$]icosa -1(20),2(7),3,5,16,18-hexaen-9-one trifluoroacetate (Diastereomer A);

(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7), 3,5,15,17-hexaene-4-carboxylate trifluoroacetate;

(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7), 3,5,15,17-hexaene-4-carboxylic acid trifluoroacetate;

(10R,14S)-14-[4-(3-chloro-2,6-difluorophenyl)-6-oxo-1, 6-dihydropyrimidin-1-yl]-4-fluoro-10-methyl-8,16-diazatricyclo[13.3.1.0$^{2,7}$]nonadeca-1(19),2(7),3,5,15,17-hexaen -9-one trifluoroacetate;

(14S)-14-{4-[5-chloro-2-(4-chloro-1H-1,2,3-triazol-1-yl) phenyl]-6-oxo-1,6-dihydropyrimidin-1-yl}-4-fluoro-10-methyl-11-oxa-8,16-diazatricyclo[13.3.1.0$^{2,7}$]nonadeca-1 (19),2(7),3,5,15,17-hexaen-9-one trifluoroacetate (Diastereomer A);

(14S)-14-{4-[5-chloro-2-(4-chloro-1H-1,2,3-triazol-1-yl) phenyl]-6-oxo-1,6-dihydropyrimidin-1-yl}-4-fluoro-10- methyl-11-oxa-8,16-diazatricyclo[13.3.1.0²,⁷]nonadeca-1 (19),2(7),3,5,15,17-hexaen-9-one trifluoroacetate (Diastereomer B);

methyl N-[(14S)-14-{4-[5-chloro-2-(4-chloro-1H-1,2,3-triazol-1-yl)phenyl]-6-oxo-1,6-dihydropyrimidin-1-yl}-16,18-diazatricyclo[13.2.1.0²,⁷]octadeca -1(17),2,4,6,15(18)-pentaen-5-yl]carbamate trifluoroacetate;

methyl N-[(14S)-14-{4-[5-chloro-2-(1H-1,2,3,4-tetrazol-1-yl)phenyl]-6-oxo-1,6-dihydropyrimidin-1-yl}-16,18-diazatricyclo[13.2.1.0²,⁷]octadeca-1(17),2,4,6,15(18) -pentaen-5-yl]carbamate trifluoroacetate;

(15S)-15-(4-{5-chloro-2-[4-(difluoromethyl)-1H-1,2,3-triazol-1-yl]phenyl}-6-oxo-1,6-dihydropyrimidin-1-yl)-4-fluoro-11-methyl-8,17-diazatricyclo[14.3.1.0²,⁷]icosa -1(20),2(7),3,5,16,18-hexaen-9-one trifluoroacetate (Diastereomer B);

(10R,14S)-14-(4-{3-chloro-6-[4-(difluoromethyl)-1H-1,2,3-triazol-1-yl]-2-fluorophenyl}-6-oxo-1,6-dihydropyrimidin-1-yl)-4-fluoro-10-methyl-8,16-diazatricyclo [13.3.1.0²,⁷]nonadeca-1(19),2(7),3,5,15,17-hexaen-9-one trifluoroacetate;

(10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,16-diazatricyclo[13.3.1.0²,⁷]nonadeca-1(19),2(7),3,5,15,17-hexaen-9-one trifluoroacetate;

(10R,14S)-14-{4-[3-chloro-6-(4-ethoxy-1H-1,2,3-triazol-1-yl)-2-fluorophenyl]-6-oxo-1,6-dihydropyrimidin-1-yl}-4-fluoro-10-methyl-8,16-diazatricyclo[13.3.1.0²,⁷]nonadeca-1 (19),2(7),3,5,15,17-hexaen-9-one trifluoroacetate;

(10R,14S)-14-{4-[3-chloro-2-fluoro-6-(4-methyl-1H-1,2,3-triazol-1-yl)phenyl]-6-oxo-1,6-dihydropyrimidin-1-yl}-4-fluoro-10-methyl-8,16-diazatricyclo[13.3.1.0²,⁷]nonadeca-1 (19),2(7),3,5,15,17-hexaen-9-one;

(10R,14S)-14-(4-{5-chloro-2-[4-(difluoromethyl)-1H-1,2,3-triazol-1-yl]phenyl}-6-oxo-1,6-dihydropyrimidin-1-yl)-4-fluoro-10-methyl-8,16-diazatricyclo[13.3.1.0²,⁷]nonadeca-1(19),2(7),3,5,15,17-hexaen-9-one;

(10R,14S)-14-{4-[5-chloro-2-(4-hydroxy-1H-1,2,3-triazol-1-yl)phenyl]-6-oxo -1,6-dihydropyrimidin-1-yl}-4-fluoro-10-methyl-8,16-diazatricyclo[13.3.1.0²,⁷]nonadeca -1(19),2(7),3,5,15,17-hexaen-9-one trifluoroacetate;

(10R,14S)-14-{4-[5-chloro-2-(4-chloro-1H-1,2,3-triazol-1-yl)phenyl]-6-oxo-1,6-dihydropyrimidin-1-yl}-4-fluoro-10-methyl-8,16-diazatricyclo[13.3.1.0²,⁷]nonadeca -1(19),2(7),3,5,15,17-hexaen-9-one trifluoroacetate;

(10R,14S)-14-{4-[5-chloro-2-(trifluoromethyl)phenyl]-6-oxo-1,6-dihydropyrimidin-1-yl}-4-fluoro-10-methyl-8,16-diazatricyclo[13.3.1.0²,⁷]nonadeca -1(19),2(7),3,5,15,17-hexaen-9-one trifluoroacetate;

(10R,14S)-14-{4-[3-chloro-6-(4-chloro-1H-1,2,3-triazol-1-yl)-2-fluorophenyl]-6-oxo-1,6-dihydropyrimidin-1-yl}-4-fluoro-10-methyl-8,16-diazatricyclo[13.3.1.0²,⁷]nonadeca-1 (19),2(7),3,5,15,17-hexaen-9-one trifluoroacetate;

(10R,14S)-14-{4-[3-chloro-2-fluoro-6-(trifluoromethyl) phenyl]-6-oxo-1,6-dihydropyrimidin-1-yl}-4-fluoro-10-methyl-8,16-diazatricyclo[13.3.1.0²,⁷]nonadeca -1(19),2(7),3,5,15,17-hexaen-9-one trifluoroacetate;

(10R,14S)-14-{4-[5-chloro-2-(4-ethoxy-1H-1,2,3-triazol-1-yl)phenyl]-6-oxo-1,6-dihydropyrimidin-1-yl}-4-fluoro-10-methyl-8,16-diazatricyclo[13.3.1.0²,⁷]nonadeca -1(19),2 (7),3,5,15,17-hexaen-9-one trifluoroacetate;

(10S,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,18-diazatricyclo[13.3.1.0²,⁷]nonadeca-1(19),2,4,6,15,17-hexaen-9-one;

(10R,14S)-14-{4-[5-chloro-2-(trifluoromethoxy)phenyl]-6-oxo-1,6-dihydropyrimidin-1-yl}-4-fluoro-10-methyl-8, 16-diazatricyclo[13.3.1.0²,⁷]nonadeca -1(19),2(7),3,5,15,17-hexaen-9-one trifluoroacetate;

(10R,14S)-14-[4-(3,6-dichloro-2-fluorophenyl)-6-oxo-1,6-dihydropyrimidin-1-yl]-4-fluoro-10-methyl-8,16-diazatricyclo[13.3.1.0²,⁷]nonadeca-1(19),2(7),3,5,15,17-hexaen -9-one trifluoroacetate;

1-(4-chloro-2-{1-[(10R,14S)-4-fluoro-10-methyl-9-oxo-8,16-diazatricyclo [13.3.1.0²,⁷]nonadeca-1(19),2(7),3,5,15,17-hexaen-14-yl]-6-oxo-1,6-dihydropyrimidin-4yl}phenyl)-1H-1,2,3 -triazole-4-carbonitrile trifluoroacetate;

1-(4-chloro-2-{1-[(10R,14S)-4-fluoro-10-methyl-9-oxo-8,16-diazatricyclo [13.3.1.0²,⁷]nonadeca-1(19),2(7),3,5,15,17-hexaen-14-yl]-6-oxo-1,6-dihydropyrimidin-4-yl}phenyl)-N'-hydroxy-1H-1,2,3-triazole-4-carboximidamide bis-trifluoroacetate, and (10R,14S)-14-[4-(5-chloro-2-methoxyphenyl)-6-oxo-1,6-dihydropyrimidin-1-yl]-4-fluoro-10-methyl-8,16-diazatricyclo[13.3.1.0²,⁷]nonadeca-1(19),2(7),3,5,15,17-hexaen -9-one trifluoroacetate.

In another embodiment, the compounds of the present invention have Factor XIa or plasma kallikrein Ki values ≤10 μM.

In another embodiment, the compounds of the present invention have Factor XIa or plasma kallikrein Ki values ≤1 μM. In another embodiment, the compounds of the present invention have Factor XIa or plasma kallikrein Ki values ≤0.5 μM.

In another embodiment, the compounds of the present invention have Factor XIa or plasma kallikrein Ki values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a factor Xa inhibitor such as apixaban, rivaroxaban, betrixaban, edoxaban, eribaxaban, an anti-coagulant agent, an anti-platelet agent, a thrombin inhibiting agent such as dabigatran, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a method for the prophylaxis of a disease or condition in which plasma kallikrein activity is implicated comprising administering to a patient in need of such treatment and/or prophylaxis a therapeutically effective amount of at least one of the compounds of the present invention or a stereoisomer, a tautomer, a pharmaceutically acceptable salt, or a solvate thereof.

The disease or condition in which plasma kallikrein activity is implicated includes, but not limited to, impaired visual acuity, diabetic retinopathy, diabetic macular edema, hereditary angioedema, diabetes, pancreatitis, nephropathy, cardio myopathy, neuropathy, inflammatory bowel disease, arthritis, inflammation, septic shock, hypotension, cancer, adult respiratory distress syndrome, disseminated intravascular coagulation, and cardiopulmonary bypass surgery.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form.

Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond. "Alkyl" also includes deuteroalkyl such as $CD_3$.

"Alkenyl" or "alkenylene" is intended to include hydrocarbon chains of either straight or branched configuration having one or more, preferably one to three, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups; such as ethenyl, propenyl, butenyl, pentenyl, and hexenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Alkoxy also includes deuteroalkoxy such as $OCD_3$. Similarly, "alkylthio" or "thioalkoxy" represents an alkyl group as defined above with the indicated number of carbon atoms attached through a sulphur bridge; for example methyl-S- and ethyl-S-.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S-, and pentafluoroethyl-S-.

The term "amino", as used herein, refers to —$NH_2$.

The term "substituted amino", as used herein, refers to the defined terms below having the suffix "amino" such as "arylamino", "alkylamino", "arylamino", etc.

The term "alkoxycarbonyl", as used herein, refers to an alkoxy group attached to the parent molecular moiety through a carbonyl group.

The term "alkoxycarbonylamino", as used herein, refers to an —NHR wherein R is an alkoxycarbonyl group.

The term "alkylamino", as used herein refers to —NHR, wherein R is an alkyl group.

The term "alkylcarbonyl", as used herein, refers to an alkyl group attached to the parent molecular moiety through a carbonyl group.

The term "alkylcarbonylamino", as used herein, refers to —NHR wherein R is an alkylcarbonyl group.

The term "aminosulfonyl", as used herein, refers to —$SO_2NH_2$.

The term "arylalkyl", as used herein, refers to an alkyl group substituted with one, two, or three aryl groups.

The term "arylamino", as used herein, refers to —NHR wherein R is an aryl group.

The term "arylcarbonyl", as used herein, refers to an aryl group attached to the parent molecular moiety through a carbonyl group.

The term "arylcarbonylamino", as used herein refers to —NHR wherein R is an arylcarbonyl group.

The term "cyano", as used herein, refers to —CN.

The term "cycloalkylamino", as used herein, refers to —NHR wherein R is a cycloalkyl group.

The term "cycloalkylcarbonyl", as used herein, refers to a cycloalkyl group attached to the parent molecular moiety through a carbonyl group.

The term "cycloalkylcarbonylamino", as used herein, refers to —NHR wherein R is a cycloalkylcarbonyl group.

The term "cycloalkyloxy", as used herein, refers to a cycloalkyl group attached to the parent molecular moiety through an oxygen atom.

The term "dialkylamino", as used herein, refers to $NR_2$, wherein each R is an alkyl group. The two alkyl groups are the same or different.

The term "haloalkoxy", as used herein, refers to a haloalkyl group attached to the parent molecular moiety through an oxygen atom.

The term "haloalkyl", as used herein, refers to an alkyl group substituted by one, two, three, or four halogen atoms.

The term "haloalkylamino", as used herein, refers to —NHR wherein R is a haloalkyl group.

The term "carbonyl" refers to C(=O) or C(O).

The term "carboxy" or "carboxyl" refers to C(=O)OH.

The terms "carboxy ester" and "oxycarbonyl" refer to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-cycloalkyl, —C(O)O-substituted cycloalkyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "aminoacyl" or "amide", or the prefix "carbamoyl", "carboxamide", "substituted carbamoyl" or "substituted carboxamide" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic.

The term "haloalkylcarbonyl", as used herein, refers to a haloalkyl group attached to the parent molecular moiety through a carbonyl group. The term "haloalkylcarbonylamino", as used herein, refers to —NHR wherein R is a haloalkylcarbonyl group.

The terms "alkylcarbonyl" refer to an alkyl or substituted alkyl bonded to a carbonyl.

The term "alkoxycarbonyl", as used herein, refers to an alkoxy group attached to the parent molecular moiety through a carbonyl group.

The term "hydroxy" or "hydroxyl" refers to OH.

As used herein the term "thiol" means —SH. A thiol may be substituted with a substituent disclosed herein, in particular alkyl(thioalkyl), aryl(thioaryl), or alkoxy(thioalkoxy).

As used herein the term "sulfonyl", used alone or linked to other terms such as alkylsulfonyl or arylsulfonyl, refers to the divalent radicals —$SO_2$—. In aspects of the invention a sulfonyl group, the sulfonyl group may be attached to a substituted or unsubstituted hydroxyl, alkyl group, ether group, alkenyl group, alkynyl group, aryl group, cycloalkyl group, cycloalkenyl group, cycloalkynyl group, heterocyclic group, carbohydrate, peptide, or peptide derivative.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997).

"$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, C(=O)$CH_3$, $SCH_3$, S(=O)$CH_3$, S(=O)$_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, C(=O)$CH_3$, $SCH_3$, S(=O)$CH_3$, S(=O)$_2CH_3$, $CH_3$, $CH_2CH_3$, $CO_2H$, and $CO_2CH_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5: "Design and Application of Prodrugs", *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, $C_{1-6}$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_{1-6}$ alkoxycarbonyloxy -$C_{1-6}$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1 x" for once, "2 x" for twice, "3 x" for thrice, "°C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| Boc or BOC | tert-butyloxycarbonyl |
| Boc$_2$O | di-tert-butyl dicarbonate |
| AcOH or HOAc | acetic acid |
| AlCl$_3$ | aluminum chloride |
| AIBN | azobisisobutyronitrile |
| aqueous | aq |
| BBr$_3$ | boron tribromide |
| BCl$_3$ | boron trichloride |
| BEMP | 2-tert-butylimino-2-diethylamino-1,3-dimethylperhydro-1,3,2-diazaphosphorine |
| BOP reagent | benzotriazol-1-yloxytris(dimethylamino)phosphonium hexafluorophosphate |
| Burgess reagent | 1-methoxy-N-triethylammoniosulfonyl-methanimidate |
| Cbz | carbobenzyloxy |
| DCM Or CH$_2$Cl$_2$ | dichloromethane |
| CH$_3$CN or ACN | acetonitrile |
| CDCl$_3$ | deutero-chloroform |
| CHCl$_3$ | chloroform |
| mCPBA or m-CPBA | meta-chloroperbenzoic acid |
| Cs$_2$CO$_3$ | cesium carbonate |
| Cu(OAc)$_2$ | copper (II) acetate |
| CuI | copper(I) iodide |
| CuSO$_4$ | copper(II) sulfate |
| Cy$_2$NMe | N-cyclohexyl-N-methylcyclohexanamine |
| DBU | 1,8-diazabicyclo[5.4.0]undec-7-ene |
| DCE | 1,2-dichloroethane |
| DEA | diethylamine |
| Dess-Martin | 1,1,1-tris(acetyloxy)-1,1-dihydro-1,2-beniziodoxo1-3-(1H)-one |
| DIC or DIPCDI | diisopropylcarbodiimide |
| DIEA, DIPEA or Hunig's base | diisopropylethylamine |
| DMAP | 4-dimethylaminopyridine |
| DME | 1,2-dimethoxyethane |
| DMF | dimethyl formamide |
| DMSO | dimethyl sulfoxide |
| cDNA | complimentary DNA |
| Dppp | (R)-(+)-1,2-bis(diphenylphosphino)propane |
| DuPhos | (+)-1,2-bis((2S,5S)-2,5-diethylphospholano)benzene |
| EDC | N-(3-dimethylaminopropyl)-N'-ethylcarbodiimide |
| EDCI | N-(3-dimethylaminopropyl)-N'-ethylcarbodiimide hydrochloride |
| EDTA | ethylenediaminetetraacetic acid |
| (S,S)-EtDuPhosRh(I) | (+)-1,2-bis((2S,5S)-2,5-diethylphospholano)benzene(1,5-cyclooctadiene)rhodium(I) trifluoromethanesulfonate |
| Et$_3$N or TEA | triethylamine |
| EtOAc | ethyl acetate |
| Et$_2$O | diethyl ether |
| EtOH | ethanol |
| GMF | glass microfiber filter |
| Grubbs II | (1,3-bis(2,4,6-trimethylphenyl)-2-imidazolidinylidene)dichloro(phenylmethylene)(triycyclohexylphosphine)ruthenium |
| HCl | hydrochloric acid |
| HATU | O-(7-azabenzotriazol-1-yl)-N,N,N',N'-tetramethyluronium hexafluorophosphate |
| HEPES | 4-(2-hydroxyethyl)piperazine-1-ethanesulfonic acid |
| Hex | hexane |
| HOBt or HOBT | 1-hydroxybenzotriazole |
| H$_2$O$_2$ | hydrogen peroxide |
| H$_2$SO$_4$ | sulfuric acid |
| IBX | 2-iodoxybenzoic acid |
| InCl$_3$ | Indium(III) chloride |
| Jones reagent | CrO$_3$ in aqueous H$_2$SO$_4$, 2 M |
| K$_2$CO$_3$ | potassium carbonate |
| K$_2$HPO$_4$ | potassium phosphate dibasic |
| K$_3$PO$_4$ | potassium phosphate tribasic |
| KOAc | potassium acetate |
| K$_3$PO$_4$ | potassium phosphate |
| LAH | lithium aluminum hydride |
| LG | leaving group |
| LiOH | lithium hydroxide |
| MeOH | methanol |
| MgSO$_4$ | magnesium sulfate |
| MsOH | or MSA methylsulfonic acid |
| NaCl | sodium chloride |
| NaH | sodium hydride |
| NaHCO$_3$ | sodium bicarbonate |
| Na$_2$CO$_3$ | sodium carbonate |
| NaOH | sodium hydroxide |
| Na$_2$SO$_3$ | sodium sulfite |

-continued

| | |
|---|---|
| Na$_2$SO$_4$ | sodium sulfate |
| NBS | N-bromosuccinimide |
| NCS | N-chlorosuccinimide |
| NH$_3$ | ammonia |
| NH$_4$Cl | ammonium chloride |
| NH$_4$OH | ammonium hydroxide |
| NH$_4$COOH | ammonium formate |
| NMM | N-methylmorpholine |
| OTf | triflate or trifluoromethanesulfonate |
| Pd$_2$(dba)$_3$ | tris(dibenzylideneacetone)dipalladium(0) |
| Pd(OAc)$_2$ | palladium(II) acetate |
| Pd/C | palladium on carbon |
| Pd(dppf)Cl$_2$ | [1,1'-bis(diphenylphosphino)-ferrocene]dichloropalladium(II) |
| Ph$_3$PCl$_2$ | triphenylphosphine dichloride |
| PG | protecting group |
| POCl$_3$ | phosphorus oxychloride |
| i-PrOH or IPA | isopropanol |
| PS | Polystyrene |
| rt | room temperature |
| SEM-Cl | 2-(trimethysilyl)ethoxymethyl chloride |
| SiO$_2$ | silica oxide |
| SnCl$_2$ | tin(II) chloride |
| TBAI | tetra-n-butylammonium iodide |
| TBN | t-butyl nitrite |
| TFA | trifluoroacetic acid |
| THF | tetrahydrofuran |
| TMSCHN$_2$ | trimethylsilyldiazomethane |
| T3P ® | propane phosphonic acid anhydride |
| TRIS | tris (hydroxymethyl) aminomethane |
| pTsOH | p-toluenesulfonic acid |

The compounds of the present invention can be prepared in a number of ways known to one skilled in the art of organic synthesis, which are described in more detail in Section VI.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, atrial fibrillation, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (Colman, R. W. et al., eds., Hemostasis and Thrombosis, Basic Principles and Clinical Practice, Fifth Edition, p. 853, Lippincott Williams & Wilkins (2006)).

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., Blood, 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", Hemostasis and Thrombosis, pp. 103-122, Lippincott Williams & Wilkins (2001); Schmaier, A. H., "Contact Activation", Thrombosis and Hemorrhage, pp. 105-128

(1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.*, 202:271-281 (2005); Kleinschmitz et al., *J. Exp. Med.*, 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.*, 10:198-204 (2000)).

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001).) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, factor XI deficiency rescues the perinatal lethal phenotype of complete protein C deficiency (Chan et al., *Amer. J. Pathol.*, 158:469-479 (2001)). Furthermore, baboon cross-reactive, function blocking antibodies to human factor XI protect against baboon arterial—venous shunt thrombosis (Gruber et al., *Blood*, 102:953-955 (2003)). Evidence for an antithrombotic effect of small molecule inhibitors of factor XIa is also disclosed in published U.S. Publication No. 2004/0180855 A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or post-traumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, Second Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial and venous thrombosis, at doses that preserved hemostasis. (Wong P. C. et al., *Journal of Thrombosis and Thrombolysis*, 32(2):129-137 (Aug. 2011); Schumacher, W. et al., *Journal of Thrombosis and Haemostasis*, 3(Suppl. 1):P1228 (2005); Schumacher, W. A. et al., *European Journal of Pharmacology*, 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo. Preclinical and clinical studies using FXI antisense (ASO) has been shown to be effective in various venous and arterial thrombosis models, comparable to warfarin or enoxaparin without increased bleeding (Bueller et al., DOI: 10.1056/NEJMoa1405760 (2014)).

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; Chromogenix or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; Chromogenix or BMPM -2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu -Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA (SEQ ID NO. 1); Chromogenix) at a concentration of 0.0002-0.00035 M.

Factor XIIa determinations were made in 0.05 M HEPES buffer at pH 7.4 containing 0.145 M NaCl, 0.05 M KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L -Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human plasma kallikrein (Enzyme Research Laboratories) at a final assay concentration of 200 pM and the synthetic substrate S-2302 (H-(D)-Pro-Phe -Arg-pNA; Chromogenix) at a concentration of 0.00008-0.0004 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix or AnaSpec) at a concentration of 0.0002-0.0004 M.

The Michaelis constant, $K_m$, for substrate hydrolysis by each protease, was determined at 25° C. or 37° C. in the absence of inhibitor. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$(V_{max}*S)/(K_m+S)$;

$(v_o-v_s)/v_s=I/(K_i(1+S/K_m))$ for a competitive inhibitor with one binding site; or $v_s/v_o=A+((B-A)/1+((IC_{50}/(I)^n)))$; and $K_i=IC_{50}/(1+S/K_m)$ for a competitive inhibitor where:

$v_o$ is the velocity of the control in the absence of inhibitor;

$v_s$ is the velocity in the presence of inhibitor;

$V_{max}$ is the maximum reaction velocity;

I is the concentration of inhibitor;

A is the minimum activity remaining (usually locked at zero);

B is the maximum activity remaining (usually locked at 1.0);

n is the Hill coefficient, a measure of the number and cooperativity of potential inhibitor binding sites;

$IC_{50}$ is the concentration of inhibitor that produces 50% inhibition under the assay conditions;

$K_i$ is the dissociation constant of the enzyme inhibitor complex;

S is the concentration of substrate; and $K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5x or IC2x, the inhibitor concentration required to increase the clotting time by 1.5-time or 2-times, respectively, relative to the clotting time in the absence of the inhibitor. The IC1.5x or IC2x is found by linear interpolation from relative clotting time versus inhibitor concentration plots using inhibitor concentration that spans the IC1.5x or IC2x.

Clotting times are determined using citrated normal human plasma as well as plasma obtained from a number of laboratory animal species (e.g., rat or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Activated Partial Thromboplastin Time (aPTT) is determined using ACTIN® (Dade-Behring, Illinois) following the directions in the package insert. Plasma (0.05 mL) is warmed to 37° C. for 1 minute. ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Innovin, Dade -Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

Chymotrypsin determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human chymotrypsin at a final concentration of 0.2-2 nM (Calbiochem) and the synthetic substrate S-2586 (Methoxy-Succinyl-Arg-Pro-Tyr-pNA; Chromogenix) at a concentration of 0.0005-0.005 M.

Trypsin determinations were made in 0.1 M sodium phosphate buffer at a pH of 7.5 containing 0.2 M sodium chloride and 0.5% PEG 8000. Determinations were made using purified human trypsin (Sigma) at a final assay concentration of 0.1-1 nM and the synthetic substrate S-2222 (Bz-Ile-Glu (gamma-OMe, 50%)-Gly-Arg-pNA (SEQ ID NO. 1); Chromogenix) at a concentration of 0.0005-0.005 M.

The Examples disclosed below were tested in the Factor XIa assay described above and found having Factor XIa inhibitory activity. A range of Factor XIa inhibitory activity (Ki values) of ≤10 µM (10000 nM) was observed.

The Examples disclosed below were tested in the Plasma Kallikrein assay described above, with some Examples having both Factor XIa and Plasma Kallikrein inhibitory activity. For those Examples where the Plasma Kallikrein inhibitory activity was observed as Ki values of ≤10 µM (10000 nM), the inhibitory activity is reported.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arteriovenous Shunt Thrombosis Models.

a. In Vivo Electrically-induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In vivo Rabbit Arteriovenous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient. In one embodiment, the pharmaceutical composition is a solid formulation, e.g., a spray-dried composition, which may be used as is, or whereto the physician or the patient adds solvents, and/or diluents prior to use.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Solid dispersions are also called solid-state dispersions. In some embodiments, any compound described herein is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences,* Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 300 milligrams per dosage unit, and the second anti-coagulant in an amount of about 1 to about 500 milligrams per dosage unit.

Where the compounds of the present invention are administered in combination with an anti-platelet agent, by way of general guidance, typically a daily dosage may be about 0.01 to about 300 milligrams of the compound of the present invention and about 50 to about 150 milligrams of the anti-platelet agent, preferably about 0.1 to about 4 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 100 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (aliskirin) and vasopepsidase inhibitors, an antiarrythmic agent selected from $I_{Kur}$ inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti -ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153, SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin -mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., -gemfibrozil, clofibrate, fenofibrate and benzafibrate) and other peroxisome proliferator activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X -receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention can also be combined with soluble guanylate cyclase inhibitors, Chymase inhibitors, ROMK inhibitors, ACE inhibitors, ATII inhibitors, ATR inhibitors, NEP inhibitors and other compounds to treat heart failure.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 4th Edition, Wiley-Interscience (2006)).

Representative pyrimidinone compounds 1a of this invention can be prepared as described in Scheme 1. Using a modified procedure described by Xiao (*Organic Letters*, 11:1421 (2009)), suitably substituted pyrimidin-4-ol derivatives 1b can be coupled with an appropriately substituted macrocycle amine 1c in the presence of HATU and DBU in a solvent such as $CH_3CN$ to provide pyrimidinone compounds 1a. When ring A is a SEM-protected imidazole ring, an additional deprotection step employing 4N HCl in dioxane or TFA in DCM is used to afford compounds of this invention.

Scheme 1

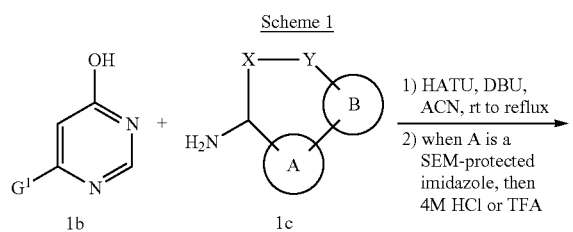

Scheme 2 describes the synthesis of suitably substituted pyrimidin-4-ol derivatives 1b. Suzuki-Miyaura coupling between 6-chloropyrimidin-4-ol (2a) and an appropriately substituted aryl boronic acid or ester 2c in the presence of a base such as Hunig's base or potassium phosphate tribasic, in a solvent mixture, such as toluene and ethanol, or THF, using a precatalyst such as $Pd(PPh_3)_4$ or 2nd generation XPhos provides 1b. Alternatively, when 4-chloro-6-methoxypyrimidine 2b is used, an additional deprotection step, employing aqueous HBr at elevated temperatures, is required to provide pyrimidin-4-ol derivatives 1b.

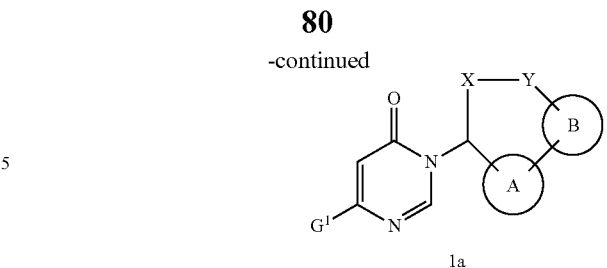

Scheme 2

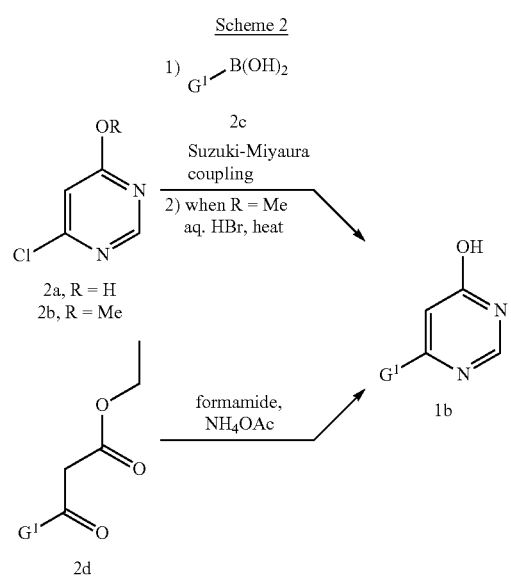

Intermediates for preparation of compounds of the present invention wherein ring A is a 6-membered heterocycle (example-pyridine) can be derived from appropriately substituted aldehydes 3a according to the general method outlined in Scheme 3. Condensation of aldehyde 3a (X=N) prepared according to a modified procedure described by Negi (*Synthesis*, 991 (1996)), with (S)-2-methylpropane-2-sulfinamide in the presence of anhydrous copper sulfate or cesium carbonate in a solvent such as DCM gives the sulfinimine 3b (Ellman, J., *J. Org. Chem.*, 64:1278 (1999)). Using a modified procedure described by Kuduk (*Tetrahedron Letters*, 45:6641 (2004)), suitably substituted Grignard reagents, for example allylmagnesium bromide, can be added to sulfinimine 3b to give a sulfinamide 3c, as a mixture of diastereomers which can be separated at various stages of the sequence. The diastereoselectivity for the addition of allylmagnesium bromide to sulfinimine 3b can be improved by employing indium(III) chloride according to a modified procedure of Xu (Xu, M.—H., *Organic Letters*, 10(6):1259 (2008)). Suzuki-Miyaura coupling between 4-chloropyridine 3c and an appropriately substituted aryl boronic acid or ester 3e in the presence of a base such as potassium phosphate, in a solvent mixture, such as DMSO and H$_2$O, or DMF, using a precatalyst such as Pd(dppf)Cl$_2$●CH$_2$Cl$_2$ complex provides 3g. Alternatively, the Suzuki-Miyaura coupling between boronic acid 3d and an appropriately substituted aryl halide 3f can be used to prepare 3g. Protecting group interconversion can be accomplished in two steps to give 3h. Alternatively, the protecting group interconversion can take place initially on 3c followed by the Suzuki-Miyaura coupling. The aniline 3h can then be coupled with an appropriately substituted carboxylic acid 3i using T3P® and a base, such as pyridine, to give the amide 3j. Using a modified procedure described by Lovely (*Tetrahedron Letters*, 44:1379 (2003)), 3j, following pretreatment with p-toluenesulfonic acid to form the pyridinium ion, can be cyclized via ring-closing metathesis using a catalyst, such as Second Generation Grubbs (II) Catalyst, in a suitable solvent, such as DCM, DCE, or toluene at elevated temperature, to give the pyridine-containing macrocycle 3k. The alkene can be reduced with hydrogen over either palladium on carbon or platinum oxide, and subsequent deprotection with TFA in DCM or 4M HCl in dioxane provides amine 3l. Compounds of the formula 3l can be converted to compounds in this invention according to Scheme 1.

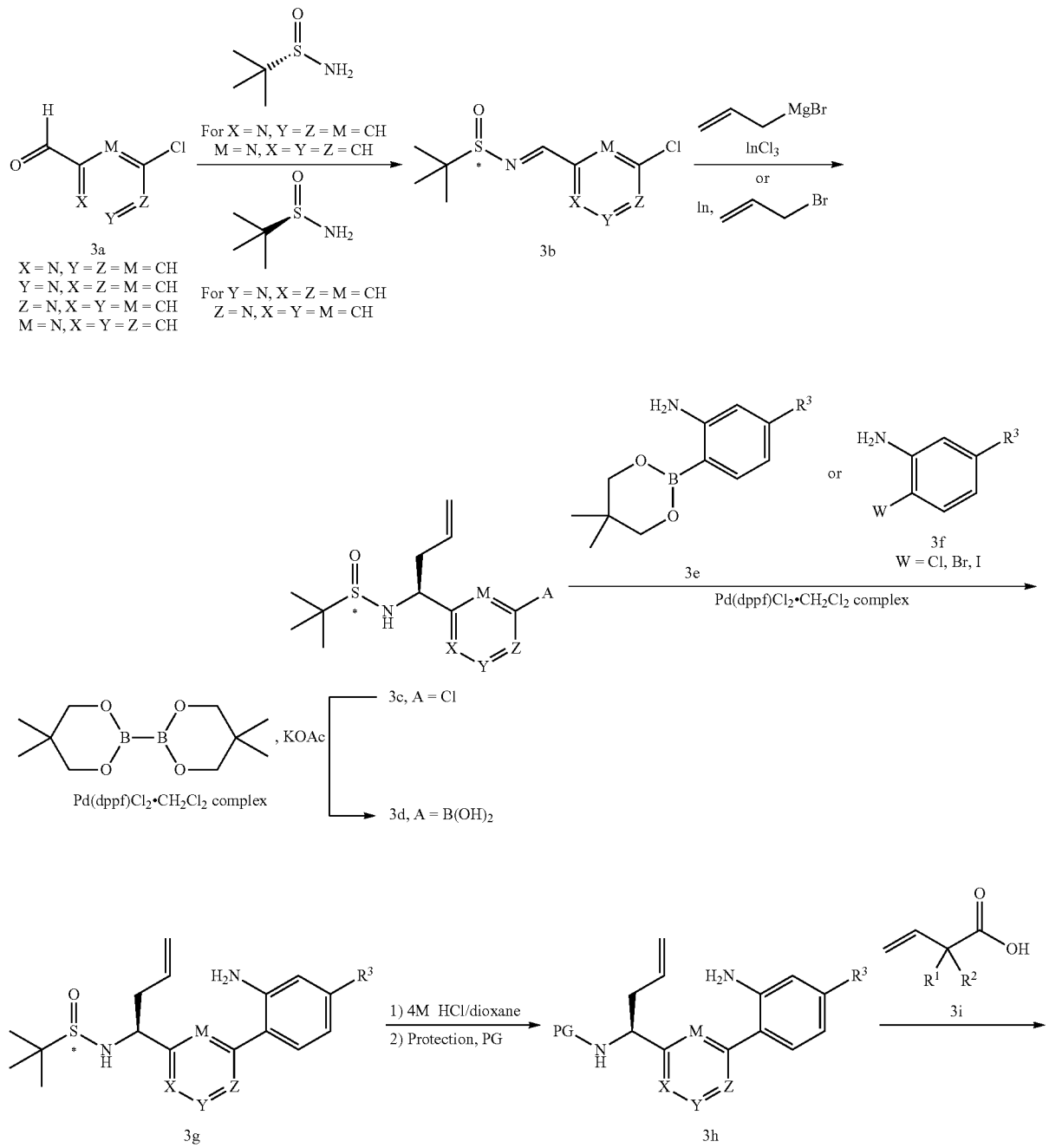

Scheme 3

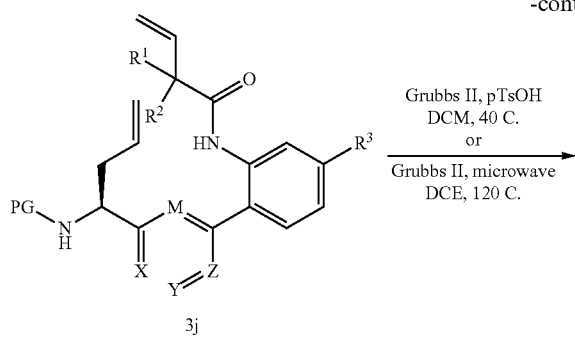

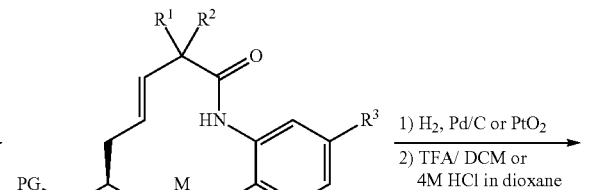

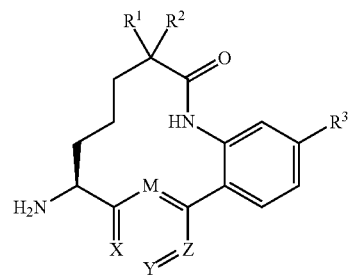

Additional pyridine containing macrocycles useful for the synthesis of compounds of this invention can also be prepared according to Scheme 3. In cases where the pyridine core is a 4-pyridine (Z=N, X=Y=M=CH) rather than the 2-pyridine (X=N, Y=Z=M=CH), conversion of 3h to 3j can be easily accomplished by using an acid chloride of 3i.

Methods for synthesis of a large variety of substituted pyridine compounds useful as starting materials for the preparation of compounds of the present invention are well known in the art and have been extensively reviewed. (For examples of methods useful for the preparation of pyridine starting materials see: Kroehnke, F., Synthesis, 1 (1976); Abramovitch, R. A., ed., "Pyridine and Its Derivatives", *The Chemistry of Heterocyclic Compounds*, 14(Suppl. 1-4), John Wiley & Sons, New York (1974); Boulton, A. J. et al., eds., *Comprehensive Heterocyclic Chemistry*, 2:165-524, Pergamon Press, New York (1984); McKillop, A., ed., *Comprehensive Heterocyclic Chemistry*, 5:1-300, Pergamon Press, New York (1996)).

In cases where suitably substituted boronic acids are not commercially available, a modification to this approach may be adopted wherein an aryl halide is subjected to a palladium mediated coupling with a diboron species such as bis(pinacolato)diboron or bis(neopentyl glycolato)diboron to provide the corresponding 4,4,5,5-tetramethyl -[1,3,2]dioxaborolane or the 5,5-dimethyl-[1,3,2]dioxaborolane intermediates using the method of Ishiyama, T. et al. (*J. Org. Chem.*, 60(23):7508-7510 (1995)). Alternately, this same intermediate can be prepared by reaction of the intermediate halide with the corresponding dialkoxyhydroborane as described by Murata et al. (*J. Org. Chem.*, 62(19):6458-6459 (1997)). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N. et al., *Chem. Rev.*, 95:2457 (1995)).

It is also realized that the scope of intermediate synthesis can be further extended outside the use of Suzuki-Miyaura coupling methodology since the precursor aryl halides or triflates described above are also precursors for Stille, Negishi, Hiyama, and Kumada -type cross coupling methodologies (Tsuji, J., *Transition Metal Reagents and Catalysts: Innovations in Organic Synthesis*, John Wiley & Sons (2000); Tsuji, J.,*Palladium Reagents and Catalysts: Innovations in Organic Synthesis*, John Wiley & Sons (1996)).

Intermediates for preparation of compounds of the present invention wherein ring A is an imidazole ring, can be prepared from an appropriately N-protected allylglycine (4a) according to the general method outlined in Scheme 4 (Contour-Galcera et al., *Bioorg. Med. Chem. Lett.*, 11(5): 741-745 (2001)). Condensation of 4a with a suitably substituted bromoacetophenone (4b) in the presence of a suitable base such as potassium bicarbonate, potassium carbonate or cesium carbonate in a suitable solvent such as DMF provides a keto ester intermediate which can be cyclized to afford an imidazole (4c) by heating in the presence of excess ammonium acetate in a solvent such as toluene or xylene. This latter transformation can be conveniently carried out on small scale at 160° C. in a microwave reactor or on larger scale by refluxing the mixture while removing water via a Dean-Stark trap. The resulting imidazole intermediate (4c) is then protected by treatment with SEM-Cl in the presence of a base such as sodium hydride or dicyclohexylmethylamine in a solvent such as THF or DCM. The resulting aryl bromide (4d) is then converted to the corresponding aniline (4e) by heating in a sealed vessel with excess ammonium hydroxide, in the presence of copper iodide, a base such as potassium carbonate and a catalytic amount of proline in DMSO as solvent. Acylation of 4e with the appropriate alkenoic acid and a coupling agent such as T3P® or BOP reagent, or alternately, by treatment with an alkenoic acid chloride in the presence of a base such as TEA, DIPEA, or pyridine provides diene 4f, which undergoes ring closing metathesis by heating in dilute solution in the presence of p-toluene sulfonic acid and Second Generation Grubbs Catalyst in a suitable solvent such as DCM or DCE to provide the corresponding macrocycle (4g). Alternately, the RCM can be run in a microwave at elevated temperatures without pTsOH. Reduction of the double bond followed by bromination with NBS at room temperature affords 4h. Suzuki-Miyaura coupling with methylboronic acid or tetramethylstannane and removal of the protecting group (PG), provides intermediate 4i. Intermediate 4i can be converted to compounds of the present invention following the steps described in Scheme 1.

Scheme 4

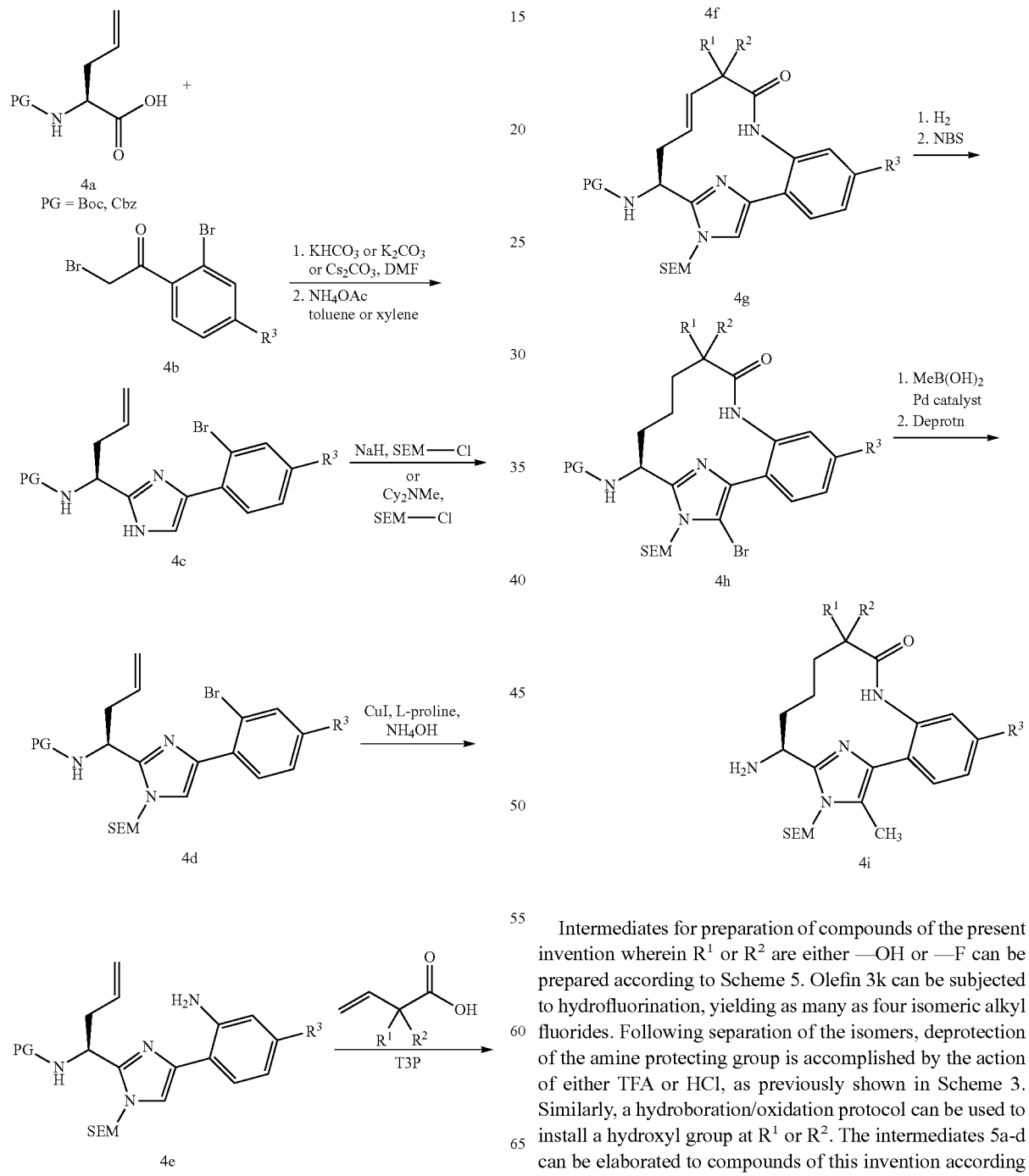

Intermediates for preparation of compounds of the present invention wherein $R^1$ or $R^2$ are either —OH or —F can be prepared according to Scheme 5. Olefin 3k can be subjected to hydrofluorination, yielding as many as four isomeric alkyl fluorides. Following separation of the isomers, deprotection of the amine protecting group is accomplished by the action of either TFA or HCl, as previously shown in Scheme 3. Similarly, a hydroboration/oxidation protocol can be used to install a hydroxyl group at $R^1$ or $R^2$. The intermediates 5a-d can be elaborated to compounds of this invention according to the procedure described in Scheme 1.

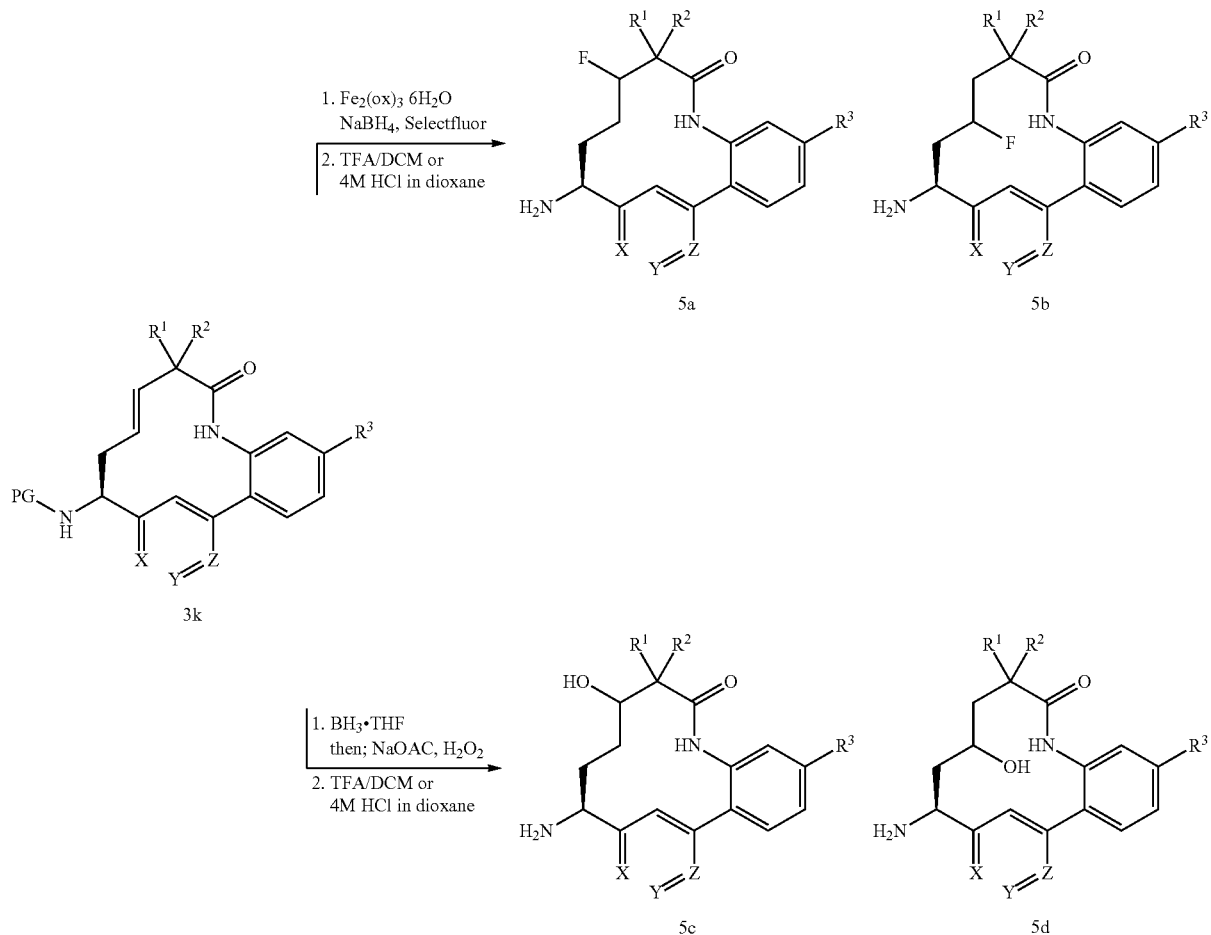

Scheme 6 describes the synthesis of suitably substituted pyrimidin-4-ol derivatives where $G^1$ is a substituted phenyl. Aniline 6a can be converted to a suitably substituted triazole 6b in a one pot, two step sequence. Specifically, the aniline 6a is converted to the aryl azide in situ followed by cycloaddition with a suitably substituted alkyne in the presence of a copper catalyst, such as $Cu_2O$, to provide 6b. Demethylation of 6b according to Scheme 2 provides the pyrimidin-4-ol derivatives 6c. When $R^{10}$ is a trimethylsilyl group, the silyl moiety can be converted to a chloride at elevated temperature with NCS in the presence of silica gel. Aniline 6a can be converted to the iodide 6d with p-TsOH, $NaNO_2$, and NaI. Subjecting iodide 6d to a variety of N-arylation or Suzuki-Miyaura couplings, followed by demethylation according to Scheme 2, gives additional pyrimidin-4-ol derivatives 6e.

Scheme 6

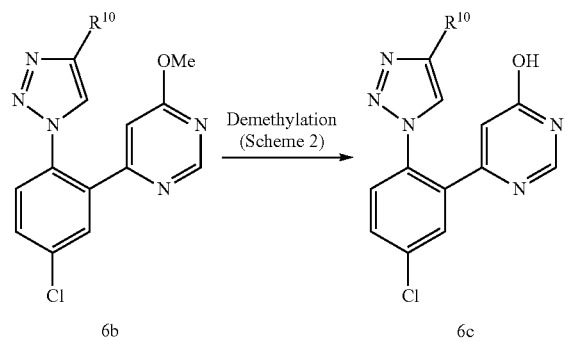

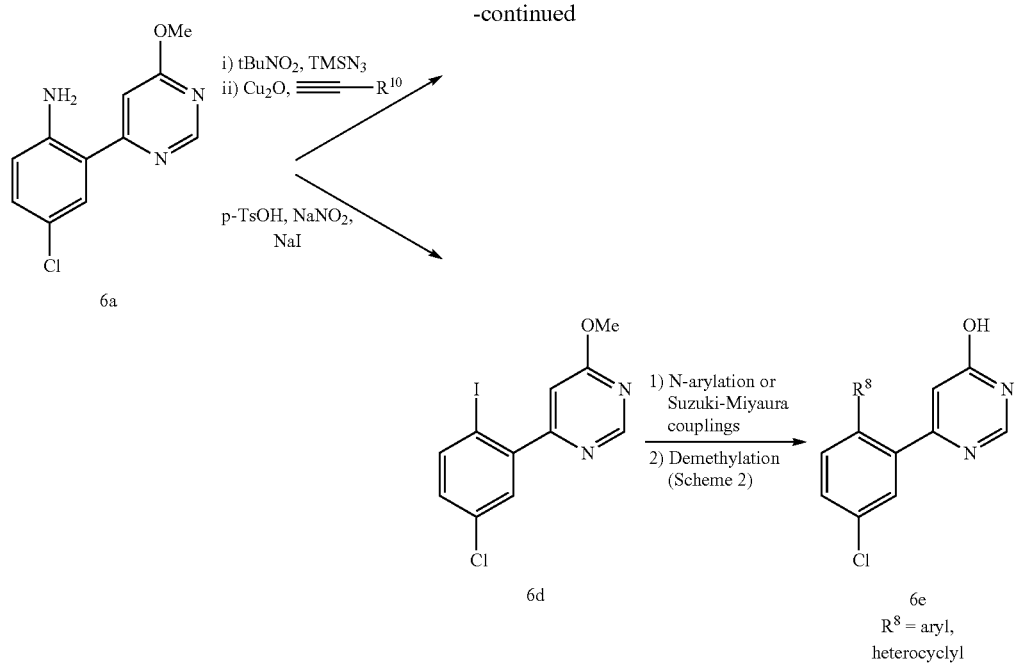

Imidazole containing macrocycles of this invention wherein Y is —CH₂— can be prepared according to Scheme 7. Suzuki-Miyaura coupling between 4d, prepared as described in Scheme 4, and a suitably substituted alkyl boronic acid 7a in the presence of silver(I) oxide and a base, such as potassium carbonate, using a precatalyst such as Pd(dppf)Cl₂●CH₂Cl₂ complex, in a solvent such as tetrahydrofuran at elevated temperatures provides 7b (Falck, J. R., *Tetrahedron Letters*, 42:7213 (2001)). Using a modified procedure described by Lovely (*Tetrahedron Letters*, 44:1379 (2003)), 7b, following pretreatment with p-toluenesulfonic acid to form the imidazolium ion, can be cyclized via ring-closing metathesis using a catalyst, such as Grubbs II, in a suitable solvent, such as dichloromethane, dichloroethane, or toluene at elevated temperature, to give the imidazole-containing macrocycle 7c as a mixture of olefin isomers. Alkene 7c can be reduced with hydrogen over either palladium on carbon or platinum oxide and subsequent deprotection as described above gives the amine 7d. Amine 7d can be converted to compounds of the present invention following the steps described in Scheme 1.

Scheme 7

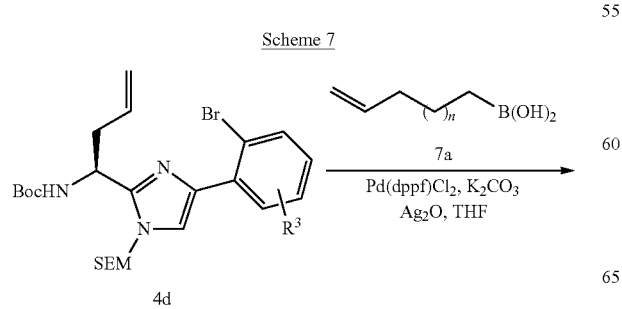

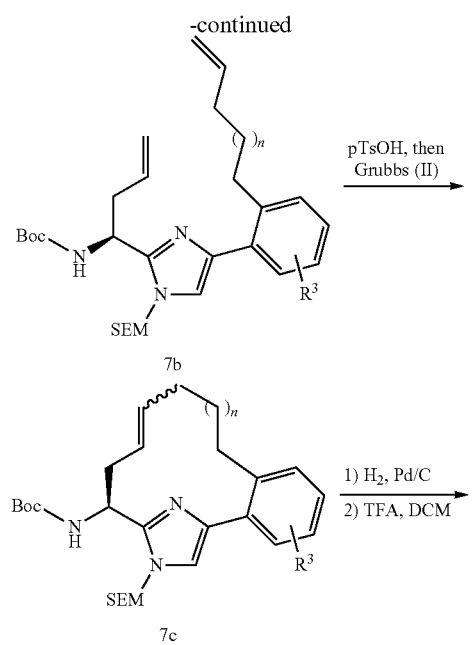

Pyridine containing macrocycles of this invention wherein W=O and Y=—C(=O)NH— can be prepared according to Scheme 8. Lemieux oxidation of alkene 8a, followed by reduction of the aldehyde with NaBH₄ will provide alcohol 8b. Alkylation of alcohol 8b with appropriately substituted α-bromo esters 8c will give 8d. Suzuki-Miyaura coupling between 4-chloropyridine 8d and an appropriately substituted aryl boronic acid or ester 3e in the presence of a base such as potassium phosphate, in a solvent mixture, such as DMSO and H₂O, or DMF, using a precatalyst such as Pd(dppf)Cl₂•CH₂Cl₂ complex provides, after saponification, 8e. Macrolactamization of 8e, followed by deprotection, provides amine 8f. Amine 8f can be converted to compounds of the present invention following the steps described in Scheme 1.

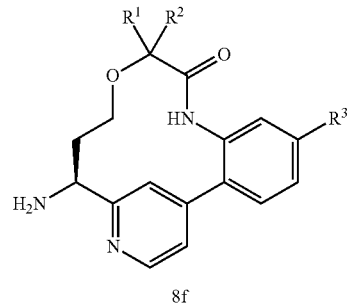

8f

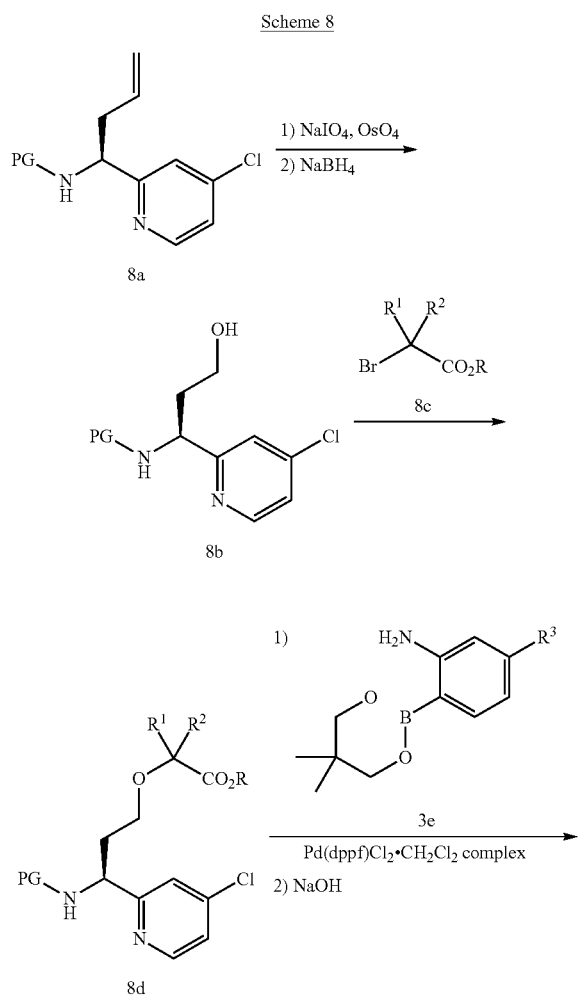

Intermediates for preparation of compounds of the present invention wherein nitrogen is part of the linker can be prepared according to Scheme 9. Olefin 9a can be oxidized to the aldehyde 9b by osmium tetraoxide and sodium periodate. Reductive amination of the aldehyde 9b with aminoester 9c provides 9d, which can be coupled with substituted boronate 9e via Suzuki coupling to give 9f. The methyl ester 9f can be hydrolyzed to acid 9g. The macrolactamation can be achieved via BOP and DMAP under dilute condition. Amine protecting group is accomplished by the action of either TFA or HCl, as previously shown in Scheme 3. The intermediate 9i can be elaborated to compounds of this invention according to the procedure described in Scheme 1.

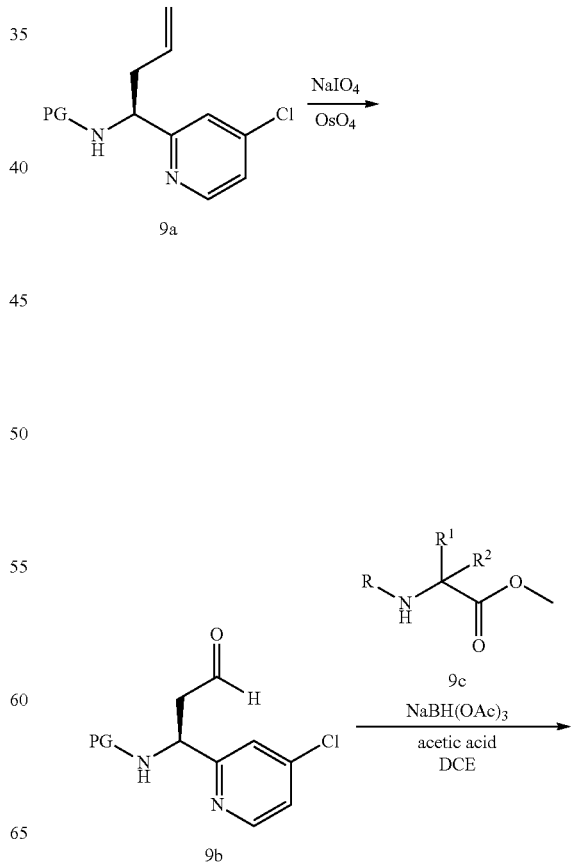

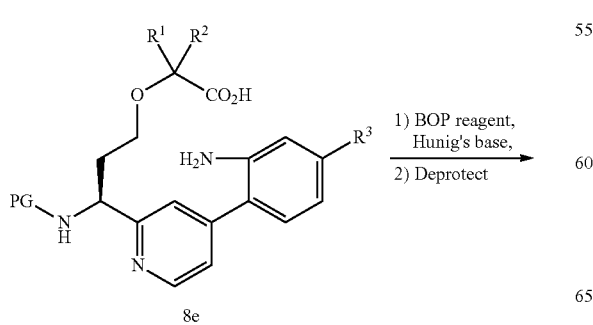

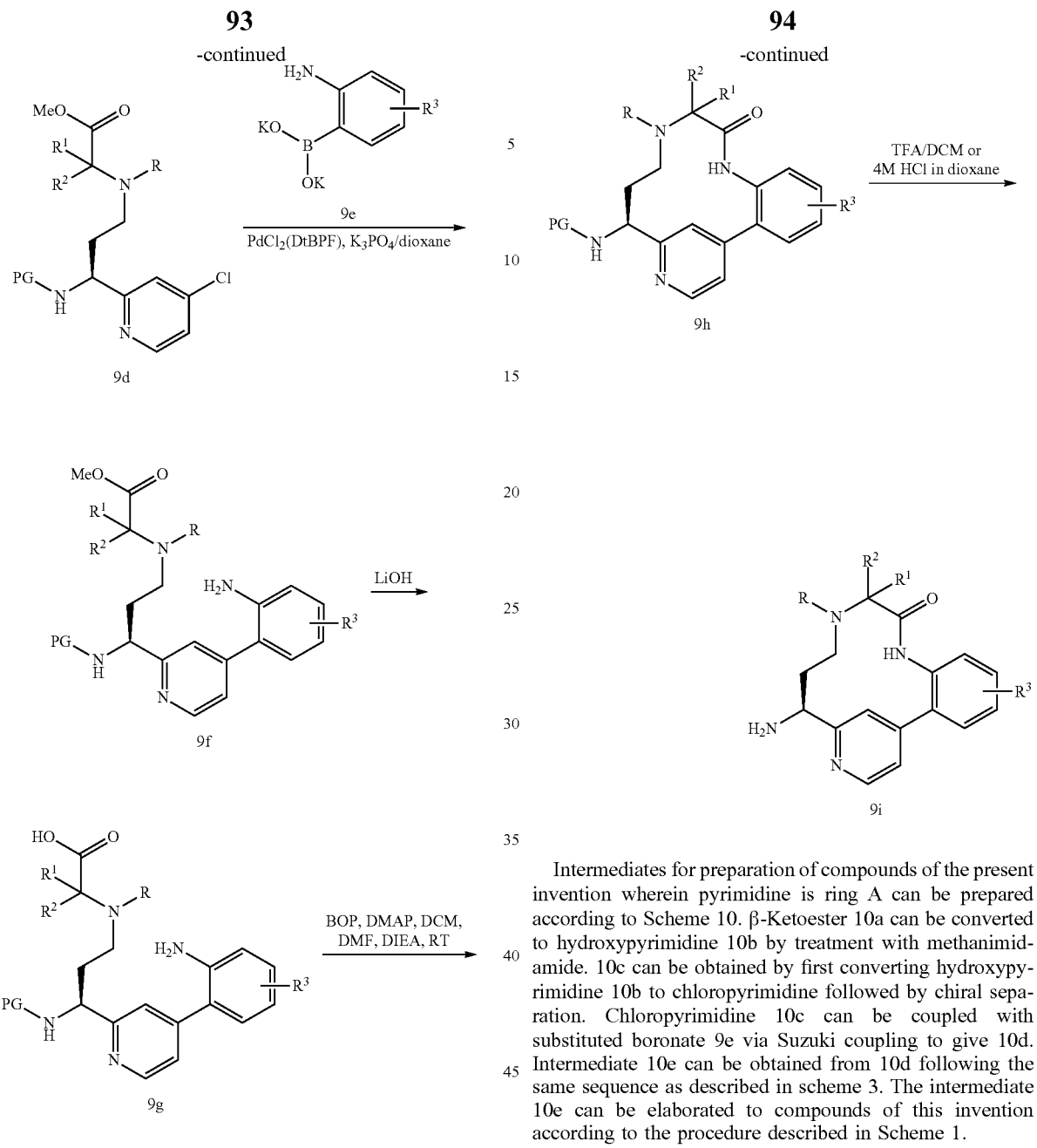

Intermediates for preparation of compounds of the present invention wherein pyrimidine is ring A can be prepared according to Scheme 10. β-Ketoester 10a can be converted to hydroxypyrimidine 10b by treatment with methanimidamide. 10c can be obtained by first converting hydroxypyrimidine 10b to chloropyrimidine followed by chiral separation. Chloropyrimidine 10c can be coupled with substituted boronate 9e via Suzuki coupling to give 10d. Intermediate 10e can be obtained from 10d following the same sequence as described in scheme 3. The intermediate 10e can be elaborated to compounds of this invention according to the procedure described in Scheme 1.

Scheme 10

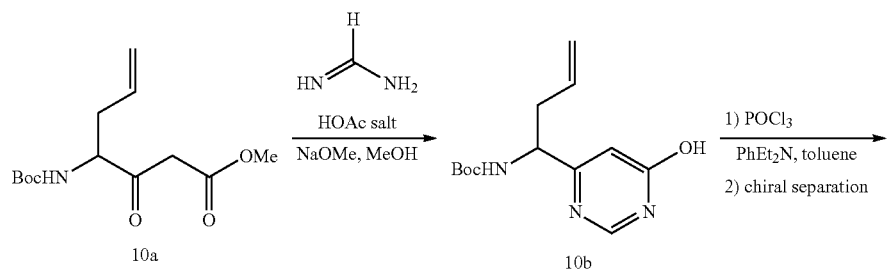

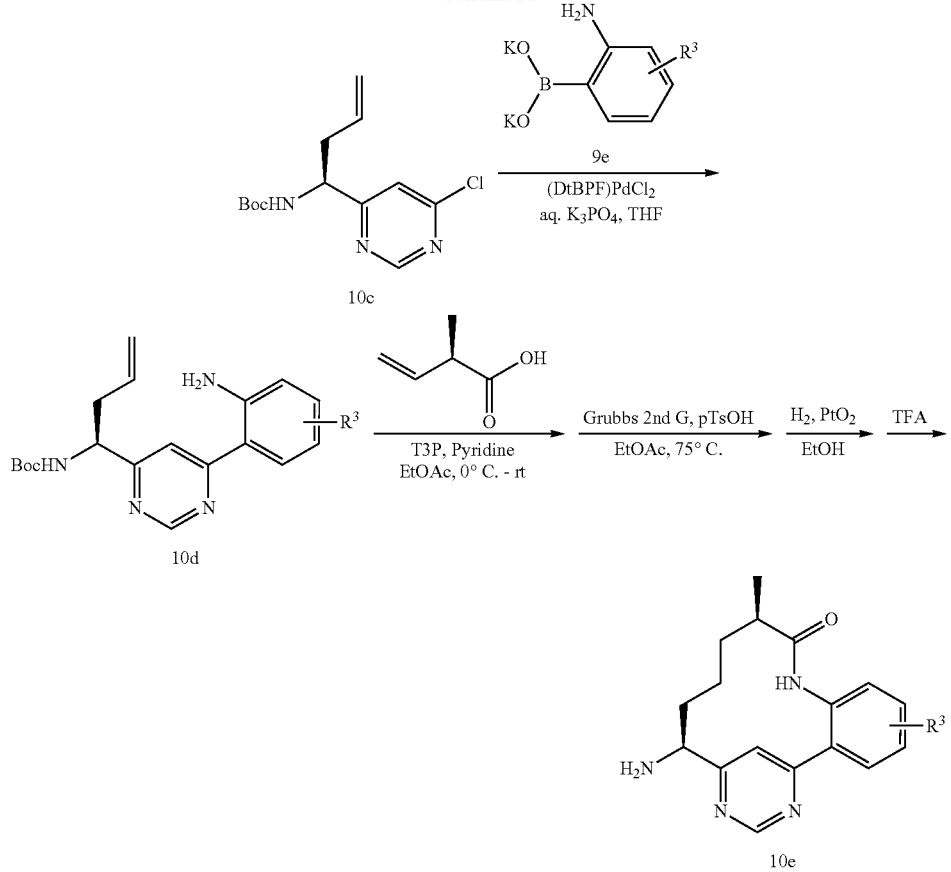

Purification of intermediates and final products was carried out via either normal or reverse phase chromatography. Normal phase chromatography was carried out using pre-packed SiO$_2$ cartridges eluting with either gradients of hexanes and EtOAc or DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm) (or) SunFire Prep C18 OBD 5 μ 30×100 mm, 25 min gradient from 0-100% B. A=H$_2$O/ACN/TFA 90:10:0.1. B=ACN/H$_2$O/TFA 90:10:0.1.

Unless otherwise stated, analysis of final products was carried out by reverse phase analytical HPLC.

Method A: Waters SunFire column (3.5 μm C18, 3.0×150 mm). Gradient elution (0.5 mL/min) from 10-100% Solvent B for 12 min and then 100% Solvent B for 3 min was used. Solvent A is (95% water, 5% acetonitrile, 0.05% TFA) and Solvent B is (5% water, 95% acetonitrile, 0.05% TFA, UV 254 nm).

Method B: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method C: Waters Acquity UPLC BEH C18, 2.1×50 mm, 1.7-μm particles; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes, then a 0.75-minute hold at 100% B; Flow: 1.11 mL/min.

Method X: ZORBAX® SB C18 column (4.6×75mm). Gradient elution (2.5 mL/min) from 0-100% Solvent B for 8 min and then 100% Solvent B for 2 min was used. Solvent A is (90% water, 10% MeOH, 0.02% H$_3$PO$_4$) and Solvent B is (10% water, 90% MeOH, 0.02% H$_3$PO$_4$, UV 220 nm).

EXAMPLE 1

Preparation of 2-(5,5-dimethyl-1,3,2-dioxaborinan-2-yl)-5-nitro-phenylamine

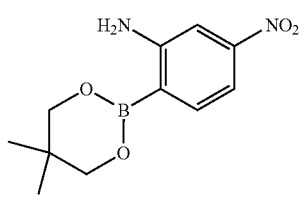 [SMILES: CC1(C)COB(c2ccc([N+](=O)[O-])cc2N)OC1]

To a flame-dried flask, equipped with a reflux condenser, containing 2-bromo-5-nitroaniline (10.0 g, 46.1 mmol), bis(neopentyl glycolato)diboron (13.01 g, 57.6 mmol), KOAc (13.57 g, 138 mmol), and PdCl₂(dppf)—CH₂Cl₂ adduct (0.941 g, 1.152 mmol) was added DMSO (132 mL). The resulting dark red-brown suspension was degassed with Ar for 30 min and then the reaction was warmed to 80° C. After 4 h, the reaction was cooled to rt. The reaction was poured slowly into vigorously stirred ice-cold water (300 mL) to give a brown suspension. After stirring for 10 min, the suspension was filtered to collect the solid. The solid was rinsed with water (3×125 mL), air-dried, and then dried under a vacuum to give a brown solid. Purification by normal phase chromatography gave 4.36 g of 2-(5,5-dimethyl-1,3,2-dioxaborinan-2-yl)-5-nitro-phenylamine as an orange solid. MS(ESI) m/z: 183.1 (M-C₅H₈+H)⁺.

EXAMPLE 2

Preparation of (R)-2-methylbut-3-enoic acid

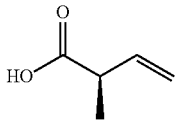

2A. Preparation of (R)-4-benzyl-3-((R)-2-methylbut-3-enoyl)oxazolidin-2-one

To the solution of 2-methylbut-3-enoic acid (5.59 g, 55.9 mmol) and NMM (6.14 mL, 55.9 mmol) in THF (62 mL) at 0° C. was added pivaloyl chloride (6.87 mL, 55.9 mmol) dropwise. The reaction mixture was cooled to −78° C., and stirred for ~2 h. In a separate flask: To the solution of (R)-4-benzyloxazolidin-2-one (8.25 g, 46.6 mmol) in THF (126 mL) at −78° C. was added 2.5 M nBuLi in hexane (20.49 mL, 51.2 mmol) dropwise. After 35 min, this reaction was transferred via cannula to the first reaction. The reaction mixture was stirred at −78° C. for 2 h, then the cold bath was removed, and the reaction was quenched with sat NH₄Cl. The reaction was diluted with water and extracted with EtOAc (3 x). The combined organic layers were washed with brine, dried over Na₂SO₄, filtered, and concentrated to give a yellow oil (15 g). Purification by silica gel chromatography afforded (R)-4-benzyl-3-((R)-2-methylbut-3-enoyl)oxazolidin-2-one (6.59 g, 55%) as a colorless oil. MS(ESI) m/z: 282.1 (M+Na)⁺. ¹H NMR (500 MHz, CDCl₃)d 7.36-7.19 (m, 5H), 6.03-5.93 (m, 1H), 5.23-5.10 (m, 2H), 4.69-4.63 (m, 1H), 4.51-4.43 (m, 1H), 4.23-4.15 (m, 2H), 3.29 (dd, J=13.5, 3.3 Hz, 1H), 2.79 (dd, J=13.5, 9.6 Hz, 1H), 1.35 (d, J=6.9 Hz, 3H) ppm. The other diastereomer (R)-4-benzyl -3-((S)-2-methylbut-3-enoyl)oxazolidin-2-one (4.6 g, 38%) also obtained as a white solid. MS(ESI) m/z: 260.1 (M+H)⁺.

2B. Preparation of (R)-2-methylbut-3-enoic acid

To a clear colorless solution of (R)-4-benzyl-3-((R)-2-methylbut-3-enoyl) oxazolidin-2-one (6.05 g, 23.33 mmol) in THF (146 mL) at 0° C. was added dropwise 30% aq H₂O₂ (9.53 mL, 93 mmol) followed by 2 N LiOH (23.33 mL, 46.7 mmol). After 30 min, the reaction was quenched with 25 mL of sat Na₂SO₃ and 25 mL of sat NaHCO₃. The reaction was then concentrated to remove the THF. The residue was diluted with water and extracted with CHCl₃ (3 x). The aqueous layer was acidified with conc. HCl to pH~3 and then it was extracted with EtOAc (3 x). The EtOAc layers were combined, washed with brine, dried over MgSO₄, filtered and concentrated to afford (R)-2-methylbut-3-enoic acid (2.15 g, 92%) as a colorless oil. ¹H NMR (500 MHz, CDCl₃)δ 10.84 (br. s., 1H), 5.94 (ddd, J=17.4, 10.1, 7.4 Hz, 1H), 5.22-5.13 (m, 2H), 3.23-3.15 (m, 1H), 1.31 (d, J=7.2 Hz, 3H) ppm.

EXAMPLE 3

Preparation of 6-(3-chloro-2-fluorophenyl)pyrimidin-4-ol

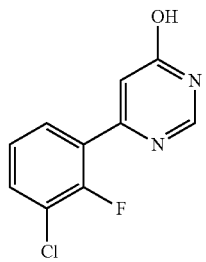 [SMILES: Oc1cc(-c2cccc(Cl)c2F)ncn1]

A microwave vial containing 6-chloropyrimidin-4-ol (0.100 g, 0.766 mmol), (3-chloro-2-fluorophenyl)boronic acid (0.534 g, 3.06 mmol), and Pd(Ph₃P)₄ (0.089 g, 0.077 mmol) was purged with Ar for several min. Then degassed toluene (1.53 mL) and EtOH (1.53 mL) were added followed by DIEA (0.54 mL, 3.06 mmol). The vial was capped and the reaction was microwaved at 120° C. for 1 h. The resulting clear, orange solution was allowed to cool to rt and a precipitate formed. The yellow solid was removed by filtration, rinsing with 1:1 toluene/EtOH. A precipitate formed in the filtrate. The solid was collected by filtration, rinsed with cold 1:1 toluene/EtOH, air-dried, and dried under vacuum to give 6-(3-chloro-2-fluorophenyl)pyrimidin-4-ol (0.0357 g, 21% yield) as a white solid. MS(ESI) m/z: 225.1 (M+H)⁺ and 227.1 (M+2+H)⁺. ¹H NMR (500 MHz, DMSO-d₆) δ 12.71 (br. s., 1H), 8.31 (d, J=1.1 Hz, 1H), 7.87 (ddd, J=8.0, 7.2, 1.7 Hz, 1H), 7.74-7.69 (m, 1H), 7.36 (td, J=8.0, 1.1 Hz, 1H), 6.72 (br. s, 1H). ¹⁹F NMR (471 MHz, DMSO-d₆) δ-117.48.

EXAMPLE 4

Preparation of 6-(3-chloro-2,6-difluorophenyl)pyrimidin-4-ol, hydrobromide

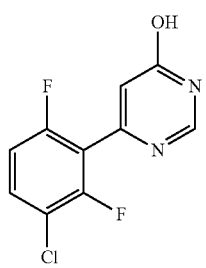 [SMILES: Oc1cc(-c2c(F)ccc(Cl)c2F)ncn1]

4A. Preparation of 4-(3-chloro-2,6-difluorophenyl)-6-methoxypyrimidine

A flask containing 4-chloro-6-methoxypyrimidine (1.0 g, 6.92 mmol), (3-chloro -2,6-difluorophenyl)boronic acid (1.996 g, 10.38 mmol), and 2nd generation XPhos precatalyst (0.272 g, 0.346 mmol) was purged with Ar for several min. Then degassed THF (13.8 mL) and degassed 0.5 M K₃PO₄ (27.7 mL, 13.84 mmol) were added. The resulting cloudy, pink reaction mixture was stirred vigorously at rt. After 2h, the reaction was diluted with water and extracted with EtOAc (2x). The organic layers were combined and washed with brine, dried over Na₂SO₄, filtered and concentrated to give an orange-brown residue weighing 1.5 g. Purification by normal phase chromatography gave 4-(3-chloro-2,6-difluorophenyl)-6-methoxypyrimidine (0.242 g, 13.6% yield) as an off-white solid. MS(ESI) m/z: 257.0 (M+H)⁺ and 259.0 (M+2+H)⁺. ¹H NMR (500 MHz, CD₃OD) δ 8.86 (d, J=1.1 Hz, 1H), 7.68-7.63 (m, 1H), 7.17 (td, J=9.0, 1.8 Hz, 1H), 7.10-7.08 (m, 1H), 4.07 (s, 3H). ¹⁹F NMR (471 MHz, CD₃OD) δ-115.84 (d, J=4.3 Hz), -116.49 (d, J=5.7 Hz).

4B. Preparation of 6-(3-chloro-2,6-difluorophenyl)pyrimidin-4-ol

A clear, yellow solution of 4-(3-chloro-2,6-difluorophenyl)-6-methoxypyrimidine (0.240 g, 0.935 mmol) in AcOH (9.35 mL) and 48% HBr in water (5.3 mL, 46.8 mmol) was warmed to 85° C. After 1 h, the reaction was cooled to rt and then concentrated under high vacuum to give a yellow solid. Et₂O (10 mL) was added to give a suspension. The solid was collected by filtration, rinsed with Et₂O, air-dried, and then dried under vacuum to give 6-(3-chloro-2,6-difluorophenyl) pyrimidin-4-ol (0.258 g, 85% yield) as an off-white solid. MS(ESI) m/z: 243.0 (M+H)⁺ and 245.0 (M+2+H)⁺. ¹H NMR (500 MHz, DMSO-d₆) δ 8.33 (d, J=1.1 Hz, 1H), 7.77 (td, J=8.7, 5.6 Hz, 1H), 7.32 (td, J=9.1, 1.7 Hz, 1H), 6.63 (d, J=0.6 Hz, 1H). ¹⁹F NMR (471 MHz, DMSO-d₆) δ-113.79 (d, J=4.3 Hz), -113.88 (d, J=5.7 Hz).

EXAMPLE 5

Preparation of 6-(5-chloro-2-fluorophenyl)pyrimidin-4-ol

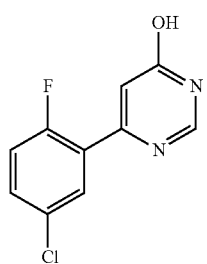

5A. Preparation of 4-(5-chloro-2-fluorophenyl)-6-methoxypyrimidine

A microwave vial containing 4-chloro-6-methoxypyrimidine (0.290 g, 2.007 mmol), (5-chloro-2-fluorophenyl)boronic acid (0.35 g, 2.007 mmol) and Na₂CO₃ (0.213 g, 2.007 mmol) in DME (10 mL), EtOH (1.25 mL) and water (1.25 mL) was purged with N₂ for several min. Then PdCl₂(dppf)—CH₂Cl₂ adduct (0.082 g, 0.100 mmol) was added and the vial was capped. The reaction was heated in a microwave at 100° C. for 1 h. The reaction mixture was then diluted with water and extracted with EtOAc. The organic layer was washed with brine and then concentrated to give an orange-brown residue. Purification by normal phase chromatography gave 4-(5-chloro-2-fluorophenyl)-6-methoxypyrimidine (400 mg, 84% yield) as white crystals. MS(ESI) m/z: 239.3 (M+H)⁺. ¹H NMR (400 MHz, CDCl₃) δ 8.86 (s, 1H), 8.16 (dd, J=6.7, 2.8 Hz, 1H), 7.39 (ddd, J=8.8, 4.2, 2.9 Hz, 1H), 7.28-7.23 (m, 1H), 7.12 (dd, J=10.8, 8.8 Hz, 1H), 4.04 (s, 3H).

5B. Preparation of 6-(5-chloro-2-fluorophenyl)pyrimidin-4-ol

A clear, yellow solution of 4-(5-chloro-2-fluorophenyl)-6-methoxypyrimidine (300 mg, 1.257 mmol) in AcOH (12.57 mL) and 48% HBr in water (7 mL, 61.9 mmol) was warmed to 85° C. After 0.5 h, the reaction was cooled to rt and concentrated under high vacuum to dryness. To the residue was added sat aq NaHCO₃ carefully to give a suspension. The solid was collected by filtration, rinsed with water, a small amount of acetone and air dried to give 6-(5-chloro-2-fluorophenyl)pyrimidin-4-ol (140 mg, 36.5% yield) as a white solid. MS(ESI) m/z: 225.2 (M+H)⁺. ¹H NMR (400 MHz, DMSO-d₆) δ 12.73 (br. s., 1H), 8.33 (d, J=0.9 Hz, 1H), 7.99 (dd, J=6.6, 2.9 Hz, 1H), 7.61 (ddd, J=6.6, 4.3, 2.1 Hz, 1H), 7.43 (dd, J=11.1, 8.9 Hz, 1H), 6.76 (s, 1H).

EXAMPLE 6

Preparation of 4-fluoro-2-(tetra-methyl-1,3,2-dioxaborolan-2-yl)aniline

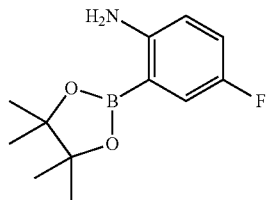 [SMILES: CC1(C)OB(c2cc(F)ccc2N)OC1(C)C]

A solution of 2-bromo-4-fluoroaniline (2.08 g, 10.95 mmol) and Et₃N (6.10 mL, 43.8 mmol) in dioxane (40 mL) was bubbled with N₂ for 5 min. Then, PdCl₂(dppf)-CH₂Cl₂ Adduct (0.447 g, 0.547 mmol) was added followed by dropwise addition of pinacolborane (4.77 mL, 32.8 mmol). The resulting purple mixture was heated at 100° C. for 15 h. The mixture was cooled to rt, quenched with sat NH₄Cl, and extracted CH₂Cl₂ (3 x). The organic layers were combined and washed with brine, dried over MgSO₄, filtered, and concentrated. Purification by normal phase chromatography gave 4-fluoro-2-(tetramethyl-1,3,2-dioxaborolan-2-yl)aniline (1.67 g, 64.3% yield) as yellow crystals. MS(ESI) m/z: 156.1 (M+H)⁺ boronic acid. ¹H NMR (400 MHz, CDCl₃) δ 7.30-7.23 (m, 1H), 6.92 (td, J=8.5, 3.2 Hz, 1H), 6.53 (dd, J=8.8, 4.4 Hz, 1H), 4.58 (br. s., 2H), 1.34 (s, 12H).

EXAMPLE 7

Preparation of 6-(3-chloro-2-fluoro-6-(1H-1,2,3-triazol-1-yl)phenyl)pyrimidin-4-ol

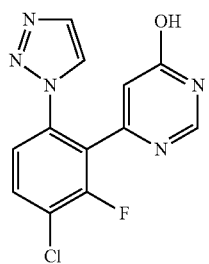 [SMILES: Oc1cc(-c2c(-n3ccnn3)ccc(Cl)c2F)ncn1]

7A. Preparation of N-(4-chloro-3-fluorophenyl)-2,2,2-trifluoroacetamide

To a cooled (−10° C.) suspension of 4-chloro-3-fluoroaniline (10.67 g, 73.3 mmol) and Na$_2$CO$_3$ (13.21 g, 125 mmol) in Et$_2$O (300 mL) was added dropwise TFAA (12.23 mL, 88 mmol). The mixture was allowed to warm to rt overnight. The mixture was diluted with hexane (300 mL) and filtered. The filtrate was washed with ice water, 10% aq NaHCO$_3$, and brine, dried over Na$_2$SO$_4$, filtered, and concentrated to give N-(4-chloro-3-fluorophenyl)-2,2,2-trifluoroacetamide (17 g, 96% yield), as a pale, yellow solid. MS(ESI) m/z: 242.1 (M+H)$^+$.

7B. Preparation of N-(4-chloro-3-fluorophenyl)-2,2,2-trifluoroacetamide hydrochloride To a cooled (−78° C.) clear, colorless solution of N-(4-chloro-3-fluorophenyl)-2,2,2-trifluoroacetamide (0.500 g, 2.070 mmol) in THF (8.28 mL) was added dropwise 2.5 M nBuLi in hexane (1.74 mL, 4.35 mmol) over 15 min keeping the internal temperature below −65° C. The resulting clear, yellow solution was stirred at −78° C. for 10 min. The reaction was allowed to warm to −50° C. over 1 h. The reaction was then cooled to −78° C. and (iPrO)$_3$B (1.05 mL, 4.55 mmol) was added dropwise. The reaction was stirred at −78° C. for 30 min. The ice bath was removed and the reaction was allowed to warm to rt and stirred at rt for 1 h. After this time, the reaction was cooled to −5° C. and then quenched with the dropwise addition of 1.0 M HCl (5 mL) followed by the addition of water (5 mL). The resulting cloudy yellow reaction mixture was stirred at rt for 45 min. The reaction was diluted with EtOAc and the layers were separated. The organic layer was washed with brine, dried over Na$_2$SO$_4$, filtered and concentrated to give a pale, orange solid. The solid was partitioned between THF (10 mL) and 0.5 M HCl (20 mL) and stirred vigorously for 4 h. The layers were then separated and the clear, colorless aqueous layer was concentrated under high vacuum to give N-(4-chloro-3-fluorophenyl)-2,2,2-trifluoroacetamide (0.1599 g, 34.2% yield) as a white solid. MS(ESI) m/z: 189.9 [M+H]$^+$.

7C. Preparation of 4-chloro-3-fluoro-2-(6-methoxypyrimidin-4-yl)aniline

4-Chloro-3-fluoro-2-(6-methoxypyrimidin-4-yl)aniline was prepared according to the procedures described in Example 3 for the synthesis of 6-(3-chloro-2-fluorophenyl)pyrimidin-4-ol by replacing (3-chloro-2-fluorophenyl)boronic acid with N-(4-chloro-3-fluorophenyl)-2,2,2-trifluoroacetamide. MS(ESI) m/z: 253.9 (M+H)$^+$. $^1$H NMR (500 MHz, CD$_3$OD) δ 8.82 (d, J=1.1 Hz, 1H), 7.18 (dd, J=8.8, 8.3 Hz, 1H), 7.01 (dd, J=3.0, 1.1 Hz, 1H), 6.61 (dd, J=8.9, 1.5 Hz, 1H), 4.04 (s, 3H). $^{19}$F NMR (471MHz, CD$_3$OD) δ-119.92 (s, 1F).

7D. Preparation of 4-(3-chloro-2-fluoro-6-(1H-1,2,3-triazol-1-yl)phenyl)-6-methoxypyrimidine trifluoroacetate In a microwave vial, 4-chloro-3-fluoro-2-(6-methoxypyrimidin-4-yl)aniline (0.045 g, 0.177 mmol) in CH$_3$CN (1.8 mL), cooled to 0° C., was added isoamyl nitrite (0.036 mL, 0.266 mmol), followed by the dropwise addition of TMSN$_3$ (0.035 mL, 0.266 mmol). Gas evolution was observed. After 5 min, the cold bath was removed, and the reaction was allowed to warm to rt. After 1 h, trimethylsilylacetylene (0.076 mL, 0.532 mmol) was added. The septum was replaced with a microwave cap and sealed. The reaction was heated in a microwave at 120° C. for a total of 4 h. The reaction was concentrated almost to dryness and then purified by reverse phase chromatography to give 4-(3-chloro-2-fluoro-6-(1H-1,2,3-triazol-1-yl)phenyl)-6-methoxypyrimidine (27 mg, 0.088 mmol) as a clear glass. MS(ESI) m/z: 306.3 (M+H)$^+$. $^1$H NMR (400 MHz, CDCl$_3$) δ 8.74 (d, J=0.4 Hz, 1H), 7.80 (d, J=0.9 Hz, 1H), 7.77-7.69 (m, 2H), 7.38 (dd, J=8.6, 1.5 Hz, 1H), 6.88 (s, 1H), 4.06 (s, 3H). $^{19}$F NMR (376MHz, CDCl$_3$) δ −76.02 (s), −112.27 (s).

7E. Preparation of 6-(3-chloro-2-fluoro-6-(1H-1,2,3-triazol-1-yl)phenyl)pyrimidin-4-ol 6-(3-Chloro-2-fluoro-6-(1H-1,2,3-triazol-1-yl)phenyl)pyrimidin-4-ol was prepared according to the procedures in described in Example 5 for the synthesis of 6-(5-chloro-2-fluorophenyl)pyrimidin-4-ol, by replacing 4-(5-chloro-2-fluorophenyl)-6-methoxypyrimidine with 4-(3-chloro-2-fluoro-6-(1H-1,2,3-triazol-1-yl)phenyl)-6-methoxypyrimidine, monotrifluoroacetate. MS(ESI) m/z: 292.3 (M+H)$^+$. $^1$H NMR (400 MHz, CD$_3$OD) δ 8.20 (d, J=1.1 Hz, 1H), 8.06 (d, J=0.7 Hz, 1H), 7.89-7.81 (m, 1H), 7.80 (d, J=0.9 Hz, 1H), 7.54 (dd, J=8.6, 1.5 Hz, 1H), 6.52 (s, 1H).

EXAMPLE 8

Preparation of 6-(5-chloro-2-(1H-1,2,3-triazol-1-yl)phenyl)pyrimidin-4-ol

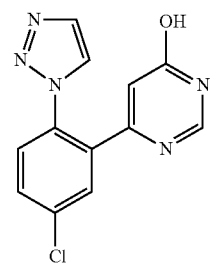 [SMILES: Oc1cc(-c2cc(Cl)ccc2-n2ccnn2)ncn1]

8A. Preparation of 4-chloro-2-(6-methoxypyrimidin-4-yl)aniline

4-Chloro-2-(6-methoxypyrimidin-4-yl)aniline was synthesized according to the procedure described in Example 5 for the synthesis of 4-(5-chloro-2-fluorophenyl)-6-methoxypyrimidine, by replacing (5-chloro-2-fluorophenyl)boronic acid with 4-chloro-2-(4,4,5,5-tetramethyl-1,3,2-dioxaborolan-2-yl)aniline. MS(ESI) m/z: 236.3 (M+H)$^+$. $^1$H NMR (400 MHz, CDCl$_3$) δ 8.78 (s, 1H), 7.49 (d, J=2.4 Hz, 1H), 7.15 (dd, J=8.6, 2.4 Hz, 1H), 6.99 (d, J=0.9 Hz, 1H), 6.66 (d, J=8.6 Hz, 1H), 4.02 (s, 3H).

8B. Preparation of 6-(5-chloro-2-(1H-1,2,3-triazol-1-yl)phenyl)pyrimidin-4-ol 6-(5-Chloro-2-(1H-1,2,3-triazol-1-yl)phenyl)pyrimidin-4-ol was synthesized according to the procedures described for the synthesis of 6-(3-chloro-2-fluoro-6-(1H-1,2,3-triazol-1-yl)phenyl)pyrimidin-4-ol, by replacing 4-chloro-3-fluoro-2-(6-methoxypyrimidin-4-yl)aniline with 4-chloro-2-(6-methoxypyrimidin-4-yl)aniline. MS(ESI) m/z: 274.3 (M+H)$^+$. $^1$H NMR (400 MHz, CD$_3$OD) δ 8.51 (d, J=0.9 Hz, 1H), 8.35 (d, J=1.1 Hz, 1H), 7.92 (d, J=1.1 Hz, 1H), 7.88 (d, J=2.4 Hz, 1H), 7.83-7.78 (m, 1H), 7.74-7.69 (m, 1H), 6.39 (d, J=0.9 Hz, 1H).

EXAMPLE 9

Preparation of 6-[5-chloro-2-(4-chloro-1H-1,2,3-triazol-1-yl)phenyl]pyrimidin-4-ol

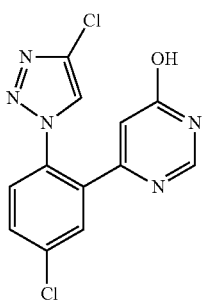 [SMILES: Oc1cc(-c2cc(Cl)ccc2-n2cc(Cl)nn2)ncn1]

9A. Preparation of 4-chloro-2-(tetramethyl-1,3,2-dioxaborolan-2-yl)aniline

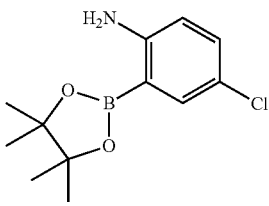 [SMILES: CC1(C)OB(c2cc(Cl)ccc2N)OC1(C)C]

In a 20 mL microwave vial was added 2-bromo-4-chloroaniline (3 g, 14.53 mmol), 4,4,5,5-tetramethyl-2-(tetramethyl-1,3,2-dioxaborolan-2-yl)-1,3,2-dioxaborolane (5.53 g, 21.80 mmol), KOAc (3.66 g, 37.3 mmol), Pd(dppf)Cl$_2$-CH$_2$Cl$_2$ adduct (0.32 g, 0.44 mmol) and DMSO (9 mL). The resulting suspension was purged with N$_2$, capped and heated at 80° C. for 22 h. The reaction was cooled to rt. Water was added to dissolve the salts, then the reaction was filtered. The remaining solid was suspended in DCM and the insoluble solid was filtered. The filtrate was concentrated and then purified by normal phase chromatography to give 4-chloro-2-(tetramethyl-1,3,2-dioxaborolan-2-yl)aniline (3.15 g, 86% yield) as a white solid. MS(ESI) m/z:172.3 (M-C$_6$H$_{10}$+H)$^+$. $^1$H NMR (400 MHz, CDCl$_3$) δ 7.54 (d, J=2.6 Hz, 1H), 7.13 (dd, J=8.8, 2.6 Hz, 1H), 6.52 (d, J=8.6 Hz, 1H), 4.72 (br. s., 2H), 1.34 (s, 12H).

9B. Preparation of 4-chloro-2-(6-methoxypyrimidin-4-yl)aniline

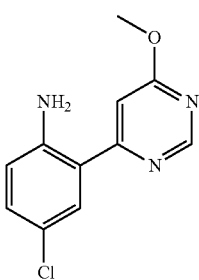 [SMILES: COc1cc(-c2cc(Cl)ccc2N)ncn1]

A RBF containing 4-chloro-6-methoxypyrimidine (3.13 g, 21.62 mmol), 4-chloro-2-(tetramethyl-1,3,2-dioxaborolan-2-yl)aniline (7.31 g, 21.62 mmol), Na$_2$CO$_3$ (2.29 g, 21.62 mmol), DME (86 ml), EtOH (10.8 ml) and water (10.8 ml) was equipped with a condenser. The mixture was purged with Ar for several min then Pd(dppf)Cl$_2$—CH$_2$Cl$_2$ adduct (1.77 g, 2.16 mmol) was added. The reaction was heated at 90° C. for 5 h. The reaction was cooled to rt, diluted with water and extracted with EtOAc. The organic layer was washed with brine, concentrated and purified by normal phase chromatography to give 4-chloro-2-(6-methoxypyrimidin-4-yl)aniline (2.86 g, 56.1% yield) as yellow solid. MS(ESI) m/z: 236.0 (M+H)$^+$. $^1$H NMR (500 MHz, CDCl$_3$) δ 8.78 (d, J=1.1 Hz, 1H), 7.49 (d, J=2.5 Hz, 1H), 7.15 (dd, J=8.8, 2.5 Hz, 1H), 6.99 (d, J=1.1 Hz, 1H), 6.67 (d, J=8.8 Hz, 1H), 5.89 (br. s., 2H), 4.03 (s, 3H).

9C. Preparation of 4-{5-chloro-2-[4-(trimethylsilyl)-1H-1,2,3-triazol-1-yl]phenyl}-6-methoxypyrimidine

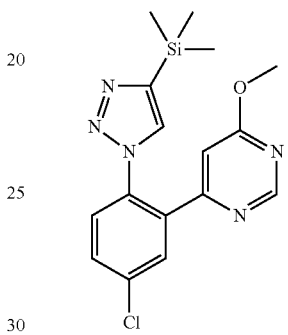

To a solution of 4-chloro-2-(6-methoxypyrimidin-4-yl)aniline (1.5 g, 6.36 mmol) in ACN (90 ml) at 0° C. was added 3-methylbutyl nitrite (1.28 ml, 9.55 mmol), followed by the dropwise addition of TMSN$_3$ (1.26 ml, 9.55 mmol). Gas evolution was observed. After 10 min, the ice bath was removed, and the reaction was allowed to warm to rt. After 1 h, ethynyltrimethylsilane (2.72 ml, 19.09 mmol) and Cu$_2$O (0.09 g, 0.64 mmol) were added and the reaction was stirred for an additional 1 h. The reaction was partitioned in EtOAc and sat NH$_4$Cl, and the layers were separated. The organic layer was washed with brine, dried over MgSO$_4$, filtered and concentrated. Purification by normal phase chromatography gave 4-{5-chloro-2-[4-(trimethylsilyl)-1H-1,2,3-triazol-1-yl]phenyl}-6-methoxypyrimidine (2.13 g, 5.92 mmol, 93% yield) as a yellow solid. MS(ESI) m/z: 360.3 (M+H)$^+$. $^1$H NMR (400 MHz, CDCl$_3$) δ 8.71 (d, J=1.1 Hz, 1H), 7.82 (d, J=2.2 Hz, 1H), 7.61-7.56 (m, 1H), 7.54-7.48 (m, 2H), 6.20 (d, J=1.1 Hz, 1H), 3.92 (s, 3H), 0.32-0.28 (m, 9H).

9D. Preparation of 4-[5-chloro-2-(4-chloro-1H-1,2,3-triazol-1-yl)phenyl]-6-methoxypyrimidine

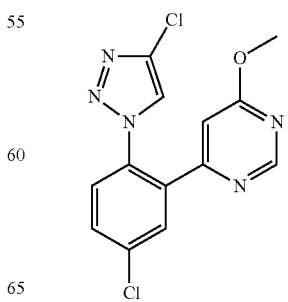

To a solution of 4-{5-chloro-2-[4-(trimethylsilyl)-1H-1,2,3-triazol-1-yl]phenyl}-6-methoxypyrimidine (1.56 g, 4.33 mmol) in ACN (28.9 ml) was added NCS (2.03 g, 15.17 mmol) and silica gel (6.51 g, 108 mmol). The reaction was stirred at 80° C. for 1 h. Then, the reaction was filtered to remove the silica gel and the collected silica gel was washed with EtOAc. The filtrate was washed with water (2x), brine and concentrated. Purification by normal phase chromatography gave 4-[5-chloro-2-(4-chloro-1H-1,2,3-triazol-1-yl)phenyl]-6-methoxypyrimidine (0.90 g, 64.5% yield) as a yellow foam. MS(ESI) m/z: 322.3 (M+H)+. 1H NMR (400 MHz, CDCl3) δ 8.70 (d, J=1.1 Hz, 1H), 7.75 (d, J=2.4 Hz, 1H), 7.66-7.55 (m, 2H), 7.50 (d, J=8.6 Hz, 1H), 6.52 (d, J=0.9 Hz, 1H), 3.98 (s, 3H).

9E. Preparation of 6-[5-chloro-2-(4-chloro-1H-1,2,3-triazol-1-yl)phenyl]pyrimidin-4-ol

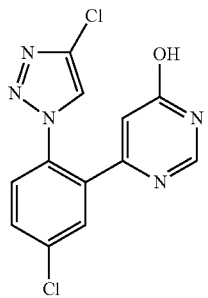 [SMILES: Oc1cc(-c2cc(Cl)ccc2-n2cc(Cl)nn2)ncn1]

To a solution of 4-[5-chloro-2-(4-chloro-1H-1,2,3-triazol-1-yl)phenyl]-6-methoxypyrimidine (900 mg, 2.79 mmol) in AcOH (6 ml) was added 48% HBr in water (3 ml, 26.5 mmol). The mixture was stirred at 85° C. for 1 h. The reaction was concentrated to dryness and then partitioned between EtOAc and sat NaHCO3 solution. The mixture was separated and the aqueous layer was extracted with EtOAc (2x). The organic layers were combined, concentrated, and then the residue was purified by normal phase chromatography to give a white solid. The solid was suspended in Et2O, filtered and washed with Et2O to give 6-[5-chloro-2-(4-chloro-1H-1,2,3-triazol-1-yl)phenyl]pyrimidin-4-ol (610 mg, 70.9% yield) as a white solid. MS(ESI) m/z: 308.3 (M+H)+. 1H NMR (400 MHz, CDCl3) δ 7.96 (s, 1H), 7.74-7.67 (m, 2H), 7.62 (dd, J=8.5, 2.3 Hz, 1H), 7.47 (d, J=8.4 Hz, 1H), 6.44 (d, J=0.9 Hz, 1H).

EXAMPLE 10

Preparation of 6-(3-chloro-6-(4-chloro-1H-1,2,3-triazol-1-yl)-2-fluorophenyl) pyrimidin-4-ol

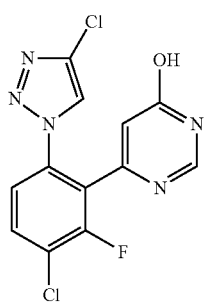

10A. Preparation of N-(4-chloro-3-fluorophenyl)-2,2,2-trifluoroacetamide

To a suspension of 4-chloro-3-fluoroaniline (10.67 g, 73.3 mmol) and Na2CO3 (24.5 g, 125 mmol) in Et2O (300 mL) at -10° C. under N2 was added TFAA (12.23 mL, 88 mmol) dropwise. The mixture was allowed to warm to rt for 18 h. The reaction mixture was diluted with hexane (300 mL), and filtered. The filtrate was washed with ice water, 10% aq NaHCO3, and brine, dried over Na2SO4, and concentrated. A pale yellow solid obtained as N-(4-chloro-3-fluorophenyl)-2,2,2-trifluoroacetamide (17 g, 96% yield). MS(ESI) m/z: 242.1 (M+H)+.

10B. Preparation of (6-amino-3-chloro-2-fluorophenyl)boronic acid

To a cooled (-78° C.) clear, colorless solution of N-(4-chloro-3-fluorophenyl)-2,2,2-trifluoroacetamide (5 g, 20.70 mmol) in THF (69.0 ml) was added dropwise 2.5 M nBuLi in hexane (16.56 ml, 41.4 mmol) over 15 min, keeping the internal temperature below -60° C. The resulting clear, yellow solution was stirred at -78° C. for 10 min, then most of the dry ice chunks were removed. The reaction was allowed to warm to -50° C. over 1 h. The resulting clear brown solution was cooled to -78° C. and then triisopropyl borate (10.51 ml, 45.5 mmol) was added dropwise. The reaction was stirred at -78° C. for 10 min, and then the ice bath was removed and the reaction was allowed to warm to rt. The resulting orange suspension was stirred at rt for 2 h, then cooled in ice bath and quenched with 1N HCl (40 ml). The reaction mixture was warmed to 40° C. for 1 h and then cooled to rt. The reaction was diluted with EtOAc and the layers were separated. The organic layer was washed with brine and concentrated. Purification by normal phase chromatography afforded (6-amino-3-chloro-2-fluorophenyl)boronic acid (3 g, 76.6% yield). MS(ESI) m/z: 190.1 (M+H)+.

10C. Preparation of 4-chloro-3-fluoro-2-(6-methoxypyrimidin-4-yl)aniline

Reaction was done in a 350 ml pressure bottle. A solution of 4-chloro-6-methoxypyrimidine (1.784 g, 12.34 mmol), (6-amino-3-chloro-2-fluorophenyl)boronic acid (3.3 g, 12.34 mmol)) in toluene (24.68 ml) and EtOH (24.68 ml)) was purged with N2 for several min. DIEA (4.31 ml, 24.68 mmol) followed by Pd(Ph3P)4 (1.426 g, 1.234 mmol) were added. The flask was capped and the reaction was heated (oil bath) at 120° C. for 2 h, then cooled to rt, and concentrated. Purification by normal phase chromatography afforded 4-chloro-3-fluoro-2-(6-methoxypyrimidin-4-yl)aniline (2 g, 45.2% yield) as a yellow solid. MS(ESI) m/z: 254.0 (M+H)+.

10D. Preparation of 4-(3-chloro-2-fluoro-6-(4-(trimethylsilyl)-1H-1,2,3-triazol-1-yl)phenyl)-6-methoxypyrimidine

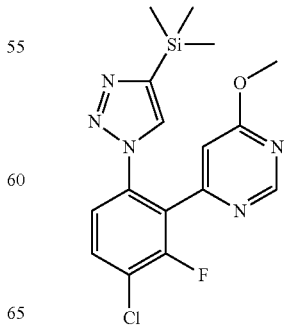

To a cooled (0° C.), clear, yellow solution of 4-chloro-3-fluoro-2-(6-methoxypyrimidin-4-yl)aniline (2.1 g, 8.28 mmol) in ACN (118 ml) was added isoamyl nitrite (1.67 ml, 12.42 mmol), followed by the dropwise addition of TMSN$_3$ (1.63 ml, 12.42 mmol). After 10 min, the cold bath was removed, and the reaction was allowed to warm to rt. After 2 h, ethynyltrimethylsilane (3.54 ml, 24.84 mmol) and Cu$_2$O (0.118 g, 0.83 mmol) were added, and the reaction was stirred at rt for 1.5 h. The reaction was then diluted with EtOAc and washed with sat NH$_4$Cl, brine, dried over MgSO$_4$, filtered and concentrated to give a brown oil. Purification by normal phase chromatography afforded 4-(3-chloro-2-fluoro-6-(4-(trimethylsilyl)-1H-1,2,3-triazol-1-yl)phenyl)-6-methoxypyrimidine (2.71 g, 87% yield) as a brown solid. MS(ESI) m/z: 378.1 (M+H)$^+$.

10E. Preparation of 4-(3-chloro-6-(4-chloro-1H-1,2,3-triazol-1-yl)-2-fluorophenyl)-6-methoxypyrimidine

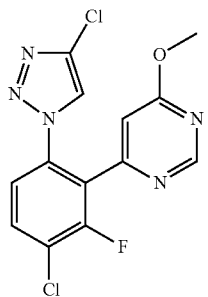 [SMILES: COc1cc(-c2c(-n3cc(Cl)nn3)ccc(Cl)c2F)ncn1]

In a RBF equipped with stirring bar and condenser was added 4-(3-chloro-2-fluoro-6-(4-(trimethylsilyl)-1H-1,2,3-triazol-1-yl)phenyl)-6-methoxypyrimidine (2.71 g, 7.17 mmol), NCS (3.35 g, 25.1 mmol), and silica gel (10.77 g, 179 mmol), followed by ACN (47.8 ml). The reaction was heated at 80° C. for 1 h, and then cooled to rt. The reaction was filtered, and the filtrate was concentrated. The residue was redissolved in EtOAc and washed with sat NaHCO$_3$, water, brine, and concentrated. Purification by normal phase chromatography afforded 4-(3-chloro-6-(4-chloro-1H-1,2,3-triazol-1-yl)-2-fluorophenyl)-6-methoxypyrimidine (1.05 g, 43.0% yield) as a yellow solid. MS(ESI) m/z: 340.0 (M+H)$^+$. $^1$H NMR (400 MHz, CDCl$_3$) δ 8.68 (d, J=0.7 Hz, 1H), 7.71-7.62 (m, 2H), 7.37 (dd, J=8.6, 1.8 Hz, 1H), 6.84 (s, 1H), 4.02 (s, 3H).

10F. Preparation of 6-(3-chloro-6-(4-chloro-1H-1,2,3-triazol-1-yl)-2-fluorophenyl) pyrimidin-4-ol

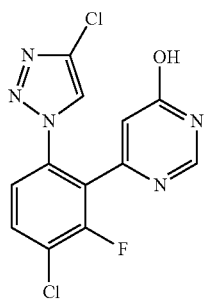 [SMILES: Oc1cc(-c2c(-n3cc(Cl)nn3)ccc(Cl)c2F)ncn1]

A clear, yellow solution of 4-(3-chloro-6-(4-chloro-1H-1,2,3-triazol-1-yl)-2-fluorophenyl)-6-methoxypyrimidine (1.05 g, 3.09 mmol) in HOAc (15.43 ml) and 48% HBr in water (17.46 ml, 154 mmol) was warmed to 65° C. for 3 h, and then cooled to rt and concentrated. The yellow gum was suspended in EtOAc and washed with sat NaHCO$_3$ (2x), brine, dried over Na$_2$SO$_4$, filtered, and concentrated. To the residue was added Et$_2$O (10 ml), sonicated, and filtered. The solid was rinsed with Et$_2$O (2 ml), air-dried with suction to afford 6-(3-chloro-6-(4-chloro-1H-1,2,3-triazol-1-yl)-2-fluorophenyl)pyrimidin-4-ol (0.79 g, 78% yield) as a white solid. MS(ESI) m/z: 326.3 (M+H)$^+$. $^1$H NMR (400 MHz, CD$_3$OD) δ 8.35 (s, 1H), 8.08 (d, J=0.7 Hz, 1H), 7.85 (dd, J=8.7, 7.6 Hz, 1H), 7.54 (dd, J=8.6, 1.5 Hz, 1H), 6.57 (s, 1H).

EXAMPLE 11

Preparation of 6-(3-chloro-2-fluoro-6-(4-(trifluoromethyl)-1H-1,2,3-triazol-1-yl)phenyl)pyrimidin-4-ol

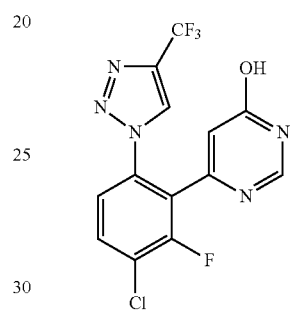

11A. Preparation of 4-(3-chloro-2-fluoro-6-(4-(trifluoromethyl)-1H-1,2,3-triazol-1-yl)phenyl)-6-methoxypyrimidine To a cooled (0° C.), clear, yellow solution of 4-chloro-3-fluoro-2-(6-methoxypyrimidin-4-yl)aniline (0.2 g, 0.79 mmol) in ACN (11.26 ml) was added isoamyl nitrite (0.16 mL, 1.18 mmol), followed by the dropwise addition of TMSN$_3$ (0.16 mL, 1.18 mmol). After 10 min, the cold bath was removed, and the reaction was allowed to warm to rt. After 2 h, Cu$_2$O (0.011 g, 0.079 mmol) was added, then 3,3,3-trifluoroprop-1-yne (0.5 mL, 0.79 mmol) gas was bubbled in through the reaction for 5 min, then the reaction was capped and stirred at rt. After 1 h, the reaction was diluted with EtOAc and washed with sat NH$_4$Cl, brine, dried over MgSO$_4$, filtered and concentrated to give a brown oil. Purification by normal phase chromatography afforded 4-(3-chloro-2-fluoro-6-(4-(trifluoromethyl)-1H-1,2,3-triazol-1-yl)phenyl)-6-methoxypyrimidine (0.24 g, 81% yield) as a yellow solid. MS(ESI) m/z: 374.3 (M+H)$^+$.

11B. Preparation of 6-(3-chloro-2-fluoro-6-(4-(trifluoromethyl)-1H-1,2,3-triazol-1-yl)phenyl)pyrimidin-4-ol A clear, yellow solution of 4-(3-chloro-2-fluoro-6-(4-(trifluoromethyl)-1H-1,2,3-triazol-1-yl)phenyl)-6-methoxypyrimidine (0.1 g, 0.268 mmol) in HOAc (1.34 ml) and 48% HBr in water (1.51 ml, 13.38 mmol) was warmed to 65° C. for 3 h, and then cooled to rt and concentrated. The yellow gum was suspended with EtOAc, washed with sat NaHCO$_3$ (2x), brine, dried over Na$_2$SO$_4$, filtered, and concentrated. To the residue was added Et$_2$O (3 ml), sonicated, and filtered. The solid was rinsed with Et$_2$O (2 ml), air-dried with suction to afford 6-(3-chloro-2-fluoro-6-(4-(trifluoromethyl)-1H-1,2,3-triazol-1-yl)phenyl)pyrimidin-4-ol (0.07 g, 72.7% yield) as a white solid. MS(ESI) m/z: 360.0 (M+H)$^+$. $^1$H NMR (400 MHz, CD$_3$OD) δ 8.84 (s, 1H), 8.03 (br. s., 1H), 7.91-7.84 (m, 1H), 7.58 (dd, J=8.8, 1.5 Hz, 1H), 6.61 (br. s., 1H).

EXAMPLE 12

Preparation of 1-(4-chloro-3-fluoro-2-(6-hydroxypyrimidin-4-yl)phenyl)-1H-1,2,3-triazole-4-carbonitrile

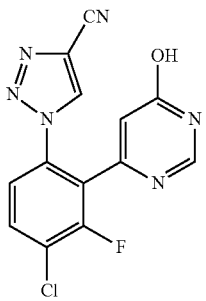 [SMILES: N#Cc1cn(-c2ccc(Cl)c(F)c2-c2cc(O)ncn2)nn1]

12A. Preparation of 1-(4-chloro-3-fluoro-2-(6-methoxypyrimidin-4-yl)phenyl)-1H-1,2,3-triazole-4-carboxamide To a cooled (0° C.), clear, yellow solution of 4-chloro-3-fluoro-2-(6-methoxypyrimidin-4-yl)aniline (1 g, 3.94 mmol) in ACN (56.3 ml) was added isoamyl nitrite (0.79 ml, 5.91 mmol), followed by the dropwise addition of TMSN$_3$ (0.79 ml, 5.91 mmol). After 10 min, the cold bath was removed, and the reaction was allowed to warm to rt and stirred at rt for 1 h. Next, propiolamide (0.817 g, 11.83 mmol) and Cu$_2$O (0.056 g, 0.394 mmol) were added. After 1 h, the yellow cloudy reaction was diluted with EtOAc, and washed with sat NH$_4$Cl, brine, dried over MgSO$_4$, filtered and concentrated to give a yellow solid. DCM (10 ml) was added and the resulting mixture was sonicated. The suspension was filtered and the solid was air-dried to give 1-(4-chloro-3-fluoro-2-(6-methoxypyrimidin-4-yl)phenyl)-1H-1,2,3-triazole-4-carboxamide (1.003 g, 73.0% yield) as a yellow solid. MS(ESI) m/z: 349.0 (M+H)$^+$.

12B. Preparation of 1-(4-chloro-3-fluoro-2-(6-methoxypyrimidin-4-yl)phenyl)-1H-1,2,3-triazole-4-carbonitrile To a suspension of 1-(4-chloro-3-fluoro-2-(6-methoxypyrimidin-4-yl)phenyl)-1H -1,2,3-triazole-4-carboxamide (1.003 g, 2.88 mmol) in EtOAc (13 ml) was added TEA (1.20 ml, 8.63 mmol), followed by the dropwise addition of T3P® (50% in EtOAc) (5.14 ml, 8.63 mmol). The reaction was microwaved at 120° C. for 30 min and then it was cooled to rt. The reaction was diluted with EtOAc, washed with sat NaHCO$_3$, brine, dried over Na$_2$SO$_4$, filtered, and concentrated to afford a brown solid. Purification by normal phase chromatography afforded 1-(4-chloro-3-fluoro-2-(6-methoxypyrimidin-4-yl) phenyl)-1H-1,2,3-triazole-4-carbonitrile (0.815 g, 86% yield) as a yellow solid. MS(ESI) m/z: 331.1 (M+H)$^+$. $^1$H NMR (400 MHz, CDCl$_3$) δ 8.62 (d, J=1.1 Hz, 1H), 8.21 (s, 1H), 7.72 (dd, J=8.6, 7.5 Hz, 1H), 7.39 (dd, J=8.6, 1.8 Hz, 1H), 6.89 (dd, J=1.9, 1.2 Hz, 1H), 4.03 (s, 3H).

12C. Preparation of 1-(4-chloro-3-fluoro-2-(6-hydroxypyrimidin-4-yl)phenyl)-1H-1,2,3-triazole-4-carbonitrile To a suspension of 1-(4-chloro-3-fluoro-2-(6-methoxypyrimidin-4-yl)phenyl)-1H -1,2,3-triazole-4-carbonitrile (0.81 g, 2.449 mmol) in ACN (16.33 ml) was added TMS-I (2.00 ml, 14.70 mmol) at rt then the clear solution was heated to 50° C. After 18 h, the reaction was cooled to rt. The reaction was poured into a 10% Na$_2$S$_2$O$_3$ solution and extracted with EtOAc (3x). The combined organic layers were washed with sat NaHCO$_3$, brine, dried over Na$_2$SO$_4$, filtered, and concentrated to give a residue. The residue was suspended in DCM (20 ml), filtered, and the solid was rinsed with DCM, and air-dried to afford 1-(4-chloro-3-fluoro-2-(6-hydroxypyrimidin-4-yl)phenyl)-1H-1,2,3-triazole-4-carbonitrile (0.73 g, 94% yield) as a white solid. MS(ESI) m/z: 317.1 (M+H)$^+$. $^1$H NMR (400MHz, CD$_3$OD) δ 8.97 (s, 1H), 8.04 (s, 1H), 7.91-7.85 (m, 1H), 7.58 (dd, J=8.8, 1.5 Hz, 1H), 6.62 (s, 1H). $^{19}$F NMR (376 MHz, CD$_3$OD) δ −114.93 (s, 1F).

EXAMPLE 13

Preparation of 6-(5-chloro-2-(4-cyclopropyl-1H-1,2,3-triazol-1-yl)phenyl)pyrimidin-4-ol, hydrobromide

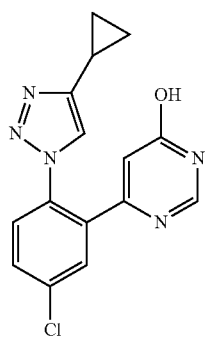 [SMILES: Oc1cc(-c2cc(Cl)ccc2-n2cc(C3CC3)nn2)ncn1]

13A. Preparation of 4-(5-chloro-2-(4-cyclopropyl-1H-1,2,3-triazol-1-yl)phenyl)-6-methoxypyrimidine To a cooled (0° C.), clear, yellow solution of 4-chloro-2-(6-methoxypyrimidin-4-yl)aniline (0.100 g, 0.42 mmol) in ACN (6.06 ml) was added isoamyl nitrite (0.086 ml, 0.64 mmol), followed by the dropwise addition of TMSN$_3$ (0.084 ml, 0.64 mmol). After 10 min, the cold bath was removed, and the reaction was allowed to warm to rt and the reaction was stirred at rt for 1 h. Next, ethynylcyclopropane (0.120 g, 1.27 mmol) and Cu$_2$O (6.07 mg, 0.042 mmol) were added. The flask was equipped with a reflux condenser and the reaction was heated to 50° C. for 1 h, then the reaction was cooled to rt. The reaction was diluted with DCM and washed with sat NH$_4$Cl, brine, dried over MgSO$_4$, filtered and concentrated to give a brown oil. Purification by normal phase chromatography then reverse phase chromatography afforded 4-(5-chloro-2-(4-cyclopropyl-1H-1,2,3-triazol-1-yl)phenyl)-6-methoxypyrimidine (0.024 g, 17.3% yield) as a yellow oil. MS(ESI) m/z: 328.1 (M+H)$^+$. $^1$H NMR (400 MHz, CDCl$_3$) δ 8.75 (d, J=0.9 Hz, 1H), 7.79 (d, J=2.2 Hz, 1H), 7.61-7.56 (m, 1H), 7.51-7.47 (m, 1H), 7.29 (s, 1H), 6.35 (d, J=0.9 Hz, 1H), 3.96 (s, 3H), 1.96 (tt, J=8.4, 5.0 Hz, 1H), 1.02-0.95 (m, 2H), 0.88-0.81 (m, 2H).

13B. Preparation of 6-(5-chloro-2-(4-cyclopropyl-1H-1,2,3-triazol-1-yl)phenyl) pyrimidin-4-ol hydrobromide A clear, yellow solution of 4-(5-chloro-2-(4-cyclopropyl-1H-1,2,3-triazol-1-yl)phenyl)-6-methoxypyrimidine (0.024 g, 0.073 mmol) in HOAc (0.73 ml) and 48% HBr in water (0.41 ml, 3.66 mmol) was warmed to 65° C. for 3 h, and then cooled to rt and concentrated. The yellow gum was suspended in EtOAc and washed with brine, dried over Na$_2$SO$_4$, filtered, and concentrated. To the residue was added Et$_2$O (3 ml), sonicated, and filtered. The solid was rinsed with Et$_2$O (2 ml), air-dried with suction to afford 6-(5-chloro-2-(4-cyclopropyl-1H-1,2,3-triazol-1-yl)phenyl) pyrimidin-4-ol hydrobromide (0.03 g, 100% yield) as a yellow solid. MS(ESI) m/z: 314.0 (M+H)$^+$. $^1$H NMR (400 MHz, CD$_3$OD) δ 8.67 (d, J=0.7 Hz, 1H), 8.22 (s, 1H), 7.89

(d, J=2.4 Hz, 1H), 7.82 (dd, J=8.6, 2.2 Hz, 1H), 7.74 (d, J=8.6 Hz, 1H), 6.48 (d, J=0.9 Hz, 1H), 2.11-2.01 (m, 1H), 1.11-1.04 (m, 2H), 0.91-0.84 (m, 2H).

EXAMPLE 14

Preparation of 6-(3-chloro-6-(4-cyclopropyl-1H-1,2,3-triazol-1-yl)-2-fluorophenyl)pyrimidin-4-ol

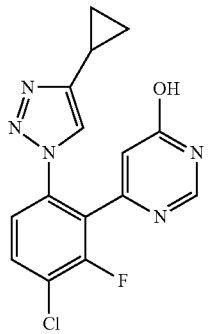 [SMILES: Oc1cc(-c2c(-n3cc(C4CC4)nn3)ccc(Cl)c2F)ncn1]

14A. Preparation of 4-(3-chloro-6-(4-cyclopropyl-1H-1,2,3-triazol-1-yl)-2-fluorophenyl)-6-methoxypyrimidine To a cooled (0° C.), clear, yellow solution of 4-chloro-3-fluoro-2-(6-methoxypyrimidin-4-yl)aniline (0.100 g, 0.39 mmol) in ACN (5.63 ml) was added isoamyl nitrite (0.079 ml, 0.59 mmol), followed by the dropwise addition of TMSN$_3$ (0.078 ml, 0.59 mmol). After 10 min, the cold bath was removed, and the reaction was allowed to warm to rt. After 1 h, ethynylcyclopropane (0.112 g, 1.18 mmol) and Cu$_2$O (5.64 mg, 0.039 mmol) were added. The flask was equipped with a reflux condenser and the reaction was heated to 50° C. for 1 h, then the reaction was cooled to rt. The reaction was diluted with DCM and washed with sat NH$_4$Cl, brine, dried over MgSO$_4$, filtered and concentrated to give a brown oil. Purification by normal phase chromatography afforded 4-(3-chloro-6-(4-cyclopropyl-1H-1,2,3-triazol-1-yl)-2-fluorophenyl)-6-methoxypyrimidine (0.05 g, 36.7% yield) as a yellow oil. MS(ESI) m/z: 346.0 (M+H)$^+$. $^1$H NMR (400 MHz, CDCl$_3$) δ 8.69 (d, J=0.9 Hz, 1H), 7.63 (dd, J=8.6, 7.5 Hz, 1H), 7.35 (dd, J=8.6, 1.5 Hz, 1H), 7.30 (s, 1H), 6.76 (t, J=1.2 Hz, 1H), 4.00 (s, 3H), 1.90 (tt, J=8.4, 5.0 Hz, 1H), 0.98-0.91 (m, 2H), 0.82-0.76 (m, 2H).

14B. Preparation of 6-(3-chloro-6-(4-cyclopropyl-1H-1,2,3-triazol-1-yl)-2-fluorophenyl) pyrimidin-4-ol A clear, yellow solution of 4-(3-chloro-6-(4-cyclopropyl-1H-1,2,3-triazol-1-yl)-2-fluorophenyl)-6-methoxypyrimidine (0.05 g, 0.145 mmol) in HOAc (1.45 ml) and 48% HBr in water (0.82 ml, 7.23 mmol) was warmed to 65° C. for 3 h, and then the reaction was cooled to rt and concentrated. Purification by reverse phase chromatography afforded 6-(3-chloro-6-(4-cyclopropyl-1H-1,2,3-triazol-1-yl)-2-fluorophenyl)pyrimidin-4-ol (0.04 g, 83% yield) as a yellow solid. MS(ESI) m/z: 332.0 (M+H)$^+$. $^1$H NMR (400 MHz, CD$_3$OD) δ 8.09 (d, J=0.9 Hz, 1H), 7.91 (s, 1H), 7.82 (dd, J=8.6, 7.7 Hz, 1H), 7.49 (dd, J=8.8, 1.5 Hz, 1H), 6.50-6.47 (m, 1H), 1.97 (tt, J=8.5, 5.1 Hz, 1H), 1.01-0.95 (m, 2H), 0.81-0.75 (m, 2H). $^{19}$F NMR (376 MHz, CD$_3$OD) δ -115.39 (s).

EXAMPLE 15

Preparation of 6-{5-chloro-2-[4-(trifluoromethyl)-1H-1,2,3-triazol-1-yl]phenyl}pyrimidin-4-ol

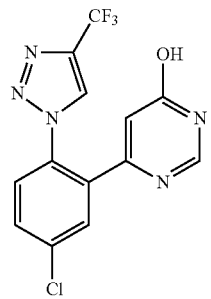

15A. Preparation of 4-{5-chloro-2[4-(trifluoromethyl)-1H-1,2,3-triazol-1-yl]phenyl} -6-methoxypyrimidine

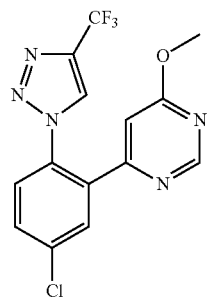

To a solution of 4-chloro-2-(6-methoxypyrimidin-4-yl) aniline (1.0 g, 4.24 mmol), prepared as described in Example 9B, in ACN (60.6 ml) at 0° C. was added 3-methylbutyl nitrite (0.86 ml, 6.36 mmol) followed by the dropwise addition of TMSN$_3$ (0.84 ml, 6.36 mmol). Gas evolution was observed. After 10 min, the ice bath was removed, and the reaction was allowed to warm to rt. After 2 h, Cu$_2$O (61 mg, 0.42 mmol) was added followed by a slow bubbling of 3,3,3-trifluoroprop-1-yne gas over a period of 5 min. After an additional 10 min, the reaction was partitioned between DCM and sat NH$_4$Cl and then the layers were separated. The organic layer was washed with brine, dried over MgSO$_4$, filtered and concentrated. Purification by normal phase chromatography gave 4-{5-chloro-2-[4-(trifluoromethyl)-1H-1,2,3-triazol-1-yl]phenyl}-6-methoxypyrimidine (1.46 g, 97% yield) as a yellow solid. MS(ESI) m/z: 356.1 (M+H)$^+$. $^1$H NMR (400 MHz, CDCl$_3$) δ 8.62 (d, J=1.1 Hz, 1H), 8.00 (d, J=0.7 Hz, 1H), 7.75 (d, J=2.4 Hz, 1H), 7.66-7.60 (m, 1H), 7.52 (d, J=8.6 Hz, 1H), 6.60 (d, J=1.1 Hz, 1H), 3.98 (s, 3H). $^{19}$F NMR (376 MHz, CDCl$_3$) δ -61.10 (s).

15B. Preparation of 6-{5-chloro-2-[4-(trifluoromethyl)-1H-1,2,3-triazol-1-yl]phenyl}pyrimidin-4-ol

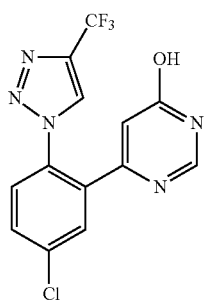

To a solution of 4-{5-chloro-2-[4-(trifluoromethyl)-1H-1,2,3-triazol-1-yl]phenyl}-6-methoxypyrimidine (1.46 g, 4.10 mmol) in AcOH (10 ml) was added 48% HBr in water (5 ml, 44.2 mmol). The mixture was stirred at 85° C. for 1 h. The reaction was concentrated to dryness and then partitioned between EtOAc and sat aq NaHCO₃. The layers were separated and the aqueous layer was extracted with EtOAc (2x). The organic layers were combined and washed with sat NaHCO₃, brine, dried over MgSO₄, filtered and the solvent was reduced under vacuum until some solid started to form. The resulting suspension was triturated with Et₂O. The solid was filtered and washed with Et₂O to give 6-{5-chloro-2-[4-(trifluoromethyl)-1H-1,2,3-triazol-1-yl]phenyl}pyrimidin-4-ol (1 g, 71.3% yield) as a pale yellow solid. MS(ESI) m/z: 342.0 (M+H)⁺. ¹H NMR (400 MHz, CD₃OD) δ 8.83 (d, J=0.7 Hz, 1H), 7.99 (d, J=0.9 Hz, 1H), 7.87 (d, J=2.2 Hz, 1H), 7.79-7.72 (m, 1H), 7.70-7.62 (m, 1H), 6.45 (d, J=0.9 Hz, 1H). ¹⁹F NMR (376 MHz, CD₃OD) δ −62.61 (s).

EXAMPLE 16

Preparation of 6-{5-chloro-2-[4-(difluoromethyl)-1H-1,2,3-triazol-1-yl]phenyl}pyrimidin-4-ol

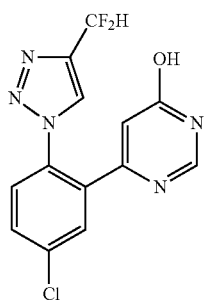 [SMILES: Oc1cc(-c2cc(Cl)ccc2-n2cc(C(F)F)nn2)ncn1]

16A. Preparation of {1-[4-chloro-2-(6-methoxypyrimidin-4-yl)phenyl]-1H-1,2,3-triazol-4-yl}methanol

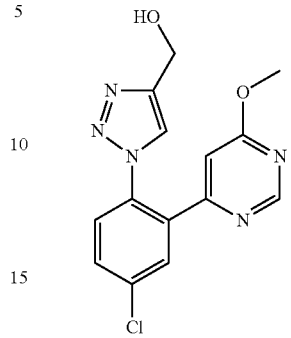

{1-[4-Chloro-2-(6-methoxypyrimidin-4-yl)phenyl]-1H-1,2,3-triazol-4-yl}methanol (0.44 g, 52.5% yield) was prepared in a similar manner as the procedure described for the preparation of 4-{5-chloro-2-[4-(trimethylsilyl)-1H-1,2,3-triazol-1-yl]phenyl}-6-methoxypyrimidine, as described in Example 9C, by replacing ethynyltrimethylsilane with propargyl alcohol (0.38 ml, 6.36 mmol). MS(ESI) m/z: 318.3 (M+H)⁺. ¹H NMR (400 MHz, CDCl₃) δ 8.66 (d, J=1.1 Hz, 1H), 7.77 (d, J=2.2 Hz, 1H), 7.63 (s, 1H), 7.61-7.55 (m, 1H), 7.51-7.46 (m, 1H), 6.42 (d, J=1.1 Hz, 1H), 4.77 (d, J=5.9 Hz, 2H), 3.93 (s, 3H).

16B. Preparation of 1-[4-chloro-2-(6-methoxypyrimidin-4-yl)phenyl]-1H-1,2,3-triazole-4-carbaldehyde

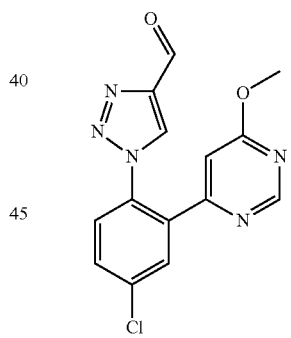

To a solution of {1-[4-chloro-2-(6-methoxypyrimidin-4-yl)phenyl]-1H-1,2,3-triazol-4-yl}methanol (95 mg, 0.3 mmol) in DMSO (1 mL) was added IBX (92 mg, 0.33 mmol) and the reaction was stirred at rt for 14 h. Water and sat NaHCO₃ were added and the mixture was extracted with EtOAc (2x). The organic layers were combined, concentrated and purified by normal phase chromatography to give 1-[4-chloro-2-(6-methoxy pyrimidin-4-yl)phenyl]-1H-1,2,3-triazole-4-carbaldehyde (82 mg, 87% yield) as a white solid. MS(ESI) m/z: 316.3 (M+H)⁺. ¹H NMR (400 MHz, CDCl₃) δ 10.16 (s, 1H), 8.62 (d, J=1.1 Hz, 1H), 8.21 (s, 1H), 7.76 (d, J=2.2 Hz, 1H), 7.64 (dd, J=8.5, 2.3 Hz, 1H), 7.53 (d, J=8.4 Hz, 1H), 6.59 (d, J=1.1 Hz, 1H), 3.97 (s, 3H).

16C. Preparation of 4-{5-chloro-2-[4-(difluoromethyl)-1H-1,2,3-triazol-1-yl]phenyl}-6-methoxypyrimidine

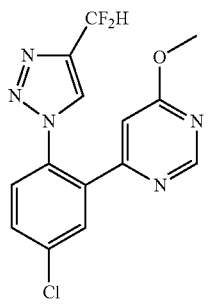 [SMILES: COc1cc(-c2cc(Cl)ccc2-n2cc(C(F)F)nn2)ncn1]

To a solution of 1-[4-chloro-2-(6-methoxypyrimidin-4-yl)phenyl]-1H-1,2,3-triazole-4-carbaldehyde (427 mg, 1.35 mmol) in DCM (30 ml) was added DAST (0.54 ml, 4.1 mmol) and the reaction was stirred overnight at rt. The reaction was quenched with water and extracted with DCM. The organic layer was concentrated and purified by normal phase chromatography to give 4-{5-chloro-2-[4-(difluoromethyl)-1H-1,2,3-triazol-1-yl]phenyl}-6-methoxypyrimidine (441 mg, 97% yield) as a yellow solid. MS(ESI) m/z: 338.3 (M+H)$^+$. $^1$H NMR (400 MHz, CDCl$_3$) δ 8.65 (d, J=0.9 Hz, 1H), 7.89 (s, 1H), 7.76 (d, J=2.4 Hz, 1H), 7.62 (dd, J=8.5, 2.3 Hz, 1H), 7.55-7.47 (m, 1H), 6.89 (t, J=54.6 Hz, 1H), 6.52 (d, J=1.1 Hz, 1H), 4.03-3.87 (m, 3H). $^{19}$F NMR (376 MHz, CDCl$_3$) δ -112.40 (s).

16D. Preparation of 6-{5-chloro-2-[4-(difluoromethyl)-1H-1,2,3-triazol-1-yl]phenyl}pyrimidin-4-ol

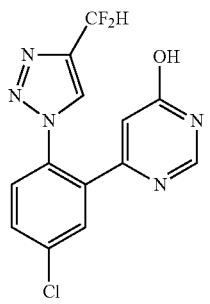 [SMILES: Oc1cc(-c2cc(Cl)ccc2-n2cc(C(F)F)nn2)ncn1]

6-{5-Chloro-2-[4-(difluoromethyl)-1H-1,2,3-triazol-1-yl]phenyl}pyrimidin-4-ol (370 mg, 88% yield) was prepared in a similar manner as the procedure described in Example 9E, by replacing 4-[5-chloro-2-(4-chloro-1H-1,2,3-triazol-1-yl)phenyl]-6-methoxypyrimidine with 4-{5-chloro-2-[4-(difluoromethyl)-1H-1,2,3-triazol-1yl]phenyl}-6-methoxypyrimidine (441 mg, 1.31 mmol). MS(ESI) m/z: 324.3 (M+H)$^+$. $^1$H NMR (400 MHz, CDCl$_3$) δ 8.04 (s, 1H), 7.86 (s, 1H), 7.71 (d, J=2.2 Hz, 1H), 7.67-7.61 (m, 1H), 7.51 (d, J=8.6 Hz, 1H), 6.92 (t, J=54.6 Hz, 1H), 6.43 (d, J=0.7 Hz, 1H). $^{19}$F NMR (376 MHz, CDCl$_3$) δ -112.69 (s).

EXAMPLE 17

Preparation of 6-[3-chloro-2-fluoro-6-(1H-1,2,3,4-tetrazol-1-yl)phenyl]pyrimidin-4-ol 17A. Preparation of 4-[3-chloro-2-fluoro-6-(1H-1,2,3,4-tetrazol-1-yl)phenyl]-6-methoxypyrimidine 4-Chloro-3-fluoro-2-(6-methoxypyrimidin-4-yl)aniline (300 mg, 1.183 mmol) dissolved in AcOH (3 mL) was added trimethoxymethane (377 mg, 3.55 mmol) and the solution was stirred at rt for 30 min. NaN$_3$ (231 mg, 3.55 mmol) was added and the solution stirred at rt for 16 h. To the reaction mixture was added water and a precipitate formed. The mixture was filtered to collect the solid residue, and filtrate was extracted with EtOAc, and the organic later was then washed with brine, dried over MgSO$_4$, filtered and concentrated to give a crude solid, which was then combined with original solid residue collected. The crude material was purified by normal phase chromatography to afford 4-(3-chloro-2-fluoro-6-(1H-tetrazol-1-yl)phenyl)-6-methoxypyrimidine (367 mg, 100% yield). MS(ESI) m/z: 307.08 (M+H)$^+$. $^1$H NMR (400 MHz, CDCl$_3$) δ 8.78 (s, 1H), 8.59 (d, J=1.1 Hz, 1H), 7.71 (dd, J=8.7, 7.4 Hz, 1H), 7.38 (dd, J=8.6, 1.8 Hz, 1H), 6.86 (dd, J=1.9, 1.2 Hz, 1H), 3.98 (s, 3H).

17B. Preparation of 6-[3-chloro-2-fluoro-6-(1H-1,2,3,4-tetrazol-1-yl)phenyl]pyrimidin- 4-ol To a solution of 4-(3-chloro-2-fluoro-6-(1H-tetrazol-1-yl)phenyl)-6-methoxypyrimidine (50 mg, 0.163 mmol), NaI (244 mg, 1.630 mmol) dissolved in ACN (1.6 ml) was added TMSCl (0.2 ml, 1.630 mmol). The resulting reaction mixture was stirred at rt for 23 h. To the reaction mixture was added CELITE®, the slurry was filtered and the collected organics were concentrated to yield a crude solid. Purification by normal phase chromatography, followed by trituration with Et$_2$O, afforded 6-[3-chloro-2-fluoro-6-(1H-1,2,3,4-tetrazol-1-yl)phenyl]pyrimidin-4-ol (46 mg, 96% yield) as a white solid. MS(ESI) m/z: 293.08 (M+H)$^+$. $^1$H NMR (400 MHz, CD$_3$OD) δ 9.75 (s, 1H), 8.40 (s, 1H), 8.28 (dd, J=8.7, 7.6 Hz, 1H), 7.97 (dd, J=8.7, 1.7 Hz, 1H), 7.02 (s, 1H).

EXAMPLE 18

Preparation of 1-[4-chloro-2-(6-hydroxypyrimidin-4-yl)phenyl]-1H-1,2,3-triazole-4-carbonitrile

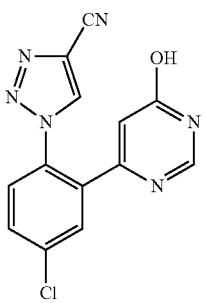 [SMILES: N#Cc1cn(-c2ccc(Cl)cc2-c2cc(O)ncn2)nn1]

18A. Preparation of 1-[4-chloro-2-(6-methoxypyrimidin-4-yl)phenyl]-1H-1,2,3-triazole -4-carboxamide

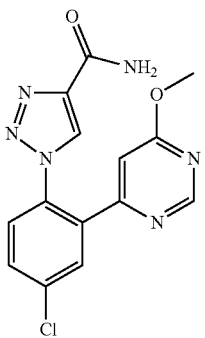 [SMILES: COc1cc(-c2cc(Cl)ccc2-n2cc(C(N)=O)nn2)ncn1]

1-[4-Chloro-2-(6-methoxypyrimidin-4-yl)phenyl]-1H-1,2,3-triazole-4-carboxamide (300 mg, 80% yield) was prepared in a similar manner as the procedure described in Example 9C, by replacing ethynyltrimethylsilane with prop-2-ynamide (176 mg, 2.55 mmol). MS(ESI) m/z: 331.4 (M+H)$^+$. $^1$H NMR (400 MHz, CDCl$_3$) δ 8.66 (d, J=0.7 Hz, 1H), 8.16 (s, 1H), 7.76 (d, J=2.4 Hz, 1H), 7.62 (dd, J=8.5, 2.3 Hz, 1H), 7.51 (d, J=8.6 Hz, 1H), 7.05 (br. s., 1H), 6.53 (d, J=0.9 Hz, 1H), 5.66 (br. s., 1H), 3.97 (s, 3H).

18B. Preparation of 1-[4-chloro-2-(6-methoxypyrimidin-4-yl)phenyl]-1H-1,2,3-triazole -4-carbonitrile

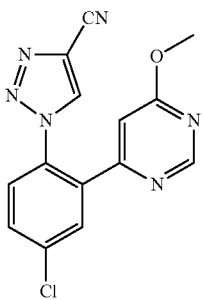

To a suspension of 1[4-chloro-2-(6-methoxypyrimidin-4-yl)phenyl]-1H-1,2,3-triazole-4-carboxamide (91 mg, 0.28 mmol) and TEA (115 µl, 0.83 mmol) in EtOAc (6.88 ml) was added T3P® (50% in EtOAc) (0.49 ml, 0.83 mmol) dropwise. The reaction was microwaved at 120° C. for 1 h. Additional TEA (115 µl, 0.83 mmol) and T3P® (50% in EtOAc) (0.49 ml, 0.83 mmol) were added and the reaction was microwaved at 120° C. for an additional 30 min. The reaction was diluted with EtOAc and washed with water, sat NaHCO$_3$, brine, dried over MgSO$_4$, filtered, and concentrated. Purification by normal phase chromatography gave 1[4-chloro-2-(6-methoxypyrimidin -4-yl)phenyl]-1H-1,2,3-triazole-4-carbonitrile (91 mg, 100% yield) as a white solid. MS(ESI) m/z: 313.3 (M+H)$^+$. $^1$H NMR (400 MHz, CDCl$_3$) δ 8.62 (d, J=0.9 Hz, 1H), 8.17 (s, 1H), 7.73 (d, J=2.4 Hz, 1H), 7.65 (dd, J=8.5, 2.3 Hz, 1H), 7.51 (d, J=8.6 Hz, 1H), 6.65 (d, J=1.1 Hz, 1H), 4.00 (s, 3H).

18C. Preparation of 1-[4-chloro-2-(6-hydroxypyrimidin-4-yl)phenyl]-1H-1,2,3-triazole -4-carbonitrile

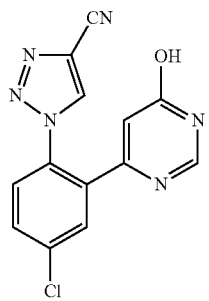 [SMILES: N#Cc1cn(-c2ccc(Cl)cc2-c2cc(O)ncn2)nn1]

To a suspension of 1[4-chloro-2-(6-methoxypyrimidin-4-yl)phenyl]-1H-1,2,3-triazole-4-carbonitrile (91 mg, 0.29 mmol) in ACN (3 mL) was added TMSI (0.2 mL, 1.47 mmol) at rt and the solution was heated at 50° C. for 15 h. The reaction was poured into 10% Na$_2$S$_2$O$_3$ and sat NaHCO$_3$ then extracted with EtOAc (3x). The combined organic layers were washed with brine. On standing, a solid precipitated out from the organic layer. The solid was filtered and rinsed with EtOAc and air-dried to give 1[4-chloro-2-(6-hydroxypyrimidin-4-yl)phenyl]-1H-1,2,3-triazole-4-carbonitrile (60 mg, 69.0% yield) as a white solid. MS(ESI) m/z: 299.3 (M+H)$^+$. $^1$H NMR (400 MHz, CDCl$_3$) δ 8.22 (s, 1H), 7.91 (s, 1H), 7.72 (d, J=2.2 Hz, 1H), 7.66 (dd, J=8.5, 2.3 Hz, 1H), 7.49 (d, J=8.4 Hz, 1H), 6.55 (s, 1H).

EXAMPLE 19

Preparation of 4-chloro-2-[(E)-2-[(S)-2-methylpropane-2-sulfinyl]ethenyl]pyridine

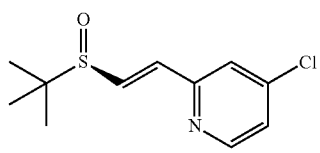

To a solution of S-(−)-t-butyl-sulfinamide (0.856 g, 7.06 mmol) in DCM (14.13 mL) was added sequentially CuSO$_4$ (2.481 g, 15.54 mmol) and 4-chloropicolinaldehyde (1.0 g, 7.06 mmol). The resulting white suspension was stirred at rt. After 3 h, the brown suspension was filtered through CELITE®, eluting with DCM, to give a clear brown filtrate. Concentration of the filtrate gave a brown oil weighing 1.85 g. Purification by normal phase chromatography gave 1.31 g of 4-chloro-2-[(E)-2-[(S)-2-methylpropane-2-sulfinyl] ethenyl]pyridine as a clear, yellow oil. MS(ESI) m/z: 245.0 (M+H)+.

EXAMPLE 20

Preparation of 6-[5-chloro-2-(1H-1,2,3,4-tetrazol-1-yl)phenyl]pyrimidin-4-ol

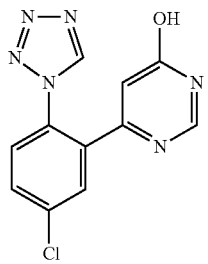 [SMILES: Oc1cc(-c2cc(Cl)ccc2-n2cnnn2)ncn1]

20A. Preparation of 4-[5-chloro-2-(1H-1,2,3,4-tetrazol-1-yl)phenyl]-6-methoxypyrimidine To a solution of 4-chloro-2-(6-methoxypyrimidin-4-yl) aniline (0.507 g, 2.151 mmol) dissolved in AcOH (5.4 ml) was added trimethoxymethane (0.685 g, 6.45 mmol) and the resulting solution was stirred at rt for 30 min. NaN$_3$ (0.420 g, 6.45 mmol) was then added and the reaction mixture was stirred at rt for 16 h. Water was added to form a precipitate. The precipitate was collected by filtration, and filtrate was extracted with EtOAc, which was then washed with brine, dried over MgSO$_4$, filtered and concentrated to give a crude solid, that was then combined with solid residue collected before. Purification by normal phase chromatography afforded 4-(5-chloro-2-(1H-tetrazol-1-yl)phenyl)-6-methoxypyrimidine (0.59 g, 95% yield) as an off-white solid. MS(ESI) m/z: 289.08 (M+H)+. $^1$H NMR (400 MHz, CDCl$_3$) δ 8.76 (s, 1H), 8.62 (d, J=0.9 Hz, 1H), 7.74 (d, J=2.2 Hz, 1H), 7.66 (dd, J=8.5, 2.3 Hz, 1H), 7.52 (d, J=8.4 Hz, 1H), 6.65 (d, J=1.1 Hz, 1H), 3.99 (s, 3H).

20B. Preparation of 6-[5-chloro-2-(1H-1,2,3,4-tetrazol-1-yl) phenyl]pyrimidin-4-ol To a solution of 4-(5-chloro-2-(1H-tetrazol-1-yl)phenyl)-6-methoxypyrimidine (0.59 g, 2.044 mmol), NaI (3.06 g, 20.44 mmol) in ACN (20.44 ml) was added TMSCl (2.6 ml, 20.44 mmol), and the reaction was stirred at rt for 16 h. CELITE® was added to the reaction mixture, the slurry was filtered, and concentrated to give a crude solid mixture. The solid was purified by normal phase chromatography, then recrystallized from EtOAc to give 6-[5-chloro-2-(1H-1,2,3,4-tetrazol-1-yl)phenyl]pyrimidin-4-ol (370 mg, 66% yield) as a white solid. MS(ESI) m/z: 275.08 (M+H)+. $^1$H NMR (400 MHz, DMSO-d$_6$) δ 12.62 (br. s., 1H), 9.72 (s, 1H), 7.97 (d, J=0.7 Hz, 1H), 7.92 (d, J=2.2 Hz, 1H), 7.87-7.83 (m, 1H), 7.82-7.78 (m, 1H), 6.48 (d, J=0.7 Hz, 1H).

EXAMPLE 21

Preparation of 6-(3-chloro-6-(4-(difluoromethyl)-1H-1,2,3-triazol-1-yl)-2-fluorophenyl)pyrimidin-4-ol

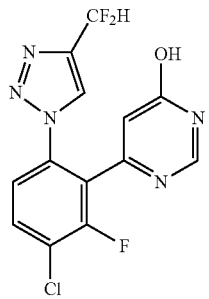 [SMILES: Oc1cc(-c2c(-n3cc(C(F)F)nn3)ccc(Cl)c2F)ncn1]

21A. Preparation of (1-(4-chloro-3-fluoro-2-(6-methoxypyrimidin-4-yl)phenyl)-1H-1,2,3-triazol-4-yl)methanol To a cooled (0° C.), clear, yellow solution of 4-chloro-3-fluoro-2-(6-methoxypyrimidin-4-yl)aniline (1.058 g, 4.17 mmol) in ACN (59.6 ml) was added isoamyl nitrite (0.84 ml, 6.26 mmol), followed by the dropwise addition of TMSN$_3$ (0.82 ml, 6.26 mmol). After 10 min, the cold bath was removed, and the reaction was allowed to warm to rt. After 1 h, propargyl alcohol (0.75 ml, 12.51 mmol) and Cu$_2$O (0.060 g, 0.42 mmol) were added. After 1 h, the reaction was diluted with EtOAc and washed with sat NH$_4$Cl, brine, dried over MgSO$_4$, filtered and concentrated to give a brown oil. The crude product was purified by normal phase chromatography to give (1-(4-chloro-3-fluoro-2-(6-methoxypyrimidin-4-yl)phenyl)-1H-1,2,3-triazol-4-yl)methanol (0.8 g, 57.1% yield) as a yellow foam. MS(ESI) m/z: 336.1 (M+H)+. $^1$H NMR (400MHz, CDCl$_3$) δ 8.65 (d, J=1.1 Hz, 1H), 7.69-7.62 (m, 2H), 7.37 (dd, J=8.6, 1.5 Hz, 1H), 6.81 (t, J=1.2 Hz, 1H), 4.76 (d, J=5.9 Hz, 2H), 4.00 (s, 3H), 2.18 (t, J=6.1 Hz, 1H).

21B. Preparation of 1-(4-chloro-3-fluoro-2-(6-methoxypyrimidin-4-yl)phenyl)-1H-1,2,3-triazole-4-carbaldehyde To the solution of (1-(4-chloro-3-fluoro-2-(6-methoxypyrimidin-4-yl)phenyl)-1H-1,2,3-triazol-4-yl)methanol (0.8 g, 2.38 mmol) in DMSO (9.53 ml) was added IBX (0.734 g, 2.62 mmol), and the reaction was stirred at rt. After 18 h, water and sat NaHCO$_3$ were added and the reaction mixture was extracted with EtOAc (2×). The organic layers were combined and dried over Na$_2$SO$_4$, filtered, and concentrated. Purification by normal phase chromatography afforded 1-(4-chloro-3-fluoro-2-(6-methoxypyrimidin-4-yl)phenyl)-1H-1,2,3-triazole-4-carbaldehyde (0.64 g, 80% yield) as a white solid. MS(ESI) m/z: 334.4 (M+H)+. $^1$H NMR (400 MHz, CDCl$_3$) δ 10.12 (s, 1H), 8.60 (d, J=1.1 Hz, 1H), 8.25 (s, 1H), 7.71 (dd, J=8.6, 7.5 Hz, 1H), 7.39 (dd, J=8.6, 1.8 Hz, 1H), 6.88 (dd, J=1.8, 1.1 Hz, 1H), 4.01 (s, 3H).

21C. Preparation of 4-(3-chloro-6-(4-(difluoromethyl)-1H-1,2,3-triazol-1-yl)-2-fluorophenyl)-6-methoxypyrimidine To the solution of 1-(4-chloro-3-fluoro-2-(6-methoxypyrimidin-4-yl)phenyl)-1H-1,2,3-triazole-4-carbaldehyde (0.3 g, 0.9 mmol) in DCM (24 ml) was added DAST (0.54 ml, 4.09 mmol). The reaction was stirred at rt for 22 h. To the reaction was added water and the resulting mixture was extracted with DCM. The organic layer was washed with brine, dried over Na$_2$SO$_4$, filtered, and concentrated. Purification by normal phase chromatography afforded 4-(3-chloro-6-(4-(difluoromethyl)-1H-1,2,3-triazol-1-yl)-2-fluorophenyl)-6-methoxypyrimidine (0.256 g, 80% yield) as a white solid. MS(ESI) m/z: 356.1 (M+H)+. $^1$H NMR (400 MHz, CDCl$_3$) δ 8.62 (d, J=0.9 Hz, 1H), 7.94 (t, J=1.3 Hz, 1H), 7.69 (dd, J=8.6, 7.5 Hz, 1H), 7.39 (dd, J=8.6, 1.8 Hz, 1H), 7.00-6.69 (m, 2H), 4.00 (s, 3H).

21D. Preparation of 6-(3-chloro-6-(4-(difluoromethyl)-1H-1,2,3-triazol-1-yl)-2-fluorophenyl)pyrimidin-4-ol A clear, yellow solution of 4-(3-chloro-6-(4-(difluoromethyl)-1H-1,2,3-triazol-1-yl)-2-fluorophenyl)-6-methoxypyrimidine (0.256 g, 0.72 mmol) in HOAc (3.6 ml) and 48% HBr in water (4.07 ml, 36.0 mmol) was warmed to 65° C. for 3 h, and then the reaction was cooled to rt and concentrated. The yellow gum was suspended in EtOAc and washed with sat NaHCO$_3$ (2×), brine, dried over Na$_2$SO$_4$, filtered, and concentrated. The residue was suspended in Et$_2$O (3 ml), sonicated, and filtered. The solid was rinsed with Et$_2$O (2 ml), air-dried with suction to afford 6-(3-chloro-6-(4-(difluoromethyl)-1H-1,2,3-triazol-1-yl)-2-fluorophenyl)pyrimidin-4-ol (0.23 g, 94% yield) as a yellow solid.

MS(ESI) m/z: 342.0 (M+H)+. $^1$H NMR (400 MHz, CD$_3$OD) δ 8.56 (t, J=1.4 Hz, 1H), 8.05 (d, J=0.9 Hz, 1H), 7.86 (dd, J=8.6, 7.7 Hz, 1H), 7.57 (dd, J=8.7, 1.7 Hz, 1H), 6.98 (t, J=54.0 Hz, 1H), 6.58 (t, J=1.2 Hz, 1H). $^{19}$F NMR (376 MHz, CD$_3$OD) δ −114.68 (s), −115.20 (s).

EXAMPLE 22

Preparation of 6-(5-chloro-1-methyl-1H-indazol-7-yl)pyrimidin-4-ol

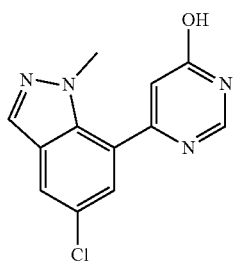 [SMILES: Cn1ncc2cc(Cl)cc(-c3cc(O)ncn3)c21]

22A. Preparation of 7-bromo-5-chloro-1-methyl-1H-indazole

To a solution of 7-bromo-5-chloro-1H-indazole (5.0 g, 21.60 mmol) and K$_2$CO$_3$ (14.93 g, 108 mmol) in DMSO (24.91 ml) was added CH$_3$I (1.62 ml, 25.9 mmol) at rt. The reaction mixture was stirred at rt overnight. Reaction was diluted with water and the resulting solid filtered through a Buchner funnel, washed with water, and dried under vacuum. The regioisomers were separate by normal phase chromatography eluting with a gradient of hexanes/EtOAc with the 1st isomer to elute off of the column being 7-bromo-5-chloro-1-methyl-1H-indazole (2.83 g, 53.4%) as confirmed by $^1$H NMR and a negative NOE. MS(ESI) m/z: 245 (M+H)+ and 247 (M+2+H)[30]. $^1$H NMR (400 MHz, DMSO-d$_6$) δ 8.12-8.09 (m, 1H), 7.88 (d, J=1.8 Hz, 1H), 7.67 (d, J=1.5 Hz, 1H), 4.32 (s, 3H).

22B. Preparation of 5-chloro-1-methyl-7-(4,4,5,5-tetramethyl-1,3,2-dioxaborolan-2-yl)-1H-indazole To a stirring solution of 7-bromo-5-chloro-1-methyl-1H-indazole (1.0 g, 4.07 mmol) in dioxane (20.37 ml) at rt was added 4,4,4',4',5,5,5',5'-octamethyl-2,2'-bi(1,3,2-dioxaborolane) (1.190 g, 4.68 mmol) and KOAc (1.839 g, 18.74 mmol). The system was purged with Ar (3×). Pd(dppf)Cl$_2$ DCM complex (0.266 g, 0.326 mmol) was added, the system was again purged with Ar, and then was heated to 90° C. After stirring overnight, the reaction mixture was cooled to rt, diluted with water, extracted with EtOAc (3×), washed with water and then brine, dried over Na$_2$SO$_4$, filtered, and concentrated. The crude residue was purified by normal phase column chromatography eluting with a gradient of hexanes/EtOAc to give 5-chloro-1-methyl-7-(4,4,5,5-tetramethyl-1,3,2-dioxaborolan-2-yl)-1H-indazole (0.47 g, 39.4% yield) an oil which slowly solidified upon standing. MS(ESI) m/z: 293.0 (M+H)+ and 295.0 (M+2+H)[1]. $^1$H NMR (400 MHz, CD$_3$OD) δ 7.94 (s, 1H), 7.80 (d, J=2.2 Hz, 1H), 7.71 (d, J=2.2 Hz, 1H), 4.23 (s, 3H), 1.40 (s, 12H).

22C. Preparation of 5-chloro-7-(6-methoxypyrimidin-4-yl)-1-methyl-1H-indazole

To a large microwave vial was added 4-chloro-6-methoxypyrimidine (0.201 g, 1.391 mmol), 5-chloro-1-methyl-7-(4,4,5,5-tetramethyl-1,3,2-dioxaborolan-2-yl)-1H-indazole (0.407 g, 1.391 mmol), and 2 M Na$_2$CO$_3$ (0.70 ml, 1.391 mmol) in DME (5.6 ml)/EtOH (0.7 ml). The mixture was purged with Ar for several min, PdCl$_2$(dppf) -CH$_2$Cl$_2$ adduct (0.114 g, 0.139 mmol) added and then heated at 90° C. After 4 h, the reaction mixture was cooled to rt, diluted with water, and extracted with EtOAc. The organic layer washed with brine, dried over Na$_2$SO$_4$, filtered, and concentrated to give an orange-brown residue. The crude material was purified by normal phase column chromatography eluting with a gradient of hexanes/EtOAc to give 5-chloro-7-(6-methoxypyrimidin-4-yl)-1-methyl-1H-indazole (0.382, 100%) as a solid. MS(ESI) m/z: 275.1 (M+H)+ and 277.1 (M+2+H)+.

22D. Preparation of 6-(5-chloro-1-methyl-1H-indazol-7-yl)pyrimidin-4-ol

A clear, yellow solution of 5-chloro-7-(6-methoxypyrimidin-4-yl)-1-methyl-1H -indazole (0.382 g, 1.391 mmol) in AcOH (3 ml) and 48% HBr in water (1.64 ml, 14.49 mmol) was warmed to 85° C. After 3 h, the reaction mixture was concentrated. The residue was dissolved in EtOAc and washed with sat NaHCO$_3$. The aqueous layer was extracted with additional EtOAc, washed with brine, dried over Na$_2$SO$_4$, filtered, and concentrated. The resulting solid was suspended with Et$_2$O, filtered, and dried under vacuum to give 6-(5-chloro-1-methyl-1H-indazol-7-yl)pyrimidin-4-ol (0.085 g, 23.5%) as a white solid. MS(ESI) m/z: 261.0 (M+H)+ and 263.0 (M+2+H)+. $^1$H NMR (400 MHz, DMSO-d$_6$) δ 12.78 (br. s., 1H), 8.32 (s, 1H), 8.13 (s, 1H), 7.97 (d, J=1.8 Hz, 1H), 7.46-7.36 (m, 1H), 6.66 (s, 1H), 3.87 (s, 3H).

EXAMPLE 23

Preparation of tert-butyl N-[(1S)-1-(4-chloropyridin-2-yl)but-3-en-1-yl]carbamate

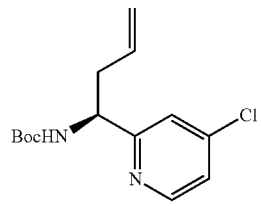 [SMILES: C=CC[C@H](NC(=O)OC(C)(C)C)c1cc(Cl)ccn1]

23A. Preparation of 4-chloro-2-[(E)-2-[(S)-2-methylpropane-2-sulfinyl]ethenyl]pyridine To a solution of S-(−)-t-butyl-sulfinamide (0.856 g, 7.06 mmol) in DCM (14.13 mL) was added sequentially CuSO₄ (2.481 g, 15.54 mmol) and 4-chloropicolinaldehyde (1.0 g, 7.06 mmol). The white suspension was stirred at rt. After 3 h, the brown suspension was filtered through CELITE®, washed with DCM to give a clear brown filtrate. Concentration gave the crude product as a brown oil weighing 1.85 g. Purification by normal phase chromatography gave tert-butyl N-[(1S)-1-(4-chloropyridin-2-yl)but-3-en-1-yl]carbamate (1.31 g) as a clear, yellow oil. MS(ESI) m/z: 245.0 (M+H)⁺.

23B. Preparation of (R)—N-[(1S)-1-(4-chloropyridin-2-yl)but-3-en-1-yl]-2-methylpropane-2-sulfinamide To a cooled (0-5° C.) mixture of InCl₃ (13.56 g, 61.3 mmol) in THF (170 mL) was added dropwise over 30 min allylmagnesium bromide (1M in Et₂O) (62 mL, 61.3 mmol). The reaction was allowed to warm to rt. After 1 h at rt, a solution of 4-chloro-2-[(E)-2-[(S)-2-methylpropane-2-sulfinyl]ethenyl]pyridine (10 g, 40.9 mmol), prepared as described in Example 19, in EtOH (170 mL) was added to the reaction mixture. After 2-3 h, the reaction was concentrated under vacuum at 50-55° C. The crude material was partitioned between EtOAc (200 ml) and water (1×50 ml) and the layers were separated. The aqueous layer was extracted with EtOAc (2×50 ml). The organic layers were combined and washed with brine (1×100ml), dried over Na₂SO₄, filtered and concentrated to give (R)—N-[(1S)-1-(4-chloropyridin-2-yl)but-3-en-1-yl]-2-methylpropane-2-sulfinamide (13.5 g, 106%) as a yellow oil. MS(ESI) m/z: 287.2 (M+H)⁺. This material was used in the next step without further purification.

23C. Preparation of (1S)-1-(4-chloropyridin-2-yl)but-3-en-1-amine (R)—N-[(1S)-1-(4-Chloropyridin-2-yl)but-3-en-1-yl]-2-methylpropane-2-sulfinamide (75 g, 261 mmol) was dissolved in MeOH (1500 mL). 6 N HCl (750 ml, 4.5 mol) was added. The reaction was stirred at rt for 2-3 h and then was concentrated. The residue was diluted with water (2 L), washed with EtOAc (500 ml). The aqueous layer was basified with sat Na₂CO₃ solution, then extracted into EtOAc (3×1 L). The combined organic layers were washed with water (1 L) and brine (1 L), dried over Na₂SO₄, filtered and concentrated under vacuum at 50-55° C. to give (1S)-1-(4-chloropyridin-2-yl)but-3-en-1-amine (43 g, 90%) which was without further purification. MS(ESI) m/z: 183.2 (M+H)⁺.

23D. Preparation of tert-butyl N-[(1S)-1-(4-chloropyridin-2-yl)but-3-en-1-yl]carbamate (1S)-1-(4-Chloropyridin-2-yl)but-3-en-1-amine (42 g, 230 mmol) was dissolved in DCM (420 mL), Et₃N (32.1 mL, 230 mmol) was added followed by dropwise addition of BOC₂O (53.4 mL, 230 mmol). The reaction was stirred at rt for 2-3 h. The reaction was diluted with excess DCM (1 L), washed with water (500 ml) and brine (500 ml). The organic layer was dried over Na₂SO₄, filtered, and concentrated. The crude product was then purified using silica gel chromatography to give tert-butyl N-[(1S)-1-(4-chloropyridin-2-yl)but-3-en-1-yl]carbamate (61 g, 86%) as a pale yellow solid. MS(ESI) m/z: 283.2 (M+H)⁺. ¹H NMR (500 MHz, CDCl₃) δ 8.44 (d, 1H), 7.26-7.16 (dd, 2H), 5.69-5.61 (m, 1H), 5.59 (bs, 1H), 5.07-5.03 (m, 2H), 4.76 (bs, 1H), 2.62-2.55 (m, 2H), 1.42 (s, 9H).

EXAMPLE 24

Preparation of tert-butyl N-[(1S)-1-(3-bromophenyl)but-3-en-1-yl]carbamate

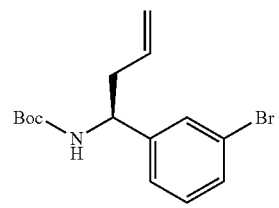 [SMILES: C=CC[C@H](NC(=O)OC(C)(C)C)c1cccc(Br)c1]

24A. Preparation of (R)—N-[(1S)-1(3-bromophenyl)methylidene]-2-methylpropane-2-sulfinamide To 3-bromobenzaldehyde (7.8 g, 42.2 mmol) was added (R)-2-methylpropane-2-sulfinamide (5.11 g, 42.2 mmol), Cs₂CO₃ (20.60 g, 63.2 mmol) in DCM (211 ml) and the resulting reaction mixture was stirred for 5 days. The reaction mixture was then partitioned with brine (50 ml) and DCM (50 ml). The aqueous layer was extracted with DCM (2×50 ml). The combined organic layers were washed with brine (25 ml), dried (Na₂SO₄), filtered and concentrated. Purification by normal phase chromatography using hexanes and EtOAc as eluents gave (R)—N-[(1E)-(3-bromophenyl)methylidene]-2-methylpropane-2-sulfinamide (11.8 g, 97%) as an amber oil. ¹H NMR (400 MHz, CDCl₃) δ 8.53 (s, 1H), 8.02 (t, J=1.8 Hz, 1H), 7.74 (dt, J=7.7, 1.2 Hz, 1H), 7.64 (ddd, J=8.0, 2.0, 1.0 Hz, 1H), 7.36 (t, J=7.8 Hz, 1H), 1.34-1.22 (m, 9H). MS(ESI) m/z: 290 (M+H)⁺.

24B. Preparation of (R)—N-[(1S)-1-(3-bromophenyl)but-3-en-1-yl]-2-methylpropane-2-sulfinamide To (R)—N-[(1E)-(3-bromophenyl)methylidene]-2-methylpropane-2-sulfinamide (11.8 g, 40.9 mmol) in THF (186 ml), in a 3 neck flask, cooled to 0° C., was added allyl bromide (3.90 ml, 45.0 mmol) and In (6.58 g, 57.3 mmol). After stirring at rt for 18 h, the reaction was not complete. The reaction was heated to 50° C. for 6 h, then stirred at rt for 18 h. The reaction mixture was filtered through CELITE® and the filtrate was quenched with water (100 ml). A thick clear gelatinous material formed in the aqueous layer. The organics were extracted with EtOAc (4×75 ml). The combined organic layer was washed with brine, dried with MgSO₄, filtered and concentrated to give (R)—N-[(1S)-1-(3-bromophenyl)but-3-en-1-yl]-2-methylpropane-2-sulfinamide as a clear oil (9.6 g, 71%) which was used without further purification. ¹H NMR (400 MHz, CDCl₃) δ 7.48 (t, J=1.8 Hz, 1H), 7.41 (dt, J=7.6, 1.6 Hz, 1H), 7.26-7.18 (m, 2H), 5.79-5.66 (m, 1H), 5.23-5.16 (m, 2H), 4.46 (ddd, J=8.1, 5.6, 2.0 Hz, 1H), 3.69 (s, 1H), 2.63-2.53 (m, 1H), 2.53-2.40 (m, 1H), 1.23-1.19 (m, 9H).

24C. Preparation of tert-butyl N-[(1S)-1-(3-bromophenyl)but-3-en-1-yl]carbamate

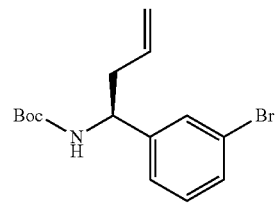 [SMILES: C=CC[C@H](NC(=O)OC(C)(C)C)c1cccc(Br)c1]

To (R)—N-[(1S)-1-(3-bromophenyl)but-3-en-1-yl]-2-methylpropane-2-sulfinamide (9.6 g, 29.1 mmol) in MeOH (300 ml) was added conc. HCl (4 ml). After 3 h, the reaction was concentrated and the residue was dissolved in DCM (300 ml), cooled to 0° C., and then TEA (16.2 ml, 116 mmol) and Boc$_2$O (6.75 ml, 29.1 mmol) in DCM (20 ml) were added. After 18 h, additional Boc$_2$O (1 g) was added and the reaction was stirred 4 h. The reaction was quenched with water (100 ml) and extracted with DCM (3×50 ml). The combined organic layers were washed with brine (50 ml), dried (Na$_2$SO$_4$), filtered and concentrated. Purification by normal phase chromatography using hexanes and EtOAc as eluents gave tert-butyl N-[(1S)-1-(3-bromophenyl)but-3-en-1-yl]carbamate (7.3 g, 77%) as a white solid. MS(ESI) m/z: 326.08 (M+H)$^+$.

EXAMPLE 25

Preparation of N-[(1S)-1-(3-bromo-5-fluorophenyl)but-3-en-1-yl]carbamate

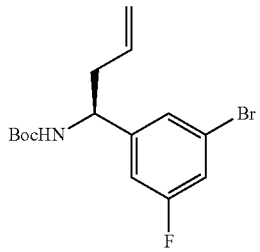

25A. Preparation of (R)—N-[(1E)-(3-bromo-5-fluorophenyl)methylidene]-2-methylpropane-2-sulfinamide To 3-bromo-5-fluorobenzaldehyde (25 g, 123 mol) dissolved in DCM (200 mL) was added (R)-2-methylpropane-2-sulfinamide (14.96 g, 123 mol) and Cs$_2$CO$_3$ (40.2 g, 123 mol). The reaction mixture was stirred at rt overnight. After this time, the reaction mixture was filtered and concentrated to give a yellow oil. The yellow oil was purified using a 120 g silica gel ISCO column eluted with hexanes and EtOAc to give (R)—N-[(1E)-(3-bromo-5-fluorophenyl)methylidene]-2-methylpropane-2-sulfinamide (35 g, 93%) as a yellow oil. $^1$H NMR (500 MHz, DMSO-d$_6$) δ 8.58-8.55 (m, 1H), 8.05-7.98 (m, 1H), 7.84-7.76 (m, 2H), 1.20 (s, 9H). LCMS m/z 306.1 (M+H).

25B. Preparation of (R)—N-[(1S)-1-(3-bromo-5-fluorophenyl)but-3-en-1-yl]-2-methylpropane-2-sulfinamide N-[(1E)-(3-Bromo-5-fluorophenyl)methylidene]-2,2-dimethylpropanamide (35 g, 114 mol) was dissolved in THF (500 mL) in a large 3 neck RB flask and flushed with Ar. The solution was cooled to 0° C. and In (18.4 g, 160 mol) was added followed by the dropwise addition of allylbromide (15.2 g, 126 mol). The reaction was stirred at 0° C. for 2 h, then the ice bath was removed and the reaction mixture was stirred at rt overnight. The reaction was quenched with water (2 L) and the gelatinous material was filtered through CELITE®. The filtrate was concentrated in vacuo to an oily mass. The crude material was dissolved in water (2 L) and the organics were extracted with EtOAc (4×200 mL), dried over MgSO$_4$, filtered and concentrated to give an oil. The oily liquid was purified via a silica gel ISCO column and eluted with DCM/MeOH to afford (R)—N-[(1S)-1-(3-bromo-5-fluorophenyl)but-3-en-1-yl]-2-methylpropane-2-sulfinamide (34.9 g, 88% yield) as a semi solid mass. LCMS m/z 348.2 (M+H). $^1$H NMR (500 MHz, DMSO-d$_6$) δ 7.44-7.38 (m, 2H), 7.26-7.20 (m, 1H), 5.79-5.65 (m, 1H), 5.46-5.42 (m, 1H), 5.04-4.98 (m, 2H), 4.41-4.34 (m, 1H), 2.69-2.59 (m, 1H), 2.49-2.43 (m, 1H), 1.09 (s, 9H).

25C. Preparation of N-[(1S)-1-(3-bromo-5-fluorophenyl)but-3-en-1-yl]carbamate

To a cooled 0° C. solution of (R)—N-[(1S)-1-(3-bromo-5-fluorophenyl)but-3-en-1-yl]-2-methylpropane-2-sulfinamide (21.9 g, 100 mol) dissolved in MeOH (100 mL) was added conc. HCl (50 mL) dropwise and then the reaction was stirred at 0° C. for 48 h. After this time, the reaction mixture was concentrated to give a white solid mass. The residue was dissolved in water (1000 mL) and the organics were extracted with EtOAc (2×200 mL), dried over MgSO$_4$, filtered and concentrated to a brown oil (11.5 g). The aqueous layer was basified with NaOH and the organics were extracted with EtOAc (2×300 mL), dried over MgSO$_4$, filtered and concentrated to a brown oil (18 g). The combined oils were dissolved in DCM (500 mL) and to this was added Boc$_2$O (22 g) followed by TEA (15 mL) and the reaction mixture was stirred at rt overnight. The reaction mixture was concentrated in vacuo and purified via a 330 g silica gel Isco column eluting with hexanes and EtOAc to give a white solid. The white solid was triturated with hexanes and the precipitate was collected by filtration to give N-[(1S)-1-(3-bromo-5-fluorophenyl)but-3-en-1-yl]carbamate (29.5 g, 87% yield).

EXAMPLE 26

Preparation of N-[(1S)-1-(5-bromopyridin-3-yl)but-3-en-1-yl]carbamate

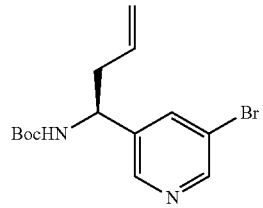

26A. Preparation of (R)—N-[(1E)-(5-chloropyridin-3-yl)methylidene]-2-methylpropane-2-sulfinamide 5-Bromonicotinaldehyde (6.6 g, 35.9 mmol) was dissolved in DCM (200 mL). To the solution was added Cs$_2$CO$_3$ (11.68 g, 35.9 mmol) and (R)-2-methylpropane-2-sulfinamide (4.34 g, 35.9 mol) and then the reaction mixture was stirred at rt overnight. The inorganics were filtered and the filtrate was concentrated to afford (R)—N-[(1E)-(5-chloropyridin-3-yl)methylidene]-2-methylpropane-2-sulfinamide as an oil (10.4 g, 100% yield). LCMS m/z =291.3.

26B. Preparation of (R)—N-[(1S)-1-(5-chloropyridin-3-yl)but-3-en-1-yl]-2-methylpropane-2-sulfinamide To a solution of (R)—N-[(1E)-(5-chloropyridin-3-yl)methylidene]-2-methylpropane-2-sulfinamide (10.36 g, 35.8 mmol) in THF (150 mL) at 0° C. was added p In (5.76 g, 50.2 mmol) followed by allylbromide (3.72 mL, 43.0 mmol). The reaction mixture was sealed and was stirred vigorously at 0° C. for 1 h and then allowed to warm gradually to rt and stirred overnight. The reaction gradually turned from pale yellow to greenish yellow to dark greenish yellow with the In forming fine particles. The solution was filtered through a pad of CELITE® and washed with EtOAc. The solution was concentrated to afford a yellow solid mass.

The solids were dissolved in MeOH (100 mL) and a solution of 4 N HCl in dioxane (25 mL) was added. The resultant solution was stirred at rt. After 6 h, conc. HCl (1 mL) was added and stirring was continued for 1 h. The reaction mixture was concentrated in vacuo to give a yellow solid. The solid was dissolved in a mixture of THF and dioxane and DCM (1:1;1, 200 mL). To this solution was added TEA (20 mL) followed by Boc$_2$O (8.1 g, 37.1 mmol) and the resulting reaction mixture was stirred overnight. LCMS confirmed the desired product formation. To the reaction mixture was added water (200 mL) and the mixture was filtered through a pad of CELITE® and washed with EtOAc (200 mL). The aqueous layer was extracted with EtOAc (2×100 mL). The combined organic layer was dried over MgSO$_4$, filtered and concentrated to give a reddish brown oil. The crude material was purified via a 80 g silica gel ISCO column and eluted with hexanes and EtOAc. (R)—N-[(1S)-1-(5-Chloropyridin -3-yl)but-3-en-1-yl]-2-methyl-propane-2-sulfinamide was obtained as a pale yellow semi solid mass (4.3 g, 36.7% yield). LCMS m/z 327.1 (M+H). $^1$H NMR (400 MHz, CDCl$_3$) δ 8.61-8.59 (m, 1H), 8.51-8.48 (m, 1H), 7.77-7.74 (m, 1H), 5.76-5.63 (m, 1H), 5.23 -5.14 (m, 2H), 5.00-4.84 (m, 1H), 4.83-4.70 (m, 1H), 2.60-2.44 (m, 2H), 1.48-1.35 (m, 9H).

EXAMPLE 27

Preparation of tert-butyl N-[(1S)-1-(2-bromopyridin-4-yl)but-3-en-1-yl]carbamate

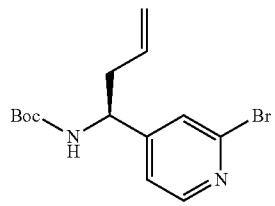 [SMILES: C=CC[C@H](NC(=O)OC(C)(C)C)c1ccnc(Br)c1]

27A. Preparation of (R)—N-[(1E)-(2-bromopyridin-4-yl) methylidene]-2-methylpropane -2-sulfinamide

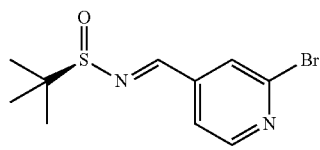

To a stirred suspension of (R)-2-methylpropane-2-sulfinamide (13.03 g, 108 mmol) and Cs$_2$CO$_3$ (52.5 g, 161 mmol) in DCM (400 ml) was added 2-bromopyridine-4-carbaldehyde (20 g, 108 mmol) over 10 min. The reaction mixture was then stirred for 18.5 h at rt. The reaction mixture was concentrated and the residue was diluted with EtOAc (50 ml) and washed with brine (3×20 ml). The organic layer was dried over MgSO$_4$, filtered and concentrated. The residue was purified by normal phase chromatography using hexanes and EtOAc as eluents to afford (27.2 g, 87%) of (R)—N -[(1E)-(2-bromopyridin-4-yl)methylidene]-2-methylpropane-2-sulfinamide as a white solid. MS(ESI) m/z: 289-291.0 (M+H)$^+$.

27B. Preparation of (R)—N-[(1S)-1-(2-bromopyridin-4-yl)but-3-en-1-yl]-2-methylpropane-2-sulfonamide

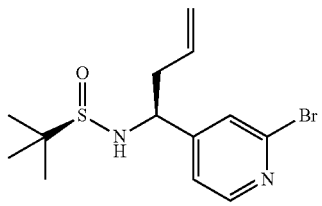 [SMILES: C=CC[C@H](N[S@](=O)C(C)(C)C)c1ccnc(Br)c1]

To a solution of (R)—N-[(1E)-(2-bromopyridin-4-yl) methylidene]-2-methylpropane-2-sulfinamide (0.73 g, 2.52 mmol) and In (0.435 g, 3.79 mmol) in THF (6 ml) was slowly added 3-bromoprop-1-ene (0.458 g, 3.79 mmol) and resulting solution was heated at 60° C. for 18 h. The reaction mixture was cooled, filtered through CELITE® and the filtrate was concentrated. To the residue was added EtOAc (100 ml) and 5% aq NaHCO$_3$ (1000 ml) and an emulsion formed immediately. The suspension was filtered through paper. The organic layer was washed with brine, dried over Na$_2$SO$_4$ filtered, and concentrated. The resulting residue was purified by normal phase chromatography using hexanes and EtOAc as eluents to afford (0.62 g, 74%) of (R)—N -[(1S)-1-(2-bromopyridin-4-yl)but-3-en-1-yl]-2-methylpropane-2-sulfonamide as a yellow liquid. MS(ESI) m/z: 331-333.0 (M+H)$^+$.

27C. Preparation of tert-butyl N-[(1S)-1-(2-bromopyridin-4-yl)but-3-en-1-yl]carbamate

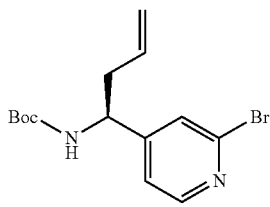 [SMILES: C=CC[C@H](NC(=O)OC(C)(C)C)c1ccnc(Br)c1]

To a solution of (R)—N-[(1S)-1-(2-bromopyridin-4-yl) but-3-en-1-yl]-2-methylpropane-2-sulfinamide (1.38 g, 4.17 mmol) in MeOH (10 ml) was added 4 N HCl in dioxane (5.21 mL, 20.83 mmol). The reaction mixture was stirred for 1.5 h at rt, then was concentrated. To the resulting residue was added ACN (10 ml), TEA (5.81 ml, 41.7 mmol) and Boc$_2$O (1.818 g, 8.33 mmol). After 18 h, the reaction mixture was concentrated and the residue was taken up in EtOAc, washed with water, brine, dried over MgSO$_4$, filtered and concentrated. The resulting residue was purified by normal phase chromatography using hexanes and EtOAc as eluents to afford (0.80 g, 58.7%) of tert-butyl N-[(1S)-1-(2-bromopyridin-4-yl)but-3-en-1-yl]carbamate as a pale yellow oil. MS(ESI) m/z: 324-326.1 (M+H)$^+$.

EXAMPLE 28

Preparation of (10R,14S)-14-amino-4-fluoro-10-methyl-8,16-diazatricyclo[13.3.1.0$^{2,7}$]nonadeca-1(19),2,4,6,15,17-hexaen-9-one

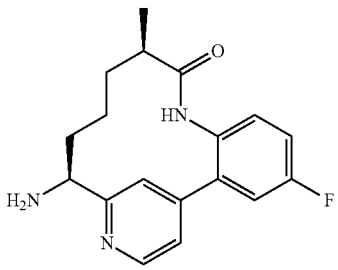 [SMILES: C[C@@H]1CCC[C@H](N)c2cc(ccn2)-c2cc(F)ccc2NC1=O]

28A. Preparation of tert-butyl N-[(1S)-1-[4-(2-amino-5-fluorophenyl)pyridin-2-yl]but-3-en-1-yl]carbamate A thick-walled flask containing tert-butyl N-[(1S)-1-(4-chloropyridin-2-yl)but-3-en-1-yl]carbamate (3.8 g, 13.44 mmol), 3 M aq K$_3$PO$_4$ (13.5 ml, 40.3 mmol), 2-(5,5-dimethyl-1,3,2-dioxaborinan-2-yl)-4-fluoroaniline (3.54 g, 14.93 mmol), and (DtBPF)PdCl$_2$ (0.44 g, 0.67 mmol) in dioxane (67.2 ml) was purged with Ar (3×x). The flask was sealed with a teflon screw cap and the reaction was heated at 65° C. for 16 h. The reaction was cooled to rt, diluted with EtOAc, and filtered to remove the solid. The filtrate was concentrated to a small volume, diluted with EtOAc, washed with water, brine, dried over MgSO$_4$, filtered, and concentrated. Purification by normal phase chromatography gave tert-butyl N-[(1S)-1-[4-(2-amino-5-fluorophenyl)pyridin-2-yl]but-3-en-1-yl]carbamate (4.32 g, 90% yield) as a brown solid. $^1$H NMR (400 MHz, CDCl$_3$) δ 8.63 (dd, J=5.1, 0.7 Hz, 1H), 7.33 (s, 1H), 7.30-7.27 (m, 1H), 6.92 (td, J=8.4, 3.0 Hz, 1H), 6.85 (dd, J=9.0, 2.9 Hz, 1H), 6.71 (dd, J=8.8, 4.6 Hz, 1H), 5.78-5.65 (m, 1H), 5.60 (br. s., 1H), 5.05 (d, J=12.3 Hz, 2H), 4.85 (d, J=6.4 Hz, 1H), 3.64 (br. s., 2H), 2.62 (t, J=6.8 Hz, 2H), 1.44 (s, 9H).

28B. Preparation of tert-butyl N-[(1S)-1-(4-{5-fluoro-2-[(2R)-2-methylbut-3-enamido]phenyl}pyridin-2-yl)but-3-en-1-yl]carbamate To a solution of tert-butyl N-[(1S)-1-[4-(2-amino-5-fluorophenyl)pyridin-2-yl]but-3-en-1-yl]carbamate (405 mg, 1.13 mmol), (R)-2-methylbut-3-enoic acid (142 mg, 1.42 mmol), prepared as described in Example 2, in EtOAc (11.2 mL) was added pyridine (0.28 mL, 3.40 mmol). The reaction was cooled to 0° C. under Ar. T3P® (1.35 mL, 2.27 mmol) was added dropwise. The reaction was then gradually warmed up to rt and stirred overnight. The reaction mixture was diluted and washed with sat NaHCO$_3$. The aqueous layer was extracted with EtOAc. The combined EtOAc phases was washed with brine, dried over MgSO$_4$, filtered and concentrated. Purification by normal phase chromatography gave tert-butyl N-[(1S)-1-(4-{5-fluoro-2-[(2R)-2-methylbut-3-enamido]phenyl}pyridin-2-yl)but-3-en-1-yl]carbamate (417 mg, 84% yield) as a white foam. MS(ESI) m/z: 440.2 (M+H)$^+$.

28C. Preparation of tert-butyl N-[(10R,11E,14S)-4-fluoro-10-methyl-9-oxo-8,16-diazatricyclo[13.3.1.0$^{2,7}$]nonadeca-1(19),2(7),3,5,11,15,17-heptaen-14-yl]carbamate

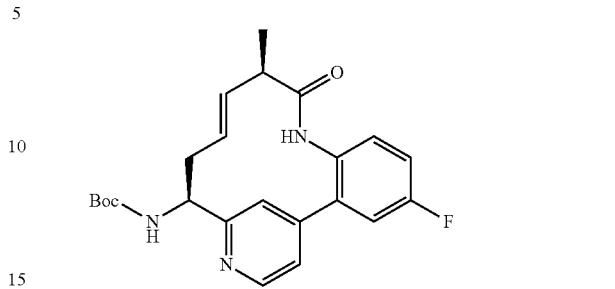

To a solution of tert-butyl N-[(1S)-1-(4-{5-fluoro-2-[(2R)-2-methylbut-3-enamido]phenyl}pyridin-2-yl)but-3-en-1-yl]carbamate (417 mg, 0.95 mmol) in DCM (63.30 ml) was added pTsOH.H$_2$O (189 mg, 0.10 mmol). The reaction solution was bubbled through with Ar for 30 min. The reaction mixture was then warmed to 40° C. for 40 min. A solution of Second Generation Grubbs Catalyst (161 mg, 0.19 mmol) in degassed DCM (2 mL) was added dropwise. The reaction mixture was heated at 40° C. overnight. The reaction was cooled to rt and was diluted with DCM, washed with sat NaHCO$_3$, brine, dried over MgSO$_4$, filtered, and concentrated. Purification by normal phase chromatography gave tert-butyl N-[(10R,11E,14S)-4-fluoro-10-methyl-9-oxo-8,16-diazatricyclo[13.3.1.0$^{2,7}$]nonadeca-1(19),2(7),3,5,11,15,17-heptaen-14-yl]carbamate (320 mg, 82% yield) as a yellow foam. MS(ESI) m/z: 412.2 (M+H)$^+$.

28D. Preparation of tert-butyl N-[(10R,14S)-4-fluoro-10-methyl-9-oxo-8,16-diazatricyclo[13.3.1.0$^{2,7}$]nonadeca-1(19),2(7),3,5,15,17-hexaen-14-yl]carbamate tert-Butyl N-[(10R,11E,14S)-4-fluoro-10-methyl-9-oxo-8,16-diazatricyclo [13.3.1.0$^{2,7}$]nonadeca-1(19),2(7),3,5,11,15,17-heptaen-14-yl]carbamate (320 mg, 0.78 mmol) in EtOAc (15.6 ml) was purged with Ar. PtO$_2$ (13.68 mg, 0.06 mmol) was added. The reaction was purged with H$_2$ several times and the reaction was then stirred under a H$_2$ atmosphere overnight. The reaction mixture was filtered through CELITE®, rinsed with DCM, and the filtrate was concentrated. The resulting residue was purified by normal phase chromatography to give tert-butyl N-[(10R,14S)-4-fluoro-10-methyl-9-oxo -8,16-diazatricyclo[13.3.1.0$^{2,7}$]nonadeca-1(19),2(7),3,5,15,17-hexaen-14-yl]carbamate (276 mg, 86% yield) as a light brownish gel-like film. MS(ESI) m/z: 414.2 (M+H)$^+$.

28E. Preparation of (10R,14S)-14-amino-4-fluoro-10-methyl-8,16-diazatricyclo [13.3.1.0$^{2,7}$]nonadeca-1(19),2(7),3,5,15,17-hexaen-9-one To a solution of tert-butyl N-[(10R,14S)-4-fluoro-10-methyl-9-oxo-8,16-diazatricyclo[13.3.1.0$^{2,7}$]nonadeca-1(19),2(7),3,5,15,17-hexaen-14-yl]carbamate (276 mg, 0.68 mmol) in DCM (10 mL) was added TFA (2 mL, 26.0 mmol). The reaction was stirred at rt for 1.5 h. After this time, the reaction mixture was concentrated to give (10R,14S)-14-amino-4-fluoro-10-methyl-8,16-diazatricyclo[13.3.1.0$^{2,7}$] nonadeca -1(19),2(7),3,5,15,17-hexaen-9-one (408 mg, 100%) as a light grayish foam. MS(ESI) m/z: 314.2 (M+H)$^+$.

EXAMPLE 29

Preparation of (10R,14S)-14-amino-10-methyl-8,16-diazatricyclo [13.3.1.0$^{2,7}$]nonadeca-1(19),2,4,6,15,17-hexaen-9-one

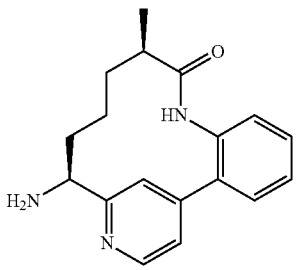 [SMILES: C[C@@H]1CCC[C@H](N)c2cc(ccn2)-c2ccccc2NC1=O]

29A. Preparation of tert-butyl N-[(1S)-1-[4-(2-aminophenyl)pyridin-2-yl]but-3-en-1-yl]carbamate To a dioxane (22.63 ml) solution of tert-butyl N-[(1S)-1-(4-chloropyridin-2-yl)but-3-en-1-yl]carbamate (3.2 g, 11.32 mmol), prepared as described in Example 23, was added (2-aminophenyl)boronic acid (2.015 g, 14.71 mmol), 3 M K$_3$PO$_4$ (11.32 ml, 34.0 mmol). The mixture was purged with N$_2$ for 15 min followed by the addition of (DtBPF)PdCl$_2$ (0.369 g, 0.566 mmol) and the reaction was then heated to 65° C. After 18 h, the reaction was partitioned between water (30 mL) and EtOAc (50 mL). The aqueous layer was extracted with EtOAc (2×50 ml). The combined organic layers were washed with brine, dried over MgSO$_4$, filtered, and concentrated. The residue was purified by normal phase chromatography using hexanes and EtOAc as eluents to afford (3.64 g, 95% yield) of tert-butyl N-[(1S)-1-[4-(2-aminophenyl)pyridin-2-yl]but-3-en-1-yl]carbamate as a brown foam. MS(ESI) m/z: 340.5 (M+H)$^+$. $^1$H NMR (500 MHz, CDCl$_3$) δ 8.63 (dd, J=5.1, 0.4 Hz, 1H), 7.37 (s, 1H), 7.32 (dd, J=5.1, 1.5 Hz, 1H), 7.23 (td, J=7.7, 1.5 Hz, 1H), 7.18-7.09 (m, 1H), 6.92-6.83 (m, 1H), 6.80 (dd, J=8.1, 0.9 Hz, 1H), 5.85-5.58 (m, 2H), 5.17-5.02 (m, 2H), 4.88 (d, J=6.2 Hz, 1H), 3.82 (br. s., 2H), 2.65 (t, J=6.7 Hz, 2H), 1.47 (s, 9H).

29B. Preparation of tert-butyl N-[(1S)-1-(4-{2-[(2R)-2-methylbut-3-enamido]phenyl}pyridin-2-yl)but-3-en-1-yl]carbamate To a cooled, 0° C., EtOAc (70 mL) solution of tert-butyl N-[(1S)-1-[4-(2-aminophenyl)pyridin-2-yl]but-3-en-1-yl]carbamate (3.6 g, 10.61 mmol), (R)-2-methylbut-3-enoic acid (1.274 g, 12.73 mmol), prepared as described in Example 2, and Hunig's Base (5.56 mL, 31.8 mmol), was slowly added a 50% EtOAc solution of T3P® (12.63 mL, 21.21 mmol). The reaction was allowed to warm to rt and after 18 h, the reaction was partitioned with sat NaHCO$_3$ (30 ml) and EtOAc (50 mL). The aqueous layer was extracted with EtOAc (2×50 ml). The combined organic layers were washed with brine and dried over (MgSO$_4$). The mixture was filtered and concentrated and the residue was purified by normal phase chromatography using hexanes and EtOAc as eluents to afford (3.3 g, 73% yield) of tert-butyl N-[(1S)-1-(4-{2-[(2R)-2-methylbut-3-enamido]phenyl}pyridin-2-yl)but-3-en-1-yl]carbamate as a tan foam. MS(ESI) m/z: 422.6 (M+H)$^+$.

29C. Preparation of tert-butyl N-[(10R,11E,14S)-10-methyl-9-oxo-8,16-diazatricyclo [13.3.1.0$^{2,7}$]nonadeca-1(19),2,4,6,11,15,17-heptaen-14-yl]carbamate A DCM (758 mL) solution of tert-butyl N-[(1S)-1-(4-{2-[(2R)-2-methylbut-3-enamido]phenyl}pyridin-2-yl)but-3-en-1-yl]carbamate (2.97 g, 7.05 mmol) and pTsOH.H$_2$O (1.474 g, 7.75 mmol) was purged with Ar for 20 min. The solution was then heated to 40° C. for 1 h. The reaction mixture was removed from oil bath and Second Generation Grubbs Catalyst (0.897 g, 1.057 mmol) was then added. The reaction was heated to 40° C. After 24 h, the reaction was cooled to rt and quenched with sat NaHCO$_3$ (50 mL) and extracted with DCM (3×75 mL). The combined organic layers were washed with brine (100 mL) and dried (MgSO$_4$). The mixture was filtered and concentrated and the residue was purified by normal phase chromatography using hexanes and EtOAc as eluents to afford (1.5 g, 54% yield) tert-butyl N-[(10R,11E,14S) -10-methyl-9-oxo-8,16-diazatricyclo[13.3.1.0$^{2,7}$]nonadeca-1(19),2,4,6,11,15,17-heptaen-14-yl]carbamate as a tan foam. MS(ESI) m/z: 394.5 (M+H)$^+$. $^1$H NMR (400 MHz, CDCl$_3$) δ 8.72 (d, J=5.1 Hz, 1H), 8.31 (d, J=8.1 Hz, 1H), 8.14 (br. s., 1H), 7.50-7.43 (m, 1H), 7.39 (dd, J=7.6, 1.2 Hz, 1H), 7.27-7.18 (m, 2H), 7.07 (s, 1H), 6.46 (d, J=7.3 Hz, 1H), 5.89 (ddd, J=15.5, 11.2, 4.0 Hz, 1H), 4.97 (dd, J=15.3, 9.1 Hz, 1H), 4.81 (t, J=7.9 Hz, 1H), 3.29-3.19 (m, 1H), 3.07 (d, J=12.8 Hz, 1H), 1.52-1.48 (m, 9H), 1.33-1.26 (m, 3H).

29D. Preparation of N-[(10R,14S)-10-methyl-9-oxo-8,16-diazatricyclo[13.3.1.0$^{2,7}$]nonadeca-1(19),2,4,6,15,17-hexaen-14-yl]carbamate To a solution of tert-butyl N-[(10R,11E,14,5)-10-methyl-9-oxo-8,16-diazatricyclo [13.3.1.0$^{2,7}$]nonadeca-1(19),2,4,6,11,15,17-heptaen-14-yl]carbamate (1.3g, 3.3 mmol) in EtOH (50 mL) was added PtO$_2$ (0.1 g). The reaction was purged with H$_2$ and then hydrogenated at 60 psi overnight. After this time, the reaction mixture was filtered through CELITE® and washed with EtOH. The filtrate was concentrated to give N -[(10R,14S)-10-methyl-9-oxo-8,16-diazatricyclo[13.3.1.0$^{2,7}$]nonadeca-1(19),2,4,6,15,17-hexaen-14-yl]carbamate as a reddish brown solid which was used without further purification. LCMS m/z: 396.3(M+H). $^1$H NMR (400 MHz, CDCl$_3$) δ 8.79-8.67 (m, 1H), 7.29 (s, 5H), 6.99-6.87 (m, 1H), 6.01-5.77 (m, 1H), 4.91-4.63 (m, 1H), 3.82-3.64 (m, 1H), 2.63-2.36 (m, 1H), 2.21-2.03 (m, 1H), 2.00-1.77 (m, 3H), 1.46 (s, 9H), 1.28 (d, 3H).

29E. Preparation of (10R,14S)-14-amino-10-methyl-8,16-diazatricyclo[13.3.1.0$^{2,7}$]nonadeca-1(19),2,4,6,15,17-hexaen-9-one To a DCM (5 mL) solution of N-[(10R,14S)-10-methyl-9-oxo-8,16-diazatricyclo [13.3.1.0$^{2,7}$]nonadeca-1(19),2,4,6,15,17-hexaen-14-yl]carbamate (97 mg, 0.245 mmol) was added 4 N HCl in dioxane (2 mL). The reaction was stirred at rt for 3 h and after this time, the reaction mixture was concentrated to give colorless foam. The foam was dissolved in EtOAc, washed with sat NaHCO$_3$ (50 mL). the organic layer was dried over MgSO$_4$, filtered and concentrated to a give (10R,14S)-14-amino-10-methyl-8,16-diazatricyclo [13.3.1.0$^{2,7}$]nonadeca-1(19),2,4,6,15,17-hexaen-9-one (70 mg, 86% yield) as semi solid mass.

EXAMPLE 30

Preparation of (10R,14S)-14-amino-10-methyl-9-oxo-8,16-diazatricyclo[13.3.1.0²,⁷]nonadeca-1(19),2,4,6,15,17-hexaene-5-carbonitrile

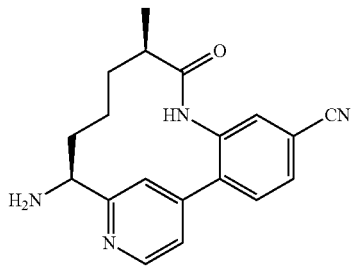 [SMILES: C[C@@H]1CCC[C@H](N)c2cc(ccn2)-c2ccc(C#N)cc2NC1=O]

30A. Preparation of tert-butyl N-[(10R,14S)-5-amino-10-methyl-9-oxo-8,16-diazatricyclo[13.3.1.0²,⁷]nonadeca-1(19),2(7),3,5,15,17-hexaen-14-yl]carbamate

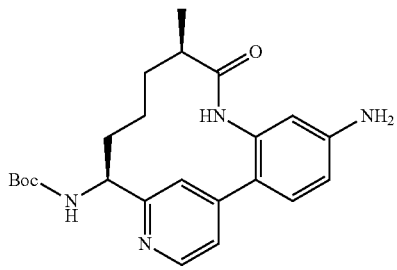 [SMILES: C[C@@H]1CCC[C@H](NC(=O)OC(C)(C)C)c2cc(ccn2)-c2ccc(N)cc2NC1=O]

To a suspension of methyl N-[(10R,14S)-14-{[(tert-butoxy)carbonyl]amino}-10-methyl-9-oxo-8,16-diazatricyclo[13.3.1.0²,⁷]nonadeca-1(19),2(7),3,5,15,17-hexaen-5-yl]carbamate (3.6 g, 7.68 mmol) in THF (59 mL) was added MeOH (5 ml) and 1 N NaOH (46.1 mL, 46.1 mmol). The reaction mixture was stirred in a sealed tube at 60° C. for 3 days. After this time, the reaction mixture was diluted with small amount of H₂O, extracted with EtOAc (2 ×) with 10%MeOH/DCM (2 ×) with 15%IPA/CHCl₃ until there was no product in aqueous layer. The combined organic layers was washed with brine, dried over MgSO₄, filtered, and concentrated. Purification by normal phase chromatography gave tert-butyl N-[(10R,14S)-5-amino-10-methyl-9-oxo-8,16-diazatricyclo[13.3.1.0²,⁷]nonadeca-1(19),2(7),3,5,15,17-hexaen-14-yl]carbamate (2.6 g, 82% yield) as a yellow solid. MS(ESI) m/z: 411.2 (M+H)⁺.

30B. Preparation of tert-butyl N-[(10R,14S)-5-iodo-10-methyl-9-oxo-8,16-diazatricyclo [13.3.1.0²,⁷]nonadeca-1(19),2(7),3,5,15,17-hexaen-14-yl]carbamate To a solution of tert-butyl N-[(10R,14S)-5-amino-10-methyl-9-oxo-8,16-diazatricyclo[13.3.1.0²,⁷]nonadeca-1(19),2(7),3,5,15,17-hexaen-14-yl]carbamate (934 mg, 2.28 mmol) in ACN (10 mL) at 0° C. was added pTsOH.H₂O (1.08 g, 5.69 mmol), followed by addition of NaNO₂ (314 mg, 4.55 mmol) and NaI (853 mg, 5.69 mmol) in water (5 mL). The reaction was gradually warmed up to rt and stirred at rt for 3 h. The reaction mixture was diluted with EtOAc, washed with sat NaHCO₃, aq Na₂S₂O₃ and brine. The organic layer was dried over MgSO₄, filtered and concentrated. Purification by normal phase chromatography gave tert-butyl N-[(10R,14S)-5-iodo-10-methyl-9-oxo -8,16-diazatricyclo[13.3.1.0²,⁷]nonadeca-1(19),2(7),3,5,15,17-hexaen-14-yl]carbamate (772 mg, 65% yield) as a white solid. MS(ESI) m/z: 522.2 (M+H)⁺.

30C. Preparation of tert-butyl N-[(10R,14S)-5-cyano-10-methyl-9-oxo-8,16-diazatricyclo [13.3.1.0²,⁷]nonadeca-1(19),2(7),3,5,15,17-hexaen-14-yl]carbamate

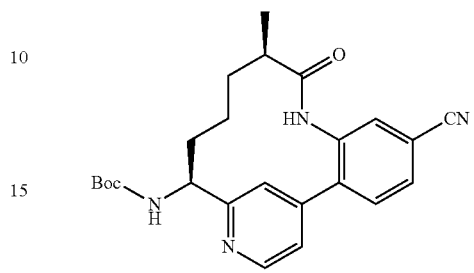

To a DMF (4 mL) solution tert-butyl N-[(10R,14S)-5-iodo-10-methyl-9-oxo-8,16-diazatricyclo[13.3.1.0²,⁷]nonadeca-1(19),2(7),3,5,15,17-hexaen-14-yl]carbamate (208 mg, 0.40 mmol), was added Zn (26.1 mg, 0.40 mmol), Zn(CN)₂ (115 mg, 0.98 mmol) and the reaction mixture was purged with Ar. Pd(P(t-Bu₃))₂ (27 mg, 0.05 mmol) was added. The reaction was purged with Ar. The reaction vial was sealed and heated at 80° C. overnight. The reaction mixture was filtered to remove the solid and the filtrate was concentrated. Purification by normal phase chromatography followed by reverse phase HPLC gave tert -butyl N-[(10R,14S)-5-cyano-10-methyl-9-oxo-8,16-diazatricyclo [13.3.1.0²,⁷]nonadeca -1(19),2(7),3,5,15,17-hexaen-14-yl] carbamate trifluoroacetate (93 mg, 44% yield) as a white solid. MS(ESI) m/z: 421.3 (M+H)⁺.

30D. Preparation of (10R,14S)-14-amino-10-methyl-9-oxo-8,16-diazatricyclo[13.3.1.0²,⁷]nonadeca-1(19),2(7),3,5,15,17-hexaene-5-carbonitrile To a solution of tert-butyl N-[(10R,14S)-5-cyano-10-methyl-9-oxo-8,16-diazatricyclo[13.3.1.0²,⁷]nonadeca-1(19),2(7),3,5,15,17-hexaen-14-yl]carbamate trifluoroacetate (41 mg, 0.077 mmol) in DCM (1.2 mL) was added TFA (0.30 mL, 3.84 mmol). The reaction was stirred at rt for 1 h before it was concentrated. The residue was redissolved in MeOH, passed through a NaHCO₃ cartridge. Removal of the solvent gave (10R,14S)-14-amino-10-methyl-9-oxo-8,16-diazatricyclo[13.3.1.0²,⁷]nonadeca -1(19),2(7),3,5,15,17-hexaene-5-carbonitrile (21 mg, 85%) as a white solid. MS(ESI) m/z: 321.5 (M+H)⁺.

EXAMPLE 31

Preparation of 6-(2-bromo-5-chlorophenyl)pyrimidin-4-ol

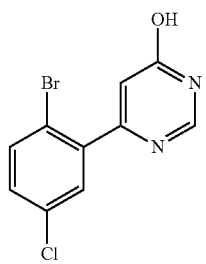 [SMILES: Oc1cc(-c2cc(Cl)ccc2Br)ncn1]

31A. Preparation of 4-(2-bromo-5-chlorophenyl)-6-methoxypyrimidine

To a suspension of 4-chloro-2-(6-methoxypyrimidin-4-yl)aniline (100 mg, 0.424 mmol) and pTsOH.H₂O (97 mg, 0.509 mmol) in CH₃CN (20 mL) was added CuBr₂ (9.48 mg, 0.042 mmol). Then t-butyl nitrite (0.067 mL, 0.509 mmol) was added followed by TBAB (274 mg, 0.849 mmol) and the reaction was stirred at rt. After 2 h, water was added and the mixture was extracted with CH₂Cl₂ (2×). The organic layers were combined, dried over MgSO₄, filtered, and concentrated. Purification by normal phase chromatography gave 4-(2-bromo-5-chlorophenyl)-6-methoxypyrimidine (115 mg, 90% yield) as a white solid. MS(ESI) m/z: 299.2 (M+H)⁺. ¹H NMR (400 MHz, CDCl₃) δ 8.88 (d, J=1.1 Hz, 1H), 7.61 (d, J=8.6 Hz, 1H), 7.56 (d, J=2.6 Hz, 1H), 7.30-7.24 (m, 1H), 7.04 (d, J=1.1 Hz, 1H), 4.05 (s, 3H).

31B. Preparation of 6-(2-bromo-5-chlorophenyl)pyrimidin-4-ol 6-(2-Bromo-5-chlorophenyl)pyrimidin-4-ol was prepared according to the procedures described in Example 5 for the synthesis of 6-(5-chloro-2-fluorophenyl) pyrimidin-4-ol, by replacing 6-(5-chloro-2-fluorophenyl)pyrimidin-4-ol with 4-(2-bromo -5-chlorophenyl)-6-methoxypyrimidine. MS(ESI) m/z: 285.2 (M+H)⁺. ¹H NMR (400 MHz, DMSO-d₆) δ 8.19 (s, 1H), 7.72 (d, J=8.6 Hz, 1H), 7.52 (d, J=2.6 Hz, 1H), 7.41 (dd, J=8.6, 2.6 Hz, 1H), 6.21 (s, 1H).

EXAMPLE 32

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0²,⁷]nonadeca-1(19),2(7),3,5,15,17-hexaene-4,5-dicarbonitrile trifluoroacetate

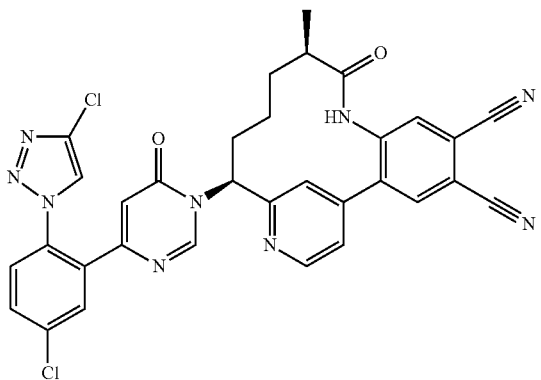 [SMILES: C[C@@H]1CCC[C@H](n2cnc(-c3cc(Cl)ccc3-n3cc(Cl)nn3)cc2=O)c2cc(ccn2)-c2cc(C#N)c(C#N)cc2NC1=O]

32A. tert-Butyl N-[(10R,14S)-4,5-dibromo-10-methyl-9-oxo-8,16-diazatricyclo [13.3.1.0²,⁷]nonadeca-1(19),2(7),3,5,15,17-hexaen-14-yl]carbamate

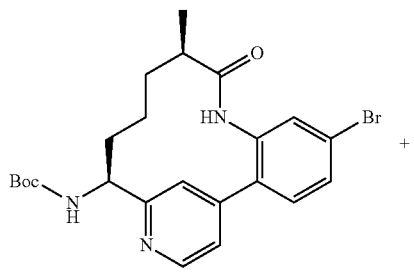

+

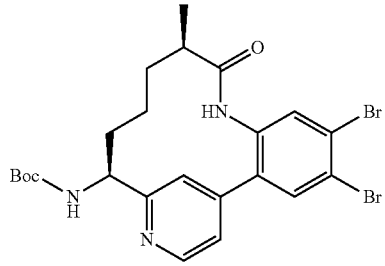

To a suspension of tert-butyl N-[(10R,14S)-5-amino-10-methyl-9-oxo-8,16-diazatricyclo[13.3.1.0²,⁷]nonadeca-1(19),2(7),3,5,15,17-hexaen-14-yl]carbamate (490 mg, 1.19 mmol) in ACN (47.7 mL) was added and pTsOH.H₂O (454 mg, 2.39 mmol). CuBr₂ (26.7 mg, 0.12 mmol) was added followed by addition of t-butyl nitrite (0.19 mL, 1.43 mmol) and Bu₄NBr (770 mg, 2.39 mmol). Water was added and the solution was extracted DCM (2 ×). The combined organic layers were washed with sat NaHCO₃, brine, dried over MgSO₄, filtered and concentrated. Purification by normal phase chromatography gave 1:1 mixture of tert-butyl N-[(10R,14S)-4,5-dibromo-10-methyl-9-oxo-8,16-diazatricyclo[13.3.1.0²,⁷]nonadeca-1(19),2(7),3,5,15,17-hexaen-14-yl]carbamate and tert-butyl N-[(10R,14S)-5-bromo-10-methyl-9-oxo-8,16-diazatricyclo[13.3.1.0²,⁷]nonadeca-1(19),2(7),3,5,15,17-hexaen-14-yl]carbamate (168 mg) as an white solid. MS(ESI) m/z: 552.1 (M+H)⁺.

32B. tert-Butyl N-[(10R,14S)-4,5-dicyano-10-methyl-9-oxo-8,16-diazatricyclo [13.3.1.0²,⁷]nonadeca-1(19),2(7),3,5,15,17-hexaen-14-yl]carbamate

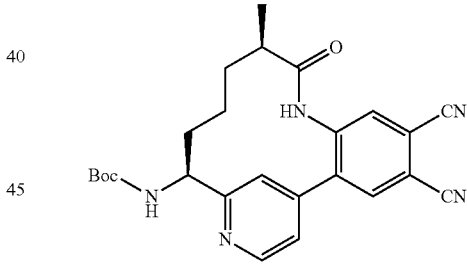

A 1:1 mixture of tert-butyl N-[(10R,14S)-4,5-dibromo-10-methyl-9-oxo-8,16-diazatricyclo[13.3.1.0²,⁷]nonadeca-1(19),2(7),3,5,15,17-hexaen-14-yl]carbamate and tert -butyl N-[(10R,14S)-5-bromo-10-methyl-9-oxo-8,16-diazatricyclo [13.3.1.0²,⁷]nonadeca -1(19),2(7),3,5,15,17-hexaen-14-yl] carbamate (168 mg, 0.35 mmol) in a microwave tube was added Zn(CN)₂ (62.4 mg, 0.53 mmol), Zn (6.95 mg, 0.11 mmol) and DMF (3.5 ml). The reaction was bubbled through with Ar for several min. Pd((P-tBu₃))₂ (18.10 mg, 0.04 mmol) was then added. The reaction was sealed and heated at 80° C. overnight then was cooled to rt. The reaction mixture was filtered and concentrated. The residue was purified by reverse phase preparative HPLC give tert-butyl N-[(10R,14S)-4,5-dicyano -10-methyl-9-oxo-8,16-diazatricyclo[13.3.1.0²,⁷]nonadeca-1(19),2(7),3,5,15,17-hexaen -14-yl]carbamate trifluoroacetate (30 mg, 15%) as a white solid. MS(ESI) m/z: 446.3 (M+H)⁺.

32C. Preparation of (10R,14S)-14-amino-10-methyl-9-oxo-8,16-diazatricyclo [13.3.1.0²,⁷]nonadeca-1(19),2(7),3,5,15,17-hexaene-4,5-dicarbonitrile

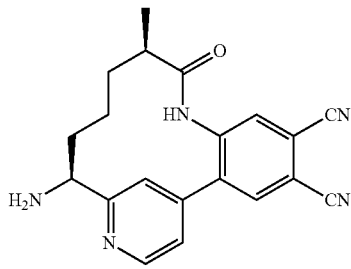 [SMILES: C[C@@H]1CCC[C@H](N)c2cc(ccn2)-c2cc(C#N)c(C#N)cc2NC1=O]

To tert-butyl N-[(10R,14S)-4,5-dicyano-10-methyl-9-oxo-8,16-diazatricyclo [13.3.1.0²,⁷]nonadeca-1(19),2(7),3,5,15,17-hexaen-14-yl]carbamate trifluoroacetate (10 mg, 0.02 mmol) in a 20 ml vial was added 4 N HCl in dioxane (223 µl, 0.89 mmol). The reaction was stirred at rt for 30 min, then concentrated to give (10R,14S)-14-amino-10-methyl-9-oxo-8,16-diazatricyclo[13.3.1.0²,⁷]nonadeca-1(19),2(7),3,5,15,17-hexaene-4,5-dicarbonitrile bis-hydrochloride (7.5 mg, 100%) as a yellow solid.

32D. Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo [13.3.1.0²,⁷]nonadeca-1(19),2(7),3,5,15,17-hexaene-4,5-dicarbonitrile trifluoroacetate

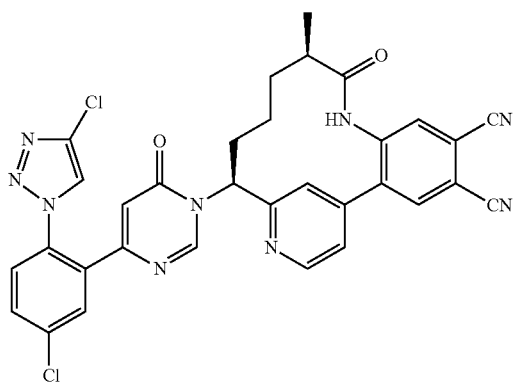 [SMILES: C[C@@H]1CCC[C@H](n2cnc(-c3cc(Cl)ccc3-n3cc(Cl)nn3)cc2=O)c2cc(ccn2)-c2cc(C#N)c(C#N)cc2NC1=O]

(10R,14S)-14-{4-[5-Chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0²,⁷]nonadeca -1(19),2(7),3,5,15,17-hexaene-4,5-dicarbonitrile trifluoroacetate (1.68 mg, 12% yield) was prepared in a similar manner as the procedure described in Example 129I, by using 6-[5-chloro-2-(4-chloro-1H-1,2,3-triazol-1-yl)phenyl]pyrimidin-4-ol (6.1 mg, 0.02 mmol), prepared as described in Example 9, and (10R,14S)-14-amino-10-methyl-9-oxo-8,16-diazatricyclo[13.3.1.0²,⁷]nonadeca-1(19),2(7),3,5,15,17-hexaene-4,5-dicarbonitrile.bis -hydrochloride (7.5 mg, 0.02 mmol). MS(ESI) m/z: 636.1 (M+H)⁺. ¹H NMR (400 MHz, CD₃OD) δ 9.03 (br. s., 1H), 8.77 (br. s., 1H), 8.29-8.06 (m, 2H), 7.88-7.55 (m, 6H), 7.46 (br. s., 1H), 6.34 (br. s., 1H), 6.07 (br. s., 1H), 2.70 (br. s., 1H), 2.19 (br. s., 1H), 2.09-1.83 (m, 2H), 1.60-1.25 (m, 2H), 0.93 (br. s., 3H), 0.52 (s, 1H). Analytical HPLC (Method A): RT=9.82 min, purity=98%; Factor XIa Ki=2.1 nM, Plasma Kallikrein Ki=84 nM.

EXAMPLE 33

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-8,16-diazatricyclo [13.3.1.0²,⁷]nonadeca -1(19),2,4,6,15,17-hexaen-9-one trifluoroacetate

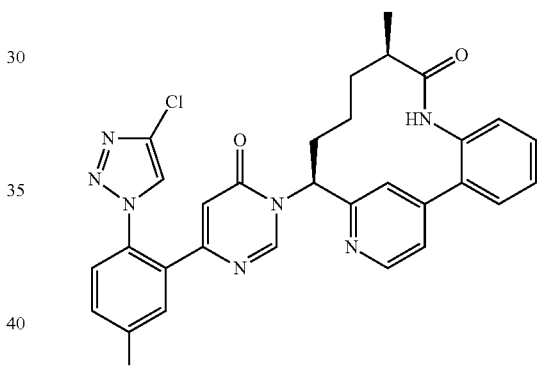

(10R,14S)-14-{4-[5-Chloro-2-(4-chloro-1H-1,2,3-triazol-1-yl)phenyl]-6-oxo-1,6dihydropyrimidin-1-yl}-10-methyl-8,16-diazatricyclo[13.3.1.0²,⁷]nonadeca -1(19),2,4,6,15,17-hexaen-9-one trifluoroacetate was prepared (97 mg, 13% yield) by treatment of (10R,14S)-14-amino-10-methyl-8,16-diazatricyclo[13.3.1.0²,⁷]nonadeca -1(19),2,4,6,15,17-hexaen-9-one (28 mg, 0.091 mmol) with 6-[5-chloro-2-(4-chloro-1H -1,2,3-triazol-1-yl)phenyl]pyrimidin-4-ol (27 mg, 0.091 mmol) following the procedures described in Example 129I. LCMS m/z 586.2 (M+H). ¹H NMR (400 MHz, CD₃OD) δ 8.82-8.74 (m, 1H), 8.40 (s, 1H), 8.07-8.01 (m, 1H), 7.92-7.89 (m, 1H), 7.76 (d, J=2.4 Hz, 2H), 7.68 (s, 2H), 7.61-7.49 (m, 2H), 7.35-7.30 (m, 1H), 6.42 (s, 1H), 5.96-5.88 (m, 1H), 2.78-2.66 (m, 1H), 2.47-2.34 (m, 1H), 2.20-2.09 (m, 1H), 2.04-1.89 (m, 1H), 1.62-1.47 (m, 2H), 1.01 (d, J=6.8 Hz, 3H), 0.84-0.67 (m, 1H). Orthogonal purity 99% with RT of 7.78 min; Factor XIa Ki=0.28 nM, Plasma Kallikrein Ki=23 nM.

EXAMPLE 34

(10R,14,5)-14-{4-[3-Chloro-6-(4-chloro-1H-1,2,3-triazol-1-yl)-2-fluorophenyl]-6-oxo-1,6-dihydropyrimidin-1-yl}-5-(hydroxymethyl)-10-methyl-8,16-diazatricyclo[13.3.1.0$^{2,7}$]nonadeca-1(19),2(7),3,5,15,17-hexaen-9-one trifluoroacetate

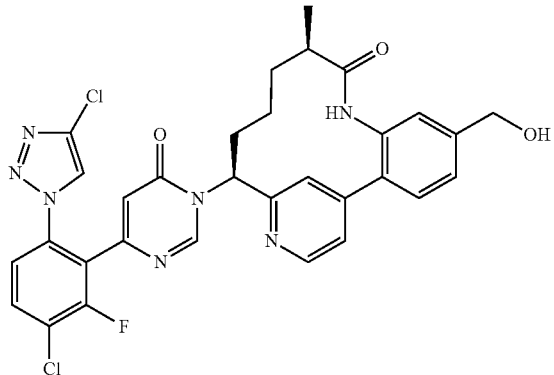 [SMILES: C[C@@H]1CCC[C@H](n2cnc(-c3c(-n4cc(Cl)nn4)ccc(Cl)c3F)cc2=O)c2cc(ccn2)-c2ccc(CO)cc2NC1=O]

34A. Preparation of (10R,14S)-14-{[(tert-butoxy)carbonyl]amino}-10-methyl-9-oxo -8,16-diazatricyclo[13.3.1.0$^{2,7}$]nonadeca-1(19),2(7),3,5,15,17-hexaene-5-carboxylic acid trifluoroacetate

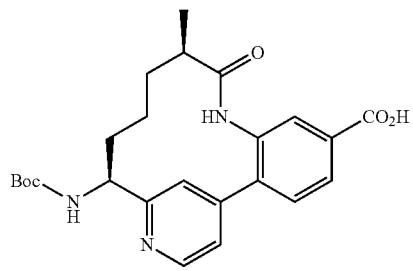 [SMILES: C[C@@H]1CCC[C@H](NC(=O)OC(C)(C)C)c2cc(ccn2)-c2ccc(C(=O)O)cc2NC1=O]

To a solution of (10R,14S)-14-{[(tert-butoxy)carbonyl]amino}-10-methyl-9-oxo -8,16-diazatricyclo[13.3.1.0$^{2,7}$]nonadeca-1(19),2(7),3,5,15,17-hexaene-5-carboxylate (60 mg, 0.13 mmol), prepared in a similar manner as described in Example 126D, in MeOH (2 mL) at rt was added LiOH (0.40 mL, 0.79 mmol) and the resulting solution was stirred at rt overnight. Purification by reverse phase chromatography gave (10R,14S)-14-{[(tert -butoxy)carbonyl]amino}-10-methyl-9-oxo-8,16-diazatricyclo[13.3.1.0$^{2,7}$]nonadeca -1(19),2(7),3,5,15,17-hexaene-5-carboxylic acid trifluoroacetate (63 mg, 86% yield as a white solid. MS(ESI) m/z: 440.5 (M+H)$^+$.

34B. Preparation of tert-butyl N-[(10R,14S)-5-(hydroxymethyl)-10-methyl-9-oxo-8,16-diazatricyclo[13.3.1.0$^{2,7}$]nonadeca-1(19),2(7),3,5,15,17-hexaen-14-yl]carbamate

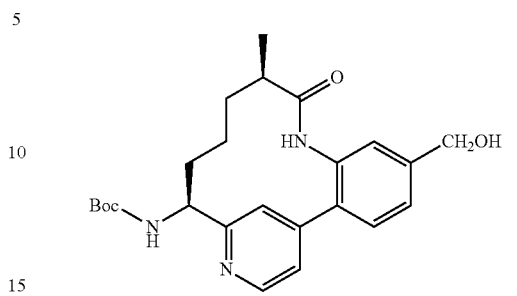

To a solution of (10R,14,5)-14- {[(tert-butoxy)carbonyl]amino}-10-methyl-9-oxo 8,16-diazatricyclo[13.3.1.0$^{2,7}$]nonadeca-1(19),2(7),3,5,15,17-hexaene-5-carboxylic acid trifluoroacetate (63 mg, 0.11 mmol) in THF (1 mL) was added BOP (127 mg, 0.28 mmol) and DIEA (0.1 mL, 0.57 mmol). The solution was stirred at rt for 30 min, then NaBH$_4$ (86 mg, 2.28 mmol) was added portionwise. After 5 min, the reaction mixture was quenched with MeOH, cooled to rt, and concentrated to yield a crude white solid product, which was redissolved in EtOAc, washed with water and brine, dried over MgSO$_4$, filtered and concentrated. The residue was purified by normal phase chromatography to give tert-butyl N-[(10R,14S)-5-(hydroxymethyl)-10-methyl-9-oxo-8,16-diazatricyclo [13.3.1.0$^{2,7}$]nonadeca-1(19),2(7),3,5,15,17-hexaen-14-yl]carbamate (30 mg, 61.9% yield) as a white solid. MS(ESI) m/z: 426.3 (M+H)$^+$ 34C. Preparation of (10R,14S)-14-amino-5-(hydroxymethyl)-10-methyl-8,16-diazatricyclo[13.3.1.0$^{2,7}$]nonadeca-1(19),2(7),3,5,15,17-hexaen-9-one

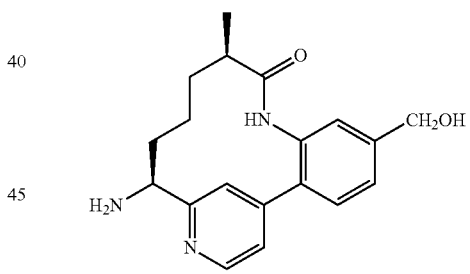

To a solution of tert-butyl N-[(10R,14S)-5-(hydroxymethyl)-10-methyl-9-oxo -8,16-diazatricyclo[13.3.1.0$^{2,7}$]nonadeca-1(19),2(7),3,5,15,17-hexaen-14-yl]carbamate (30 mg, 0.07 mmol) in DCM (1 mL) was added TFA (0.16 mL, 2.11 mmol). The solution was stirred at rt for 1 h, then was concentrated. The residue was dissolved in MeOH, passed through HCO$_3$ resin cartridge, rinsed with MeOH. The filtrate was concentrated to give (10R,14S)-14-amino-5-(hydroxymethyl)-10-methyl-8,16-diazatricyclo[13.3.1.0$^{2,7}$]nonadeca-1(19),2(7),3,5,15,17-hexaen-9-one (23 mg, 100% yield) as a white solid. MS(ESI) m/z: 326.08 (M+H)$^+$.

34D. Preparation of (10R,14S)-14-{4-[3-chloro-6-(4-chloro-1H-1,2,3-triazol-1-yl)-2-fluorophenyl]-6-oxo-1,6-dihydropyrimidin-1-yl}-5-(hydroxymethyl)-10-methyl-8,16-diazatricyclo[13.3.1.0$^{2,7}$]nonadeca-1(19),2(7),3,5,15,17-hexaen-9-one trifluoroacetate (10R,14S)-14-{4-[3-Chloro-6-(4-chloro-1H-1,2,3-triazol-1-yl)-2-fluorophenyl]-6-oxo-1,6-dihydropyrimidin-1- yl}-5-(hydroxymethyl)-10-methyl-8,16-diazatricyclo[13.3.1.0²,⁷]nonadeca-1(19),2(7),3,5,15,17-hexaen-9-one trifluoroacetate (5.37 mg, 22% yield) was prepared in a similar manner as the procedure described In Example 98, by replacing (10R,14S)-14-amino-10-methyl-9-oxo-8,16-diazatricyclo[13.3.1.0²,⁷]nonadeca -1(19),2(7),3,5,15,17-hexaene-4-carbonitrile with (10R,14S)-14-amino-5-(hydroxymethyl)-10-methyl-8,16-diazatricyclo[13.3.1.0²,⁷]nonadeca -1(19),2(7),3,5,15,17-hexaen-9-one. MS(ESI) m/z: 634.2 (M+H)⁺. ¹H NMR (400 MHz, CD₃OD) δ 8.95 (s, 1H), 8.70 (d, J=5.1 Hz, 1H), 8.36 (s, 1H), 7.90 (dd, J=8.6, 7.7 Hz, 1H), 7.79 (s, 1H), 7.67-7.56 (m, 2H), 7.53-7.44 (m, 2H), 7.31 (s, 1H), 6.63 (s, 1H), 6.09-5.96 (m, 1H), 4.72 (s, 2H), 2.72 (br. s., 1H), 2.35-2.18 (m, 1H), 2.14-1.99 (m, 1H), 1.63-1.45 (m, 2H), 1.41-1.29 (m, 1H), 1.01 (d, J=7.0 Hz, 3H), 0.86-0.58 (m, 1H). Analytical HPLC (Method A): RT=7.28 min, purity>99%; Factor XIa Ki=5.7 nM, Plasma Kallikrein Ki=120 nM.

EXAMPLE 35

Preparation of (10R,14S)-14-{4-[3-chloro-2-fluoro-6-(1H-1,2,3,4-tetrazol-1-yl)phenyl]-6-oxo-1,6-dihydropyrimidin-1-yl}-4-fluoro-10-methyl-8,16-diazatricyclo[13.3.1.0²,⁷]nonadeca-1(19),2(7),3,5,15,17-hexaen-9-one trifluoroacetate

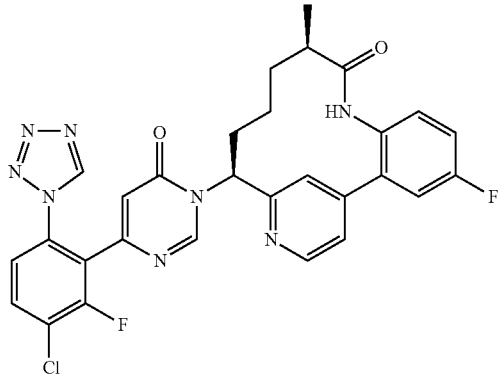 [SMILES: C[C@@H]1CCC[C@H](n2cnc(-c3c(-n4cnnn4)ccc(Cl)c3F)cc2=O)c2cc(ccn2)-c2cc(F)ccc2NC1=O]

(10R,14S)-14-{4-[3-Chloro-2-fluoro-6-(1H-1,2,3,4-tetrazol-1-yl)phenyl]-6-oxo -1,6-dihydropyrimidin-1-yl}-4-fluoro-10-methyl-8,16-diazatricyclo[13.3.1.0²,⁷]nonadeca -1(19),2(7),3,5,15,17-hexaen-9-one trifluoroacetate (6.4 mg, 43% yield) was prepared in a similar manner as the procedure described in Example 126 by using 6-[3-chloro-2-fluoro -6-(1H-1,2,3,4-tetrazol-1-yl)phenyl]pyrimidin-4-ol, prepared as described in Example 17, and (10R,14S)-14-amino-4-fluoro-10-methyl-8,16-diazatricyclo[13.3.1.0²,⁷]nonadeca -1(19),2(7),3,5,15,17-hexaen-9-one, prepared as described in Example 28. MS(ESI) m/z: 589.2 (M+H)⁺. ¹H NMR (400 MHz, CD₃OD) δ 9.46 (s, 1H), 8.89 (s, 1H), 8.71 (d, J=5.1 Hz, 1H), 7.93 (dd, J=8.7, 7.6 Hz, 1H), 7.78 (s, 1H), 7.63 (dd, J=8.6, 1.5 Hz, 1H), 7.49 (dd, J=5.2, 1.7 Hz, 1H), 7.43 (dd, J=9.0, 2.9 Hz, 1H), 7.35-7.22 (m, 2H), 6.69 (d, J=0.7 Hz, 1H), 6.01 (dd, J=12.5, 4.6 Hz, 1H), 2.73-2.62 (m, 1H), 2.29-2.16 (m, 1H), 2.12-1.91 (m, 2H), 1.59-1.39 (m, 2H), 1.00 (d, J=7.0 Hz, 3H), 0.74 (br. s., 1H) Analytical HPLC (Method A): RT=8.27 min, purity=>98%; Factor XIa Ki=0.1 nM, Plasma Kallikrein Ki=8 nM.

EXAMPLE 36

Preparation of (10R,14S)-14-{4-[5-chloro-2-(1H-1,2,3,4-tetrazol-1-yl)phenyl]-6-oxo-1,6-dihydropyrimidin-1-yl}-4-fluoro-10-methyl-8,16-diazatricyclo[13.3.1.0²,⁷]nonadeca -1(19),2(7),3,5,15,17-hexaen-9-one trifluoroacetate

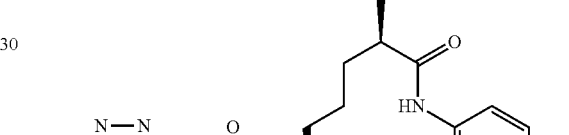

(10R,14S)-14-{4-[5-Chloro-2-(1H-1,2,3,4-tetrazol-1-yl)phenyl]-6-oxo-1,6-dihydropyrimidin-1-yl}-4-fluoro-10-methyl-8,16-diazatricyclo[13.3.1.0²,⁷]nonadeca -1(19),2(7),3,5,15,17-hexaen-9-one trifluoroacetate (17.6 mg, 46% yield) was prepared in a similar manner as the procedure described in Example 35 by replacing 6-[3-chloro-2- fluoro-6-(1H-1,2,3,4-tetrazol-1-yl)phenyl]pyrimidin-4-ol, with 6-[5-chloro-2-(1H-1,2,3,4-tetrazol-1-yl)phenyl]pyrimidin-4-ol, prepared as described in Example 20. MS(ESI) m/z: 571.2 (M+H)⁺. ¹H NMR (400 MHz, CD₃OD) δ 9.41 (s, 1H), 8.75 (d, J=5.7 Hz, 1H), 8.49 (s, 1H), 8.15 (s, 1H), 7.85 (d, J=2.2 Hz, 2H), 7.76-7.69 (m, 1H), 7.67-7.61 (m, 1H), 7.47 (d, J=8.4 Hz, 1H), 7.29 (d, J=5.9 Hz, 2H), 6.54 (s, 1H), 5.74 (dd, J=12.7, 4.7 Hz, 1H), 2.69-2.54 (m, 1H), 2.47-2.30 (m, 1H), 2.22-2.07 (m, 1H), 1.90-1.79 (m, 1H), 1.61-1.35 (m, 1H), 0.92 (d, J=7.0 Hz, 3H), 0.77-0.51 (m, 1H) Analytical HPLC (Method A): RT=8.22 min, purity=>99%; Factor XIa Ki=0.1 nM, Plasma Kallikrein Ki=8 nM.

143
EXAMPLE 37

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-5-(hydroxymethyl)-10-methyl-8,16-diazatricyclo[13.3.1.0$^{2,7}$]nonadeca-1(19),2(7),3,5,15,17-hexaen-9-one trifluoroacetate

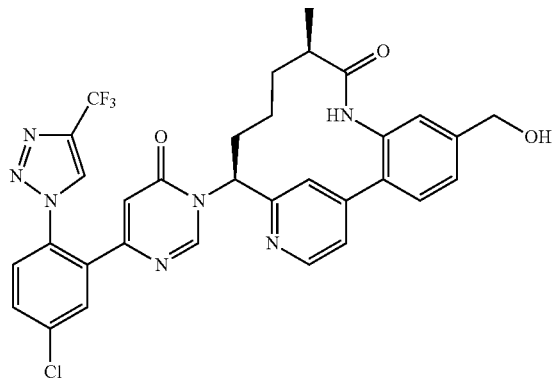 [SMILES: C[C@@H]1CCC[C@H](n2cnc(-c3cc(Cl)ccc3-n3cc(C(F)(F)F)nn3)cc2=O)c2cc(ccn2)-c2ccc(CO)cc2NC1=O]

(10R,14S)-14-(4-{5-Chloro-2-[4-(trifluoromethyl)-1H-1,2,3-triazol-1-yl]phenyl}-6-oxo-1,6-dihydropyrimidin-1-yl)-5-(hydroxymethyl)-10-methyl-8,16-diazatricyclo [13.3.1.0$^{2,7}$]nonadeca-1(19),2(7),3,5,15,17-hexaen-9-one trifluoroacetate (7.7 mg, 29% yield) was prepared in a similar manner as the procedure described in Example 34 by replacing 6-[3-chloro-6-(4-chloro-1H-1,2,3-triazol-1-yl)-2-fluorophenyl]pyrimidin-4-ol with 6-{5-chloro-2-[4-(trifluoromethyl)-1H-1,2,3-triazol-1-yl]phenyl}pyrimidin-4-ol, prepared as described in Example 15. MS(ESI) m/z: 650.08 (M+H)$^+$. $^1$H NMR (400MHz, CD$_3$OD) δ 8.86 (s, 2H), 8.68 (d, J=5.3 Hz, 1H), 7.93 (d, J=2.2 Hz, 1H), 7.86-7.75 (m, 2H), 7.74-7.69 (m, 1H), 7.62 (d, J=7.9 Hz, 1H), 7.55 (dd, J=5.1, 1.5 Hz, 1H), 7.48 (dd, J=7.9, 1.3 Hz, 1H), 7.30 (d, J=1.3 Hz, 1H), 6.47 (s, 1H), 5.99 (dd, J=12.5, 4.6 Hz, 1H), 4.71 (s, 2H), 2.77-2.65 (m, 1H), 2.34-2.21 (m, 1H), 2.12-1.93 (m, 2H), 1.60-1.44 (m, 2H), 1.00 (d, J=6.8 Hz, 3H), 0.74 (br. s., 1H). Analytical HPLC (Method A): RT=8.19 min, purity=>98%; Factor XIa Ki=0.18 nM, Plasma Kallikrein Ki=18 nM.

144
EXAMPLE 38

Preparation of (10R,14,5)-14-{4-[5-chloro-2-(4-cyano-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-5-carbonitrile trifluoroacetate

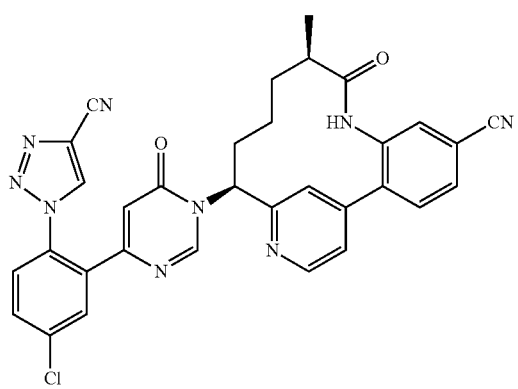 [SMILES: C[C@@H]1CCC[C@H](n2cnc(-c3cc(Cl)ccc3-n3cc(C#N)nn3)cc2=O)c2cc(ccn2)-c2ccc(C#N)cc2NC1=O]

(10R,14S)-14-{4-[5-Chloro-2-(4-cyano-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7),3,5,15,17-hexaene-5-carbonitrile trifluoroacetate (8.8 mg, 27% yield) was prepared in a similar manner as the procedure described in Example 194 by replacing 6-[5-chloro-2-(4-chloro-1H-1,2,3-triazol-1-yl)phenyl]pyrimidin-4-ol with 1-[4-chloro-2-(6-hydroxypyrimidin-4-yl)phenyl]-1H-1,2,3-triazole-4-carbonitrile, prepared as described in Example 18. MS(ESI) m/z: 602.20 (M+H)$^+$. $^1$H NMR (500 MHz, DMSO-d$_6$) δ 10.02 (s, 1H), 9.25 (s, 1H), 8.76 (s, 1H), 8.64 (d, J=4.9 Hz, 1H), 7.93-7.70 (m, 5H), 7.65 (s, 2H), 7.43 (d, J=4.9 Hz, 1H), 6.45 (s, 1H), 5.84 (d, J=8.2 Hz, 1H), 2.60 (br. s., 1H), 2.15 (br. s., 1H), 1.84 (br. s., 2H), 1.34 (br. s., 2H), 0.80 (d, J=6.4 Hz, 3H), 0.37 (br. s., 1H) Analytical HPLC (Method C): RT=1.717 min, purity=100%; Factor XIa Ki=0.21 nM, Plasma Kallikrein Ki=19 nM.

EXAMPLE 39

Preparation of (10R,14S)-14-{4-[5-chloro-2-(4-chloro-1H-1,2,3-triazol-1-yl)phenyl]-6-oxo-1,6-dihydropyrimidin-1-yl}-4-fluoro-12-hydroxy-10-methyl-8,16-diazatricyclo [13.3.1.0$^{2,7}$]nonadeca-1(19),2(7),3,5,15,17-hexaen-9-one trifluoroacetate

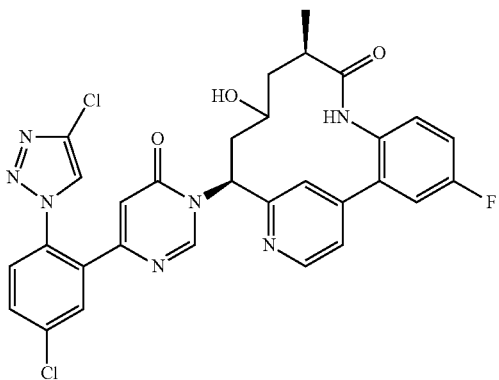 [SMILES: C[C@@H]1CC(O)C[C@H](n2cnc(-c3cc(Cl)ccc3-n3cc(Cl)nn3)cc2=O)c2cc(ccn2)-c2cc(F)ccc2NC1=O]

39A. Preparation of tert-butyl N-[(10R,14S)-4-fluoro-12-hydroxy-10-methyl-9-oxo -8,16-diazatricyclo[13.3.1.0$^{2,7}$]nonadeca-1(19),2(7),3,5,15,17-hexaen-14-yl]carbamate, and tert-butyl N-[(10R,14S)-4-fluoro-11-hydroxy-10-methyl-9-oxo-8,16-diazatricyclo [13.3.1.0$^{2,7}$]nonadeca-1(19),2(7),3,5,15,17-hexaen-14-yl]carbamate

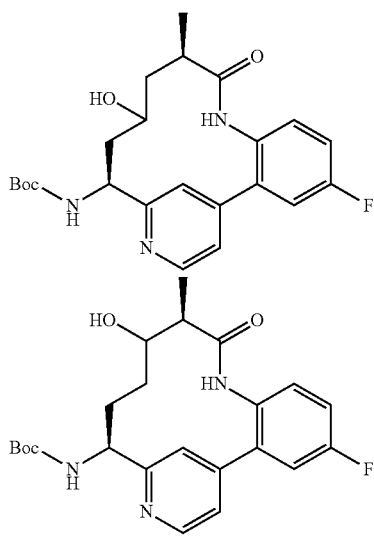

To a solution of tert-butyl N-[(10R,11E,14S)-4-fluoro-10-methyl-9-oxo-8,16-diazatricyclo[13.3.1.0$^{2,7}$]nonadeca-1(19),2(7),3,5,11,15,17-heptaen-14-yl]carbamate (829 mg, 2.02 mmol) in THF (20.1 ml) was added dropwise BH$_3$.THF (2.02 ml, 2.02 mmol) at 0° C. After addition, the ice water bath was removed and the reaction was warmed up to rt and stirred for 3 h. Additional BH$_3$.THF (3.02 ml, 3.02 mmol) was added. The reaction mixture was cooled to 0° C. and NaOAc solution (13.43 ml, 40.3 mmol) was added followed by addition of H$_2$O$_2$ (5.29 ml, 60.4 mmol) dropwise. The reaction was then warmed to rt and stirred at rt for 1 h. The reaction was then quenched with water (5 ml). The layers were separated. The aqueous layer was extracted with EtOAc (2 ×). The combined EtOAc layers was washed with water and brine, dried over MgSO$_4$, filtered and concentrated. Purification by normal phase chromatography gave tert-butyl N -[(10R,14S)-4-fluoro-12-hydroxy-10-methyl-9-oxo-8,16-diazatricyclo[13.3.1.0$^{2,7}$]nonadeca-1(19),2(7),3,5,15,17-hexaen-14-yl]carbamate and tert-butyl N-[(10R,14S)-4-fluoro-11-hydroxy-10-methyl-9-oxo-8,16-diazatricyclo [13.3.1.0$^{2,7}$]nonadeca -1(19),2(7),3,5,15,17-hexaen-14-yl] carbamate (625 mg, 72% yield) as a pale yellow solid (mixture of 4 diastereomers). MS(ESI) m/z: 430.1 (M+H)$^+$.

39B. Preparation of tert-butyl N-[(10R,14S)-4-fluoro -10-methyl-9,12-dioxo-8,16-diazatricyclo[13.3.1.0$^{2,7}$]nonadeca-1(19),2(7),3,5,15,17-hexaen-14-yl]carbamate

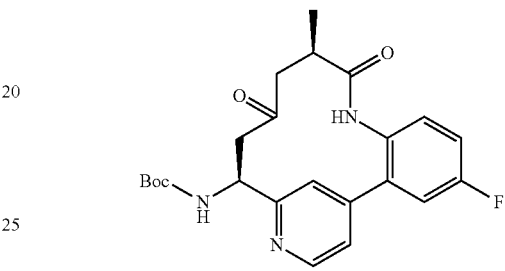

To a solution of tert-butyl N-[(10R,14S)-4-fluoro-12-hydroxy-10-methyl-9-oxo -8,16-diazatricyclo[13.3.1.0$^{2,7}$]nonadeca-1(19),2(7),3,5,15,17-hexaen-14-yl]carbamate and tert-butyl N-[(10R,14S)-4-fluoro-11-hydroxy-10-methyl-9-oxo-8,16-diazatricyclo [13.3.1.0$^{2,7}$]nonadeca-1(19),2(7),3,5,15,17-hexaen-14-yl]carbamate (391 mg, 0.91 mmol) in DCM (9.10 ml) was added Dess Martin's reagent (502 mg, 1.184 mmol) at rt. After 1 h, the reaction mixture was diluted with DCM, washed with H$_2$O, NaHCO$_3$, and brine. The combined organic layers was dried over MgSO$_4$, filtered, and concentrated. Purification by normal phase chromatography gave tert-butyl N-[(10R,14S)-4-fluoro-10-methyl-9,12-dioxo-8,16-diazatricyclo[13.3.1.0$^{2,7}$]nonadeca-1(19),2(7),3,5,15,17-hexaen -14-yl]carbamate (257 mg, 66%). MS(ESI) m/z: 428.1 (M+H)$^+$.

39C. Preparation of tert-butyl N-[(10R,14S)-4-fluoro-12-hydroxy-10-methyl-9-oxo-8,16-diazatricyclo[13.3.1.0$^{2,7}$]nonadeca-1(19),2(7),3,5,15 ,17-hexaen-14-yl]carbamate

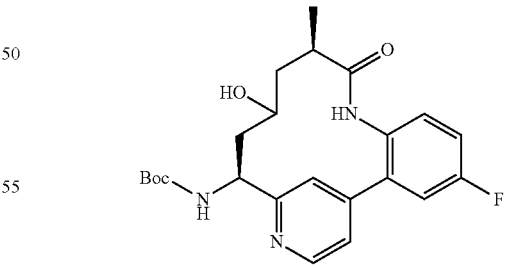

To a suspension of tert-butyl N-[(10R,14S)-4-fluoro-10-methyl-9,12-dioxo-8,16-diazatricyclo[13.3.1.0$^{2,7}$]nonadeca-1(19),2(7),3,5,15,17-hexaen-14-yl]carbamate (53 mg, 0.12 mmol) in MeOH (1.3 ml) at 0° C. was added NaBH$_4$ (23.45 mg, 0.620 mmol). Bubbles formed and the reaction became clear within several min. Sat NH$_4$Cl was added. The reaction was concentrated and partitioned between DCM and NH$_4$Cl. The organic layer was washed with brine, dried over MgSO$_4$, filtered and concentrated. Purification by normal phase chromatography gave tert-butyl N-[(10R,14S)-4-fluoro-12-hydroxy-10-methyl-9-oxo-8,16-diazatricyclo[13.3.1.0$^{2,7}$]nonadeca-1(19),2(7),3,5,15,17-hexaen-14-yl]carbamate (33 mg, 62%) as a white solid. MS(ESI) m/z: 430.2 (M+H)$^+$.

39D. Preparation of (10R,14S)-14-amino-4-fluoro-12-hydroxy-10-methyl-8,16-diazatricyclo[13.3.1.0$^{2,7}$]nonadeca-1(19),2(7),3,5,15,17-hexaen-9-one

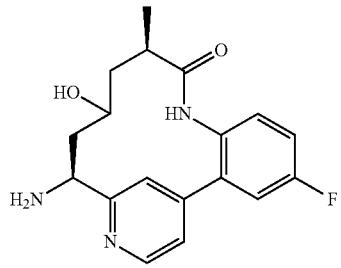 [SMILES: C[C@@H]1CC(O)C[C@H](N)c2cc(ccn2)-c2cc(F)ccc2NC1=O]

To a solution of tert-butyl N-[(10R,14S)-4-fluoro-12-hydroxy-10-methyl-9-oxo -8,16-diazatricyclo[13.3.1.0$^{2,7}$]nonadeca-1(19),2(7),3,5,15,17-hexaen-14-yl]carbamate (25 mg, 0.06 mmol) in DCM (1 mL) was added TFA (0.14 mL, 1.75 mmol). The reaction was stirred at rt for 1 h. The reaction was concentrated and the residue was dissolved in MeOH, passed through NaHCO$_3$ cartridge, and concentrated to give (10R,14S)-14-amino -4-fluoro-12-hydroxy-10-methyl-8,16-diazatricyclo[13.3.1.0$^{2,7}$]nonadeca -1(19),2(7),3,5,15,17-hexaen-9-one (19 mg, 99%) as a white solid. MS(ESI) m/z: 330.4 (M+H)$^+$.

39E. Preparation of (10R,14S)-14-{4-[5-chloro-2-(4-chloro-1H-1,2,3-triazol-1-yl)phenyl]-6-oxo-1,6-dihydropyrimidin-1-yl}-4-fluoro-12-hydroxy-10-methyl-8,16-diazatricyclo[13.3.1.0$^{2,7}$]nonadeca-1(19),2(7),3,5,15,17-hexaen-9-one trifluoroacetate (10R,14S)-14-{4-[5-Chloro-2-(4-chloro-1H-1,2,3-triazol-1-yl)phenyl]-6-oxo-1,6-dihydropyrimidin-1-yl}-4-fluoro-12-hydroxy-10-methyl-8,16-diazatricyclo[13.3.1.0$^{2,7}$]nonadeca-1(19),2(7),3,5,15,17-hexaen-9-one trifluoroacetate (17.5 mg, 61% yield) was prepared in a similar manner as the procedure described In Example 129I by using 6-[5-chloro-2-(4-chloro-1H-1,2,3-triazol-1-yl)phenyl]pyrimidin-4-ol (11.7 mg, 0.04 mmol), prepared as described in Example 9 and (10R,14S)-14-amino-4-fluoro-12-hydroxy-10-methyl-8,16-diazatricyclo[13.3.1.0$^{2,7}$]nonadeca-1(19),2(7),3,5,15,17-hexaen-9-one (12.5 mg, 0.04 mmol), prepared as described in Example 28. MS(ESI) m/z: 620.1 (M+H)$^+$. $^1$H NMR (400 MHz, CD$_3$OD) δ 9.16 (s, 1H), 8.68 (d, J=5.1 Hz, 1H), 8.34-8.33 (m, 1H), 7.88 (d, J=2.4 Hz, 1H), 7.72 (dd, J=6.2, 2.4 Hz, 1H), 7.69 (d, J=0.9 Hz, 1H), 7.64 (d, J=8.4 Hz, 1H), 7.46 (dd, J=5.1, 1.8 Hz, 1H), 7.40 (dd, J=9.0, 2.9 Hz, 1H), 7.29-7.19 (m, 2H), 6.36 (d, J=0.7 Hz, 1H), 6.05 (dd, J=11.3, 5.8 Hz, 1H), 3.35 (s, 1H), 2.80 (ddd, J=7.0, 5.6, 3.3 Hz, 2H), 2.44-2.34 (m, 1H), 2.21-2.08 (m, 2H), 1.61 (ddd, J=14.8, 8.6, 5.8 Hz, 1H), 1.11 (d, J=7.0 Hz, 3H). Analytical HPLC (Method A): RT=8.09 min, purity=97%; Factor XIa Ki=0.87 nM, Plasma Kallikrein Ki=40 nM.

EXAMPLE 40

Preparation of (10R,14S)-14-{4-[3-chloro-6-(4-chloro-1H-1,2,3-triazol-1-yl)-2-fluorophenyl]-6-oxo-1,6-dihydropyrimidin-1-yl}-4-fluoro-12-hydroxy-10-methyl-8,16-diazatricyclo[13.3.1.0$^{2,7}$]nonadeca-1(19),2(7),3,5,15,17-hexaen-9-one trifluoroacetate

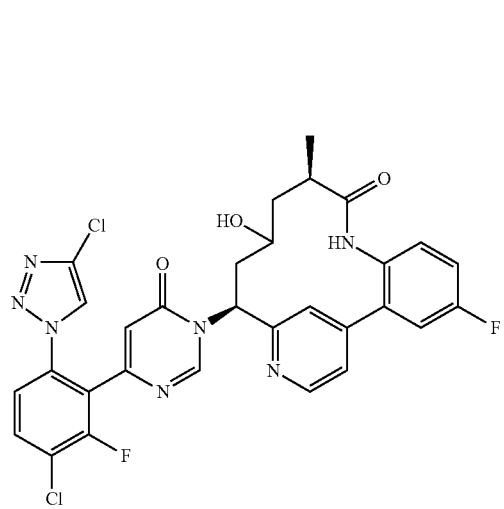 [SMILES: C[C@@H]1CC(O)C[C@H](n2cnc(-c3c(-n4cc(Cl)nn4)ccc(Cl)c3F)cc2=O)c2cc(ccn2)-c2cc(F)ccc2NC1=O]

(10R,14S)-14-{4-[3-Chloro-6-(4-chloro-1H-1,2,3-triazol-1-yl)-2-fluorophenyl]-6-oxo-1,6-dihydropyrimidin-1-yl}-4-fluoro-12-hydroxy-10-methyl-8,16-diazatricyclo[13.3.1.0$^{2,7}$]nonadeca-1(19),2(7),3,5,15,17-hexaen-9-one trifluoroacetate (14.0 mg, 40% yield) was prepared in a similar manner as the procedure described in Example 129I, by using 6-[3-chloro-6-(4-chloro-1H-1,2,3-triazol-1-yl)-2-fluorophenyl]pyrimidin-4-ol hydrobromide (19 mg, 0.05 mmol), prepared as described in Example 10, and (10R,14S)-14-amino-4-fluoro-12-hydroxy-10-methyl-8,16-diazatricyclo[13.3.1.0$^{2,7}$]nonadeca -1(19),2(7),3,5,15,17-hexaen-9-one (15 mg, 0.05 mmol), prepared as described in Example 28. MS(ESI) m/z: 638.1 (M+H)$^+$. $^1$H NMR (400 MHz, CD$_3$OD) δ 9.14 (s, 1H), 8.76 (d, J=5.3 Hz, 1H), 8.38 (s, 1H), 7.89 (dd, J=8.7, 7.6 Hz, 1H), 7.83 (s, 1H), 7.58 (dt, J=7.0, 1.7 Hz, 2H), 7.47 (dd, J=8.9, 2.5 Hz, 1H), 7.35-7.25 (m, 2H), 6.66 (s, 1H), 6.07 (dd, J=11.1, 5.8 Hz, 1H), 2.91-2.79 (m, 2H), 2.53-2.42 (m, 1H), 2.28-2.13 (m, 2H), 1.72-1.60 (m, 1H), 1.15 (d, J=7.0 Hz, 3H). Analytical HPLC (Method A): RT=8.40 min, purity=98%; Factor XIa Ki=0.24 nM, Plasma Kallikrein Ki=13 nM.

EXAMPLE 41

Preparation of methyl (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo [13.3.1.0$^{2,7}$]nonadeca-1(19),2(7),3,5,15,17-hexaene-5-carboxylate trifluoroacetate

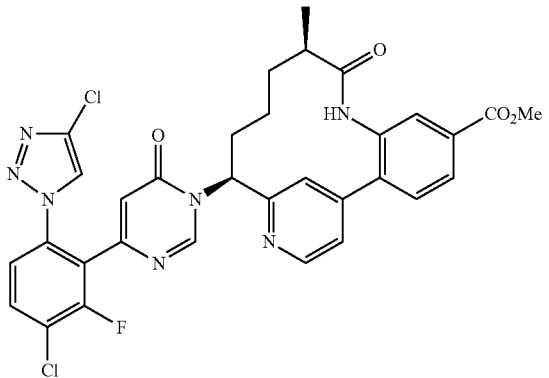 [SMILES: COC(=O)c1ccc2c(c1)NC(=O)[C@H](C)CCC[C@H](n1cnc(-c3c(-n4cc(Cl)nn4)ccc(Cl)c3F)cc1=O)c1cc-2ccn1]

41A. Preparation of methyl 3-amino-4-{2-[(1S)-1-{[(tert-butoxy)carbonyl]amino}but-3-en-1-yl]pyridin-4-yl}benzoate

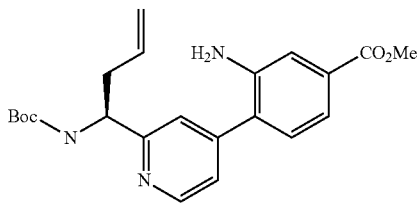 [SMILES: C=CC[C@H](NC(=O)OC(C)(C)C)c1cc(-c2ccc(C(=O)OC)cc2N)ccn1]

A sealable flask containing tert-butyl N-[(1S)-1-(4-chloropyridin-2-yl)but-3-en-1-yl]carbamate, prepared as described in Example 23 (2 g, 7.07 mmol) and (2-amino-4-(methoxycarbonyl)phenyl)boronic acid hydrochloride (1.72 g, 7.43 mmol) in DMSO (35.4 ml) and water (0.64 ml, 35.4 mmol) was purged with Ar for 30 min. Then 3 M K$_3$PO$_4$ (3.00 g, 14.15 mmol) and Pd(dppf)Cl$_2$.CH$_2$Cl$_2$ complex (0.52 g, 0.71 mmol) were added. The dark red reaction mixture was sealed and heated to 90° C. for 48 h. Additional (2-amino-4-(methoxycarbonyl)phenyl)boronic acid hydrochloride (0.51 g, 2.22 mmol) and Pd(dppf)Cl$_2$.CH$_2$Cl$_2$ complex (0.39 g, 0.53 mmol) were added. The reaction was purged with Ar, sealed, and reheated to 90° C. for 48 h. The reaction mixture was diluted with EtOAc and washed with water and brine, dried over MgSO$_4$, filtered and concentrated to give the crude product as a black oil. Purification by normal phase chromatography gave methyl 3-amino-4-{2-[(1S)-1-{[(tert-butoxy)carbonyl]amino}but -3-en-1-yl]pyridin-4-yl}benzoate (2.3 g, 82%) as an orange foam. MS(ESI) m/z: 398.2 (M+H)$^+$.

41B. Preparation of methyl 4-{2-[(1S)-1-{[(tert-butoxy)carbonyl]amino}but-3-en-1-yl]pyridin-4-yl}-3-[(2R)-2-methylbut-3-enamido]benzoate

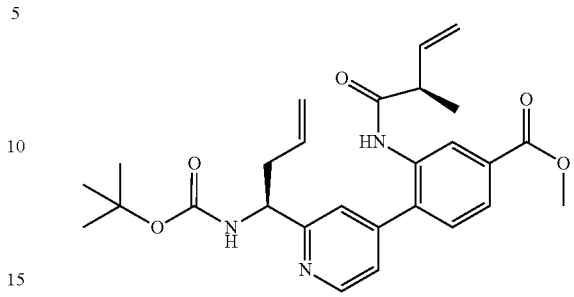

To a cooled (−10° C.) clear, yellow solution of methyl 3-amino-4-{2-[(1S)-1-{[(tert-butoxy)carbonyl]amino}but-3-en-1-yl]pyridin-4-yl}benzoate (2.3 g, 5.79 mmol) and (2R)-2-methylbut-3-enoic acid (0.87 g, 8.68 mmol), prepared as described in Example 2, in EtOAc (57.9 ml) was added pyridine (1.40 ml, 17.36 mmol) and T3P® (6.82 ml, 11.57 mmol). Following the addition, the reaction was allowed to warm to rt. The reaction was quenched with sat aq NaHCO$_3$ and diluted with EtOAc. The organic layer was washed with brine, and dried over MgSO$_4$, filtered and concentrated. Purification by normal phase chromatography gave methyl 4-{2-[(1S)-1-{[(tert -butoxy)carbonyl]amino}but-3-en-1-yl]pyridin-4-yl}-3-[(2R)-2-methylbut-3-enamido]benzoate (2.42 g, 87%) as a yellow foam. MS(ESI) m/z: 480.2 (M+H)$^+$.

41C. Preparation of methyl (10R,11E,14S)-14-{[(tert-butoxy)carbonyl]amino}-10-methyl-9-oxo-8,16-diazatricyclo [13.3.1.0$^{2,7}$]nonadeca-1(19),2(7),3,5,11,15,17-heptaene-5-carboxylate

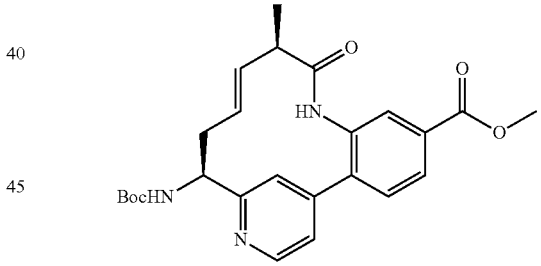

To a solution of methyl 4-{2-[(1S)-1-{[(tert-butoxy)carbonyl]amino}but-3-en-1-yl]pyridin-4-yl}-3-[(2R)-2-methylbut-3-enamido]benzoate (2.57 g, 5.04 mmol) in DCM (720 ml) was added pTsOH.H$_2$O (1.05 g, 5.54 mmol). The reaction mixture was purged with Ar for 30 min, then warmed to 40° C. and stirred at 40° C. for 1 h with under a continuous stream of Ar. In a separate flask, Second Generation Grubbs Catalyst (0.86 g, 1.01 mmol) was added to DCM (10 ml). The dark burgundy solution was added dropwise over 30 min to the solution containing the reactant. The resulting clear brown solution was stirred at 40° C. overnight. The solution was washed with sat NaHCO$_3$ and brine, dried over MgSO$_4$, filtered, and concentrated. Purification by normal phase chromatography gave methyl (10R,11E,14S)-14-{[(tert-butoxy)carbonyl]amino}-10-methyl-9-oxo-8,16-diazatricyclo[13.3.1.0$^{2,7}$]nonadeca-1(19),2(7),3,5,11,15,17-heptaene -5-carboxylate (1.63 g, 72%) as a brownish solid. MS(ESI) m/z: 452.1 (M+H)$^+$.

41D. Preparation of methyl (10R,14S)-14-{[(tert-butoxy)carbonyl]amino}-10-methyl-9-oxo-8,16-diazatricyclo[13.3.1.0²,⁷]nonadeca-1(19),2,4,6,15,17-hexaene-5-carboxylate

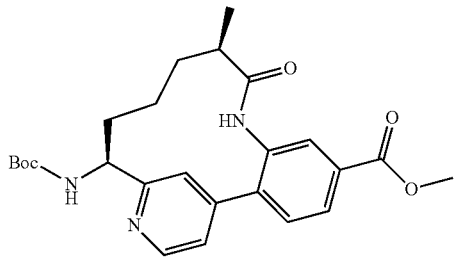 [SMILES: COC(=O)c1ccc2c(c1)NC(=O)[C@H](C)CCC[C@H](NC(=O)OC(C)(C)C)c1cc-2ccn1]

To a solution methyl (10R,11E,14S)-14-{[(tert-butoxy)carbonyl]amino}-10-methyl-9-oxo-8,16-diazatricyclo[13.3.1.0²,⁷]nonadeca-1(19),2(7),3,5,11,15,17-heptaene-5-carboxylate (1.63 g, 3.61 mmol) in EtOAc (120 ml) was added PtO₂ (0.123 g, 0.542 mmol), and the solution was purged and refilled with H₂ (3 ×). The reaction was stirred at rt under H₂ overnight. The reaction mixture was filtered, rinsed with EtOAc, MeOH and concentrated to give methyl (10R,14S)-14-{[(tert-butoxy)carbonyl]amino}-10-methyl-9-oxo-8,16-diazatricyclo[13.3.1.0²,⁷]nonadeca-1(19),2,4,6,15,17-hexaene-5-carboxylate (1.59 g, 97%) as a brownish solid. MS(ESI) m/z: 454.1 (M+H)⁺.

41E. Preparation of methyl (10R,14S)-14-amino-10-methyl-9-oxo-8,16-diazatricyclo [13.3.1.0²,⁷]nonadeca-1(19),2(7),3,5,15,17-hexaene-5-carboxylate

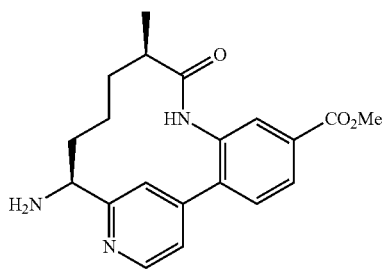

To a solution of methyl (10R,14S)-14-{[(tert-butoxy)carbonyl]amino}-10-methyl-9-oxo-8,16-diazatricyclo[13.3.1.0²,⁷]nonadeca-1(19),2,4,6,15,17-hexaene-5-carboxylate (163 mg, 0.36 mmol) in DCM (6 mL) was added TFA (0.83 mL, 10.80 mmol). The reaction was stirred at rt for 1.5 h. The reaction was concentrated and diluted with EtOAc, washed with sat NaHCO₃, extracted (2 ×), and then extracted with 10% MeOH/DCM. The combined organic layers was dried over MgSO₄, filtered and concentrated to give methyl (10R,14S)-14-amino-10-methyl-9-oxo-8,16-diazatricyclo[13.3.1.0²,⁷]nonadeca-1(19),2(7),3,5,15,17-hexaene-5-carboxylate (91 mg, 72%) as a brownish solid. MS(ESI) m/z: 454.4 (M+H)⁺.

41F. Preparation of methyl (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo[13.3.1.0²,⁷]nonadeca-1(19),2(7),3,5,15,17-hexaene-5-carboxylate

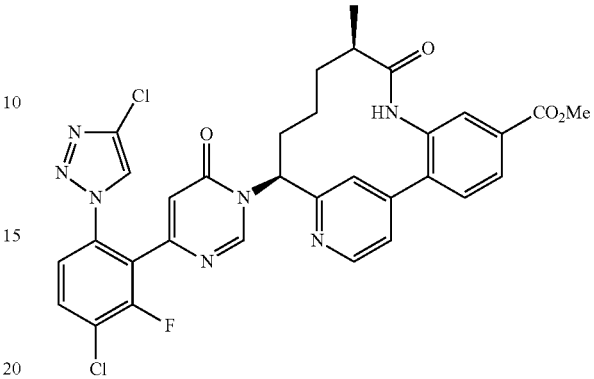

Methyl (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo [13.3.1.0²,⁷]nonadeca-1(19),2(7),3,5,15,17-hexaene-5-carboxylate (21 mg, 34%) was prepared in a similar manner as the procedure described in Example 129I by using 6-[3-chloro-6-(4-chloro-1H-1,2,3-triazol-1-yl)-2-fluorophenyl]pyrimidin-4-ol hydrobromide (32 mg, 0.08 mmol), prepared as described in Example 10, methyl (10R,14S)-14-amino -10-methyl-9-oxo-8,16-diazatricyclo[13.3.1.0²,⁷]nonadeca-1(19),2(7),3,5,15,17-hexaene -5-carboxylate (27.8 mg, 0.08 mmol). MS(ESI) m/z: 662.2.1 (M+H)⁺. ¹H NMR (400 MHz, CD₃OD) δ 8.95 (s, 1H), 8.70 (d, J=5.1 Hz, 1H), 8.31 (s, 1H), 8.08 (dd, J=7.9, 1.8 Hz, 1H), 7.88 (d, J=1.8 Hz, 1H), 7.85 (dd, J=8.6, 7.7 Hz, 1H), 7.75-7.71 (m, 2H), 7.55 (dd, J=8.6, 1.5 Hz, 1H), 7.48 (dd, J=5.1, 1.5 Hz, 1H), 6.59 (s, 1H), 6.02 (dd, J=12.3, 4.6 Hz, 1H), 3.95 (s, 3H), 2.69 (br. s., 1H), 2.22 (m, 1H), 2.08-1.91 (m, 2H), 1.57-1.40 (m, 2H), 0.97 (d, J=7.0 Hz, 3H), 0.70 (br. s., 1H). Analytical HPLC (Method A): RT=9.12 min, purity=98%; Factor XIa Ki=5.7 nM, Plasma Kallikrein Ki=120 nM.

EXAMPLE 42

Preparation of (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo [13.3.1.0²,⁷]nonadeca-1(19),2(7),3,5,15,17-hexaene-5-carbonitrile trifluoroacetate

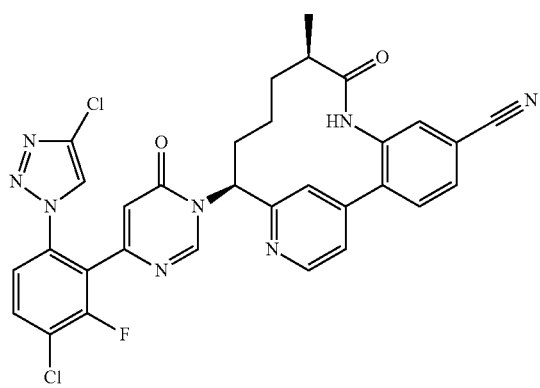 [SMILES: C[C@@H]1CCC[C@H](n2cnc(-c3c(-n4cc(Cl)nn4)ccc(Cl)c3F)cc2=O)c2cc(ccn2)-c2ccc(C#N)cc2NC1=O]

(10R,14S)-14-{4-[3-Chloro-6-(4-chloro-1H-1,2,3-triazol-1-yl)-2-fluorophenyl]-6-oxo-1,6-dihydropyrimidin-1- yl}-10-methyl-9-oxo-8,16-diazatricyclo[13.3.1.0²,⁷]non-adeca-1(19),2(7),3,5,15,17-hexaene-5-carbonitrile trifluoroacetate (3.9 mg, 13% yield) was prepared in a similar manner as the procedure described in Example 129I, by using 6-[3-chloro-6-(4-chloro-1H-1,2,3-triazol-1-yl)-2-fluorophenyl]pyrimidin-4-ol (13 mg, 0.04 mmol), prepared as described in Example 10, and (10R,14S)-14-amino-10-methyl-9-oxo-8,16-diazatricyclo[13.3.1.0²,⁷]nonadeca-1(19),2,4,6,15,17-hexaene-5-carbonitrile (16 mg, 0.04 mmol), prepared as described in Example 30. MS(ESI) m/z: 629.1 (M+H)⁺. ¹H NMR (400 MHz, CD₃OD) δ 9.00 (s, 1H), 8.75 (d, J=5.1 Hz, 1H), 8.35 (s, 1H), 7.89 (dd, J=8.6, 7.7 Hz, 1H), 7.85-7.78 (m, 2H), 7.74 (s, 1H), 7.66 (d, J=1.3 Hz, 1H), 7.58 (dd, J=8.8, 1.5 Hz, 1H), 7.49 (dd, J=5.1, 1.5 Hz, 1H), 6.62 (s, 1H), 6.06 (dd, J=13.1, 4.7 Hz, 1H), 2.70 (br. s., 1H), 2.24 (t, J=12.5 Hz, 1H), 2.12-1.90 (m, 2H), 1.63-1.29 (m, 2H), 0.98 (d, J=6.8 Hz, 3H), 0.68 (br. s., 1H). Analytical HPLC (Method A): RT=9.27 min, purity=98%; Factor XIa Ki=0.12 nM, Plasma Kallikrein Ki=8 nM.

EXAMPLE 43

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-9-oxo-8,16-diazatricyclo [13.3.1.0²,⁷]nonadeca-1(19),2(7),3,5,15,17-hexaene-5-carbonitrile trifluoroacetate

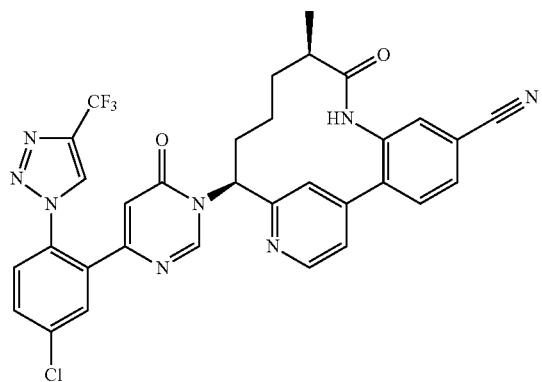 [SMILES: C[C@@H]1CCC[C@H](n2cnc(-c3cc(Cl)ccc3-n3cc(C(F)(F)F)nn3)cc2=O)c2cc(ccn2)-c2ccc(C#N)cc2NC1=O]

(10R,14S)-14-(4-{5-Chloro-2-[4-(trifluoromethyl)-1H-1,2,3-triazol-1-yl]phenyl}-6-oxo-1,6-dihydropyrimidin-1-yl)-10-methyl-9-oxo-8,16-diazatricyclo[13.3.1.0²,⁷]nonadeca-1(19),2(7),3,5,15,17-hexaene-5-carbonitrile trifluoroacetate (10.5 mg, 62% yield) was prepared in a similar manner as the procedure described in Example 129I, by replacing (9R,13S)-13-amino-3,9-dimethyl-3,4,7,15-tetraazatricyclo[12.3.1.0²,⁶]octadeca-1(18),2(6),4,14,16-pentaen-8-one, with (10R,14S)-14-amino-10-methyl-9-oxo-8,16-diazatricyclo[13.3.1.0²,⁷]nonadeca-1(19),2,4,6,15,17-hexaene-5-carbonitrile (10 mg, 0.03 mmol), prepared as described in Example 30. MS(ESI) m/z: 645.3 (M+H)⁺. ¹H NMR (400 MHz, CD₃OD) δ 8.90 (s, 1H), 8.81 (s, 1H), 8.68 (d, J=5.1 Hz, 1H), 7.89 (d, J=2.2 Hz, 1H), 7.83-7.73 (m, 3H), 7.72-7.66 (m, 2H), 7.63 (d, J=1.3 Hz, 1H), 7.46 (dd, J=5.1, 1.5 Hz, 1H), 6.42 (s, 1H), 6.01 (dd, J=12.7, 5.0 Hz, 1H), 2.67 (d, J=6.6 Hz, 1H), 2.25-2.13 (m, 1H), 2.06-1.87 (m, 2H), 1.57-1.36 (m, 2H), 0.95 (d, J=6.8 Hz, 3H), 0.62 (br. s., 1H). Analytical HPLC (Method A): RT=10.1 min, purity=100%; Factor XIa Ki=3 nM, Plasma Kallikrein Ki=32 nM.

EXAMPLE 44

Preparation of (10R,14S)-14-(4-{5-chloro-2-[4-(difluoromethyl)-1H-1,2,3-triazol-1-yl]phenyl}-6-oxo-1,6-dihydropyrimidin-1-yl)-10-methyl-9-oxo-8,16-diazatricyclo [13.3.1.0²,⁷]nonadeca-1(19),2(7),3,5,15,17-hexaene-5-carbonitrile trifluoroacetate

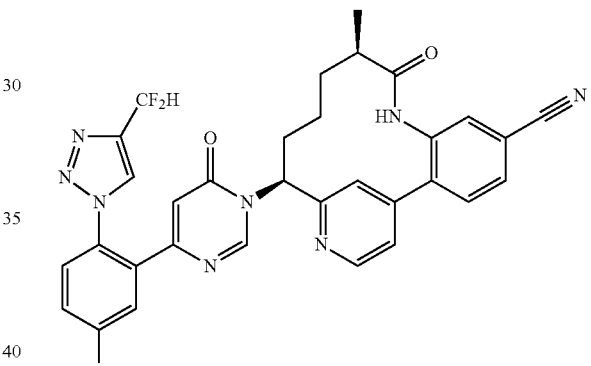

(10R,14S)-14-(4-{5-Chloro-2-[4-(difluoromethyl)-1H-1,2,3-triazol-1-yl]phenyl}-6-oxo-1,6-dihydropyrimidin-1-yl)-10-methyl-9-oxo-8,16-diazatricyclo[13.3.1.0²,⁷]nonadeca-1(19),2(7),3,5,15,17-hexaene-5-carbonitrile trifluoroacetate (10.5 mg, 53% yield) was prepared in a similar manner as described in Example 129I, by using 6-{5-chloro-2-[4-(difluoromethyl)-1H-1,2,3-triazol-1-yl]phenyl}pyrimidin-4-ol (8.6 mg, 0.03 mmol), prepared as described in Example 16, and (10R,14S)-14-amino-10-methyl-9-oxo -8,16-diazatricyclo[13.3.1.0²,⁷]nonadeca-1(19),2,4,6,15,17-hexaene-5-carbonitrile (10 mg, 0.03 mmol), prepared as described in Example 30. MS(ESI) m/z: 627.3 (M+H)⁺. ¹H NMR (400 MHz, CD₃OD) δ 8.93 (s, 1H), 8.70 (d, J=5.1 Hz, 1H), 8.55-8.52 (m, 1H), 7.88 (d, J=2.4 Hz, 1H), 7.82-7.70 (m, 4H), 7.68-7.64 (m, 1H), 7.62 (d, J=1.3 Hz, 1H), 7.47 (dd, J=5.1, 1.8 Hz, 1H), 7.15-6.83 (m, 1H), 6.33 (s, 1H), 5.99 (dd, J=12.5, 5.1 Hz, 1H), 2.67 (d, J=6.2 Hz, 1H), 2.26-2.13 (m, 1H), 2.07-1.85 (m, 2H), 1.59-1.32 (m, 2H), 0.95 (d, J=6.8 Hz, 3H), 0.63 (br. s., 1H). Analytical HPLC (Method A): RT=8.51 min, purity=100%; Factor XIa Ki=0.8 nM, Plasma Kallikrein Ki=60 nM.

EXAMPLE 45

Preparation of methyl N-[(10R,14S)-14-[4-(3-chloro-2-fluorophenyl)-6-oxo-1,6-dihydropyrimidin-1-yl]-10-methyl-9-oxo-8,16-diazatricyclo[13.3.1.0$^{2,7}$]nonadeca -1(18),2,4,6,15(19),16-hexaen-5-yl] carbamate trifluoroacetate

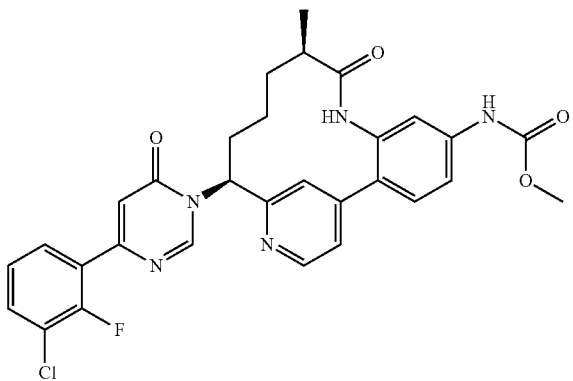 [SMILES: COC(=O)Nc1ccc2c(c1)NC(=O)[C@H](C)CCC[C@H](n1cnc(-c3cccc(Cl)c3F)cc1=O)c1cc-2ccn1]

45A. Preparation of (S)—N—((S)-1-(4-chloropyridin-2-yl)but-3-enyl)-2-methylpropane-2-sulfinamide.

To a cooled (0-5° C.) mixture of InCl$_3$ (13.56 g, 61.3 mmol) in THF (170 mL) was added dropwise over 30 min. allylmagnesium bromide (1 M in Et$_2$O) (62 mL, 61.3 mmol). The reaction was allowed to warm to rt. After 1 h at rt, a solution of chloro-2-[(E)-2-[(S)-2-methylpropane-2-sulfinyl]ethenyl]pyridine (10 g, 40.9 mmol), prepared as described in Example 19, in EtOH (170 mL) was added. After 2-3 h, the reaction was concentrated under vacuum at 50-55° C. The crude material was partitioned between EtOAc (200 mL) and water (50 mL) and the layers were separated. The aqueous layer was extracted with EtOAc (2×50 mL). The organic layers were combined and washed with brine (100 mL), dried over Na$_2$SO$_4$, filtered and concentrated to give (S)—N—((S)-1-(4-chloropyridin-2-yl)but-3-enyl)-2-methylpropane-2-sulfinamide (13.5 g, 106%) as a yellow oil. MS(ESI) m/z: 287.2 (M+H)$^+$. This material was used in the next step without further purification.

45B. Preparation of (S)-tert-butyl 1-(4-chloropyridin-2-yl)but-3-enylcarbamate (S)—N—((S)-1-(4-Chloropyridin-2-yl)but-3-enyl)-2-methylpropane-2-sulfinamide (75 g, 261 mmol) was dissolved in MeOH (1500 mL). 6 N HCl (750 mL, 4.5 mol) was added. The reaction was stirred at rt for 2-3 h and then was concentrated. The residue was diluted with water (2 L), washed with EtOAc (500 mL). The aqueous layer was basified with sat Na$_2$CO$_3$, extracted into EtOAc (3×1 L). The combined organic layers were washed with water (1 L) and brine (1×1 L), dried over Na$_2$SO$_4$, filtered and concentrated under vacuum at 50-55° C. to give crude product (43 g, 90%). MS(ESI) m/z: 183.2 (M+H)$^+$. The crude product (42 g, 230 mmol) was dissolved in DCM (420 mL), Et$_3$N (32.1 mL, 230 mmol) was added followed by dropwise addition of BOC$_2$O (53.4 mL, 230 mmol). The reaction was stirred at rt for 2-3 h. The reaction was diluted with excess DCM (1 L), washed with water (500 mL) and brine (500 mL). The organic layer was dried over Na$_2$SO$_4$, filtered, and concentrated. The crude product was then purified using silica gel chromatography to give (S)-tert-butyl 1-(4-chloropyridin-2-yl)but-3-enylcarbamate (61 g, 86%) as a pale yellow solid. MS(ESI) m/z: 283.2 (M+H)$^+$.

45C. Preparation of (S)-tert-butyl 1-(4-(2-amino-4-nitrophenyl)pyridin-2-yl)but-3-enylcarbamate To a RBF was added (S)-tert-butyl 1-(4-chloropyridin-2-yl)but-3-enylcarbamate (3.33 g, 11.78 mmol), 2-(5,5-dimethyl-1,3,2-dioxaborinan-2-yl)-5-nitro-phenylamine, prepared as described in Example 1, (5.89 g, 23.55 mmol), PdCl$_2$(dppf)-CH$_2$Cl$_2$ Adduct (0.962 g, 1.178 mmol), and K$_3$PO$_4$ (5.00 g, 23.55 mmol). The RBF was equipped with a reflux condenser, then the apparatus was purged with Ar for several min. Next, degassed DMSO (58.9 mL) was added followed by degassed water (1.1 mL, 58.9 mmol). The bright orange suspension was warmed to 90° C. for 6 h and then was cooled to rt and stirred overnight. The reaction was filtered via Buchner funnel, rinsing with EtOAc to remove the solid. The filtrate was then partitioned between EtOAc and water which gave an emulsion. Brine was added to break up the emulsion and the layers were separated. The aqueous layer was extracted with EtOAc. The combined organic layers were washed with brine, dried over Na$_2$SO$_4$, filtered and concentrated to give a thick black oil weighing 10.2 g. Purification by column chromatography gave (S)-tert-butyl 1-(4-(2-amino-4-nitrophenyl)pyridin-2-yl)but-3-enylcarbamate as an orange foam (2.90 g, 64%). MS(ESI) 385.1 (M+H)$^+$.

45D. Preparation of (S)-tert-butyl 1-(4-(2,4-diaminophenyl)pyridin-2-yl)but-3-enylcarbamate To a clear, orange solution of (S)-tert-butyl 1-(4-(2-amino-4-nitrophenyl)pyridin -2-yl)but-3-enylcarbamate (2.9 g, 7.54 mmol) in MeOH (75 mL) was added sequentially Zn (4.93 g, 75 mmol) and NH$_4$Cl (4.04 g, 75 mmol). The resulting suspension was stirred vigorously for 4 h. The reaction was filtered and the solution was concentrated to give a produced a yellow-black residue. The residue was partitioned between EtOAc and 0.25 M HCl (50 mL) and the layers were separated. The organic layer was extracted with 0.25 M HCl (50 mL). The combined aqueous layers were basified with 1.5 M K$_2$HPO$_4$ and then extracted with EtOAc (3×). The combined organic layers were washed with brine, dried over Na$_2$SO$_4$, filtered and concentrated to give (S)-tert-butyl 1-(4-(2,4-diaminophenyl)pyridin-2-yl)but-3-enylcarbamate (2.63 g, 98%) as a brown foam. MS(ESI) m/z: 355.2 (M+H)$^+$.

45E. Preparation of {3-amino-4-[24(S)-1-tert-butoxycarbonylamino-but-3-enyl)-pyridin -4-yl]phenyl}carbamic acid methyl ester To a cooled (−78° C.) clear, brown solution of (S)-tert-butyl 1-(4-(2,4-diaminophenyl)pyridin-2-yl)but-3-enylcarbamate (2.63 g, 7.42 mmol) and pyridine (0.600 mL, 7.42 mmol) in DCM (74.2 mL) was added dropwise over 30 min methyl chloroformate (0.516 mL, 6.68 mmol). The reaction was stirred at −78° C. After 1.5 h, the reaction was quenched with sat NH$_4$Cl and the reaction was to warm to rt. The reaction was diluted with DCM and water, and the layers were separated. The aqueous layer was extracted with DCM. The combined organic layers were washed with sat NaHCO$_3$, brine, dried over Na$_2$SO$_4$, filtered and concentrated. The residue was dissolved in DCM (10 mL) and then hexane (300 mL) was added to give a brown suspension with a brown gummy sticky substance at the bottom. The mixture was sonicated to give a mostly clear solution with the brown substance at the bottom. The solution was decanted and the bottom substance rinsed with hexane, and dried to give {3-amino-4-[2-((S)-1-tert -butoxycarbonylamino-but-3-enyl)-pyridin-4-yl]phenyl}carbamic acid methyl ester (2.7 g, 88%) as a slightly brown foam. MS(ESI) m/z: 413.2 (M+H)$^+$.

45F. Preparation of methyl N-(4-{2-[(1S)-1-{[(tert-butoxy)carbonyl]amino}but-3-en-1-yl]pyridin-4-yl}-3-[(2R)-2-methylbut-3-enamido]phenyl)carbamate To a solution of (R)-2-methylbut-3-enoic acid, prepared as described in Example 2, (1.201 g, 12.00 mmol), {3-amino-4-[2-(S)-1-tert-butoxycarbonylamino-but-3-enyl)-pyridin-4-yl]phenyl}carbamic acid methyl ester (3.3 g, 8.00 mmol), pyridine (1.937 mL, 24.00 mmol) in EtOAc (40.0 mL) at −10° C. under Ar, was added dropwise a solution of T3P® (50%wt in EtOAc) (9.52 mL, 16.00 mmol). The resulting solution was stirred at −10° C., then was allowed to gradually warmed up to rt over night. The reaction mixture was washed with sat aq NaHCO$_3$ twice, then the combined aqueous layer was back extracted with EtOAc. The combined EtOAc phases were washed with brine, dried over MgSO$_4$, filtered, concentrated. The crude product was then purified using silica gel chromatography to give methyl N-(4-{2-[(1S)-1-{[(tert-butoxy)carbonyl]amino}but-3-en-1-yl]pyridin-4-yl}-3-[(2R)-2-methylbut-3-enamido]phenyl)carbamate (4.06 g, 97%) as a white solid. $^1$H NMR (500 MHz, CD$_3$OD) δ 8.46 (d, J=5.0 Hz, 1H), 7.64 (s, 1H), 7.47 (dd, J=8.4, 2.1 Hz, 1H), 7.35 (s, 1H), 7.29 (d, J=8.3 Hz, 1H), 7.25 (m, 1H), 5.87-5.73 (m, 2H), 5.16-5.02 (m, 4H), 4.79-4.71 (m, 1H), 3.75 (s, 3H), 3.14-3.05 (m, 1H), 2.64-2.55 (m, 1H), 2.52-2.43 (m, 1H), 1.42 (s, 9H), 1.16 (d, J=6.9 Hz, 3H). MS(ESI) m/z: 495.1 (M+H)$^+$.

45G. Preparation of methyl N-[(10R,11E,14S)-14-{[(tert-butoxy)carbonyl]amino}-10-methyl-9-oxo-8,16-diazatricyclo[13.3.1.0$^{2,7}$]nonadeca-1(19),2(7),3,5,11,15,17-heptaen-5-yl]carbamate To a RBF was added methyl N-(4-{2-[(1S)-1-{[(tert-butoxy)carbonyl]amino}but-3-en-1-yl]pyridin-4-yl}-3-[(2R)-2-methylbut-3-enamido]phenyl)carbamate (0.5 g, 1.011 mmol), TsOH.H$_2$O (0.212 g, 1.112 mmol), and DCM (84 mL). The flask was equipped with a reflux condenser and the clear yellow solution was degassed with Ar for 30 min. The reaction was then warmed to reflux for 1 h. Then a solution of Second Generation Grubbs Catalyst (0.172 g, 0.202 mmol) in DCM (2 mL) was added dropwise to the reaction mixture. After 4 h at reflux, the reaction was cooled to rt, washed with sat Na$_2$CO$_3$, brine, dried over MgSO$_4$, filtered, and concentrated to give a brown solid. The crude product was then purified using silica gel chromatography to give methyl N-[(10R,11E,14S)-14-{[(tert-butoxy)carbonyl]amino}-10-methyl-9-oxo-8,16-diazatricyclo[13.3.1.0$^{2,7}$]nonadeca-1(19),2(7),3,5,11,15,17-heptaen-5-yl]carbamate (0.336 g, 71.2% yield) as a yellow solid. $^1$H NMR (500 MHz, CD$_3$OD) δ 8.52 (d, J=5.2 Hz, 1H), 7.54 (d, J=1.4 Hz, 1H), 7.48-7.43 (m, 1H), 7.38 (d, J=8.3 Hz, 1H), 7.24 (dd, J=5.1, 1.5 Hz, 1H), 6.89 (s, 1H), 5.75-5.65 (m, 1H), 4.60 (dd, J=11.3, 3.6 Hz, 1H), 4.39 (dd, J=15.1, 9.6 Hz, 1H), 3.75 (s, 3H), 3.14-3.06 (m, 1H), 2.75-2.68 (m, 1H), 2.04-1.94 (m, 1H), 1.44 (s, 9H), 1.30 (br. s., 1H), 1.04 (d, J=6.6 Hz, 3H). MS(ESI) m/z: 467.2 (M+H)$^+$.

45H. Preparation of methyl N-[(10R,14S)-14-{[(tert-butoxy)carbonyl]amino}-10-methyl-9-oxo-8,16-diazatricyclo[13.3.1.0$^{2,7}$]nonadeca-1(19),2(7),3,5,15,17-hexaen-5-yl]carbamate.

Methyl N-[(10R,11E,14S)-14-{[(tert-butoxy)carbonyl]amino}-10-methyl-9-oxo-8,16-diazatricyclo[13.3.1.0$^{2,7}$]nonadeca-1(19),2(7),3,5,11,15,17-heptaen-5-yl]carbamate was dissolved in 200 mL MeOH, purged and refilled with Ar. 10% Pd/C (0.684 g, 0.643 mmol) was then added, and the reaction vessel was purged and refilled with Ar, then purged and refilled with H$_2$ (3 ×), and then stirred at rt under 55 psi H$_2$ for 16 h. The reaction mixture was filtered through a pad of CELITE® under N$_2$ to remove the solid material, and the collected solid was washed with copious amounts of MeOH. The resulting dark filtrate was further filtered through 6×Whatman autovials and 6×target2 nylon 0.2 μM syringe filters under N$_2$ to yield a colorless clear solution, which was concentrated under vacuum to afford methyl N-[(10R,14S)-14-{[(tert-butoxy)carbonyl]amino}-10-methyl-9-oxo-8,16-diazatricyclo[13.3.1.0$^{2,7}$]nonadeca-1(19),2(7),3,5,15,17-hexaen-5-yl]carbamate (3 g, 6.4 mmol, 100% yield) as a white solid. $^1$H NMR (500 MHz, DMSO-d$_6$) δ 9.87 (s, 1H), 9.65 (s, 1H), 8.54 (d, J=5.0 Hz, 1H), 7.50-7.43 (m, 2H), 7.40 (s, 1H), 7.33 (s, 1H), 7.23 (dd, J=5.0, 1.7 Hz, 1H), 7.03 (d, J=7.4 Hz, 1H), 4.65-4.55 (m, 1H), 3.69 (s, 3H), 2.60 (br. s., 1H), 1.84-1.55 (m, 3H), 1.34 (s, 9H), 1.21-1.06 (m, 2H), 0.79 (d, J=7.2 Hz, 3H), 0.11 (d, J=12.1 Hz, 1H). MS(ESI) m/z: 469.0 (M+H)$^+$.

45I. Preparation of methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate, monotrifluoroacetate To methyl N-[(10R,14S)-14-{[(tert-butoxy)carbonyl]amino}-10-methyl-9-oxo-8,16-diazatricyclo[13.3.1.0$^{2,7}$]nonadeca-1(19),2(7),3,5,15,17-hexaen-5-yl]carbamate (3 g, 6.40 mmol) in CH$_2$Cl$_2$ (100 mL) was added TFA (14.80 mL, 192 mmol). After 4 h, the reaction mixture was concentrated under vacuum to afford methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate, monotrifluoroacetate (3.8 g, 6.4 mmol) as a yellow solid. MS(ESI) m/z: 369.0 (M+H)$^+$.

45J. Preparation of methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate, dihydrochloride To a flask containing methyl N-[(10R,14S)-14-{[(tert-butoxy)carbonyl]amino}-10-methyl-9-oxo-8,16-diazatricyclo[13.3.1.0$^{2,7}$]nonadeca-1(19),2(7),3,5,15,17-hexaen-5-yl]carbamate (0.880 g, 1.878 mmol) was added 4.0 M HCl in dioxane (21.13 mL, 85 mmol). The resulting suspension was sonicated to give a clear, yellow solution. After 5 to 10 min, a precipitate formed. After 1 h, the reaction was stopped and the precipitate was collected by filtration. The solid was rinsed with dioxane and air-dried to give a hygroscopic, yellow solid. The solid was dissolved in MeOH, concentrated, and lyophilized to give methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate, dihydrochloride (0.7171 g, 87% yield) as a yellow solid. MS(ESI) m/z: 369.3 (M+H)$^+$.

45K. Preparation of methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate Methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate dihydrochloride (0.100 g, 0.227 mmol) was dissolved in MeOH (1 mL) to give a clear, pale green solution. The solution was added to a pre-rinsed AGILENT® StratoSpheres SPE PL-HCO$_3$ MP Resin cartridge. Gravity filtration, eluting with MeOH, gave a clear, slightly pink filtrate. Concentration provided methyl N-[(10R,14S)-14-amino-10-methyl-9-oxo-8,16-diazatricyclo [13.3.1.0$^{2,7}$]nonadeca-1(19),2(7),3,5,15,17-hexaen-5-yl]carbamate (0.080 g, 84%) as a pink solid.

45L. Preparation of methyl N-[(10R,14S)-14-[4-(3-chloro-2-fluorophenyl)-6-oxo-1,6-dihydropyrimidin-1-yl]-10-methyl-9-oxo-8,16-diazatricyclo[13.3.1.0$^{2,7}$]nonadeca-1(18),2,4,6,15(19),16-hexaen-5-yl]carbamate trifluoroacetate To a 1-dram, pressure vial containing a white suspension of methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate (15.0 mg, 0.041 mmol) in CH$_3$CN (0.27 mL) was added 6-(3-chloro-2-fluorophenyl)pyrimidin-4-ol, Example 3, (10.97 mg, 0.049 mmol) and HATU (0.020 g, 0.053 mmol). Additional CH$_3$CN (0.1 mL) was added to facilitate mixing. Next, DBU (9.21 μL, 0.061 mmol) was added and the resulting bright yellow suspension was stirred at rt. After 2 h, 5:1 DMF/MeOH (1.5 mL) was added to the reaction to give a clear, yellow solution. Purification by reverse phase chromatography afforded, after concentration and lyophilization, methyl N-[(10R,14S)-14-[4-(3-chloro-2-fluorophenyl) -6-oxo-1,6-dihydropyrimidin-1-yl]-10-methyl-9-oxo-8,16-diazatricyclo[13.3.1.0$^{2,7}$]nonadeca-1(18),2,4,6,15(19),16-hexaen-5-yl]carbamate trifluoroacetate (0.0112 g, 38% yield) as a white solid. MS(ESI) m/z: 576.3 (M+H)' and 578.3 (M+2+H)'. $^1$H NMR (500 MHz, DMSO-d$_6$) δ 9.10 (s, 1H), 8.58 (d, J=5.0 Hz, 1H), 7.95-7.89 (m, 1H), 7.74-7.68 (m, 1H), 7.67 (s, 1H), 7.50 (d, J=8.5 Hz, 1H), 7.46 (dd, J=8.3, 1.9 Hz, 1H), 7.39-7.33 (m, 3H), 6.78 (s, 1H), 5.95-5.89 (m, 1H), 3.69 (s, 3H), 2.68-2.62 (m, 1H), 2.32-2.23 (m, 1H), 2.03-1.86 (m, 2H), 1.46-1.34 (m, 2H), 0.83 (d, J=7.2 Hz, 3H), 0.50-0.34 (m, 1H). $^{19}$F NMR (471 MHz, DMSO-d$_6$) δ −73.42, −117.25. Analytical HPLC (Method A): RT=8.46 min, purity=97%; Factor XIa Ki=7 nM, Plasma Kallikrein Ki=78 nM.

EXAMPLE 46

Preparation of methyl N-[(10R,14S)-14-[4-(3-chloro-2,6-difluorophenyl)-6-oxo-1,6-dihydropyrimidin-1-yl]-10-methyl-9-oxo-8,16-diazatricyclo [13.3.1.0$^{2,7}$]nonadeca -1(18),2,4,6,15(19),16-hexaen-5-yl]carbamate trifluoroacetate

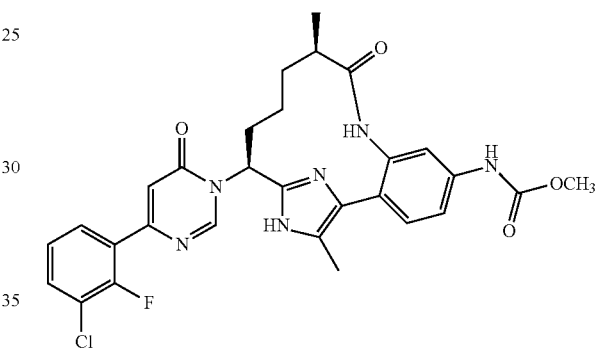

To a 1-dram vial containing a white suspension of methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate (20 mg, 0.054 mmol) in CH$_3$CN (0.36 mL) was added 6-(3-chloro-2,6-difluorophenyl)pyrimidin-4-ol, hydrobromide, prepared as described in Example 4, (0.021 g, 0.065 mmol) and HATU (0.027 g, 0.071 mmol). Next, DBU (0.022 mL, 0.147 mmol) was added and the resulting bright yellow solution was stirred at rt. Overtime a precipitate formed. After 2 h, was diluted with 5:1 DMF/MeOH (1.5 mL) to give a clear, yellow solution. Purification by reverse phase chromatography (2 ×) gave after concentration and lyophilization methyl N-[(10R,14S)-14-[4-(3-chloro-2,6-difluorophenyl)-6-oxo-1,6-dihydropyrimidin-1-yl]-10-methyl-9-oxo-8,16-diazatricyclo [13.3.1.0$^{2,7}$]nonadeca-1(18),2,4,6,15(19),16-hexaen-5-yl]carbamate trifluoroacetate (0.0059 g, 15.3% yield) as a white solid. MS(ESI) m/z: 594.2 (M+H)$^+$ and 596.2 (M+2+H)$^+$. $^1$H NMR (500 MHz, DMSO-d$_6$) δ 9.92 (s, 1H), 9.76 (s, 1H), 9.12 (s, 1H), 8.61 (d, J=5.2 Hz, 1H), 7.79 (td, J=8.7, 5.6 Hz, 1H), 7.69 (s, 1H), 7.52-7.46 (m, 2H), 7.40-7.35 (m, 2H), 7.33 (td, J=9.1, 1.7 Hz, 1H), 6.70 (s, 1H), 5.98-5.91 (m, 1H), 3.70 (s, 3H), 2.71-2.62 (m, 1H), 2.35-2.26 (m, 1H), 2.05-1.89 (m, 2H), 1.48-1.35 (m, 2H), 0.85 (d, J=6.9 Hz, 3H), 0.49-0.33 (m, 1H). $^{19}$F NMR (471 MHz, DMSO-d$_6$) δ −73.42 (s), −113.62 (d, J=4.3 Hz), −113.76 (d, J=4.3 Hz). Analytical HPLC (Method A): RT=7.97 min, purity=98.9%; Factor XIa Ki=0.57 nM, Plasma Kallikrein Ki=13 nM.

EXAMPLE 47

Preparation of methyl N-[(10R,14S)-14-[4-(3 -chloro-2-fluorophenyl)-6-oxo-1,6-dihydropyrimidin-1-yl]-10,17-dimethyl-9-oxo-8,16,18-triazatricyclo[13.2.1.0$^{2,7}$]octadeca-1(17),2,4,6,15(18)-pentaen-5-yl]carbamate trifluoroacetate

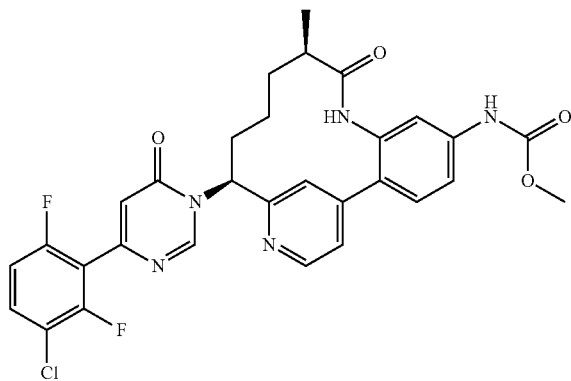 [SMILES: COC(=O)Nc1ccc2c(c1)NC(=O)[C@H](C)CCC[C@H](n1cnc(-c3c(F)ccc(Cl)c3F)cc1=O)c1cc-2ccn1]

47A. Preparation of {3-bromo-4-[2-((S)-1-tert-butoxycarbonylamino-but-3-enyl)-3H -imidazol-4-yl]phenyl}carbamic acid methyl ester To a 500-mL RBF containing a clear, yellow solution of 2-{2-bromo-4-[(methoxycarbonyl)amino]phenyl}-2-oxoethyl (2S)-2-{[(tert-butoxy)carbonyl]amino}pent-4-enoate (8.77 g, 18.07 mmol) in xylene (181 mL) was added NH$_4$OAc (13.93 g, 181 mmol). The flask was equipped with a Dean-stark trap and a reflux condenser, and then the reaction was warmed to 140° C. After 3 h, the reaction was cooled to rt. The dark orange reaction was diluted with EtOAc (400 mL) and then washed with 1.5 M K$_2$HPO$_4$ (2×150 mL), brine, dried over Na$_2$SO$_4$, filtered, and concentrated to give a brown foam weighing 11.06 g. Purification by normal phase chromatography gave 4.61 g (55%) of {3-bromo-4-[2-((S)-1-tert-butoxycarbonylamino-but-3-enyl)-3H-imidazol-4-yl]phenyl}carbamic acid methyl ester as a pale, yellow foam. MS(ESI) m/z: 467.1 (M+2+H)$^+$.

47B. Preparation of {3 -bromo-4-[2-((S)-1-tert-butoxycarbonylamino-but-3- enyl)-1-(2-trimethylsilanyl-ethoxymethyl)-1H-imidazol-4-yl]phenyl}carbamic acid methyl ester To a 0° C. solution of {3-bromo-4-[2-((S)-1-tert-butoxycarbonylamino-but-3-enyl)-3H-imidazol-4-yl] phenyl}carbamic acid methyl ester (15 g, 32.2 mmol) in THF (77 mL) was added N,N-dicyclohexylmethylamine (7.52 mL, 35.5 mmol) followed by the dropwise addition of SEM-Cl (6.29 mL, 35.5 mmol). The reaction was stirred at 0° C. for 2 h and then it was allowed to warm slowly to rt. After 18 h, the yellow suspension was diluted with EtOAc, washed with sat NaHCO$_3$, brine, dried over MgSO$_4$, filtered and concentrated. Purification by normal phase chromatography gave 12.24 g (63.8%) of {3-bromo-4-[2-((S)-1-tert-butoxycarbonylamino-but-3-enyl)-1-(2-trimethylsilanyl-ethoxymethyl)-1H-imidazol-4-yl]phenyl}carbamic acid methyl ester as an off-white solid. MS(ESI) m/z: 595.1 (M+H)$^+$ and 597.2 (M+2+H)$^+$.

47C. Preparation of {3-amino-4-[2-((S)-1-tert-butoxycarbonylamino-but-3-enyl)-1-(2-trimethylsilanyl-ethoxymethyl)-1H-imidazol-4-yl]phenyl}carbamic acid methyl ester A thick-walled vial containing {3-bromo-4-[2-((S)-1-tert-butoxycarbonylamino -but-3-enyl)-1-(2-trimethylsilanyl-ethoxymethyl)-1H-imidazol-4-yl]phenyl}carbamic acid methyl ester (2 g, 3.36 mmol), CuI (128 mg, 0.672 mmol), L-proline (155 mg, 1.343 mmol) and K$_2$CO$_3$ (1.392 g, 10.07 mmol) in DMSO (6.72 mL) was purged and back-filled with Ar (3 x). Then 28% aq NH$_4$OH (0.61 mL, 4.37 mmol) was added. The vial was sealed with a teflon-coated screw cap and the reaction was warmed to 85° C. After 20 h, the reaction was cooled to rt, diluted with EtOAc, washed with water, brine, dried over Na$_2$SO$_4$, filtered and concentrated. Purification by normal phase chromatography afforded 1.05 g (58.8%) of {3-amino-4-[2-((S)-1-tert-butoxycarbonylamino-but-3-enyl) -1-(2-trimethylsilanyl-ethoxymethyl)-1H-imidazol-4-yl]phenyl}carbamic acid methyl ester as a yellow solid. MS(ESI) m/z: 532.5 (M+H)$^+$.

47D. Preparation of tert-butyl N-[(1S)-1-(4-{4-[(methoxycarbonyl)amino]-2-[(2R)-2-methylbut-3-enamido]phenyl}-1-{[2-(trimethylsilyl)ethoxy]methyl}-1H-imidazol-2-yl)but-3-en-1-yl]carbamate To a cooled (0° C.) solution of {3-amino-4-[2-((S)-1-tert-butoxycarbonylamino -but-3-enyl)-1-(2-trimethylsilanyl-ethoxymethyl)-1H-imidazol-4-yl]phenyl}carbamic acid methyl ester (7.71 g, 14.50 mmol) in EtOAc (72.5 mL) was added (R)-2-methylbut-3-enoic acid, prepared as described in Example 2, (1.742 g, 17.40 mmol) and pyridine (3.52 mL, 43.5 mmol). Next, T3P® (50% in EtOAc) (17.26 mL, 29.0 mmol) was added dropwise. Following the addition, the reaction was allowed to warm to rt. After 1.5 h, the reaction was quenched with sat NaHCO$_3$ and the reaction was stirred until gas evolution ceased. The layers were separated and the organic layer was washed with water, brine, dried over MgSO$_4$, filtered and concentrated to give an orange oil. Purification by normal phase chromatography provided tert-butyl N-[(1S)-1-(4-{4-[(methoxycarbonyl)amino]-2-[(2R)-2-methylbut-3-enamido]phenyl}-1-{[2-(trimethylsilyl)ethoxy]methyl}-1H imidazol-2-yl)but-3-en-1-yl]carbamate (7.03 g, 79% yield) as a brown solid. MS(ESI) m/z: 614.5 (M+H)$^+$.

47E. Preparation of tert-butyl N-[(10R,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,11,15(18)-hexaen-14-yl]carbamate To a solution of tert-butyl N-[(1S)-1-(4-{4-[(methoxycarbonyl)amino]-2-[(2R)-2-methylbut-3-enamido]phenyl}-1-{[2-(trimethylsilyl)ethoxy]methyl}-1H-imidazol-2-yl)but-3-en-1-yl]carbamate (7.03 g, 11.45 mmol) in DCM (1,000 mL) was added TsOH.H$_2$O (2.396 g, 12.60 mmol) and the mixture was purged with Ar for 30 min. Next, the flask was equipped with a reflux condenser and the reaction was warmed to 40° C. for 1 h. Then, the reaction was cooled to 30° C. and Second Generation Grubbs Catalyst (1.070 g, 1.260 mmol) was added in one portion and the reaction was refluxed overnight. The next day, additional Second Generation Grubbs Catalyst (0.5 g) was added and the reaction was refluxed for 7 h. The reaction was cooled to rt and sat NaHCO$_3$ (25 mL) was added to the reaction and the reaction was stirred for 15 min. The layers were separated and the organic layer was washed with sat NaHCO$_3$ (200 mL), brine (200 mL), dried over MgSO$_4$, filtered and concentrated. Purification by normal phase chromatography gave a brown solid. Trituration from DCM provided tert-butyl N-[(10R,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,11,15(18)-hexaen-14-yl]carbamate (2.2 g, 32.8% yield) as an off-white solid. MS(ESI) m/z: 586.4 (M+H)$^+$.

47F. Preparation of tert-butyl N-[(10R,14S)-5-[(methoxycarbonyl)amino]-10-methyl-9oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate A dark brown solution of tert-butyl N-[(10R,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,11,15(18)-hexaen-14-yl]carbamate (1.71 g, 2.92 mmol) in EtOAc (97 mL) was purged with Ar for 30 min. Next PtO$_2$ (0.066 g, 0.292 mmol) was added and H$_2$ gas from a balloon was bubbled through the reaction mixture for several min. The reaction was stirred under a H$_2$ atmosphere. After 24 h, an additional amount of PtO$_2$ (0.192 g, 0.876 mmol) was added and the reaction was stirred under a H$_2$ atmosphere. After 21 h, the reaction was stopped. The vessel was purged with Ar (3 x), then CELITE® was added, and the reaction was filtered rinsing with EtOAc. The resulting clear, yellow brown filtrate was concentrated to give an off-white solid weighing 1.66 g. Recrystallization from MeOH (30 mL) gave tert-butyl N-[(10R,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate (0.575 g, 34%) as a white solid. MS(ESI) m/z: 588.4 (M+H)$^+$.

47G. Preparation of tert-butyl N-[(10R,14S)-17-bromo-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate To a RBF was added tert-butyl N-[(10R,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate (1.32 g, 2.246 mmol) and CHCl$_3$ (100 mL). The reaction was cooled to 0° C. and then NBS (400 mg, 2.246 mmol) was added to the reaction. The reaction was stirred at ° C. for 20 min. After this time, the reaction was concentrated and the crude product was purified by normal phase chromatography to give tert-butyl N-[(10R,14S)-17-bromo-5-[(methoxycarbonyl)amino]-10-methyl-9-oxo-16-{[2-(trimethylsilyl)ethoxy]methyl}-8,16,18-triazatricyclo [13.2.1.0$^{2,7}$]octadeca-1(17),2,4,6,15(18)-pentaen-14-yl]carbamate as an off-white solid. MS(ESI) m/z: 666.3 (M+H)$^+$.

47H. Preparation of tert-butyl N-[(10R,14S)-5-[(methoxycarbonyl)amino]-10,17-dimethyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate To a microwave vial was added tert-butyl N-[(10R,14S)-17-bromo-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate (300 mg, 0.450 mmol), PdCl$_2$(dppf)-CH$_2$Cl$_2$ adduct (73.5 mg, 0.090 mmol), methylboronic acid (404 mg, 6.75 mmol) and dioxane (15 mL). The reaction was purged with Ar and then sealed. The reaction was then stirred at 150° C. in a microwave for 15 min. The reaction was then cooled to rt and partitioned between EtOAc (15 mL) and water (15 mL). The organic layer was separated, washed with sat NaCl (10 mL), dried over MgSO$_4$, filtered and concentrated. The residue was purified by normal phase chromatography to give tert-butyl N-[(10R,14S)-5-[(methoxycarbonyl)amino]-10,17-dimethyl-9-oxo-16-{[2-(trimethylsilyl)ethoxy]methyl}-8,16,18-triazatricyclo [13.2.1.0$^{2,7}$]octadeca-1(17),2,4,6,15(18)-pentaen-14-yl] carbamate (175 mg, 64.6% yield) as an off -white solid. MS(ESI) m/z: 602.5 (M+H)$^+$. $^1$H NMR (400 MHz, CD$_3$OD) δ 7.51 (s, 1H), 7.39 (d, J=0.9 Hz, 2H), 5.58-5.47 (m, 2H), 4.97 (br. s., 1H), 3.74-3.62 (m, 5H), 2.63 (br. s., 1H), 2.35 (s, 3H), 1.99 (br. s., 2H), 1.52 (d, J=11.7 Hz, 2H), 1.43-1.24 (m, 10H), 0.98-0.89 (m, 5H), 0.80-0.57 (m, 1H), 0.03 (m, 9H).

47I. Preparation of methyl N-[(10R,14S)-14-amino-10,17-dimethyl-9-oxo-16-{[2-(trimethylsilyl)ethoxy]methyl}-8,16,18-triazatricyclo[13.2.1.0$^{2,7}$]octadeca -1(17),2,4,6,15 (18)-pentaen-5-yl]carbamate To a brown solution of tert-butyl N-[(10R,14S)-5-[(methoxycarbonyl)amino]-10,17-dimethyl-9-oxo-16-{[2-(trimethylsilyl)ethoxy]methyl}-8,16,18-triazatricyclo [13.2.1.0$^{2,7}$]octadeca-1(17),2,4,6,15(18)-pentaen-14-yl]carbamate (0.51 g, 0.847 mmol) in DCM (10 mL) was added TFA (2.50 mL). The resulting dark green solution was stirred at rt for 1 h and then the reaction was concentrated. The resulting yellow solid was dissolved in EtOAc and washed with sat NaHCO$_3$ (2×), brine, dried over Na$_2$SO$_4$, filtered, and concentrated to give methyl N-[(10R,14S)-14-amino-10,17-dimethyl-9-oxo -16-{[2-(trimethylsilyl)ethoxy] methyl}-8,16,18-triazatricyclo[13.2.1.0$^{2,7}$]octadeca -1(17), 2,4,6,15(18)-pentaen-5-yl]carbamate (0.38 g, 89% yield), as a yellow solid. MS(ESI) m/z: 502.4 (M+H)$^+$.

47J. Preparation of methyl N-[(10R,14S)-14-[4-(3-chloro-2-fluorophenyl)-6-oxo-1,6-dihydropyrimidin-1-yl]-10,17-dimethyl-9-oxo-16-{[2-(trimethylsilyl)ethoxy]methyl}-8,16,18-triazatricyclo[13.2.1.0$^{2,7}$]octadeca-1(17),2,4,6,15 (18)-pentaen-5-yl]carbamate trifluoroacetate To a 1-dram, pressure vial containing a white suspension of methyl N-[(10R,14S) -14-amino-10,17-dimethyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl] carbamate (0.023 g, 0.046 mmol) in CH$_3$CN (0.31 mL) was added 6-(3-chloro-2-fluorophenyl)pyrimidin-4-ol, prepared as described in Example 3, (0.012 g, 0.055 mmol) and HATU (0.023 g, 0.060 mmol). The resulting yellow suspension was stirred at rt for a few min. Next, DBU (10.37 μL, 0.069 mmol) was added and the resulting bright yellow solution was stirred at rt. After 2 h, 5:1 DMF/MeOH (1.5 mL) was added to give a clear, yellow solution. Purification by reverse phase chromatography gave, after concentration, methyl N -[(10R,14)-14[4-(3 -chloro-2-fluorophenyl)-6-oxo-1,6-dihydropyrimidin-1-yl] -10,17dimethyl-9-oxo-16-{[2-(trimethylsilyl)ethoxy]methyl}-8,16,18-triazatricyclo [13.2.1.0$^{2,7}$]octadeca-1(17),2,4,6,15(18)-pentaen-5-yl] carbamate trifluoroacetate (0.0130 g, 34.4% yield) as a clear, colorless residue. MS(ESI) m/z: 709.5 (M+H)$^+$.

47K. Preparation of methyl N-[(10R,14S)-14-[4-(3-chloro-2-fluorophenyl)-6-oxo-1,6-dihydropyrimidin-1-yl]-10,17-dimethyl-9-oxo-8,16,18-triazatricyclo[13.2.1.0$^{2,7}$]octadeca -1(17),2,4,6,15(18)-pentaen-5-yl]carbamate trifluoroacetate A clear, pale yellow solution of methyl N-[(10R,14S)-14-[4-(3-chloro-2-fluorophenyl)-6-oxo-1,6-dihydropyrimidin-1-yl]-10,17-dimethyl-9-oxo-16-{[2-(trimethylsilyl)ethoxy] methyl}-8,16,18-triazatricyclo[13.2.1.0$^{2,7}$]octadeca -1(17), 2,4,6,15(18)-pentaen-5-yl]carbamate trifluoroacetate (0.0130 g, 0.016 mmol) dissolved in 4 M HCl in dioxane (1.0 mL, 4.00 mmol) was warmed to 60° C. After 1 h the resulting suspension was cooled to rt and was concentrated. The residue was dissolved in 1:1 DMF/MeOH. Purification by reverse phase chromatography gave, after concentration and lyophilization, methyl N-[(10R,14S)-14-[4-(3-chloro-2-fluorophenyl) -6-oxo-1,6-dihydropyrimidin-1-yl]-10,17-dimethyl-9-oxo-8,16,18-triazatricyclo [13.2.1.0$^{2,7}$]octadeca-1 (17),2,4,6,15(18)-pentaen-5-yl]carbamate trifluoroacetate (0.0080 g, 72.4% yield) as a white solid. MS(ESI) m/z: 579.3 (M+H)$^+$ and 581.3 (M+2+H)$^+$. $^1$H NMR (500 MHz, 60° C., CD$_3$OD) δ 8.66 (s, 1H), 7.96 (ddd, J=8.0, 6.7, 1.8 Hz, 1H), 7.63-7.57 (m, 2H), 7.47-7.43 (m, 2H), 7.29 (td, J=8.0, 1.1 Hz, 1H), 6.96 (s, 1H), 5.80 (dd, J=11.7, 5.4 Hz, 1H), 3.77 (s, 3H), 2.66-2.59 (m, 1H), 2.56-2.47 (m, 1H), 2.39-2.31 (m, 4H), 1.85-1.76 (m, 1H), 1.62-1.52 (m, 1H), 1.51-1.41 (m, 1H), 1.31-1.21 (m, 1H), 1.10 (d, J=7.2 Hz, 3H). $^{19}$F NMR (471MHz, CDCl$_3$) δ −77.01 (s), −118.10 (s). Analytical HPLC (Method A): RT=6.04 min, purity=99.8%; Factor XIa Ki=1.1 nM, Plasma Kallikrein Ki=340 nM.

EXAMPLE 48

Preparation of methyl N-[(10R,14S)-14-[4-(3-chloro-2,6-difluorophenyl)-6-oxo-1,6-dihydropyrimidin-1-yl]-10,17-dimethyl-9-oxo-8,16,18-triazatricyclo[13.2.1.0$^{2,7}$]octadeca-1(17),2,4,6,15(18)-pentaen-5-yl]carbamate trifluoroacetate

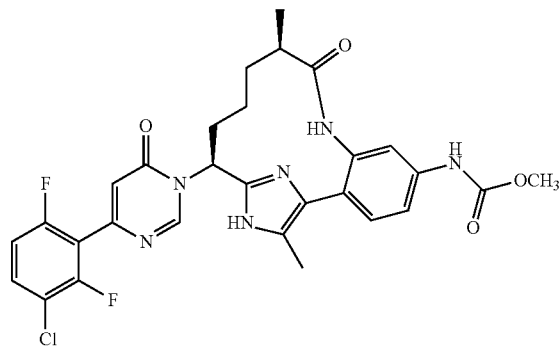 [SMILES: COC(=O)Nc1ccc2c(c1)NC(=O)[C@H](C)CCC[C@H](n1cnc(-c3c(F)ccc(Cl)c3F)cc1=O)c1nc-2c(C)[nH]1]

Methyl N-[(10R,14S)-14-[4-(3 -chloro-2,6-difluorophenyl)-6-oxo-1,6-dihydropyrimidin-1-yl]-10,17-dimethyl-9-oxo-8,16,18-triazatricyclo[13.2.1.0$^{2,7}$]octadeca -1(17),2,4, 6,15(18)-pentaen-5-yl]carbamate trifluoroacetate (0.0045 g, 11.7% over two steps) was prepared according to the procedures described in Example 47 for the preparation of methyl N-[(10R,14S)-14-[4-(3 -chloro-2-fluorophenyl)-6-oxo-1,6-dihydropyrimidin-1-yl]-10,17-dimethyl-9-oxo-8, 16,18-triazatricyclo[13.2.1.0$^{2,7}$]octadeca -1(17),2,4,6,15 (18)-pentaen-5-yl]carbamate trifluoroacetate, by replacing 6-(3-chloro-2-fluorophenyl)pyrimidin-4-ol with 6-(3-chloro-2,6-difluorophenyl)pyrimidin-4-ol, hydrobromide, prepared as described in Example 4. MS(ESI) m/z: 597.4 (M+H)$^+$. $^1$H NMR (500 MHz, CD$_3$OD, 60° C.) δ 8.68 (s, 1H), 7.62 (ddd, J=9.1, 8.3, 5.5 Hz, 1H), 7.59-7.57 (m, 1H), 7.49-7.44 (m, 2H), 7.13 (td, J=9.1, 1.8 Hz, 1H), 6.73 (d, J=0.5 Hz, 1H), 5.81 (dd, J=11.8, 5.5 Hz, 1H), 3.77 (s, 3H), 2.69-2.61 (m, 1H), 2.58-2.50 (m, 1H), 2.43-2.37 (m, 1H), 2.35 (s, 3H), 1.84-1.76 (m, 1H), 1.61-1.43 (m, 2H), 1.27-1.17 (m, 1H), 1.09 (d, J=6.9 Hz, 3H). $^{19}$F NMR (471 MHz, methanol-d$_4$) δ −77.10 (s), −114.74 (d, J=4.3 Hz), −115.50 (d, J=4.3 Hz). Analytical HPLC (Method A): RT=5.70 min, purity=99.4%; Factor XIa Ki=0.42 nM, Plasma Kallikrein Ki=19 nM.

EXAMPLE 49

Preparation of methyl N-[(10R,14S)-14-[4-(5-chloro-2-fluorophenyl)-6-oxo-1,6-dihydropyrimidin-1-yl]-10-methyl-9-oxo-8,16-diazatricyclo[13.3.1.0$^{2,7}$]nonadeca-1(19),2(7),3,5,15,17-hexaen-5-yl] carbamate trifluoroacetate

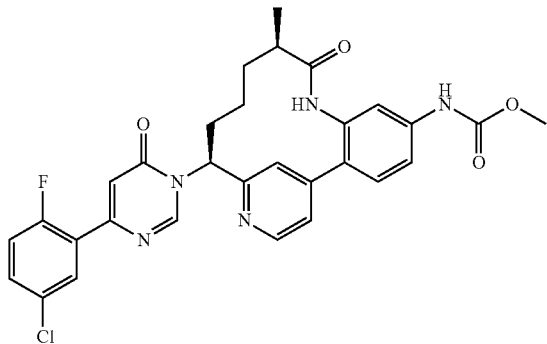 [SMILES: COC(=O)Nc1ccc2c(c1)NC(=O)[C@H](C)CCC[C@H](n1cnc(-c3cc(Cl)ccc3F)cc1=O)c1cc-2ccn1]

Methyl N-[(10R,14S)-14-[4-(5-chloro-2-fluorophenyl)-6-oxo-1,6-dihydropyrimidin-1-yl]-10-methyl-9-oxo-8,16-diazatricyclo[13.3.1.0$^{2,7}$]nonadeca-1(19),2(7),3,5,15,17-hexaen-5-yl]carbamate trifluoroacetate was prepared according to the procedures described in Example 45 for the synthesis of methyl N-[(10R,14S)-14-[4-(3-chloro-2-fluorophenyl)-6-oxo-1,6-dihydropyrimidin-1-yl]-10-methyl-9-oxo-8,16-diazatricyclo[13.3.1.0$^{2,7}$]nonadeca-1(18),2,4,6,15(19),16-hexaen-5-yl]carbamate trifluoroacetate., by replacing 6-(3-chloro-2-fluorophenyl)pyrimidin-4-ol with 6-(5-chloro-2-fluorophenyl)pyrimidin-4-ol, prepared as described in Example 5. MS(ESI) m/z: 576.05 (M+H)$^+$; $^1$H NMR (500 MHz, DMSO-d$_6$) δ 9.91 (s, 1H), 9.77 (s, 1H), 9.12 (s, 1H), 8.59 (d, J=4.9 Hz, 1H), 8.06-7.96 (m, 1H), 7.68 (s, 1H), 7.61 (d, J=8.5 Hz, 1H), 7.52-7.30 (m, 6H), 6.81 (s, 1H), 5.93 (d, J=8.9 Hz, 1H), 3.69 (s, 3H), 3.05 (m., 1H), 2.66 m., 1H), 2.32-2.23 (m, 1H), 2.02-1.84 (m, 2H), 1.40 (m, 2H), 0.84 (d, J=7.0 Hz, 3H), 0.42 (m., 1H). Analytical HPLC (Method C): RT=1.52 min, purity=91%; Factor XIa Ki=0.57 nM, Plasma Kallikrein Ki=13 nM.

EXAMPLE 50

Preparation of (10R,14S)-14-[4-(5-chloro-2-fluorophenyl)-6-oxo-1,6-dihydropyrimidin-1-yl]-4-fluoro-10-methyl-8,16-diazatricyclo[13.3.1.0$^{2,7}$]nonadeca-1(19),2(7),3,5,15,17-hexaen-9-one trifluoroacetate

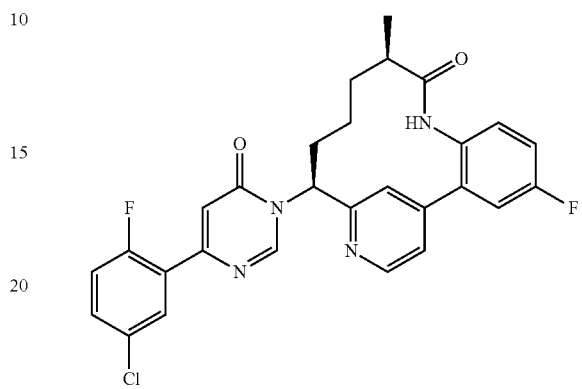

50A. Preparation of tert-butyl N-[(1S)-1-[4-(2-amino-5-fluorophenyl)pyridin-2-yl]but-3-en-1-yl]carbamate A thick-walled flask containing (S)-tert-butyl 1-(4-chloropyridin-2-yl)but-3-enylcarbamate, prepared as described in Example 45C, (3.8 g, 13.44 mmol), 3 M K$_3$PO$_4$ aq (13.44 mL, 40.3 mmol), 4-fluoro-2-(tetra-methyl-1,3,2-dioxaborolan-2-yl)aniline, prepared as described in Example 6, (3.54 g, 14.93 mmol), and (DtBPF)PdCl$_2$ (0.438 g, 0.672 mmol) in dioxane (67.2 mL) was purged and refilled with Ar (3 ×). The flask was then sealed with a teflon screw cap and the reaction was heated at 65° C. for 16 h. The reaction was then cooled to rt, diluted with EtOAc, and the reaction was filtered to remove the solid. The filtrate was concentrated to a small volume, diluted with EtOAc, washed with water, brine, dried over MgSO$_4$, filtered, and concentrated. Purification by normal phase chromatography gave tert-butyl N-[(1S)-1-[4-(2-amino-5-fluorophenyl) pyridin-2-yl]but-3-en-1-yl]carbamate (4.32 g, 90% yield) as a brown solid. $^1$H NMR (400 MHz, CDCl$_3$) δ 8.63 (dd, J=5.1, 0.7 Hz, 1H), 7.33 (s, 1H), 7.30-7.27 (m, 1H), 6.92 (td, J=8.4, 3.0 Hz, 1H), 6.85 (dd, J=9.0, 2.9 Hz, 1H), 6.71 (dd, J=8.8, 4.6 Hz, 1H), 5.78-5.65 (m, 1H), 5.60 (br. s., 1H), 5.05 (d, J=12.3 Hz, 2H), 4.85 (d, J=6.4 Hz, 1H), 3.64 (br. s., 2H), 2.62 (t, J=6.8 Hz, 2H), 1.44 (s, 9H).

50B. Preparation of (10R,14S)-14-amino-4-fluoro-10-methyl-8,16-diazatricyclo [13.3.1.0$^{2,7}$]nonadeca-1(19),2(7),3,5,15,17-hexaen-9-one (10R,14S)-14-Amino-4-fluoro-10-methyl-8,16-diazatricyclo[13.3.1.0$^{2,7}$]nonadeca -1(19),2(7),3,5,15,17-hexaen-9-one was prepared according to the procedure described for the synthesis in 45 G for the synthesis of methyl N-(4-{2-[(1S)-1-{[(tert-butoxy)carbonyl]amino}but-3-en-1-yl]pyridin-4-yl}-3-[(2R)-2-methylbut-3-enamido]phenyl)carbamate, by replacing {3-amino-4-[2-((S)-1-tert-butoxycarbonylamino-but-3-enyl)-pyridin-4-yl] phenyl}carbamic acid methyl ester, prepared as described in Example 45E with tert-butyl N-[(1S)-1-[4-(2-amino-5-fluorophenyl)pyridin-2-yl]but-3-en-1-yl]carbamate, and then procedures 45G, 45H, 45I, 45J and 45K were followed. MS(ESI) m/z: 314.1 (M+H)$^+$.

50C. Preparation of (10R,14S)-14-[4-(5-chloro-2-fluorophenyl)-6-oxo-1,6-dihydropyrimidin-1-yl]-4-fluoro-10- methyl-8,16-diazatricyclo[13.3.1.0²,⁷]nonadeca -1(19),2(7),3,5,15,17-hexaen-9-one trifluoroacetate (10R,14S)-14-[4-(5-Chloro-2-fluorophenyl)-6-oxo-1,6-dihydropyrimidin-1-yl]-4-fluoro-10-methyl-8,16-diazatricyclo[13.3.1.0²,⁷]nonadeca-1(19),2(7),3,5,15,17-hexaen-9-one trifluoroacetate was prepared according to the procedure described in Examples 45K and 45L, by using (10R,14S)-14-amino-4-fluoro-10-methyl-8,16-diazatricyclo[13.3.1.0²,⁷]nonadeca-1(19),2,4,6,15,17-hexaen-9-one prepared as described in Example 28 and 6-(5-chloro-2-fluorophenyl)pyrimidin-4-ol, prepared as described in Example 5. MS(ESI) m/z: 512.15 (M+H)⁺. ¹H NMR (500 MHz, DMSO-d₆) δ 9.71 (s, 1H), 9.11 (s, 1H), 8.65 (d, J=5.2 Hz, 1H), 8.03 (dd, J=6.6, 2.6 Hz, 1H), 7.74 (s, 1H), 7.65-7.56 (m, 1H), 7.52-7.36 (m, 3H), 7.35-7.22 (m, 2H), 6.81 (m, 1H), 5.92 (m, 1H), 2.89 (m, 1H), 2.73 (m, 1H), 2.62 (m, 1H), 2.29 (m, 1H), 1.95 (m, 2H), 1.39 (m, 2H), 0.84 (d, J=7.0 Hz, 3H), 0.45 (m., 1H). Analytical HPLC (Method C): RT=1.97 min, purity=98%; Factor XIa Ki=290 nM, Plasma Kallikrein Ki=3,600 nM.

EXAMPLE 51

Preparation of (10R,14S)-14-{4-[5-chloro-2-(1H-1,2,3-triazol-1-yl)phenyl]-6-oxo-1,6dihydropyrimidin-1-yl}-4-fluoro-10-methyl-8,16-diazatricyclo [13.3.1.0²,⁷]nonadeca -1(19),2(7),3,5,15,17-hexaen-9-one trifluoroacetate.

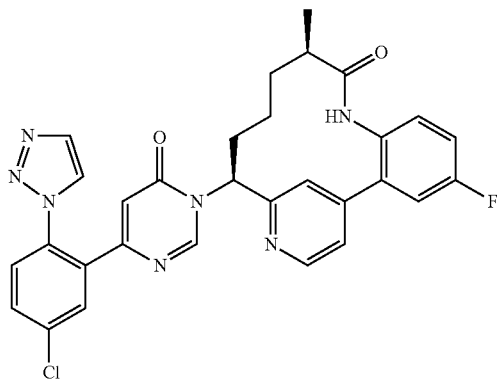

(10R,14S)-14-{4-[5-Chloro-2-(1H-1,2,3-triazol-1-yl)phenyl]-6-oxo-1,6-dihydropyrimidin-1-yl}-4-fluoro-10-methyl-8,16-diazatricyclo[13.3.1.0²,⁷]nonadeca -1(19),2(7),3,5,15,17-hexaen-9-one trifluoroacetate was prepared according to the procedure described in Examples 45K and 45L by using methyl N-[(10R,14S)-14-amino -10-methyl-9-oxo-8,16-diazatricyclo[13.3.1.0²,⁷] nonadeca-1(19),2(7),3,5,15,17-hexaen-5-yl]carbamate, described in Example 50B, and 6-(3-chloro-2-fluoro-6-(1H-1,2,3-triazol-1-yl)phenyl)pyrimidin-4-ol prepared as described in Example 7. MS(ESI) m/z: 570.1 (M+H)⁺. ¹H NMR (400 MHz, CD₃OD) δ 9.83-9.79 (m, 1H), 8.95 (s, 1H), 8.66 (d, J=5.1 Hz, 1H), 8.21 (d, J=1.1 Hz, 1H), 7.90 (d, J=2.4 Hz, 1H), 7.83 (d, J=0.9 Hz, 1H), 7.76-7.70 (m, 1H), 7.69 (s, 1H), 7.63 (d, J=8.6 Hz, 1H), 7.43-7.40 (m, 1H), 7.40-7.35 (m, 1H), 7.31-7.18 (m, 2H), 6.17 (d, J=0.9 Hz, 1H), 5.98 (dd, J=12.5, 4.6 Hz, 1H), 2.70-2.60 (m, 1H), 2.26-2.14 (m, 1H), 2.04-1.88 (m, 2H), 1.54-1.35 (m, 3H), 0.98-0.91 (m, 3H), 0.71-0.54 (m, 1H). Analytical HPLC (Method A): RT=7.84 min, purity=93%; Factor XIa Ki=3.8 nM, Plasma Kallikrein Ki=240 nM.

EXAMPLE 52

Preparation of (10R,14S)-14-{4-[3-chloro-2-fluoro-6-(1H-1,2,3-triazol-1-yl)phenyl]-6-oxo-1,6-dihydropyrimidin-1-yl}-4-fluoro-10-methyl-8,16-diazatricyclo[13.3.1.0²,⁷]nonadeca-1(19),2(7),3,5,15,17-hexaen-9-one trifluoroacetate

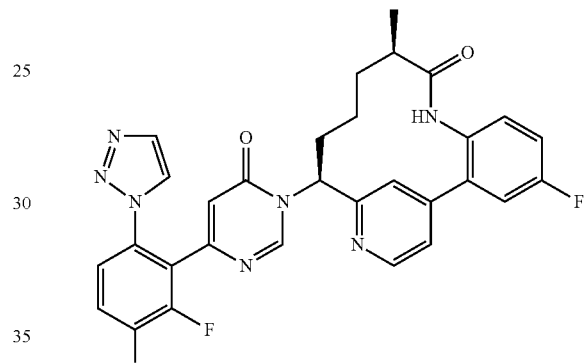

(10R,14S)-14-{4-[3-Chloro-2-fluoro-6-(1H-1,2,3-triazol-1-yl)phenyl]-6-oxo-1,6-dihydropyrimidin-1-yl}-4-fluoro-10-methyl-8,16-diazatricyclo[13.3.1.0²,⁷]nonadeca -1(19),2(7),3,5,15,17-hexaen-9-one trifluoroacetate was prepared according to the procedure described in Example 45K, by using (10R,14S)-14-amino-4-fluoro-10-methyl -8,16-diazatricyclo[13.3.1.0²,⁷]nonadeca-1(19),2(7),3,5,15,17-hexaen-9-one, preparation described in Example 28, and 6-(5-chloro-2-(1H-1,2,3-triazol-1-yl)phenyl)pyrimidin-4-ol.

MS(ESI) m/z: 588.4 (M+H)⁺. ¹H NMR (400 MHz, CD₃OD) δ 8.92 (s, 1H), 8.69 (d, J=5.1 Hz, 1H), 8.20 (d, J=1.1 Hz, 1H), 7.85 (dd, J=8.6, 7.7 Hz, 1H), 7.78 (d, J=1.1 Hz, 1H), 7.77-7.75 (m, 1H), 7.54 (dd, J=8.7, 1.7 Hz, 1H), 7.48 (dd, J=5.2, 1.7 Hz, 1H), 7.41 (dd, J=9.0, 2.6 Hz, 1H), 7.32-7.20 (m, 2H), 6.53 (s, 1H), 5.98 (dd, J=12.7, 4.7 Hz, 1H), 2.66 (m, 1H), 2.28-2.16 (m, 1H), 2.10-1.89 (m, 2H), 1.56-1.38 (m, 2H), 0.95 (d, J=6.8 Hz, 3H), 0.65 (m., 1H). Analytical HPLC (Method A): RT=11.6 min, purity=99%; Factor XIa Ki=0.47 nM, Plasma Kallikrein Ki=58 nM.

EXAMPLE 53

Preparation of (10R,14S)-14-[4-(2-bromo-5-chlorophenyl)-6-oxo-1,6-dihydropyrimidin-1-yl]-4-fluoro-10-methyl-8,16-diazatricyclo[13.3.1.0$^{2,7}$]nonadeca-1(19),2(7),3,5,15,17-hexaen-9-one trifluoroacetate

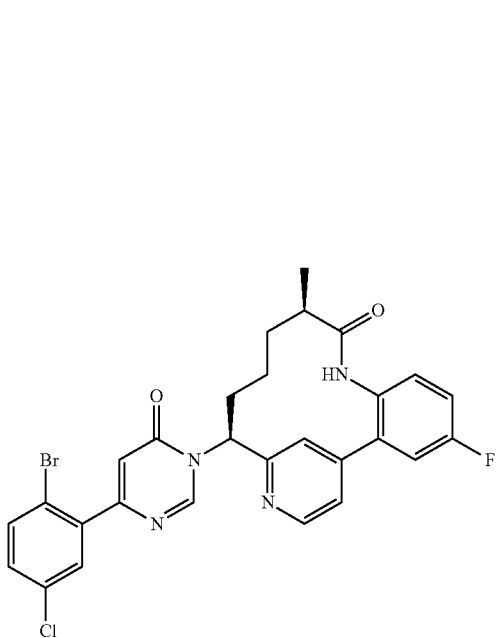 [SMILES: C[C@@H]1CCC[C@H](n2cnc(-c3cc(Cl)ccc3F)cc2=O)c2cc(ccn2)-c2cc(F)ccc2NC1=O]

(10R,14S)-14-[4-(2-Bromo-5-chlorophenyl)-6-oxo-1,6-dihydropyrimidin-1-yl]-4-fluoro-10-methyl-8,16-diazatricyclo[13.3.1.0$^{2,7}$]nonadeca-1(19),2(7),3,5,15,17-hexaen-9-one trifluoroacetate was prepared according to the procedure described in Examples 45K and 45L, by using (10R,14S)-14-amino-4-fluoro-10-methyl-8,16-diazatricyclo[13.3.1.0$^{2,7}$]nonadeca-1(19),2(7),3,5,15,17-hexaen-9-one, preparation described in Example 28, and 6-(2-bromo-5-chlorophenyl)pyrimidin-4-ol, prepared as described in Example 31. MS(ESI) m/z: 581.1 (M+H)$^+$. $^1$H NMR (400 MHz, CD$_3$OD) δ 9.14 (s, 1H), 8.70 (d, J=5.1 Hz, 1H), 7.77 (d, J=0.9 Hz, 1H), 7.70 (d, J=8.6 Hz, 1H), 7.60 (d, J=2.4 Hz, 1H), 7.45 (dd, J=5.2, 1.7 Hz, 1H), 7.39 (ddd, J=8.7, 5.7, 2.8 Hz, 2H), 7.33-7.18 (m, 2H), 6.69 (d, J=0.9 Hz, 1H), 6.07 (dd, J=12.7, 4.7 Hz, 1H), 2.66 (m, 1H), 2.38-2.23 (m, 1H), 2.16-2.05 (m, 1H), 2.03-1.91 (m, 1H), 1.61-1.39 (m, 2H), 0.97 (d, J=7.0 Hz, 3H), 0.74 (m., 1H). Analytical HPLC (Method A): RT=10.2 min, purity=99%; Factor XIa Ki=37 nM, Plasma Kallikrein Ki=310 nM.

EXAMPLE 54

Preparation of (10R,14S)-14-{4-[3-chloro-2-fluoro-6-(1H-1,2,3-triazol-1-yl)phenyl]-6-oxo-1,6-dihydropyrimidin-1-yl}-3,4-difluoro-10-methyl-8,16-diazatricyclo[13.3.1.0$^{2,7}$]nonadeca-1(19),2(7),3,5,15,17-hexaen-9-one trifluoroacetate

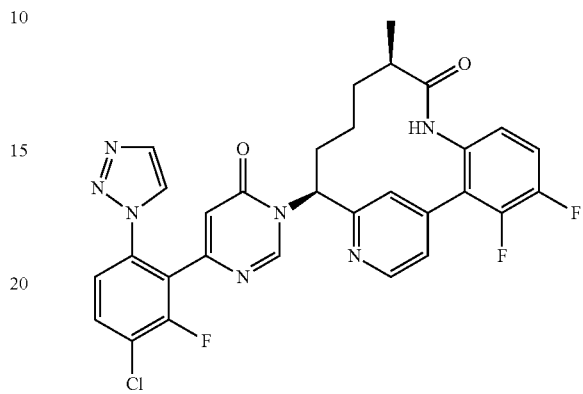

54A. Preparation of (S)-(2-(1-((tert-butoxycarbonyl)amino)but-3-en-1-yl)pyridin-4-yl)boronic acid, trifluoroacetate To a solution of 5,5,5',5'-tetramethyl-2,2'-bi(1,3,2-dioxaborinane) (1.198 g, 5.30 mmol) and (1.0 g, 3.54 mmol), (S)-tert-butyl 1-(4-chloropyridin-2-yl)but-3-enylcarbamate, prepared as described in Example 45C, in DMSO (10 mL) was added KOAc (1.041 g, 10.61 mmol) and PdCl$_2$(dppf)-CH$_2$Cl$_2$ adduct (0.289 g, 0.354 mmol). The reaction was purged with Ar for 10 min. The reaction mixture was then sealed and stirred for 12 h at 85° C. The reaction mixture was cooled to rt and then it was diluted with EtOAc and washed with water. The aqueous layer was extracted with EtOAc. The organic layers were combined and was washed with brine, dried over Na$_2$SO$_4$, filtered, and concentrated. Purification by reverse phase chromatography afforded the (S)-(2-(1-((tert-butoxycarbonyl)amino)but-3-en-1-yl)pyridin-4-yl)boronic acid trifluoroacetate (1.1 g, 77%) as a white solid. MS(ESI) m/z: 293.2 (M+H)$^+$. $^1$H NMR (500 MHz, CD$_3$OD) d 8.54 (d, J=5.8 Hz, 1H), 8.11 (s, 1H), 8.02 (dd, J=5.8, 0.6 Hz, 1H), 5.79 (ddt, J=17.1, 10.2, 7.1 Hz, 1H), 5.11-5.03 (m, 2H), 4.86 (t, J=7.0 Hz, 1H), 2.69-2.55 (m, 2H), 1.40 (br. s., 9H) ppm.

54B. Preparation of tert-butyl N-[(1S)-1-[4-(2-amino-6-fluorophenyl)pyridin-2-yl]but-3en-1-yl]carbamate A sealed tube was charged with (S)-(2-(1-((tert-butoxycarbonyl)amino)but-3-en-1-yl)pyridin-4-yl)boronic acid trifluoroacetate (0.5 g, 1.712 mmol), 2-chloro-3,4-difluoroaniline (0.31 g, 1.88 mmol), (DtBPF)PdCl$_2$ (0.056 g, 0.086 mmol), 3 M K$_2$PO$_3$ (1.71 mL, 5.13 mmol), and THF (17.1 mL). The reaction vessel was purged and back-filled with Ar (3 ×), then the tube was sealed, and the reaction was heated at 90° C. After 18 h, the reaction was cooled to rt. The reaction was diluted with EtOAc, washed with brine, dried over Na$_2$SO$_4$, filtered, and concentrated. Purification by normal phase chromatography afforded tert-butyl N-[(1S)-1-[4-(2-amino-6-fluorophenyl)pyridin-2-yl]but-3-en-1-yl]carbamate (0.35 g, 54.5% yield). MS(ESI) m/z: 376.4 (M+H)$^+$. $^1$H NMR (400 MHz, CDCl$_3$) δ 8.67 (dd, J=5.1, 0.4 Hz, 1H), 7.28 (s, 1H), 7.23 (dd, J=5.1, 1.1 Hz, 1H), 7.04-6.96 (m, 1H), 6.48-6.42 (m, 1H), 5.78-5.57 (m, 2H), 5.09-5.01 (m, 2H), 4.90-4.80 (m, 1H), 3.60 (br. s., 2H), 2.63 (t, J=6.6 Hz, 2H), 1.43 (s, 9H).

54C. Preparation of (10R,14S)-14-amino-3,4-difluoro-10-methyl-8,16-diazatricyclo [13.3.1.0$^{2,7}$]nonadeca-1(19),2(7),3,5,15,17-hexaen-9-one (10R,14S)-14-Amino-3,4-difluoro-10-methyl-8,16-diazatricyclo[13.3.1.0$^{2,7}$]nonadeca-1(19),2(7),3,5,15,17-hexaen-9-one was prepared according to the procedure described in 45G by replacing {3-amino-4[2-((S)-1-tert-butoxycarbonylamino-but-3-enyl)-pyridin-4-yl]phenyl}carbamic acid methyl ester with tert-butyl N-[(1S)-1-[4-(2-amino-6-fluorophenyl)pyridin-2-yl]but-3-en-1-yl]carbamate and then procedures described in Examples 45G, 45H, 45I, and 45K were followed.

54D. Preparation of (10R,14S)-14-{4-[3-chloro-2-fluoro-6-(1H-1,2,3-triazol-1-yl)phenyl]-6-oxo-1,6-dihydropyrimidin-1-yl}-3,4-difluoro-10-methyl-8,16-diazatricyclo [13.3.1.0$^{2,7}$]nonadeca-1(19),2(7),3,5,15,17-hexaen-9-one trifluoroacetate (10R,14S)-14-{4-[3-Chloro-2-fluoro-6-(1H-1,2,3-triazol-1-yl)phenyl]-6-oxo-1,6dihydropyrimidin-1-yl}-3,4-difluoro-10-methyl-8,16-diazatricyclo[13.3.1.0$^{2,7}$]nonadeca-1(19),2(7),3,5,15,17-hexaen-9-one trifluoroacetate was prepared according to the procedure described in Examples 45K and 45L, by using (10R,14S)-14-amino-3,4-difluoro-10-methyl-8,16-diazatricyclo[13.3.1.0$^{2,7}$]nonadeca-1(19),2(7),3,5,15,17-hexaen -9-one and 6-(3-chloro-2-fluoro-6-(1H-1,2,3-triazol-1-yl)phenyl)pyrimidin-4-ol, prepared as described in Example 7. MS(ESI) m/z: 606.3 (M+H)$^+$. $^1$H NMR (400 MHz, CD$_3$OD) δ 8.96 (s, 1H), 8.69 (d, J=4.8 Hz, 1H), 8.18 (d, J=1.1 Hz, 1H), 7.84 (dd, J=8.6, 7.7 Hz, 1H), 7.78 (d, J=1.1 Hz, 1H), 7.58 (s, 1H), 7.53 (dd, J=8.6, 1.5 Hz, 1H), 7.47 (ddd, J=4.8, 2.9, 1.5 Hz, 1H), 7.43-7.35 (m, 1H), 7.10 (ddd, J=8.9, 4.5, 1.9 Hz, 1H), 6.53 (s, 1H), 5.98 (dd, J=12.3, 4.8 Hz, 1H), 2.61-2.51 (m, 1H), 2.21-1.97 (m, 2H), 1.86-1.74 (m, 1H), 1.53-1.40 (m, 1H), 1.31-1.15 (m, 1H), 0.93 (d, J=6.8 Hz, 3H), 0.85-0.64 (m, 1H). Analytical HPLC, RT=8.32 min, 99.9% purity; Factor XIa Ki=0.49 nM, Plasma Kallikrein Ki=41 nM.

EXAMPLE 55

Preparation of (10R,12R,14S)-14-{4-[3-chloro-6-(4-chloro-1H-1,2,3-triazol-1-yl)-2-fluorophenyl]-6-oxo-1,6-dihydropyrimidin-1-yl}-4,17-difluoro-12-hydroxy-10-methyl-8-azatricyclo[13.3.1.0$^{2,7}$]nonadeca-1(19),2(7),3,5,15,17-hexaen-9-one

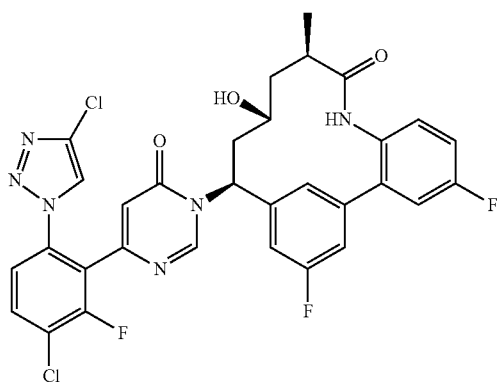 [SMILES: C[C@@H]1C[C@@H](O)C[C@H](n2cnc(-c3c(-n4cc(Cl)nn4)ccc(Cl)c3F)cc2=O)c2cc(F)cc(c2)-c2cc(F)ccc2NC1=O]

55A. Preparation of tert-butyl N-[(1S)-1-[3-(2-amino-5-fluorophenyl)-5-fluorophenyl]but-3-en-1-yl]carbamate

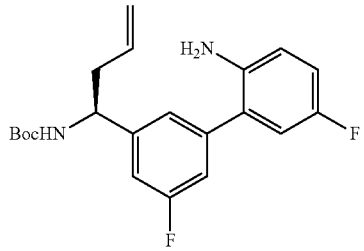 [SMILES: C=CC[C@H](NC(=O)OC(C)(C)C)c1cc(F)cc(-c2cc(F)ccc2N)c1]

To a solution of (S)-tert-butyl (1-(3-bromo-5-fluorophenyl)but-3-en-1-yl)carbamate (483 mg, 1.403 mmol) in dioxane (7 ml) was added potassium (2-amino-5-fluorophenyl)boronate (454 mg, 1.96 mmol) and 3 M K$_3$PO$_4$ (1.4 ml, 4.20 mmol). The resulting solution was purged with Ar for several min, then (DtBPF)PdCl$_2$ (45.7 mg, 0.07 mmol) was added, the reaction vessel sealed and heated at 75 ° C. overnight. The reaction mixture was filtered, rinsed with EtOAc and the filtrate concentrated to yield a dark brown crude product which was dissolved in EtOAc. The resulting solution was washed with water and brine, dried over MgSO$_4$, filtered and concentrated. Purification by normal phase chromatography gave tert-butyl N-[(1S)-14-1-[3-(2-amino-5-fluorophenyl)-5-fluorophenyl]but-3-en-1-yl]carbamate (425 mg, 81% yield) as a light brownish oil. MS(ESI) m/z: 375.4 (M+H)$^+$.

55B. Preparation of tert-butyl N-[(1S)-1-(3-fluoro-5-{5-fluoro-2-[(2R)-2-methylbut-3-enamido]phenyl}phenyl)but-3-en-1-yl]carbamate

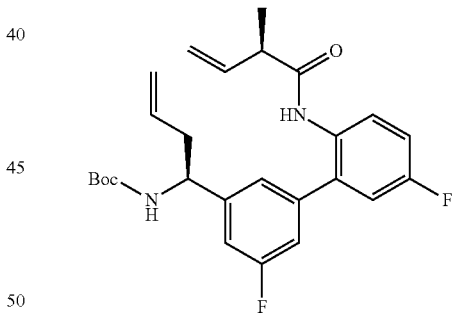

To a solution of tert-butyl N-[(1S)-1-[3-(2-amino-5-fluorophenyl)-5-fluorophenyl]but-3-en-1-yl]carbamate in EtOAc (6 mL) was added (R)-2-methylbut-3-enoic acid (136 mg, 1.362 mmol), prepared as described in Example 2, and pyridine (0.275 mL, 3.41 mmol). The solution was cooled to 0° C. and T3P® (50% wt in EtOAc) (1.351 mL, 2.270 mmol) was added. The reaction mixture was stirred at 0° C., for 1 h, then gradually warmed up to rt and stirred overnight. The reaction mixture was concentrated and the residue was purified by normal phase chromatography to give tert-butyl N-[(1S)-1-(3-fluoro-5-{5-fluoro-2-[(2R)-2-methylbut-3-enamido]phenyl}phenyl)but-3-en-1-yl]carbamate (431 mg, 83% yield). MS(ESI) m/z: 457.08 (M+H)$^+$.

55C. Preparation of tert-butyl N-[(10R,11E,14S)-4,17-difluoro-10-methyl-9-oxo-8-azatricyclo[13.3.1.0²,⁷]nonadeca-1(19),2(7),3,5,11,15,17-heptaen-14-yl]carbamate

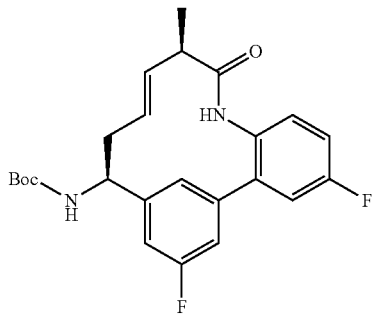 [SMILES: C[C@@H]1/C=C/C[C@H](NC(=O)OC(C)(C)C)c2cc(F)cc(c2)-c2cc(F)ccc2NC1=O]

A solution of tert-butyl N-[(1S)-1-(3-fluoro-5-{5-fluoro-2-[(2R)-2-methylbut-3-enamido]phenyl}phenyl)but-3-en-1-yl]carbamate (431 mg, 0.944 mmol) in DCM (380 mL) was purged with Ar. Second Generation Grubbs Catalyst (180 mg, 0.212 mmol) was then added and the reaction was sealed and heated at 40° C. overnight. The reaction mixture was cooled to rt and concentrated. The residue was purified by normal phase chromatography to give tert-butyl N-[(10R,11E,14S)-4,17-difluoro-10-methyl-9-oxo-8-azatricyclo[13.3.1.0²,⁷]nonadeca-1(19),2(7),3,5,11,15,17-heptaen-14-yl]carbamate (284 mg, 0.66 mmol, 70% yield) as a white solid. MS(ESI) m/z: 373.1 (M+H—ᵗBu)⁺.

55D. Preparation of tert-butyl N-[(10R,14S)-4,17-difluoro-11-hydroxy-10-methyl-9-oxo-8-azatricyclo[13.3.1.0²,⁷]nonadeca-1(19),2(7),3,5,15,17-hexaen-14-yl]carbamate, and tert-butyl N-[(10R,14S)-4,17-difluoro-12-hydroxy-10-methyl-9-oxo-8-azatricyclo[13.3.1.0²,⁷]nonadeca-1(19),2(7),3,5,15,17-hexaen-14-yl]carbamate

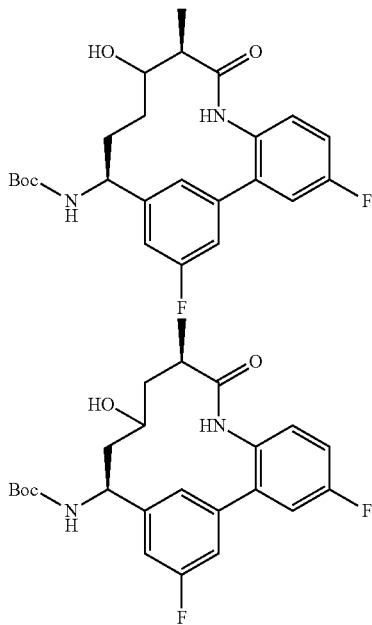

A solution of tert-butyl N-[(10R,11E,14S)-4,17-difluoro-10-methyl-9-oxo-8-azatricyclo[13.3.1.0²,⁷]nonadeca-1(19),2(7),3,5,11,15,17-heptaen-14-yl]carbamate (54.5 mg, 0.127 mmol) in THF (1.5 mL) was cooled to 0° C. and 1M BH₃.THF complex (0.38 mL, 0.38 mmol) was added dropwise. After addition, the reaction mixture was warmed to rt and stirred for 2 h. After this time, 3M NaOAc (0.85 mL, 2.54 mmol), and 35% aq H₂O₂ (0.33 mL, 3.82 mmol) were added. After 2.5 h, to the reaction mixture was added water, and the resulting solution was extracted with EtOAc (2 ×). The combined EtOAc phases were washed with brine, dried over MgSO₄, filtered, concentrated. The residue was purified by normal phase chromatography to give a mixture of tert-butyl N -[(10R,14S)-4,17-difluoro-11-hydroxy-10-methyl-9-oxo-8-azatricyclo[13.3.1.0²,⁷]nonadeca-1(19),2(7),3,5,15,17-hexaen-14-yl]carbamate and tert-butyl N-[(10R,14S)-4,17-difluoro-12-hydroxy-10-methyl-9-oxo-8-azatricyclo[13.3.1.0²,⁷]nonadeca-1(19),2(7),3,5,15,17-hexaen-14-yl]carbamate (38 mg, 67% yield). MS(ESI) m/z: 347.4 (M+H-Boc)⁺.

55E. Preparation of tert-butyl N-[(10R,14S)-4,17-difluoro-10-methyl-9,12-dioxo-8-azatricyclo[13.3.1.0²,⁷]nonadeca-1(19),2(7),3,5,15,17-hexaen-14-yl]carbamate

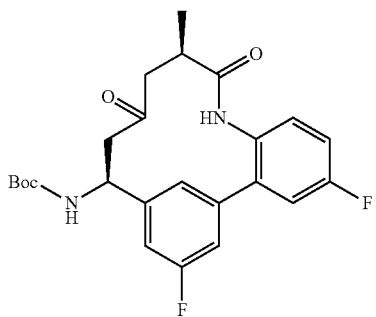 [SMILES: C[C@@H]1CC(=O)C[C@H](NC(=O)OC(C)(C)C)c2cc(F)cc(c2)-c2cc(F)ccc2NC1=O]

To the mixture of tert-butyl N-[(10R,14S)-4,17-difluoro-11-hydroxy-10-methyl-9-oxo-8-azatricyclo[13.3.1.0²,⁷]nonadeca-1(19),2(7),3,5,15,17-hexaen-14-yl]carbamate and tert-butyl N-[(10R,14S)-4,17-difluoro-12-hydroxy-10-methyl-9-oxo-8-azatricyclo [13.3.1.0²,⁷]nonadeca-1(19),2(7),3,5,15,17-hexaen-14-yl]carbamate (117 mg, 0.262 mmol) in DCM (5 mL) was added Dess Martin's reagent (144 mg, 0.341 mmol), and the reaction was stirred at rt. After 1 h, the reaction mixture was diluted with DCM, washed with water and concentrated. The residue was purified by normal phase chromatography, followed by chiral reverse phase chromatography to give tert-butyl N-[(10R,14S)-4,17-difluoro-10-methyl-9,12-dioxo-8-azatricyclo[13.3.1.0²,⁷]nonadeca-1(19),2(7),3,5,15,17-hexaen-14-yl]carbamate (47 mg, 40% yield) as a white solid. MS(ESI) m/z: 347.4 (M+H ᵗBu)⁺.

55F. Preparation of tert-butyl N-[(10R,12R,14S)-4,17-difluoro-12-hydroxy-10-methyl-9-oxo-8-azatricyclo[13.3.1.0²,⁷]nonadeca-1(19),2(7),3,5,15,17-hexaen-14-yl]carbamate

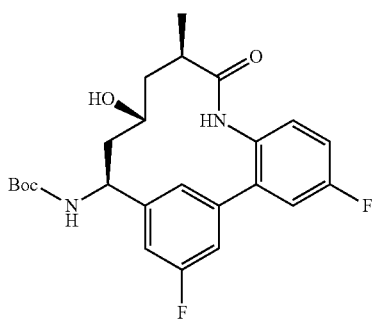 [SMILES: C[C@@H]1C[C@@H](O)C[C@H](NC(=O)OC(C)(C)C)c2cc(F)cc(c2)-c2cc(F)ccc2NC1=O]

A solution of tert-butyl N-[(10R,14S)-4,17-difluoro-10-methyl-9,12-dioxo-8-azatricyclo[13.3.1.0$^{2,7}$]nonadeca-1(19),2(7),3,5,15,17-hexaen-14-yl]carbamate (47 mg, 0.106 mmol) in MeOH (3 mL) was cooled to 0° C. and NaBH$_4$ (20.0 mg, 0.53 mmol) was added portionwise. The solution was warmed to rt after 10 min the reaction mixture was quenched with water, concentrated, redissolved in DMSO/MeOH, filtered, and purified by reverse phase chromatography to give tert-butyl N-[(10R,12R,14S)-4,17-difluoro-12-hydroxy-10-methyl-9-oxo-8-azatricyclo[13.3.1.0$^{2,7}$]nonadeca-1(19),2(7),3,5,15,17-hexaen-14-yl]carbamate (36.8 mg, 78% yield) as a white solid. $^1$H NMR (400 MHz, CD$_3$OD) δ 7.41-6.98 (m, 6H), 4.77 (d, J=5.5 Hz, 1H), 2.99-2.83 (m, 1H), 2.76-2.62 (m, 1H), 2.19-2.08 (m, 1H), 1.90-1.81 (m, 1H), 1.80-1.73 (m, 1H), 1.63-1.53 (m, 1H), 1.51-1.39 (m, 9H), 1.14 (d, J=7.0 Hz, 3H).

55G. Preparation of (10R,12R,14S)-14-amino-4,17-difluoro-12-hydroxy-10-methyl-8-azatricyclo[13.3.1.0$^{2,7}$]nonadeca-1(19),2(7),3,5,15,17-hexaen-9-one To a solution of tert-butyl N-[(10R,12R,14S)-4,17-difluoro-12-hydroxy-10-methyl-9-oxo-8-azatricyclo[13.3.1.0$^{2,7}$]nonadeca-1(19),2(7),3,5,15,17-hexaen-14-yl]carbamate (36.8 mg, 0.082 mmol) in DCM (2 mL) was added TFA (0.4 mL, 5.12 mmol). The reaction was stirred at rt for 1.5 h. The reaction mixture was concentrated then redissolved in MeOH, passed through HCO$_3$ resin cartridge, rinsed with MeOH, and the filtrate was concentrated to give (10R,12R,14S)-14-amino-4,17-difluoro-12-hydroxy-10-methyl-8-azatricyclo[13.3.1.0$^{2,7}$]nonadeca-1(19),2(7),3,5,15,17-hexaen-9-one (28 mg, 98% yield). MS(ESI) m/z: 347.4 (M+H)$^+$.

55H. Preparation of (10R,12R,14S)-14-{4-[3-chloro-6-(4-chloro-1H-1,2,3-triazol-1-yl)-2-fluorophenyl]-6-oxo-1,6-dihydropyrimidin-1-yl}-4,17-difluoro-12-hydroxy-10-methyl-8-azatricyclo[13.3.1.0$^{2,7}$]nonadeca-1(19),2(7),3,5,15,17-hexaen-9-one (10R,12R,14S)-14-{4-[3-Chloro-6-(4-chloro-1H-1,2,3-triazol-1-yl)-2-fluorophenyl]-6-oxo-1,6-dihydropyrimidin-1-yl}-4,17-difluoro-12-hydroxy-10-methyl-8-azatricyclo[13.3.1.0$^{2,7}$]nonadeca-1(19),2(7),3,5,15,17-hexaen-9-one (10 mg, 34% yield) was prepared in a similar manner as the procedure described in Example 114 by replacing (10R,14S)-14-amino-10-methyl-9-oxo-8,16-diazatricyclo[13.3.1.0$^{2,7}$]nonadeca-1(19),2(7),3,5,15,17-hexaene-4-carbonitrile with (10R,12R,14S)-14-amino-4,17-difluoro-12-hydroxy-10-methyl-8-azatricyclo[13.3.1.0$^{2,7}$]nonadeca-1(19),2(7),3,5,15,17-hexaen-9-one. MS(ESI) m/z: 655.2 (M+H)$^+$. $^1$H NMR (400 MHz, CD$_3$OD) δ 8.91 (s, 1H), 8.35 (s, 1H), 7.88 (t, J=8.0 Hz, 1H), 7.63-7.54 (m, 2H), 7.42-7.36 (m, 1H), 7.32-7.14 (m, 3H), 6.88(d, J=9.0 Hz, 1H), 6.64 (s, 1H), 5.92 (dd, J=9.7, 4.8 Hz, 1H), 3.18 (br. s., 1H), 2.83-2.72 (m, 1H), 2.54-2.41 (m, 1H), 2.30-2.17 (m, 1H), 2.06-1.95 (m, 1H), 1.75-1.59-(m, 1H), 1.18 (d, J=7.0 Hz, 3H). Analytical HPLC (Method A): RT=9.21 min, purity>92%; Factor XIa Ki=0.11 nM, Plasma Kallikrein Ki=5 nM.

EXAMPLE 56

Preparation of (10R,12R,14S)-14-{4-[5-chloro-2-(4-chloro-1H-1,2,3-triazol-1-yl)phenyl]-6-oxo-1,6-dihydropyrimidin-1-yl}-4,17-difluoro-12-hydroxy-10-methyl-8-azatricyclo[13.3.1.0$^{2,7}$]nonadeca-1(19),2(7),3,5,15,17-hexaen-9-one

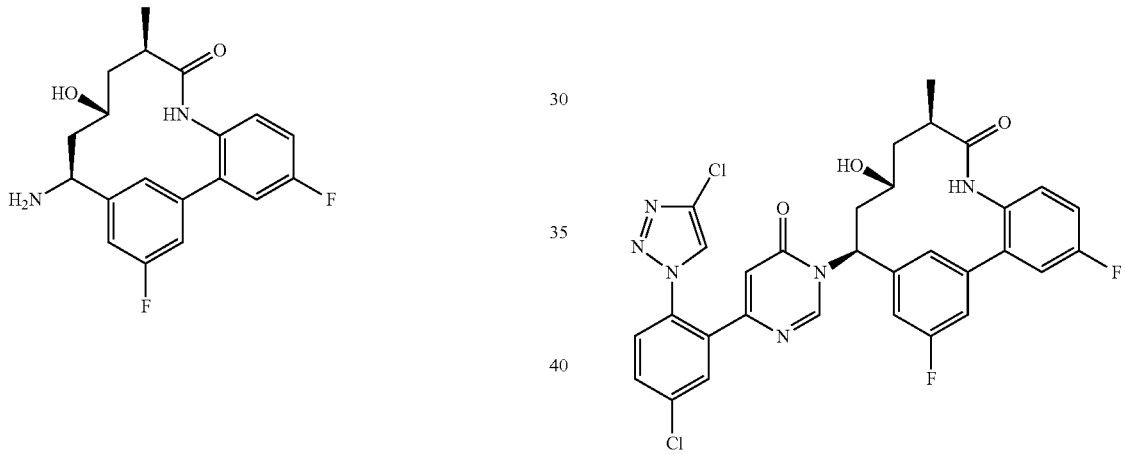

(10R,12R,14S)-14-{4-[5-Chloro-2-(4-chloro-1H-1,2,3-triazol-1-yl)phenyl]-6-oxo-1,6-dihydropyrimidin-1-yl}-4,17-difluoro-12-hydroxy-10-methyl-8-azatricyclo[13.3.1.0$^{2,7}$]nonadeca-1(19),2(7),3,5,15,17-hexaen-9-one (6.1 mg, 23% yield) was prepared in a similar manner as the procedure described in Example 98 by replacing 6-[3-chloro-6-(4-chloro-1H-1,2,3-triazol-1-yl)-2-fluorophenyl]pyrimidin-4-ol with 6-[5-chloro-2-(4-chloro-1H-1,2,3-triazol-1-yl)phenyl]pyrimidin-4-ol, prepared as described in Example 9. MS(ESI) m/z: 637.2 (M+H)$^+$. $^1$H NMR (400 MHz, CD$_3$OD) δ 8.88 (s, 1H), 8.37 (s, 1H), 7.92 (d, J=2.4 Hz, 1H), 7.78-7.74 (m, 1H), 7.70-7.65 (m, 1H), 7.56 (s, 1H), 7.38 (dd, J=9.2, 2.9 Hz, 1H), 7.29 (dd, J=8.6, 5.3 Hz, 1H), 7.25-7.15 (m, 2H), 6.96-6.90 (m, 1H), 6.41 (d, J=0.7 Hz, 1H), 5.89 (dd, J=10.1, 4.8 Hz, 1H), 3.20 (br. s., 1H), 2.83-2.73 (m, 1H), 2.55-2.44 (m, 1H), 2.25-2.18 (m, 1H), 2.07-1.97 (m, 1H), 1.73-1.63 (m, 1H), 1.19 (d, J=7.0 Hz, 3H). Analytical HPLC (Method A): RT=9.15 min, purity=>97%; Factor XIa Ki=0.19 nM, Plasma Kallikrein Ki=16 nM.

EXAMPLE 57

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-8,16-diazatricyclo[13.3.1.0$^{2,7}$]nonadeca-1(19),2,4,6,15,17-hexaen-9-one

EXAMPLE 58

Preparation of (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-8,16-diazatricyclo[13.3.1.0$^{2,7}$]nonadeca-1(19),2,4,6,15,17-hexaen-9-one

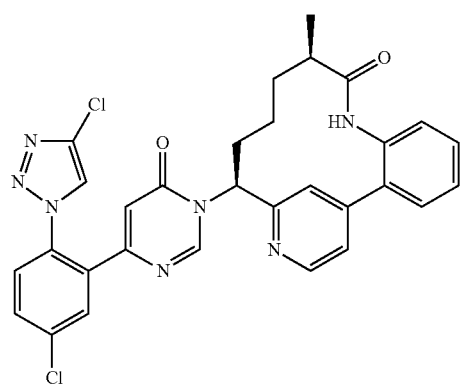 [SMILES: C[C@@H]1CCC[C@H](n2cnc(-c3cc(Cl)ccc3-n3cc(Cl)nn3)cc2=O)c2cc(ccn2)-c2ccccc2NC1=O]

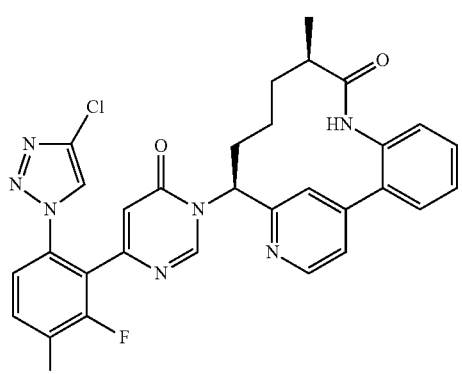

(10R,14S)-14-{4-[5-Chloro-2-(4-chloro-1H-1,2,3-triazol-1-yl)phenyl]-6-oxo-1,6-dihydropyrimidin-1-yl}-10-methyl-8,16-diazatricyclo[13.3.1.0$^{2,7}$]nonadeca-1(19),2,4,6,15,17-hexaen-9-one was prepared in 21% yield as a solid (7 mg), via the coupling of 6-[5-chloro-2-(4-chloro-1H-1,2,3-triazol-1-yl)phenyl]pyrimidin-4-ol (0.03 g, 0.09 mmol) and (10R,14S)-14-amino-10-methyl-8,16-diazatricyclo[13.3.1.0$^{2,7}$]nonadeca-1(19),2,4,6,15,17-hexaen-9-one (0.028 g, 0.09 mmol) using the HATU, DBU coupling methodology described in Examples 45K and 45L. MS(ESI) m/z: 620.1 (M+H)$^+$. $^1$H NMR (400 MHz, CD$_3$OD) δ 8.82-8.74 (m, 1H), 8.40 (s, 1H), 8.07-8.01 (m, 1H), 7.92-7.89 (m, 1H), 7.76 (d, J=2.4 Hz, 2H), 7.68 (s, 2H), 7.61-7.49 (m, 2H), 7.35-7.30 (m, 1H), 6.42 (s, 1H), 5.96-5.88 (m, 1H), 2.78-2.66 (m, 1H), 2.47-2.34 (m, 1H), 2.20-2.09 (m, 1H), 2.04-1.89 (m, 1H), 1.62-1.47 (m, 2H), 1.01 (d, J=6.8 Hz, 3H), 0.84-0.67 (m, 1H). Analytical HPLC (Method A): RT=7.78 min, purity=98%; Factor XIa Ki=0.28 nM, Plasma Kallikrein Ki=18nM.

(10R,14S)-14-{4-[3-Chloro-6-(4-chloro-1H-1,2,3-triazol-1-yl)-2-fluorophenyl]-6-oxo-1,6-dihydropyrimidin-1-yl}-10-methyl-8,16-diazatricyclo[13.3.1.0$^{2,7}$]nonadeca-1(19),2,4,6,15,17-hexaen-9-one was prepared in 22% yield as a solid (8 mg), via the coupling of 6-[3-chloro-6-(4-chloro-1H-1,2,3-triazol-1-yl)-2-fluorophenyl]pyrimidin-4-ol (0.017 g, 0.06 mmol) and (10R,14S)-14-amino-10-methyl-8,16-diazatricyclo[13.3.1.0$^{2,7}$]nonadeca-1(19),2,4,6,15,17-hexaen-9-one (0.024 g, 0.06 mmol) using the HATU, DBU coupling methodology described in Examples 45K and 45L. MS(ESI) m/z =638.1 (M+H)$^+$. $^1$H NMR (400 MHz, CD$_3$OD) δ 8.79 (d, J=2.4 Hz, 2H), 8.40 (s, 1H), 8.06 (s, 1H), 7.89 (s, 1H), 7.78-7.74 (m, 1H), 7.72-7.68 (m, 1H), 7.59 (d, J=1.3 Hz, 3H), 7.35-7.30 (m, 1H), 6.68-6.65 (m, 1H), 5.98-5.90 (m, 1H), 2.77-2.68 (m, 1H), 2.47-2.33 (m, 1H), 2.21-2.11 (m, 1H), 2.03-1.91 (m, 1H), 1.63-1.49 (m, 2H), 1.01 (d, J=7.0 Hz, 3H), 0.87-0.65 (m, 1H). Analytical HPLC (Method A) RT=7.78 min, purity=99%; Factor XIa Ki=0.11 nM, Plasma Kallikrein Ki=5 nM.

EXAMPLE 59

Preparation of (10S,14S)-14-{4-[5-chloro-2-(4-chloro-1H-1,2,3-triazol-1-yl)phenyl]-6-oxo-1,6-dihydropyrimidin-1-yl}-4-fluoro-10,11-dimethyl-8,11,16-triazatricyclo [13.3.1.0$^{2,7}$]nonadeca-1(19),2(7),3,5,15,17-hexaen-9-one

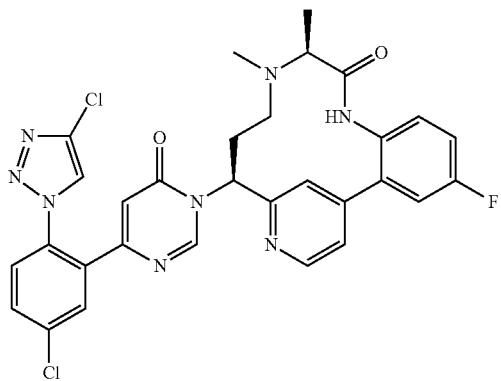 [SMILES: C[C@H]1C(=O)Nc2ccc(F)cc2-c2ccnc(c2)[C@@H](n2cnc(-c3cc(Cl)ccc3-n3cc(Cl)nn3)cc2=O)CCN1C]

59A. Preparation of tert-butyl N-[(1S)-1-(4-chloropyridin-2-yl)-3-oxopropyl]carbamate To a solution of tert-butyl N-[(1S)-1-(4-chloropyridin-2-yl)but-3-en-1-yl]carbamate, prepared as described in Example 23, (2 g, 7.07 mmol) in MeOH (79 ml) and H$_2$O (39.3 ml) was added OsO$_4$ (17.68 ml, 0.354 mmol). After 5-10 min of stirring, a dark tan solution formed. NaIO$_4$ (4.54 g, 21.22 mmol) was added with vigorous stirring. The reaction mixture was stirred at rt for 2 h. The reaction mixture was concentrated to remove most MeOH, then extracted 2× with EtOAc. The combined EtOAc phases were washed with brine, dried over MgSO$_4$, filtered and concentrated. The crude product was then purified using silica gel chromatography to give tert-butyl N-[(1S)-1-(4-chloropyridin-2-yl)but-3-en-1-yl]carbamate (1.29 g, 64%) as a dark greenish oil. MS(ESI) m/z: 285.3 (M+H)$^+$.

59B. Preparation of methyl (2S)-2-{[(3S)-3-{[(tert-butoxy)carbonyl]amino}-3-(4-chloropyridin-2-yl)propyl](methyl)amino}propanoate (S)-Methyl 2-(methylamino)propanoate hydrochloride (138 mg, 0.901 mmol) was dissolved in MeOH, passing through an AGILENT® PL-HCO$_3$ MP resin cartridge and concentrated. tert-Butyl N-[(1S)-1-(4-chloropyridin-2-yl)but-3-en-1-yl]carbamate (190 mg, 0.667 mmol) in DCE (8341 µl) was added followed by addition of 1 drop of AcOH. The reaction mixture was stirred at rt for 1.5 h, then NaBH(OAc)$_3$ (424 mg, 2.002 mmol) was added and the reaction was stirred at rt overnight. The reaction was diluted with DCM, washed with sat NaHCO$_3$, brine, dried over MgSO$_4$, filtered and concentrated. The crude product was then purified using silica gel chromatography to give methyl (2S)-2-{[(3S)-3-{[(tert-butoxy)carbonyl]amino}-3-(4-chloropyridin-2-yl)propyl](methyl)amino}propanoate (200 mg, 78%) as a light greenish oil. MS(ESI) m/z: 386.1 (M+H)$^+$.

59C. Preparation of methyl (2S)-2-{[(3S)-3-[4-(2-amino-5-fluorophenyl)pyridin-2-yl]-3-{[(tert-butoxy)carbonyl]amino}propyl](methyl)amino}propanoate A solution of methyl (2S)-2-{[(3S)-3-{[(tert-butoxy)carbonyl]amino}-3-(4-chloropyridin-2-yl)propyl](methyl)amino}propanoate (200 mg, 0.518 mmol), potassium (2-amino-5-fluorophenyl)boronate (180 mg, 0.777 mmol), aq 3 M K$_3$PO$_4$ (518 µl, 1.555 mmol) in dioxane (2591 µl) was purged with Ar for several min, (DtBPF)PdCl$_2$ (16.89 mg, 0.026 mmol) was added. The reaction was sealed and heated at 90° C. overnight. The reaction mixture was filtered off solid, rinsed with EtOAc, filtrate was concentrated to yield a dark brown crude product which was dissolved in EtOAc, washed with water and brine, dried over MgSO$_4$, filtered, and concentrated. The crude product was then purified using silica gel chromatography to give methyl (2S)-2-{[(3S)-3-[4-(2-amino-5-fluorophenyl)pyridin-2-yl]-3-{[(tert-butoxy)carbonyl]amino}propyl](methyl)amino}propanoate (159 mg, 67%) as a light brownish oil. MS(ESI) m/z: 461.2 (M+H)$^+$.

59D. Preparation of (2S)-2-{[(3S)-3-[4-(2-amino-5-fluorophenyl)pyridin-2-yl]-3-{[(tert-butoxy)carbonyl]amino}propyl](methyl)amino}propanoic acid To a solution of methyl (2S)-2-{[(3S)-3-[4-(2-amino-5-fluorophenyl)pyridin-2-yl]-3-{[(tert-butoxy)carbonyl]amino}propyl](methyl)amino}propanoate (194 mg, 0.421 mmol) in MeOH (4200 µl) was added 2 M LiOH (1000 µl, 2.106 mmol). The reaction was stirred at rt overnight. The reaction was concentrated, diluted with EtOAc/H$_2$O, extracted with EtOAc (2×), and 10% MeOH/DCM (2×). The organic layers were combined, dried over MgSO$_4$, filtered and concentrated to give (2S)-2-{[(3S)-3-[4-(2amino-5-fluorophenyl)pyridin-2-yl]-3-{[(tert-butoxy)carbonyl]amino}propyl](methyl) -amino}propanoic acid (140 mg, 74%) as a dark brownish solid. MS(ESI) m/z: 447.5 (M+H)$^+$.

59E. Preparation of tert-butyl N-[(10S,14S)-4-fluoro-10,11-dimethyl-9-oxo-8,11,16-triazatricyclo[13.3.1.0$^{2,7}$]nonadeca-1(19),2,4,6,15,17-hexaen-14-yl]carbamate To a clear, colorless solution of BOP (74.3 mg, 0.168 mmol) and DMAP (16.42 mg, 0.134 mmol) in DCM (66.500 ml) and DMF (0.665 ml) at rt was added dropwise a brown solution of (2S)-2-{[(3S)-3-[4-(2-amino-5-fluorophenyl)pyridin-2-yl]-3-{[(tert -butoxy)carbonyl]amino}propyl](methyl)amino}propanoic acid (30 mg, 0.067 mmol) and DIEA (0.117 ml, 0.672 mmol) in DMF (5 mL) via a syringe pump over 1.5 h. The reaction was allowed to stir overnight. More BOP (40 mg) was added, the reaction was stirred at rt overnight. MeOH was added to quench the reaction. The reaction was concentrated. Purification by reverse phase chromatography afforded, after concentration, tert-butyl N-[(10S,14S)-4-fluoro-10,11-dimethyl-9-oxo-8,11,16-triazatricyclo[13.3.1.0$^{2,7}$]nonadeca-1(19),2,4,6,15,17-hexaen-14-yl]carbamate, bis-trifluoroacetate (14 mg, 32% yield) as a pale yellow solid. MS(ESI) m/z: 429.2 (M+H)$^+$.

59F. Preparation of (10S,14S)-14-amino-4-fluoro-10,11-dimethyl-8,11,16-triazatricyclo [13.3.1.0$^{2,7}$]nonadeca-1(19),2,4,6,15,17-hexaen-9-one tert-Butyl N-[(10S,14S)-4-fluoro-10,11-dimethyl-9-oxo-8,11,16-triazatricyclo [13.3.1.0$^{2,7}$]nonadeca-1(19),2,4,6,15,17-hexaen-14-yl]carbamate, bis-trifluoroacetate (11 mg, 0.017 mmol) in DCM (0.5 mL) was added TFA (0.052 mL, 0.670 mmol). The reaction was stirred at rt for 2.5 h, concentrated. The residue was dissolved in MeOH, passed through a NaHCO$_3$ cartridge to give (10S,14S)-14-amino-4-fluoro-10,11-dimethyl-8,11,16-triazatricyclo[13.3.1.0$^{2,7}$]nonadeca-1(19),2,4,6,15,17-hexaen-9-one (5.5 mg, 100%) as an white solid.

59G. Preparation of (10S,14S)-14-{4-[5-chloro-2-(4-chloro-1H-1,2,3-triazol-1-yl)phenyl]-6-oxo-1,6-dihydropyrimidin-1-yl}-4-fluoro-10,11-dimethyl-8,11,16-triazatricyclo [13.3.1.0$^{2,7}$]nonadeca-1(19),2(7),3,5,15,17-hexaen-9-one (10S,14S)-14-{4-[5-Chloro-2-(4-chloro-1H-1,2,3-triazol-1-yl)phenyl]-6-oxo-1,6-dihydropyrimidin-1-yl}-4-fluoro-10, 11-dimethyl-8,11,16-triazatricyclo[13.3.1.0²,⁷]nonadeca-1(19),2(7),3,5,15,17-hexaen-9-one bis-trifluoroacetate (7.6 mg, 49% yield) was prepared in a similar manner as the procedure described in Example 129 by replacing (14S)-14-amino-4-fluoro-10-methyl-11-oxa-8,16-diazatricyclo [13.3.1.0²,⁷]nonadeca -1(19),2,4,6,15,17-hexaen-9-one with (10S,14S)-14-amino-4-fluoro-10,11-dimethyl -8,11,16-triazatricyclo[13.3.1.0²,⁷]nonadeca-1(19),2,4,6,15,17-hexaen-9-one (5.6 mg, 0.017 mmol). MS(ESI) m/z: 619.2 (M+H)⁺. ¹H NMR (400 MHz, CDCl₃) δ 11.19 (br. s., 1H), 9.14 (br. s., 1H), 8.78-8.62 (m, 1H), 7.95 (br. s., 1H), 7.66 (s, 1H), 7.62 (d, J=2.2 Hz, 1H), 7.54 (dd, J=8.5, 2.3 Hz, 1H), 7.42-7.33 (m, 2H), 7.18-7.15 (m, 1H), 7.13-7.06 (m, 1H), 6.60 (d, J=9.2 Hz, 1H), 6.43 (s, 1H), 4.34 (d, J=6.2 Hz, 1H), 2.88 (s, 3H), 2.75-2.53 (m, 2H), 2.30 (t, J=11.8 Hz, 2H), 1.25 (d, J=5.9 Hz, 3H). Analytical HPLC (Method A): RT=6.22 min, purity=92.5%; Factor XIa Ki=11 nM, Plasma Kallikrein Ki=960 nM.

EXAMPLE 60

Preparation of (10S,14S)-14-{4-[3-chloro-6-(4-chloro-1H-1,2,3-triazol-1-yl)-2-fluorophenyl]-6-oxo-1,6-dihydropyrimidin-1-yl}-4-fluoro-10,11-dimethyl-8,11,16-triazatricyclo[13.3.1.0²,⁷]nonadeca-1(19),2(7),3,5,15,17-hexaen-9-one

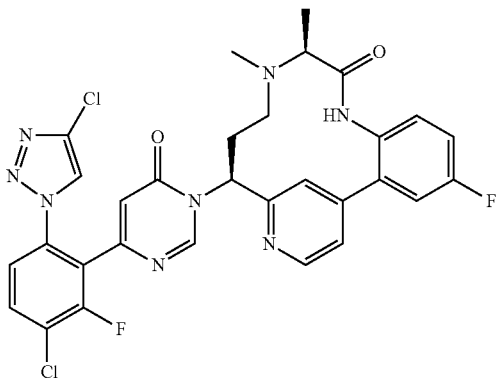 [SMILES: C[C@H]1C(=O)Nc2ccc(F)cc2-c2ccnc(c2)[C@@H](n2cnc(-c3c(-n4cc(Cl)nn4)ccc(Cl)c3F)cc2=O)CCN1C]

(10S,14S)-14-{4-[3-Chloro-6-(4-chloro-1H-1,2,3-triazol-1-yl)-2-fluorophenyl]-6-oxo-1,6-dihydropyrimidin-1-yl}-4-fluoro-10,11-dimethyl-8,11,16-triazatricyclo [13.3.1.0²,⁷]nonadeca-1(19),2(7),3,5,15,17-hexaen-9-one bis-trifluoroacetate (16.6 mg, 43% yield) was prepared in a similar manner as the procedure described in Example 129 by using 6-[3-chloro-6-(4-chloro-1H-1,2,3-triazol-1-yl)-2-fluorophenyl]pyrimidin-4-ol, prepared as described in Example 10 (14.4 mg, 0.044 mmol) and (10S,14S)-14-{4-[5-chloro-2-(4-chloro-1H-1,2,3-triazol-1-yl)phenyl]-6-oxo-1,6-dihydropyrimidin-1-yl}-4-fluoro-10,11-dimethyl-8,11,16-triazatricyclo[13.3.1.0²,⁷]nonadeca-1(19),2(7),3,5,15,17-hexaen-9-one, prepared as described in Example 59G. MS(ESI) m/z: 637.1 (M+H)⁺. ¹H NMR (400 MHz, CDCl₃) δ 11.26 (br. s., 1H), 9.14 (br. s., 1H), 8.71 (d, J=4.8 Hz, 1H), 7.93 (br. s., 1H), 7.62 (s, 1H), 7.34 (d, J=4.0 Hz, 1H), 7.28 (dd, J=8.6, 1.5 Hz, 1H), 7.23-7.15 (m, 2H), 7.12-7.05 (m, 1H), 6.63 (br. s., 1H), 6.58 (s, 1H), 4.33 (br. s., 1H), 2.87 (br. s., 3H), 2.74-2.51 (m, 2H), 2.28 (br. s., 2H), 1.25 (d, J=5.7 Hz, 3H). Analytical HPLC (Method A): RT=6.45 min, purity=99.1%; Factor XIa Ki=6 nM, Plasma Kallikrein Ki=380 nM.

EXAMPLE 61

Preparation of 6-[3-chloro-6-(4-chloro-1H-1,2,3-triazol-1-yl)-2-fluorophenyl]-3-[(10R,14S)-4-fluoro-10-methyl-8,16-diazatricyclo[13.3.1.0²,⁷]nonadeca-1(19),2(7),3,5,15,17-hexaen-14-yl]-3,4-dihydropyrimidin-4-one

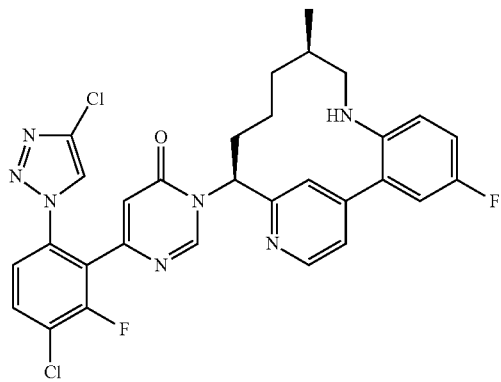 [SMILES: C[C@@H]1CCC[C@H](n2cnc(-c3c(-n4cc(Cl)nn4)ccc(Cl)c3F)cc2=O)c2cc(ccn2)-c2cc(F)ccc2NC1]

61A. Preparation of (10R,14S)-4-fluoro-10-methyl-8,16-diazatricyclo[13.3.1.0²,⁷]nonadeca-1(19),2(7),3,5,15,17-hexaen-14-amine To a solution of (10R,14S)-14-amino-4-fluoro-10-methyl-8,16-diazatricyclo [13.3.1.0²,⁷]nonadeca-1(19),2(7),3,5,15,17-hexaen-9-one, prepared as described in Example 28 (47 mg, 0.150 mmol) in THF (7,500 µl) was added 1 M BH₃.THF complex (1500 µl, 1.500 mmol). The reaction was sealed and heated at 60° C. for 2 MeOH was added followed by addition of 1.25M HCl in MeOH (1 ml). The mixture was sealed and heated at 60° C. for 10 min then cooled to rt. The reaction mixture was concentrated, redissolved in MeOH, and filtered. The crude product was purified by reverse phase chromatography. After concentration, the product was dissolved in MeOH, passed through NaHCO₃ cartridge, and concentrated to give (10R,14S)-4-fluoro-10-methyl-8,16-diazatricyclo[13.3.1.0²,⁷]nonadeca-1(19),2(7),3,5,15,17-hexaen-14-amine (7 mg, 16%) as a colorless oil. MS(ESI) m/z: 300.2 (M+H)⁺.

61B. Preparation of 6-[3-chloro-6-(4-chloro-1H-1,2,3-triazol-1-yl)-2-fluorophenyl]-3-[(10R,14S)-4-fluoro-10-methyl-8,16-diazatricyclo[13.3.1.0²,⁷]nonadeca -1(19),2(7),3,5,15,17-hexaen-14-yl]-3,4-dihydropyrimidin-4-one 6-[3-Chloro-6-(4-chloro-1H-1,2,3-triazol-1-yl)-2-fluorophenyl]-3-[(10R,14S)-4fluoro-10-methyl-8,16-diazatricyclo [13.3.1.0²,⁷]nonadeca-1(19),2(7),3,5,15,17-hexaen -14-yl]-3,4-dihydropyrimidin-4-one bis-trifluoroacetate (11 mg, 55% yield) was prepared in a similar manner as the procedure described in Example 129 by using (10R,14S)-4-fluoro-10-methyl-8,16-diazatricyclo[13.3.1.0²,⁷]nonadeca-1(19),2(7),3,5,15,17-hexaen -14-amine (7 mg, 0.023 mmol) and 6-[3-chloro-6-(4-chloro-1H-1,2,3-triazol-1-yl)-2-fluorophenyl]pyrimidin-4-ol, prepared as described in Example 10 (7.6 mg, 0.023 mmol). MS(ESI) m/z: 608.2 (M+H)⁺. ¹H NMR (400 MHz, CD₃OD) δ 8.84 (br. s., 1H), 8.74 (d, J=5.3 Hz, 1H), 8.46-8.36 (m, 1H), 8.35-8.32 (m, 1H), 7.90-7.82 (m, 1H), 7.58-7.48 (m, 2H), 7.34-7.10 (m, 3H), 6.62 (s, 1H), 6.02 (dd, J=12.0, 5.0 Hz, 1H), 2.87 (d, J=5.7 Hz, 1H), 2.55 (br. s., 1H), 2.30-2.07 (m, 2H), 1.79 (br. s., 1H), 1.59-1.43 (m, 1H), 1.10-0.87 (m, 1H), 0.83 (d, J=7.0 Hz, 3H). Ana-

EXAMPLE 62

Preparation of (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo [13.3.1.0$^{2,7}$]nonadeca-1(19),2(7),3,5,15,17-hexaene-5-carbonitrile

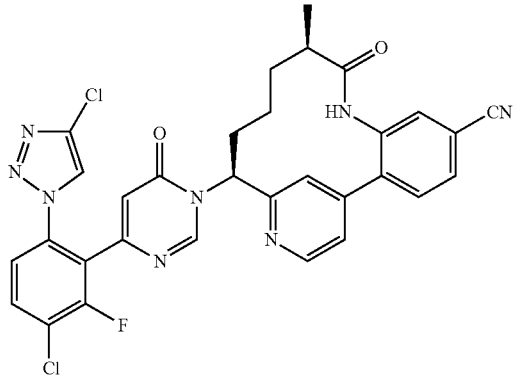 [SMILES: C[C@@H]1CCC[C@H](n2cnc(-c3c(-n4cc(Cl)nn4)ccc(Cl)c3F)cc2=O)c2cc(ccn2)-c2ccc(C#N)cc2NC1=O]

(10R,14S)-14-{4-[3-Chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-5-carbonitrile trifluoroacetate (13.5 mg, 50%) was prepared in a similar manner as the procedure described in Example 129 by using (10R,14 S)-14-amino-10-methyl-9-oxo-8,16-diazatricyclo [13.3.1.0$^{2,7}$]nonadeca -1(19),2,4,6,15,17-hexaene-5-carbonitrile hydrochloride (16.5 mg, 0.036mmol), prepared as described in Example 30, and 6-[3-chloro-6-(4-chloro-1H-1,2,3-triazol-1-yl)-2-fluorophenyl]pyrimidin-4-ol, prepared as described in Example 10 (11.6 mg, 0.036 mmol). MS(ESI) m/z: 629.1 (M+H)$^+$. $^1$H NMR (400 MHz, CD$_3$OD) δ 8.96 (s, 1H), 8.72 (d, J=5.1 Hz, 1H), 7.89-7.75 (m, 3H), 7.72 (s, 1H), 7.63 (d, J=1.3 Hz, 1H), 7.54 (dd, J=8.6, 1.5 Hz, 1H), 7.46 (dd, J=5.1, 1.5 Hz, 1H), 6.58 (s, 1H), 6.02 (dd, J=12.7, 5.0 Hz, 1H), 2.67 (d, J=6.6 Hz, 1H), 2.28-2.15 (m, 1H), 2.10-1.87 (m, 2H), 1.59-1.34 (m, 2H), 0.95 (d, J=7.0 Hz, 3H), 0.65 (br. s., 1H). Analytical HPLC (Method A): RT=9.27 min, purity=99.1%; Factor XIa Ki=0.12 nM, Plasma Kallikrein Ki=7.8 nM.

EXAMPLE 63

Preparation of (10S,17S)-17-{4-[3-chloro-6-(4-chloro-1H-1,2,3-triazol-1-yl)-2-fluorophenyl]-6-oxo-1,6-dihydropyrimidin-1-yl}-4-fluoro-8,14,19-triazatetracyclo [16.3.1.0$^{2,7}$.0$^{10,14}$]docosa-1(22),2(7),3,5,18,20-hexaen-9-one

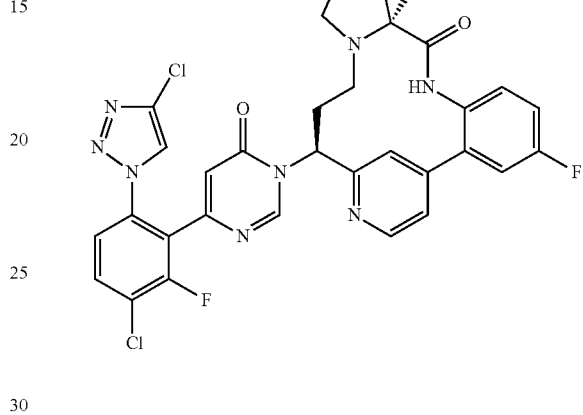

63A. Preparation of (10S,17S)-17-amino-4-fluoro-8,14,19-triazatetracyclo [16.3.1.0$^{2,7}$.0$^{10,14}$]docosa-1(22),2,4,6,18,20-hexaen-9-one (10S,17S)-17-Amino-4-fluoro-8,14,19-triazatetracyclo[16.3.1.0$^{2,7}$.0$^{10,14}$]docosa -1(22),2,4,6,18,20-hexaen-9-one was prepared in a similar manner as the procedure described in Example 59F by replacing (S)-methyl 2-(methylamino)propanoate hydrochloride, with (S)-methyl pyrrolidine-2-carboxylate hydrochloride (149 mg, 0.901 mmol). MS(ESI) m/z: 341.5 (M+H)$^+$.

63B. Preparation of (10S,17S)-17-{4-[3-chloro-6-(4-chloro-1H-1,2,3-triazol-1-yl)-2-fluorophenyl]-6-oxo-1,6-dihydropyrimidin-1-yl}-4-fluoro-8,14,19-triazatetracyclo [16.3.1.0$^{2,7}$.0$^{10,14}$]docosa-1(22),2(7),3,5,18,20-hexaen-9-one (10S,17S)-17-{4-[3-Chloro-6-(4-chloro-1H-1,2,3-triazol-1-yl)-2-fluorophenyl]-6-oxo-1,6-dihydropyrimidin-1-yl}-4-fluoro-8,14,19-triazatetracyclo[16.3.1.0$^{2,7}$.0$^{10,14}$]docosa-1 (22),2(7),3,5,18,20-hexaen-9-one, bis-trifluoroacetate (11.5 mg, 44% yield) was prepared in a similar manner as the procedure described in Example 59G by using (10S ,17S)-17-amino-4-fluoro-8,14,19-triazatetracyclo[16.3.1.0$^{2,7}$.0$^{10,14}$]docosa -1(22),2,4,6,18,20-hexaen-9-one (10 mg, 0.029 mmol) and 6-[3-chloro-6-(4-chloro-1H -1,2,3-triazol-1-yl)-2-fluorophenyl]pyrimidin-4-ol, prepared as described in Example 10 (9.6 mg, 0.029 mmol). MS(ESI) m/z: 649.2 (M+H)$^+$. $^1$H NMR (400 MHz, CD$_3$OD) δ 8.73 (d, J=5.1 Hz, 1H), 8.45 (s, 1H), 8.35-8.33 (m, 1H), 7.90-7.82 (m, 2H), 7.56-7.43 (m, 4H), 7.30 (td, J=8.4, 3.0 Hz, 1H), 6.60 (s, 1H), 5.65 (br. s., 1H), 3.98 (br. s., 1H), 3.84-3.52 (m, 2H), 3.39-3.32 (m, 1H), 3.24-3.10 (m, 1H), 2.99-2.83 (m, 1H), 2.73-2.58 (m, 1H), 2.51-2.39 (m, 1H), 2.26-1.99 (m, 3H). Analytical HPLC (Method A): RT=6.61 min, purity=99.2%; Factor XIa Ki=100 nM, Plasma Kallikrein Ki=4,300 nM.

EXAMPLE 64

Preparation of (10R,14S)-14-(4-{2,3-difluoro-6-[4-(trifluoromethyl)-1H-1,2,3-triazol-1-yl]phenyl}-6-oxo-1,6-dihydropyrimidin-1-yl)-4-fluoro-10-methyl-8,18-diazatricyclo [13.3.1.0$^{2,7}$]nonadeca-1(19),2(7),3,5,15,17-hexaen-9-one

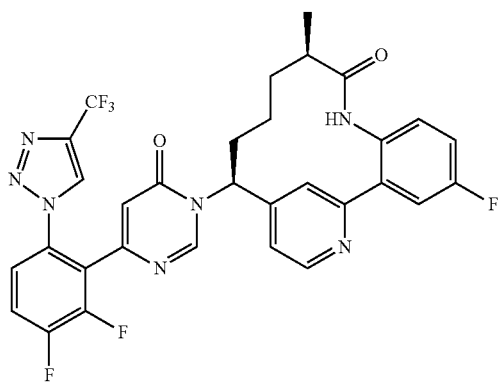 [SMILES: C[C@@H]1CCC[C@H](n2cnc(-c3c(-n4cc(C(F)(F)F)nn4)ccc(F)c3F)cc2=O)c2ccnc(c2)-c2cc(F)ccc2NC1=O]

(10R,14S)-14-(4-{2,3-Difluoro-6-[4-(trifluoromethyl)-1H-1,2,3-triazol-1-yl]phenyl}-6-oxo-1,6-dihydropyrimidin-1-yl)-4-fluoro-10-methyl-8,18-diazatricyclo [13.3.1.0$^{2,7}$]nonadeca-1(19),2(7),3,5,15,17-hexaen-9-one was prepared in 15% yield as a solid (1.9 mg), via the coupling of 6-{2,3-difluoro-6-[4-(trifluoromethyl)-1H-1,2,3-triazol-1-yl]phenyl}pyrimidin-4-ol (0.007 g, 0.02 mmol) and (10R,14S)-14-amino-4-fluoro-10-methyl-8,18-diazatricyclo [13.3.1.0$^{2,7}$]nonadeca-1(19),2,4,6,15,17-hexaen-9-one (0.0064 g, 0.02 mmol) using the HATU,DBU coupling methodology described in 45K and 45L. MS(ESI) m/z: 656.1 (M+H)$^+$. $^1$H NMR (500 MHz, DMSO-d$_6$) δ 9.75-9.71 (m, 1H), 9.22-9.18 (m, 1H), 8.66-8.61 (m, 2H), 7.95-7.88 (m, 1H), 7.87-7.83 (m, 1H), 7.81-7.74 (m, 1H), 7.61-7.55 (m, 1H), 7.36-7.22 (m, 2H), 7.02-6.96 (m, 1H), 6.72-6.66 (m, 1H), 5.64-5.52 (m, 1H), 2.45-2.31 (m, 1H), 1.98-1.81 (m, 2H), 1.50-1.22 (m, 2H), 1.01-0.75 (m, 3H), −0.71, −0.78 (m, 1H). Analytical HPLC (Method B) RT=1.73 min, purity=100%; Factor XIa Ki=1.92 nM, Plasma Kallikrein Ki=156 nM.

EXAMPLE 65

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-5-carboxamide, hydrochloride

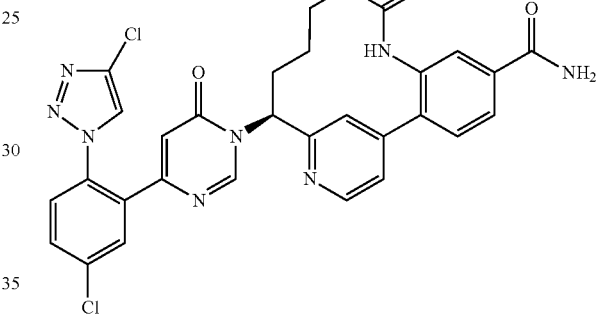

(10R,14S)-14-{4-[5-Chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-5-carbonitrile, prepared as described in Example 89, was treated with HCl in MeOH. The solution was concentrated and the residue was purified by reverse phase chromatography to give (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-5-carboxamide hydrochloride as white solid. MS(ESI) m/z: 629.2 (M+H)$^+$. $^1$H NMR (400 MHz, CD$_3$OD) δ 8.85 (d, J=5.7 Hz, 1H), 8.76 (s, 1H), 8.43 (s, 1H), 8.19 (s, 1H), 8.01 (dd, J=8.1, 1.8 Hz, 1H), 7.95-7.88 (m, 2H), 7.86-7.75 (m, 3H), 7.72-7.65 (m, 1H), 6.46 (s, 1H), 5.91 (dd, J=12.5, 4.6 Hz, 1H), 2.81-2.70 (m, 1H), 2.56-2.42 (m, 1H), 2.28-2.15 (m, 1H), 2.05-1.91 (m, 1H), 1.67-1.49 (m, 2H), 1.02 (d, J=7.0 Hz, 3H), 0.79 (br. s., 1H). Analytical HPLC (Method A): RT=7.10 min, purity=>99%; Factor XIa Ki=0.7 nM, Plasma Kallikrein Ki=40 nM.

EXAMPLE 66

Preparation of (10R,14S)-14-{4-[5-chloro-2-(1-methyl-1H-pyrazol-4-yl)phenyl]-6-oxo -1,6-dihydropyrimidin-1-yl}-4-fluoro-10-methyl-8,16-diazatricyclo[13.3.1.0²,⁷]nonadeca -1(19),2(7),3,5,15,17-hexaen-9-one

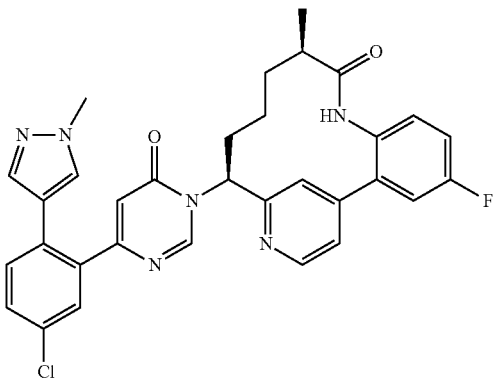 [SMILES: C[C@@H]1CCC[C@H](n2cnc(-c3cc(Cl)ccc3-c3cnn(C)c3)cc2=O)c2cc(ccn2)-c2cc(F)ccc2NC1=O]

66A. Preparation of 4-(5-chloro-2-(1-(difluoromethyl)-1H-pyrazol-4-yl)phenyl)-6-methoxypyrimidine To a sealable vial was added 4-(2-bromo-5-chlorophenyl)-6-methoxypyrimidine (0.08 g, 0.267 mmol), 1-(difluoromethyl)-4-(4,4,5,5-tetramethyl-1,3,2-dioxaborolan-2-yl)-1H-pyrazole (0.072 g, 0.294 mmol), 3 M aq K$_3$PO$_4$ (0.267 ml, 0.801 mmol) and THF (2.67 ml). Ar was bubbled through the reaction mixture for several min and then (DtBPF)PdCl$_2$ (8.70 mg, 0.013 mmol) was added. The vial was sealed and heated at 90° C. After 15 h, the reaction was cooled to rt. The reaction was diluted with EtOAc, washed with brine, dried over Na$_2$SO$_4$, filtered, and concentrated. Purification by normal phase chromatography afforded 4-(5-chloro-2-(1-(difluoromethyl)-1H-pyrazol-4-yl)phenyl)-6-methoxypyrimidine (0.05 g, 56% yield) as a white solid. MS(ESI) m/z: 337.2 (M+H)⁺. ¹H NMR (400 MHz, CDCl$_3$) δ 8.81 (d, J=0.9 Hz, 1H), 7.69 (s, 1H), 7.54 (d, J=2.2 Hz, 1H), 7.48-7.43 (m, 1H), 7.41-7.35 (m, 2H), 7.17 (t, J=54.0 Hz, 1H), 6.61 (d, J=1.1 Hz, 1H), 3.99 (s, 3H).

66B. Preparation of 6-(5-chloro-2-(1-(difluoromethyl)-1H-pyrazol-4-yl)phenyl) pyrimidin-4-ol A clear solution of 4-(5-chloro-2-(1-(difluoromethyl)-1H-pyrazol-4-yl)phenyl)-6-methoxypyrimidine (0.05 g, 0.148 mmol) in HOAc (0.742 ml) and 48% HBr in water (0.84 ml, 7.42 mmol) was warmed to 65° C. After 3 h, the reaction was cooled to rt and concentrated. The yellow residue was dissolved in EtOAc, washed with sat NaHCO$_3$, brine, dried over Na$_2$SO$_4$, filtered, and concentrated. Et$_2$O (3 ml) was added and the mixture was sonicated. The solid was collected by filtration, rinsed with Et$_2$O (2 ml), air-dried to give 6-(5-chloro-2-(1-(difluoromethyl)-1H-pyrazol-4-yl)phenyl) pyrimidin-4-ol (0.03 g, 63% yield) as a white solid. MS(ESI) m/z: 323.2 (M+H)⁺. ¹FINMR (400MHz, CD$_3$OD) δ 8.20 (d, J=1.1 Hz, 1H), 8.05 (s, 1H), 7.61-7.27 (m, 5H), 6.40 (d, J=1.1 Hz, 1H).

66C. Preparation of (10R,14S)-14-{4-[5-chloro-2-(1-methyl-1H-pyrazol-4-yl)phenyl]-6-oxo-1,6-dihydropyrimidin-1-yl}-4-fluoro-10-methyl-8,16-diazatricyclo[13.3.1.0²,⁷]nonadeca-1(19),2(7),3,5,15,17-hexaen-9-one trifluoroacetate (10R,14S)-14-{4-[5-Chloro-2-(1-methyl-1H-pyrazol-4-yl)phenyl]-6-oxo-1,6dihydropyrimidin-1-yl}-4-fluoro-10-methyl-8,16-diazatricyclo[13.3.1.0²,⁷]nonadeca -1(19),2(7), 3,5,15,17-hexaen-9-one trifluoroacetate (0.007 g, 31% yield) was prepared in a similar manner as the procedure described in Example 124D, by replacing 6-(5-chloro-2-(1-(difluoromethyl)-1H-pyrazol-4-yl)phenyl)pyrimidin-4-ol with 6-(5-chloro-2-(1-methyl-1H-pyrazol-4-yl)phenyl)pyrimidin-4-ol (9.15 mg, 0.032 mmol), prepared as described in Example 66B. MS(ESI) m/z: 583.3 (M+H)⁺. ¹H NMR (400 MHz, CD$_3$OD) δ 9.06 (br. s., 1H), 8.71 (d, J=4.4 Hz, 1H), 7.79 (br. s., 1H), 7.63-7.20 (m, 9H), 6.39 (s, 1H), 6.02 (d, J=8.4 Hz, 1H), 3.83 (s, 3H), 2.72-2.60 (m, 1H), 2.35-2.24 (m, 1H), 2.17-1.91 (m, 2H), 1.60-1.38 (m, 2H), 0.97 (d, J=6.8 Hz, 3H), 0.85-0.63 (m, 1H). Analytical HPLC (Method A): RT=8.46 min, 99.6% purity.; Factor XIa Ki=13 nM, Plasma Kallikrein Ki=900 nM.

EXAMPLE 67

Preparation of (10R,14S)-14-{4-[5-chloro-2-(4-chloro-1H-1,2,3-triazol-1-yl)phenyl]-6-oxo-1,6-dihydropyrimidin-1-yl}-4-methanesulfonyl-10-methyl-8,16-diazatricyclo[13.3.1.0²,⁷]nonadeca-1(19),2(7),3,5,15,17-hexaen-9-one

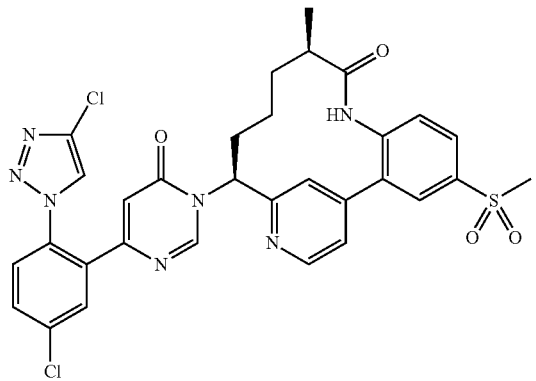 [SMILES: C[C@@H]1CCC[C@H](n2cnc(-c3cc(Cl)ccc3-n3cc(Cl)nn3)cc2=O)c2cc(ccn2)-c2cc(S(C)(=O)=O)ccc2NC1=O]

67A. Preparation of tert-butyl N-[(1S)-1-[4-(2-amino-5-methanesulfonylphenyl)pyridin -2-yl]but-3-en-1-yl]carbamate To {3-[(1S)-1-{[(tert-butoxy)carbonyl]amino}but-3-en-1-yl]phenyl}boronic acid (0.36 g, 0.886 mmol), prepared as described in Example 38A, in dioxane (3 ml), was added 2-bromo-4-(methylsulfonyl)aniline (0.244 g, 0.975 mmol), and Na$_2$CO$_3$ (1.55 ml, 3.10 mmol). The resulting reaction mixture was degassed with Ar for 10 min, then Pd(PPh$_3$)$_4$ (0.051 g, 0.044 mmol) was added and the reaction mixture was then heated to 130° C. in a microwave for a total of 50 min. The reaction mixture was diluted with EtOAc (30 ml), dried (MgSO$_4$), filtered, concentrated and the residue was purified by normal phase chromatography using hexanes and EtOAc as eluents to afford tert-butyl N -[(1S)-1-[4-(2-amino-5-methanesulfonylphenyl)pyridin-2-yl]but-3-en-1-yl]carbamate (0.255 g, 68.9%) as a bright yellow foam. MS(ESI) m/z: 418.3 (M+H)⁺.

67B. Preparation of tert-butyl N-[(1S)-1-(4-{5-methanesulfonyl-2-[(2R)-2-methylbut-3-enamido]phenyl}pyridin-2-yl)but-3-en-1-yl]carbamate To a solution of tert-butyl N-[(1S)-1-[4-(2-amino-5-methanesulfonylphenyl) pyridin-2-yl]but-3-en-1-yl]carbamate (0.255 g, 0.611 mmol) in EtOAc (8 ml), was added (R)-2-methylbut-3-enoic acid (0.073 g, 0.733 mmol), prepared as described in Example 2, and pyridine (0.198 mL, 2.443 mmol). The resulting solution was cooled to 0° C. and a 50% solution of T3P® in EtOAc (0.364 ml, 1.221 mmol) was added. The reaction mixture was stirred at rt for 18 h. The reaction was incomplete and an additional amount of pyridine (0.198 mL, 2.443 mmol) and T3P® solution (0.364 ml, 1.221 mmol) were added. After 18 h, the reaction was partitioned between sat NaHCO₃ (20 ml) and EtOAc (50 ml). The aqueous layer was extracted with EtOAc (2×20 ml). The combined organic layers were washed with brine (15 ml), dried (MgSO₄), filtered and concentrated. The residue was purified by normal phase chromatography using hexanes and EtOAc as eluents to afford tert-butyl N-[(1S)-1-(4-{5-methanesulfonyl-2-[(2R)-2-methylbut-3-enamido]phenyl}pyridin-2-yl)but-3-en-1-yl]carbamate (0.22 g, 72%) as a clear oil. MS(ESI) m/z: 500.6 (M+H)$^+$. $^1$H NMR (400 MHz, CDCl₃) δ 8.78-8.64 (m, 2H), 7.98 (dd, J=8.8, 2.2 Hz, 1H), 7.86-7.75 (m, 1H), 7.61 (br. s., 1H), 7.29-7.23 (m, 1H), 7.23-7.13 (m, 1H), 5.85-5.65 (m, 2H), 5.20-5.00 (m, 3H), 4.13 (q, J=7.1 Hz, 1H), 3.16-3.01 (m, 4H), 2.66 (dq, J=13.5, 6.9 Hz, 1H), 1.48-1.39 (m, 9H), 1.32-1.24 (m, 4H).

67C. Preparation of tert-butyl N-[(10R,11E,14S)-4-methanesulfonyl-10-methyl-9-oxo -8,16-diazatricyclo[13.3.1.0$^{2,7}$]nonadeca-1(19),2,4,6,11,15,17-heptaen-14-yl]carbamate To solution of tert-butyl N-[(1S)-1-(4-{5-methanesulfonyl-2-[(2R)-2-methylbut-3-enamido]phenyl}pyridin-2-yl)but-3-en-1-yl]carbamate (0.22 g, 0.440 mmol) in DCM (44.0 ml) was added pTsOH.H₂O (0.092 g, 0.484 mmol) and the mixture was degassed for 10 min, then heated to 40° C. for 1 h. The reaction was removed from heat and Second Generation Grubbs Catalyst (0.112 g, 0.132 mmol) was added and the reaction was heated at 40° C. for 24 h. The reaction was cooled to rt and quenched with sat NaHCO₃ (20 ml) and extracted with EtOAc (3×30 ml). The combined organic layers were washed with brine (15 ml), dried (MgSO₄), filtered and concentrated. The residue purified by normal phase chromatography using hexanes and EtOAc as eluents to afford tert-butyl N -[(10R,11E,14S)-4-methanesulfonyl-10-methyl-9-oxo-8,16-diazatricyclo[13.3.1.0$^{2,7}$]nonadeca-1(19),2,4,6,11,15,17-heptaen-14-yl]carbamate (81.7 mg, 39%) as a brown solid. MS(ESI) m/z: 472.6 (M+H)$^+$. $^1$H NMR (400 MHz, CDCl₃) δ 8.77-8.66 (m, 1H), 8.58 (d, J=8.6 Hz, 1H), 8.54-8.46 (m, 1H), 7.98-7.83 (m, 2H), 7.17-7.14 (m, 1H), 7.00 (s, 1H), 6.37 (d, J=6.8 Hz, 1H), 5.86 (ddd, J=15.2, 11.3, 3.9 Hz, 1H), 4.93 (dd, J=15.4, 8.8 Hz, 1H), 4.77 (t, J=7.9 Hz, 1H), 3.27-3.16 (m, 1H), 3.06-2.99 (m, 3H), 1.61-1.52 (m, 2H), 1.46-1.39 (m, 9H), 1.27-1.19 (m, 3H).

67D. Preparation of tert-butyl N-[(10R,14S)-4-methanesulfonyl-10-methyl-9-oxo-8,16-diazatricyclo[13.3.1.0$^{2,7}$]nonadeca-1(19),2,4,6,15,17-hexaen-14-yl]carbamate A solution of tert-butyl N-[(10R,11E,14S)-4-methanesulfonyl-10-methyl-9-oxo -8,16-diazatricyclo[13.3.1.0$^{2,7}$]nonadeca-1(19),2,4,6,11,15,17-heptaen-14-yl]carbamate (81 mg, 0.172 mmol) in EtOH (4 ml) was hydrogenated at 55 psi in the presence of PtO₂ (10 mg). After 3 h, the reaction was filtered through CELITE® and concentrated to afford tert-butyl N-[(10R,14S)-4-methanesulfonyl-10-methyl-9-oxo-8,16-diazatricyclo [13.3.1.0$^{2,7}$]nonadeca-1(19),2,4,6,15,17-hexaen-14-yl]carbamate (0.83mg, 102%) as a brown film.

MS(ESI) m/z: 474.5 (M+H)$^+$. $^1$H NMR (400 MHz, CDCl₃) δ 8.57 (d, J=4.6 Hz, 1H), 8.13 (br. s., 1H), 7.72 (br. s., 1H), 7.28 - 7.13 (m, 3H), 5.83 (br. s., 1H), 4.68 (br. s., 1H), 3.17-2.96 (m, 3H), 2.55 (br. s., 1H), 1.96 (br. s., 1H), 1.72-1.52 (m, 2H), 1.43-1.24 (m, 9H), 1.17 (t, J=6.9 Hz, 3H), 0.50-0.34 (m, 3H).

67E. Preparation of (10R,14S)-14-amino-4-methanesulfonyl-10-methyl-8,16-diazatricyclo[13.3.1.0$^{2,7}$]nonadeca-1(19),2,4,6,15,17-hexaen-9-one bis-hydrochloride

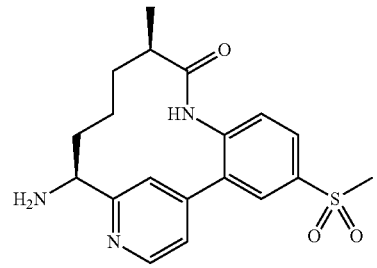 [SMILES: C[C@@H]1CCC[C@H](N)c2cc(ccn2)-c2cc(S(C)(=O)=O)ccc2NC1=O]

To a solution of tert-butyl N-[(10R,14S)-4-methanesulfonyl-10-methyl-9-oxo -8,16-diazatricyclo[13.3.1.0$^{2,7}$]-1(19),2,4,6,15,17-hexaen-14-yl]carbamate (81 mg, 0.171 mmol) in a mixture of dioxane (1 ml), DCM (0.5 ml) and MeOH (1 ml) was added 4 M HCl in dioxane (1 ml). After 3 h, the reaction was concentrated to give (10R,14S)-14-amino-4-methanesulfonyl-10-methyl-8,16-diazatricyclo[13.3.1.0$^{2,7}$] nonadeca -1(19),2,4,6,15,17-hexaen-9-one bis-hydrochloride (80mg, 105%). MS(ESI) m/z: 374.5 (M+H)$^+$.

67F. Preparation of (10R,14S)-14-{4-[5-chloro-2-(4-chloro-1H-1,2,3-triazol-1-yl)phenyl]-6-oxo-1,6-dihydropyrimidin-1-yl}-4-methanesulfonyl-10-methyl-8,16diazatricyclo [13.3.1.0$^{2,7}$]nonadeca-1(19),2(7),3,5,15,17-hexaen-9-one

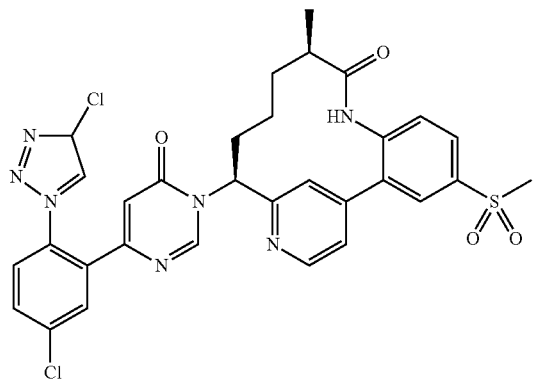

To a 1-dram vial containing a white suspension of 6-[5-chloro-2-(4-chloro-1H -1,2,3-triazol-1-yl)phenyl]pyrimidin-4-ol (0.012 g, 0.040 mmol), prepared as described in Example 9, in ACN (0.3 ml) was added HATU (0.020 g, 0.052 mmol) and a solution of DBU (9.08 μl, 0.060 mmol) in CH₃CN (0.3 ml). After 20 min, (10R,14S)-14-amino-4-methane sulfonyl-10-methyl-8,16-diazatricyclo[13.3.1.0$^{2,7}$] nonadeca-1(19),2,4,6,15,17-hexaen-9-one (15 mg, 0.040 mmol), which had been dissolved in MeOH and filtered through basic cartridge to give the free base, in CH₃CN (0.2 ml )/DMF (0.1 ml) was added. The reaction was stirred for 24 h. After this time, the reaction was diluted with DMF, filtered and concentrated. The resulting residue was purified by reverse phase HPLC using PHENOMENEX® Luna 5U 30×100 mm (10:90 MeOH/H$_2$O to 90:10 MeOH/H$_2$O, 0.1% TFA) (25%B start, 14 min gradient). The desired fractions were concentrated and freeze-dried to afford (10R,14S)-14-{4-[5-chloro-2-(4-chloro-1H-1,2,3-triazol-1-yl)phenyl]-6-oxo-1,6-dihydropyrimidin-1-yl}-4-methanesulfonyl-10-methyl-8,16-diazatricyclo[13.3.1.0$^{2,7}$]nonadeca-1(19),2(7),3,5,15,17-hexaen-9-one (6 mg, 19%) as a pink solid. MS(ESI) m/z: 664.3 (M+H)$^+$. $^1$H NMR (400 MHz, CD$_3$OD) δ 9.01 (s, 1H), 8.76 (d, J=5.1 Hz, 1H), 8.39-8.34 (m, 1H), 8.16 (d, J=2.0 Hz, 1H), 8.12-8.05 (m, 1H), 7.95-7.87 (m, 1H), 7.81-7.74 (m, 2H), 7.70-7.65 (m, 1H), 7.63-7.56 (m, 1H), 7.52 (d, J=8.1 Hz, 1H), 6.47-6.35 (m, 1H), 6.04 (dd, J=12.7, 5.0 Hz, 1H), 3.28-3.20 (m, 3H), 2.73 (d, J=6.6 Hz, 1H), 2.27 (t, J=12.8 Hz, 1H), 2.12-2.03 (m, 1H), 2.02-1.91 (m, 1H), 1.60-1.45 (m, 2H), 0.98 (d, J=6.8 Hz, 3H). Analytical HPLC (Method A) RT=8.52 min, 95% purity; Factor XIa Ki=11 nM, Plasma Kallikrein Ki=540 nM.

EXAMPLE 68

Preparation of methyl 4-chloro-2-{1-[(10R,14S)-4-fluoro-10-methyl-9-oxo-8,16-diazatricyclo[13.3.1.0$^{2,7}$]nonadeca-1(19),2(7),3,5,15,17-hexaen-14-yl]-6-oxo-1,6-dihydropyrimidin-4-yl}benzoate

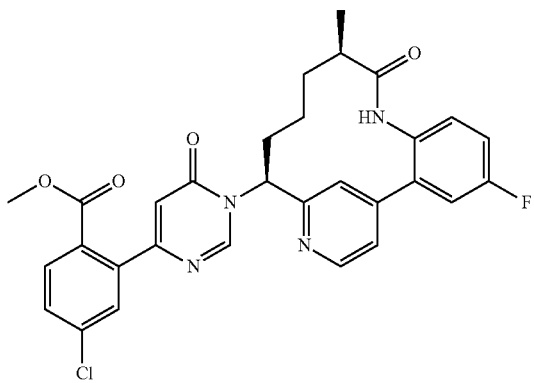 [SMILES: COC(=O)c1ccc(Cl)cc1-c1cc(=O)n([C@H]2CCC[C@@H](C)C(=O)Nc3ccc(F)cc3-c3ccnc2c3)cn1]

68A. Preparation of methyl 4-chloro-2-(6-methoxypyrimidin-4-yl)benzoate 4-chloro-2-(6-methoxypyrimidin-4-yl)benzoic acid A suspension of 4-chloro-6-methoxypyrimidine (0.067 g, 0.466 mmol), (5-chloro-2-(methoxycarbonyl)phenyl)boronic acid (0.1 g, 0.466 mmol) in ACN (1.8 ml) was purged with Ar for several min. 2 M aq Na$_2$CO$_3$ (0.47 ml, 0.94 mmol) followed by Pd(Ph$_3$P)$_4$ (0.027 g, 0.023 mmol) were added to the reaction mixture. The vial was capped and microwaved at 130° C. for 0.5 h, and then cooled to rt. The reaction was diluted with EtOAc, washed with brine, dried over Na$_2$SO$_4$, filtered, and concentrated. Purification by normal phase chromatography afforded methyl 4-chloro-2-(6-methoxypyrimidin-4-yl)benzoate (0.086 g, 66% yield) as a colorless oil. MS(ESI) m/z: 279.0 (M+H)$^+$.

68B. Preparation of methyl 4-chloro-2-(6-hydroxypyrimidin-4-yl)benzoate

A clear solution of methyl 4-chloro-2-(6-methoxypyrimidin-4-yl)benzoate (0.086 g, 0.309 mmol) in HOAc(1.54 ml) and 48% HBr in water (1.75 ml, 15.43 mmol) was warmed to 65° C. After 3 h, the reaction was cooled to rt and then concentrated. The residue was dissolved in EtOAc, washed with sat NaHCO$_3$, brine, dried over Na$_2$SO$_4$, filtered, and concentrated. Et$_2$O (3 ml) was added and the mixture was sonicated. The solid was collected by filtration, rinsed with Et$_2$O (2 ml), air-dried to afford methyl 4-chloro-2-(6-hydroxypyrimidin-4-yl)benzoate (0.046 g, 56% yield) as a white solid. MS(ESI) m/z: 265.1 (M+H)$^+$. $^1$H NMR (500 MHz, CD$_3$OD) δ 8.19 (d, J=1.1 Hz, 1H), 7.83 (d, J=8.3 Hz, 1H), 7.62-7.57 (m, 2H), 6.57 (d, J=0.8 Hz, 1H), 3.76 (s, 3H).

68C. Preparation of methyl 4-chloro-2-{1-[(10R,14S)-4-fluoro-10-methyl-9-oxo-8,16-diazatricyclo[13.3.1.0$^{2,7}$]nonadeca-1(19),2(7),3,5,15,17-hexaen-14-yl]-6-oxo-1,6-dihydropyrimidin-4-yl}benzoate trifluoroacetate Methyl 4-chloro-2-{1-[(10R,14S)-4-fluoro-10-methyl-9-oxo-8,16-diazatricyclo[13.3.1.0$^{2,7}$]nonadeca-1(19),2(7),3,5,15,17-hexaen-14-yl]-6-oxo-1,6-dihydropyrimidin-4-yl}benzoate trifluoroacetate (0.008 g, 46% yield) was prepared in a similar manner as the procedure described in Example 124D, by replacing 6-(5-chloro-2-(1-(difluoromethyl)-1H-pyrazol-4-yl)phenyl)pyrimidin-4-ol with methyl 4-chloro-2-(6-hydroxypyrimidin-4-yl)benzoate (6.76 mg, 0.026 mmol), prepared as described in Example 68B. MS(ESI) m/z: 561.3 (M+H)$^+$. $^1$H NMR (400 MHz, CD$_3$OD) δ 9.06 (s, 1H), 8.70 (d, J=5.1 Hz, 1H), 7.86 - 7.79 (m, 2H), 7.65 - 7.56 (m, 2H), 7.49 (d, J=4.4 Hz, 1H), 7.40 (dd, J=9.0, 2.6 Hz, 1H), 7.33-7.20 (m, 2H), 6.61 (s, 1H), 6.07 (d, J=8.1 Hz, 1H), 3.75 (s, 3H), 2.71-2.62 (m, 1H), 2.37-2.25 (m, 1H), 2.16-1.92 (m, 2H), 1.60-1.39 (m, 2H), 0.98 (d, J=6.8 Hz, 3H), 0.84-0.65 (m, 1H). Analytical HPLC (Method A): RT=9.09 min, 99.1% purity; Factor XIa Ki=39 nM, Plasma Kallikrein Ki=580 nM.

EXAMPLE 69

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-8,16-diazatricyclo [13.3.1.0$^{2,7}$]nonadeca-1(19),2(7),3,5,15,17-hexaen-9-one

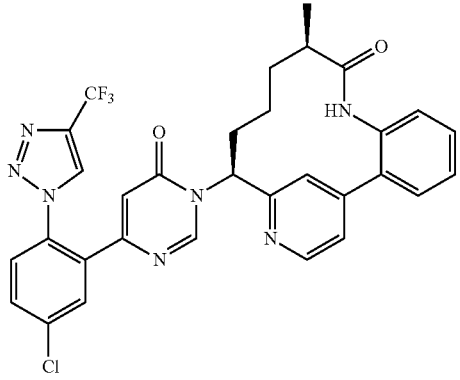

(10R,14S)-14-(4-{5-Chloro-2-[4-(trifluoromethyl)-1H-1,2,3-triazol-1-yl]phenyl}-6-oxo-1,6-dihydropyrimidin-1-yl)-10-methyl-8,16-diazatricyclo[13.3.1.0$^{2,7}$]nonadeca-1(19),2(7),3,5,15,17-hexaen-9-one (0.0179 g, 56% yield) was prepared in a similar manner as the procedure described in Example 129, by using 6-{5-chloro-2-[4-(trifluoromethyl)-1H-1,2,3-triazol-1-yl]phenyl}pyrimidin-4-ol, prepared as described in Example 15, and (10R,14S)-14-amino-10-methyl-8,16-diazatricyclo[13.3.1.0$^{2,7}$]nonadeca-1(19),2,4,6,15,17-hexaen-9-one, prepared as described in Example 29. MS(ESI) m/z: 620.2 (M+H)$^+$ and 622.1 (M+2+H)$^+$. $^1$H NMR (500 MHz, DMSO-d$_6$) δ 9.57 (s, 1H), 9.11 (d, J=0.6

Hz, 1H), 8.80 (s, 1H), 8.59 (d, J=5.0 Hz, 1H), 7.93 (d, J=1.9 Hz, 1H), 7.82 (dd, J=8.3, 2.2 Hz, 1H), 7.79 (d, J=8.5 Hz, 1H), 7.68 (s, 1H), 7.57 (dd, J=7.4, 1.7 Hz, 1H), 7.49-7.45 (m, 1H), 7.44-7.40 (m, 1H), 7.38 (dd, J=5.0, 1.4 Hz, 1H), 7.22 (d, J=7.7 Hz, 1H), 6.39 (d, J=0.8 Hz, 1H), 5.91 (dd, J=12.7, 5.0 Hz, 1H), 2.65-2.57 (m, 1H), 2.21-2.12 (m, 1H), 1.96-1.81 (m, 2H), 1.44-1.31 (m, 2H), 0.86 (d, J=6.9 Hz, 3H), 0.61-0.49 (m, 1H). $^{19}$F NMR (471MHz, DMSO-d$_6$) δ −59.56 (s). Analytical HPLC (Method A): RT=8.91 min, purity=99.7%; Factor XIa Ki=0.29 nM, Plasma Kallikrein Ki=22 nM.

EXAMPLE 70

Preparation of 1-(4-chloro-2-{1-[(10R,14S)-5-(difluoromethyl)-10-methyl-9-oxo-8,16-diazatricyclo[13.3.1.0$^{2,7}$]nonadeca-1(19),2(7),3,5,15,17-hexaen-14-yl]-6-oxo-1,6-dihydropyrimidin-4-yl}phenyl)-1H-1,2,3-triazole-4-carbonitrile

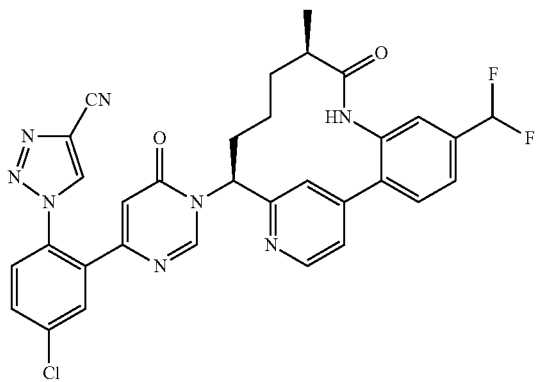 [SMILES: C[C@@H]1CCC[C@H](n2cnc(-c3cc(Cl)ccc3-n3cc(C#N)nn3)cc2=O)c2cc(ccn2)-c2ccc(C(F)F)cc2NC1=O]

70A. Preparation of tert-butyl N-[(10R,14S)-5-formyl-10-methyl-9-oxo-8,16-diazatricyclo[13.3.1.0$^{2,7}$]nonadeca-1(19),2(7),3,5,15,17-hexaen-14-yl]carbamate To a suspension of tert-butyl N-[(10R,14S)-5-(hydroxymethyl)-10-methyl-9-oxo -8,16-diazatricyclo[13.3.1.0$^{2,7}$]nonadeca-1(19),2(7),3,5,15,17-hexaen-14-yl]carbamate, prepared as described in Example 34B, (41 mg, 0.096 mmol) in DCM (964 μl) was added Dess Martin's reagent (53.1 mg, 0.125 mmol). After 20 min, the reaction mixture was diluted with DCM, washed with NaHCO$_3$, brine. The combined organic layers were dried over MgSO$_4$, filtered, and concentrated. The crude product was then purified using silica gel chromatography to give tert-butyl N-[(10R,14S)-5-formyl-10-methyl-9-oxo-8,16-diazatricyclo[13.3.1.0$^{2,7}$]nonadeca-1(19),2(7),3,5,15,17-hexaen-14-yl]carbamate (31 mg, 76%) as a white solid. MS(ESI) m/z: 424.3 (M+H)$^+$.

70B. Preparation of tert-butyl N-[(10R,14S)-5-(difluoromethyl)-10-methyl-9-oxo-8,16-diazatricyclo[13.3.1.0$^{2,7}$]nonadeca-1(19),2(7),3,5,15,17-hexaen-14-yl]carbamate To a clear solution of tert-butyl N-[(10R,14S)-5-formyl-10-methyl-9-oxo-8,16-diazatricyclo[13.3.1.0$^{2,7}$]nonadeca-1(19),2(7),3,5,15,17-hexaen-14-yl]carbamate (31 mg, 0.073 mmol) in DCM (1464 μl) was added DAST (21.31 μl, 0.161 mmol). The reaction was stirred at rt for 4 h. Another 30 mg of DAST was added and the reaction was stirred at rt overnight. The crude product was then purified using silica gel chromatography to give tert-butyl N-[(10R,14S)-5-(difluoromethyl)-10-methyl-9-oxo-8,16-diazatricyclo[13.3.1.0$^{2,7}$]nonadeca-1(19),2(7),3,5,15,17-hexaen-14-yl] carbamate (12 mg, 37%) as a white solid. MS(ESI) m/z: 446.4 (M+H)$^+$.

70C. Preparation of (10R,14S)-14-amino-5-(difluoromethyl)-10-methyl-8,16-diazatricyclo[13.3.1.0$^{2,7}$]nonadeca-1(19),2(7),3,5,15,17-hexaen-9-one tert-Butyl N-[(10R,14S)-5-(difluoromethyl)-10-methyl-9-oxo-8,16-diazatricyclo[13.3.1.0$^{2,7}$]nonadeca-1(19),2(7),3,5,15,17-hexaen-14-yl] carbamate (22.28 mg, 0.05 mmol) in a 20 ml vial was added 4 M HCl in dioxane (625 μl, 2.500 mmol). The reaction was stirred at rt for 1 h. The reaction mixture was then concentrated. The residue was redissolved in MeOH, passed through NaHCO$_3$ cartridge, concentrated to give (10R,14S)-14-amino-5-(difluoromethyl)-10-methyl-8,16-diazatricyclo[13.3.1.0$^{2,7}$]nonadeca-1(19),2(7),3,5,15,17-hexaen-9-one (18.2 mg, 100%) as an off-white solid. MS(ESI) m/z: 346.3 (M+H)$^+$.

70D. Preparation of 1-(4-chloro-2-{1-[(10R,14S)-5-(difluoromethyl)-10-methyl-9-oxo -8,16-diazatricyclo[13.3.1.0$^{2,7}$]nonadeca-1(19),2(7),3,5,15,17-hexaen-14-yl]-6-oxo-1,6-dihydropyrimidin-4-yl}phenyl)-1H-1,2,3-triazole-4-carbonitrile 1-(4-Chloro-2-{1-[(10R,14S)-5-(difluoromethyl)-10-methyl-9-oxo-8,16-diazatricyclo[13.3.1.0$^{2,7}$]nonadeca-1(19),2(7),3,5,15,17-hexaen-14-yl]-6-oxo-1,6-dihydropyrimidin-4-yl}phenyl)-1H-1,2,3-triazole-4-carbonitrile trifluoroacetate (9.5 mg, 51% yield) was prepared in a similar manner as the procedure described in Example 129 by using (10R,14S)-14-amino-5-(difluoromethyl)-10-methyl-8,16-diazatricyclo [13.3.1.0$^{2,7}$]nonadeca-1(19),2(7),3,5,15,17-hexaen-9-one (8.63 mg, 0.025 mmol) and 1-[4-chloro-2-(6-hydroxypyrimidin-4-yl)phenyl]-1H-1,2,3-triazole-4-carbonitrile, prepared as described in Example 18 (8.2 mg, 0.028 mmol). MS(ESI) m/z: 627.3 (M+H)$^+$. $^1$H NMR (500 MHz, DMSO-d$_6$) δ 9.89 (br. s., 1H), 9.37 (br. s., 1H), 8.82 (br. s., 1H), 8.67 (br. s., 1H), 7.96 (br. s., 1H), 7.89-7.79 (m, 2H), 7.77-7.68 (m, 2H), 7.64 (d, J=7.3 Hz, 1H), 7.44 (d, J=16.8 Hz, 2H), 7.28-6.97 (m, 1H), 6.53 (br. s., 1H), 5.90 (d, J=8.5 Hz, 1H), 2.64 (br. s., 1H), 2.23 (br. s., 1H), 2.00-1.78 (m, 2H), 1.38 (br. s., 2H), 0.85 (d, J=6.1 Hz, 3H), 0.45 (br. s., 1H). Analytical HPLC (Method C): RT=1.79 min, purity=100.0%; Factor XIa Ki=0.26 nM, Plasma Kallikrein Ki=26 nM.

EXAMPLE 71

Preparation of (10R,14S)-14-[4-(5-chloro-1-methyl-1H-indazol-7-yl)-6-oxo-1,6-dihydropyrimidin-1-yl]-4-fluoro-10-methyl-8,16-diazatricyclo[13.3.1.0$^{2,7}$]nonadeca-1(19),2(7),3,5,15,17-hexaen-9-one

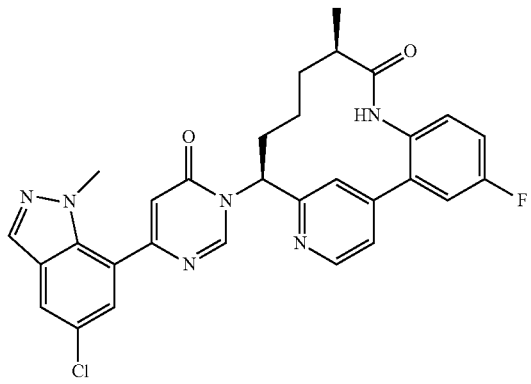 [SMILES: C[C@@H]1CCC[C@H](n2cnc(-c3cc(Cl)cc4cnn(C)c34)cc2=O)c2cc(ccn2)-c2cc(F)ccc2NC1=O]

To a scintillation vial containing 6-(5-chloro-1-methyl-1H-indazol-7-yl)pyrimidin-4-ol (19 mg, 0.073 mmol), prepared as described in Example 22, HATU (36 mg, 0.095 mmol) in ACN (1.0 mL) was added DBU (17 µl, 0.110 mmol). After 15 min, (10R,14S)-14-amino-4-fluoro-10-methyl-8,16-diazatricyclo[13.3.1.0$^{2,7}$]nonadeca -1(19),2,4,6,15,17-hexaen-9-one (23 mg, 0.073 mmol), prepared as described in Example 28, in DMF (1.0 mL) was added. The resulting solution was stirred at rt for 3 h then purified by reverse phase chromatography (XBridge C18, 19×200 mm, 5-µm particles; Mobile Phase A: 5:95 ACN: H$_2$O with 0.1% TFA; Mobile Phase B: 95:5 acetonitrile:water with 0.1% TFA; Gradient: 20-60% B over 14 minutes, then a 5-minute hold at 100% B; Flow: 20 mL/min) to give (10R,14S)-14-[4-(5-chloro-1-methyl-1H indazol-7-yl)-6-oxo-1,6-dihydropyrimidin-1-yl]-4-fluoro-10-methyl-8,16-diazatricyclo [13.3.1.0$^{2,7}$]nonadeca-1(19),2,4,6,15,17-hexaen-9-one trifluoroacetate (2.4 mg, 4.9% yield). MS(ESI) m/z: 557.3 (M+H)$^+$. $^1$H NMR (500 MHz, DMSO-d$_6$) δ 9.75 (s, 1H), 9.13 (s, 1H), 8.68 (d, J=4.9 Hz, 1H), 8.16 (s, 1H), 8.00 (s, 1H), 7.77 (s, 1H), 7.52-7.43 (m, 3H), 7.37-7.24 (m, 2H), 6.74 (s, 1H), 5.99 (d, J=7.9 Hz, 1H), 3.90 (s, 3H), 2.68-2.61 (m, 1H), 2.38-2.28 (m, 1H), 2.04-1.93 (m, 2H), 1.48-1.36 (m, 2H), 0.87 (d, J=6.7 Hz, 3H). Analytical HPLC (Method B): 1.83 min, purity=100%; Factor XIa Ki=350 nM.

EXAMPLE 72

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-3,10-dimethyl-8,16-diazatricyclo [13.3.1.0$^{2,7}$]nonadeca-1(19),2(7),3,5,15,17-hexaen-9-one

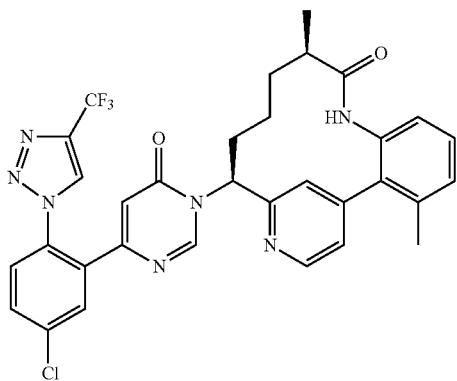

72A. Preparation of 3-methyl-2-(tetramethyl-1,3,2-dioxaborolan-2-yl)aniline

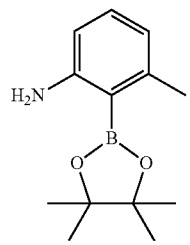

To a solution of 2-bromo-3-methylaniline (0.850 g, 4.6 mmol), Et$_3$N (3.8 ml, 27.4 mmol), 4,4,5,5-tetramethyl-1,3,2-dioxaborolane (2 ml, 13.7 mmol) in dioxane (9 ml) was purged with Ar. PdCl$_2$(PPh$_3$)$_2$ (0.16 g, 0.23 mmol) was added, and Ar was again bubbled through the solution The reaction vessel was sealed and heated at 100° C. for 32 h, then cooled to rt. The reaction mixture was diluted with EtOAc, filtered and the organic solution was washed with water and brine, dried over MgSO$_4$, filtered and concentration followed by purification with normal phase chromatography to afford 3-methyl-2-(tetramethyl-1,3,2-dioxaborolan-2-yl)aniline (0.696 g, 65%) as a pale yellow oil. $^1$H NMR (400 MHz, CDCl$_3$) δ 7.05 (t, J=7.7 Hz, 1H), 6.50 (d, J=7.3 Hz, 1H), 6.44 (d, J=8.1 Hz, 1H), 4.80 (br. s., 2H), 2.46 (s, 3H), 1.35 (s, 12H).

72B. Preparation of (10R,14S)-14-amino-3,10-dimethyl-8,16-diazatricyclo[13.3.1.0$^{2,7}$]nonadeca-1(19),2(7),3,5,15,17-hexaen-9-one

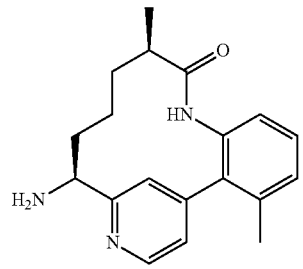 [SMILES: Cc1cccc2c1-c1ccnc(c1)[C@@H](N)CCC[C@@H](C)C(=O)N2]

(10R,14S)-14-Amino-3,10-dimethyl-8,16-diazatricyclo [13.3.1.0$^{2,7}$]nonadeca -1(19),2(7),3,5,15,17-hexaen-9-one was prepared in a similar manner as the procedure described in Example 29, by replacing (2-aminophenyl)boronic acid, with 3-methyl-2-(tetramethyl-1,3,2-dioxaborolan-2-yl)aniline.

72C. Preparation of (10R,14S)-14-(4-{5-chloro-2-[4-(trifluoromethyl)-1H-1,2,3-triazol -1-yl]phenyl}-6-oxo-1,6-dihydropyrimidin-1-yl)-3,10-dimethyl-8,16-diazatricyclo [13.3.1.0$^{2,7}$]nonadeca-1(19),2(7),3,5,15,17-hexaen-9-one trifluoroacetate (10R,14S)-14-(4-{5-Chloro-2-[4-(trifluoromethyl)-1H-1,2,3-triazol-1-yl]phenyl}-6-oxo-1,6-dihydropyrimidin-1-yl)-3,10-dimethyl-8,16-diazatricyclo[13.3.1.0$^{2,7}$]nonadeca -1(19),2(7),3,5,15,17-hexaen-9-one trifluoroacetate (0.0095 g, 47%) was prepared in a similar manner as the procedure described in Example 129 by using 6-{5-chloro-2-[4-(trifluoromethyl)-1H-1,2,3-triazol-1-yl]phenyl}pyrimidin-4-ol, prepared as described in Example 15, and (10R,14S)-14-amino-3,10-dimethyl-8,16-diazatricyclo[13.3.1.0$^{2,7}$]nonadeca-1(19),2(7),3,5,15,17-hexaen-9-one. MS(ESI) m/z: 634.4 (M+H)$^+$. $^1$H NMR (500 MHz, DMSO-d$_6$) δ 9.23-9.07 (m, 2H), 8.76 (br. s., 1H), 8.51 (d, J=4.6 Hz, 1H), 7.90 (s, 1H), 7.83-7.72 (m, 2H), 7.35-7.16 (m, 4H), 7.00 (d, J=7.6 Hz, 1H), 6.42 (s, 1H), 5.77 (br. s., 1H), 2.29-2.11 (m, 4H), 1.98-1.77 (m, 2H), 1.51-1.27 (m, 2H), 1.01-0.70 (m, 4H), 0.61 (br. s., 1H). Analytical HPLC (Method B) RT=2.31 min, 100% purity; Factor XIa Ki=1.8 nM, Plasma Kallikrein Ki=720 nM.

EXAMPLE 73

Preparation of (10R,14S)-14-{4-[5-chloro-2-(4-chloro-1H-1,2,3-triazol-1-yl)phenyl]-6oxo-1,6-dihydropyrimidin-1-yl}-3,10-dimethyl-8,16-diazatricyclo[13.3.1.0$^{2,7}$]nonadeca -1(19),2(7),3,5,15,17-hexaen-9-one

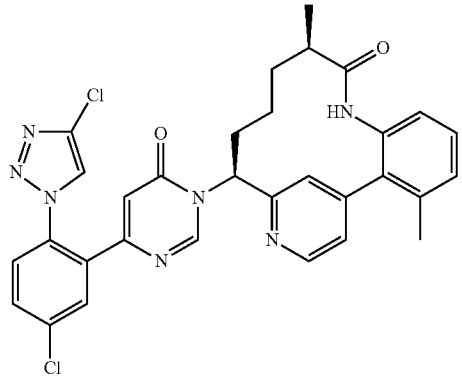

(10R,14S)-14-{4-[5-Chloro-2-(4-chloro-1H-1,2,3-triazol-1-yl)phenyl]-6-oxo-1,6-dihydropyrimidin-1-yl}-3,10-dimethyl-8,16-diazatricyclo[13.3.1.0$^{2,7}$]nonadeca -1(19),2(7),3,5,15,17-hexaen-9-one trifluoroacetate (0.0114 g, 57%) was prepared in a similar manner as the procedure described in Example 72 by replacing 6-{5-chloro-2-[4-(trifluoromethyl)-1H-1,2,3-triazol-1-yl]phenyl}pyrimidin-4-ol with 6-(5-chloro-2-(4-chloro-1H-1,2,3-triazol-1-yl)phenyl)pyrimidin-4-ol, prepared as described in Example 9. MS(ESI) m/z: 600.3 (M+H)$^+$. $^1$H NMR (500 MHz, DMSO-d$_6$) δ 9.18 (br. s., 1H), 8.83 (br. s., 1H), 8.65 (s, 1H), 8.55 (d, J=4.9 Hz, 1H), 7.86 (s, 1H), 7.79-7.73 (m, 1H), 7.68 (d, J=8.5 Hz, 1H), 7.32-7.17 (m, 4H), 7.00 (d, J=7.6 Hz, 1H), 6.29 (s, 1H), 5.75 (br. s., 1H), 2.27-2.14 (m, 4H), 2.03-1.78 (m, 2H), 1.49-1.29 (m, 2H), 1.03-0.71 (m, 4H), 0.68-0.46 (m, 1H). Analytical HPLC (Method B) RT=2.20 min, 96% purity; Factor XIa Ki=2 nM, Plasma Kallikrein Ki=580 nM.

EXAMPLE 74

Preparation of (10R,14S)-14-{4-[5-chloro-2-(4-chloro-1H-1,2,3-triazol-1-yl)phenyl]-6-oxo-1,6-dihydropyrimidin-1-yl}-5-(difluoromethyl)-10-methyl-8,16-diazatricyclo[13.3.1.0$^{2,7}$]nonadeca-1(19),2(7),3,5,15,17-hexaen-9-one

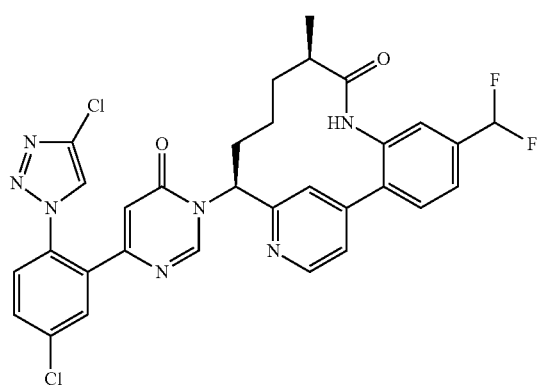 [SMILES: C[C@@H]1CCC[C@H](n2cnc(-c3cc(Cl)ccc3-n3cc(Cl)nn3)cc2=O)c2cc(ccn2)-c2ccc(C(F)F)cc2NC1=O]

(10R,14S)-14-{4-[5-Chloro-2-(4-chloro-1H-1,2,3-triazol-1-yl)phenyl]-6-oxo-1,6-dihydropyrimidin-1-yl}-5-(difluoromethyl)-10-methyl-8,16-diazatricyclo[13.3.1.0$^{2,7}$]nonadeca-1(19),2(7),3,5,15,17-hexaen-9-one trifluoroacetate (8.3 mg, 41% yield) was prepared in a similar manner as the procedure described in Example 70 by replacing 1-[4-chloro-2-(6-hydroxypyrimidin-4-yl)phenyl]-1H-1,2,3-triazole-4-carbonitrile with 6-(5-chloro-2-(4-chloro-1H-1,2,3-triazol-1-yl)phenyl)pyrimidin-4-ol, prepared as described in Example 9 (8.5 mg, 0.028 mmol). MS(ESI) m/z: 636.3 (M+H)$^+$. $^1$H NMR (500 MHz, DMSO-d$_6$) δ 9.68 (s, 1H), 8.66 (br. s., 1H), 8.48-8.39 (m, 2H), 7.73-7.63 (m, 1H), 7.58-7.34 (m, 5H), 7.24-7.14 (m, 2H), 7.00-6.71 (m, 1H), 6.09 (s, 1H), 5.66 (d, J=9.2 Hz, 1H), 2.40 (br. s., 1H), 1.99 (t, J=11.9 Hz, 1H), 1.75-1.55 (m, 2H), 1.14 (br. s., 2H), 0.60 (d, J=6.7 Hz, 3H), 0.19 (br. s., 1H). Analytical HPLC (Method C): RT=1.80 min, purity=93.0%; Factor XIa Ki=0.7 nM, Plasma Kallikrein Ki=40 nM.

EXAMPLE 75

Preparation of (10R,14S)-5-chloro-14-{4-[5-chloro-2-(4-chloro-1H-1,2,3-triazol-1-yl)phenyl]-6-oxo-1,6-dihydropyrimidin-1-yl}-10-methyl-8,16-diazatricyclo [13.3.1.0$^{2,7}$]nonadeca-1(19),2(7),3,5,15,17-hexaen-9-one

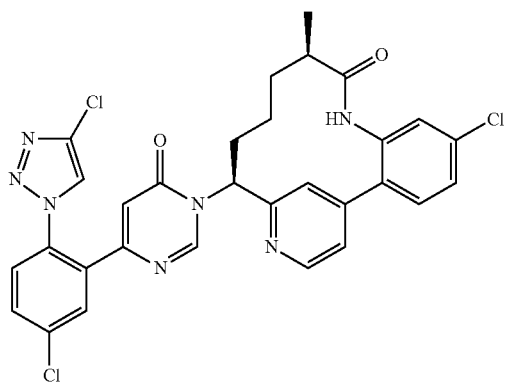 [SMILES: C[C@@H]1CCC[C@H](n2cnc(-c3cc(Cl)ccc3-n3cc(Cl)nn3)cc2=O)c2cc(ccn2)-c2ccc(Cl)cc2NC1=O]

75A. Preparation of (10R,14S)-14-amino-5-chloro-10-methyl-8,16-diazatricyclo [13.3.1.0$^{2,7}$]nonadeca-1(19),2(7), 3,5,15,17-hexaen-9-one

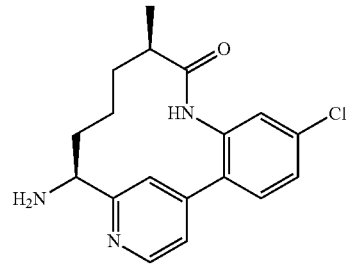 [SMILES: C[C@@H]1CCC[C@H](N)c2cc(ccn2)-c2ccc(Cl)cc2NC1=O]

tert-Butyl N-[(10R,14S)-5-amino-10-methyl-9-oxo-8,16-diazatricyclo [13.3.1.0$^{2,7}$]nonadeca-1(19),2(7),3,5,15,17-hexaen-14-yl]carbamate, prepared as described in Example 30A, (0.134 g, 0.326 mmol) in CH$_2$Cl$_2$ (10 mL) was added NOBF$_4$ (0.060 g, 0.514 mmol). The reaction vessel was sealed and microwaved at 120° C. for 30 min then cooled to rt. The reaction mixture was concentrated and the residue purified by reverse phase chromatography, followed by treatment with HCl in water. Concentration afforded (10R, 14S)-14-amino-5-chloro-10-methyl-8,16-diazatricyclo [13.3.1.0$^{2,7}$]nonadeca -1(19),2(7),3,5,15,17-hexaen-9-one (0.0095 g, 9%). MS(ESI) m/z: 330.2 (M+H)$^+$.

75B. Preparation of (10R,14S)-5-chloro-14-{4-[5-chloro-2-(4-chloro-1H-1,2,3-triazol-1-yl)phenyl]-6-oxo-1,6-dihydropyrimidin-1-yl}-10-methyl-8,16-diazatricyclo[13.3.1.0$^{2,7}$] nonadeca-1(19),2(7),3,5,15,17-hexaen-9-one trifluoroacetate (10R,14S)-5-Chloro-14-{4-[5-chloro-2-(4-chloro-1H-1, 2,3-triazol-1-yl)phenyl]-6-oxo-1,6-dihydropyrimidin-1-yl}-10-methyl-8,16-diazatricyclo[13.3.1.0$^{2,7}$]nonadeca -1(19),2 (7),3,5,15,17-hexaen-9-one trifluoroacetate (0.0089 g, 48%) was prepared in a similar manner as the procedure described in Example 73, by using(10R,14S)-14-amino -5-chloro-10-methyl-8,16-diazatricyclo[13.3.1.0$^{2,7}$]nonadeca-1(19),2(7), 3,5,15,17-hexaen -9-one. MS(ESI) m/z: 620.1 (M+H)$^+$. $^1$H NMR (500 MHz, DMSO-d$_6$) δ 9.83 (s, 1H), 8.83 (br. s., 1H), 8.62 (s, 1H), 8.57 (d, J=4.9 Hz, 1H), 7.84 (s, 1H), 7.75-7.71 (m, 1H), 7.69-7.64 (m, 1H), 7.61 (s, 1H), 7.54 (d, J=8.2 Hz, 1H), 7.42 (d, J=7.9 Hz, 1H), 7.34 (d, J=4.3 Hz, 1H), 7.24 (s, 1H), 6.25 (s, 1H), 5.83 (d, J=8.8 Hz, 1H), 2.56 (br. s., 1H), 2.15 (t, J=12.2 Hz, 1H), 1.90-1.74 (m, 2H), 1.31 (br. s., 2H), 0.77 (d, J=6.4 Hz, 3H), 0.34 (br. s., 1H). Analytical HPLC (Method B) RT=1.97 min, 93% purity; Factor XIa Ki=1.0 nM, Plasma Kallikrein Ki=100 nM.

EXAMPLE 76

Preparation of (10R,14S)-14-(4-{5-chloro-2-[4-(trifluoromethyl)-1H-1,2,3-triazol-1-yl]phenyl}-6-oxo-1, 6-dihydropyrimidin-1-yl)-10-methyl-9-oxo-8,16-diazatricyclo [13.3.1.0$^{2,7}$]nonadeca-1(19),2(7),3,5, 15,17-hexaene-5-carboxamide

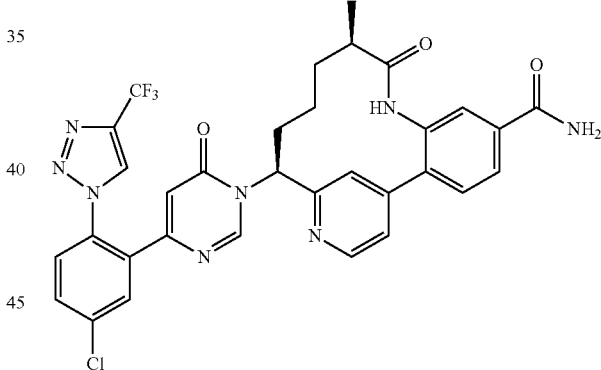

(10R,14S)-14-(4-{5-Chloro-2-[4-(trifluoromethyl)-1H-1, 2,3-triazol-1-yl]phenyl}-6-oxo-1,6-dihydropyrimidin-1-yl)-10-methyl-9-oxo-8,16-diazatricyclo[13.3.1.0$^{2,7}$]nonadeca-1 (19),2(7),3,5,15,17-hexaene-5-carboxamide was isolated as a side product during the synthesis of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-9-oxo-8, 16-diazatricyclo[13.3.1.0$^{2,7}$]nonadeca-1(19),2(7),3,5,15,17-hexaene-5-carbonitrile, as described in Example 43. MS(ESI) m/z: 663.2 (M+H)$^+$. $^1$H NMR (400 MHz, CDCl$_3$) δ 8.86 (s, 1H), 8.81 (s, 1H), 8.67 (d, J=5.1 Hz, 1H), 7.94 (dd, J=8.0, 1.4 Hz, 1H), 7.89 (d, J=2.2 Hz, 1H), 7.79-7.64 (m, 5H), 7.49 (dd, J=5.1, 1.3 Hz, 1H), 6.43 (s, 1H), 5.99 (dd, J=12.5, 4.6 Hz, 1H), 2.67 (d, J=6.4 Hz, 1H), 2.21 (t, J=12.8 Hz, 1H), 2.10-1.89 (m, 2H), 1.59-1.37 (m, 2H), 0.97 (d, J=7.0 Hz, 3H), 0.70 (br. s., 1H). Analytical HPLC (Method A): RT=7.87 min, purity=99.0%; Factor XIa Ki=0.44 nM, Plasma Kallikrein Ki=36 nM.

EXAMPLE 77

Preparation of 4-chloro-2-{1-[(10R,14S)-4-fluoro-10-methyl-9-oxo-8,16-diazatricyclo [13.3.1.0$^{2,7}$] nonadeca-1(19),2(7),3,5,15,17-hexaen-14-yl]-6-oxo-1,6-dihydropyrimidin-4-yl}benzoic acid

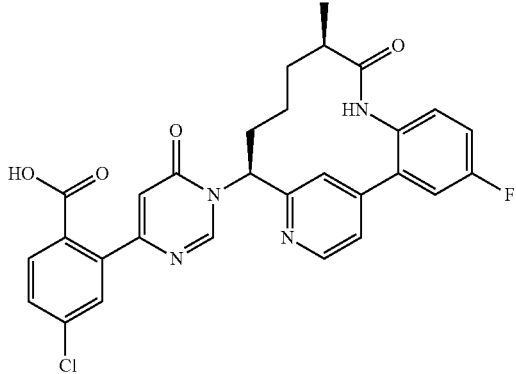 [SMILES: C[C@@H]1CCC[C@H](n2cnc(-c3cc(Cl)ccc3C(=O)O)cc2=O)c2cc(ccn2)-c2cc(F)ccc2NC1=O]

To a solution of methyl 4-chloro-2-{1-[(10R,14S)-4-fluoro-10-methyl-9-oxo-8,16-diazatricyclo[13.3.1.0$^{2,7}$]nonadeca-1(19),2(7),3,5,15,17-hexaen-14-yl]-6-oxo-1,6-dihydropyrimidin-4-yl}benzoate trifluoroacetate (0.005 g, 7.41 µmol), prepared as described in Example 68, in THF (1 ml) was added 2 N LiOH (0.019 ml, 0.037 mmol). The reaction was stirred at rt for 1 h, then 1 N NaOH (0.030 ml, 0.030 mmol) was added, followed by a few drops of MeOH. After stirring at rt for 3 h, the reaction was neutralized with 1 N HCl and concentrated. Purification by reverse phase chromatography afforded 4-chloro-2-{1-[(10R,14S)-4-fluoro-10-methyl-9-oxo-8,16-diazatricyclo[13.3.1.0$^{2,7}$]nonadeca-1 (19),2(7),3,5,15,17-hexaen-14-yl]-6-oxo-1,6-dihydropyrimidin-4-yl}benzoic acid trifluoroacetate (1.54 mg, 31% yield) as a white solid. MS(ESI) m/z: 547.3 (M+H)$^+$. $^1$H NMR (400 MHz, CD$_3$OD) δ 9.09 (s, 1H), 8.69 (d, J=5.1 Hz, 1H), 7.89 (d, J=8.8 Hz, 1H), 7.75 (s, 1H), 7.60-7.55 (m, 2H), 7.44 (dd, J=5.1, 1.5 Hz, 1H), 7.39 (dd, J=9.0, 2.9 Hz, 1H), 7.32-7.20 (m, 2H), 6.56 (s, 1H), 6.09 (dd, J=12.4, 4.5 Hz, 1H), 2.73-2.62 (m, 1H), 2.34-2.23 (m, 1H), 2.13-1.91 (m, 2H), 1.59-1.38 (m, 2H), 0.97 (d, J=7.0 Hz, 3H), 0.79-0.59 (m, 1H). Analytical HPLC (Method A): RT=7.53 min, 98.4% purity; Factor XIa Ki=500 nM.

EXAMPLE 78

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-5,10-dimethyl-8,16-diazatricyclo [13.3.1.0$^{2,7}$]nonadeca-1(19),2(7),3,5,15,17-hexaen-9-one

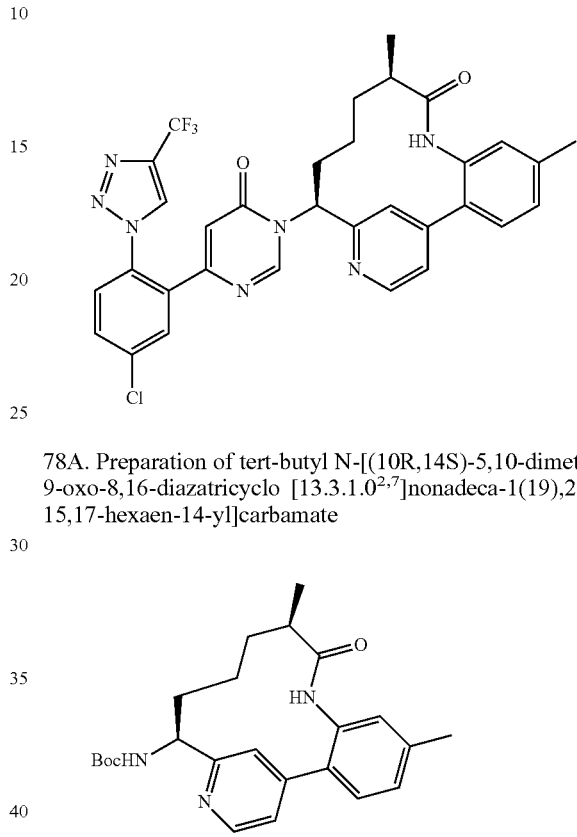

78A. Preparation of tert-butyl N-[(10R,14S)-5,10-dimethyl-9-oxo-8,16-diazatricyclo [13.3.1.0$^{2,7}$]nonadeca-1(19),2,4,6,15,17-hexaen-14-yl]carbamate tert-Butyl N-[(10R,14S)-5-bromo-10-methyl-9-oxo-8,16-diazatricyclo[13.3.1.0$^{2,7}$]nonadeca-1(19),2,4,6,15,17-hexaen-14-yl]carbamate (0.074 g, 0.156 mmol), CH$_3$B (OH)$_2$ (0.0187 g, 0.312 mmol), 3 M K$_3$PO$_4$ (0.15 ml, 0.468 mmol) and THF (1.5 ml) in a 20-drum vial was bubbled through Ar for several min and (DtBPF)PdCl$_2$ (0.010 g, 0.016 mmol) was added. The reaction vessel was sealed and heated at 60° C. for 16 h then more CH$_3$B(OH)$_2$ (0.020 g) and C$_3$H$_9$B$_3$O$_3$ (0.030 g) were added. The reaction was heated at 80° C. for 4 h then cooled to rt. Purification with normal phase chromatography, followed by reverse phase chromatography afforded (0.040 g, 49%) tert-butyl N-[(10R, 14S)-5,10-dimethyl-9-oxo-8,16-diazatricyclo[13.3.1.0$^{2,7}$] nonadeca-1(19),2,4,6,15,17-hexaen-14-yl]carbamate as a white solid. MS(ESI) m/z: 410.1 (M+H)$^+$.

78B. Preparation of (10R,14S)-14-(4-{5-chloro-2[4-(trifluoromethyl)-1H-1,2,3-triazol -1-yl]phenyl}-6-oxo-1,6-dihydropyrimidin-1-yl)-5,10-dimethyl-8,16-diazatricyclo [13.3.1.0$^{2,7}$]nonadeca-1(19),2(7),3,5,15,17-hexaen-9-one trifluoroacetate (10R,14S)-14-(4-{5-Chloro-2-[4-(trifluoromethyl)-1H-1, 2,3-triazol-1-yl]phenyl}-6-oxo-1,6-dihydropyrimidin-1-yl)-5,10-dimethyl-8,16-diazatricyclo[13.3.1.0$^{2,7}$]nonadeca -1(19),2(7),3,5,15,17-hexaen-9-one trifluoroacetate (0.011 g, 33%) was prepared in a similar manner as the procedure described in Example 67, by using tert-butyl N-[(10R,14S)-5,10-dimethyl-9-oxo-8,16-diazatricyclo[13.3.1.0$^{2,7}$]nonadeca-1(19),2,4,6,15,17-hexaen-14-yl]carbamate, prepared as described in Example 78A, and 6-{5-chloro-2-[4-(trifluoromethyl)-1H-1,2,3-triazol-1-yl]phenyl}pyrimidin-4-ol, prepared as described in Example 15B. MS(ESI) m/z: 634.2 (M+H)$^+$. $^1$H NMR (400 MHz, CDCl$_3$) δ 8.84 (s, 1H), 8.79 (s, 1H), 8.65 (d, J=5.3 Hz, 1H), 7.90 (d, J=2.4 Hz, 1H), 7.84 (s, 1H), 7.79-7.73 (m, 1H), 7.72-7.66 (m, 1H), 7.58-7.48 (m, 2H), 7.30 (d, J=7.7 Hz, 1H), 7.10 (s, 1H), 6.44 (s, 1H), 5.94 (dd, J=12.5, 4.6 Hz, 1H), 2.73-2.61 (m, J=4.0 Hz, 1H), 2.42 (s, 3H), 2.35-2.21 (m, 1H), 2.11-1.89 (m, 2H), 1.57-1.41 (m, 2H), 0.98 (d, J=7.0 Hz, 3H), 0.85-0.58 (m, 1H). Analytical HPLC (Method A) RT=9.04 min, 90% purity; Factor XIa Ki=0.42 nM, Plasma Kallikrein Ki=40 nM.

EXAMPLE 79

Preparation of (10R,14S)-14-{4-[5-chloro-2-(4-chloro-1H-1,2,3-triazol-1-yl)phenyl]-6-oxo-1,6-dihydropyrimidin-1-yl}-5,10-dimethyl-8,16-diazatricyclo[13.3.1.0$^{2,7}$]nonadeca-1(19),2(7),3,5,15,17-hexaen-9-one

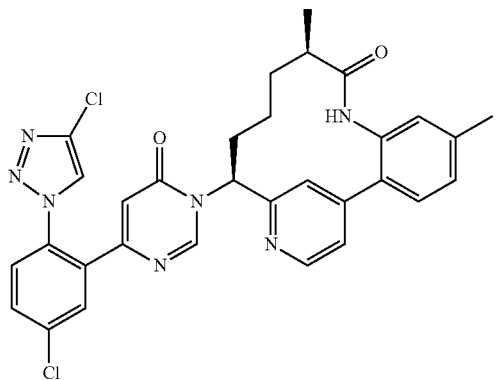 [SMILES: Cc1ccc2c(c1)NC(=O)[C@H](C)CCC[C@H](n1cnc(-c3cc(Cl)ccc3-n3cc(Cl)nn3)cc1=O)c1cc-2ccn1]

(10R,14S)-14-{4-[5-Chloro-2-(4-chloro-1H-1,2,3-triazol-1-yl)phenyl]-6-oxo-1,6-dihydropyrimidin-1-yl}-5,10-dimethyl-8,16-diazatricyclo[13.3.1.0$^{2,7}$]nonadeca-1(19),2(7),3,5,15,17-hexaen-9-one trifluoroacetate (0.0059 g, 19%) was prepared in a similar manner as the procedure described in Example 78B, by using 6-[5-chloro-2-(4-chloro-1H-1,2,3-triazol-1-yl)phenyl]pyrimidin-4-ol, prepared as described in Example 9.

MS(ESI) m/z: 600.2 (M+H)$^+$. $^1$H NMR (400 MHz, CD$_3$OD) δ 8.84 (s, 1H), 8.79 (s, 1H), 8.65 (d, J=5.3 Hz, 1H), 7.90 (d, J=2.4 Hz, 1H), 7.84 (s, 1H), 7.79-7.73 (m, 1H), 7.72-7.66 (m, 1H), 7.58-7.48 (m, 2H), 7.30 (d, J=7.7 Hz, 1H), 7.10 (s, 1H), 6.44 (s, 1H), 5.94 (dd, J=12.5, 4.6 Hz, 1H), 2.73-2.61 (m, J=4.0 Hz, 1H), 2.42 (s, 3H), 2.35-2.21 (m, 1H), 2.11-1.89 (m, 2H), 1.57-1.41 (m, 2H), 0.98 (d, J=7.0 Hz, 3H), 0.85-0.58 (m, 1H). Analytical HPLC (Method A) RT=8.42 min, 90% purity; Factor XIa Ki=0.56 nM, Plasma Kallikrein Ki=45 nM.

EXAMPLE 80

Preparation of methyl N-[(10R,14S)-14-[4-(3-chloro-2-methylphenyl)-6-oxo-1,6-dihydropyrimidin-1-yl]-10-methyl-9-oxo-8,16-diazatricyclo[13.3.1.0$^{2,7}$]nonadeca-1(19),2(7),3,5,15,17-hexaen-5-yl]carbamate 80A. Preparation of 6-(3-chloro-2-methylphenyl)pyrimidin-4-ol 6-(3-Chloro-2-methylphenyl)pyrimidin-4-ol (25 mg, 15%) was prepared in a similar manner as the procedure described in Example 3 by replacing (3-chloro-2-fluorophenyl)boronic acid with (3-chloro-2-methylphenyl)boronic acid (0.1 g, 0.766 mmol). MS(ESI) m/z: 221.0 (M+H)$^+$.

80B. Preparation of methyl N-[(10R,14S)-14-[4-(3-chloro-2-methylphenyl)-6-oxo-1,6-dihydropyrimidin-1-yl]-10-methyl-9-oxo-8,16-diazatricyclo[13.3.1.0$^{2,7}$]nonadeca-1(19),2(7),3,5,15,17-hexaen-5-yl]carbamate Methyl N-[(10R,14S)-14-[4-(3-chloro-2-methylphenyl)-6-oxo-1,6-dihydropyrimidin-1-yl]-10-methyl-9-oxo-8,16-diazatricyclo[13.3.1.0$^{2,7}$]nonadeca-1(19),2(7),3,5,15,17-hexaen-5-yl]carbamate trifluoroacetate (11 mg, 64% yield) was prepared in a similar manner as the procedure described in Example 129 by using methyl N-[(10R,14 S)-14-amino-10-methyl-9-oxo-8,16-diazatricyclo[13.3.1.0$^{2,7}$]nonadeca-1(19),2(7),3,5,15,17-hexaen-5-yl]carbamate (9.21 mg, 0.025 mmol), prepared as described in Example 45K and 6-(3-chloro-2-methylphenyl)pyrimidin-4-ol (6.1 mg, 0.028 mmol). MS(ESI) m/z: 572.3 (M+H)$^+$. $^1$H NMR (500 MHz, DMSO-d$_6$) δ 9.92 (s, 1H), 9.80 (s, 1H), 9.07 (br. s., 1H), 8.62 (d, J=4.9 Hz, 1H), 7.69 (s, 1H), 7.57-7.45 (m, 3H), 7.42-7.29 (m, 4H), 7.28-7.03 (m, 1H), 6.47 (s, 1H), 5.96 (d, J=8.8 Hz, 1H), 3.60 (s, 3H), 2.67 (br. s., 1H), 2.34 (s, 3H), 2.33-2.23 (m, 1H), 2.05-1.86 (m, 2H), 1.42 (br. s., 2H), 0.85 (d, J=6.7 Hz, 3H), 0.42 (br. s., 1H). Analytical HPLC (Method C): RT=1.65 min, purity=99.0%; Factor XIa Ki=275 nM, Plasma Kallikrein Ki=5,600 nM.

EXAMPLE 81

Preparation of (10R,14S)-10-methyl-14-(4-{5-methyl-2[4-(trifluoromethyl)-1H-1,2,3-triazol-1-yl]phenyl}-6-oxo-1,6-dihydropyrimidin-1-yl)-8,16-diazatricyclo [13.3.1.0$^{2,7}$]nonadeca-1(19),2(7),3,5,15,17-hexaen-9-one

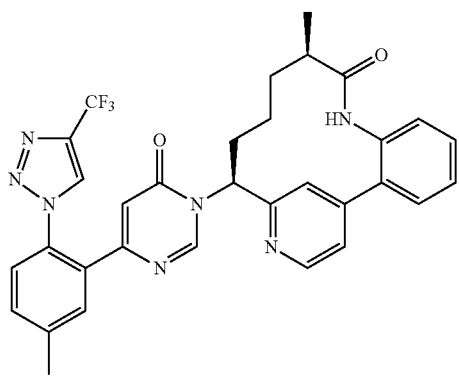 [SMILES: Cc1ccc(-n2cc(C(F)(F)F)nn2)c(-c2cc(=O)n([C@H]3CCC[C@@H](C)C(=O)Nc4ccccc4-c4ccnc3c4)cn2)c1]

81A. Preparation of 4-methyl-2-(4,4,5,5-tetramethyl-1,3,2-dioxaborolan-2-yl)aniline 2-Bromo-4-methylaniline (3 g, 16.12 mmol), bis(pinacolato)diboron (6.14 g, 24.19 mmol), KOAc (4.07 g, 41.4 mmol) were added to DMSO (9 mL) under $N_2$ atm and then the solution was purged with Ar for 10 min. PdCl$_2$(dppf)-CH$_2$Cl$_2$Adduct (0.395 g, 0.484 mmol) was added and the resulting suspension was stirred overnight at 80° C. The reaction mixture was partitioned between DCM and water. The organic layer was washed with brine, dried over Na$_2$SO$_4$, filtered, and concentrated, then purified normal phase chromatography using hexane and EtOAc as eluents to give 4-methyl-2-(4,4,5,5-tetramethyl-1,3,2-dioxaborolan-2-yl)aniline (3.52 g, 94% yield) as a clear oil which solidified into a white solid upon standing. MS(ESI) m/z: 152.3 (M-C$_6$H$_{10}$+H)$^+$. $^1$H NMR (400MHz, CDCl$_3$-d) δ 7.43 (d, J=1.8 Hz, 1H), 7.04 (dd, J=8.3, 2.3 Hz, 1H), 6.55 (d, J=8.1 Hz, 1H), 4.60 (br. s., 2H), 2.23-2.20 (m, 3H), 1.38-1.32 (m, 12H).

81B. Preparation of 2-(6-methoxypyrimidin-4-yl)-4-methylaniline

To a RBF (250 mL) equipped with a reflux condenser containing DME (42.9 mL), EtOH (5.36 mL) was added 4-chloro-6-methoxypyrimidine (1.55 g, 10.72 mmol), 4-methyl-2-(4,4,5,5-tetramethyl-1,3,2-dioxaborolan-2-yl)aniline (2.5 g, 10.72 mmol) and 2 M Na$_2$CO$_3$ (5.36 mL, 10.72 mmol). The mixture was purged with Ar for 10 min, then PdCl$_2$(dppf)-CH$_2$Cl$_2$Adduct (0.876 g, 1.072 mmol) was added and the reaction mixture was heated at 90° C. After 2 h, the reaction was diluted with water and extracted with EtOAc. The organic layer washed with brine and concentrated to give a brown oil. The crude product was purified by normal phase chromatography using heptane and EtOAc as eluents to give 2-(6-methoxypyrimidin-4-yl)-4-methylaniline (670 mg, 29%) as a solid. MS(ESI) m/z: 216.1 (M+H)$^+$. $^1$H NMR (500 MHz, CDCl$_3$-d) δ 8.79 (d, J=1.1 Hz, 1H), 7.33 (d, J=1.4 Hz, 1H), 7.08-7.01 (m, 2H), 6.67 (d, J=8.3 Hz, 1H), 5.68 (br. s., 2H), 4.03 (s, 3H), 2.29 (s, 3H).

81C. Preparation of 4-methoxy-6-(5-methyl-2-(4-(trifluoromethyl)-1H-1,2,3-triazol-1-yl)phenyl)pyrimidine To a clear, yellow solution of 2-(6-methoxypyrimidin-4-yl)-4-methylaniline (0.670 g, 3.11 mmol) in ACN (44.5 mL) at 0° C. was added isoamyl nitrite (0.627 mL, 4.67 mmol), followed by dropwise addition of TMSN$_3$ (0.614 mL, 4.67 mmol). After 10 min, the cold bath was removed, and the reaction allowed to warm to rt. After 4.5 h, Cu$_2$O (0.045 g, 0.311 mmol) was added. After a few min, 3,3,3-trifluoroprop-1-yne (0.293 g, 3.11 mmol) gas was bubbled into the dark green solution at rt. After 1 h, the reaction was diluted with DCM and washed with sat NH$_4$Cl, brine, dried over MgSO$_4$, filtered and concentrated to give a brown oil. The crude product was purified by normal phase chromatography using heptane and EtOAc as eluents to give 4-methoxy-6-(5-methyl-2-(4-(trifluoromethyl)-1H-1,2,3-triazol-1-yl)phenyl)pyrimidine (941 mg, 90%) as a solid. MS(ESI) m/z: 336.1 (M+H)$^+$. $^1$H NMR (500 MHz, CDCl$_3$) δ 8.63 (s, 1H), 7.98 (s, 1H), 7.56 (s, 1H), 7.45 (s, 2H), 6.58 (s, 1H), 3.97 (s, 3H), 2.53 (s, 3H).

81D. Preparation of 6-(5-methyl-2-(4-(trifluoromethyl)-1H-1,2,3-triazol-1-yl)phenyl) pyrimidin-4-ol A clear, yellow solution of 4-methoxy-6-(5-methyl-2-(4-(trifluoromethyl)-1H -1,2,3-triazol-1-yl)phenyl)pyrimidine (0.941 g, 2.81 mmol) in AcOH (14.03 mL) and 48% HBr in water (15.88 mL, 140 mmol) was warmed to 85 ° C. After 3 h, the reaction was cooled to rt and concentrated. The yellow gum was dissolved in EtOAc, washed with sat NaHCO$_3$, brine, dried over Na$_2$SO$_4$, filtered, and concentrated. Et$_2$O (3 mL) was added and the mixture was sonicated and filtered. The solid was rinsed with Et$_2$O (5 mL), air-dried with suction overnight to afford 6-(5-methyl-2-(4-(trifluoromethyl)-1H-1,2,3-triazol-1-yl)phenyl)pyrimidin-4-ol (0.609 g, 67.5% yield) as a light yellow solid. MS(ESI) m/z: 322.1 (M+H)$^+$. $^1$H NMR (400 MHz, CDCl$_3$) δ 12.90 (br. s., 1H), 8.06 (s, 1H), 7.93 (d, J=0.7 Hz, 1H), 7.57-7.40 (m, 3H), 6.51 (d, J=0.9 Hz, 1H), 2.53 (s, 3H).

81E. Preparation of (10R,14S)-10-methyl-14-(4-{5-methyl-2[4-(trifluoromethyl)-1H -1,2,3 -triazol-1-yl]phenyl}-6-oxo-1,6-dihydropyrimidin-1-yl)-8,16-diazatricyclo [13.3.1.0$^{2,7}$]nonadeca-1(19),2,4,6,15,17-hexaen-9-one trifluoroacetate (10R,14S)-10-Methyl-14-(4-{5-methyl-2-[4-(trifluoromethyl)-1H-1,2,3-triazol-1-yl]phenyl}-6-oxo-1,6-dihydropyrimidin-1-yl)-8,16-diazatricyclo[13.3.1.0$^{2,7}$] nonadeca -1(19),2,4,6,15,17-hexaen-9-one trifluoroacetate (37 mg, 60%) was prepared in a similar manner as Example 129, using 6-(5-methyl-2-(4-(trifluoromethyl)-1H-1,2,3-triazol-1-yl)phenyl)pyrimidin-4-ol and (10R,14S)-14-amino-10-methyl-8,16-diazatricyclo [13.3.1.0$^{2,7}$]nonadeca-1(19), 2,4,6,15,17-hexaen-9-one, prepared as described in Example 29. MS(ESI) m/z: 600 (M+H)$^+$. $^1$H NMR (500 MHz, DMSO-d$_6$) δ 9.76 (s, 1H), 9.14 (s, 1H), 8.81 (br. s., 1H), 8.59 (d, J=4.6 Hz, 1H), 7.68 (s, 2H), 7.62 (d, J=7.9 Hz, 1H), 7.56 (t, J=9.2 Hz, 2H), 7.49-7.39 (m, 3H), 7.22 (d, J=7.6 Hz, 1H), 6.34 (s, 1H), 5.90 (d, J=9.2 Hz, 1H), 3.55 (d, J=5.8 Hz, 1H), 2.65-2.61 (m, 1H), 2.47 (s, 3H), 2.19 (t, J=12.1 Hz, 1H), 1.98-1.91 (m, 1H), 1.86-1.80 (m, 1H), 1.43-1.33 (m, 2H), 0.83 (d, J=6.7 Hz, 3H). Analytical HPLC (Method C): RT=1.72 min, purity=99%; Factor XIa Ki=0.63 nM, Plasma Kallikrein Ki=66 nM.

EXAMPLE 82

Preparation of (10R,14S)-10-methyl-14-(4-{5-methyl-2-[4-(trifluoromethyl)-1H-1,2,3-triazol-1-yl]phenyl}-6-oxo-1,6-dihydropyrimidin-1-yl)-9-oxo-8,16-diazatricyclo [13.3.1.0$^{2,7}$]nonadeca-1(19),2(7),3,5,15,17-hexaene-5-carbonitrile

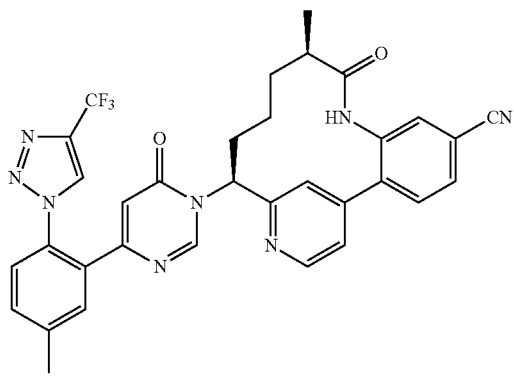 [SMILES: Cc1ccc(-n2cc(C(F)(F)F)nn2)c(-c2cc(=O)n([C@H]3CCC[C@@H](C)C(=O)Nc4cc(C#N)ccc4-c4ccnc3c4)cn2)c1]

(10R,14S)-10-Methyl-14-(4-{5-methyl-2-[4-(trifluoromethyl)-1H-1,2,3-triazol-1-yl]phenyl}-6-oxo-1,6-dihydropyrimidin-1-yl)-9-oxo-8,16-diazatricyclo[13.3.1.0$^{2,7}$]nonadeca-1(19),2(7),3,5,15,17-hexaene-5-carbonitrile trifluoroacetate (7.9 mg, 42%) was prepared in a similar manner as Example 129, using 6-(5-methyl-2-(4-(trifluoromethyl)-1H-1,2,3-triazol-1-yl)phenyl)pyrimidin-4-ol prepared as described in Example 81D and (10R,14S)-14-amino-10-methyl-9-oxo-8,16-diazatricyclo[13.3.1.0$^{2,7}$] nonadeca -1(19),2,4,6,15,17-hexaene-5-carbonitrile, prepared as described in Example 30. MS(ESI) m/z: 625 (M+H. $^1$H NMR (500 MHz, DMSO-d$_6$) δ 9.98 (s, 1H), 9.16 (s, 1H), 8.82 (br. s., 1H), 8.65 (d, J=4.6 Hz, 1H), 7.90 (d, J=7.6 Hz, 1H), 7.79 (br. s., 1H), 7.70 (d, J=9.2 Hz, 2H), 7.66-7.61 (m, 1H), 7.59-7.55 (m, 1H), 7.48 (br. s., 1H), 6.34 (s, 1H), 3.52-3.38 (m, 2H), 2.64 (br. s., 1H), 2.48 (s, 3H), 2.25-2.16 (m, 1H), 1.96-1.81 (m, 2H), 1.44-1.34 (m, 2H), 0.84 (d, J=6.4 Hz, 3H), 0.45-0.34 (m, 1H). Analytical HPLC (Method C): RT=1.82 min, purity=99%; Factor XIa Ki=1.9 nM, Plasma Kallikrein Ki=176 nM.

EXAMPLE 83

Preparation of (10R,14S)-14-{4-[3-chloro-2-fluoro-6-(1H-1,2,3-triazol-1-yl)phenyl]-6-oxo-1,6-dihydropyrimidin-1-yl}-10-methyl-9-oxo-8,16-diazatricyclo [13.3.1.0$^{2,7}$]nonadeca-1(19),2(7),3,5,15,17-hexaene-5-carbonitrile

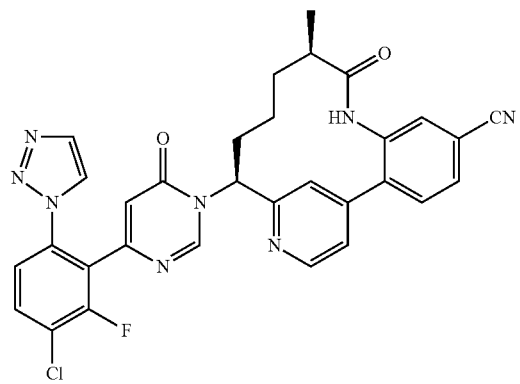 [SMILES: C[C@@H]1CCC[C@H](n2cnc(-c3c(-n4ccnn4)ccc(Cl)c3F)cc2=O)c2cc(ccn2)-c2ccc(C#N)cc2NC1=O]

(10R,14S)-14-{4-[3-Chloro-2-fluoro-6-(1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7),3,5,15,17-hexaene-5-carbonitrile (6 mg, 21% yield) was prepared in a similar manner as the procedure described in Example 129, by using 6-(3-chloro-2-fluoro-6-(1H -1,2,3-triazol-1-yl)phenyl)pyrimidin-4-ol, prepared as described in Example 7, and (10R,14S)-14-amino-10-methyl-9-oxo-8,16-diazatricyclo[13.3.1.0$^{2,7}$]nonadeca -1(19),2,4,6,15,17-hexaene-5-carbonitrile, prepared as described in Example 37. MS(ESI) m/z: 595.2 (M+H)$^+$. $^1$H NMR (400 MHz, CD$_3$OD) δ 10.00 (s, 1H), 9.00 (s, 1H), 8.71 (d, J=5.1 Hz, 1H), 8.15 (s, 1H), 7.88-7.70 (m, 5H), 7.69 (s, 1H), 7.61 (d, J=1.1 Hz, 1H), 7.52 (dd, J=8.7, 1.4 Hz, 1H), 7.44 (dd, J=5.0, 1.4 Hz, 1H), 6.51 (s, 1H), 6.03 (dd, J=12.5, 4.8 Hz, 1H), 2.75-2.62 (m, 1H), 2.25-2.11 (m, 1H), 2.09-1.83 (m, 2H), 1.59-1.36 (m, 2H), 0.95 (d, J=7.0 Hz, 3H), 0.70-0.47 (m, 1H). Analytical HPLC (Method A): RT=8.34 min, purity=99%; Factor XIa Ki=1.4 nM, Plasma Kallikrein Ki=92 nM.

EXAMPLE 84

Preparation of (10R,14S)-14-{4-[5-chloro-2-(4-chloro-1H-1,2,3-triazol-1-yl)phenyl]-6-oxo-1,6-dihydropyrimidin-1-yl}-5-methoxy-10-methyl-8,16-diazatricyclo[13.3.1.0$^{2,7}$]nonadeca-1(19),2(7),3,5,15,17-hexaen-9-one

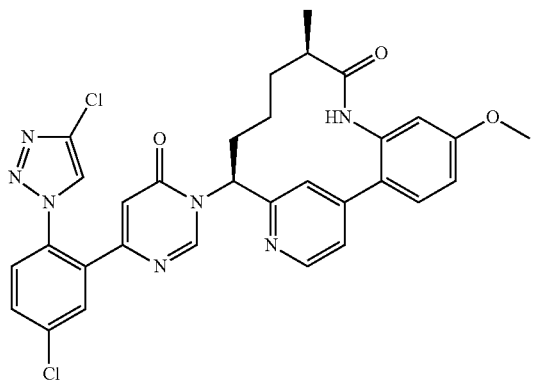 [SMILES: COc1ccc2c(c1)NC(=O)[C@H](C)CCC[C@H](n1cnc(-c3cc(Cl)ccc3-n3cc(Cl)nn3)cc1=O)c1cc-2ccn1]

84A. Preparation of tert-butyl N-[(10R,14S)-5-methoxy-10-methyl-9-oxo-8,16-diazatricyclo[13.3.1.0$^{2,7}$]nonadeca-1(19),2(7),3,5,15,17-hexaen-14-yl]carbamate

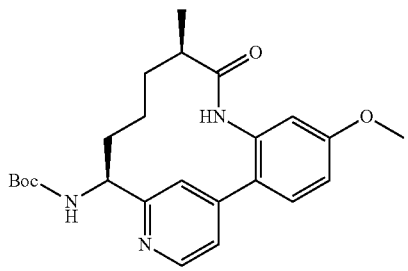 [SMILES: COc1ccc2c(c1)NC(=O)[C@H](C)CCC[C@H](NC(=O)OC(C)(C)C)c1cc-2ccn1]

tert-Butyl N-[(10R,14S)-5-iodo-10-methyl-9-oxo-8,16-diazatricyclo[13.3.1.0$^{2,7}$]-nonadeca-1(19),2(7),3,5,15,17-hexaen-14-yl]carbamate (0.059 g, 0.113 mmol), prepared as described in Example 30B, 1,10-phenanthroline (0.004 g, 0.023 mmol), CuI (0.002 g, 0.011 mmol), Cs$_2$CO$_3$ (0.074 g, 0.226 mmol) in MeOH (1 mL) was sealed and heated at 110° C. for 16 h, then was cooled to rt. The reaction mixture was diluted with EtOAc, washed with water and brine, dried over MgSO$_4$, filtered and concentrated. The resulting crude product was purified by normal phase chromatography to afford tert-butyl N-[(10R,14S)-5-iodo-10-methyl-9-oxo-8,16-diazatricyclo[13.3.1.0$^{2,7}$]nonadeca-1(19),2(7),3,5,15,17-hexaen-14-yl]carbamate (0.035 g, 73% yield) as a white solid. MS(ESI) m/z: 426.08 (M+H)$^+$.

84B. Preparation of (10R,14S)-14-{4-[5-chloro-2-(4-chloro-1H-1,2,3-triazol-1-yl)phenyl]-6-oxo-1,6-dihydropyrimidin-1-yl}-5-methoxy-10-methyl-8,16-diazatricyclo[13.3.1.0$^{2,7}$]nonadeca-1(19),2(7),3,5,15,17-hexaen-9-one trifluoroacetate (10R,14S)-14-{4-[5-Chloro-2-(4-chloro-1H-1,2,3-triazol-1-yl)phenyl]-6-oxo-1,6-dihydropyrimidin-1-yl}-5-methoxy-10-methyl-8,16-diazatricyclo[13.3.1.0$^{2,7}$]nonadeca-1(19),2(7),3,5,15,17-hexaen-9-one trifluoroacetate (0.031 g, 52%) was prepared in a similar manner as the procedure described in Example 79, by using tert-butyl N-[(10R,14S)-5-methoxy-10-methyl-9-oxo-8,16-diazatricyclo[13.3.1.0$^{2,7}$]nonadeca-1(19),2(7),3,5,15,17-hexaen-14-yl]carbamate. MS(ESI) m/z: 616.2 (M+H)$^+$. $^1$H NMR (400 MHz, CD$_3$OD) δ 8.87 (s, 1H), 8.67 (d, J=5.3 Hz, 1H), 8.38 (s, 1H), 7.91 (d, J=2.2 Hz, 1H), 7.84 (d, J=0.9 Hz, 1H), 7.80-7.73 (m, 1H), 7.70-7.64 (m, 1H), 7.58 (d, J=8.8 Hz, 1H), 7.54 (dd, J=5.3, 1.5 Hz, 1H), 7.07 (dd, J=8.6, 2.6 Hz, 1H), 6.86 (d, J=2.6 Hz, 1H), 6.39 (d, J=0.4 Hz, 1H), 5.97 (dd, J=12.5, 4.8 Hz, 1H), 3.90 (s, 3H), 2.77-2.66 (m, 1H), 2.38-2.26 (m, 1H), 2.14-1.96 (m, 2H), 1.62-1.47 (m, 2H), 1.00 (d, J=6.8 Hz, 3H), 0.71 (br. s., 1H). Analytical HPLC (Method A) RT=9.46 min, 98% purity; Factor XIa Ki=5.1 nM, Plasma Kallikrein Ki=190 nM.

EXAMPLE 85

Preparation of (10R,14S)-14-{4-[5-chloro-2-(4-chloro-1H-1,2,3-triazol-1-yl)phenyl]-6-oxo-1,6-dihydropyrimidin-1-yl}-5-hydroxy-10-methyl-8,16-diazatricyclo[13.3.1.0$^{2,7}$]nonadeca-1(19),2(7),3,5,15,17-hexaen-9-one trifluoroacetate

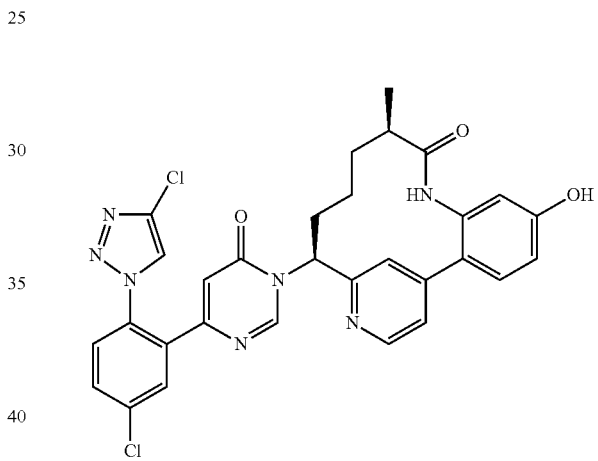

To a solution of (10R,14S)-14-{4-[5-Chloro-2-(4-chloro-1H-1,2,3-triazol-1-yl)phenyl]-6-oxo-1,6-dihydropyrimidin-1-yl}-5-methoxy-10-methyl-8,16-diazatricyclo [13.3.1.0$^{2,7}$] nonadeca-1(19),2(7),3,5,15,17-hexaen-9-one trifluoroacetate (0.029 g, 0.040 mmol) in CH$_2$Cl$_2$ (1 mL) was added BBr$_3$ (0.008 ml, 0.079 mmol) at 0° C. The reaction was allowed to warm to rt and stirred at rt for 16 h. The reaction mixture was quenched with MeOH, reverse phase chromatography purification to afford (10R,14S)-14-{4-[5-chloro-2-(4-chloro-1H-1,2,3-triazol-1-yl)phenyl]-6-oxo-1,6-dihydropyrimidin-1-yl}-5-methoxy-10-methyl-8,16-diazatricyclo[13.3.1.0$^{2,7}$]nonadeca-1(19),2(7),3,5,15,17-hexaen-9-one trifluoroacetate (0.0091 g, 32%) as a pale yellow solid. MS(ESI) m/z: 602.3 (M+H)$^+$. $^1$H NMR (400 MHz, CD$_3$OD) δ 8.81 (s, 1H), 8.65 (d, J=5.5 Hz, 1H), 8.37 (s, 1H), 7.89 (dd, J=3.7, 1.8 Hz, 2H), 7.79-7.73 (m, 1H), 7.69-7.63 (m, 1H), 7.57 (dd, J=5.4, 1.7 Hz, 1H), 7.49 (d, J=8.4 Hz, 1H), 6.91 (dd, J=8.5, 2.5 Hz, 1H), 6.73 (d, J=2.4 Hz, 1H), 6.39 (s, 1H), 5.93 (dd, J=12.5, 4.6 Hz, 1H), 2.76-2.67 (m, 1H), 2.34 (tt, J=12.7, 3.9 Hz, 1H), 2.15-1.94 (m, 2H), 1.63-1.46 (m, 2H), 1.00 (d, J=7.0 Hz, 3H), 0.74 (br. s., 1H). Analytical HPLC (Method A) RT=7.44 min, 99% purity; Factor XIa Ki=0.1 nM, Plasma Kallikrein Ki=6 nM.

EXAMPLE 86

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-5-(2-hydroxypropan-2-yl)-10-methyl-8,16-diazatricyclo[13.3.1.0^{2,7}]nonadeca-1(19),2(7),3,5,15,17-hexaen-9-one

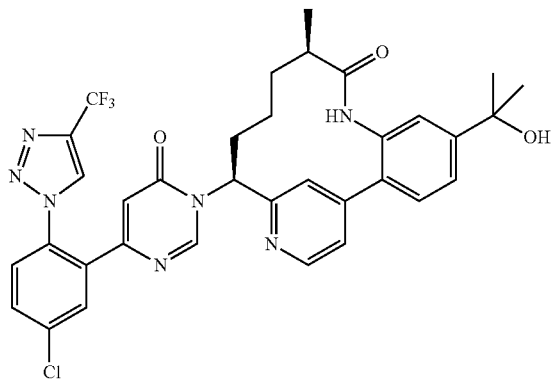 [SMILES: C[C@@H]1CCC[C@H](n2cnc(-c3cc(Cl)ccc3-n3cc(C(F)(F)F)nn3)cc2=O)c2cc(ccn2)-c2ccc(C(C)(C)O)cc2NC1=O]

86A. Preparation of tert-butyl N-[(10R,14S)-5-(2-hydroxypropan-2-yl)-10-methyl-9-oxo-8,16-diazatricyclo[13.3.1.0^{2,7}]nonadeca-1(19),2(7),3,5,15,17-hexaen-14-yl]carbamate To a solution of methyl (10R,14S)-14-{[(tert-butoxy)carbonyl]amino}-10-methyl -9-oxo-8,16-diazatricyclo[13.3.1.0^{2,7}]nonadeca-1(19),2,4,6,15,17-hexaene-5-carboxylate, prepared in Example 41D (20 mg, 0.044 mmol) in THF (1470 μA) at 0° C., was added 3 M MeMgBr in Et$_2$O (588 μl, 1.76 mmol). The mixture was slowly warmed to rt and stirred at for 3 days. The reaction mixture was quenched with addition of sat NH$_4$Cl and the solution was extracted EtOAc (2 ×). The organic phase was washed with brine, dried over MgSO$_4$, filtered and concentrated. The residue was purified by reverse phase -chromatography purification to give tert-butyl N-[(10R,14S)-5-(2-hydroxypropan-2-yl)-10-methyl-9-oxo-8,16-diazatricyclo[13.3.1.0^{2,7}]nonadeca-1(19),2(7),3,5,15,17-hexaen -14-yl]carbamate (9.3 mg, 37.2% yield) as a colorless solid. MS(ESI) m/z: 454.2 (M+H)$^+$.

86B. Preparation of (10R,14S)-14-amino-5-(2-hydroxypropan-2-yl)-10-methyl-8,16-diazatricyclo[13.3.1.0^{2,7}]nonadeca-1(19),2(7),3 ,5,15,17-hexaen-9-one To a clear colorless solution of tert-butyl N-[(10R,14S)-5-(2-hydroxypropan-2-yl)-10-methyl-9-oxo-8,16-diazatricyclo[13.3.1.0^{2,7}]nonadeca-1(19),2(7),3,5,15,17-hexaen-14-yl]carbamate (9.3 mg, 0.016 mmol) in DCM (1 mL) was added TFA (0.063 mL, 0.819 mmol). The reaction was stirred at rt for 2 h. Reaction mixture was then concentrated. The residue was redissolved in MeOH, passed through a NaHCO$_3$ cartridge, solvents were removed to give (10R,14S)-14-amino-5-(2-hydroxypropan-2-yl) -10-methyl-8,16-diazatricyclo[13.3.1.0^{2,7}]nonadeca-1(19),2(7),3,5,15,17-hexaen-9-one (6 mg, 100%) as a white solid. MS(ESI) m/z: 354.3 (M+H)$^+$.

86C. Preparation of (10R,14S)-14-(4-{5-chloro-2-[4-(trifluoromethyl)-1H-1,2,3-triazol -1-yl]phenyl}-6-oxo-1,6-dihydropyrimidin-1-yl)-5-(2-hydroxypropan-2-yl)-10-methyl -8,16-diazatricyclo[13.3.1.0^{2,7}]nonadeca-1(19),2(7),3,5,15,17-hexaen-9-one (10R,14S)-14-(4-{5 -Chloro-2-[4-(trifluoromethyl)-1H-1,2,3 -triazol-1-yl]phenyl}-6-oxo-1,6-dihydropyrimidin-1-yl)-5-(2-hydroxypropan-2-yl)-10-methyl-8, 16-diazatricyclo[13.3.1.0^{2,7}]nonadeca-1(19),2(7),3,5,15,17-hexaen-9-one trifluoroacetate (7 mg, 54% yield) was prepared in a similar manner as the procedure described in Example 129 by using (10R,14S)-14-amino-5-(2-hydroxypropan-2-yl)-10-methyl-8,16-diazatricyclo[13.3.1.0^{2,7}]nonadeca-1(19),2(7),3,5,15,17-hexaen-9-one (5.7 mg, 0.016 mmol and 6-{5-chloro-2-[4-(trifluoromethyl)-1H-1,2,3-triazol-1-yl]phenyl}pyrimidin-4-ol (5.5 mg, 0.016 mmol), prepared as described in Example 15. MS(ESI) m/z: 678.2 (M+H)$^+$. $^1$H NMR (400 MHz, CD$_3$OD) δ 8.84-8.79 (m, 2H), 8.65 (d, J=5.3 Hz, 1H), 7.89 (d, J=2.2 Hz, 1H), 7.83 (s, 1H), 7.77-7.73 (m, 1H), 7.70-7.66 (m, 1H), 7.58 (d, J=1.1 Hz, 2H), 7.54 (dd, J=5.3, 1.5 Hz, 1H), 7.40 (s, 1H), 6.43 (s, 1H), 5.95 (dd, J=12.5, 4.8 Hz, 1H), 2.68 (br. s., 1H), 2.32-2.20 (m, 1H), 2.09-1.94 (m, 2H), 1.57 (s, 6H), 1.54-1.43 (m, 2H), 0.97 (d, J=6.8 Hz, 3H), 0.69 (br. s., 1H). Analytical HPLC (Method A): RT=8.94 min, purity=100.0%; Factor XIa Ki=0.66 nM, Plasma Kallikrein Ki=28 nM.

EXAMPLE 87

Preparation of (10R,14S)-14-{4-[5-chloro-2-(5-fluoropyridin-3-yl)phenyl]-6-oxo-1,6-dihydropyrimidin-1-yl}-10-methyl-9-oxo-8,16-diazatricyclo[13.3.1.0^{2,7}]nonadeca -1(19),2(7),3,5,15,17-hexaene-5-carbonitrile

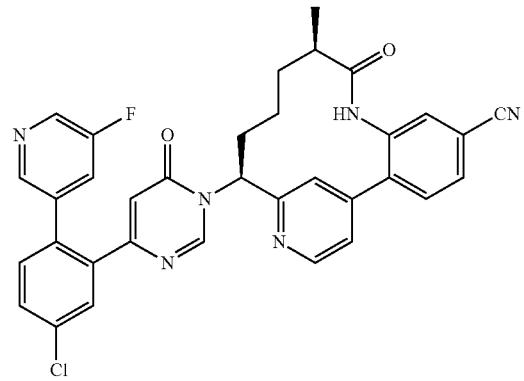 [SMILES: C[C@@H]1CCC[C@H](n2cnc(-c3cc(Cl)ccc3-c3cncc(F)c3)cc2=O)c2cc(ccn2)-c2ccc(C#N)cc2NC1=O]

87A. Preparation of 4-(2-bromo-5-chlorophenyl)-6-methoxypyrimidine

To a suspension of 4-chloro-2-(6-methoxypyrimidin-4-yl) aniline (2 g, 8.49 mmol) and p-toluenesulfonic acid monohydrate (1.937 g, 10.18 mmol) in ACN (424 ml) was added CuBr$_2$ (0.190 g, 0.849 mmol). t-Butyl nitrite (1.346 ml, 10.18 mmol) was added followed by tetrabutylammonium bromide (5.47 g, 16.97 mmol). The solution was stirred at rt for 2 h. The mixture was partitioned between DCM and water and the layers were separated. The organic layer was washed with brine, dried with MgSO$_4$, filtered, and concentrated. Purification by normal phase chromatography gave 4-(2-bromo-5-chlorophenyl)-6-methoxypyrimidine (2.0g, 76% yield) as a yellow solid. MS(ESI) m/z: 299.0 (M+H)$^+$. $^1$H NMR (400 MHz, CDCl$_3$) δ 8.88 (d, J=1.1 Hz, 1H), 7.61 (d, J=8.6 Hz, 1H), 7.56 (d, J=2.6 Hz, 1H), 7.30-7.23 (m, 1H), 7.04 (d, J=1.3 Hz, 1H), 4.05 (s, 3H).

87B. Preparation of 4-(5-chloro-2-(5-fluoropyridin-3-yl) phenyl)-6-methoxypyrimidine (5-Fluoropyridin-3-yl)boronic acid (56.4 mg, 0.401 mmol), and Na$_2$CO$_3$ (53.1 mg, 0.501 mmol) were combined in dioxane (2 mL) and water (0.75 mL). The suspension was purged with Ar then Pd(PPH$_3$)$_4$ (38.6 mg, 0.033 mmol), [1,1'-biphenyl]-2-yldicyclohexylphosphine (47 mg, 0.134 mmol) and 4-(2-bromo-5-chlorophenyl)-6-methoxypyrimidine (100 mg, 0.334 mmol) were added. The mixture was heated at 90° C. overnight. The reaction was cooled to rt and partitioned between EtOAc and water and the layers were separated. The organic layer was washed with brine and concentrated. Purification by normal phase chromatography afforded 4-(5-chloro-2-(5-fluoropyridin-3-yl)phenyl)-6-methoxypyrimidine (20 mg, 19% yield) as an orange solid. MS(ESI) m/z: 316.2 (M+H)$^+$. $^1$H NMR (400 MHz, CDCl$_3$) δ 8.70 (d, J=0.9 Hz, 1H), 8.40 (br. s., 1H), 8.20 (s, 1H), 7.68 (d, J=2.2 Hz, 1H), 7.53 (dd, J=8.4, 2.2 Hz, 1H), 7.36 (d, J=8.1 Hz, 1H), 7.31-7.16 (m, 1H), 6.48 (d, J=1.1 Hz, 1H), 3.95 (s, 3H).

87C. Preparation of 6-(5-chloro-2-(5-fluoropyridin-3-yl)phenyl)pyrimidin-4-ol 6-(5-Chloro-2-(5-fluoropyridin-3-yl)phenyl)pyrimidin-4-ol (20 mg, 105% yield) was prepared according to the procedure described in Example 15B for the preparation of 6-{5-chloro-2-[4-(trifluoromethyl)-1H-1,2,3-triazol-1-yl]phenyl}pyrimidin-4-ol by replacing 4-{5-chloro-2-[4-(trifluoromethyl)-1H-1,2,3-triazol-1-yl]phenyl}-6-methoxypyrimidine with 4-(5-chloro-2-(5-fluoropyridin-3-yl)phenyl)-6-methoxypyrimidine. MS(ESI) m/z: 302.1 (M+H)$^+$. $^1$H NMR (400 MHz, CD$_3$OD) δ 8.42 (br. s., 1H), 8.29-8.18 (m, 1H), 8.08 (s, 1H), 7.70 (d, J=2.0 Hz, 1H), 7.64-7.58 (m, 2H), 7.50 (d, J=8.4 Hz, 1H), 6.35 (s, 1H).

87D. Preparation of (10R,14S)-14-{4-[5-chloro-2-(5-fluoropyridin-3-yl)phenyl]-6-oxo -1,6-dihydropyrimidin-1-yl}4-10-methyl-9-oxo-8,16-diazatricyclo[13.3.1.0$^{2,7}$]nonadeca-1(19),2(7),3,5,15,17-hexaene-5-carbonitrile bis-trifluoroacetate (10R,14S)-14-{4-[5-Chloro-2-(5-fluoropyridin-3-yl)phenyl]-6-oxo-1,6-dihydropyrimidin-1-yl}-10-methyl-9-oxo-8,16-diazatricyclo[13.3.1.0$^{2,7}$]nonadeca -1(19),2(7),3,5,15,17-hexaene-5-carbonitrile bis-trifluoroacetate (10 mg, 38% yield) was prepared in a similar manner as the procedure described in Example 129, by using 6-(5-chloro-2-(5-fluoropyridin-3-yl)phenyl)pyrimidin-4-ol, prepared as described in Example 87C, and with (10R,14S)-14-amino-10-methyl-9-oxo-8,16-diazatricyclo[13.3.1.0$^{2,7}$]nonadeca-1(19),2,4,6,15,17-hexaene-5-carbonitrile, prepared as described in Example 37. MS(ESI) m/z: 605.3 (M+H)$^+$. $^1$H NMR (400 MHz, CD$_3$OD) δ 8.97 (s, 1H), 8.69 (d, J=5.1 Hz, 1H), 8.44 (d, J=2.6 Hz, 1H), 8.26 (s, 1H), 7.82-7.78 (m, 1H), 7.77 (s, 1H), 7.75-7.73 (m, 1H), 7.71 (s, 1H), 7.66-7.60 (m, 3H), 7.51 (d, J=8.1 Hz, 1H), 7.46 (dd, J=5.1, 1.8 Hz, 1H), 6.35 (d, J=0.7 Hz, 1H), 5.99 (dd, J=12.4, 4.7 Hz, 1H), 2.71-2.62 (m, 1H), 2.26-2.15 (m, 1H), 2.07-1.87 (m, 2H), 1.57-1.34 (m, 2H), 0.95 (d, J=6.8 Hz, 3H), 0.66 (m., 1H). Analytical HPLC (Method A): RT=8.21 min, purity=99%. Factor XIa Ki=90 nM, Plasma Kallikrein Ki=4,400 nM.

EXAMPLE 88

Preparation of (10R,14S)-14-{4-[5-chloro-2-(4-chloro-1H-1,2,3-triazol-1-yl)phenyl]-6-oxo-1,6-dihydropyrimidin-1-yl}-5 -(1,1-difluoro-2-hydroxyethyl)-10-methyl-8,16-diazatricyclo[13.3.1.0$^{2,7}$] nonadeca-1(19),2(7),3,5,15,17-hexaen-9-one

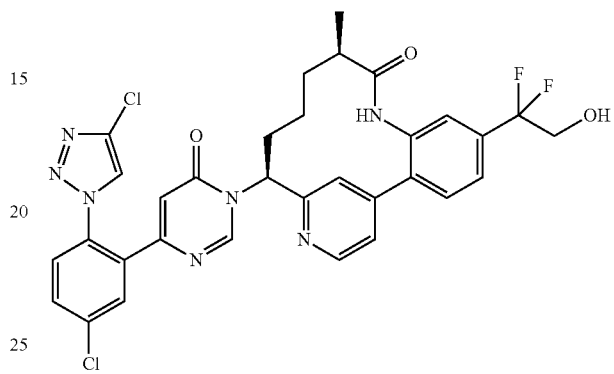

88A. Preparation of ethyl 2-[(10R,14S)-14-{[(tert-butoxy)carbonyl]amino}-10-methyl-9-oxo-8,16-diazatricyclo [13.3.1.0$^{2,7}$]nonadeca-1(19),2(7),3,5,15,17-hexaen-5-yl]-2,2-difluoroacetate trifluoroacetate

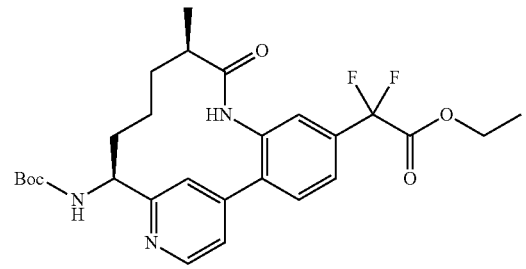 [SMILES: CCOC(=O)C(F)(F)c1ccc2c(c1)NC(=O)[C@H](C)CCC[C@H](NC(=O)OC(C)(C)C)c1cc-2ccn1]

A solution of ethyl 2-bromo-2,2-difluoroacetate (0.046 g, 0.227 mmol), Cu (0.014 g, 0.227 mmol), CuI (0.0086 g, 0.045 mmol) in Ar degassed DMSO (1 mL) was purged and refilled with Ar (3 ×). The reaction vessel was sealed and heated at 55° C. for 10 min. After this time, tert-butyl N-[(10R,14S)-5-iodo-10-methyl-9-oxo-8,16-diazatricyclo [13.3.1.0$^{2,7}$]nonadeca-1(19),2(7),3 ,5,15,17-hexaen-14-yl] carbamate (0.0473 g, 0.091 mmol) in 0.5 ml Ar degassed DMSO was added, and the reaction was heated at 55° C. for 16 h. The reaction mixture was cooled to rt then filtered to collect the crude material as a solid which was then purified by reverse phase chromatography to afford ethyl 2-[(10R,14 S)-14-{[(tert-butoxy)carbonyl]amino}-10-methyl-9-oxo-8,16-diazatricyclo [13 .3 .1.0$^{2,7}$]nonadeca-1(19),2(7),3 ,5,15,17-hexaen-5-yl] -2,2-difluoroacetate trifluoroacetate (0.012 g, 21%) as a white solid. MS(ESI) m/z: 518.4 (M+H)$^+$.

88B. Preparation of tert-butyl N- [(10R,14 S)-5 -(1,1-difluoro-2-hydroxyethyl)-10-methyl -9-oxo-8,16-diazatricyclo [13.3.1.0$^{2,7}$]nonadeca-1(19),2(7),3,5,15,17-hexaen-14-yl] carbamate trifluoroacetate

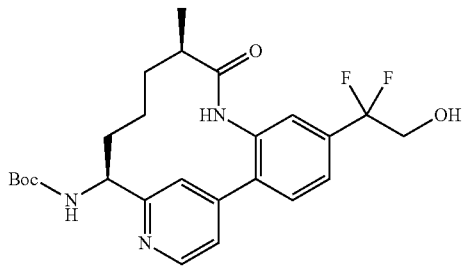 [SMILES: C[C@@H]1CCC[C@H](NC(=O)OC(C)(C)C)c2cc(ccn2)-c2ccc(C(F)(F)CO)cc2NC1=O]

To a solution of ethyl 2-[(10R,14S)-14-{[(tert-butoxy) carbonyl]amino}-10-methyl-9-oxo-8,16-diazatricyclo [13.3.1.0$^{2,7}$]nonadeca-1(19),2(7),3,5,15,17-hexaen-5-yl]-2, 2-difluoroacetate trifluoroacetate (0.012 g, 0.019 mmol) in EtOH (0.5 mL) was added NaBH$_4$ (0.0036 g, 0.095 mmol), and the reaction mixture stirred at rt. After 30 min, reaction mixture was added a drop of 1.25 M HCl in MeOH, purification by reverse phase chromatography to afford tert-butyl N-[(10R,14S)-5-(1,1-difluoro-2-hydroxyethyl)-10-methyl-9-oxo-8,16-diazatricyclo[13.3.1.0$^{2,7}$]nonadeca -1(19),2(7),3,5,15,17-hexaen-14-yl]carbamate trifluoroacetate (0.008 g, 71%) as a white solid. MS(ESI) m/z: 476.4 (M+H)$^+$.

88C. Preparation of (10R,14S)-14-{4-[5-chloro-2-(4-chloro-1H-1,2,3-triazol-1-yl)phenyl]-6-oxo-1,6-dihydropyrimidin-1-yl}-5-(1,1-difluoro-2-hydroxyethyl)-10-methyl-8,16-diazatricyclo[13.3.1.0$^{2,7}$]nonadeca-1(19),2(7),3,5,15, 17-hexaen-9-one trifluoroacetate (10R,14S)-14-{4-[5-Chloro-2-(4-chloro-1H-1,2,3-triazol-1-yl)phenyl]-6-oxo-1,6-dihydropyrimidin-1-yl}-5 -(1, 1-difluoro-2-hydroxyethyl)-10-methyl-8,16-diazatricyclo [13.3.1.0$^{2,7}$]nonadeca-1(19),2(7),3,5,15,17-hexaen-9-one trifluoroacetate (0.0051 g, 46%) was prepared in a similar manner as the procedure described in Example 79, by replacing tert-butyl N-[(10R,14S)-5,10-dimethyl-9-oxo-8, 16-diazatricyclo[13.3.1.0$^{2,7}$]nonadeca 1(19),2,4,6,15,17-hexaen-14-yl]carbamate, with tert-butyl N-[(10R,14S)-5-(1, 1-difluoro -2-hydroxyethyl)-10-methyl-9-oxo-8,16-diazatricyclo[13.3.1.0$^{2,7}$]nonadeca -1(19),2(7),3,5,15,17-hexaen-14-yl]carbamate trifluoroacetate. MS(ESI) m/z: 666.2 (M+H)$^+$. $^1$H NMR (400MHz, CD$_3$OD) δ 8.88 (s, 1H), 8.77 (d, J=5.5 Hz, 1H), 8.39 (s, 1H), 7.96-7.89 (m, 2H), 7.80-7.73 (m, 2H), 7.70-7.63 (m, 3H), 7.48 (d, J=1.3 Hz, 1H), 6.41 (s, 1H), 5.98 (dd, J=12.4, 4.7 Hz, 1H), 3.98 (t, J=13.2 Hz, 2H), 2.78-2.66 (m, 1H), 2.41-2.28 (m, 1H), 2.18-2.08 (m, 1H), 2.04-1.91 (m, 1H), 1.64-1.46 (m, 2H), 1.01 (d, J=6.8 Hz, 3H), 0.72 (br. s., 1H). Analytical HPLC (Method A) RT=8.15 min, 99% purity; Factor XIa Ki=5.4 nM, Plasma Kallikrein Ki=120 nM.

EXAMPLE 89

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-5-carbonitrile trifluoroacetate

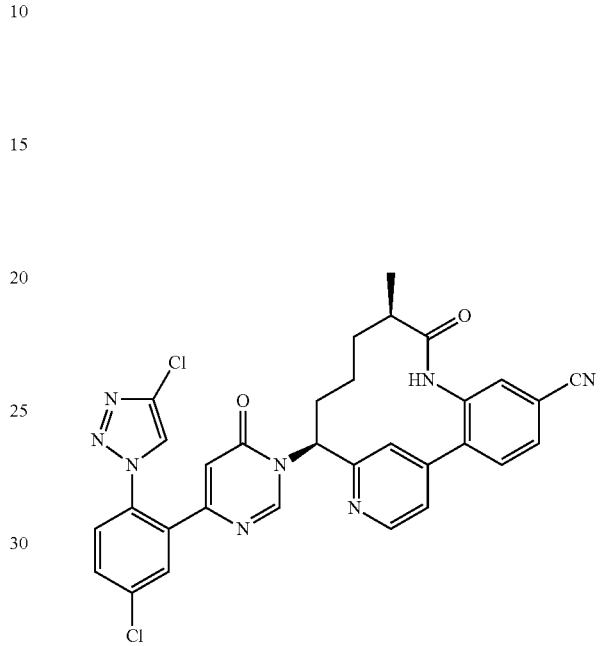

(10R,14S)-14-{4-[5-Chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7),3,5,15,17-hexaene-5-carbonitrile trifluoroacetate (3.81 mg, 14% yield) was prepared in a similar manner as the procedure described in Example 114 by replacing (10R,14S)-14-amino-10-methyl-9-oxo-8,16-diazatricyclo [13.3.1.0$^{2,7}$]nonadeca -1(19),2(7),3,5,15,17-hexaene-4-carbonitrile with (10R,14 S)-14-amino-10-methyl-9-oxo -8,16-diazatricyclo[13.3.1.0$^{2,7}$]nonadeca-1(19),2(7),3 ,5,15,17-hexaene-5-carbonitrile, prepared as described in Example 30. MS(ESI) m/z: 611.2 (M+H)$^+$. $^1$H NMR (400MHz, CD$_3$OD) δ 8.94 (s, 1H), 8.75 (d, J=5.1 Hz, 1H), 8.36 (s, 1H), 7.89 (s, 1H), 7.85-7.71 (m, 4H), 7.66 (d, J=6.2 Hz, 2H), 7.55 (d, J=4.6 Hz, 1H), 6.37 (s, 1H), 6.00 (dd, J=12.5, 4.4 Hz, 1H), 2.76-2.63 (m, 1H), 2.32-2.20 (m, 1H), 2.13-1.88 (m, 2H), 1.60-1.38 (m, 2H), 0.97 (d, J=7.0 Hz, 3H), 0.66 (br. s., 1H). Analytical HPLC (Method A): RT=9.19 min, purity>99%; Factor XIa Ki=0.12 nM, Plasma Kallikrein Ki=8 nM.

EXAMPLE 90

Preparation of 2-[(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0²,⁷]nonadeca-1(19),2(7),3,5,15,17-hexaen-5-yl]-2,2-difluoroacetamide trifluoroacetate

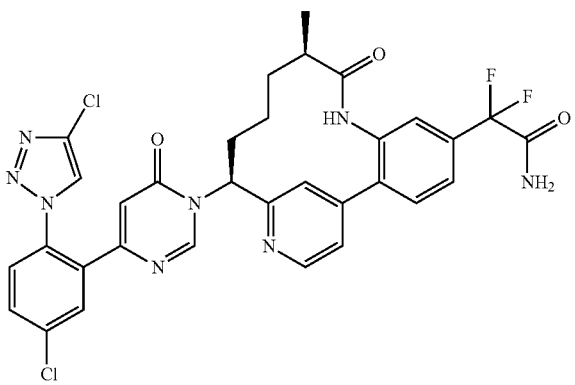 [SMILES: C[C@@H]1CCC[C@H](n2cnc(-c3cc(Cl)ccc3-n3cc(Cl)nn3)cc2=O)c2cc(ccn2)-c2ccc(C(F)(F)C(N)=O)cc2NC1=O]

90A. Preparation of tert-butyl N-[(10R,14S)-5-(carbamoyldifluoromethyl)-10-methyl-9-oxo-8,16-diazatricyclo[13.3.1.0²,⁷]nonadeca-1(19),2(7),3,5,15,17-hexaen-14-yl]carbamate trifluoroacetate

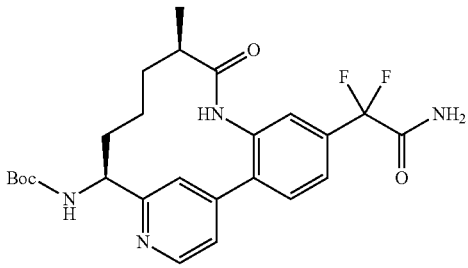 [SMILES: C[C@@H]1CCC[C@H](NC(=O)OC(C)(C)C)c2cc(ccn2)-c2ccc(C(F)(F)C(N)=O)cc2NC1=O]

A solution of 2-bromo-2,2-difluoroacetamide (0.083 g, 0.479 mmol), Cu (0.030 g, 0.479 mmol), CuI (0.018 g, 0.096 mmol) in DMSO (1 mL) was purged and backfilled with Ar (3 x). The reaction vessel was sealed and heated at 55° C. for 10 min. tert-Butyl N-[(10R,14S)-5-iodo-10-methyl-9-oxo-8,16-diazatricyclo[13.3.1.0²,⁷]nonadeca -1(19),2(7),3,5,15, 17-hexaen-14-yl]carbamate (0.050 g, 0.096 mmol) in 0.5 ml Ar degassed DMSO was added and the reaction vessel was sealed and heated at 55° C. for 16 h. The reaction mixture was cooled to rt and filtered. The collected solid was purified by reverse phase chromatography to afford tert-butyl N-[(10R,14S)-5-(carbamoyldifluoromethyl)-10-methyl-9-oxo-8,16-diazatricyclo[13.3.1.0²,⁷]nonadeca -1(19),2(7),3, 5,15,17-hexaen-14-yl]carbamate trifluoroacetate (8 mg, 14%) as a white solid. MS(ESI) m/z: 489.4 (M+H)⁺.

90B. Preparation of 2-[(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0²,⁷]nonadeca-1(19),2(7),3,5,15,17-hexaen-5-yl]-2, 2-difluoroacetamide trifluoroacetate 2-[(10R,14S)-14-{4-[5-Chloro-2-(4-chloro-1H-1,2,3-triazol-1-yl)phenyl]-6-oxo -1,6-dihydropyrimidin-1-yl}-10-methyl-9-oxo-8,16-diazatricyclo[13.3.1.0²,⁷]nonadeca -1(19),2(7),3,5,15,17-hexaen-5-yl]-2,2-difluoroacetamide trifluoroacetate (0.0025 g, 23%) was prepared in a similar manner as the procedure described in Example 79, by using tert-butyl N-[(10R,14S)-5-(carbamoyldifluoromethyl)-10-methyl-9-oxo-8,16-diazatricyclo[13.3.1.0²,⁷]nonadeca-1(19),2(7),3,5,15,17-hexaen-14-yl] carbamate. MS(ESI) m/z: 679.2 (M+H)⁺. ¹H NMR (400 MHz, CDCl₃) δ 8.95 (s, 1H), 8.75 (d, J=5.3 Hz, 1H), 8.38 (s, 1H), 7.92 (d, J=2.4 Hz, 1H), 7.84 (s, 1H), 7.81-7.73 (m, 3H), 7.70-7.64 (m, 1H), 7.60-7.55 (m, 2H), 6.40 (d, J0.9 =Hz, 1H), 6.02 (dd, J=12.5, 4.8 Hz, 1H), 2.78-2.66 (m, 1H), 2.35-2.22 (m, 1H), 2.14-1.92 (m, 2H), 1.63-1.42 (m, 2H), 1.00 (d, J=6.8 Hz, 3H), 0.71 (br. s., 1H). Analytical HPLC (Method A) RT=8.23 min, 95% purity; Factor XIa Ki=7.1 nM, Plasma Kallikrein Ki=260 nM.

EXAMPLE 91

Preparation of (10R,14S)-14-{4-[5-chloro-2-(4-chloro-1H-1,2,3-triazol-1-yl)phenyl]-6-oxo-1,6-dihydropyrimidin-1-yl}-5-ethynyl-10-methyl-8,16-diazatricyclo[13.3.1.0²,⁷]nonadeca-1(19),2(7),3,5,15, 17-hexaen-9-one

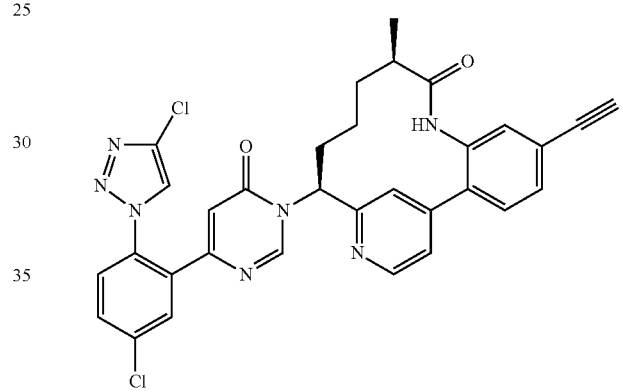

91A. Preparation of (10R,14S)-14-{4-[5-chloro-2-(4-chloro-1H-1,2,3 -triazol-1-yl)phenyl]-6-oxo-1,6-dihydropyrimidin-1-yl}-5-iodo-10-methyl-8,16-diazatricyclo[13.3.1.0²,⁷]nonadeca-1(19),2(7),3,5,15,17-hexaen-9-one trifluoroacetate

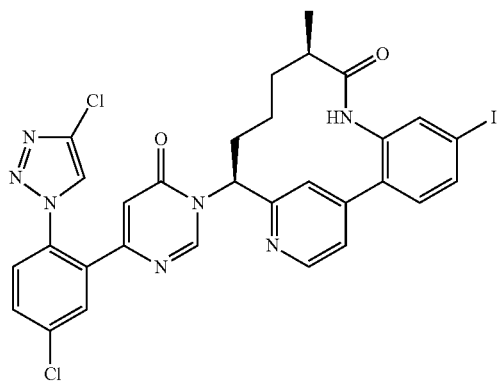 [SMILES: C[C@@H]1CCC[C@H](n2cnc(-c3cc(Cl)ccc3-n3cc(Cl)nn3)cc2=O)c2cc(ccn2)-c2ccc(I)cc2NC1=O]

(10R,14S)-14-{4-[5-Chloro-2-(4-chloro-1H-1,2,3-triazol-1-yl)phenyl]-6-oxo-1,6-dihydropyrimidin-1-yl}-5-iodo-10-methyl-8,16-diazatricyclo[13.3.1.0²,⁷]nonadeca -1(19),2(7),3,5,15,17-hexaen-9-one trifluoroacetate (0.013 g, 41%) was prepared in a similar manner as the procedure described in Example 79, by using tent-butyl N -[(10R,14S)-5-iodo-10-methyl-9-oxo-8,16-diazatricyclo[13.3.1.0$^{2,7}$] nonadeca -1(19),2(7),3,5,15,17-hexaen-14-yl]carbamate, prepared as described in Example 30B. MS(ESI) m/z: 712.2 (M+H)$^+$.

91B. Preparation of (10R,14S)-14-{4-[5-chloro-2-(4-chloro-1H-1,2,3-triazol-1-yl)phenyl]-6-oxo-1,6-dihydropyrimidin-1-yl}-5-ethynyl-10-methyl-8,16-diazatricyclo [13.3.1.0$^{2,7}$]nonadeca-1(19),2(7),3,5,15,17-hexaen-9-one trifluoroacetate (10R,14S)-14-{4-[5-Chloro-2-(4-chloro-1H-1,2,3-triazol-1-yl)phenyl]-6-oxo-1,6-dihydropyrimidin-1-yl}-5-iodo-10-methyl-8,16-diazatricyclo[13.3.1.0$^{2,7}$]nonadeca -1(19),2(7),3,5,15,17-hexaen-9-one (0.007 g, 9.83 μmol), CuI (0.001 g, 4.91 μmol), Pd(PPh$_3$)$_2$Cl$_2$ (0.0003 g, 0.491 μmol) in DMF (1 mL) was added Et$_3$N (0.004 ml, 0.029 mmol), followed by ethynyltrimethylsilane (0.003 g, 0.029 mmol), and then was stirred at rt for 5 h. KF (0.010 g, 0.172 mmol) was added to the reaction mixture and stirring was continued at rt for 16 h. The reaction mixture was filtered to collect the crude product which was purified by reverse phase chromatography to afford (10R,14S)-14-{4-[5-chloro-2-(4-chloro-1H-1,2,3-triazol-1-yl)phenyl]-6-oxo-1,6-dihydropyrimidin-1-yl}-5-ethynyl-10-methyl-8,16-diazatricyclo[13.3.1.0$^{2,7}$]nonadeca-1(19),2(7),3,5,15,17-hexaen -9-one trifluoroacetate (0.0052 g, 72%) as a white solid. MS(ESI) m/z: 610.1 (M+H)$^+$. $^1$H NMR (400 MHz, CD$_3$OD) δ 8.97 (s, 1H), 8.70 (d, J=5.1 Hz, 1H), 8.37 (s, 1H), 7.91 (d, J=2.4 Hz, 1H), 7.80-7.73 (m, 2H), 7.70-7.55 (m, 3H), 7.50-7.46 (m, 1H), 7.40-7.36 (m, 1H), 6.38 (s, 1H), 6.03 (dd, J=12.3, 4.4 Hz, 1H), 3.70 (s, 1H), 2.76-2.65 (m, 1H), 2.32-2.20 (m, 1H), 2.12-1.93 (m, 2H), 1.61-1.42 (m, 2H), 0.99 (d, J=7.0 Hz, 3H), 0.70 (br. s., 1H). Analytical HPLC (Method A) RT=8.67 min, 99% purity; Factor XIa Ki=8.9 nM, Plasma Kallikrein Ki=660 nM.

EXAMPLE 92

Preparation of (10R,14S)-14-(4-{5-chloro-2-[4-(trifluoromethyl)-1H-1,2,3-triazol-1-yl]phenyl}-6-oxo-1, 6-dihydropyrimidin-1-yl)-10-methyl-9-oxo-8,17-diazatricyclo[13.3.1.0$^{2,7}$]nonadeca-1(19),2(7),3,5,15, 17-hexaene-5-carbonitrile trifluoroacetate

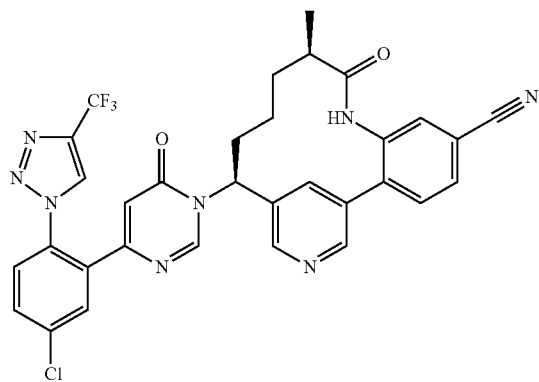 [SMILES: C[C@@H]1CCC[C@H](n2cnc(-c3cc(Cl)ccc3-n3cc(C(F)(F)F)nn3)cc2=O)c2cncc(c2)-c2ccc(C#N)cc2NC1=O]

92A. Preparation of tert-butyl N-[(1S)-1-[5-(2-amino-4-cyanophenyl)pyridin-3-yl]but-3-en-1l-yl]carbamate

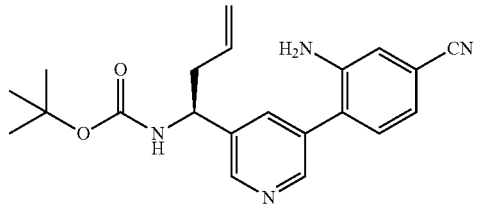 [SMILES: C=CC[C@H](NC(=O)OC(C)(C)C)c1cncc(-c2ccc(C#N)cc2N)c1]

To N-[(1S)-1-(5-bromopyridin-3-yl)but-3-en-1-yl]carbamate (0.8 g, 2.44 mmol), prepared as described in Example 26, and (2-amino-4-cyanophenyl)boronic acid hydrochloride (0.97 g, 4.89 mmol) in DMSO (25 ml) was added aq 3 M K$_3$PO$_4$ (3.2 ml, 9.78 mmol). The resulting solution was purged and refilled with Ar (3 ×), PdCl$_2$(dppf) -CH$_2$Cl$_2$Adduct (0.200 g, 0.244 mmol) was added, and the reaction mixture was purged and backfilled with Ar, capped and heated at 90° C. for 3 h. The reaction was cooled to rt and the reaction mixture was diluted with EtOAc, washed with water and brine, dried over MgSO$_4$, filtered and concentrated. Purification by normal phase chromatography afforded tert-butyl N-[(1S)-1-[5-(2-amino-4-cyanophenyl) pyridin-3-yl]but-3-en-1-yl]carbamate (0.8 g, 90%) as a pale yellow solid. MS(ESI) m/z: 365.2 (M+H)$^+$.

92B. Preparation of tert-butyl N-[(1S)-1-(5-{4-cyano-2-[(2R)-2-methylbut-3-enamido]phenyl}pyridin-3-yl)but-3-en-1-yl]carbamate

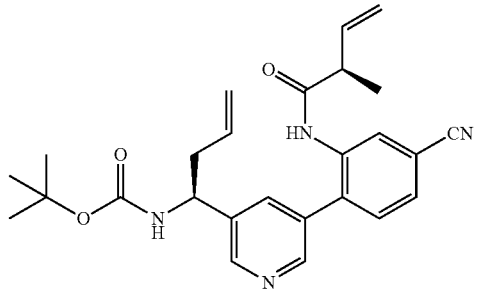 [SMILES: C=CC[C@H](NC(=O)OC(C)(C)C)c1cncc(-c2ccc(C#N)cc2NC(=O)[C@H](C)C=C)c1]

To a solution of (S)-tert-butyl (1-(5-(2-amino-4-cyanophenyl)pyridin-3-yl)but-3-en-1-yl)carbamate (0.8 g, 2.195 mmol) in EtOAc (10 mL) was added (R)-2-methylbut-3-enoic acid (0.330 g, 3.29 mmol), prepared as described in Example 2, and pyridine (0.53 mL, 6.59 mmol). The solution was cooled to 0° C. and T3P® (50% in EtOAc) (2.79 g, 4.39 mmol) was added. The solution was allowed to gradually warmed to rt and stirred at rt for 16 h. Reaction mixture was neutralized with sat aq NaHCO$_3$, extracted with EtOAc (3 ×). The combined EtOAc phase was washed with brine, dried over MgSO$_4$, purification with normal phase chromatography to afford tert-butyl ((S)-1-(5-(4-cyano-2-((R)-2-methylbut-3-enamido)phenyl)pyridin-3 -yl)but-3 -en-1-yl)carbamate(0.87 g, 89%). MS(ESI) m/z: 447.4 (M+H)$^+$.

92C. Preparation of tert-butyl N-[(10R,11E,14S)-5-cyano-10-methyl-9-oxo-8,17-diazatricyclo[13.3.1.0$^{2,7}$]nonadeca-1(19),2(7),3,5,11,15,17-heptaen-14-yl]carbamate

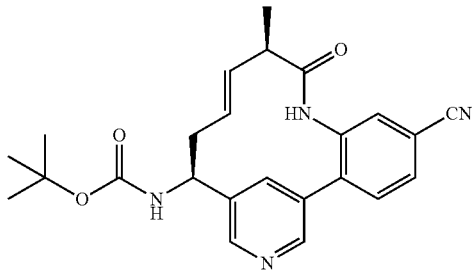 [SMILES: C[C@@H]1/C=C/C[C@H](NC(=O)OC(C)(C)C)c2cncc(c2)-c2ccc(C#N)cc2NC1=O]

tert-Butyl ((S)-1-(5-(4-cyano-2-((R)-2-methylbut-3-enamido)phenyl)pyridin-3-yl)but-3-en-1-yl)carbamate (0.87 g, 1.948 mmol) and pTsOH (0.389 g, 2.046 mmol) in CH$_2$Cl$_2$ (200 ml) was degassed with Ar, heated at 40 °C. under Ar for 30 min. After this time, Second Generation Grubbs Catalyst (0.662 g, 0.779 mmol) in 10 ml Ar degassed DCM was added and the reaction was heated at 40° C. for 16 h, then cooled to rt. The reaction mixture was neutralized with sat aq NaHCO$_3$. The DCM phase was separated and washed with brine, dried over MgSO$_4$, filtered and concentrated. Purification with normal phase chromatography gave tert-butyl N-[(10R,11E,14S)-5-cyano-10-methyl-9-oxo-8,17-diazatricyclo[13.3.1.0$^{2,7}$]nonadeca-1(19),2(7),3,5,11,15,17-heptaen-14-yl]carbamate (0.124 g, 15%) as a pale yellow solid. MS(ESI) m/z: 419.3 (M+H)$^+$.

92D. Preparation of tert-butyl N-[(10R,14S)-5-(aminomethyl)-10-methyl-9-oxo-8,17-diazatricyclo[13.3.1.0$^{2,7}$]nonadeca-1(19),2(7),3,5,15,17-hexaen-14-yl]carbamate trifluoroacetate

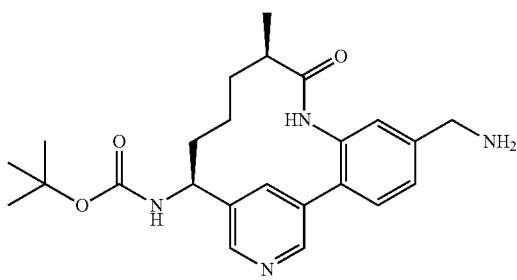 [SMILES: C[C@@H]1CCC[C@H](NC(=O)OC(C)(C)C)c2cncc(c2)-c2ccc(CN)cc2NC1=O]

To a solution of tert-butyl N-[(10R,11E,14S)-5-cyano-10-methyl-9-oxo-8,17-diazatricyclo[13.3.1.0$^{2,7}$]nonadeca-1(19),2(7),3,5,11,15,17-heptaen-14-yl]carbamate (0.124 g, 0.296 mmol) in EtOH (5 mL), under Ar was added PtO$_2$ (0.027 g, 0.119 mmol). The solution was purged and backfilled with H$_2$ (3 ×), then stirred at rt under balloon H$_2$. After 2 h, 4 ml DMSO was added to the reaction mixture and the suspension was filtered under Ar. Purification with reverse chromatography afforded tert-butyl N-[(10R,14S)-5-(aminomethyl)-10-methyl-9-oxo-8,17-diazatricyclo [13.3.1.0$^{2,7}$]nonadeca-1(19),2(7),3,5,15,17-hexaen-14-yl]carbamate trifluoroacetate (0.123 g, 64%) as a white solid. MS(ESI) m/z: 425.4 (M+H)$^+$.

92E. Preparation of tert-butyl N-[(10R,14S)-5-cyano-10-methyl-9-oxo-8,17-diazatricyclo[13.3.1.0$^{2,7}$]nonadeca-1(19),2(7),3,5,15,17-hexaen-14-yl]carbamate trifluoroacetate

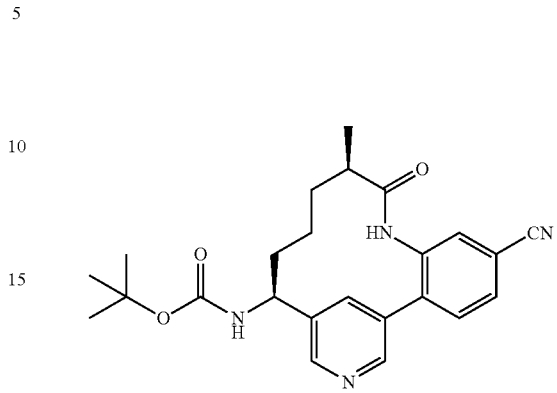

To a solution of tert-butyl N-[(10R,14S)-5-(aminomethyl)-10-methyl-9-oxo-8,17-diazatricyclo[13.3.1.0$^{2,7}$]nonadeca-1(19),2(7),3,5,15,17-hexaen-14-yl]carbamate trifluoroacetate (76 mg, 0.116 mmol) in CH$_2$Cl$_2$ (2 mL) was added Et$_3$N (0.049 mL, 0.349 mmol), followed by Dess-Martin reagents (198 mg, 0.466 mmol). The solution was stirred at rt. After 1 h the reaction was quenched with aq Na$_2$S$_2$O$_3$ and sat aq NaHCO$_3$, extracted with 10% MeOH in DCM, dried over MgSO$_4$, filtered and concentrated. Purification with normal phase chromatography, followed by reverse phase chromatography afforded tert-butyl N-[(10R,14S)-5-cyano-10-methyl-9-oxo-8,17-diazatricyclo[13.3.1.0$^{2,7}$]nonadeca-1(19),2(7),3,5,15,17-hexaen-14-yl]carbamate trifluoroacetate (14 mg, 22%) as a white solid.

92F. Preparation of (10R,14S)-14-(4-{5-chloro-2-[4-(trifluoromethyl)-1H-1,2,3-triazol -1-yl]phenyl}-6-oxo-1,6-dihydropyrimidin-1-yl)-10-methyl-9-oxo-8,17-diazatricyclo [13.3.1.0$^{2,7}$]nonadeca-1(19),2(7),3,5,15,17-hexaene-5-carbonitrile trifluoroacetate (10R,14S)-14-(4-{5-Chloro-2-[4-(trifluoromethyl)-1H-1,2,3-triazol-1-yl]phenyl}-6-oxo-1,6-dihydropyrimidin-1-yl)-10-methyl-9-oxo-8,17-diazatricyclo[13.3.1.0$^{2,7}$]nonadeca-1(19),2(7),3,5,15,17-hexaene-5-carbonitrile trifluoroacetate (0.0067 g, 34% over 2 steps) was prepared in a similar manner as the procedure described in Example 78B, by using tert-butyl N-[(10R,14S)-5-cyano-10-methyl-9-oxo-8,17-diazatricyclo [13.3.1.0$^{2,7}$]nonadeca-1(19),2(7),3,5,15,17-hexaen-14-yl] carbamate trifluoroacetate. MS(ESI) m/z: 645.2 (M+H)$^+$. $^1$H NMR (400 MHz, CD$_3$OD) δ 8.86 (d, J=0.7 Hz, 1H), 8.83 (d, J=1.5 Hz, 1H), 8.68 (d, J=1.8 Hz, 1H), 8.49 (s, 1H), 8.45 (s, 1H), 7.92-7.85 (m, 3H), 7.80-7.75 (m, 2H), 7.72-7.68 (m, 1H), 6.47 (s, 1H), 5.75 (dd, J=13.0, 4.0 Hz, 1H), 2.56-2.44 (m, 2H), 2.27-2.16 (m, 1H), 1.90-1.78 (m, 1H), 1.57-1.40 (m, 2H), 1.30-1.17 (m, 1H), 1.13 (d, J=7.0 Hz, 3H). Analytical HPLC (Method A) RT=7.79 min, 100% purity; Factor XIa Ki=0.24 nM, Plasma Kallikrein Ki=24 nM.

EXAMPLE 93

Preparation of (10R,14S)-14-{4-[5-chloro-2-(4-chloro-1H-1,2,3-triazol-1-yl)phenyl]-6-oxo-1,6-dihydropyrimidin-1-yl}-5-(difluoromethoxy)-10-methyl-8,16-diazatricyclo [13.3.1.0$^{2,7}$]nonadeca-1(19),2(7),3,5,15,17-hexaen-9-one trifluoroacetate

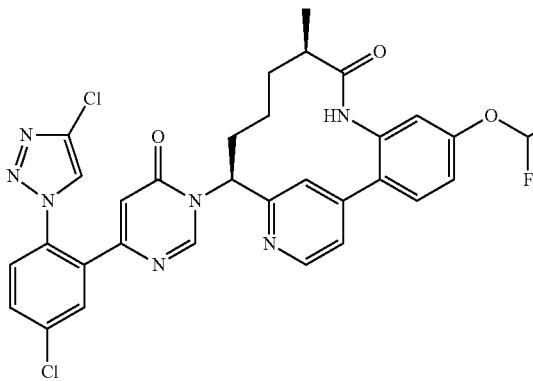

93A. Preparation of tert-butyl N-[(10R,14S)-5-hydroxy-10-methyl-9-oxo-8,16-diazatricyclo[13.3.1.0$^{2,7}$]nonadeca-1(19),2(7),3,5,15,17-hexaen-14-yl]carbamate

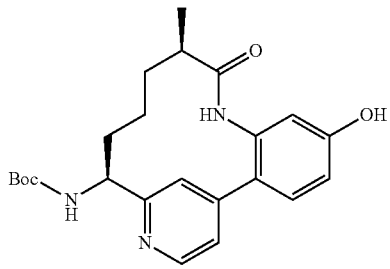

A solution of tert-butyl N-[(10R,14S)-5-iodo-10-methyl-9-oxo-8,16-diazatricyclo [13.3.1.0$^{2,7}$]nonadeca-1(19),2(7),3,5,15,17-hexaen-14-yl]carbamate (346 mg, 0.664 mmol), prepared as described in Example 30B, quinolin-8-ol (38.5 mg, 0.265 mmol), CuI (25 mg, 0.133 mmol), KOH (223 mg, 3.98 mmol) in water (2.2 ml) and DMSO (2.2 ml) was heated at 100° C. for 16 h, then cooled to rt. (Boc)$_2$O (218 mg, 1 mmol) and 1 ml THF was added to the reaction mixture and stirred at rt for 4 h. The reaction mixture was diluted with EtOAc, washed with water and brine, concentrated and purified with normal phase chromatography to afford tert-butyl N-[(10R,14S)-5-hydroxy-10-methyl-9-oxo-8,16-diazatricyclo[13.3.1.0$^{2,7}$]nonadeca-1(19),2(7),3,5,15,17-hexaen-14-yl]carbamate (120 mg, 44%) as a white solid. MS(ESI) m/z: 412.3 (M+H)$^+$.

93B. Preparation of tert-butyl N-[(10R,14S)-5-(difluoromethoxy)-10-methyl-9-oxo-8,16-diazatricyclo[13.3.1.0$^{2,7}$]nonadeca-1(19),2(7),3,5,15,17-hexaen-14-yl]carbamate trifluoroacetate

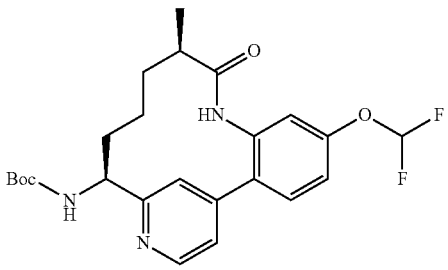 [SMILES: C[C@@H]1CCC[C@H](NC(=O)OC(C)(C)C)c2cc(ccn2)-c2ccc(OC(F)F)cc2NC1=O]

tert-Butyl N-[(10R,14S)-5-hydroxy-10-methyl-9-oxo-8,16-diazatricyclo [13.3.1.0$^{2,7}$]nonadeca-1(19),2(7),3,5,15,17-hexaen-14-yl]carbamate (33 mg, 0.080 mmol), C$_2$ClF$_2$NaO$_2$ (31 mg, 0.200 mmol), Cs$_2$CO$_3$ (52 mg, 0.160 mmol) in DMF (1 mL) was heated at 100° C. for 4 h, then cooled to rt. The reaction mixture was filtered and concentrated. The crude product was purified with reverse phase chromatography to afford tert-butyl N-[(10R,14S)-5-(difluoromethoxy)-10-methyl-9-oxo-8,16-diazatricyclo [13.3.1.0$^{2,7}$]nonadeca-1(19),2(7),3,5,15,17-hexaen-14-yl]carbamate trifluoroacetate (8 mg, 17%). MS(ESI) m/z: 462.1 (M+H)$^+$.

93C. Preparation of (10R,14S)-14-{4-[5-chloro-2-(4-chloro-1H-1,2,3-triazol-1-yl)phenyl]-6-oxo-1,6-dihydropyrimidin-1-yl}-5-(difluoromethoxy)-10-methyl-8,16-diazatricyclo[13.3.1.0$^{2,7}$]nonadeca-1(19),2(7),3,5,15,17-hexaen-9-one trifluoroacetate (10R,14S)-14-{4-[5-Chloro-2-(4-chloro-1H-1,2,3-triazol-1-yl)phenyl]-6-oxo-1,6-dihydropyrimidin-1-yl}-5-(difluoromethoxy)-10-methyl-8,16-diazatricyclo[13.3.1.0$^{2,7}$]nonadeca-1(19),2(7),3,5,15,17-hexaen-9-one trifluoroacetate (1.6 mg, 15% over 2 steps) was prepared in a similar manner as described in Example 79, by using tert-butyl N-[(10R,14S)-5-(difluoromethoxy)-10-methyl-9-oxo-8,16-diazatricyclo[13.3.1.0$^{2,7}$]nonadeca-1(19),2(7),3,5,15,17-hexaen-14-yl]carbamate trifluoroacetate. MS(ESI) m/z: 652.1. (M+H)$^+$. $^1$H NMR (400 MHz, CD$_3$OD) δ 8.89 (s, 1H), 8.68 (d, J=5.1 Hz, 1H), 8.37 (s, 1H), 7.93 (d, J=2.2 Hz, 1H), 7.81-7.74 (m, 1H), 7.73-7.64 (m, 2H), 7.60 (s, 1H), 7.41 (dd, J=5.1, 1.5 Hz, 1H), 7.32 (dd, J=8.5, 2.5 Hz, 1H), 7.19-6.76 (m, 2H), 6.40 (s, 1H), 6.02 (dd, J=12.4, 4.5 Hz, 1H), 2.41-2.28 (m, 1H), 2.26-2.13 (m, 1H), 2.12-2.02 (m, 1H), 1.96-1.82 (m, 1H), 1.61 (br. s., 1H), 1.45-1.32 (m, 1H), 1.28 (d, J=7.0 Hz, 3H), 1.08-0.90 (m, 1H). Analytical HPLC (Method A) RT=8.83 min, 100% purity; Factor XIa Ki=100 nM, Plasma Kallikrein Ki=4,000 nM.

EXAMPLE 94

Preparation of (10R,14S)-14-(4-{5-chloro-2-[4-(difluoromethyl)-1H-1,2,3-triazol-1-yl]phenyl}-6-oxo-1,6-dihydropyrimidin-1-yl)-10-methyl-8,16-diazatricyclo[13.3.1.0$^{2,7}$]nonadeca-1(19),2(7),3,5,15,17-hexaen-9-one

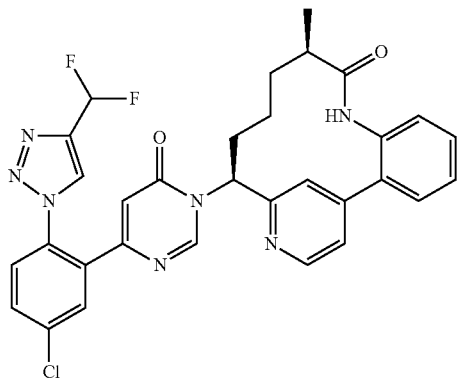 [SMILES: C[C@@H]1CCC[C@H](n2cnc(-c3cc(Cl)ccc3-n3cc(C(F)F)nn3)cc2=O)c2cc(ccn2)-c2ccccc2NC1=O]

(10R,14S)-14-(4-{5-Chloro-2[4-(difluoromethyl)-1H-1,2,3-triazol-1-yl]phenyl}-6-oxo-1,6-dihydropyrimidin-1-yl)-10-methyl-8,16-diazatricyclo[13.3.1.0$^{2,7}$]nonadeca -1(19),2(7),3,5,15,17-hexaen-9-one (0.0117 g, 32% yield) was prepared in a similar manner as the procedure described in Example 129, by using 6-{5-chloro-2-[4-(difluoromethyl)-1H-1,2,3-triazol-1-yl]phenyl}pyrimidin-4-ol, prepared as described in Example 16, and (10R,14S)-14-amino-10-methyl-8,16-diazatricyclo[13.3.1.0$^{2,7}$]nonadeca-1(19),2,4,6,15,17-hexaen-9-one, prepared as described in Example 29. MS(ESI) m/z: 602.1 (M+H)$^+$ and 604.1 (M+2+H)$^+$. $^1$H NMR (500 MHz, DMSO-d$_6$) δ 9.64 (s, 1H), 8.80 (s, 1H), 8.78-8.76 (m, 1H), 8.54 (d, J=5.0 Hz, 1H), 7.86 (d, J=2.5 Hz, 1H), 7.75 (dd, J=8.5, 2.5 Hz, 1H), 7.69 (d, J=8.5 Hz, 1H), 7.61 (s, 1H), 7.50 (dd, J=7.4, 1.7 Hz, 1H), 7.42-7.32 (m, 3H), 7.19 (t, J=54.2 Hz, 1H), 7.15 (dd, J=7.7, 1.4 Hz, 1H), 6.26 (d, J=0.8 Hz, 1H), 5.85-5.79 (m, 1H), 2.59-2.52 (m, 1H), 2.17-2.09 (m, 1H), 1.92-1.81 (m, 1H), 1.79-1.71 (m, 1H), 1.35-1.24 (m, 2H), 0.76 (d, J=6.9 Hz, 3H), 0.42-0.25 (m, 1H). Analytical HPLC (Method A): RT=8.11 min, purity=99.8%; Factor XIa Ki=0.46 nM, Plasma Kallikrein Ki=30 nM.

EXAMPLE 95

Preparation (10R,14S)-14-(4-{3-chloro-6-[4-(difluoromethyl)-1H-1,2,3-triazol-1-yl]-2fluorophenyl}-6-oxo-1,6-dihydropyrimidin-1-yl)-10-methyl-8,16-diazatricyclo [13.3.1.0$^{2,7}$]nonadeca-1(19),2(7),3,5,15,17-hexaen-9-one

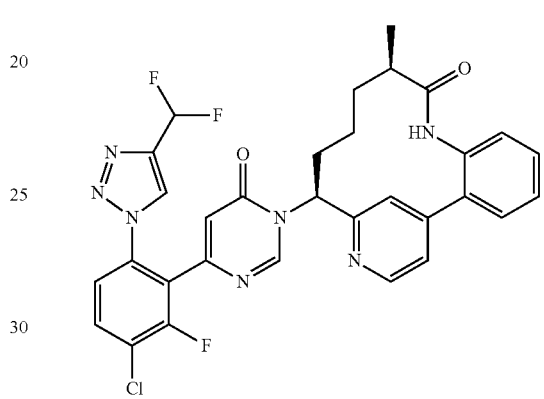

(10R,14S)-14-(4-{3-Chloro-6[4-(difluoromethyl)-1H-1,2,3 -triazol-1-yl]-2-fluorophenyl}-6-oxo-1,6-dihydropyrimidin-1-yl)-10-methyl-8,16-diazatricyclo [13.3.1.0$^{2,7}$]nonadeca-1(19),2(7),3,5,15,17-hexaen-9-one (0.0168 g, 45% yield) was prepared in a similar manner as the procedure described in Example 129, by using 6-(3-chloro-6-(4-(difluoromethyl)-1H-1,2,3-triazol-1-yl)-2-fluorophenyl)pyrimidin-4-ol, prepared as described in Example 21, and (10R,14S)-14-amino-10-methyl-8,16-diazatricyclo [13.3.1.0$^{2,7}$]nonadeca-1(19),2,4,6,15,17-hexaen-9-one, prepared as described in Example 29. MS(ESI) m/z: 620.1 (M+H)$^+$ and 622.1 (M+2+H)$^+$. $^1$h NMR (500MHz, DMSO-d$_6$) δ 9.72 (s, 1H), 8.89 (s, 1H), 8.82-8.79 (m, 1H), 8.62 (d, J=5.2 Hz, 1H), 8.02 (dd, J=8.5, 7.7 Hz, 1H), 7.73-7.68 (m, 2H), 7.58 (dd, J=7.4, 1.7 Hz, 1H), 7.50-7.40 (m, 3H), 7.36-7.12 (m, 2H), 6.63 (s, 1H), 5.94-5.87 (m, 1H), 2.67-2.59 (m, 1H), 2.26-2.17 (m, 1H), 2.00-1.90 (m, 1H), 1.89-1.80 (m, 1H), 1.44-1.31 (m, 2H), 0.84 (d, J=6.9 Hz, 3H), 0.52-0.32 (m, 1H). Analytical HPLC (Method A): RT=8.20 min, purity=99.9%; Factor XIa Ki=0.16 nM, Plasma Kallikrein Ki=13 nM.

EXAMPLE 96

Preparation of 1-(4-chloro-2-{1-[(10R,14S)-10-methyl-9-oxo-8,16-diazatricyclo [13.3.1.0$^{2,7}$]nonadeca-1(19),2(7),3,5,15,17-hexaen-14-yl]-6-oxo-1,6-dihydropyrimidin-4-yl}phenyl)-1H-1,2,3-triazole-4-carbonitrile

EXAMPLE 97

Preparation of (10R,14S)-14-{5-chloro-4-[3-chloro-2-fluoro-6-(1H-1,2,3-triazol-1-yl)phenyl]-6-oxo-1,6-dihydropyrimidin-1-yl}-10-methyl-9-oxo-8,16-diazatricyclo [13.3.1.0$^{2,7}$]nonadeca-1(19),2(7),3,5,15,17-hexaene-5-carbonitrile

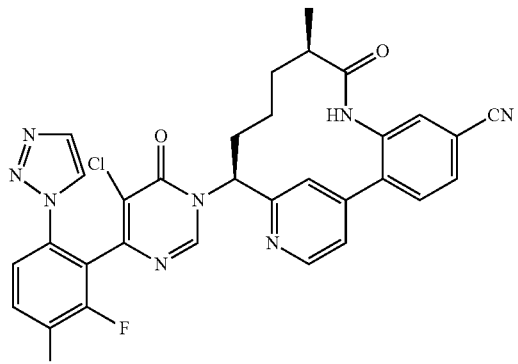

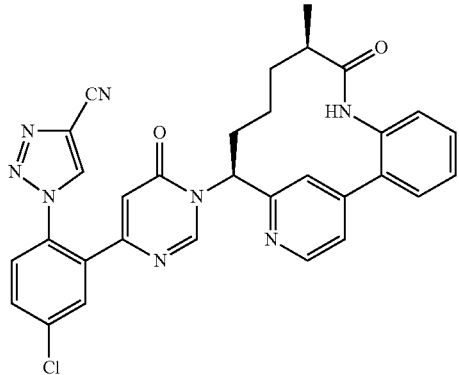 [SMILES: C[C@@H]1CCC[C@H](n2cnc(-c3cc(Cl)ccc3-n3cc(C#N)nn3)cc2=O)c2cc(ccn2)-c2ccccc2NC1=O]

1-(4-Chloro-2-{1-[(10R,14S)-10-methyl-9-oxo-8,16-diazatricyclo[13.3.1.0$^{2,7}$]nonadeca-1(19),2(7),3,5,15,17-hexaen-14-yl]-6-oxo-1,6-dihydropyrimidin-4-yl}phenyl) -1H-1,2,3-triazole-4-carbonitrile (0.0098 g, 29% yield) was prepared in a similar manner as the procedure described in Example 129, by using 1-[4-chloro-2-(6-hydroxypyrimidin -4-yl)phenyl]-1H-1,2,3-triazole-4-carbonitrile, prepared as described in Example 18, and (10R,14S)-14-amino-10-methyl-8,16-diazatricyclo[13.3.1.0$^{2,7}$]nonadeca -1(19),2,4,6,15,17-hexaen-9-one, prepared as described in Example 29. MS(ESI) m/z: 577.1 (M+H)$^+$ and 579.1 (M+2+H)$^+$. $^1$H NMR (500MHz, DMSO-d$_6$) δ 9.72 (s, 1H), 9.39 (s, 1H), 8.83 (s, 1H), 8.63 (d, J=5.0 Hz, 1H), 7.97 (d, J=2.2 Hz, 1H), 7.87 (dd, J=8.5, 2.5 Hz, 1H), 7.82 (d, J=8.5 Hz, 1H), 7.69 (s, 1H), 7.58 (dd, J=7.4, 1.7 Hz, 1H), 7.50-7.40 (m, 3H), 7.23 (dd, J=7.7, 1.1 Hz, 1H), 6.54 (d, J=0.8 Hz, 1H), 5.93-5.86 (m, 1H), 2.67-2.59 (m, 1H), 2.28-2.19 (m, 1H), 2.00-1.90 (m, 1H), 1.88-1.79 (m, 1H), 1.44 -1.32 (m, 2H), 0.84 (d, J=6.9 Hz, 3H), 0.50-0.35 (m, 1H). Analytical HPLC (Method A): RT=8.13 min, purity=99.6%; Factor XIa Ki=0.1 nM, Plasma Kallikrein Ki=12 nM.

97A. Preparation of 5-chloro-6-(3-chloro-2-fluoro-6-(1H-1,2,3-triazol-1-yl)phenyl) pyrimidin-4-ol To a solution of 6-(3-chloro-2-fluoro-6-(1H-1,2,3-triazol-1-yl)phenyl)pyrimidin -4-ol (53 mg, 0.182 mmol) in CH$_3$CN (2 mL) was added NCS (26.7 mg, 0.200 mmol). After 2 h, DMF (0.5 mL) was added. The reaction was heated at 60° C. overnight. The reaction was concentrated. Purification by normal phase chromatography yielded 5-chloro-6-(3-chloro-2-fluoro-6-(1H-1,2,3-triazol-1-yl)phenyl)pyrimidin-4-ol (32 mg, 54% yield) as a clear glass. MS(ESI) m/z: 326.3 (M+H)$^+$. $^1$H NMR (400 MHz, CD$_3$OD) δ 8.24 (d, J=1.1 Hz, 1H), 8.09 (s, 1H), 7.90 (dd, J=8.6, 7.7 Hz, 1H), 7.79 (d, J=1.1 Hz, 1H), 7.61 (dd, J=8.8, 1.5 Hz, 1H).

97B. Preparation of (10R,14S)-14-{5-chloro-4-[3-chloro-2-fluoro-6-(1H-1,2,3-triazol-1-yl)phenyl]-6-oxo-1,6-dihydro-pyrimidin-1-yl}-10-methyl-9-oxo-8,16-diazatricyclo [13.3.1.0$^{2,7}$]nonadeca-1(19),2(7),3,5,15,17-hexaene-5-carbonitrile trifluoroacetate (10R,14S)-14-{5-Chloro-4-[3-chloro-2-fluoro-6-(1H-1,2,3-triazol-1-yl)phenyl]-6-oxo-1, 6-dihydropyrimidin-1-yl}-10-methyl-9-oxo-8,16-diazatricyclo[13.3.1.0$^{2,7}$]nonadeca-1(19),2(7),3,5,15,17-hexaene-5-carbonitrile trifluoroacetate (10mg, 27% yield) was prepared in a similar manner as the procedure described in Example 129, by using 5-chloro-6-(3-chloro-2-fluoro-6-(1H-1,2,3-triazol-1-yl)phenyl)pyrimidin-4-ol and (10R, 14S)-14-amino-10-methyl-9-oxo-8,16-diazatricyclo [13.3.1.0$^{2,7}$]nonadeca -1(19),2,4,6,15,17-hexaene-5-carbonitrile, prepared as described in Example 30. MS(ESI) m/z: 629.1 (M+H)$^+$. $^1$H NMR (400 MHz, CD$_3$OD) δ 9.07-8.96 (m, 1H), 8.72 (dd, J=7.9, 5.1 Hz, 1H), 8.33-8.14 (m, 1H), 7.90 (dd, J=8.7, 7.8 Hz, 1H), 7.84-7.68 (m, 4H), 7.66-7.56 (m, 2H), 7.47 (td, J=4.5, 1.8 Hz, 1H), 6.02 (ddd, J=17.0, 12.4, 5.0 Hz, 1H), 2.68 (br. s., 1H), 2.29-2.14 (m, 1H), 2.08 (dt, J=8.4, 4.3 Hz, 1H), 1.99-1.84 (m, 1H), 1.59-1.33 (m, 2H), 0.95 (dd, J=6.9, 2.5 Hz, 3H), 0.65 (m., 1H). Analytical HPLC (Method A): RT=9.00 min, purity=100%; Factor XIa Ki=2 nM, Plasma Kallikrein Ki=50 nM.

EXAMPLE 98

Preparation of 10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo [13.3.1.0$^{2,7}$]nonadeca-1(19),2(7),3,5,15,17-hexaene-4-carbonitrile trifluoroacetate

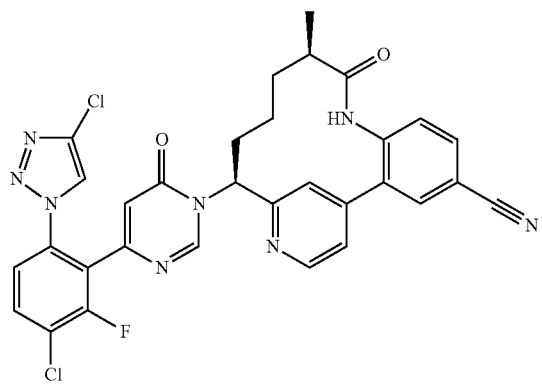 [SMILES: C[C@@H]1CCC[C@H](n2cnc(-c3c(-n4cc(Cl)nn4)ccc(Cl)c3F)cc2=O)c2cc(ccn2)-c2cc(C#N)ccc2NC1=O]

(10R,14S)-14-{4-[3-Chloro-6-(4-chloro-1H-1,2,3-triazol-1-yl)-2-fluorophenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-4-carbonitrile trifluoroacetate (4.64 mg, 29% yield) was prepared in a similar manner as the procedure described in Example 114 by replacing 6-[5-chloro-2-(4-chloro-1H-1,2,3-triazol-1-yl)phenyl]pyrimidin-4-ol with 6-[3-chloro-6-(4-chloro-1H-1,2,3-triazol-1-yl)-2-fluorophenyl]pyrimidin-4-ol, prepared as described in Example 10. MS(ESI) m/z: 629.2 (M+H)$^+$. $^1$H NMR (400 MHz, DMF) δ 10.17 (s, 1H), 9.06 (s, 1H), 8.75 (d, J=4.8 Hz, 1H), 8.71 (s, 1H), 8.13 (d, J=2.0 Hz, 1H), 8.09-8.06 (m, 1H), 7.96 (dd, J=8.4, 2.0 Hz, 1H), 7.82-7.74 (m, 2H), 7.60 (dd, J=5.1, 1.5 Hz, 1H), 7.52 (d, J=8.1 Hz, 1H), 6.70 (s, 1H), 6.08 (dd, J=12.4, 5.0 Hz, 1H), 2.28 (t, J=12.7 Hz, 1H), 1.98 (d, J=12.8 Hz, 2H), 1.57-1.40 (m, 2H), 1.28 (br. s., 1H), 0.90 (d, J=7.0 Hz, 3H), 0.58 (br. s., 1H). Analytical HPLC (Method A): RT=8.97 min, purity>99%; Factor XIa Ki=0.26 nM, Plasma Kallikrein Ki=40 nM.

EXAMPLE 99

Preparation of 2-{[(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaen-5-yl]oxy}acetic acid

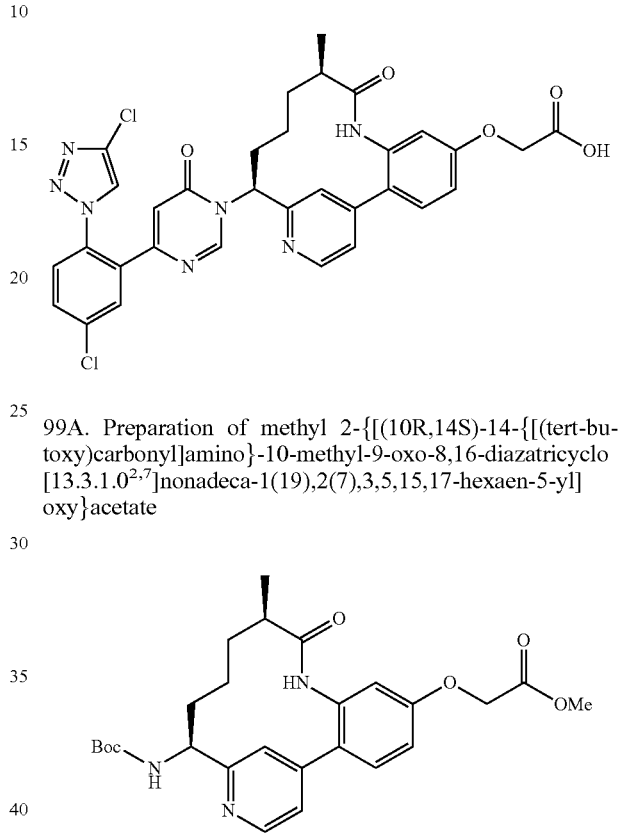

99A. Preparation of methyl 2-{[(10R,14S)-14-{[(tert-butoxy)carbonyl]amino}-10-methyl-9-oxo-8,16-diazatricyclo [13.3.1.0$^{2,7}$]nonadeca-1(19),2(7),3,5,15,17-hexaen-5-yl]oxy}acetate To a solution of tert-butyl N-[(10R,14S)-5-hydroxy-10-methyl-9-oxo-8,16-diazatricyclo[13.3.1.0$^{2,7}$]nonadeca-1 (19),2(7),3,5,15,17-hexaen-14-yl]carbamate (64 mg, 0.156 mmol), prepared as described in Example 93A, in DMF (1 mL) was added methyl bromoacetate (26 mg, 0.171 mmol) and Cs$_2$CO$_3$ (63 mg, 0.194 mmol). The reaction was stirred at rt for 16 h, then diluted with EtOAc, washed with water and brine, dried over MgSO$_4$, filtered and concentrated. Purification with normal phase chromatography afforded methyl 2-{[(10R,14S)-14-{[(tert-butoxy)carbonyl]amino}-10-methyl-9-oxo -8,16-diazatricyclo[13.3.1.0$^{2,7}$]nonadeca-1(19),2(7),3,5,15,17-hexaen-5-yl]oxy}acetate (72 mg, 96%) as a pale yellow solid. MS(ESI) m/z: 484.2. (M+H)$^+$.

99B. Preparation of methyl 2-{[(10R,14S)-14-{4-[5-chloro-2-(4-chloro-1H-1,2,3-triazol -1-yl)phenyl]-6-oxo-1,6-dihydropyrimidin-1-yl}-10-methyl-9-oxo-8,16-diazatricyclo [13.3.1.0$^{2,7}$]nonadeca-1(19),2(7),3 ,5,15,17-hexaen-5-yl]oxy}acetate trifluoroacetate Methyl 2-{[(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaen-5-yl]oxy}acetate trifluoroacetate (6.5 mg, 15% over 2 steps) was prepared in a similar manner as described in Example 79, by using methyl 2-{[(10R,14S)-14-{[(tert-butoxy)carbonyl]amino}-10-methyl-9-oxo-8,16-diazatricyclo[13.3.1.0$^{2,7}$]nonadeca-1(19),2(7),3,5,15,17-hexaen-5-yl]oxy}acetate. MS(ESI) m/z: 674.2. (M+H)$^+$. $^1$H NMR (400 MHz, CD$_3$OD) δ 8.76 (s, 1H), 8.72 (d, J=5.5 Hz, 1H), 8.40 (s, 1H), 7.96 (s, 1H), 7.92 (d, J=2.4 Hz, 1H), 7.81-7.74 (m, 1H), 7.72-7.65 (m, 3H), 7.13 (dd, J=8.8, 2.6 Hz, 1H), 6.95 (d, J=2.6 Hz, 1H), 6.44 (s, 1H), 5.86 (dd, J=12.3, 4.2 Hz, 1H), 3.84 (s, 2H), 2.46 (t, J=7.4 Hz, 1H), 2.37 (t, J=12.9 Hz, 1H), 2.26-2.13 (m, 1H), 1.88-1.77 (m, 1H), 1.76-1.66 (m, 1H), 1.60-1.46 (m, 1H), 1.35 (d, J=18.7 Hz, 2H), 1.27 (d, J=7.0 Hz, 2H), 1.15 (br. s., 1H). Analytical HPLC (Method A) RT=8.07 min, 99% purity.

99C. Preparation of 2-{[(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaen-5-yl]oxy}acetic acid trifluoroacetate To a solution of methyl 2-{[(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaen-5-yl]oxy}acetate trifluoroacetate (5 mg, 6.34 μmol) in MeOH (1 mL), was added aq 1 N NaOH (0.10 mL, 0.10 mmol) and the reaction was stirred at rt for 3 days. To the reaction mixture was added a small amount of DMF, and the resulting solution was purified by reverse phase chromatography to afford 2-{[(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo [13.3.1.0$^{2,7}$]nonadeca-1(19),2(7),3,5,15,17-hexaen-5-yl]oxy}acetic acid trifluoroacetate (3.7 mg, 75% yield) as a white solid. MS(ESI) m/z: 660.1. (M+H)$^+$. $^1$H NMR (500 MHz, CD$_3$OD) δ 8.84 (s, 1H), 8.65 (d, J=5.2 Hz, 1H), 8.37 (s, 1H), 7.91 (d, J=2.2 Hz, 1H), 7.79-7.74 (m, 1H), 7.72 (s, 1H), 7.68 (d, J=8.5 Hz, 1H), 7.60 (d, J=8.5 Hz, 1H), 7.48 (dd, J=5.2, 1.7 Hz, 1H), 7.11 (dd, J=8.5, 2.5 Hz, 1H), 6.93 (d, J=2.5 Hz, 1H), 6.40 (d, J=0.6 Hz, 1H), 5.96 (dd, J=12.5, 4.3 Hz, 1H), 4.79 (s, 2H), 2.40-2.31 (m, 1H), 2.29-2.20 (m, 1H), 2.13-2.03 (m, 1H), 1.93-1.84 (m, 1H), 1.57-1.40 (m, 2H), 1.27 (d, J=6.9 Hz, 3H), 1.07-0.95 (m, 1H). Analytical HPLC (Method A) RT=7.07 min, 100% purity; Factor XIa Ki=90 nM, Plasma Kallikrein Ki=4,900 nM.

EXAMPLE 100

Preparation of N-{[(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,17-diazatricyclo[13.3.1.0$^{2,7}$]nonadeca-1(19),2(7),3,5,15,17-hexaen-5-yl]methyl}-2,2,2-trifluoroacetamide

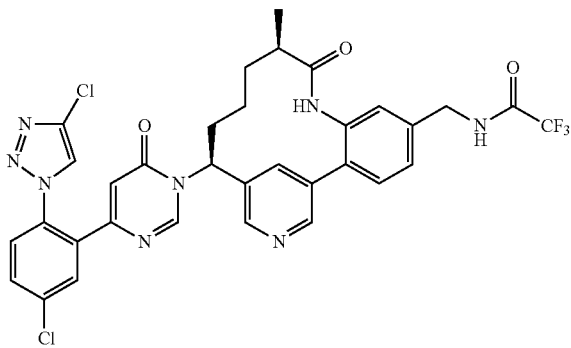 [SMILES: C[C@@H]1CCC[C@H](n2cnc(-c3cc(Cl)ccc3-n3cc(Cl)nn3)cc2=O)c2cncc(c2)-c2ccc(CNC(=O)C(F)(F)F)cc2NC1=O]

100A. Preparation of tert-butyl N-[(10R,14S)-10-methyl-9-oxo-5-[(trifluoroacetamido)methyl]-8,17-diazatricyclo[13.3.1.0$^{2,7}$]nonadeca-1(19),2(7),3,5,15,17-hexaen-14-yl]carbamate trifluoroacetate

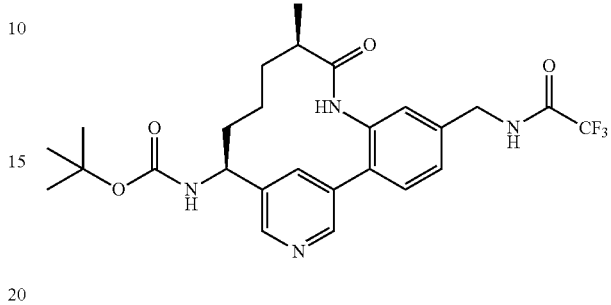

To a solution of tert-butyl N-[(10R,14S)-5-(aminomethyl)-10-methyl-9-oxo-8,17-diazatricyclo[13.3.1.0$^{2,7}$]nonadeca-1(19),2(7),3,5,15,17-hexaen-14-yl]carbamate trifluoroacetate (51 mg, 0.078 mmol), prepared as described in Example 92D, in DMF (1 mL) was added Et$_3$N (0.033 mL, 0.234 mmol) and ethyl 2,2,2-trifluoroacetate (13 mg, 0.094 mmol). The solution was stirred at rt for 16 h. The solution was concentrated. Purification with reverse phase chromatography afforded tert-butyl N-[(10R,14S)-5-(aminomethyl)-10-methyl-9-oxo-8,17-diazatricyclo[13.3.1.0$^{2,7}$]nonadeca-1(19),2(7),3,5,15,17-hexaen-14-yl]carbamate trifluoroacetate (30 mg, 60% yield) as a white solid. MS(ESI) m/z: 521.6.

100B. Preparation of N-{[(10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,17-diazatricyclo[13.3.1.0$^{2,7}$]nonadeca-1(19),2(7),3,5,15,17-hexaen-5-yl]methyl}-2,2,2-trifluoroacetamide trifluoroacetate N-{[(10R,14S)-14-{4-[5-Chloro-2-(4-chloro-1H-1,2,3-triazol-1-yl)phenyl]-6-oxo-1,6-dihydropyrimidin-1-yl}-10-methyl-9-oxo-8,17-diazatricyclo[13.3.1.0$^{2,7}$]nonadeca-1(19),2(7),3,5,15,17-hexaen-5-yl]methyl}-2,2,2-trifluoroacetamide trifluoroacetate (9.5 mg, 24% over 2 steps) was prepared in a similar manner as described in Example 79, by using tert-butyl N-[(10R,14S)-10-methyl-9-oxo-5-[(trifluoroacetamido)methyl]-8,17-diazatricyclo[13.3.1.0$^{2,7}$]nonadeca-1(19),2(7),3,5,15,17-hexaen-14-yl]carbamate trifluoroacetate. MS(ESI) m/z: 711.2. (M+H)$^+$. $^1$H NMR (400 MHz, CD$_3$OD) δ 8.91-8.87 (m, 1H), 8.80-8.75 (m, 1H), 8.50 (s, 1H), 8.38 (s, 1H), 7.86 (d, J=2.2 Hz, 1H), 7.78-7.60 (m, 3H), 7.49 (dd, J=7.9, 1.8 Hz, 1H), 7.33 (d, J=1.5 Hz, 1H), 6.38 (d, J=0.7 Hz, 1H), 5.71 (dd, J=12.9, 3.9 Hz, 1H), 4.59-4.53 (m, 2H), 2.61-2.46 (m, 2H), 2.31-2.16 (m, 1H), 1.91-1.76 (m, 1H), 1.60-1.33 (m, 3H), 1.25 (br. s., 1H), 1.09 (d, J=6.8 Hz, 3H). Analytical HPLC (Method A) RT=7.45 min, 95% purity; Factor XIa Ki=1.3 nM, Plasma Kallikrein Ki=110 nM.

EXAMPLE 101

Preparation of (10R,14S)-5-(aminomethyl)-14-{4-[5-chloro-2-(4-chloro-1H-1,2,3-triazol-1-yl)phenyl]-6-oxo-1,6-dihydropyrimidin-1-yl}-10-methyl-8,17-diazatricyclo [13.3.1.0$^{2,7}$]nonadeca-1(19),2(7),3,5,15,17-hexaen-9-one trifluoroacetate

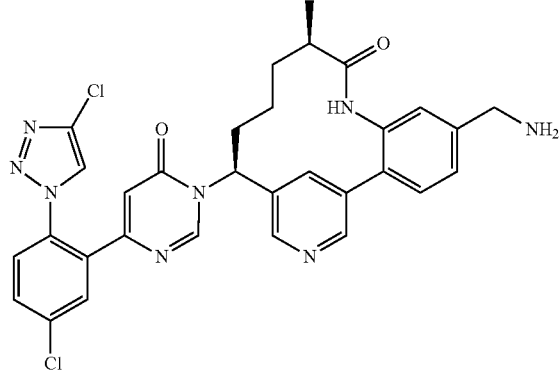 [SMILES: C[C@@H]1CCC[C@H](n2cnc(-c3cc(Cl)ccc3-n3cc(Cl)nn3)cc2=O)c2cncc(c2)-c2ccc(CN)cc2NC1=O]

N-{[(10R,14S)-14-{4-[5-Chloro-2-(4-chloro-1H-1,2,3-triazol-1-yl)phenyl]-6-oxo -1,6-dihydropyrimidin-1-yl}-10-methyl-9-oxo-8,17-diazatricyclo[13.3.1.0$^{2,7}$]nonadeca-1(19),2(7),3,5,15,17-hexaen-5-yl]methyl}-2,2,2-trifluoroacetamide trifluoroacetate (8.5 mg, 10.30 μmol) in MeOH (0.5 mL) was added aq 1 N NaOH (0.1 mL, 0.10 mmol), and the solution was stirred at rt. After 4 h, the reaction mixture was purified by reverse phase chromatography to afford (10R,14S)-5-(aminomethyl)-14-{4-[5-chloro-2-(4-chloro-1H -1,2,3-triazol-1-yl)phenyl]-6-oxo-1,6-dihydropyrimidin-1-yl}-10-methyl-8,17-diazatricyclo[13.3.1.0$^{2,7}$]nonadeca-1(19),2(7),3,5,15,17-hexaen-9-one trifluoroacetate (4.0 mg, 42% yield) as a white solid. MS(ESI) m/z: 615.2. (M+H)$^+$.
$^1$H NMR (400 MHz, CD$_3$OD) δ 8.69 (d, J=1.5 Hz, 1H), 8.60 (d, J=1.8 Hz, 1H), 8.41 (s, 1H), 8.36 (s, 1H), 8.30 (t, J=1.9 Hz, 1H), 7.88 (d, J=2.2 Hz, 1H), 7.80-7.73 (m, 2H), 7.68-7.60 (m, 2H), 7.49 (d, J=1.8 Hz, 1H), 6.42 (d, J=0.7 Hz, 1H), 5.74 (dd, J=12.8, 3.5 Hz, 1H), 4.25 (s, 2H), 2.55-2.43 (m, 2H), 2.28-2.17 (m, 1H), 1.84 (dt, J=8.6, 5.7 Hz, 1H), 1.70-1.49 (m, 2H), 1.34 (d, J=19.4 Hz, 1H), 1.17 (d, J=6.8 Hz, 3H). Analytical HPLC (Method A) RT=5.40 min, 90% purity; Factor XIa Ki=7.9 nM, Plasma Kallikrein Ki=630 nM.

EXAMPLE 102

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-8,17-diazatricyclo [13.3.1.0$^{2,7}$]nonadeca-1(19),2(7),3,5,15,17-hexaen-9-one

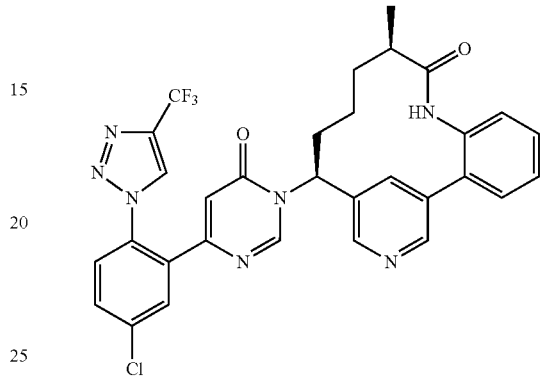

102A. Preparation of (S)-tert-butyl (1-(5-(2-aminophenyl)pyridin-3-yl)but-3-en-1-yl)carbamate (S)-tert-Butyl (1-(5-bromopyridin-3-yl)but-3-en-1-yl)carbamate (0.50 g, 1.53 mmol), as prepared by Example 26, (2-aminophenyl)boronic acid (0.23 g, 1.68 mmol), and 2 M Na$_2$CO$_3$ (3.06 mL, 6.11 mmol) were added to dioxane (8.83 mL) and purged with a stream of argon for 10 min. Pd(PPh$_3$)$_4$ (0.088 g, 0.076 mmol) was added and the mixture irradiated at 120° C. for 30 min. The reaction mixture was partition between EtOAc and water. The organic layer was washed with brine, dried over Na$_2$SO$_4$, filtered, and concentrated to afford (S)-tert-butyl (1-(5-(2-aminophenyl)pyridin-3-yl)but-3-en-1-yl)carbamate which was used in the next reaction. MS(ESI) m/z: 340.1 (M+H)$^+$.

102B. Preparation of tert-butyl ((S)-1-(5-(2-((R)-2-methylbut-3-enamido)phenyl)pyridin -3-yl)but-3-en-1-yl)carbamate To (S)-tert-butyl (145-(2-aminophenyl)pyridin-3-yl)but-3-en-1-yl)carbamate (0.519 g, 1.529 mmol) in EtOAc (5.10 mL), was added (R)-2-methylbut-3-enoic acid (0.230 g, 2.294 mmol) in EtOAc (1 mL) at 0° C. T3P® (50% EtOAc) (1.820 ml, 3.06 mmol) and pyridine (0.371 mL, 4.59 mmol) were then added. After stirring overnight, the reaction was partitioned with sat NaHCO$_3$ (100 mL) and EtOAc (100 mL). The aqueous layer was extracted with EtOAc (2×50 mL). The combined organic layer was washed with brine (50 mL), dried (Na$_2$SO$_4$), filtered, and concentrated. The residue was purified by normal phase chromatography hexanes and EtOAc as eluents to afford the tert-butyl ((S)-1-(5-(24(R)-2-methylbut-3-enamido)phenyl)pyridin-3-yl)but-3-en-1-yl)carbamate (0.565 g, 88%). MS(ESI) m/z: 422.3 (M+H)$^+$. $^1$H NMR (500 MHz, CDCl$_3$-d) δ 8.61 (d, J=1.9 Hz, 1H), 8.50 (d, J=2.2 Hz, 1H), 8.27 (d, J=8.3 Hz, 1H), 7.56 (t, J=2.1 Hz, 1H), 7.43 (dt, J+8.5, 4.4 Hz, 1H), 7.21 (d, J=4.4 Hz, 2H), 5.81-5.66 (m, 2H), 5.21-5.15 (m, 2H), 5.08-5.01 (m, 2H), 3.07-2.98 (m, 1H), 2.63-2.49 (m, 2H), 1.56 (s, 4H), 1.43 (br. s., 9H).

102C. Preparation of tert-butyl N-[(10R,11E,14S)-10-methyl-9-oxo-8,17-diazatricyclo [13.3.1.0$^{2,7}$]nonadeca-1(19),2(7),3,5,11,15,17-heptaen-14-yl]carbamate To a solution of tert-butyl ((S)-1-(5-(24(R)-2-methylbut-3-enamido)phenyl) -pyridin-3-yl)but-3-en-1-yl)carbamate (565 mg, 1.34 mmol) in DCM (335 mL) was added pTsOH.H$_2$O (268 mg, 1.407 mmol). The mixture was heated at 40° C. while bubbling Ar through for 1 h. Second Generation Grubbs Catalyst ((455 mg, 0.536 mmol) was added and stirring continued at 40° C. under Ar. After 2 h, the reaction was cooled to rt and stirred under Ar overnight. The reaction mixture was neutralized with sat aq NaHCO$_3$. The organic phase was separated, washed with brine, dried over MgSO$_4$, filtered, and concentrated. The crude residue was purified by normal phase chromatography hexanes and EtOAc as eluants to give the desired product (527 mg, 100%). MS(ESI) m/z: 394.2 (M+H)$^+$.

102D. Preparation of tert-butyl N-[(10R,14S)-10-methyl-9-oxo-8,17-diazatricyclo [13.3.1.0$^{2,7}$]nonadeca-1(19),2(7),3,5,15,17-hexaen-14-yl]carbamate PtO$_2$ (0.030 g, 0.134 mmol) was added to a solution of tert-butyl N -[(10R,11E,14S)-10-methyl-9-oxo-8,17-diazatricyclo[13.3.1.0$^{2,7}$]nonadeca -1(19),2(7),3,5,11,15,17-heptaen-14-yl]carbamate (0.527 g, 1.34 mmol) in EtOH (50 mL) and subjected to a H$_2$ atmosphere (55 psi). After 4 h, the catalyst was filtered off through a plug of CELITE® and the filtrate concentrated. The product was carried forward to the next reaction. MS(ESI) m/z: 396.5 (M+H)$^+$.

102E. Preparation of (10R,14 S)-14-amino-10-methyl-8,17-diazatricyclo [13.3.1.0$^{2,7}$]nonadeca-1(19),2(7),3,5,15,17-hexaen-9-one TFA (2.065 mL, 26.8 mmol) was added to a stirring solution of tent-butyl N -[(10R,14S)-10-methyl-9-oxo-8,17-diazatricyclo[13.3.1.0$^{2,7}$]nonadeca -1(19),2(7),3,5,15,17-hexaen-14-yl]carbamate (0.530 g, 1.34 mmol) in DCM (5.0 mL) at rt. After 1 h, the reaction mixture was concentrated to dryness and neutralized with sat NaHCO$_3$. The mixture was extracted with a CHCl$_3$/IPA (3:1) solution (3×). The combined organic layer was dried over MgSO$_4$, filtered, and concentrated to give the desired product which was carried forward to the next reaction. MS(ESI) m/z: 296.1 (M+H)$^+$.

102F. Preparation of (10R,14S)-14-(4-{5-chloro-2-[4-(trifluoromethyl)-1H-1,2,3 -triazol -1-yl]phenyl}-6-oxo-1,6-dihydropyrimidin-1-yl)-10-methyl-8,17-diazatricyclo [13.3.1.0$^{2,7}$]nonadeca-1(19),2,4,6,15,17-hexaen-9-one trifluoroacetate To a vial containing a white suspension 6-(5-chloro-2-(4-(trifluoromethyl)-1H -1,2,3-triazol-1-yl)phenyl)pyrimidin-4-ol (0.023 g, 0.068 mmol), prepared in Example 15, in ACN (1.830 mL) was added HATU (0.033 g, 0.088 mmol) and DBU (0.015 ml, 0.102 mmol). After 30 min, (10R,14S)-14-amino-10-methyl-8,17-diazatricyclo [13.3.1.0$^{2,7}$]nonadeca-1(19),2(7),3,5,15,17-hexaen-9-one (0.020 g, 0.068 mmol) in DMF (1.0 mL) was added. The resulting solution was stirred at rt overnight. The crude reaction mixture was purified by reverse phase chromatography (PHENOMENEX® Luna Axia C18 5 µ 30 ×100 mm column, 10-minute gradient; Solvent A: 20% MeOH-80% H$_2$O-0.1% TFA; Solvent B: 90% MeOH-10% H$_2$O-0.1% TFA) and lyopholized to give (10R,14S)-14-(4-{5-chloro-2[4-(trifluoromethyl)-1H-1,2,3-triazol-1-yl]phenyl}-6-oxo-1,6-dihydropyrimidin-1-yl)-10-methyl-8,17-diazatricyclo[13.3.1.0$^{2,7}$]nonadeca -1(19),2,4,6,15,17-hexaen-9-one trifluoroacetate (5.4 mg, 10%) as a white solid. MS(ESI) m/z: 620 (M+H)$^+$.
$^1$H NMR (400 MHz, CD$_3$OD) δ 8.90-8.83 (m, 1H), 8.51 (s, 1H), 8.42 (s, 1H), 7.94-7.89 (m, 1H), 7.82-7.76 (m, 1H), 7.74-7.67 (m, 2H), 7.63-7.52 (m, 2H), 7.39 (dd, J=7.4, 1.7 Hz, 1H), 6.52-6.42 (m, 1H), 5.79 (d, J=9.2 Hz, 1H), 2.60-2.44 (m, 2H), 2.22 (d, J=9.5 Hz, 1H), 1.89-1.77 (m, 1H), 1.54 (d, J=7.0 Hz, 2H), 1.30-1.06 (m, 4H). Analytical HPLC (Method X) RT=5.78 min, 92% purity. Factor XIa Ki=0.2 nM, Plasma Kallikrein Ki=15 nM.

EXAMPLE 103

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,17-diazatricyclo[13.3.1.0$^{2,7}$]nonadeca-1(19),2(7),3,5,15,17-hexaen-9-one

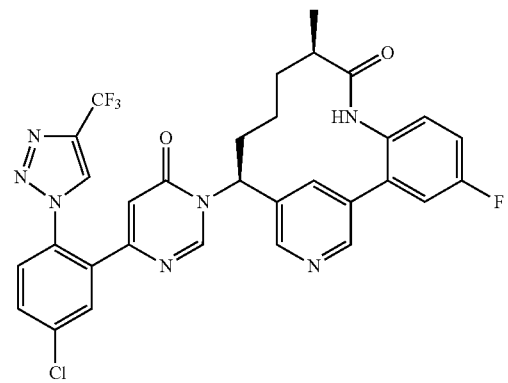 [SMILES: C[C@@H]1CCC[C@H](n2cnc(-c3cc(Cl)ccc3-n3cc(C(F)(F)F)nn3)cc2=O)c2cncc(c2)-c2cc(F)ccc2NC1=O]

103A. Preparation of 2-(5,5-dimethyl-1,3,2-dioxaborinan-2-yl)-4-fluoroaniline hydrochloride tert-Butyl (2-(5,5-dimethyl-1,3,2-dioxaborinan-2-yl)-4-fluorophenyl)carbamate (0.500 g, 1.547 mmol) was added to MeOH (1 mL) and treated with 4 M HCl in dioxane (7.74 ml, 30.9 mmol) and stirred overnight. The reaction mixture was concentrated and the residue dried further under high vacuum for 3 h to give 2-(5,5-dimethyl-1,3,2-dioxaborinan-2-yl)-4-fluoroaniline hydrochloride (0.390g, 97% yield) as a white solid. $^1$H NMR (400 MHz, DMSO-d$_6$) δ 7.49-7.42 (m, 1H), 7.42-7.32 (m, 2H), 3.78 (s, 4H), 0.98 (s, 6H).

103B. Preparation of (S)-tert-butyl (1-(5-(2-amino-5-fluorophenyl)pyridin-3-yl)but-3-en -1-yl)carbamate (S)-tert-Butyl (1-(5-bromopyridin-3-yl)but-3-en-1-yl)carbamate (0.485 g, 1.484 mmol), prepared as described for Example 26, 2-(5,5-dimethyl-1,3,2-dioxaborinan-2-yl) -4-fluoroaniline hydrochloride (0.385 g, 1.484 mmol), and aq 2 M Na$_2$CO$_3$ (2.97 mL, 5.93 mmol) were added to dioxane (8.58 mL) and purged with a stream of Ar for 10 min. Pd(PPh$_3$)$_4$ (0.086 g, 0.074 mmol) was added and the mixture irradiated at 120° C. for 30 min. The reaction mixture was partition between EtOAc and water. The organic layer was washed with brine, dried over Na$_2$SO$_4$, filtered, and concentrated. Crude (S)-tert -butyl (1-(5 -(2-amino-5 -fluorophenyl)pyridin-3 -yl)but-3 -en-1-yl)carbamate was carried forward to the next reaction without further purification. MS(ESI) m/z: 358.1 (M+H)$^+$.

103C. Preparation of tert-butyl ((S)-1-(5-(5-fluoro-2-((R)-2-methylbut-3-enamido) phenyl)pyridin-3-yl)but-3-en-l-yl) carbamate To (S)-tert-butyl (1-(5-(2-amino-5-fluorophenyl)pyridin-3-yl)but-3-en-1-yl)carbamate (0.530 g, 1.483 mmol) in EtOAc (4.94 ml) was added (R)-2-methylbut-3-enoic acid (0.223 g, 2.224 mmol) in EtOAc (1 mL) at 0° C. T3P® (50% in EtOAc) (1.765 mL, 2.97 mmol) and pyridine (0.360 ml, 4.45 mmol) were added. After 18 h, the reaction was partitioned with sat NaHCO$_3$ (100 mL) and EtOAc (100 mL). The aqueous layer was extracted with EtOAc (2×50 mL). The combined organic layer was washed with brine (50 mL) and dried (Na$_2$SO$_4$), filtered, and concentrated. The residue was purified by normal phase chromatography with hexane and EtOAc as eluents to give tert -butyl ((S)-1-(5-(5-fluoro-2-((R)-2-methylbut-3-enamido)phenyl)pyridin-3-yl)but-3-en-1-yl)carbamate (583 mg, 89%) as an oil. MS(ESI) m/z: 440 (M+H)$^+$.

103D. Preparation of tert-butyl N-[(10R,11E,14S)-4-fluoro-10-methyl-9-oxo-8,17-diazatricyclo[13.3.1.0$^{2,7}$]nonadeca-1(19),2(7),3,5,11,15,17-heptaen-14-yl]carbamate tert-Butyl ((S)-1-(5-(5-fluoro-24(R)-2-methylbut-3-enamido)phenyl)pyridin-3-yl)but-3-en-1-yl)carbamate (580 mg, 1.320 mmol) in DCM (335.00 mL) was added pTsOH (264 mg, 1.386 mmol), and the solution was heated at 40° C. while bubbling Ar through the solution. After 1 h, Second Generation Grubbs Catalyst (448 mg, 0.528 mmol) was added and heating continued. After 2 h, the reaction was cooled to rt and stirred under Ar. After 18 h, the reaction mixture was neutralized with sat aq NaHCO$_3$. The organic phase was separated, washed with brine, dried over MgSO$_4$, filtered, and concentrated. The crude residue was purified by normal phase chromatography using hexane and EtOAc as eluents to give tert-butyl N-[(10R,11E,14S)-4-fluoro-10-methyl-9-oxo-8,17-diazatricyclo[13.3.1.0$^{2,7}$]nonadeca-1(19),2(7),3,5,11,15,17-heptaen-14-yl]carbamate (468 mg, 86%) as a brown oil. MS(ESI) m/z: 412 (M+H)$^+$.

103E. Preparation of tert-butyl N-[(10R,14S)-4-fluoro-10-methyl-9-oxo-8,17-diazatricyclo[13.3.1.0$^{2,7}$]nonadeca-1(19),2(7),3,5,15,17-hexaen-14-yl]carbamate PtO$_2$ (0.026 g, 0.114 mmol) was added to a solution of tert-butyl N -[(10R,11E,14S)-4-fluoro-10-methyl-9-oxo-8,17-diazatricyclo[13.3.1.0$^{2,7}$]nonadeca -1(19),2(7),3,5,11,15,17-heptaen-14-yl]carbamate (0.468 g, 1.137 mmol) in EtOH (50 mL) and subjected to a H$_2$ atmosphere (55 psi). The catalyst was filtered off through a plug of CELITE® and the filtrate concentrated to give tert-butyl N-[(10R,14S)-4-fluoro -10-methyl-9-oxo-8,17-diazatricyclo[13.3.1.0$^{2,7}$]nonadeca-1(19),2(7),3,5,15,17-hexaen -14-yl]carbamate. MS(ESI) m/z: 414 (M+H)$^+$.

103F. Preparation of (10R,14S)-14-amino-4-fluoro-10-methyl-8,17-diazatricyclo [13.3.1.0$^{2,7}$]nonadeca-1(19),2(7),3,5,15,17-hexaen-9-one TFA (1.751 mL, 22.73 mmol) was added to a stirring solution of tert-butyl N -[(10R,14S)-4-fluoro-10-methyl-9-oxo-8,17-diazatricyclo[13.3.1.0$^{2,7}$]nonadeca -1(19),2(7),3,5,15,17-hexaen-14-yl]carbamate (0.470 g, 1.137 mmol) in DCM (5 mL) at rt. After 1 h, the reaction mixture was concentrated and neutralized with sat aq NaHCO$_3$. The mixture was extracted with a CHCl$_3$/IPA (3:1) solution (3×). The combined organic layer was dried over MgSO$_4$, filtered, and concentrated to give (10R,14S)-14-amino-4-fluoro-10-methyl-8,17-diazatricyclo[13.3.1.0$^{2,7}$]nonadeca-1(19),2(7),3,5,15,17-hexaen-9-one as a brown oil (0.30 g, 84%). MS(ESI) m/z: 314 (M+H)$^+$.

103G. Preparation of (10R,14S)-14-(4-{5-chloro-2-[4-(trifluoromethyl)-1H-1,2,3-triazol -1-yl]phenyl}-6-oxo-1,6-dihydropyrimidin-1-yl)-4-fluoro-10-methyl-8,17-diazatricyclo [13.3.1.0$^{2,7}$]nonadeca-1(19),2(7),3,5,15,17-hexaen-9-one trifluoroacetate To a vial containing a white suspension 6-(5-chloro-2-(4-(trifluoromethyl)-1H -1,2,3-triazol-1-yl)phenyl)pyrimidin-4-ol (0.022 g, 0.064 mmol), prepared as described for Example 15, in ACN (1.725 mL) was added HATU (0.032 g, 0.083 mmol) and DBU (0.014 mL, 0.096 mmol). After 30 min, (10R,14S)-14-amino-4-fluoro-10-methyl-8,17-diazatricyclo[13.3.1.0$^{2,7}$]nonadeca-1(19),2(7),3,5,15,17-hexaen-9-one (0.020 g, 0.064 mmol) in DMF (1 mL) was added. After stirring for 18 h, the crude reaction mixture was purified by reverse phase chromatography (PHENOMENEX® Luna Axia C18 5 μ 30×100 mm column, 10-minute gradient; Solvent A: 20% ACN - 80% H$_2$O- 0.1% TFA; Solvent B: 80% ACN - 20% H$_2$O- 0.1% TFA) and lyopholized to give (10R,14S)-14-(4-{5-Chloro-2-[4-(trifluoromethyl)-1H-1,2,3-triazol-1-yl]phenyl}-6-oxo-1,6-dihydropyrimidin-1-yl)-4-fluoro-10-methyl-8,17-diazatricyclo [13.3.1.0$^{2,7}$]nonadeca -1(19),2(7),3,5,15,17-hexaen-9-one trifluoroacetate (6.9 mg, 13.7%) as a white solid. MS(ESI) m/z: 638.1 (M+H)$^+$. $^1$H NMR (400 MHz, CD$_3$OD) δ 8.73 (s, 1H), 8.36 (s, 1H), 8.28 (s, 1H), 7.77 (d, J=2.2 Hz, 1H), 7.67-7.62 (m, 1H), 7.62-7.54 (m, 1H), 7.37 (dd, J=8.8, 2.9 Hz, 1H), 7.31-7.24 (m, 1H), 7.25-7.15 (m, 1H), 6.35 (s, 1H), 5.63 (dd, J=12.9, 3.4 Hz, 1H), 2.43-2.28 (m, 3H), 2.15-2.04 (m, 1H), 1.70 (dd, J=9.9, 3.5 Hz, 1H), 1.48-1.36 (m, 2H), 1.01 (d, J=7.0 Hz, 4H). Analytical HPLC (Method A) RT=7.40 min, 95% purity; Factor XIa Ki=0.22 nM, Plasma Kallikrein Ki=32 nM.

EXAMPLE 104

Preparation (10R,14S)-3-chloro-14-{4-[5-chloro-2-(4-chloro-1H-1,2,3-triazol-1-yl)phenyl]-6-oxo-1,6-dihydropyrimidin-1-yl}-10-methyl-8,16-diazatricyclo [13.3.1.0$^{2,7}$]nonadeca-1(19),2(7),3,5,15,17-hexaen-9-one

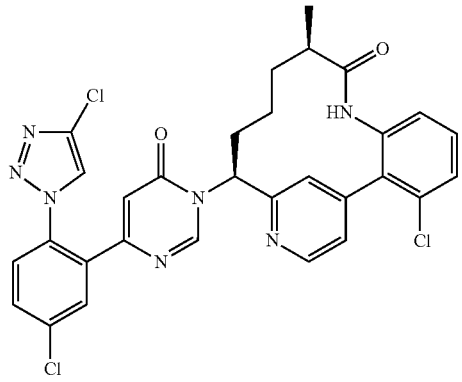 [SMILES: C[C@@H]1CCC[C@H](n2cnc(-c3cc(Cl)ccc3-n3cc(Cl)nn3)cc2=O)c2cc(ccn2)-c2c(Cl)cccc2NC1=O]

(10R,14S)-3-Chloro-14-{4-[5-chloro-2-(4-chloro-1H-1,2,3 -triazol-1-yl)phenyl]-6-oxo-1,6-dihydropyrimidin-1-yl}-10-methyl-8,16-diazatricyclo[13.3.1.0$^{2,7}$]nonadeca -1(19),2(7),3,5,15,17-hexaen-9-one trifluoroacetate was prepared in a similar manner as the procedure described in Example 54 by replacing 2-chloro-3,4-difluoroaniline (0.31 g, 1.88 mmol), with 2-bromo-3-chloroaniline in Example 54B and by replacing 6-(3-chloro -2-fluoro-6-(1H-1,2,3-triazol-1-yl)phenyl)pyrimidin-4-ol, prepared as described in Example 7, with 6-(5-chloro-2-(4-chloro-1H-1,2,3-triazol-1-yl)phenyl)pyrimidin-4-ol, prepared as described in Example 9, in Example 54H. MS(ESI) m/z: 622.1 (M+H)$^+$. $^1$H NMR (400 MHz, methanol-d$_4$) δ 8.95 (br. s., 1H), 8.69 (d, J=5.1 Hz, 1H), 8.39-8.32 (m, 1H), 7.91 (d, J=2.2 Hz, 1H), 7.80-7.73 (m, 1H), 7.72-7.64 (m, 1H), 7.57 (d, J=7.9 Hz, 1H), 7.53-7.46 (m, 2H), 7.42 (br. s., 1H), 7.28 (d, J=7.7 Hz, 1H), 6.40 (d, J=0.7 Hz, 1H), 5.94 (d, J=9.9 Hz, 1H), 2.40 (br. s., 1H), 2.21-1.98 (m, 2H), 1.57 (br. s., 2H), 1.32-1.13 (m, 1H), 0.98 (d, J=5.7 Hz, 3H), 0.69 (br. s., 1H). Analytical HPLC (Method A): RT=9.53 min, purity=100%; Factor XIa Ki=0.63 nM, Plasma Kallikrein Ki=190 nM.

EXAMPLE 105

Preparation of (10R,14S)-3-chloro-14-(4-{5-chloro-2-[4-(trifluoromethyl)-1H-1,2,3triazol-1-yl]phenyl}-6-oxo-1,6-dihydropyrimidin-1-yl)-10-methyl-8,16-diazatricyclo[13.3.1.0²,⁷]nonadeca-1(19),2(7),3,5,15,17-hexaen-9-one

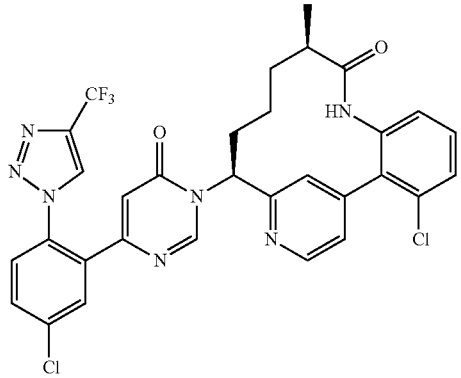 [SMILES: C[C@@H]1CCC[C@H](n2cnc(-c3cc(Cl)ccc3-n3cc(C(F)(F)F)nn3)cc2=O)c2cc(ccn2)-c2c(Cl)cccc2NC1=O]

(10R,14S)-3-Chloro-14-(4-{5-chloro-2[4-(trifluoromethyl)-1H-1,2,3-triazol-1-yl]phenyl}-6-oxo-1,6-dihydropyrimidin-1-yl)-10-methyl-8,16-diazatricyclo[13.3.1.0²,⁷]nonadeca-1(19),2(7),3,5,15,17-hexaen-9-one trifluoroacetate was prepared in a similar manner as the procedure described in Example 54 by using 2-bromo-3-chloroaniline and 6-{5-chloro-2-[4-(trifluoromethyl)-1H-1,2,3-triazol-1-yl]phenyl}pyrimidin-4-ol, prepared as described in Example 15, in Example 54H. MS(ESI) m/z: 654.1 (M+H)⁺. ¹H NMR (400 MHz, CD₃OD) δ 8.90 (br. s., 1H), 8.84 (s, 1H), 8.66 (d, J=5.1 Hz, 1H), 7.93 (d, J=2.0 Hz, 1H), 7.82-7.70 (m, 2H), 7.57 (d, J=7.9 Hz, 1H), 7.49 (t, J=7.8 Hz, 2H), 7.40 (br. s., 1H), 7.28 (d, J=7.7 Hz, 1H), 6.48 (d, J=0.7 Hz, 1H), 6.00-5.88 (m, 1H), 2.39 (br. s., 1H), 2.18-1.97 (m, 2H), 1.56 (br. s., 2H), 1.22 (br. s., 1H), 0.98 (d, J=5.9 Hz, 3H), 0.68 (br. s., 1H). Analytical HPLC (Method A): RT=10.25 min, purity=99.7%.; Factor XIa Ki=0.41 nM, Plasma Kallikrein Ki=200 nM.

EXAMPLE 106

Preparation of methyl N-[(10R,14S)-14-[4-(3-chloro-2,6-difluorophenyl)-6-oxo-1,6-dihydropyrimidin-1-yl]-10-methyl-9-oxo-8,18-diazatricyclo[13.3.1.0²,⁷]nonadeca-1(19),2(7),3,5,15,17-hexaen-5-yl]carbamate

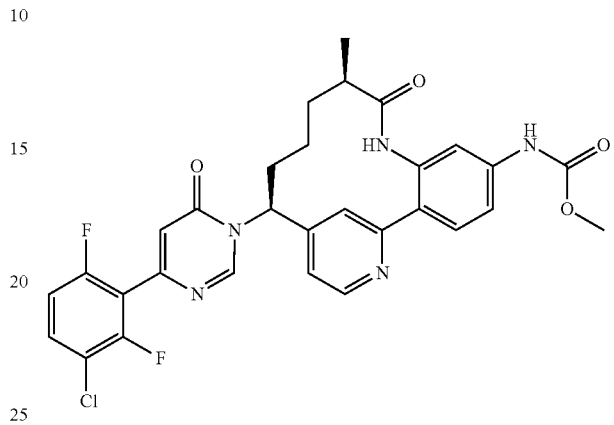

106A. Preparation of tert-butyl N-[(1S)-1-(2-{2-amino-4-[(methoxycarbonyl)amino]phenyl}pyridin-4-yl)but-3-en-1-yl]carbamate To a scintillation vial was added 2-((5-((methoxycarbonyl)amino)-2-(4,4,5,5-tetramethyl-1,3,2-dioxaborolan-2-yl)phenyl)amino)-4,4,5,5-tetramethyl-2-(4,4,5,5-tetramethyl-1,3,2-dioxaborolan-2-yl)-1,3,2-dioxaborolan-2-uide (916 mg, 1.681 mmol), K₂CO₃ (845 mg, 6.11 mmol), water (2.55 mL) and dioxane (10.200 mL) and the mixture heated to 65° C. for 1 h. The mixture was cooled to ambient temperature and (S)-tert-butyl (1-(2-bromopyridin-4-yl)but-3-en-1-yl)carbamate (500 mg, 1.528 mmol), prepared as described in Example 27, was added. The reaction was purged by bubbling through Ar. Tricyclohexylphosphine tetrafluoroborate (56.3 mg, 0.153 mmol) and Pd(OAc)₂ (17.15 mg, 0.076 mmol) were added as solids and the mixture heated to 70° C. overnight and cooled to rt over the weekend. The reaction was degassed and another 27 mg of ligand and 8 mg of Pd(OAc)₂ were added. The reaction was heated at 85° C. for 5h. Reaction mixture is diluted with water/EtOAc, phases separated and aqueous layer extracted again with EtOAc. Combined organics was washed with brine, dried over MgSO₄, filtered and concentrated. The crude product was purified using silica gel chromatography to give tert-butyl N-[(1S)-1-(2-{2-amino-4-[(methoxycarbonyl)amino]phenyl}pyridin-4-yl)but-3-en-1-yl]carbamate (573 mg, 91%) as a off-white foam. MS(ESI) m/z: 413.1 (M+H)⁺.

106B. Preparation of tert-butyl N-[(10R,14S)-5-[(methoxycarbonyl)amino]-10-methyl-9-oxo-8,18-diazatricyclo[13.3.1.0²,⁷]nonadeca-1(19),2,4,6,15,17-hexaen-14-yl]carbamate tert-Butyl N-[(10R,14S)-5-[(methoxycarbonyl)amino]-10-methyl-9-oxo-8,18-diazatricyclo[13.3.1.0²,⁷]nonadeca-1(19),2,4,6,15,17-hexaen-14-yl]carbamate was prepared in a similar manner as the procedures described in Examples 45F to 45H by replacing tert-butyl N-[(1S)-1-(4-{2-amino-4-[(methoxycarbonyl)amino]phenyl}pyridin-2-yl)but-3-en-1-yl]carbamate, with tert-butyl N-[(1S)-1-(2-{2-amino-4-[(methoxycarbonyl)amino]phenyl}pyridin-4-yl)but-3-en-1-yl]carbamate. MS(ESI) m/z: 469.2 (M+H)⁺.

106C. Preparation of methyl N-[(10R,14S)-14-amino-10-methyl-9-oxo-8,18-diazatricyclo[13.3.1.0²,⁷]nonadeca-1(19),2,4,6,15,17-hexaen-5-yl]carbamate To a solution of tert-butyl N-[(10R,14S)-5-[(methoxycarbonyl)amino]-10-methyl -9-oxo-8,18-diazatricyclo[13.3.1.0²,⁷]nonadeca-1(19),2,4,6,15,17-hexaen-14-yl]carbamate (10 mg, 0.021 mmol) in CH$_2$Cl$_2$ (0.5 mL) was added TFA (0.082 mL, 1.067 mmol). The reaction was stirred at rt for 30 min, then concentrated. The residue was redissolved in MeOH, passed through NaHCO$_3$ cartridge and concentrated to remove solvent to give methyl N-[(10R,14S)-14-amino-10-methyl-9-oxo-8,18-diazatricyclo[13.3.1.0²,⁷]nonadeca-1(19),2,4,6,15,17-hexaen-5-yl]carbamate (8 mg, 100%) as a white solid. MS(ESI) m/z: 369.5.

106D. Preparation of methyl N-[(10R,14S)-14-[4-(3-chloro-2,6-difluorophenyl)-6-oxo -1,6-dihydropyrimidin-1-yl]-10-methyl-9-oxo-8,18-diazatricyclo[13.3.1.0²,⁷]nonadeca-1(19),2(7),3,5,15,17-hexaen-5-yl]carbamate (10R,14S)-14-(4-{5-Chloro-2-[4-(trifluoromethyl)-1H-1,2,3-triazol-1-yl]phenyl}-6-oxo-1,6-dihydropyrimidin-1-yl)-5-(2-hydroxypropan-2-yl)-10-methyl-8,16-diazatricyclo[13.3.1.0²,⁷]nonadeca-1(19),2(7),3,5,15,17-hexaen-9-one trifluoroacetate (6.3 mg, 37% yield) was prepared in a similar manner as the procedure described in Example 129 by replacing using methyl N-[(10R,14S)-14-amino-10-methyl-9-oxo-8,18-diazatricyclo[13.3.1.0²,⁷]nonadeca-1(19),2,4,6,15,17-hexaen-5-yl]carbamate (8 mg, 0.022 mmol) and 6-(3-chloro-2,6-difluorophenyl)pyrimidin-4-ol (5.3 mg, 0.022 mmol), prepared as described in Example 4. MS(ESI) m/z: 549.2 (M+H)⁺. ¹H NMR (400 MHz, CD$_3$OD) δ 9.81 (s, 1H), 8.91 (s, 1H), 8.85 (s, 1H), 8.78 (d, J=6.2 Hz, 1H), 8.40 (d, J=1.5 Hz, 1H), 7.79 (dd, J=6.2, 1.8 Hz, 1H), 7.73 (d, J=8.6 Hz, 1H), 7.71-7.63 (m, 2H), 7.60 (dd, J=8.6, 2.2 Hz, 1H), 7.22-7.15 (m, 1H), 6.71 (s, 1H), 5.84-5.75 (m, 1H), 3.84- 3.80 (m, 3H), 2.73 (t, J=5.8 Hz, 1H), 2.58-2.29 (m, 2H), 2.02-1.88 (m, 1H), 1.72-1.41 (m, 2H), 1.18-0.97 (m, 4H). Analytical HPLC (Method A): RT=5.89 min, purity=99.5%; Factor XIa Ki=1.3 nM, Plasma Kallikrein Ki=19 nM.

EXAMPLE 107

Preparation of (10R,14S)-4-fluoro-14-(4-{5-methoxy-2-[4-(trifluoromethyl)-1H-1,2,3-1-yl]phenyl}-6-oxo-1,6-dihydropyrimidin-1-yl)-10-methyl-8,17-diazatricyclo[13.3.1.0²,⁷]nonadeca-1(19),2(7),3,5,15,17-hexaen-9-one

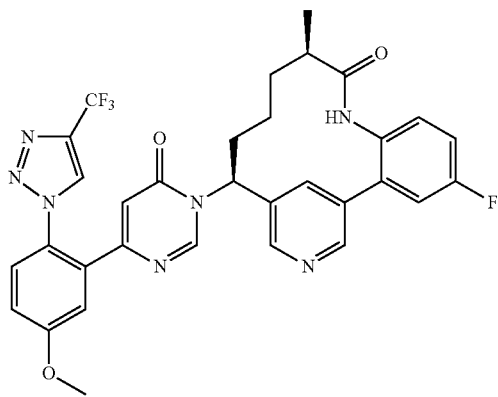 [SMILES: COc1ccc(-n2cc(C(F)(F)F)nn2)c(-c2cc(=O)n([C@H]3CCC[C@@H](C)C(=O)Nc4ccc(F)cc4-c4cncc3c4)cn2)c1]

(10R,14S)-4-Fluoro-14-(4-{5-methoxy-2-[4-(trifluoromethyl)-1H-1,2,3-triazol-1-yl]phenyl}-6-oxo-1,6-dihydropyrimidin-1-yl)-10-methyl-8,17-diazatricyclo[13.3.1.0²,⁷]nonadeca-1(19),2(7),3,5,15,17-hexaen-9-one was prepared in 4% yield as a solid (0.5 mg), via the coupling of 6-{5-methoxy-2-[4-(trifluoromethyl)-1H-1,2,3-triazol-1-yl]phenyl}pyrimidin-4-ol (0.007 g, 0.02 mmol) and (10R,14S)-14-amino-4-fluoro-10-methyl-8,17-diazatricyclo[13.3.1.0²,⁷]nonadeca-1(19),2,4,6,15,17-hexaen-9-one (0.0065 g, 0.02 mmol) using the HATU,DBU coupling methodology described in Examples 45K and 45L. MS(ESI) m/z: 634.2 (M+H)⁺. ¹H NMR (400 MHz, CD$_3$OD) d 8.77-8.75 (m, 1H), 8.70-8.62 (m, 1H), 8.43-8.35 (m, 1H), 7.61-7.56 (m, 2H), 7.53-7.47 (m, 1H), 7.44-7.39 (m, 1H), 7.36-7.24 (m, 3H), 6.46-6.42 (m, 1H), 5.97-5.76 (m, 1H), 3.96 (s, 3H), 2.57-2.40 (m, 2H), 2.35-2.18 (m, 1H), 1.86-1.73 (m, 1H), 1.57-1.37 (m, 2H), 1.16-1.06 (m, 3H), 0.44-0.36 (m, 1H) 2.21-2.12 (m, 1H), 2.00-1.72 (m, 1H), 1.46-1.30 (m, 2H), 0.92-0.74 (d, 3H), 0.46-0.21 (m, 1H). Analytical HPLC (Method A) RT=11.3 min, purity=95%; Factor XIa Ki=142 nM, Plasma Kallikrein Ki=1,400 nM.

EXAMPLE 108

Preparation of (10R,14S)-14-{4-[5-chloro-2-(4-chloro-1H-1,2,3-triazol-1-yl)phenyl]-6-oxo-1,6-dihydropyrimidin-1-yl}-4-fluoro-10-methyl-8,18-diazatricyclo[13.3.1.0²,⁷]nonadeca-1(19),2(7),3,5,15,17-hexaen-9-one

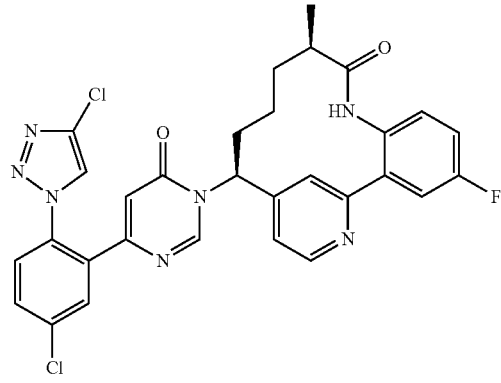 [SMILES: C[C@@H]1CCC[C@H](n2cnc(-c3cc(Cl)ccc3-n3cc(Cl)nn3)cc2=O)c2ccnc(c2)-c2cc(F)ccc2NC1=O]

108A. Preparation of tert-butyl N-[(10R,11E,14S)-4-fluoro-10-methyl-9-oxo-8,18-diazatricyclo[13.3.1.0²,⁷]nonadeca-1(19),2(7),3,5,11,15,17-heptaen-14-yl]carbamate

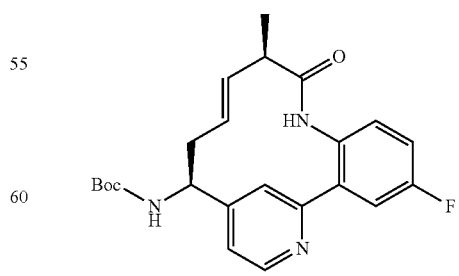

tert-Butyl N-[(10R,11E,14S)-4-fluoro-10-methyl-9-oxo-8,18-diazatricyclo [13.3.1.0²,⁷]nonadeca-1(19),2(7),3,5,11,15,17-heptaen-14-yl]carbamate (59 mg, 68%) as a clear film, was made in a similar manner as Example 28C, substituting tert-butyl N-[(1S)-1-(2-bromopyridin-4-yl)but-3-en-1-yl]carbamate for tert-butyl N-[(1S)-1-(4-chloropyridin-2-yl)but-3-en-1-yl]carbamate. MS(ESI) m/z: 412.5 (M+H)+.

108B. Preparation of (10R,14S)-14-amino-4-fluoro-10-methyl-8,18-diazatricyclo [13.3.1.0²,⁷]nonadeca-1(19),2,4,6,15,17-hexaen-9-one

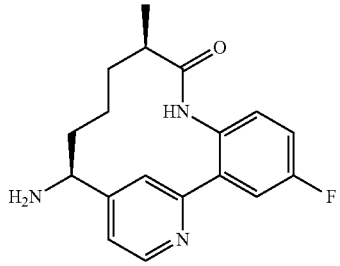 [SMILES: C[C@@H]1CCC[C@H](N)c2ccnc(c2)-c2cc(F)ccc2NC1=O]

tert-Butyl N-[(10R,11E,14S)-4-fluoro-10-methyl-9-oxo-8,18-diazatricyclo [13.3.1.0²,⁷]nonadeca-1(19),2(7),3,5,11,15,17-heptaen-14-yl]carbamate (0.059 g, 0.143 mmol) was hydrogenated at 55 psi in EtOH (10 ml) in presence of PtO₂ (15 mg). After a total of 8 h, the reaction was filtered through CELITE® and the filtrate was concentrated to give 53 mg of a tan foam. The foam was heated to 150° C. for 30 min in microwave in MeOH (1 ml) / water (4 ml). The reaction mixture was concentrated and the residue taken up in EtOAc/DCM, dried (MgSO₄), filtered and concentrated to give (10R,14S)-14-amino-4-fluoro-10-methyl-8,18-diazatricyclo[13.3.1.0²,⁷]nonadeca-1(19),2,4,6,15,17-hexaen-9-one (44 mg, 98%) as a clear film. MS(ESI) m/z: 314.5 (M+H)+. ¹H NMR (400 MHz, CDCl₃) δ 8.53 (d, J=5.1 Hz, 1H), 7.43-7.31 (m, 3H), 7.27 (d, J=3.5 Hz, 1H), 7.18-7.05 (m, 2H), 4.04 (dd, J=9.4, 4.3 Hz, 1H), 2.53-2.36 (m, 1H), 2.03-1.87 (m, 1H), 1.60-1.37 (m, 5H), 1.20-1.12 (m, 3H).

108C. Preparation of (10R,14S)-14-{4-[5-chloro-2-(4-chloro-1H-1,2,3-triazol-1-yl)phenyl]-6-oxo-1,6-dihydropyrimidin-1-yl}-4-fluoro-10-methyl-8,18-diazatricyclo[13.3.1.0²,⁷]nonadeca-1(19),2(7),3,5,15,17-hexaen-9-one (10R,14S)-14-{4-[5-Chloro-2-(4-chloro-1H-1,2,3-triazol-1-yl)phenyl]-6-oxo-1,6dihydropyrimidin-1-yl} -4-fluoro-10-methyl-8,18-diazatricyclo[13.3.1.0²,⁷]nonadeca- -1(19),2(7),3,5,15,17-hexaen-9-one (8 mg, 29%) was prepared in a manner similar to Example 129, by using (14S)-14-amino-4-fluoro-10-methyl-11-oxa-8,16-diazatricyclo [13.3.1.0²,⁷] nonadeca-1(19),2,4,6,15,17-hexaen-9-one bis-trifluoroacetate (Diastereomer A). MS(ESI) m/z: 604.5 (M+H)+. ¹H NMR (400 MHz, CD₃OD) δ 8.65 (d, J=5.7 Hz, 1H), 8.43 (s, 1H), 8.28 (s, 1H), 8.03 (d, J=1.3 Hz, 1H), 7.77 (d, J=2.4 Hz, 1H), 7.68-7.61 (m, 1H), 7.59-7.47 (m, 2H), 7.36 (dd, J=5.7, 1.8 Hz, 1H), 7.32-7.24 (m, 2H), 6.30 (d, J=0.7 Hz, 1H), 5.61 (dd, J=12.5, 4.4 Hz, 1H), 2.57-2.43 (m, 1H), 2.37-2.22 (m, 1H), 2.19-2.05 (m, 1H), 1.84-1.71 (m, 1H), 1.42-1.27 (m, 2H), 1.16 (br. s., 1H), 0.94 (d, J=6.8 Hz, 3H). Analytical HPLC (Method A) RT=6.81 min, purity=100%; Factor XIa Ki=0.21 nM, Plasma Kallikrein Ki=13 nM.

EXAMPLE 109

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,18-diazatricyclo[13.3.1.0²,⁷]nonadeca-1(19),2(7),3,5,15,17-hexaen-9-one

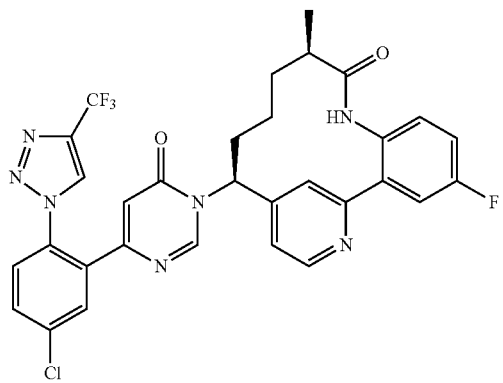 [SMILES: C[C@@H]1CCC[C@H](n2cnc(-c3cc(Cl)ccc3-n3cc(C(F)(F)F)nn3)cc2=O)c2ccnc(c2)-c2cc(F)ccc2NC1=O]

(10R,14S)-14-(4-{5-Chloro-2-[4-(trifluoromethyl)-1H-1,2,3-triazol-1-yl]phenyl}-6-oxo-1,6-dihydropyrimidin-1-yl)-4-fluoro-10-methyl-8,18-diazatricyclo[13.3.1.0²,⁷]nonadeca-1(19),2(7),3,5,15,17-hexaen-9-one (0.167g, 40.2%), a white solid, was prepared in a similar manner as Example 108, using 6-[5-chloro-2-(4-chloro-1H-1,2,3-triazol-1-yl) phenyl]pyrimidin-4-ol, as described in Example 9. Further chiral HPLC chromatography (Column: CHIRALPAK® IC, 30×250 mm, 5 g; Mobile Phase: 30% MeOH/70% CO₂; Flow Conditions: 85 ml/min, 150 Bar, 40° C.) afforded the title compound as the major diastereomer. MS(ESI) m/z: 638.1 (M+H)+. ¹H NMR (400 MHz, CD₃OD) δ 8.83 (d, J=0.9 Hz, 1H), 8.66 (d, J=5.7 Hz, 1H), 8.38 (s, 1H), 7.90 (d, J=2.2 Hz, 2H), 7.82-7.75 (m, 1H), 7.73-7.69 (m, 1H), 7.58 (dd, J=9.0, 2.9 Hz, 1H), 7.39-7.25 (m, 2H), 7.21 (dd, J=5.3, 1.8 Hz, 1H), 6.50 (d, J=0.7 Hz, 1H), 5.75 (dd, J=12.9, 3.9 Hz, 1H), 2.56 (t, J=6.5 Hz, 1H), 2.39 (dd, J=8.0, 3.4 Hz, 1H), 2.20-2.10 (m, 1H), 2.00-1.88 (m, 1H), 1.68-1.54 (m, 1H), 1.44 (d, J=8.8 Hz, 1H), 1.33 (br. s., 1H), 1.13 (d, J=7.0 Hz, 3H). Analytical HPLC (Method A) RT=7.62 min, purity=98%.

EXAMPLE 110

Preparation of methyl N-[(10R,14S)-14-{4-[5-(difluoromethoxy)-2-[4-(trifluoromethyl)-1H-1,2,3-triazol-1-yl]phenyl]-6-oxo-1,6-dihydropyrimidin-1-yl}-10-methyl-9-oxo-8,16-diazatricyclo[13.3.1.0²,⁷]nonadeca-1(19),2(7),3,5,15,17-hexaen-5-yl]carbamate

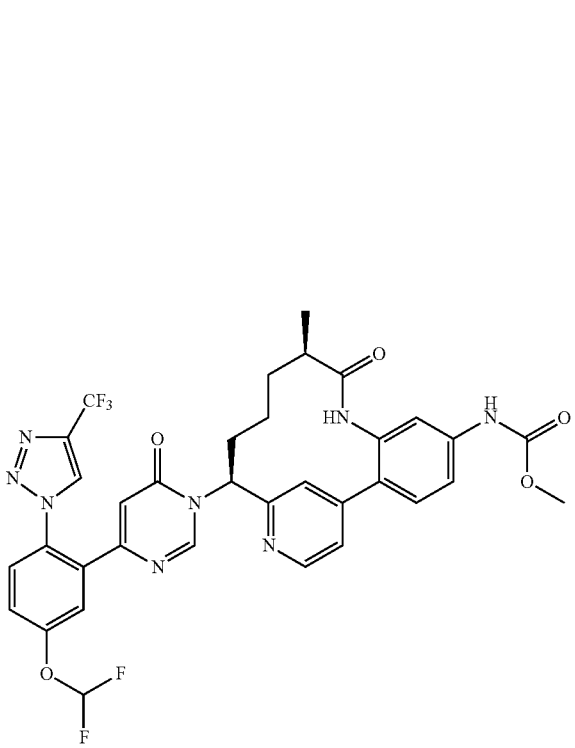 [SMILES: COC(=O)Nc1ccc2c(c1)NC(=O)[C@H](C)CCC[C@H](n1cnc(-c3cc(OC(F)F)ccc3-n3cc(C(F)(F)F)nn3)cc1=O)c1cc-2ccn1]

Using the procedures described in Examples 45K and 45L, methyl N-[(10R,14S) -14-{4-[5-(difluoromethoxy)-2-[4-(trifluoromethyl)-1H-1,2,3-triazol-1-yl]phenyl]-6-oxo-1,6-dihydropyrimidin-1-yl}-10-methyl-9-oxo-8,16-diazatricyclo[13.3.1.0²,⁷]nonadeca -1(19),2(7),3,5,15,17-hexaen-5-yl]carbamate was prepared by coupling 645-(difluoromethoxy)-2-(4-(trifluoromethyl)-1H-1,2,3-triazol-1-yl)phenyl)pyrimidin-4(3H) -one and methyl N-[(10R,14S)-14-amino-10-methyl-9-oxo-8,16-diazatricyclo[13.3.1.0²,⁷]nonadeca-1(19),2(7),3,5,15,17-hexaen-5-yl]carbamate. MS m/z=725.1 (M+H).+¹H NMR (500 MHz, DMSO-d₆) δ 9.93-9.89 (m, 1H), 9.76-9.73 (m, 1H), 9.22-9.20 (m, 1H), 8.87-8.83 (m, 1H), 8.56-8.52 (m, 1H), 7.88-7.82 (m, 1H), 7.68-7.61 (m, 2H), 7.58-7.53 (m, 1H), 7.51-7.46 (m, 2H), 7.40-7.31 (m, 2H), 6.43-6.40 (m, 1H), 5.96-5.81 (m, 1H), 3.70 (s, 3H), 2.24-2.15 (m, 1H), 2.02-1.90 (m, 1H), 1.85-1.69 (m, 1H), 1.46-1.29 (m, 2H), 0.87-0.77 (d, 3H), 0.45-0.22 (m, 1H). Analytical HPLC (Method B) RT=1.8 min, purity=96%; Factor XIa Ki=14 nM.

EXAMPLE 111

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-3-fluoro-10-methyl-8,16-diazatricyclo [13.3.1.0²,⁷]nonadeca-1(19),2(7),3,5,15,17-hexaen-9-one

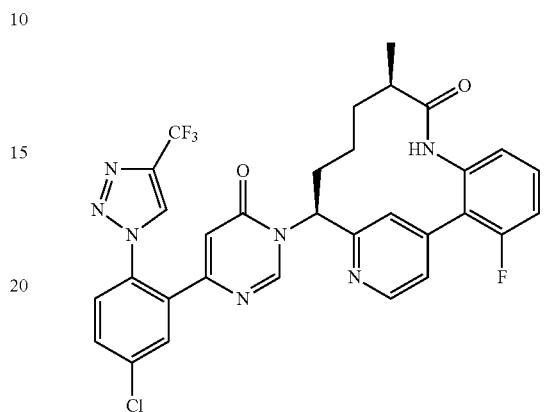

111A. Preparation of (10R,14S)-14-amino-3-fluoro-10-methyl-8,16-diazatricyclo [13.3.1.0²,⁷]nonadeca-1(19),2,4,6,15,17-hexaen-9-one (10R,14S)-14-Amino-3-fluoro-10-methyl-8,16-diazatricyclo[13.3.1.0²,⁷]nonadeca -1(19),2,4,6,15,17-hexaen-9-one was prepared according to the procedure described in Example 54B, by replacing, 2-chloro-3,4-difluoroaniline with 2-bromo-3-fluoroaniline and then the procedure described in Example 54C was followed.

111B. Preparation of (10R,14S)-14-(4-{5-chloro-2-[4-(trifluoromethyl)-1H-1,2,3-triazol 1-yl]phenyl}-6-oxo-1,6-dihydropyrimidin-1-yl)-3-fluoro-10-methyl-8,16-diazatricyclo [13.3.1.0²,⁷]nonadeca-1(19),2(7),3,5,15,17-hexaen-9-one trifluoroacetate (10R,14S)-14-(4-{5-Chloro-2-[4-(trifluoromethyl)-1H-1,2,3-triazol-1-yl]phenyl}-6-oxo-1,6-dihydropyrimidin-1-yl)-3-fluoro-10-methyl-8,16-diazatricyclo[13.3.1.0²,⁷]nonadeca-1(19),2(7),3,5,15,17-hexaen-9-one trifluoroacetate (0.05 g, 76% yield) was prepared in a similar manner as the procedure described in Example 135, by using (10R,14S)-14-amino-3-fluoro-10-methyl-8,16-diazatricyclo[13.3.1.0²,⁷]nonadeca -1(19),2,4,6,15,17-hexaen-9-one (0.030 g, 0.097 mmol). MS(ESI) m/z: 638.5 (M+H)⁺. ¹H NMR (400 MHz, CD₃OD) δ 8.88 (s, 1H), 8.81 (d, J=0.7 Hz, 1H), 8.63 (d, J=5.3 Hz, 1H), 7.89 (d, J=2.2 Hz, 1H), 7.77-7.73 (m, 1H), 7.71-7.67 (m, 1H), 7.60 (s, 1H), 7.52-7.44 (m, 2H), 7.23 (td, J=9.1, 1.0 Hz, 1H), 7.11 (d, J=7.9 Hz, 1H), 6.43 (d, J=0.7 Hz, 1H), 5.96 (dd, J=12.4, 5.0 Hz, 1H), 2.63-2.52 (m, 1H), 2.22-2.11 (m, 1H), 2.08-1.97 (m, 1H), 1.81 (t, J=12.5 Hz, 1H), 1.53-1.41 (m, 1H), 1.35-1.19 (m, 1H), 0.94 (d, J=6.8 Hz, 3H), 0.85-0.68 (m, 1H). ¹⁹F NMR (376 MHz, CD₃OD) δ −62.54 (s), −77.68 (s), −117.05 (s). Analytical HPLC (Method A): RT=10.04 min, 100% purity; Factor XIa Ki=0.17 nM, Plasma Kallikrein Ki=28 nM.

EXAMPLE 112

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,18-diazatricyclo [13.3.1.0$^{2,7}$]nonadeca-1(19),2(7),3,5,15,17-hexaene-5-carbonitrile

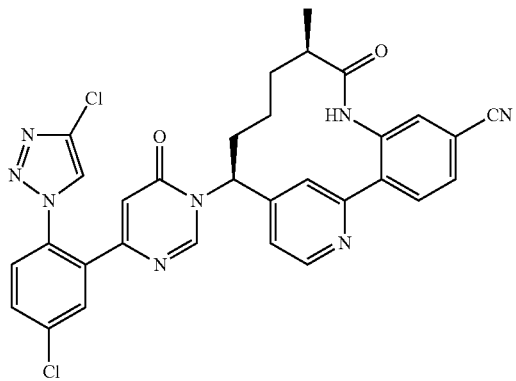 [SMILES: C[C@@H]1CCC[C@H](n2cnc(-c3cc(Cl)ccc3-n3cc(Cl)nn3)cc2=O)c2ccnc(c2)-c2ccc(C#N)cc2NC1=O]

112A. Preparation of (10R,14S)-14-amino-10-methyl-9-oxo-8,18-diazatricyclo [13.3.1.0$^{2,7}$]nonadeca-1(19),2(7),3,5,15,17-hexaene-5-carbonitrile (10R,14S)-14-Amino-10-methyl-9-oxo-8,18-diazatricyclo[13.3.1.0$^{2,7}$]nonadeca-1(19),2(7),3,5,15,17-hexaene-5-carbonitrile was prepared in a similar manner as the procedures described in Example 30 by replacing methyl N-[(10R,14S)-14-{[(tert -butoxy)carbonyl]amino}-10-methyl-9-oxo-8,16-diazatricyclo [13.3.1.0$^{2,7}$]nonadeca -1(19),2(7),3,5,15,17-hexaen-5-yl] carbamate with tert-butyl N-[(10R,14S)-5-[(methoxycarbonyl)amino]-10-methyl-9-oxo-8,18-diazatricyclo[13.3.1.0$^{2,7}$]nonadeca -1(19),2,4,6,15,17-hexaen-14-yl]carbamate, prepared as described in Example 106B. MS(ESI) m/z: 469.2 (M+H)$^+$.

112B. Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,18-diazatricyclo [13.3.1.0$^{2,7}$]nonadeca-1(19),2(7),3,5,15,17-hexaene-5-carbonitrile (10R,14S)-14-{4-[5-Chloro-2-(4-chloro-1H-1,2,3-triazol-1-yl)phenyl]-6-oxo-1,6-dihydropyrimidin-1-yl}-10-methyl-9-oxo-8,18-diazatricyclo[13.3.1.0$^{2,7}$]nonadeca -1(19),2(7),3,5,15,17-hexaene-5-carbonitrile trifluoroacetate (10.7 mg, 38% yield) was prepared in a similar manner as the procedure described in Example 129 by using (10R,14S)-14-amino-10-methyl-9-oxo-8,18-diazatricyclo [13.3.1.0$^{2,7}$]nonadeca -1(19),2(7),3,5,15,17-hexaene-5-carbonitrile (12.3 mg, 0.038 mmol). MS(ESI) m/z: 611.1 (M+H)$^+$. $^1$H NMR (400 MHz, methanol-d$_4$) d 8.78 (d, J=5.7 Hz, 1H), 8.56 (s, 1H), 8.39-8.35 (m, 1H), 8.13 (s, 1H), 7.98 (d, J=7.9 Hz, 1H), 7.89-7.83 (m, 2H), 7.76-7.68 (m, 2H), 7.66-7.62 (m, 1H), 7.46 (dd, J=5.6, 1.7 Hz, 1H), 6.38 (s, 1H), 5.69 (dd, J=12.5, 4.4 Hz, 1H), 2.66-2.55 (m, 1H), 2.40-2.14 (m, 2H), 1.92-1.80 (m, 1H), 1.55-1.38 (m, 2H), 1.18 (br. s., 1H), 1.02 (d, J=7.0 Hz, 3H). Analytical HPLC (Method A): RT=7.61 min, purity=99.4%; Factor XIa Ki=0.22 nM, Plasma Kallikrein Ki=19 nM.

EXAMPLE 113

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-9-oxo-8,18-diazatricyclo [13.3.1.0$^{2,7}$]nonadeca-1(19),2(7),3,5,15,17-hexaene-5-carbonitrile

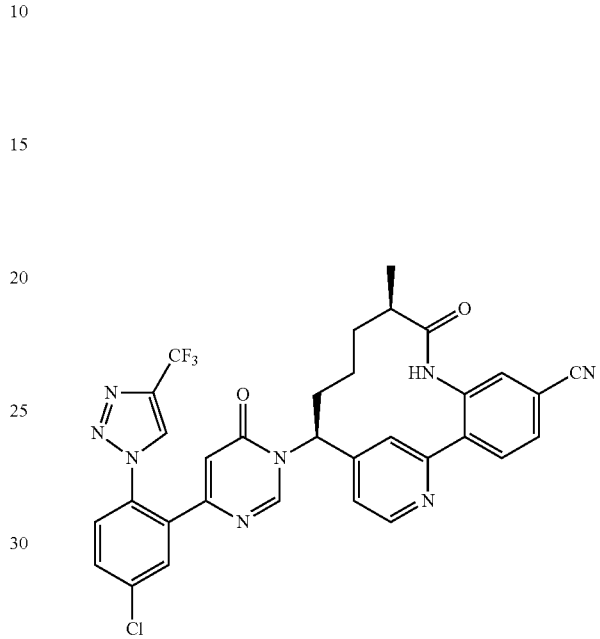

(10R,14S)-14-(4-{5-Chloro-2-[4-(trifluoromethyl)-1H-1,2,3-triazol-1-yl]phenyl}-6-oxo-1,6-dihydropyrimidin-1-yl)-10-methyl-9-oxo-8,18-diazatricyclo[13.3.1.0$^{2,7}$]nonadeca-1(19),2(7),3,5,15,17-hexaene-5-carbonitrile trifluoroacetate (12.6 mg, 42% yield) was prepared in a similar manner as the procedure described in Example 129 by using (10R,14S)-14-amino-10-methyl-9-oxo-8,18-diazatricyclo [13.3.1.0$^{2,7}$]nonadeca -1(19),2(7),3,5,15,17-hexaene-5-carbonitrile (12.3 mg, 0.038 mmol) and 6-{5-chloro-2-[4(trifluoromethyl)-1H-1,2,3-triazol-1-yl]phenyl}pyrimidin-4-ol, prepared as described in Example 15. MS(ESI) m/z: 645.1 (M+H)$^+$. $^1$H NMR (400 MHz, CD$_3$OD) d 8.85 (d, J=0.7 Hz, 1H), 8.75 (d, J=5.5 Hz, 1H), 8.50 (s, 1H), 8.08 (d, J=1.1 Hz, 1H), 7.97 (d, J=8.1 Hz, 1H), 7.90-7.82 (m, 2H), 7.78-7.72 (m, 1H), 7.71-7.63 (m, 2H), 7.39 (dd, J=5.6, 1.7 Hz, 1H), 6.47-6.41 (m, 1H), 5.69 (dd, J=12.7, 4.3 Hz, 1H), 2.66-2.53 (m, 1H), 2.39-2.26 (m, 1H), 2.23-2.10 (m, 1H), 1.93-1.80 (m, 1H), 1.56-1.37 (m, 2H), 1.29-1.11 (m, 1H), 1.03 (d, J=7.0 Hz, 3H). Analytical HPLC (Method A): RT=8.42 min, purity=97.9%.; Factor XIa Ki=0.19 nM, Plasma Kallikrein Ki=15 nM.

EXAMPLE 114

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-4-carbonitrile trifluoroacetate

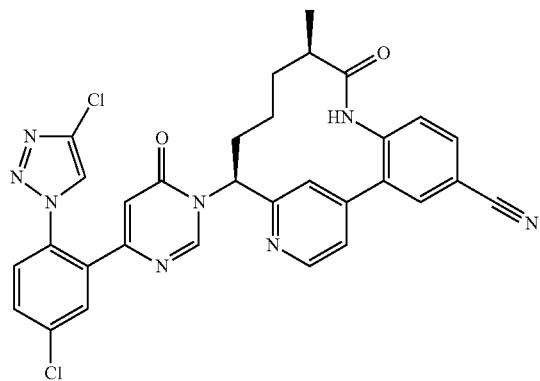 [SMILES: C[C@@H]1CCC[C@H](n2cnc(-c3cc(Cl)ccc3-n3cc(Cl)nn3)cc2=O)c2cc(ccn2)-c2cc(C#N)ccc2NC1=O]

(10R,14S)-14-{4-[5-Chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca -1(19),2(7),3,5,15,17-hexaene-4-carbonitrile trifluoroacetate (9.08 mg, 29% yield) was prepared in a similar manner as the procedure described in Example 126 by replacing methyl (10R,14 S)-14-amino-10-methyl-9-oxo-8,16-diazatricyclo[13.3.1.0$^{2,7}$]nonadeca -1(19),2(7),3,5,15,17-hexaene-4-carboxylate with (10R,14S)-14-amino-10-methyl-9-oxo -8,16-diazatricyclo[13.3.1.0$^{2,7}$]nonadeca-1(19),2(7),3,5,15,17-hexaene-4-carbonitrile, which was prepared in a similar manner as (10R,14S)-14-amino-10-methyl-9-oxo-8,16-diazatricyclo[13.3.1.0$^{2,7}$]nonadeca-1(19),2(7),3,5,15,17-hexaene-5-carbonitrile, prepared as described in Example 30. MS(ESI) m/z: 611.1 (M+H)$^+$. $^1$H NMR (400 MHz, CD$_3$OD) δ 8.99 (s, 1H), 8.71 (d, J=5.1 Hz, 1H), 8.34 (s, 1H), 7.98 (d, J=2.0 Hz, 1H), 7.88 (d, J=2.2 Hz, 1H), 7.84 (dd, J=8.3, 1.9 Hz, 1H), 7.75-7.69 (m, 2H), 7.67-7.62 (m, 1H), 7.49 (dd, J=5.1, 1.5 Hz, 1H), 7.41 (d, J=8.1 Hz, 1H), 6.35 (s, 1H), 6.02 (dd, J=12.5, 5.1 Hz, 1H), 2.75-2.65 (m, 1H), 2.28-2.17 (m, 1H), 2.08-1.88 (m, 2H), 1.59-1.40 (m, 2H), 0.94 (d, J=7.0 Hz, 3H), 0.60 (br. s., 1H). Analytical HPLC (Method A): RT=9.18 min, purity>99%; Factor XIa Ki=0.8 nM, Plasma Kallikrein Ki=26 nM.

EXAMPLE 115

Preparation of methyl N-[(10R,14S)-14-(4-{5-methoxy-2-[4-(trifluoromethyl)-1H-1,2,3-triazol-1-yl]phenyl}-6-oxo-1,6-dihydropyrimidin-1-yl)-10-methyl-9-oxo-8,16-diazatricyclo[13.3.1.0$^{2,7}$]nonadeca-1(19),2(7),3,5,15,17-hexaen-5-yl]carbamate

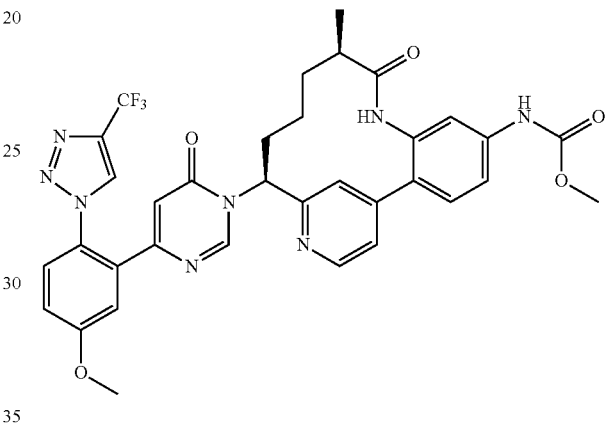

Using the procedures described in Examples 45K and 45L, methyl N-[(10R,14S) -14-(4-{5-methoxy-2-[4-(trifluoromethyl)-1H-1,2,3-triazol-1-yl]phenyl}-6-oxo-1,6-dihydropyrimidin-1-yl)-10-methyl-9-oxo-8,16-diazatricyclo [13.3.1.0$^{2,7}$]nonadeca -1(19),2(7),3,5,15,17-hexaen-5-yl] carbamate was prepared by coupling 6-(5-methoxy-2-(4-(trifluoromethyl)-1H-1,2,3-triazol-1-yl)phenyl)pyrimidin-4(3H)-one and methyl N -[(10R,14S)-14-amino-10-methyl-9-oxo-8,16-diazatricyclo[13.3.1.0$^{2,7}$]nonadeca -1(19),2(7),3,5,15,17-hexaen-5-yl]carbamate. MS m/z =689.3. $^1$H NMR (500 MHz, DMSO-d$_6$) δ 9.93-9.88 (m, 1H), 9.82-9.76 (m, 1H), 9.09-9.05 (m, 1H), 8.81-8.76 (m, 1H), 8.55-8.50 (m, 1H), 7.67-7.60 (m, 2H), 7.51-7.42 (m, 2H), 7.38-7.32 (m, 3H), 7.29-7.23 (m, 1H), 6.38-6.33 (m, 1H), 5.92-5.83 (m, 1H), 3.90 (s, 3H), 3.71-3.64 (s, 3H), 2.69 - 2.59 (m, 1H), 2.21-2.10 (m, 1H), 2.00-1.89 (m, 1H), 1.85-1.74 (m, 1H), 1.44-1.29 (m, 2H), 0.88-0.78 (d, 3H), 0.46-0.28 (m, 1H). Analytical HPLC (Method B) RT=1.75 min, purity=100%; Factor XIa Ki=0.47 nM, Plasma Kallikrein Ki=47 nM.

EXAMPLE 116

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,16,18-triazatricyclo[13.3.1.0$^{2,7}$]nonadeca-1(19),2(7),3,5,15,17-hexaen-9-one

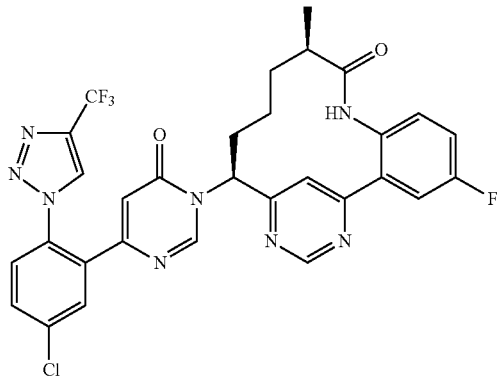

116A. Preparation of ethyl 4-{[(tert-butoxy)carbonyl]amino}-3-oxohept-6-enoate

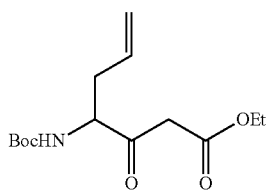 [SMILES: C=CCC(NC(=O)OC(C)(C)C)C(=O)CC(=O)OCC]

To a solution of Boc-2-allylglycine (8 g, 37.2 mmol) in THF (50 mL) was added CDI (7.23 g, 44.6 mmol) portionwise, and the reaction was stirred at rt overnight to give a solution of tert-butyl (1-(1H-imidazol-1-yl)-1-oxopent-4-en-2-yl)carbamate. In a separate RBF, to 3-ethoxy-3-oxopropanoic acid (7.37 g, 55.8 mmol) in THF (20 ml), at 0° C. was added 2 M iPrMgCl in THF (55.8 ml, 112 mmol) dropwise through syringe pump, then the reaction was allowed to warm to rt and then stirred for 1 h. After this time, the solution was cooled to 0° C., and a solution of tert-butyl (1-(1H-imidazol-1-yl)-1-oxopent-4-en-2-yl)carbamate cooled at 0° C. was then added through cannula. The reaction mixture was allowed to warm to rt and stirred for 16 h. After this time, the reaction was neutralized with aq 1 N HCl. The resulting solution was extracted with Et$_2$O (3×100 ml), washed with brine, dried over MgSO$_4$, filtered and concentrated. Purification with normal phase chromatography afforded ethyl 4-{[(tert-butoxy)carbonyl]amino}-3-oxohept-6-enoate (6.55 g, 62%) as a white solid product. MS(ESI) m/z: 308.1 (M+Na)$^+$.

116B. Preparation of tert-butyl N-[1-(6-hydroxypyrimidin-4-yl)but-3-en-1-yl]carbamate

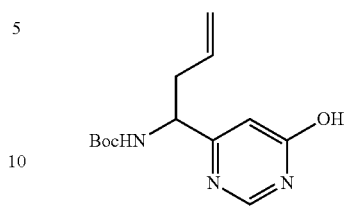

In a 200 ml RBF at rt, to NaOMe (25 wt% in MeOH) (22.30 g, 103 mmol) was added formimidamide, AcOH (5.37 g, 51.6 mmol), followed by ethyl 4-((tert-butoxycarbonyl)amino)-3-oxohept-6-enoate (10 g, 36.9 mmol), prepared as described in Example 116A. The reaction was stirred at rt for 2 days, then concentrated to remove MeOH, and sat aq NH$_4$Cl was then added. The pH was adjusted to pH 7-8 by adding aq 1 N HCl. The solution was extracted with DCM several times, and the combined DCM phase was washed with brine, dried over MgSO$_4$, filtered and concentrated. Purification by normal phase chromatography afforded tert-butyl N-[4-(6-hydroxypyrimidin-4-yl)but-3-en-1-yl]carbamate (3.44 g, 35%) as a pale yellow solid. MS(ESI) m/z: 266.4 (M+H)$^+$.

116C. Preparation of tert-butyl N-[1-(6-chloropyrimidin-4-yl)but-3-en-1-yl]carbamate

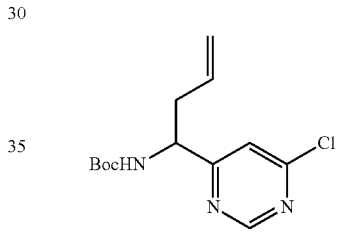

tert-Butyl N-[1-(6-hydroxypyrimidin-4-yl)but-3-en-1-yl]carbamate (3.44 g, 12.97 mmol), prepared as described in Example 116B, and N,N-diethylaniline (4.15 ml, 25.9 mmol) in toluene (64.8 ml) was cooled 0° C., PCl$_3$ (3.64 ml, 38.9 mmol) was added, and the solution was heated to 100° C. and stirred at 100° C. for 30 min. then cooled to rt, diluted with Et$_2$O, washed with water and brine, dried over MgSO$_4$, filtered and concentrated. Purification using normal phase chromatography afforded tert-butyl N-[1-(6-chloropyrimidin-4-yl)but-3-en-1-yl]carbamate (2.77 g, 75%) as a pale yellow solid. (ESI) m/z: 284.4 (M+H)$^+$.

116D. Preparation of tert-butyl N-[1-(6-{5-fluoro-2-[(2R)-2-methylbut-3-enamido]phenyl}pyrimidin-4-yl)but-3-en-1-yl]carbamate

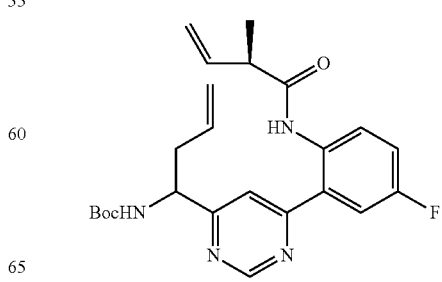

tert-Butyl N-[1-(6-{5-fluoro-2-[(2R)-2-methylbut-3-enamido]phenyl}pyrimidin-4-yl)but-3-en-1-yl]carbamate (172 mg, 37% over 2 steps) was prepared in a similar manner as described in Example 28B, by replacing tert-butyl N-[(1S)-1-[4-(2-amino-5-fluorophenyl)pyridin-2-yl]but-3-en-1-yl]carbamate with tert-butyl N-[1-(6-chloropyrimidin-4-yl)but-3-en-1-yl]carbamate.

116E1 and 116E2. Preparation of tert-butyl N-[(10R,11E)-4-fluoro-10-methyl-9-oxo -8,16,18-triazatricyclo[13.3.1.0²,⁷]nonadeca-1(19),2,4,6,11,15,17-heptaen-14-yl]carbamate

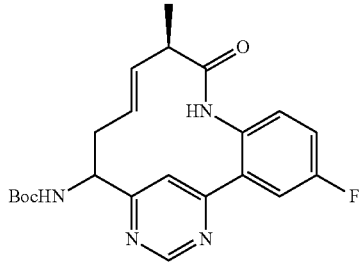 [SMILES: C[C@@H]1/C=C/CC(NC(=O)OC(C)(C)C)c2cc(ncn2)-c2cc(F)ccc2NC1=O]

A solution of tert-butyl N-[1-(6-{5-fluoro-2-[(2R)-2-methylbut-3-enamido]phenyl}pyrimidin-4-yl)but-3-en-1-yl]carbamate (172 mg, 0.390 mmol), pTsOH (82 mg, 0.430 mmol) in EtOAc (100 mL) was heated to 75° C. while bubbling Ar through the solution. After 15 min, Second Generation Grubbs Catalyst (133 mg, 0.156 mmol) was added and the solution was stirred at 75° C. under Ar for 36 h. The reaction was cooled to rt. Reaction mixture was quenched with sat aq NaHCO₃. The organic phase was separated and washed with brine, dried over MgSO₄, filtered and concentrated. Purification with normal phase chromatography, followed by reverse phase chromatography afforded as the fast eluting isomer 116E1 tert-butyl N-[(10R,11E)-4-fluoro-10-methyl-9-oxo-8,16,18-triazatricyclo[13.3.1.0²,⁷]nonadeca-1(19),2,4,6,11,15,17-heptaen-14-yl]carbamate (8 mg, 5%) (ESI) m/z: 413.5 (M+H)⁺; and as the slow eluting isomer 116E2 116E1 tert-butyl N-[(10R,11E)-4-fluoro-10-methyl-9-oxo-8,16,18-triazatricyclo[13.3.1.0²,⁷]nonadeca-1(19),2,4,6,11,15,17-heptaen-14-yl]carbamate (6 mg, 4%); (ESI) m/z: 413.5 (M+H)⁺.

116F. Preparation of (10R,14S)-14-(4-{5-chloro-2-[4-(trifluoromethyl)-1H-1,2,3-triazol -1-yl]phenyl}-6-oxo-1,6-dihydropyrimidin-1-yl)-4-fluoro-10-methyl-8,16,18-triazatricyclo [13.3.1.0²,⁷]nonadeca-1(19),2(7),3,5,15,17-hexaen-9-one (10R,14S)-14-(4-{5-Chloro-2-[4-(trifluoromethyl)-1H-1,2,3-triazol-1-yl]phenyl}-6-oxo-1,6-dihydropyrimidin-1-yl)-4-fluoro-10-methyl-8,16,18-triazatricyclo[13.3.1.0²,⁷]nonadeca-1(19),2(7),3,5,15,17-hexaen-9-one (0.0035 g, 39%) was prepared in a similar manner as the procedure described in Example 78B, by replacing (10R,14S)-14-amino -4,10-dimethyl-8,16-diazatricyclo[13.3.1.0²,⁷]nonadeca-1(19),2,4,6,15,17-hexaen-9-one, with (10R)-14-amino-4-fluoro-10-methyl-8,16,18-triazatricyclo[13.3.1.0²,⁷]nonadeca -1(19),2,4,6,15,17-hexaen-9-one, prepared in 2 steps from Example 116E1. MS(ESI) m/z: 639.0 (M+H)⁺. ¹H NMR (500 MHz, CD₃OD) δ 9.21 (d, J=1.4 Hz, 1H), 8.88 (s, 1H), 8.85 (d, J=0.8 Hz, 1H), 7.96 (d, J=1.4 Hz, 1H), 7.93 (d, J=2.5 Hz, 1H), 7.81-7.77 (m, 1H), 7.74-7.71 (m, 1H), 7.68 (dd, J=9.1, 2.8 Hz, 1H), 7.37-7.28 (m, 2H), 6.47 (d, J=0.8 Hz, 1H), 6.05 (dd, J=12.2, 5.1 Hz, 1H), 2.77 (br. s., 1H), 2.32-2.23 (m, 1H), 2.11-2.00 (m, 2H), 1.66-1.54 (m, 2H), 0.99 (d, J=6.9 Hz, 3H), 0.71 (br. s., 1H). Analytical HPLC (Method A). RT=9.11 min, 99% purity; Factor XIa Ki=1.0 nM, Plasma Kallikrein Ki=96 nM.

EXAMPLE 117

Preparation of (10R,14S)-14-{4-[5 -chloro-2-(1,2,3 -thiadiazol-4-yl)phenyl]-6-oxo-1,6-dihydropyrimidin-1-yl}-4-fluoro-10-methyl-8,16-diazatricyclo [13.3.1.0²,⁷]nonadeca -1(19),2(7),3,5,15,17-hexaen-9-one

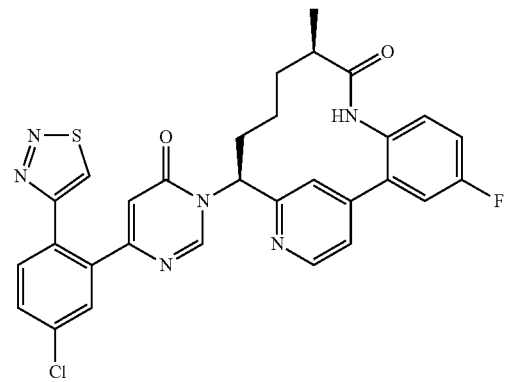 [SMILES: C[C@@H]1CCC[C@H](n2cnc(-c3cc(Cl)ccc3-c3csnn3)cc2=O)c2cc(ccn2)-c2cc(F)ccc2NC1=O]

117A. Preparation of 1-[4-chloro-2-(6-methoxypyrimidin-4-yl)phenyl]ethan-1-one

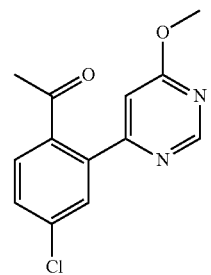 [SMILES: COc1cc(-c2cc(Cl)ccc2C(C)=O)ncn1]

A solution of 4-(2-bromo-5-chlorophenyl)-6-methoxypyrimidine (0.173 g, 0.578 mmol), CsF (0.351 g, 2.310 mmol) in DCE (3 mL) was purged with Ar. Pd(PPh₃)₄ (0.033 g, 0.029 mmol) and 1-(trimethylsilyl)ethanone (0.165 mL, 1.155 mmol) were added. The solution was bubbled with Ar, then the reaction vessel was sealed and heated at 75° C. for 2 days. After this time, the solution was cooled to rt and 1 ml hexane was added. The reaction mixture was filtered through a pad of CELITE®, rinsed with 10 ml EtOAc, filtrated and concentrated. Purification using normal phase chromatography afforded 1-[4-chloro-2-(6-methoxypyrimidin-4-yl)phenyl]ethan-1-one (0.057 g, 38% yield). MS(ESI) m/z: 263.08 (M+H)⁺.

117B. Preparation of N'-{1-[4-chloro-2-(6-methoxypyrimidin-4-yl)phenyl]ethenyl}ethoxycarbohydrazide

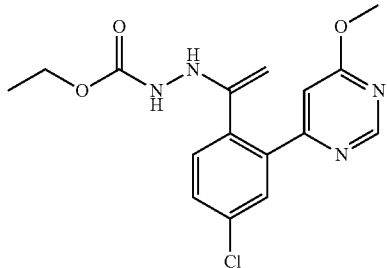 [SMILES: C=C(NNC(=O)OCC)c1ccc(Cl)cc1-c1cc(OC)ncn1]

To a solution of 1-(4-chloro-2-(6-methoxypyrimidin-4-yl) phenyl)ethanone (0.057 g, 0.217 mmol), ethyl hydrazinecarboxylate (0.022 g, 0.217 mmol) in EtOH (3 mL) was added 2 drops of conc. HCl and the solution was then heated at 75° C. for 2 h. The reaction mixture was concentrated to yield N'-{1-[4-chloro-2-(6-methoxypyrimidin-4-yl)phenyl] ethenyl}ethoxycarbohydrazide as a solid. MS(ESI) m/z: 349.4 (M+H)$^+$.

117C. Preparation of 4-[5-chloro-2-(1,2,3-thiadiazol-4-yl) phenyl]-6-methoxypyrimidine

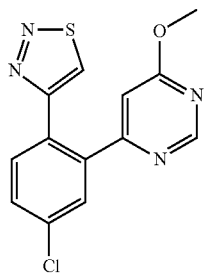 [SMILES: COc1cc(-c2cc(Cl)ccc2-c2csnn2)ncn1]

To N'-{1-[4-chloro-2-(6-methoxypyrimidin-4-yl)phenyl] ethenyl}ethoxycarbohydrazide (0.076 g, 0.217 mmol) in a vial was added SCl$_2$ (0.32 ml, 4.34 mmol), and the solution was stirred at rt for 30 min, then heated at 60° C. for 1 h. The solution was then cooled rt. To the reaction mixture was added MeOH, then the solution was concentrated. Purification using reverse phase chromatography afforded 4-(4-chloro -2-(6-methoxypyrimidin-4-yl)phenyl)-1,2,3-thiadiazole (0.017 g, 26% yield) as a yellow solid. MS(ESI) m/z: 305.0 (M+H)$^+$. $^1$H NMR (400 MHz, CD$_3$OD) δ 8.87 (s, 1H), 8.63 (d, J=1.1 Hz, 1H), 7.86 (d, J=8.6 Hz, 1H), 7.76 (d, J=2.0 Hz, 1H), 7.71 (dd, J=8.4, 2.2 Hz, 1H), 6.82 (d, J=1.1 Hz, 1H), 4.02 (s, 3H).

117D. Preparation of 6-[5-chloro-2-(1,2,3-thiadiazol-4-yl) phenyl]pyrimidin-4-ol

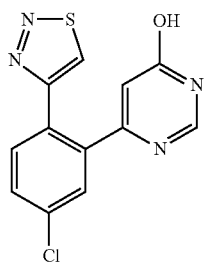 [SMILES: Oc1cc(-c2cc(Cl)ccc2-c2csnn2)ncn1]

4-(4-Chloro-2-(6-methoxypyrimidin-4-yl)phenyl)-1,2,3-thiadiazole (0.059 g, 0.194 mmol) in AcOH (2 ml) was added 48% HBr in water (1.1 ml, 9.68 mmol). The solution was heated at 85° C. for 1 h, then cooled to rt. The reaction mixture was concentrated. The residue was dissolved in EtOAc, washed with sat aq NaHCO$_3$, brine, dried over MgSO$_4$, filtered and concentrated to give 6-(5-chloro-2-(1, 2,3-thiadiazol-4-yl)phenyl)pyrimidin-4-ol (0.053 g, 94% yield) as an off-white solid. MS(ESI) m/z: 291.0 (M+H)$^+$. $^1$H NMR (400 MHz, CD$_3$OD) δ 8.84 (s, 1H), 7.94 (s, 1H), 7.70 (d, J=8.1 Hz, 1H), 7.61 (d, J=2.0 Hz, 1H), 7.55 (dd, J=8.4, 2.2 Hz, 1H), 6.27 (d, J=0.7 Hz, 1H).

117E. Preparation of (10R,14S)-14-{4-[5-chloro-2-(1,2,3-thiadiazol-4-yl)phenyl]-6-oxo -1,6-dihydropyrimidin-1-yl}-4-fluoro-10-methyl-8,16-diazatricyclo[13.3.1.0$^{2,7}$]nonadeca -1(19),2(7),3,5,15,17-hexaen-9-one (10R,14S)-14-{4-[5-Chloro-2-(1,2,3-thiadiazol-4-yl)phenyl]-6-oxo-1,6-dihydropyrimidin-1-yl}-4-fluoro-10-methyl-8,16-diazatricyclo [13.3.1.0$^{2,7}$]nonadeca -1(19),2(7),3,5,15,17-hexaen-9-one (0.0022 g, 47%) was prepared in a similar manner as the procedure described in Example 129 by using 6-[5-chloro-2-(1,2,3-thiadiazol-4-yl)phenyl]pyrimidin-4-ol and (10R, 14S)-14-amino-4-fluoro-10-methyl-8,16-diazatricyclo [13.3.1.0$^{2,7}$]nonadeca-1(19),2(7),3,5,15,17-hexaen-9-one, prepared as described in Example 28. MS(ESI) m/z: 587.5 (M+H)$^+$. $^1$H NMR (500 MHz, DMSO-d$_6$) δ 9.69 (s, 1H), 9.16 (s, 1H), 8.84 (s, 1H), 8.63 (d, J=4.9 Hz, 1H), 7.82 (d, J=8.2 Hz, 1H), 7.78-7.65 (m, 3H), 7.52-7.39 (m, 2H), 7.35-7.20 (m, 2H), 6.35 (s, 1H), 5.89 (d, J=9.2 Hz, 1H), 2.60 (br. s., 1H), 2.20 (br. s., 1H), 2.01-1.78 (m, 2H), 1.36 (br. s., 2H), 0.83 (d, J=7.0 Hz, 3H), 0.39 (br. s., 1H). Analytical HPLC (Method B) RT =1.74 min, 100% purity; Factor XIa Ki=2.7 nM, Plasma Kallikrein Ki=330 nM.

EXAMPLE 118

Preparation of (10R,14R)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,16,18-triazatricyclo[13.3.1.0$^{2,7}$]nonadeca-1(19),2 (7),3,5,15,17-hexaen-9-one

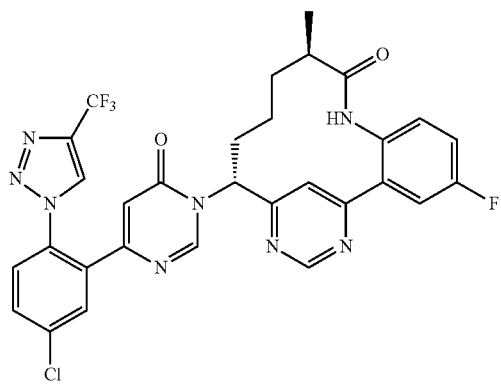 [SMILES: C[C@@H]1CCC[C@@H](n2cnc(-c3cc(Cl)ccc3-n3cc(C(F)(F)F)nn3)cc2=O)c2cc(ncn2)-c2cc(F)ccc2NC1=O]

(10R,14R)-14-(4-{5-Chloro-2-[4-(trifluoromethyl)-1H-1, 2,3-triazol-1-yl]phenyl}-6-oxo-1,6-dihydropyrimidin-1-yl)-4-fluoro-10-methyl-8,16,18-triazatricyclo [13.3.1.0$^{2,7}$]nonadeca-1(19),2(7),3,5,15,17-hexaen-9-one (0.0049 g, 34%) was prepared in a similar manner as the procedure described in Example 116F, by using (10R)-14-amino-4-fluoro -10-methyl-8,16,18-triazatricyclo[13.3.1.0$^{2,7}$]nonadeca-1(19),2, 4,6,15,17-hexaen-9-one, prepared 2 steps from Example 116E2. MS(ESI) m/z: 639.1 (M+H)+. $^1$H NMR (500 MHz, CD$_3$OD) δ 9.20 (d, J=1.1 Hz, 1H), 8.86 (d, J=0.5 Hz, 1H), 8.74 (s, 1H), 7.94 (d, J=2.2 Hz, 1H), 7.86 (d, J=1.4 Hz, 1H), 7.81-7.78 (m, 1H), 7.76-7.71 (m, 1H), 7.70-7.65 (m, 1H), 7.39-7.34 (m, 2H), 6.50 (d, J=0.8 Hz, 1H), 5.99 (dd, J=12.4, 4.4 Hz, 1H), 2.40-2.31 (m, 1H), 2.28-2.18 (m, 1H), 2.14-2.07 (m, 1H), 1.98-1.87 (m, 1H), 1.72-1.60 (m, 1H), 1.57-1.46 (m, 1H), 1.30 (d, J=6.9 Hz, 3H), 1.05-0.91 (m, 1H). Analytical HPLC (Method A). RT=9.92 min, 100% purity; Factor XIa Ki=30 nM, Plasma Kallikrein Ki=2,000 nM.

EXAMPLE 119

Preparation of (10R,14S)-14-[4-(5-chloro-1-methyl-1H-indazol-7-yl)-6-oxo-1,6-dihydropyrimidin-1-yl]-10-methyl-8,16-diazatricyclo[13.3.1.0$^{2,7}$]nonadeca-1(19),2(7),3,5,15,17-hexaen-9-one

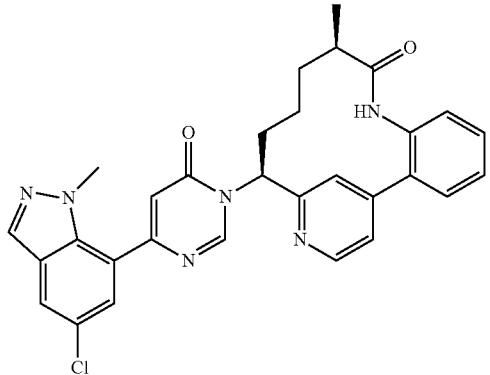 [SMILES: C[C@@H]1CCC[C@H](n2cnc(-c3cc(Cl)cc4cnn(C)c34)cc2=O)c2cc(ccn2)-c2ccccc2NC1=O]

To a vial (4 ml) containing a suspension of 6-(5-chloro-1-methyl-1H-indazol-7-yl)pyrimidin-4-ol (0.014 g, 0.054 mmol), prepared as described in Example 22, in ACN (1 ml) was added HATU (0.027 g, 0.071 mmol) and DBU (0.012 ml, 0.081 mmol). In a separate flask, (10R,14S)-14-amino-10-methyl-8,16-diazatricyclo[13.3.1.0$^{2,7}$]nonadeca-1(19),2(7),3,5,15,17-hexaen-9-one bis-hydrochloride (0.020 g, 0.054 mmol), prepared as described in Example 29, was dissolved in MeOH (2 mL), passed through a NaHCO$_3$ cartridge (StratoSpheres SPE; 500 mg, 0.90 mmol loading), and filtrate concentrated. After 30 min, the free based amine in DMF (1.0 ml) was added at rt. After 3 h, the crude mixture was purified by reverse phase chromatography (column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 35 min, then a 5-minute hold at 100% B; Flow: 20 mL/min) to give (10R,14S)-14-[4-(5-chloro-1-methyl-1H-indazol-7-yl)-6-oxo-1,6-dihydropyrimidin-1-yl]-10-methyl-8,16-diazatricyclo[13.3.1.0$^{2,7}$]nonadeca-1(19),2(7),3,5,15,17-hexaen-9-one (10 mg, 29.9%) as a white solid. MS(ESI) m/z: 578.2 (M+H)+. $^1$H NMR (400 MHz, DMSO-d$_6$) δ 9.80 (s, 1H), 9.13 (s, 1H), 8.66 (d, J=4.9 Hz, 1H), 8.16 (s, 1H), 7.99 (s, 1H), 7.74 (s, 1H), 7.59 (d, J=7.3 Hz, 1H), 7.51-7.40 (m, 4H), 7.24 (d, J=7.6 Hz, 1H), 6.73 (s, 1H), 5.98 (d, J=8.5 Hz, 1H), 3.89 (s, 3H), 2.65 (br. s., 1H), 2.36-2.28 (m, 1H), 1.98 (br. s., 2H), 1.42 (br. s., 2H), 0.86 (d, J=6.7 Hz, 3H). Analytical HPLC (Method C): 1.59 min, purity=99%; Factor XIa Ki=100 nM, Plasma Kallikrein Ki=4,900 nM.

EXAMPLE 120

Preparation of N-[(10R,14S)-14-[4-(5-chloro-1-methyl-1H-indazol-7-yl)-6-oxo-1,6-1-yl]-10-methyl-9-oxo-8,16-diazatricyclo[13.3.1.0$^{2,7}$]nonadeca-1(19),2(7),3,5,15,17-hexaen-5-yl]carbamate

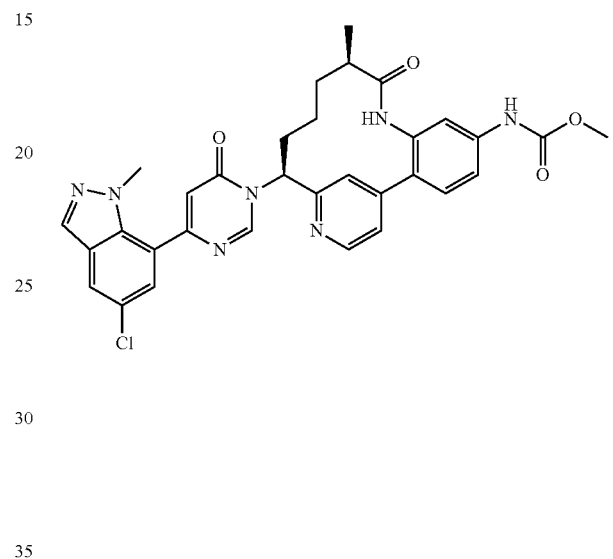

To a vial (4 ml) containing a suspension of 6-(5-chloro-1-methyl-1H-indazol-7-yl)pyrimidin-4-ol (0.013 g, 0.050 mmol), prepared as described in Example 22, in ACN (1 ml) was added HATU (0.025 g, 0.065 mmol) and DBU (0.011 ml, 0.075 mmol). In a separate flask, N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate bis-trifluoroacetate (0.000 g, 0.050 mmol), prepared as described in Example 45J, was dissolved in MeOH (2 mL), passed through a NaHCO$_3$ cartridge (StratoSpheres SPE; 500 mg, 0.90 mmol loading), and filtrate concentrated. After 30 min, the free based amine in DMF (1.0 ml) was added at rt. After 3 h, the crude mixture was purified by reverse phase chromatography (column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 35 min, then a 5-minute hold at 100% B; Flow: 20 mL/min) to give N-[(10R,14S)-14-[4-(5-chloro-1-methyl-1H-indazol-7-yl)-6-oxo-1,6-dihydropyrimidin-1-yl]-10-methyl-9-oxo-8,16-diazatricyclo[13.3.1.0$^{2,7}$]nonadeca-1(19),2(7),3,5,15,17-hexaen-5-yl]carbamate (14.1 mg, 38.6%) as a white solid. MS(ESI) m/z: 612 (M+H)+. $^1$H NMR (400 MHz, DMSO-d$_6$) δ 9.92 (s, 1H), 9.81 (s, 1H), 9.13 (s, 1H), 8.61 (d, J=4.9 Hz, 1H), 8.16 (s, 1H), 7.99 (d, J=1.5 Hz, 1H), 7.71 (s, 1H), 7.53-7.43 (m, 3H), 7.41-7.36 (m, 2H), 6.73 (s, 1H), 5.98 (d, J=7.9 Hz, 1H), 3.89 (s, 3H), 3.59 (s, 3H), 2.35-2.28 (m, 1H), 2.03-1.94 (m, 2H), 1.49 - 1.39 (m, 2H), 0.86 (d, J=6.7 Hz, 3H). Analytical HPLC (Method C): RT=1.52 min, purity=100%; Factor XIa Ki=14 nM, Plasma Kallikrein Ki=180 nM.

EXAMPLE 121

Preparation of (10S,14S)-14-{4-[5-chloro-2-(4-chloro-1H-1,2,3-triazol-1-yl)phenyl]-6-oxo-1,6-dihydropyrimidin-1-yl}-4,11-difluoro-10-methyl-8,16-diazatricyclo[13.3.1.0$^{2,7}$]nonadeca-1(19),2(7),3,5,15,17-hexaen-9-one trifluoroacetate

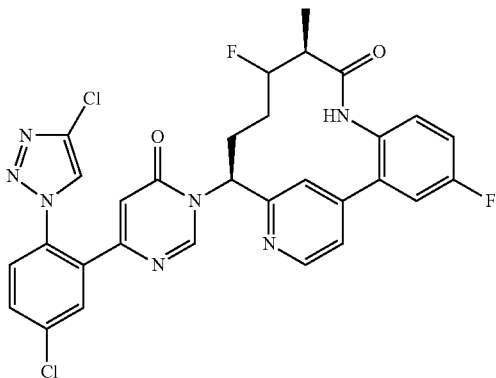 [SMILES: C[C@H]1C(=O)Nc2ccc(F)cc2-c2ccnc(c2)[C@@H](n2cnc(-c3cc(Cl)ccc3-n3cc(Cl)nn3)cc2=O)CCC1F]

121A. Preparation of (10S,14S)-14-amino-4,11-difluoro-10-methyl-8,16-diazatricyclo [13.3.1.0$^{2,7}$]nonadeca-1(19),2(7),3,5,15,17-hexaen-9-one trifluoroacetate

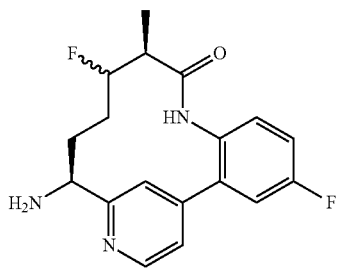 [SMILES: C[C@H]1C(=O)Nc2ccc(F)cc2-c2ccnc(c2)[C@@H](N)CCC1F]

Fe$_2$(C$_2$O$_4$)$_3$.6H$_2$O (882 mg, 1.823 mmol) was dissolved in water (40 mL) and the solution purged with Ar (3 ×). SELECTFLUOR® (646 mg, 1.823 mmol) was added, followed by addition of the solution of tert-butyl N-[(10R,11E,14S)-4-fluoro-10-methyl-9-oxo-8,16-diazatricyclo [13.3.1.0$^{2,7}$]nonadeca-1(19),2(7),3,5,11,15,17-heptaen-14-yl]carbamate in ACN (30 mL). To the resulting solution was added NaBH$_4$ (184 mg, 4.86 mmol) portionwise. After 2 h, the reaction mixture was quenched with 28%-30% aq NH$_4$OH (15 ml), then extracted with 200 ml DCM, and the combined organic phase washed with brine, dried over MgSO$_4$, filtered, concentrated. The residue was purified by reverse phase chromatography, followed by treating TFA in DCM, and concentrated to give (10S,14S)-14-amino-4,11-difluoro-10-methyl-8,16-diazatricyclo[13.3.1.0$^{2,7}$]nonadeca-1(19),2(7),3,5,15,17-hexaen-9-one trifluoroacetate (87 mg, 25% yield). MS(ESI) m/z: 332.3 (M+H)$^+$.

121B. Preparation of (10S,14S)-14-{4-[5-chloro-2-(4-chloro-1H-1,2,3-triazol-1-yl)phenyl]-6-oxo-1,6-dihydropyrimidin-1-yl}-4,11-difluoro-10-methyl-8,16-diazatricyclo [13.3.1.0$^{2,7}$]nonadeca-1(19),2(7),3,5,15,17-hexaen-9-one trifluoroacetate (10S,14S)-14-{4-[5-Chloro-2-(4-chloro-1H-1,2,3-triazol-1-yl)phenyl]-6-oxo-1,6-dihydropyrimidin-1-yl}-4,11-difluoro-10-methyl-8,16-diazatricyclo[13.3.1.0$^{2,7}$]nonadeca-1(19),2(7),3,5,15,17-hexaen-9-one trifluoroacetate (11.5 mg, 37% yield) was prepared in a similar manner as the procedure described in Examples 45K and 45L, by replacing (9S,13 S)-13-amino-10-fluoro-3,9-dimethyl-3,4,7,15-tetraazatricyclo[12.3.1.0$^{2,6}$]octadeca-1(18),2(6),4,14,16-pentaen-8-one with (10S,14S)-14-amino-4,11-difluoro-10-methyl-8,16-diazatricyclo[13.3.1.0$^{2,7}$]nonadeca-1(19),2(7),3,5,15,17-hexaen-9-one. MS(ESI) m/z: 622.1 (M+H)$^+$. $^1$H NMR (400 MHz, CD$_3$OD) δ 9.19 (s, 1H), 8.74 (d, J=5.1 Hz, 1H), 8.37 (s, 1H), 7.93 (d, J=2.2 Hz, 1H), 7.81-7.74 (m, 1H), 7.71-7.63 (m, 2H), 7.47-7.38 (m, 2H), 7.36-7.23 (m, 2H), 6.40 (s, 1H), 6.31-6.21 (m, 1H), 5.42-5.22 (m, 1H), 3.24-3.12 (m, 1H), 2.37-2.20 (m, 2H), 1.85-1.68 (m, 1H), 0.98 (d, J=7.0 Hz, 3H), 0.69-0.43 (m, 1H). Analytical HPLC (Method A): RT=11.53 min, purity>=99%.

EXAMPLE 122

Preparation of (10R,14S)-14-{4-[5-chloro-2-(4-chloro-1H-1,2,3-triazol-1-yl)phenyl]-6-oxo-1,6-dihydropyrimidin-1-yl}-N,10-dimethyl-9-oxo-8,16-diazatricyclo[13.3.1.0$^{2,7}$]nonadeca-1(19),2(7),3,5,15,17-hexaene-4-carboxamide trifluoroacetate

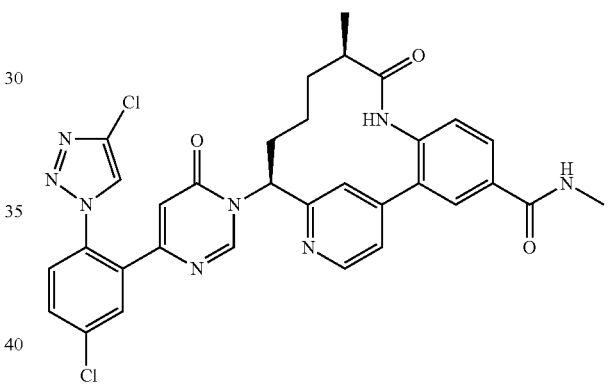

To a solution of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo [13.3.1.0$^{2,7}$]nonadeca-1(19),2(7),3,5,15,17-hexaene-4-carboxylic acid trifluoroacetate (10 mg, 0.013 mmol) in DMF (0.5 mL) was added MeNHHCl (5.4 mg, 0.08 mmol), DIEA (0.016 mL, 0.094 mmol), HOBT (4.1 mg, 0.027 mmol), and EDC (5.2 mg, 0.027 mmol). The reaction mixture was stirred at rt over night. The reaction mixture was purified by reverse phase chromatography to give (10R,14S)-14-{4-[5-chloro-2-(4-chloro-1H-1,2,3- triazol-1-yl)phenyl]-6-oxo-1,6-dihydropyrimidin-1-yl}-N,10-dimethyl-9-oxo-8,16-diazatricyclo [13.3.1.0$^{2,7}$]nonadeca-1(19),2(7),3,5,15,17-hexaene-4-carboxamide trifluoroacetate as a white solid. (6.72 mg, 65% yield). MS(ESI) m/z: 643.2 (M+H)$^+$. $^1$H NMR (400 MHz, CD$_3$OD) δ 9.00 (s, 1H), 8.74 (d, J=5.1 Hz, 1H), 8.38 (s, 1H), 8.07 (d, J=2.0 Hz, 1H), 7.96 (dd, J=8.3, 2.1 Hz, 1H), 7.92 (d, J=2.2 Hz, 1H), 7.80-7.74 (m, 2H), 7.70-7.66 (m, 1H), 7.57(dd, J=5.1, 1.5 Hz, 1H), 7.38 (d, J=8.4 Hz, 1H), 6.39 (s, 1H), 6.05 (dd, J=12.5, 4.6 Hz, 1H), 2.98 (s, 3H), 2.79-2.68 (m, 1H), 2.34-2.20 (m, 1H), 2.14-1.94 (m, 2H), 1.62-1.45 (m, 2H), 0.99 (d, J=6.8 Hz, 3H), 0.67 (br. s., 1H). Analytical HPLC (Method A): RT=7.41 min, purity=>98%; Factor XIa Ki=0.42 nM, Plasma Kallikrein Ki=50 nM.

EXAMPLE 123

Preparation of (10R,14S)-14-[4-(5-chloro-1-methyl-1H-indazol-7-yl)-6-oxo-1,6-dihydropyrimidin-1-yl]-10-methyl-9-oxo-8,16-diazatricyclo[13.3.1.0$^{2,7}$]nonadeca-1(19),2(7),3,5,15,17-hexaene-5-carbonitrile

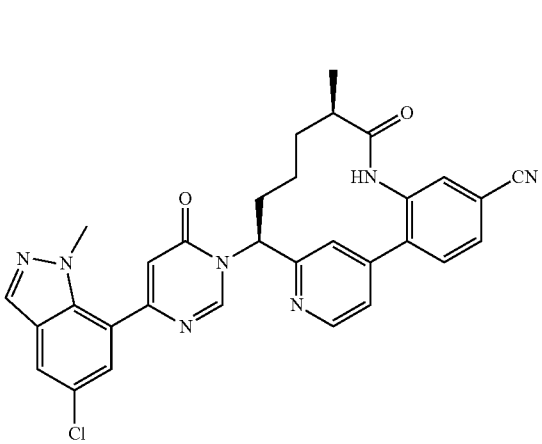 [SMILES: C[C@@H]1CCC[C@H](n2cnc(-c3cc(Cl)cc4cnn(C)c34)cc2=O)c2cc(ccn2)-c2ccc(C#N)cc2NC1=O]

To a vial (4 ml) containing a suspension of 6-(5-chloro-1-methyl-1H-indazol-7-yl)pyrimidin-4-ol (0.0069 g, 0.027 mmol), prepared as described in Example 22, in ACN (1 ml) was added HATU (0.013 g, 0.035 mmol) and DBU (0.006 ml, 0.040 mmol). In a separate flask, (10R,14S)-14-amino-10-methyl-9-oxo-8,16-diazatricyclo[13.3.1.0$^{2,7}$]nonadeca-1(19),2(7),3,5,15,17-hexaene-5-carbonitrile bis-hydrochloride (0.0105 g, 0.027 mmol), prepared as described in Example 30, was dissolved in MeOH (2 mL), passed through a NaHCO$_3$ cartridge (StratoSpheres SPE; 500 mg, 0.90 mmol loading), and filtrate concentrated. After 30 min, the free based amine in DMF (1.0 ml) was added at rt. After 3 h, the crude mixture was purified by reverse phase chromatography (column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-70% B over 35 min, then a 5-minute hold at 100% B; Flow: 20 mL/min) to give (10R,14S)-14-[4-(5-chloro-1-methyl-1H-indazol-7-yl)-6-oxo -1,6-dihydropyrimidin-1-yl]-10-methyl-9-oxo-8,16-diazatricyclo[13.3.1.0$^{2,7}$]nonadeca -1(19),2(7),3,5,15,17-hexaene-5-carbonitrile (7.1 mg, 39.2%) as a white solid. MS(ESI) m/z: 564.2 (M+H)$^+$. $^1$H NMR (500 MHz, DMSO-d$_6$) δ 10.06 (s, 1H), 9.15-9.07 (m, 1H), 8.70 (d, J=4.9 Hz, 1H), 8.16 (s, 1H), 7.88 (d, J=7.9 Hz, 1H), 7.80-7.69 (m, 3H), 7.52-7.38 (m, 2H), 6.72 (s, 1H), 5.96 (d, J=7.6 Hz, 1H), 3.87 (s, 2H), 2.65 (br. s., 1H), 2.29 (br. s., 1H), 2.05-1.88 (m, 2H), 1.42 (d, J=10.1 Hz, 2H), 0.85 (d, J=6.7 Hz, 3H), 0.47 (br. s., 1H). Analytical HPLC (Method C): RT=1.70 min, purity=100%; Factor XIa Ki=570 nM, Plasma Kallikrein Ki=6,000 nM.

EXAMPLE 124

Preparation of (10R,14S)-14-(4-{5-chloro-2-[1-(difluoromethyl)-1H-pyrazol-4-yl]phenyl}-6-oxo-1,6-dihydropyrimidin-1-yl)-4-fluoro-10-methyl-8,16-diazatricyclo [13.3.1.0$^{2,7}$]nonadeca-1(19),2(7),3,5,15,17-hexaen-9-one trifluoroacetate

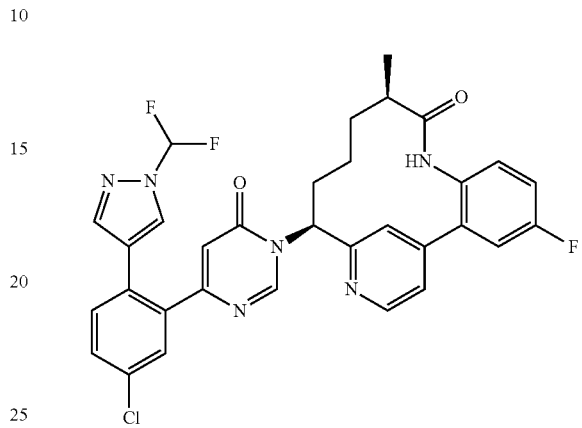

124A. Preparation of 4-(2-bromo-5-chlorophenyl)-6-methoxypyrimidine

To a yellow suspension of 4-chloro-2-(6-methoxypyrimidin-4-yl)aniline (1.0 g, 4.24 mmol) and pTsOH.H$_2$O (0.969 g, 5.09 mmol) in ACN (212 ml) was added CuBr$_2$ (0.095 g, 0.42 mmol). The yellow suspension turned to a green suspension. Next, t-butyl nitrite (0.673 ml, 5.09 mmol) was added dropwise to give a clear, green solution. Then, tetrabutylammonium bromide (2.74 g, 8.49 mmol) was added and the reaction became a dark brown/black solution. After 2 h, water (200 ml) was added to give a greenish yellow suspension. The reaction was extracted with DCM (2×). The organic layers were combined and washed with brine, dried over MgSO$_4$, filtered and concentrated. Purification by normal phase chromatography afforded 4-(2-bromo-5-chlorophenyl)-6-methoxypyrimidine (0.495 g, 38.9% yield) as a white solid. MS(ESI) m/z: 299.0 (M+H)$^+$. $^1$H NMR (500 MHz, CDCl$_3$) δ 8.88 (d, J=1.1 Hz, 1H), 7.60 (d, J=8.5 Hz, 1H), 7.56 (d, J=2.5 Hz, 1H), 7.27 (dd, J=8.5, 2.5 Hz, 1H), 7.04 (d, J=1.1 Hz, 1H), 4.05 (s, 3H).

124B. Preparation of 4-(5-chloro-2-(1-(difluoromethyl)-1H-pyrazol-4-yl)phenyl)-6-methoxypyrimidine To a microwave tube was added 4-(2-bromo-5-chlorophenyl)-6-methoxypyrimidine (0.08 g, 0.27 mmol), 1-(difluoromethyl)-4-(4,4,5,5-tetramethyl-1,3,2-dioxaborolan-2-yl)-1H-pyrazole (0.072 g, 0.29 mmol), 3 M K$_3$PO$_4$ (0.27 ml, 0.80 mmol) and THF (2.67 ml). Ar was bubbled through the reaction for several min and (DtBPF)PdCl$_2$ (8.70 mg, 0.013 mmol) was added. The vial was sealed and heated at 90° C. for 15 h, then the reaction was cooled to rt. The reaction was diluted with EtOAc, washed with brine, dried over Na$_2$SO$_4$, filtered, and concentrated. Purification by normal phase chromatography afforded 4-(5-chloro-2-(1-(difluoromethyl)-1H-pyrazol-4-yl)phenyl)-6-methoxypyrimidine (0.05 g, 55.6% yield) as a white solid. MS(ESI) m/z: 337.2 (M+H)$^+$. $^1$H NMR (400 MHz, CDCl$_3$) δ 8.81 (d, J=0.9 Hz, 1H), 7.69 (s, 1H), 7.54 (d, J=2.2 Hz, 1H), 7.48-7.43 (m, 1H), 7.41-7.35 (m, 2H), 7.17 (t, J=54.0 Hz, 1H), 6.61 (d, J=1.1 Hz, 1H), 3.99 (s, 3H).

124C. Preparation of 6-(5-chloro-2-(1-(difluoromethyl)-1H-pyrazol-4-yl)phenyl) pyrimidin-4-ol A clear solution of 4-(5-chloro-2-(1-(difluoromethyl)-1H-pyrazol-4-yl)phenyl)-6-methoxypyrimidine (0.05 g, 0.15 mmol) in HOAc (0.74 ml) and 48% HBr in water (0.84 ml, 7.42 mmol) was warmed to 65° C. for 3 h, then the reaction was cooled to rt and concentrated. The yellow gum dissolved in EtOAc, washed with sat NaHCO$_3$, brine, dried over Na$_2$SO$_4$, filtered, and concentrated. Et$_2$O (3 ml) was added and the mixture was sonicated to give a suspension. The solid was collected by filtration, rinsed with Et$_2$O (2 ml), air-dried with suction to afford 6-(5-chloro-2-(1-(difluoromethyl)-1H -pyrazol-4-yl)phenyl)pyrimidin-4-ol (0.03 g, 62.6% yield) as a white solid. MS(ESI) m/z: 323.2 (M+H)$^+$. $^1$H NMR (400 MHz, CD$_3$OD) δ 8.20 (d, J=1.1 Hz, 1H), 8.05 (s, 1H), 7.61-7.27 (m, 5H), 6.40 (d, J=1.1 Hz, 1H).

124D. Preparation of (10R,14S)-14-(4-{5-chloro-2-[1-(difluoromethyl)-1H-pyrazol-4-yl]phenyl}-6-oxo-1,6-dihydropyrimidin-1-yl)-4-fluoro-10-methyl-8,16-diazatricyclo [13.3.1.0$^{2,7}$]nonadeca-1(19),2(7),3,5,15,17-hexaen-9-one trifluoroacetate (10R,14S)-14-(4-{5-Chloro-2-[1-(difluoromethyl)-1H-pyrazol-4-yl]phenyl}-6-oxo-1,6-dihydropyrimidin-1-yl)-4-fluoro-10-methyl-8,16-diazatricyclo[13.3.1.0$^{2,7}$]nonadeca-1(19),2(7),3,5,15,17-hexaen-9-one trifluoroacetate (0.017 g, 55.4% yield) was prepared in a similar manner as the procedure described in Example 150, by using 6-(5--2-(1-(difluoromethyl)-1H-pyrazol-4-yl)phenyl)pyrimidin-4-ol. MS(ESI) m/z: 619.3 (M+H)$^+$. $^1$H NMR (400 MHz, CD$_3$OD) δ 9.04 (s, 1H), 8.69 (d, J=5.1 Hz, 1H), 8.04 (s, 1H), 7.76 (s, 1H), 7.61-7.19 (m, 9H), 6.41 (s, 1H), 6.02 (dd, J=12.5, 4.6 Hz, 1H), 2.72-2.60 (m, 1H), 2.33-2.21 (m, 1H), 2.13-1.90 (m, 2H), 1.59-1.37 (m, 2H), 0.97 (d, J=7.0 Hz, 3H), 0.85-0.65 (m, 1H). $^{19}$F NMR (376MHz, CD$_3$OD) δ −77.63 (s), −96.05 (s), −116.22 (s). Analytical HPLC (Method A): RT=9.68 min, 99.5% purity; Factor XIa Ki=0.11 nM, Plasma Kallikrein Ki=780 nM.

EXAMPLE 125

Preparation of (15S)-15-(4-{5-chloro-2[-4-(difluoromethyl)-1H-1,2,3-triazol-1-yl]phenyl}-6-oxo-1,6-dihydropyrimidin-1-yl)-4-fluoro-11-methyl-8,17-diazatricyclo [14.3.1.0$^{2,7}$]icosa-1(20),2(7),3,5,16,18-hexaen-9-one trifluoroacetate (Diastereomer A)

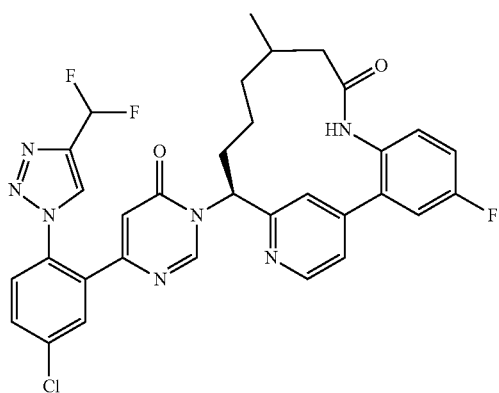 [SMILES: CC1CCC[C@H](n2cnc(-c3cc(Cl)ccc3-n3cc(C(F)F)nn3)cc2=O)c2cc(ccn2)-c2cc(F)ccc2NC(=O)C1]

125A. Preparation of (15S)-15-amino-4-fluoro-11-methyl-8,17-diazatricyclo[14.3.1.0$^{2,7}$]icosa-1(20),2(7),3,5,16,18-hexaen-9-one (Diastereomer A) (15S)-15-Amino-4-fluoro-11-methyl-8,17-diazatricyclo[14.3.1.0$^{2,7}$]icosa -1(20),2(7),3,5,16,18-hexaen-9-one (Diastereomer A) was prepared in a similar manner as the procedure described in Examples 133D and 133E, by replacing tert-butyl N -[(12E,15S)-4-fluoro-11-methyl-9-oxo-8,17-diazatricyclo[14.3.1.0$^{2,7}$]icosa -1(20),2(7),3,5,12,16,18-heptaen-15-yl]carbamate (Diastereomer B) with tert-butyl N -[(12E,15S)-4-fluoro-11-methyl-9-oxo-8,17-diazatricyclo[14.3.1.0$^{2,7}$]icosa -1(20),2(7),3,5,12,16,18-heptaen-15-yl]carbamate (Diastereomer A), both prepared as described in 180B. MS(ESI) m/z: 328.2 (M+H)$^+$.

125B. Preparation of (15S)-15-(4- {5-chloro-2-[4-(difluoromethyl)-1H-1,2,3-triazol-1-yl]phenyl}-6-oxo-1,6-dihydropyrimidin-1-yl)-4-fluoro-11-methyl-8,17-diazatricyclo [14.3.1.0$^{2,7}$]icosa-1(20),2(7),3,5,16,18-hexaen-9-one trifluoroacetate (Diastereomer A)

(15S)-15-(4-{5-Chloro-2[4-(difluoromethyl)-1H-1,2,3-triazol-1-yl]phenyl}-6-oxo-1,6-dihydropyrimidin-1-yl)-4-fluoro-11-methyl-8,17-diazatricyclo[14.3 .1.0$^{2,7}$]icosa -1(20),2(7),3,5,16,18-hexaen-9-one trifluoroacetate (Diastereomer A) (0.021 g, 60.4% yield) was prepared in a similar manner as the procedure described in Example 150, using 6-(5-chloro-2-(4-(difluoromethyl)-1H-1,2,3-triazol-1-yl) phenyl)pyrimidin-4-ol (0.015 g, 0.046 mmol), prepared as described in Example 16, and (15S)-15-amino-4-fluoro-11-methyl-8,17-diazatricyclo[14.3.1.0$^{2,7}$]icosa-1(20),2(7),3,5,16,18-hexaen-9-one (Diastereomer A) (0.015 g, 0.046 mmol). MS(ESI) m/z: 634.3 (M+H)$^+$. $^1$H NMR (400 MHz, CD$_3$OD) δ 8.73 (s, 1H), 8.65 (d, J=4.8 Hz, 1H), 8.52 (t, J=1.4 Hz, 1H), 7.87 (d, J=2.2 Hz, 1H), 7.75-7.71 (m, 1H), 7.68-7.64 (m, 1H), 7.46-7.40 (m, 2H), 7.37 (dd, J=5.0, 1.7 Hz, 1H), 7.26 - 7.19 (m, 2H), 7.00 (t, J=54.0 Hz, 1H), 6.32 (d, J=0.4 Hz, 1H), 5.93 (dd, J=12.7, 3.2 Hz, 1H), 2.42-2.29 (m, 3H), 2.12-2.03 (m, 1H), 2.02-1.92 (m, 1H), 1.85-1.76 (m, 1H), 1.62-1.50 (m, 1H), 1.27-1.11 (m, 2H), 1.01 (d, J=6.8 Hz, 3H). $^{19}$F NMR (376 MHz, CD$_3$OD) δ −77.7 (s), −114.39 (s), −116.32 (s). Analytical HPLC (Method A): RT=9.77 min, 98.9% purity; Factor XIa Ki=90 nM, Plasma Kallikrein Ki=4,400 nM.

EXAMPLE 126

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0$^{2,7}$]nonadeca-1(19),2(7),3,5,15,17-hexaene-4-carboxylate trifluoroacetate

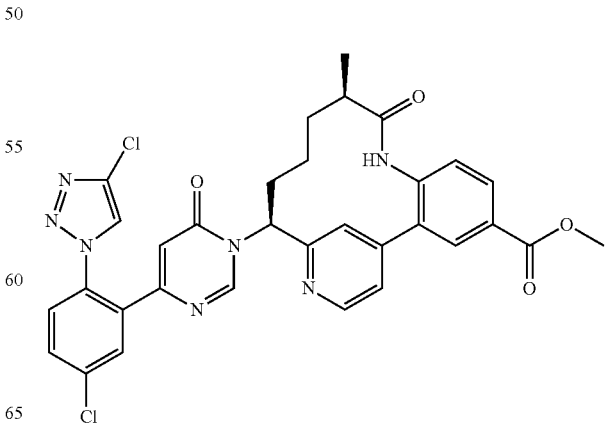

126A. Preparation of methyl 4-amino-3-{2-[(1S)-1-{[(tert-butoxy)carbonyl]amino}but-3-en-1-yl]pyridin-4-yl}benzoate

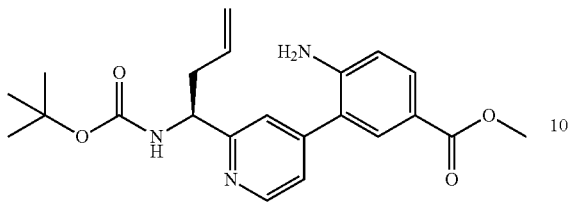

In a 100 mL flask was added methyl 4-amino-3-bromobenzoate (1.0 g, 4.35 mmol), (dihydroxyboranyl)boronic acid (1.169 g, 13.04 mmol), 2nd generation XPhos precatalyst (0.034 g, 0.043 mmol), XPHOS (0.04 g, 0.087 mmol). The vial was capped with a septum purged with Ar (3 ×). To the solution was added degassed EtOH (43.5 ml) and the reaction mixture was allowed to stir for 2 min. After this time KOAc was added (1.28 g, 13.0 mmol) and the solution was heated at 75° C. for 2 h. Degassed aq $K_2CO_3$ (7.24 ml, 13.04 mmol) was added followed by (S)-tert-butyl (1-(4-chloropyridin-2-yl)but-3-en-1-yl)carbamate (1.23 g, 4.35 mmol) as a solution in EtOH (2 mL). The solution was heated at 75° C. for 2 h, then at rt for 16 h. The reaction mixture was concentrated. The residue was dissolved in EtOAc, washed with water and brine, dried over $MgSO_4$, filtered and concentrated. Purification by normal phase chromatography gave methyl 4-amino-3-{2-[(1S)-1-{[(tert-butoxy)carbonyl]amino}but-3-en-1-yl]pyridin-4-yl}benzoate (717 mg, 41% yield) as a white foam. MS(ESI) m/z: 398.5 (M+H)+.

126B. Preparation of methyl 3-{2-[(1S)-1-{[(tert-butoxy)carbonyl]amino}but-3-en-1-yl]pyridin-4-yl}-4-[(2R)-2-methylbut-3-enamido]benzoate

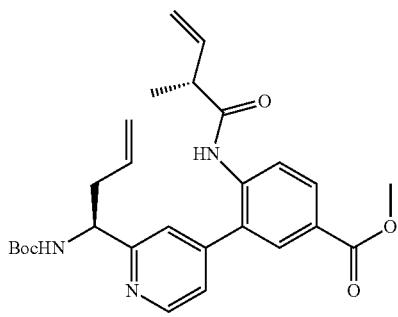 [SMILES: C=CC[C@H](NC(=O)OC(C)(C)C)c1cc(-c2cc(C(=O)OC)ccc2NC(=O)[C@H](C)C=C)ccn1]

Methyl 4-amino-3-{2-[(1S)-1-{[(tert-butoxy)carbonyl]amino}but-3-en-1-yl]pyridin-4-yl}benzoate (0.717 g, 1.80 mmol), (R)-2-methylbut-3-enoic acid (0.235 g, 2.35 mmol), prepared as described in Example 2, in EtOAc (18 ml) was added pyridine (0.44 ml, 5.41 mmol). The reaction was cooled to 0° C. under Ar, and propane phosphonic acid anhydride (2.15 ml, 3.61 mmol) was added dropwise. The reaction was then gradually warmed up to rt and stirred overnight. The reaction mixture was diluted with EtOAc and washed with sat $NaHCO_3$. The aqueous layer back extracted with EtOAc, and the combined organic layers were washed with brine, dried over $MgSO_4$, filtered, concentrated. The residue was purified by normal phase chromatography to afford methyl 3-{2-[(1S)-1-{[(tert-butoxy)carbonyl]amino}but-3-en-1-yl]pyridin-4-yl}-4-[(2R)-2-methylbut-3-enamido]benzoate (740 mg, 86% yield) as a white foam. MS(ESI) m/z: 480.2 (M+H)+.

126C. Preparation of methyl (10R,11E,14S)-14-{[(tert-butoxy)carbonyl]amino}-10-methyl-9-oxo-8,16-diazatricyclo[13.3.1.0$^{2,7}$]nonadeca-1(19),2(7),3,5,11,15,17-heptaene-4-carboxylate

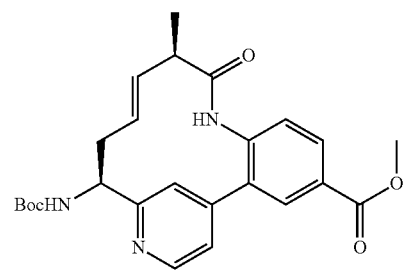 [SMILES: COC(=O)c1ccc2c(c1)-c1ccnc(c1)[C@@H](NC(=O)OC(C)(C)C)C/C=C/[C@@H](C)C(=O)N2]

To a solution of 3-{2-[(1S)-1-{[(tert-butoxy)carbonyl]amino}but-3-en-1-yl]pyridin-4-yl}-4-[(2R)-2-methylbut-3-enamido]benzoate (0.717 g, 1.495 mmol) in DCM (100 ml) was added pTsOH.H$_2$O (0.313 g, 1.645 mmol). The reaction mixture was purged with Ar for 30 min, then warmed to 40° C. and stirred at 40° C. for 40 min as the solution was bubbled with a stream of Ar. In a separate flask, Second Generation Grubbs Catalyst (0.38 g, 0.449 mmol) was added to 3 ml degassed DCM. The dark burgundy solution was added dropwise to the reaction. The resulting clear brownish solution was stirred at 40° C. overnight. The reaction was cooled to rt, washed with sat aq $NaHCO_3$ and brine, dried over $MgSO_4$, filtered, and concentrated to give a brown solid The residue was purified by normal phase chromatography to afford methyl (1OR,11E,14S)-14-{[(tert -butoxy)carbonyl]amino}-10-methyl-9-oxo-8,16-diazatricyclo [13 .3 .1.0$^{2,7}$]nonadeca -1(19),2(7),3,5,11,15,17-heptaene-4-carboxylate (270 mg, 40% yield) as a brown foam. MS(ESI) m/z: 452.5 (M+H)+.

126D. Preparation of methyl (10R,14S)-14-{[(tert-butoxy)carbonyl]amino}-10-methyl-9-oxo-8,16-diazatricyclo[13.3.1.0$^{2,7}$]nonadeca-1(19),2(7),3,5,15,17-hexaene-4-carboxylate

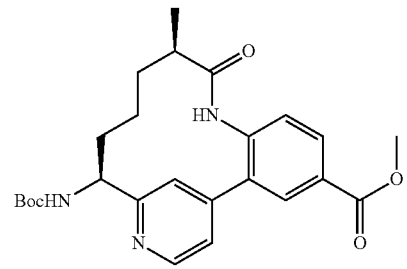 [SMILES: COC(=O)c1ccc2c(c1)-c1ccnc(c1)[C@@H](NC(=O)OC(C)(C)C)CCC[C@@H](C)C(=O)N2]

Methyl (10R,11E,14S)-14-{[(tert-butoxy)carbonyl]amino}-10-methyl-9-oxo-8,16-diazatricyclo[13.3.1.0$^{2,7}$]nonadeca-1(19),2(7),3,5,11,15,17-heptaene-4-carboxylate (270 mg, 0.60 mmol) in EtOAc (12 ml) was purged with Ar and PtO$_2$ (13.7 mg, 0.06 mmol) was added. The solution was purged with H$_2$ several and the reaction was stirred under H$_2$ overnight. The solution was then filtered through CELITE®, rinsed with DCM. The filtrate was concentrated to give a crude solid. Purification by normal phase chromatography afforded methyl (10R,145)-14-{[(tert-butoxy)carbonyl]amino}-10-methyl-9-oxo-8,16-diazatricyclo[13.3.1.0$^{2,7}$]

nonadeca-1(19),2(7),3,5,15,17-hexaene-4-carboxylate (231 mg, 85% yield) as a light brownish solid. MS(ESI) m/z: 454.6 (M+H)+.

126E. Preparation of methyl (10R,14S)-14-amino-10-methyl-9-oxo-8,16-diazatricyclo [13.3.1.0²,⁷]nonadeca-1(19),2(7),3,5,15,17-hexaene-4-carboxylate trifluoroacetate

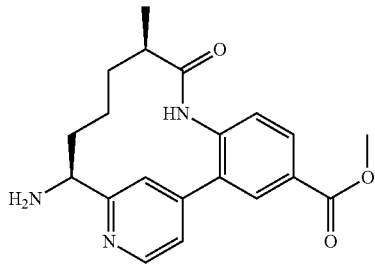 [SMILES: COC(=O)c1ccc2c(c1)-c1ccnc(c1)[C@@H](N)CCC[C@@H](C)C(=O)N2]

To a solution of methyl (10R,14S)-14-{[(tert-butoxy)carbonyl]amino}-10-methyl -9-oxo-8,16-diazatricyclo [13.3.1.0²,⁷]nonadeca-1(19),2(7),3,5,15,17-hexaene-4-carboxylate (231 mg, 0.51 mmol) in DCM (8 mL) was added TFA (1.2 mL, 15.4 mmol). The reaction was stirred at rt for 2 h. The reaction was concentrated to give methyl (10R,14S)-14-amino-10-methyl-9-oxo-8,16-diazatricyclo [13.3.1.0²,⁷]nonadeca -1(19),2(7),3,5,15,17-hexaene-4-carboxylate trifluoroacetate (294 mg, 100% yield). MS(ESI) m/z: 354.2 (M+H)+.

126F. Preparation of methyl (10R,14S)-14-amino-10-methyl-9-oxo-8,16-diazatricyclo [13.3.1.0²,⁷]nonadeca-1(19),2(7),3,5,15,17-hexaene-4-carboxylate Methyl (10R,14S)-14-amino-10-methyl-9-oxo-8,16-diazatricyclo[13.3.1.0²,⁷]nonadeca-1(19),2(7),3,5,15,17-hexaene-4-carboxylate trifluoroacetate (58 mg) was dissolved in MeOH, passed through PL-HCO₃ MP SPE 500 mg per 6 ml tube, rinsed with MeOH and the filtrate was concentrated to give methyl (10R,14S)-14-amino-10-methyl -9-oxo-8,16-diazatricyclo[13.3.1.0²,⁷]nonadeca-1(19),2(7),3,5,15,17-hexaene-4-carboxylate (46 mg, 95% yield) as a free base. MS(ESI) m/z: 354.2 (M+H)+.

126G. Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo [13.3.1.0²,⁷]nonadeca-1(19),2(7),3,5,15,17-hexaene-4-carboxylate trifluoroacetate

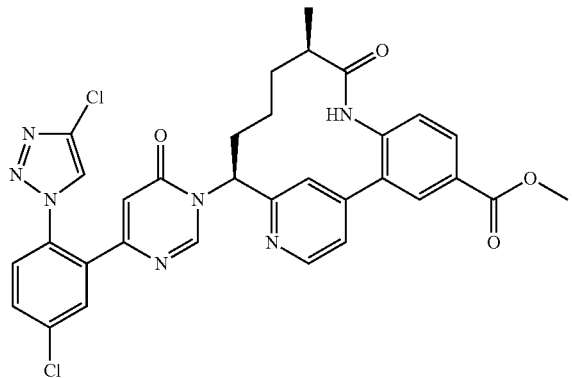

In a 2 dram vial, 9 6-[5-chloro-2-(4-chloro-1H-1,2,3-triazol-1-yl)phenyl]pyrimidin-4-ol (29.6 mg, 0.096 mmol), prepared as described in Example 9, in ACN (0.8 ml) was added HATU (47.6 mg, 0.125 mmol), followed by DBU (22 µl, 0.144 mmol). The solution turned into clear yellow brown upon addition of DBU and the reaction mixture was stirred at rt for 30 min. Methyl (10R,14S)-14-amino-10-methyl-9-oxo-8,16-diazatricyclo[13.3.1.0²,⁷]nonadeca-1(19),2(7),3,5,15,17-hexaene-4-carboxylate (34 mg, 0.096 mmol) was dissolved in DMF (0.8 ml) and added to the reaction mixture and stirred at rt overnight. The reaction mixture was purified by reverse phase chromatography to give (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo [13.3.1.0²,⁷]nonadeca-1(19),2(7),3,5,15,17-hexaene-4-carboxylate trifluoroacetate (59.5 mg, 81% yield) as a beige solid. MS(ESI) m/z: 644.08 (M+H)+. ¹H NMR (400 MHz, CD₃OD)ᵟ 8.88 (s, 1H), 8.70 (d, J=5.5 Hz, 1H), 8.33 (s, 1H), 8.17 (d, J=2.0 Hz, 1H), 8.08 (dd, J=8.1, 2.0 Hz, 1H), 7.87-7.80 (m, 2H), 7.73-7.66 (m, 1H), 7.64-7.55 (m, 2H), 7.32 (d, J=8.4 Hz, 1H), 6.34 (s, 1H), 5.93 (dd, J=12.5, 5.1 Hz, 1H), 3.92 (s, 3H), 2.77-2.65 (m, 1H), 2.35-2.22 (m, 1H), 2.11-2.00 (m, 1H), 1.98-1.85 (m, 1H), 1.58-1.41 (m, 2H), 0.93 (d, J=7.0 Hz, 3H), 0.60 (br. s., 1H). Analytical HPLC (Method A): RT=9.35 min, purity=>99%; Factor XIa Ki=3.6 nM, Plasma Kallikrein Ki=120 nM.

EXAMPLE 127

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo[13.3.1.0²,⁷]nonadeca-1(19),2(7),3,5,15,17-hexaene-4-carboxylic acid trifluoroacetate

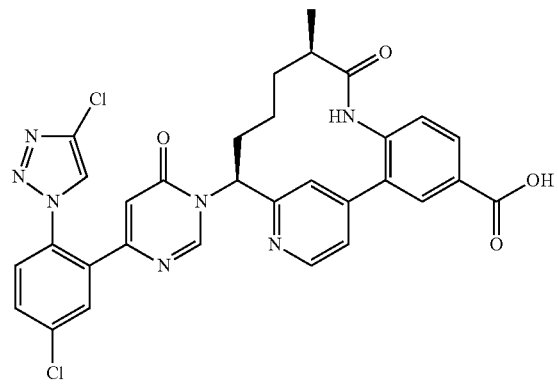 [SMILES: C[C@@H]1CCC[C@H](n2cnc(-c3cc(Cl)ccc3-n3cc(Cl)nn3)cc2=O)c2cc(ccn2)-c2cc(C(=O)O)ccc2NC1=O]

To a solution of (10R,14S)-14-{4-[5-chloro-2-(4-chloro-1H-1,2,3-triazol-1-yl)phenyl]-6-oxo-1,6-dihydropyrimidin-1-yl}-10-methyl-9-oxo-8,16-diazatricyclo [13.3.1.0²,⁷]nonadeca-1(19),2(7),3,5,15,17-hexaene-4-carboxylate trifluoroacetate (52 mg, 0.069 mmol) in MeOH (2 mL) was added 1 N NaOH (1 mL, 1.0 mmol). The solution was stirred at rt for 16 h. The solution was acidified with 1 N HCl, and the resulting solution was extracted with EtOAc. The organic layer was washed with brine, dried over MgSO₄, filtered and concentrated. The residue was purified by reverse phase chromatography to give (10R,14S)-14-{4-[5-chloro-2-(4-chloro-1H-1,2,3-triazol-1-yl)phenyl]-6-oxo-1, 6-dihydropyrimidin-1-yl}-10-methyl-9-oxo-8,16-diazatricyclo [13.3.1.0²,⁷]nonadeca-1(19),2(7),3,5,15,17-hexaene-4-carboxylic acid trifluoroacetate (27.5 mg, 53% yield) as a white solid. MS(ESI) m/z: 630.1 (M+H)+. ¹H NMR (400

MHz, CD$_3$OD) δ 8.88 (s, 1H), 8.70 (d, J=5.5 Hz, 1H), 8.33 (s, 1H), 8.17 (d, J=2.0 Hz, 1H), 8.08 (dd, J=8.1, 2.0 Hz, 1H), 7.87-7.80 (m, 2H), 7.73-7.66 (m, 1H), 7.64-7.55 (m, 2H), 7.32 (d, J=8.4 Hz, 1H), 6.34 (s, 1H), 5.93 (dd, J=12.5, 5.1 Hz, 1H), 3.92 (s, 3H), 2.772.65 (m, 1H), 2.35-2.22 (m, 1H), 2.11-2.00 (m, 1H), 1.98-1.85 (m, 1H), 1.58-1.41 (m, 2H), 0.93 (d, J32 7.0 Hz, 3H), 0.60 (br. s., 1H). Analytical HPLC (Method A): RT=7.85 min, purity=>99%; Factor XIa Ki=0.1 nM, Plasma Kallikrein Ki=40 nM.

EXAMPLE 128

Preparation of (10R,14S)-14-[4-(3-chloro-2,6-difluorophenyl)-6-oxo-1,6-dihydropyrimidin-1-yl]-4-fluoro-10-methyl-8,16-diazatricyclo[13.3.1.0$^{2,7}$] nonadeca -1(19),2(7),3,5, 15,17-hexaen-9-one trifluoroacetate

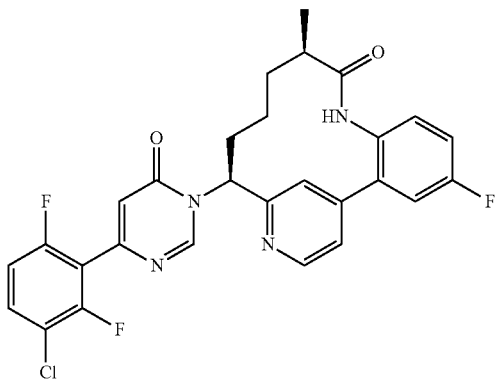 [SMILES: C[C@@H]1CCC[C@H](n2cnc(-c3c(F)ccc(Cl)c3F)cc2=O)c2cc(ccn2)-c2cc(F)ccc2NC1=O]

To a 1-dram vial containing a white suspension of 6-(3-chloro-2,6-difluorophenyl) pyrimidin-4-ol, hydrobromide (0.021 g, 0.064 mmol), prepared as described in Example 4, in ACN (0.53 ml) was added HATU (0.032 g, 0.083 mmol) and DBU (0.024 ml, 0.160 mmol). The resulting clear, yellow solution was stirred at rt. After 5 min, a solution of (10R,14S)-14-amino-4-fluoro-10-methyl-8,16-diazatricyclo [13.3.1.0$^{2,7}$]nonadeca -1(19),2(7),3,5,15,17-hexaen-9-one (0.020 g, 0.064 mmol), prepared as described in Example 28, in DMF (0.53 ml) was added and the resulting bright yellow solution was stirred at rt. After 22 h, the reaction was diluted with MeOH (0.5 mL). Purification by reverse phase chromatography gave, after concentration and lyophilization, (10R,14S) -14-[4-(3-chloro-2,6- difluorophenyl)-6-oxo-1,6-dihydropyrimidin-1-yl]-4-fluoro-10-methyl-8,16-diazatricyclo[13.3.1.0$^{2,7}$]nonadeca-1(19),2(7),3,5,15,17-hexaen-9-one trifluoroacetate (0.023 g, 55% yield) as a white solid. MS(ESI) m/z: 539.1 (M+H)$^+$ and 541.0 (M+2+H)$^+$. $^1$H NMR (500 MHz, CD$_3$OD) δ 9.13 (s, 1H), 8.70 (d, J=5.0 Hz, 1H), 7.79 (d, J=0.8 Hz, 1H), 7.63 (ddd, J=9.1, 8.3, 5.5 Hz, 1H), 7.47 (dd, J=5.2, 1.7 Hz, 1H), 7.40 (dd, J=8.9, 2.9 Hz, 1H), 7.30 (dd, J=9.1, 5.8 Hz, 1H), 7.27-7.21 (m, 1H), 7.15 (td, J=9.1, 1.9 Hz, 1H), 6.66 (d, J=0.5 Hz, 1H), 6.06 (dd, J=12.7, 4.7 Hz, 1H), 2.71-2.63 (m, 1H), 2.31 (tt, J=12.6, 4.0 Hz, 1H), 2.16-2.07 (m, 1H), 2.02-1.94 (m, 1H), 1.58-1.41 (m, 2H), 0.97 (d, J=6.9 Hz, 3H), 0.81-0.64 (m, 1H). $^{19}$F NMR (471 MHz, CD$_3$OD) δ −77.59 (s), −114.77 (d, J=4.3 Hz), −115.49 (d, J=4.3 Hz), −116.26 (s). Analytical HPLC (Method A): RT=8.99 min, purity=99.9%; Factor XIa Ki=48 nM, Plasma Kallikrein Ki−570 nM.

EXAMPLE 129

Preparation of (14S)-14-{4-[5 -chloro-2-(4-chloro-1H-1,2,3 -triazol-1-yl)phenyl]-6-oxo -1,6-dihydropyrimidin-1-yl}-4-fluoro-10-methyl-11-oxa-8,16-diazatricyclo[13.3.1.0$^{2,7}$]nonadeca-1(19),2(7),3,5,15, 17-hexaen-9-one trifluoroacetate (Diastereomer A)

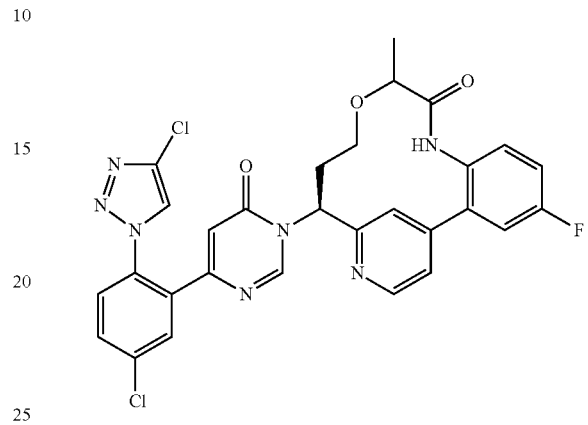

129A. Preparation of tert-butyl 2-[(3S)-3-{[(tert-butoxy)carbonyl]amino}-3-(4-chloropyridin-2-yl)propoxy]propanoate To a clear, pale yellow solution of tert-butyl N-[(1S)-1-(4-chloropyridin-2-yl)-3-hydroxypropyl]carbamate (1.20 g, 4.18 mmol) in DCM (13.9 ml) was added tetrabutylammonium hydrogen sulfate (0.355 g, 1.046 mmol) and 2-bromopropionic acid tert-butyl ester (2.187 g, 10.46 mmol). Next, 50% NaOH (6.70 ml, 84 mmol) was added and the biphasic mixture was stirred vigorously and the mixture became a bright, yellow color. After 1.5 h, additional 2-bromopropionic acid tert-butyl ester (2.187 g, 10.46 mmol) was added. After an additional 2.5 h, the reaction was stopped and partitioned between water and DCM and the layers were separated. The organic layer was dried over MgSO$_4$, filtered and concentrated to give a clear, yellow liquid. Purification by normal phase chromatography gave tert-butyl 2-[(3S)-3-{[(tert-butoxy)carbonyl]amino}-3-(4chloropyridin-2-yl) propoxy]propanoate (1.24 g, 71% yield) as a clear, colorless oil. MS(ESI) m/z: 415.2 (M+H)$^+$.

129B. Preparation of tert-butyl 2-[(3S)-3-[4-(2-amino-5-fluorophenyl)pyridin-2-yl]-3-{[(tert-butoxy)carbonyl] amino}propoxy]propanoate A thick-walled, screw thread single neck flask containing tert-butyl 2-[(3S)-3-{[(tert-butoxy)carbonyl]amino}-3-(4-chloropyridin-2-yl)propoxy]propanoate (1.20 g, 2.89 mmol), (2-amino-5-fluorophenyl)boronic acid (1.34 g, 8.68 mmol), 3M aq K$_3$PO$_4$ (2.89 ml, 8.68 mmol) in dioxane (14.5 ml) was purged and refilled with Ar (3 ×). (DtBPF)PdCl$_2$ (0.094 g, 0.145 mmol) was added, the flask was purged and refilled with Ar (3 ×), and then it was sealed with a teflon screw cap. The flask was heated to 65° C. After 3 h, the reaction was stopped and it was cooled to rt. The reaction was partitioned between EtOAc and water, and the layers were separated. The aqueous layer was extracted with EtOAc (2×). The organic layers were combined and washed with brine, dried over Na$_2$SO$_4$, filtered, and concentrated to give a brown foam. Purification by normal phase chromatography gave tert-butyl 2-[(3S)-3-[4-(2-amino-5-fluorophenyl) pyridin-2-yl]-3-{[(tert-butoxy)carbonyl] amino}propoxy]propanoate (0.771 g, 54% yield) as an off-white foam. MS(ESI) m/z: 490.3 (M+H)$^+$.

129C. Preparation of tert-butyl 2-[(3S)-3-amino-3-[4-(2-amino-5-fluorophenyl)pyridin -2-yl]propoxy]propanoate, tris-trifluoroacetate To a clear, colorless solution of tert-butyl 2-[(3S)-3-[4-(2-amino-5-fluorophenyl) pyridin-2-yl]-3-{[(tert-butoxy)carbonyl]amino}propoxy]propanoate (0.696 g, 1.42 mmol) in DCM (11.9 mL) was added dropwise TFA (2.1 mL). The resulting bright, yellow solution was stirred at rt. The reaction was stopped after 1.5 h and the reaction was concentrated to give a yellow residue. The residue was diluted with DCM and concentrated. This was repeated (2 ×) to give tert-butyl 2-[(3S)-3-amino-3-[4-(2-amino -5-fluorophenyl)pyridin-2-yl]propoxy]propanoate, tris-trifluoroacetate (1.04 g, 100% yield) as a yellow-orange viscous oil. MS(ESI) m/z: 390.2 (M+H)$^+$.

129D. Preparation of tert-butyl 2-[(3S)-3-[4-(2-amino-5-fluorophenyl)pyridin-2-yl]-3-{[(benzyloxy)carbonyl]amino}propoxy]propanoate To a flask containing tert-butyl 2-[(3S)-3-amino-3[4-(2-amino-5-fluorophenyl) pyridin-2-yl]propoxy]propanoate tris-trifluoroacetate (1.04 g, 1.422 mmol) and N -benzyloxycarbonyl- oxy)succinimide (0.354 g, 1.422 mmol) was added DMF (14.2 ml) to give a clear, orange solution. Next, Hunig's base (1.24 ml, 7.11 mmol) was added and the resulting clear, yellow solution was stirred at rt. After 2 h, additional N -(benzyloxycarbonyloxy)succinimide (0.176 g, 0.711 mmol) and Hunig's base (1.24 ml, 7.11 mmol) were added. After an additional 1 h, the reaction was stopped. The reaction was poured into a mixture of water/satNaHCO$_3$ (42 mL/22 mL) to give a suspension. The reaction mixture was extracted with EtOAc (2×). The organic layers were combined and washed with brine, dried over Na$_2$SO$_4$, filtered and concentrated to give a clear, dark brown oil weighing 0.868 g. Purification by normal phase chromatography gave tert -butyl 2-[(3S)-3-[4-(2-amino-5-fluorophenyl)pyridin-2-yl]-3-{[(benzyloxy)carbonyl]amino}propoxy]propanoate (0.232 g, 31% yield) as a clear, colorless residue. MS(ESI) m/z: 524.3 (M+H)$^+$.

129E. Preparation of 2-[(3S)-3-[4-(2-amino-5-fluorophenyl)pyridin-2-yl]-3-{[(benzyloxy)carbonyl]amino}propoxy]propanoic acid bis-hydrochloride A clear, colorless solution of tert-butyl 2-[(3S)-3-[4-(2-amino-5-fluorophenyl) pyridin-2-yl]-3-{[(benzyloxy)carbonyl]aminopropoxy]propanoate (0.220 g, 0.420 mmol) in 4 M HCl in dioxane (15.8 ml, 63.0 mmol) was stirred at rt. After 3.5 h, the reaction was stopped and concentrated to give a yellow residue. The residue was dissolved in dioxane and concentrated. This was repeated again to give 2-[(3S)-3-[4-(2-amino-5-fluorophenyl)pyridin-2-yl]-3-{[(benzyloxy)carbonyl]amino}propoxy]propanoic acid, bis -hydrochloride (0.227 g, 100% yield) as a yellow foam. MS(ESI) m/z: 468.1 (M+H)$^+$.

129F. Preparation of benzyl N-[(14S)-4-fluoro-10-methyl-9-oxo-11-oxa-8,16-diazatricyclo[13.3.1.0$^{2,7}$]nonadeca-1(19),2,4,6,15,17-hexaen-14-yl]carbamate trifluoroacetate To a clear, colorless solution of BOP (0.464 g, 1.05 mmol) and DMAP (0.103 g, 0.840 mmol) in DCM (416 ml) and DMF (4.16 ml) at rt was added a pale, yellow solution of 2-[(3S)-3-[4-(2-amino-5-fluorophenyl)pyridin-2-yl]-3-{[(benzyloxy)carbonyl]amino}propoxy]propanoic acid bis-hydrochloride (0.227 g, 0.420 mmol) and DIEA (0.734 ml, 4.20 mmol) in DMF (21 mL) dropwise via a syringe pump over 4 h. After 23 h, the reaction was concentrated to remove the DCM to give a yellow-brown solution. The solution was partitioned between water, sat NaHCO$_3$, and EtOAc and the layers were separated. The aqueous layer was extracted with EtOAc. The organic layers were combined and washed with brine, dried over Na$_2$SO$_4$, filtered and concentrated to give a brown oil weighing 0.286 g. Purification by reverse phase chromatography gave benzyl N-[(14S)-4-fluoro-10-methyl-9-oxo-11-oxa-8,16-diazatricyclo[13.3.1.0$^{2,7}$]nonadeca -1(19),2,4,6,15,17-hexaen-14-yl]carbamate trifluoroacetate (0.094 g, 39.7% yield) as a yellow residue. MS(ESI) m/z: 450.1 (M+H)$^+$.

129G. Preparation of (14S)-14-amino-4-fluoro-10-methyl-11-oxa-8,16-diazatricyclo [13.3.1.0$^{2,7}$]nonadeca-1(19),2,4,6,15 ,17-hexaen-9-one, bis-trifluoroacetate (Diastereomer A), and 129H. Preparation of (14S)-14-amino-4-fluoro-10-methyl-11-oxa-8,16-diazatricyclo [13.3.1.0$^{2,7}$]nonadeca-1(19),2,4,6,15,17-hexaen-9-one bis-trifluoroacetate (Diastereomer B)

A clear, yellow solution of benzyl N-[(14S)-4-fluoro-10-methyl-9-oxo-11-oxa -8,16-diazatricyclo[13.3.1.0$^{2,7}$]nonadeca-1(19),2,4,6,15,17-hexaen-14-yl]carbamate trifluoroacetate (0.094 g, 0.167 mmol) in EtOH (6.67 ml) was degassed with Ar for 10 min. Next, 10% Pd/C (0.018 g, 0.017 mmol) was added to give a black suspension. H$_2$ was bubbled through the reaction mixture for several min then the reaction was stirred vigorously under an atmosphere of H$_2$. After 2.5 h, CELITE® was added and the reaction was filtered. The filter cake was rinsed with EtOH. The clear, yellow filtrate was concentrated to give a clear, yellow residue. Purification by reverse phase chromatography gave (14S)-14-amino-4-fluoro-10-methyl-11-oxa-8,16-diazatricyclo [13.3.1.0$^{2,7}$]nonadeca-1(19),2,4,6,15,17-hexaen-9-one, bis-trifluoroacetate (Diastereomer A) (0.0287 g, 32% yield) as a clear, colorless residue and (14S)-14-amino-4-fluoro-10-methyl-11-oxa-8,16-diazatricyclo[13.3.1.0$^{2,7}$] nonadeca-1(19),2,4,6,15,17-hexaen-9-one, bis-trifluoroacetate (Diastereomer B) (0.0341 g, 38% yield) as a clear, pale yellow residue. For Diastereomer A: MS(ESI) m/z: 316.1 (M+H)$^+$. For Diastereomer B: MS(ESI) m/z: 316.1 (M+H)$^+$.

129.I. Preparation of (14S)-14-{4-[5-chloro-2-(4-chloro-1H-1,2,3-triazol-1-yl)phenyl]-6-oxo-1,6-dihydropyrimidin-1-yl}-4-fluoro-10-methyl-11-oxa-8,16-diazatricyclo [13.3.1.0$^{2,7}$]nonadeca-1(19),2(7),3,5,15,17-hexaen-9-one trifluoroacetate (Diastereomer A)

(14 S)-14-Amino-4-fluoro-10-methyl-11-oxa-8,16-diazatricyclo [13.3.1.0$^{2,7}$]nonadeca-1(19),2,4,6,15,17-hexaen-9-one, bis-trifluoroacetate (Diastereomer A) (0.0287 g) was dissolved in MeOH (1 mL) to give a clear, pink solution. The solution was added to a pre-rinsed AGILENT® StratoSpheres SPE PL-HCO$_3$ MP resin cartridge. Gravity filtration, eluting with MeOH, gave a clear colorless filtrate which was concentrated to give (14S)-14-amino-4-fluoro-10-methyl-11-oxa-8,16-diazatricyclo[13.3.1.0$^{2,7}$]nonadeca -1(19),2,4,6,15,17-hexaen-9-one (Diastereomer A) (0.0163 g, 0.052 mmol) as an off -white solid. To a 1-dram vial containing a white suspension of 6-(5-chloro-2-(4-chloro -1H-1,2,3-triazol-1-yl)phenyl)pyrimidin-4-ol (0.016 g, 0.052 mmol), prepared as described in Example 9, in ACN (0.43 ml) was added HATU (0.026 g, 0.067 mmol) and DBU (0.012 ml, 0.078 mmol). The resulting clear, orange brown solution was stirred at rt. After 10 min, a solution of (14S)-14-amino-4-fluoro-10-methyl-11-oxa-8,16-diazatricyclo[13.3.1.0$^{2,7}$]nonadeca-1(19),2,4,6,15,17-hexaen-9-one (Diastereomer A) (0.0163 g, 0.052 mmol) in DMF (0.43 ml) was added and the reaction was stirred at rt. After 16 h, the reaction was stopped. Purification by reverse phase chromatography gave (14S)-14-{4-[5-chloro-2-(4-chloro-1H-1,2,3-triazol-1-yl)phenyl]-6-oxo-1,6dihydropyrimidin-1-yl}-4-fluoro-10-methyl-11-oxa-8,16-diazatricyclo[13.3.1.0$^{2,7}$] nonadeca-1(19),2(7),3,5,15,17-hexaen-9-one trifluoroacetate (Diastereomer A) (0.0144 g, 37.8% yield) as an off-white solid. MS(ESI) m/z: 606.1 (M+H)⁺ and 608.0 (M+2+H)⁺. $^1$H NMR (500 MHz, CD$_3$OD) δ 8.98 (s, 1H), 8.67 (d, J=5.0 Hz, 1H), 8.33 (s, 1H), 7.88 (d, J=2.2 Hz, 1H), 7.78 (d, J=0.8 Hz, 1H), 7.75-7.71 (m, 1H), 7.64 (d, J+8.5 Hz, 1H), 7.47 (dd, J=8.9, 2.9 Hz, 1H), 7.43 (dd, J=5.1, 1.8 Hz, 1H), 7.37 (dd, J=8.8, 5.2 Hz, 1H), 7.29-7.23 (m, 1H), 6.37 (d, J=0.6 Hz, 1H), 6.21 (dd, J=12.1, 5.2 Hz, 1H), 3.70-3.61 (m, 2H), 2.75-2.68 (m, 1H), 2.42-2.34 (m, 1H), 2.33-2.25 (m, 1H), 1.45 (d, J=6.9 Hz, 3H). $^{19}$F NMR (471 MHz, CD$_3$OD) δ −77.50 (s), −115.23 (s). Analytical HPLC (Method A): RT=8.92 min, purity=99.8%; Factor XIa Ki=0.7 nM, Plasma Kallikrein Ki=500 nM.

EXAMPLE 130

Preparation of (14S)-14-{4-[5-chloro-2-(4-chloro-1H-1,2,3-triazol-1-yl)phenyl]-6-oxo-1,6-dihydropyrimidin-1-yl}-4-fluoro-10-methyl-11-oxa-8,16-diazatricyclo[13.3.1.0$^{2,7}$]nonadeca-1(19),2(7),3,5,15,17-hexaen-9-one trifluoroacetate (Diastereomer B)

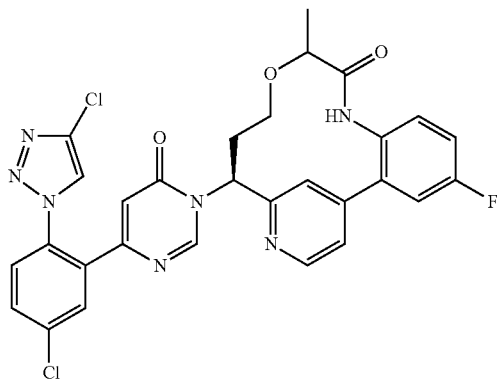 [SMILES: CC1OCC[C@H](n2cnc(-c3cc(Cl)ccc3-n3cc(Cl)nn3)cc2=O)c2cc(ccn2)-c2cc(F)ccc2NC1=O]

(14S)-14-{4-[5-Chloro-2-(4-chloro-1H-1,2,3-triazol-1-yl)phenyl]-6-oxo-1,6-dihydropyrimidin-1-yl}-4-fluoro-10-methyl-11-oxa-8,16-diazatricyclo[13.3.1.0$^{2,7}$]nonadeca-1(19),2(7),3,5,15,17-hexaen-9-one trifluoroacetate (Diastereomer B) (0.0186 g, 46% yield) was prepared in a similar manner as the procedure described for the preparation of (14S)-14-{4-[5-chloro-2-(4-chloro-1H-1,2,3-triazol-1-yl)phenyl]-6-oxo -1,6-dihydropyrimidin-1-yl}-4-fluoro-10-methyl-1 1-oxa-8,16-diazatricyclo[13.3.1.0$^{2,7}$]nonadeca-1(19),2(7),3,5,15,17-hexaen-9-one trifluoroacetate (Diastereomer A) by replacing (14S)-14-amino-4-fluoro-10-methyl-11-oxa-8,16-diazatricyclo[13.3.1.0$^{2,7}$]nonadeca-1(19),2,4,6,15,17-hexaen-9-one, bis-trifluoroacetate (Diastereomer A) with (14S)-14-amino-4-fluoro-10-methyl-11-oxa-8,16-diazatricyclo[13.3.1.0$^{2,7}$]nonadeca -1(19),2,4,6,15,17-hexaen-9-one bis-trifluoroacetate (Diastereomer B) (0.0341 g). MS(ESI) m/z: 606.0 (M+H)⁺ and 607.9 (M+2+H)⁺. $^1$H NMR (500 MHz, CD$_3$OD) δ 8.81 (d, J=0.5 Hz, 1H), 8.65 (d, J=4.7 Hz, 1H), 8.34 (s, 1H), 7.89 (d, J=2.5 Hz, 1H), 7.78 (d, J=0.8 Hz, 1H), 7.75-7.72 (m, 1H), 7.67-7.62 (m, 2H), 7.41-7.37 (m, 2H), 7.23 (td, J=8.5, 3.0 Hz, 1H), 6.36 (d, J=0.6 Hz, 1H), 6.11 (dd, J=11.6, 3.3 Hz, 1H), 4.04 (q, J=6.9 Hz, 1H), 3.75 (ddd, J=9.7, 7.4, 2.5 Hz, 1H), 3.60 (ddd, J=9.7, 7.4, 2.5 Hz, 1H), 2.55-2.47 (m, 1H), 2.34-2.27 (m, 1H), 1.26 (d, J=6.6 Hz, 3H). $^{19}$F NMR (471 MHz, CD$_3$OD) δ −77.60 (s), −116.96 (s). Analytical HPLC (Method A): RT=9.73 min, purity=99.6%; Factor XIa Ki=4.3 nM, Plasma Kallikrein Ki=12 nM.

EXAMPLE 131

Preparation of methyl N-[(14S)-14-{4-[5-chloro-2-(4-chloro-1H- 1,2,3-triazol-1-)phenyl]-6-oxo-1,6-dihydropyrimidin-1 -yl}-16,18-diazatricyclo [13.2.1.0$^{2,7}$]octadeca -1(17),2,4,6,15 (18)-pentaen-5-yl]carb amate trifluoroacetate

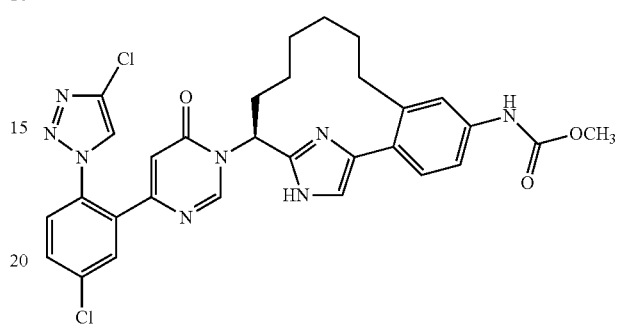

131A. Preparation of tert-butyl N-[(1S)-1-(4-{4-[(methoxycarbonyl)amino]-2-(pent-4-en-1-yl)phenyl}-1-{[2-(trimethylsilyl)ethoxy]methyl}-1H-imidazol-2-yl)but-3-en-1-yl]carbamate To a flame-dried, thick-walled flask was placed {3-bromo-4-[2-((S)-1-tert -butoxycarbonylamino-but-3-enyl)-1-(2-trimethylsilanyl-ethoxymethyl)-1H-imidazol-4-yl]phenyl}carbamic acid methyl ester (7.60 g, 12.75 mmol), prepared as described in Example 47B, pent-4-en-1-ylboronic acid (4.36 g, 38.3 mmol), K$_2$CO$_3$ (15.86 g, 115 mmol), Ag$_2$O (10.34 g, 44.6 mmol) and PdCl$_2$(dppf)-CH$_2$Cl$_2$ (1.042 g, 1.275 mmol). The flask was purged with Ar for several min and then degassed THF (63.8 ml) was added. The flask was sealed with a teflon screw cap, equipped with a viton O-ring, and then the black suspension was warmed to 80° C. After 13 h, the reaction was stopped and cooled to rt. The reaction was filtered through a plug of CELITE®, eluting with DCM. The clear, brown filtrate was concentrated to give a light, brown foam weighing 9.87 g. Purification by normal phase chromatography gave a mixture of tert-butyl N-[(1S)-1-(4-{4-[(methoxycarbonyl)amino]-2-(pent-4-en-1-yl)phenyl}-1-{[2-(trimethylsilyl)ethoxy]-methyl}-1H-imidazol-2-yl)but-3-en-1-yl]carbamate and {3-bromo-4-[2-((S)-1-tert -butoxycarbonylamino-but-3-enyl)-1-(2-trimethylsilanyl-ethoxymethyl)-1H-imidazol-4-yl] phenyl}carbamic acid methyl ester (1.09 g, 15% yield). MS(ESI) m/z: 585.3 (M+H)⁺.

131B. Preparation of methyl N-[(14S)-14-amino-16-{[2-(trimethylsilyl)ethoxy]methyl}-16,18-diazatricyclo [13.2.1.0$^{2,7}$]octadeca-1(17),2,4,6,15(18)-pentaen-5-yl]carbamate tert-Butyl N-[(1S)-1-(4-{4-[(methoxycarbonyl)amino]-2-(pent-4-en-1-yl)phenyl}-1-{[2-(trimethylsilyl)ethoxy]methyl}-1H-imidazol-2-yl)but-3 -en-1-yl]carbamate was converted to methyl N-[(14S)-14-amino-16-{[2-(trimethylsilyl)ethoxy]methyl}-16,18-diazatricyclo[13.2.1.0$^{2,7}$]octadeca-1(17),2,4,6,15(18)-pentaen-5-yl]carbamate in three steps following the procedures described in Examples 47E, 47F, and 471. MS(ESI) m/z: 459.3 (M+H)⁺. $^1$H NMR (500

MHz, CD₃OD) δ 7.34-7.30 (m, 1H), 7.28 (d, J+1.7 Hz, 1H), 7.23 (d, J+8.3 Hz, 1H), 7.10 (s, 1H), 5.47 (d, J+11.3 Hz, 1H), 5.43 (d, J=11.0 Hz, 1H), 4.37-4.32 (m, 1H), 3.73 (s, 3H), 3.70-3.60 (m, 2H), 2.76-2.67 (m, 1H), 2.53-2.44 (m, 1H), 1.98-1.83 (m, 2H), 1.54-1.36 (m, 2H), 1.35-1.06 (m, 5H), 1.02-0.89 (m, 2H), 0.82-0.69 (m, 1H), 0.01 (s, 9H).

131C. Preparation of methyl N-[(14S)-14-{4-[5-chloro-2-(4-chloro-1H-1,2,3-triazol-1-yl)phenyl]-6-oxo-1,6-dihydropyrimidin-1-yl}-16-{[2-(trimethylsilyl)ethoxy]methyl}-16,18-diazatricyclo[13.2.1.0$^{2,7}$]octadeca-1(17),2,4,6,15(18)pentaen-5-yl]carbamate trifluoroacetate Methyl N-[(14S)-14-{4-[5-chloro-2-(4-chloro-1H-1,2,3-triazol-1-yl)phenyl]-6-oxo-1,6-dihydropyrimidin-1-yl}-16-{[2-(trimethylsilyl)ethoxy]methyl}-16,18-diazatricyclo[13.2.1.0$^{2,7}$]octadeca-1(17),2,4,6,15(18)-pentaen-5-yl]carbamate trifluoroacetate (0.0279 g, 49% yield) was prepared in a similar manner as the procedure described in Example 129I, by using methyl N-[(14S)-14-amino-16-{[2-(trimethylsilyl)ethoxy]methyl}-16,18-diazatricyclo[13.2.1.0$^{2,7}$]octadeca-1(17),2,4,6,15 (18)-pentaen-5-yl]carbamate. MS(ESI) m/z: 749.4 (M+H)⁺ and 751.3 (M+2+H)⁺. ¹H NMR (500 MHz, CD₃OD) δ 8.45 (s, 1H), 8.39 (s, 1H), 7.86 (d, J+2.5 Hz, 1H), 7.74 (dd, J=8.5, 2.2 Hz, 1H), 7.65 (d, J=8.5 Hz, 1H), 7.58 (s, 1H), 7.42-7.38 (m, 2H), 7.38-7.35 (m, 1H), 6.46 (s, 1H), 5.95 (dd, J=9.9, 4.1 Hz, 1H), 5.62 (d, J=11.0 Hz, 1H), 5.35 (d, J=11.0 Hz, 1H), 3.75 (s, 3H), 3.67-3.61 (m, 2H), 2.86-2.78 (m, 1H), 2.62-2.54 (m, 1H), 2.46-2.39 (m, 1H), 2.28-2.20 (m, 1H), 1.73-1.61 (m, 1H), 1.60-1.38 (m, 5H), 1.32-1.22 (m, 1H), 0.98-0.88 (m, 3H), 0.01 (s, 9H).

131D. Preparation of methyl N-[(14S)-14-{4-[5-chloro-2-(4-chloro-1H-1,2,3-triazol-1-yl)phenyl]-6-oxo-1,6-dihydropyrimidin-1-yl}-16,18-diazatricyclo[13.2.1.0$^{2,7}$]octadeca-1(17),2,4,6,15(18)-pentaen-5-yl]carbamate trifluoroacetate Methyl N-[(14S)-14-{4-[5-chloro-2-(4-chloro-1H-1,2,3-triazol-1-yl)phenyl]-6-oxo-1,6-dihydropyrimidin-1-yl}-16,18-diazatricyclo[13.2.1.0$^{2,7}$]octadeca -1(17),2,4,6,15(18)-pentaen-5-yl]carbamate trifluoroacetate (0.0164 g, 68% yield) was prepared in a similar manner as the procedure described in Example 47K, by using methyl N-[(14S)-14-{4-[5-chloro-2-(4-chloro-1H-1,2,3-triazol-1-yl)phenyl]-6oxo-1,6- -dihydropyrimidin-1-yl}-16-{[2-(trimethylsilyl)ethoxy]methyl}-16,18-diazatricyclo [13.2.1.0$^{2,7}$]octadeca-1(17),2,4,6,15(18)-pentaen-5-yl]carbamate. MS(ESI) m/z: 619.2 (M+H)⁺. ¹H NMR (500 MHz, 60° C., DMSO-d₆) δ 8.72 (s, 1H), 8.66 (s, 1H), 7.91 (d, J=2.2 Hz, 1H), 7.81 (dd, J=8.3, 2.2 Hz, 1H), 7.72 (d, J=8.5 Hz, 1H), 7.40-7.32 (m, 3H), 7.30 (s, 1H), 6.35 (d, J=0.8 Hz, 1H), 5.84 (dd, J=10.3, 5.9 Hz, 1H), 3.69 (s, 3H), 2.73-2.63 (m, 1H), 2.61-2.53 (m, 1H), 2.21-2.07 (m, 2H), 1.38-1.19 (m, 7H), 0.82-0.67 (m, 1H). Analytical HPLC (Method A): RT=6.88 min, purity=100%; Factor XIa Ki=5 nM, Plasma Kallikrein Ki=2,200 nM.

EXAMPLE 132

Preparation of methyl N-[(14S)-14-{4-[5-chloro-2-(1H-1,2,3,4-tetrazol-1-yl)phenyl]-6-oxo-1,6-dihydropyrimidin-1-yl}-16,18-diazatricyclo[13.2.1.0$^{2,7}$]octadeca -1(17),2,4,6,15(18)-pentaen-5-yl]carbamate trifluoroacetate

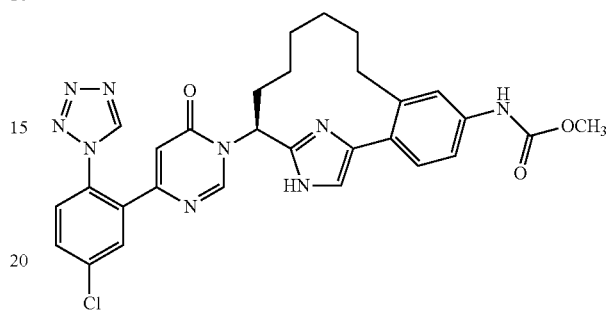

132A. Preparation of methyl N-[(14S)-14-{4-[5-chloro-2-(1H-1,2,3,4-tetrazol-1-yl)phenyl]-6-oxo-1,6-dihydropyrimidin-1-yl}-16-{[2-(trimethylsilyl)ethoxy]methyl}-16,18-diazatricyclo[13.2.1.0$^{2,7}$]octadeca-1(17),2,4,6,15(18)-pentaen-5-yl]carbamate trifluoroacetate Methyl N-[(14S)-14-{4-[5-chloro-2-(1H-1,2,3,4-tetrazol-1-yl)phenyl]-6-oxo-1,6-dihydropyrimidin-1-yl}-16-{[2-(trimethylsilyl)ethoxy]methyl}-16,18-diazatricyclo[13.2.1.0$^{2,7}$]octadeca-1(17),2,4,6,15(18)-pentaen-5-yl]carbamate trifluoroacetate (0.0312 g, 57% yield) was prepared in a similar manner as the procedure described in Example 129I, using N-[(14S)-14-amino-16-{[2-(trimethylsilyl)ethoxy]methyl}-16,18diazatricyclo[13.2.1.0$^{2,7}$]octadeca-1(17),2,4,6,15(18)-pentaen-5-yl]carbamate, prepared as described in Example 131B. MS(ESI) m/z: 716.4 (M+H)⁺ and 718.4 (M+2+H)⁺. ¹H NMR (500 MHz, CD₃OD) δ 9.45 (s, 1H), 8.35 (s, 1H), 7.88 (d, J=2.2 Hz, 1H), 7.78 (dd, J=8.5, 2.5 Hz, 1H), 7.69 (d, J=8.5 Hz, 1H), 7.55 (s, 1H), 7.41-7.34 (m, 3H), 6.61 (d, J=0.8 Hz, 1H), 5.98-5.94 (m, 1H), 5.61 (d, J=11.3 Hz, 1H), 5.38 (d, J=11.0 Hz, 1H), 3.75 (s, 3H), 3.64-3.58 (m, 2H), 2.94-2.83 (m, 1H), 2.60-2.50 (m, 1H), 2.46-2.36 (m, 1H), 2.26-2.14 (m, 1H), 1.71-1.58 (m, 1H), 1.57-1.35 (m, 4H), 1.33-1.22 (m, 1H), 1.08-0.85 (m, 4H), 0.00 (s, 9H).

132B. Preparation of methyl N-[(14S)-14-{4-[5-chloro-2-(1H-1,2,3,4-tetrazol-1-yl)phenyl]-6-oxo-1,6-dihydropyrimidin-1-yl}-16,18-diazatricyclo[13.2.1.0$^{2,7}$]octadeca -1(17),2,4,6,15(18)-pentaen-5-yl]carbamate trifluoroacetate Methyl N-[(14S)-14-{4-[5-chloro-2-(1H-1,2,3,4-tetrazol-1-yl)phenyl]-6-oxo-1,6-dihydropyrimidin-1-yl}-16,18-diazatricyclo[13.2.1.0$^{2,7}$]octadeca-1(17),2,4,6,15(18) -pentaen-5-yl]carbamate trifluoroacetate (0.0082 g, 31% yield) was prepared in a similar manner as the procedure described in Example 47K, by using methyl N-[(14S)-14-{4-[5-chloro-2-(1H-1,2,3,4-tetrazol-1-yl)phenyl]-6-oxo-1,6-dihydropyrimidin-1-yl}-16-{[2-(trimethylsilyl)ethoxy]methyl}-16,18-diazatricyclo[13.2.1.0$^{2,7}$]octadeca -1(17),2,4,6,15(18)-pentaen-5-yl]carbamate trifluoroacetate, prepared as described in Example 131A. MS(ESI) m/z: 586.3 (M+H)⁺. ¹F NMR (500 MHz, CD₃OD) δ 9.47 (s, 1H), 8.44 (s, 1H), 7.94 (d, J=2.5 Hz, 1H), 7.80 (dd, J=8.5, 2.2 Hz, 1H), 7.71 (d, J=8.5 Hz, 1H), 7.48-7.43 (m, 3H), 7.38 (d, J=8.3 Hz, 1H), 6.63 (d, J=0.6 Hz, 1H), 5.62 (dd, J=11.1, 5.1 Hz, 1H), 3.75 (s, 3H), 2.61-2.52 (m, 1H), 2.47-2.25 (m, 3H), 1.61-1.47 (m, 2H), 1.45-1.34 (m, 2H), 1.34-1.12 (m, 3H), 0.45-0.30 (m, 1H). Analytical HPLC (Method A): RT=6.23 min, purity=99.8%; Factor XIa Ki=1.1 nM, Plasma Kallikrein Ki=340 nM.

EXAMPLE 133

Preparation of (15S)-15-(4-{5-chloro-2-[4-(difluoromethyl)-1H-1,2,3-triazol-1-yl]phenyl}-6-oxo-1,6-dihydropyrimidin-1-yl)-4-fluoro-11-methyl-8,17-diazatricyclo [14.3.1.0$^{2,7}$]icosa-1(20),2(7),3,5,16,18-hexaen-9-one trifluoroacetate (Diastereomer B)

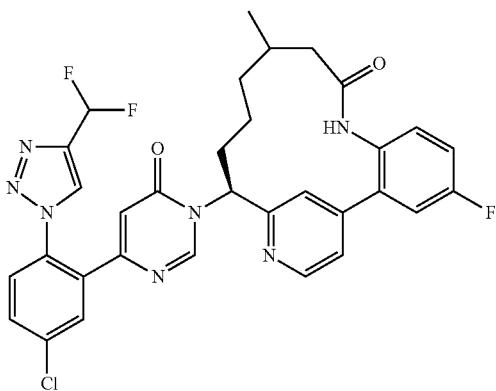 [SMILES: CC1CCC[C@H](n2cnc(-c3cc(Cl)ccc3-n3cc(C(F)F)nn3)cc2=O)c2cc(ccn2)-c2cc(F)ccc2NC(=O)C1]

133A. Preparation of tert-butyl ((1S)-1-(4-(5-fluoro-2-(3-methylpent-4-enamido)phenyl) pyridin-2-yl)but-3-en-1-yl)carbamate To a cooled (−10° C.) solution of 3-methylpent-4-enoic acid (0.479 g, 4.20 mmol), (S)-tert-butyl (1-(4-(2-amino-5-fluorophenyl)pyridin-2-yl)but-3-en-1-yl)carbamate (1 g, 2.80 mmol), and pyridine (0.68 ml, 8.39 mmol) in EtOAc (28.0 ml) was added dropwise T3P® (50%wt in EtOAc) (3.33 ml, 5.60 mmol). After a few min, the reaction was allowed to warm to rt. After 18 h, the reaction mixture was diluted with EtOAc, washed with sat NaHCO$_3$, brine, dried over MgSO$_4$, filtered, and concentrated. Purification by normal phase chromatography gave tert-butyl ((1S)-1-(4-(5-fluoro-2-(3-methylpent-4-enamido) phenyl)pyridin-2-yl)but-3-en-1-yl)carbamate (1.13 g, 89% yield) as a white foam. MS(ESI) m/z: 454.2 (M+H)$^+$. $^1$H NMR (400 MHz, CDCl$_3$) δ 8.66 (d, J=5.1 Hz, 1H), 8.07 (dd, J=8.7, 5.2 Hz, 1H), 7.24-7.08 (m, 3H), 7.02-6.91 (m, 2H), 5.78-5.65 (m, 2H), 5.56-5.45 (m, 1H), 5.13-4.78 (m, 5H), 2.72-2.57 (m, 3H), 2.31-2.15 (m, 2H), 1.43 (s, 9H), 1.07-1.00 (m, 3H).

133B and 133C. Preparation of tert-butyl N-[(12E,15S)-4-fluoro-11-methyl-9-oxo-8,17-diazatricyclo[14.3.1.0$^{2,7}$]icosa-1(20),2(7),3,5,12,16,18-heptaen-15-yl]carbamate (Diastereomer A and Diastereomer B)

To a round-bottomed flask was added tert-butyl ((lS)-1-(4-(5-fluoro-2-(3-methylpent-4-enamido)phenyl)pyridin-2-yl)but-3-en-1-yl)carbamate (1.13 g, 2.49 mmol), pTsOH.H$_2$O (0.521 g, 2.74 mmol), and DCM (249 ml). The flask was equipped with a reflux condenser and the clear, colorless solution was degassed with Ar for 30 min. The reaction was then warmed to reflux for 1 h. In a separate, flame-dried round-bottom flask was added Second Generation Grubbs Catalyst (0.423 g, 0.5 mmol) and the flask was purged with Ar for several min. Degassed DCM (2 ml) was added to give a clear, burgundy solution. The solution was added dropwise to the above reaction. The resulting clear yellow solution was stirred at reflux for 48 h and then the reaction was cooled to rt. The reaction mixture was washed with sat NaHCO$_3$, brine, dried over Na$_2$SO$_4$, filtered, and concentrated to give dark brown solid. Purification by normal phase chromatography afforded tert-butyl N-[(12E,15S)-4-fluoro-11-methyl-9-oxo-8,17-diazatricyclo [14.3.1.0$^{2,7}$]icosa-1(20),2(7),3,5,12,16,18-heptaen-15-yl] carbamate (Diastereomer A) (0.11 g, 10.4% yield). MS(ESI) m/z: 426.2 (M+H)$^+$ and tert-butyl N -[(12E,15S)-4-fluoro-11-methyl-9-oxo-8,17-diazatricyclo[14.3.1.0$^{2,7}$]icosa -1(20),2(7),3,5,12,16,18-heptaen-15-yl]carbamate (Diastereomer B) (0.23 g, 11.3% yield) also obtained as a yellow solid. MS(ESI) m/z: 426.2 (M+H)$^+$.

133D. Preparation of tert-butyl N-[(15S)-4-fluoro-11-methyl-9-oxo-8,17-diazatricyclo [14.3.1.0$^{2,7}$]icosa-1(20),2(7),3,5,16,18-hexaen-15-yl]carbamate (Diastereomer B)

To the solution of tert-butyl N-[(12E,15S)-4-fluoro-11-methyl-9-oxo-8,17-diazatricyclo[14.3.1.0$^{2,7}$]icosa-1(20),2(7),3,5,12,16,18-heptaen-15-yl]carbamate (Diastereomer B) (0.23 g, 0.28 mmol) in MeOH (3 ml) was added 10% Pd on carbon (0.030 g, 0.028 mmol). H$_2$ gas, from a balloon, was bubbled through the reaction for 3 min, then the reaction was stirred at rt under H$_2$-balloon for 18 h. The reaction mixture was filtered through CELITE® and rinsed with MeOH. The filtrate was concentrated. Purification by normal phase chromatography afforded tert-butyl N-[(15S)-4-fluoro-11-methyl-9-oxo-8,17-diazatricyclo[14.3.1.0$^{2,7}$]icosa-1(20),2(7),3,5,16,18-hexaen-15-yl]carbamate (Diastereomer B) (0.108 g, 90% yield) as a white solid. MS(ESI) m/z: 428.1 (M+H)$^+$.

133E. Preparation of (15S)-15-amino-4-fluoro-11-methyl-8,17-diazatricyclo[14.3.1.0$^{2,7}$]icosa-1(20),2(7),3,5,16,18-hexaen-9-one (Diastereomer B)

To the solution of tert-butyl N-[(15S)-4-fluoro-11-methyl-9-oxo-8,17-diazatricyclo[14.3.1.0$^{2,7}$]icosa-1(20),2(7),3,5,16,18-hexaen-15-yl]carbamate (Diastereomer B) in DCM (1 ml) was added TFA (1 ml, 12.98 mmol). The reaction was stirred at rt for 2 h, then the reaction was concentrated to dryness to afford a white solid (0.17 g). A portion of the white solid (0.05 g) was dissolved in MeOH. The solution was added to a pre-rinsed AGILENT® StratoSpheres SPE PL-HCO$_3$ MP resin cartridge, and the cartridge rinsed with MeOH. The filtrate was concentrated to afford (15S)-15-amino -4-fluoro-11-methyl-8,17-diazatricyclo[14.3.1.0$^{2,7}$] icosa-1(20),2(7),3,5,16,18-hexaen-9-one (Diastereomer B) (0.04 g) as a yellow solid. MS(ESI) m/z: 328.2 (M+H)$^+$.

133F. Preparation of (155)-15-(4-{5-chloro-2-[4-(difluoromethyl)-1H-1,2,3-triazol-1-yl]phenyl}-6-oxo-1,6-dihydropyrimidin-1-yl)-4-fluoro-11-methyl-8,17-diazatricyclo [14.3.1.0$^{2,7}$]icosa-1(20),2(7),3,5,16,18-hexaen-9-one trifluoroacetate (Diastereomer B)

(15S)-15-(4-{5-Chloro-2[4-(difluoromethyl)-1H-1,2,3-triazol-1-yl]phenyl}-6-oxo-1,6-dihydropyrimidin-1-yl)-4-fluoro-11-methyl-8,17-diazatricyclo[14.3.1.0$^{2,7}$]icosa -1(20),2(7),3,5,16,18-hexaen-9-one trifluoroacetate (Diastereomer B) (8.89 mg, 25.9% yield) was prepared in a similar manner as the procedure described in Example 147, using 6-(5-chloro-2-(4-(difluoromethyl)-1H-1,2,3-triazol-1-yl) phenyl)pyrimidin-4-ol, hydrobromide (0.019 g, 0.046 mmol), prepared as described in Example 16, and (15S) -15-amino-4-fluoro-11-methyl-8,17-diazatricyclo[14.3.1.0$^{2,7}$]icosa-1(20),2(7),3,5,16,18-hexaen-9-one (Diastereomer B) (0.015 g, 0.046 mmol). MS(ESI) m/z: 634.5 (M+H)$^+$. $^1$H NMR (400 MHz, CD$_3$OD) δ 8.67-8.62 (m, 2H), 8.51 (t, J=1.4 Hz, 1H), 7.86 (d, J=2.4 Hz, 1H), 7.76-7.71 (m, 1H), 7.67-7.63 (m, 1H), 7.58 (s, 1H), 7.46-7.38 (m, 2H), 7.30-7.19 (m, 2H), 6.99 (t, J=54.0 Hz, 1H), 6.32 (d, J=0.4 Hz, 1H), 5.85 (dd, J=12.8, 3.5 Hz, 1H), 2.35-1.91 (m, 5H), 1.55-1.31 (m, 3H), 1.04 (d, J=7.0 Hz, 3H), 0.94-0.83 (m, J=12.2, 12.2 Hz, 1H). $^{19}$F NMR (376 MHz, CD$_3$OD) δ −77.25 (s), −114.46 (s), −116.48 (s). Analytical HPLC (Method A): RT=9.60 min, 99.9% purity; Factor XIa Ki=3.3 nM, Plasma Kallikrein Ki=150 nM.

EXAMPLE 134

Preparation of (10R,14S)-14-(4-{3-chloro-6-[4-(difluoromethyl)-1H-1,2,3-triazol-1-yl]-2-fluorophenyl}-6-oxo-1,6-dihydropyrimidin-1-yl)-4-fluoro-10-methyl-8,16-diazatricyclo [13.3.1.0$^{2,7}$]nonadeca-1(19),2(7),3,5,15,17-hexaen-9-one trifluoroacetate

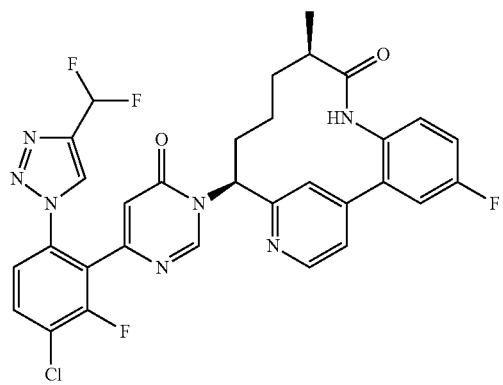 [SMILES: C[C@@H]1CCC[C@H](n2cnc(-c3c(-n4cc(C(F)F)nn4)ccc(Cl)c3F)cc2=O)c2cc(ccn2)-c2cc(F)ccc2NC1=O]

(10R,14S)-14-(4-{3-Chloro-6-[4-(difluoromethyl)-1H-1,2,3-triazol-1-yl]-2fluorophenyl}-6-oxo-1,6-dihydropyrimidin-1-yl)-4-fluoro-10-methyl-8,16-diazatricyclo [13.3.1.0$^{2,7}$]nonadeca-1(19),2(7),3,5,15,17-hexaen-9-one trifluoroacetate (0.017 g, 47.1% yield) was prepared in a similar manner as the procedure described in Example 150, by replacing 6-(5-chloro-2-methoxyphenyl)pyrimidin-4-ol with 6-(3-chloro-6-(4-(difluoromethyl)-1H-1,2,3-triazol-1-yl)-2-fluorophenyl)pyrimidin-4-ol (0.016 g, 0.048 mmol), prepared as described in Example 21. MS(ESI) m/z: 638.5 (M+H)$^+$. $^1$H NMR (400 MHz, CD$_3$OD) δ 8.91 (s, 1H), 8.66 (d, J=5.1 Hz, 1H), 8.52 (s, 1H), 7.90-7.83 (m, 1H), 7.70 (s, 1H), 7.57 (dd, J=8.7, 1.4 Hz, 1H), 7.44-7.36 (m, 2H), 7.31-7.19 (m, 2H), 6.97 (t, J=54.0 Hz, 1H), 6.59 (s, 1H), 6.00 (dd, J=12.8, 4.6 Hz, 1H), 2.70-2.60 (m, 1H), 2.24-2.13 (m, 1H), 2.06-1.89 (m, 2H), 1.56-1.35 (m, 2H), 0.96 (d, J=7.0 Hz, 3H), 0.78-0.61 (m, 1H). $^{19}$F NMR (376MHz, CD$_3$OD) δ −77.43 (s), −114.58 (d, J=5.7 Hz), −115.08 (s), −116.31 (s). Analytical HPLC (Method A): RT=9.26 min, 99.9% purity; Factor XIa Ki=0.16 nM, Plasma Kallikrein Ki=12 nM.

EXAMPLE 135

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,16-diazatricyclo [13.3.1.0$^{2,7}$]nonadeca-1(19),2(7),3,5,15,17-hexaen-9-one trifluoroacetate

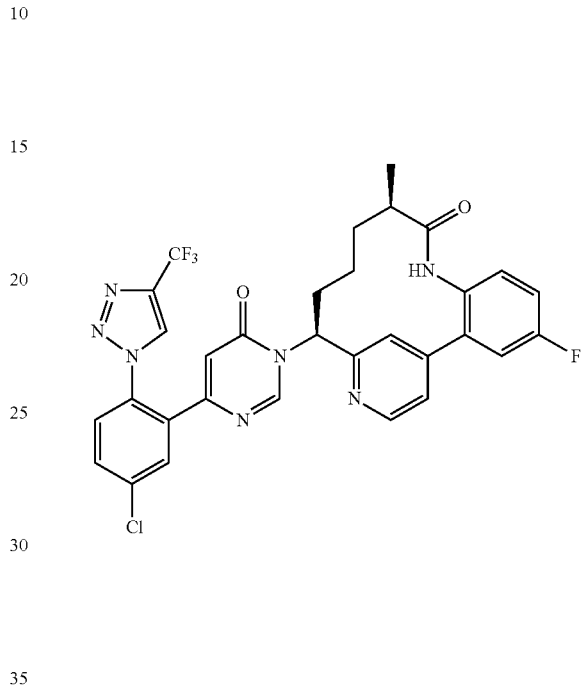

To a 1-dram vial containing an off-white suspension of 6-(5-chloro-2-(4-(trifluoromethyl)-1H-1,2,3-triazol-1-yl)phenyl)pyrimidin-4-ol (0.016 g, 0.048 mmol), prepared as described in Example 15, and HATU (0.024 g, 0.062 mmol) in ACN (0.48 ml) was added dropwise DBU (10.8 μl, 0.072 mmol). The resulting yellow solution was stirred at rt. Over time the color became an orange solution. After 20 min, a pink solution of (10R,14S)-14-amino-4-fluoro-10-methyl-8,16-diazatricyclo[13.3.1.0$^{2,7}$]nonadeca -1(19),2(7),3,5,15,17-hexaen-9-one (0.015 g, 0.048 mmol), prepared as described in Example 28, in DMF (0.48 ml) was added. The reaction was stirred overnight. Purification by reverse phase chromatography gave, after concentration and lyophilization, (10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,16-diazatricyclo [13.3.1.0$^{2,7}$] nonadeca-1(19),2(7),3,5,15,17-hexaen-9-one trifluoroacetate (0.0163 g, 44% yield) as a white solid. MS(ESI) m/z: 638.2 (M+H)$^+$ and 640.2 (M+2+H)$^+$. $^1$H NMR (500 MHz, CD$_3$OD) δ 8.87 (s, 1H), 8.81 (d, J=0.8 Hz, 1H), 8.64 (d, J=5.0 Hz, 1H), 7.89 (d, J=2.5 Hz, 1H), 7.75 (dd, J=8.5, 2.2 Hz, 1H), 7.70 (d, J=0.8 Hz, 1H), 7.68 (d, J=8.5 Hz, 1H), 7.42 (dd, J=5.0, 1.7 Hz, 1H), 7.38 (dd, J=9.1, 2.8 Hz, 1H), 7.28 (dd, J=8.5, 5.2 Hz, 1H), 7.25 - 7.20 (m, 1H), 6.42 (d, J=0.8 Hz, 1H), 5.99 (dd, J=12.4, 4.7 Hz, 1H), 2.68 -2.61 (m, 1H), 2.18 (tt, J=12.7, 3.9 Hz, 1H), 2.04-1.89 (m, 2H), 1.54-1.36 (m, 2H), 0.95 (d, J=7.2 Hz, 3H), 0.75-0.60 (m, 1H). $^{19}$F NMR (471 MHz, CD$_3$OD) δ −62.54 (s), −77.50 (s), −116.28 (s). Analytical HPLC (Method A): RT=9.37 min, purity=99.6%; Factor XIa Ki=0.2 nM, Plasma Kallikrein Ki=29 nM.

EXAMPLE 136

Preparation of (10R,14S)-14-{4-[3-chloro-6-(4-ethoxy-1H-1,2,3-triazol-1-yl)-2-fluorophenyl]-6-oxo-1,6-dihydropyrimidin-1-yl}-4-fluoro-10-methyl-8,16-diazatricyclo [13.3.1.0$^{2,7}$]nonadeca-1(19),2(7),3,5,15,17-hexaen-9-one trifluoroacetate

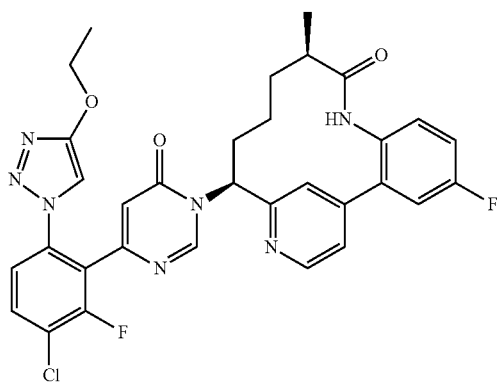 [SMILES: CCOc1cn(-c2ccc(Cl)c(F)c2-c2cc(=O)n([C@H]3CCC[C@@H](C)C(=O)Nc4ccc(F)cc4-c4ccnc3c4)cn2)nn1]

136A. Preparation of 4-(3-chloro-6-(4-ethoxy-1H-1,2,3-triazol-1-yl)-2-fluorophenyl)-6-methoxypyrimidine To a cooled (0° C.), clear, yellow solution of 4-chloro-3-fluoro-2-(6-methoxypyrimidin-4-yl)aniline (0.100 g, 0.39 mmol) in ACN (5.63 ml) was added isoamyl nitrite (0.079 ml, 0.59 mmol), followed by the dropwise addition of TMSN$_3$ (0.078 ml, 0.59 mmol). After 10 min, the cold bath was removed, and the reaction was allowed to warm to rt. After 1 h, ethoxyacetylene (40% in hexanes) (0.28 ml, 1.18 mmol) and Cu$_2$O (5.64 mg, 0.039 mmol) were added. The flask was equipped with a reflux condenser and the reaction was heated to 50° C. for 1 h and then the reaction was cooled to rt. The reaction was diluted with DCM and washed with sat NH$_4$Cl brine, dried over MgSO$_4$, filtered and concentrated to give a brown oil. Purification by normal phase chromatography afforded 4-(3-chloro-6-(4-ethoxy-1H-1,2,3-triazol-1-yl)-2-fluorophenyl)-6-methoxypyrimidine (0.1 g, 72.5% yield) as a brown solid. MS(ESI) m/z: 350.1 (M+H)$^+$. $^1$H NMR (400 MHz, CDCl$_3$) δ 8.72 (d, J=1.1 Hz, 1H), 7.65 (dd, J=8.6, 7.5 Hz, 1H), 7.39 (dd, J=8.6, 1.5 Hz, 1H), 7.05 (s, 1H), 6.78 (t, J=1.1 Hz, 1H), 4.25 (q, J=7.0 Hz, 2H), 4.01 (s, 3H), 1.38 (t, J=7.0 Hz, 3H).

136B. Preparation of 6-(3-chloro-6-(4-ethoxy-1H-1,2,3-triazol-1-yl)-2-fluorophenyl) pyrimidin-4-ol hydrobromide A clear, yellow solution of 4-(3-chloro-6-(4-ethoxy-1H-1,2,3-triazol-1-yl)-2-fluorophenyl)-6-methoxypyrimidine (0.1 g, 0.29 mmol) in HOAc (2.86 ml) and 48% HBr in water (1.62 ml, 14.30 mmol) was warmed to 65° C. After 5 h, the reaction was cooled to rt and the reaction was concentrated. Et$_2$O (3 ml) was added and the mixture was sonicated to give a yellow suspension. The solid was collected by filtration, rinsed with Et$_2$O (2×1 ml), and air-dried to give a yellow solid as 6-(3-chloro-6-(4-ethoxy-1H-1,2,3-triazol-1-yl)-2-fluorophenyl)pyrimidin-4-ol hydrobromide (0.12 g, 100% yield). MS(ESI) m/z: 336.0 (M+H)$^+$. $^1$H NMR (400 MHz, CD$_3$OD) δ 8.96 (d, J=0.9 Hz, 1H), 8.00-7.92 (m, 2H), 7.64 (dd, J=8.8, 1.8 Hz, 1H), 6.63 (s, 1H), 4.23 (q, J=7.0 Hz, 2H), 1.40 (t, J=7.0 Hz, 3H).

136C. Preparation of (10R,14S)-14-{4-[3-chloro-6-(4-ethoxy-1H-1,2,3-triazol-1-yl)-2-fluorophenyl]-6-oxo-1,6-dihydropyrimidin-1-yl}-4-fluoro-10-methyl-8,16-diazatricyclo [13.3.1.0$^{2,7}$]nonadeca-1(19),2(7),3,5,15,17-hexaen-9-one trifluoroacetate (10R,14S)-14-{4-[3-Chloro-6-(4-ethoxy-1H-1,2,3-triazol-1-yl)-2-fluorophenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate (9.2 mg, 25.7% yield) was prepared in a similar manner as the procedure described in Example 147, by replacing 6-(3,6-dichloro-2-fluorophenyl)pyrimidin-4-ol, hydrobromide with 6-(3-chloro-6-(4-ethoxy-1H-1,2,3-triazol-1-yl)-2-fluorophenyl)pyrimidin-4-ol hydrobromide (19.94 mg, 0.048 mmol). MS(ESI) m/z: 632.2 (M+H)$^+$. $^1$H NMR (400 MHz, CD$_3$OD) δ 8.96 (s, 1H), 8.68 (d, J=5.1 Hz, 1H), 7.82 (dd, J=8.6, 7.7 Hz, 1H), 7.76 (s, 1H), 7.66 (s, 1H), 7.54-7.45 (m, 2H), 7.39 (dd, J=9.0, 2.6 Hz, 1H), 7.31-7.21 (m, 2H), 6.53 (s, 1H), 6.00 (dd, J=12.5, 4.8 Hz, 1H), 4.11 (q, J=7.0 Hz, 2H), 2.71-2.60 (m, 1H), 2.30-2.18 (m, 1H), 2.10-1.90 (m, 2H), 1.56-1.38 (m, 2H), 1.34 (t, J=7.0 Hz, 3H), 0.96 (d, J7.0 Hz, 3H), 0.77-0.58 (m, 1H). $^{19}$F NMR (376MHz, CD$_3$OD) δ −77.67 (s), −115.13 (s), −116.22 (s). Analytical HPLC (Method A): RT=9.02 min, 99.9% purity; Factor XIa Ki=1.6 nM, Plasma Kallikrein Ki=76 nM.

EXAMPLE 137

Preparation of (10R,14S)-14-{4-[3-chloro-2-fluoro-6-(4-methyl-1H-1,2,3-triazol-1-yl)phenyl]-6-oxo-1,6-dihydropyrimidin-1-yl}-4-fluoro-10-methyl-8,16-diazatricyclo [13.3.1.0$^{2,7}$]nonadeca-1(19),2(7),3,5,15,17-hexaen-9-one

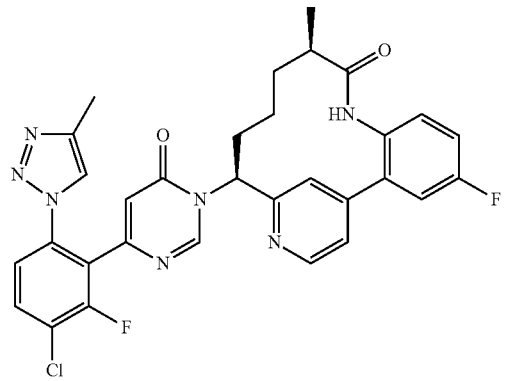 [SMILES: Cc1cn(-c2ccc(Cl)c(F)c2-c2cc(=O)n([C@H]3CCC[C@@H](C)C(=O)Nc4ccc(F)cc4-c4ccnc3c4)cn2)nn1]

137A. Preparation of 4-[3-chloro-2-fluoro-6-(4-methyl-1H-1,2,3-triazol-1-yl)phenyl]-6-methoxypyrimidine trifluoroacetate To a cooled (0° C.), clear, yellow solution of 4-chloro-3-fluoro-2-(6-methoxypyrimidin-4-yl)aniline (0.250 g, 0.986 mmol), prepared as described in Example 7C, in EtOH (12.3 ml) was added Hunig's base (1.03 ml, 5.91 mmol). The resulting mixture was stirred for 10 min. Then, a suspension of N'-[(2E)-1,1-dichloropropan-2-ylidene]-4-methylbenzene-1-sulfonohydrazide (0.591 g, 1.28 mmol) in ACN (8 mL) was added dropwise. The resulting dark orange solution was allowed to warm to rt. After 96 h, the reaction was stopped and concentrated to give a dark brown oil. Purification by reverse phase chromatography gave 4-[3-chloro-2-fluoro-6-(4-methyl-1H-1,2,3-triazol-1-yl)phenyl]-6- methoxypyrimidine trifluoroacetate (0.0725 g, 17% yield) as a yellow residue. MS(ESI) m/z: 320.1 (M+H)+. 1H NMR (500 MHz, CD3OD) δ 8.64 (d, J=1.1 Hz, 1H), 7.86-7.82 (m, 2H), 7.52 (dd, J=8.7, 1.8 Hz, 1H), 6.95 (t, J=1.1 Hz, 1H), 4.00 (s, 3H), 2.29 (d, J=0.8 Hz, 3H). 19F NMR (471 MHz, CD3OD) δ −77.68 (s), −115.91 (s).

137B. Preparation 6-[3-chloro-2-fluoro-6-(4-methyl-1H-1,2,3-triazol-1-yl)phenyl]pyrimidin-4-ol A clear, yellow solution of 4-[3-chloro-2-fluoro-6-(4-methyl-1H-1,2,3-triazol-1-yl)phenyl]-6-methoxypyrimidine trifluoroacetate (0.072 g, 0.166 mmol) in AcOH (1.66 ml) and 48% HBr in water (0.94 ml, 8.30 mmol) was warmed to 85° C. After 1 h, the reaction was cooled to rt and then was concentrated to give a yellow solid. The yellow solid was suspended in EtOAc and sat NaHCO3 was added. The layers were separated and the aqueous layer was extracted with EtOAc (2×). The organic layers were combined and washed with brine, dried over Na2SO4, filtered and concentrated to give an off-white solid weighing 0.073 g. The solid was suspended in Et2O (2 mL) and sonicated. The solid was collected by filtration, rinsed with Et2O, air-dried, and dried under vacuum to give 6-[3-chloro-2-fluoro-6-(4-methyl-1H-1,2,3-triazol-1-yl)phenyl]pyrimidin-4-ol (0.0381 g, 71% yield) as an off-white solid. MS(ESI) m/z: 306.1 (M+H)+. 1H NMR (500 MHz, CD3OD) δ 8.08 (d, J=0.8 Hz, 1H), 7.92 (d, J=0.8 Hz, 1H), 7.82 (dd, J=8.5, 7.7 Hz, 1H), 7.50 (dd, J=8.8, 1.7 Hz, 1H), 6.50 (s, 1H), 2.32 (d, J=0.6 Hz, 3H). 19F NMR (471 MHz, CD3OD) δ −115.39 (s, 1F).

137C. Preparation of (10R,14S)-14-{4-[3-chloro-2-fluoro-6-(4-methyl-1H-1,2,3-triazol -1-yl)phenyl]-6-oxo-1,6-dihydropyrimidin-1-yl}-4-fluoro-10-methyl-8,16-diazatricyclo [13.3.1.0$^{2,7}$]nonadeca-1(19),2(7),3,5,15,17-hexaen-9-one To an off-white suspension of 6-(3-chloro-2-fluoro-6-(4-methyl-1H-1,2,3-triazol -1-yl)phenyl)pyrimidin-4-ol (0.013 g, 0.043 mmol) and HATU (0.021 g, 0.055 mmol) in ACN (0.42 ml) was added dropwise DBU (9.6 μl, 0.064 mmol). The resulting yellow solution was stirred at rt. Over time the color became an orange solution. After 20 min, a pink solution of (10R,14S)-14-amino-4-fluoro-10-methyl-8,16-diazatricyclo[13.3.1.0$^{2,7}$]nonadeca-1(19),2(7),3,5,15,17-hexaen-9-one, prepared as described in Example 28, (0.013 g, 0.043 mmol) in DMF (0.42 ml) was added. Over time a precipitate formed. After 17 h, the reaction was stopped and the solid was collected by filtration, rinsed with ACN and air-dried to give an off-white solid weighing 0.017 g. The solid was suspended in a mixture of 1:1 ACN/DMF (1.5 mL) and deionized water (1 mL). The solid was collected by filtration, rinsed with ACN and water and then air-dried. Lyophilization gave (10R,14S)-14-{4-[3-chloro-2-fluoro-6-(4-methyl-1H-1,2,3-triazol-1-yl)phenyl]-6-oxo-1,6-dihydropyrimidin-1-yl}-4-fluoro-10-methyl-8,16-diazatricyclo [13.3.1.0$^{2,7}$]nonadeca-1(19),2(7),3,5,15,17-hexaen-9-one (0.0092 g, 36% yield) as a white solid. MS(ESI) m/z: 602.3 (M+H)+ and 604.2 (M+2+H)+. 1H NMR (500 MHz, 60° C., DMSO -d6) δ 9.53 (s, 1H), 8.86 (s, 1H), 8.64 (d, J=5.0 Hz, 1H), 7.95 (d, J=0.8 Hz, 1H), 7.91 (dd, J=8.5, 8.0 Hz, 1H), 7.72 (d, J=0.5 Hz, 1H), 7.56 (dd, J=8.7, 1.5 Hz, 1H), 7.46-7.41 (m, 2H), 7.32-7.24 (m, 2H), 6.48 (s, 1H), 5.90 (dd, J=12.7, 4.7 Hz, 1H), 2.64-2.56 (m, 1H), 2.26-2.17 (m, 4H), 1.97-1.86 (m, 2H), 1.44-1.30 (m, 2H), 0.87 (d, J=6.9 Hz, 3H), 0.60-0.49 (m, 1H). 19F NMR (471 MHz, DMSO-d6) δ −114.45 (s, 1F), −115.24 (s, 1F). Analytical HPLC (Method A): RT=7.81 min, purity=99.5%; Factor XIa Ki=0.16 nM, Plasma Kallikrein Ki=12 nM.

EXAMPLE 138

Preparation of (10R,14S)-14-(4-{5-chloro-2-[4-(difluoromethyl)-1H-1,2,3-triazol-1-yl]phenyl}-6-oxo-1,6-dihydropyrimidin-1-yl)-4-fluoro-10-methyl-8,16-diazatricyclo [13.3.1.0$^{2,7}$]nonadeca-1(19),2(7),3,5,15,17-hexaen-9-one

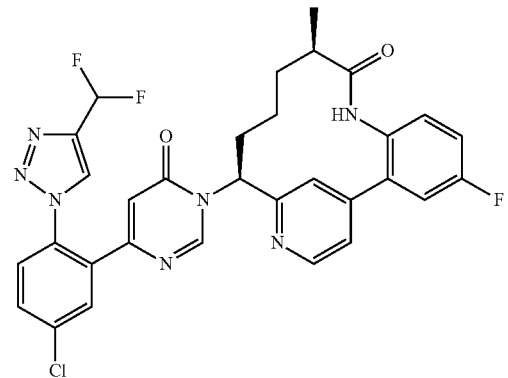 [SMILES: C[C@@H]1CCC[C@H](n2cnc(-c3cc(Cl)ccc3-n3cc(C(F)F)nn3)cc2=O)c2cc(ccn2)-c2cc(F)ccc2NC1=O]

(10R,14S)-14-(4-{5-Chloro-2-[4-(difluoromethyl)-1H-1,2,3-triazol-1-yl]phenyl}-6-oxo-1,6-dihydropyrimidin-1-yl)-4-fluoro-10-methyl-8,16-diazatricyclo[13.3.1.0$^{2,7}$] nonadeca-1(19),2(7),3,5,15,17-hexaen-9-one (24.2 mg, 60% yield) was prepared in a similar manner as the procedure described in Example 135, by replacing 6-(5-chloro-2-(4-(trifluoromethyl)-1H-1,2,3-triazol-1-yl)phenyl)pyrimidin-4-ol (0.016 g, 0.048 mmol) with 6-(5-chloro-2-(4-(difluoromethyl)-1H-1,2,3-triazol-1-yl)phenyl)pyrimidin-4-ol (0.021 g, 0.064 mmol), prepared as described in Example 16. MS(ESI) m/z: 620.3 (M+H)+ and 622.2 (M+2+H)+. 1H NMR (500 MHz, CD3OD) δ 9.76 (s, 1H), 8.90 (s, 1H), 8.65 (d, J=4.7 Hz, 1H), 8.53 (t, J=1.4 Hz, 1H), 7.88 (d, J=2.5 Hz, 1H), 7.74 (dd, J=8.5, 2.5 Hz, 1H), 7.69 (br. s, 1H), 7.66 (d, J=8.5 Hz, 1H), 7.41 (dd, J=5.1, 1.5 Hz, 1H), 7.37 (dd, J=8.9, 2.9 Hz, 1H), 7.27 (dd, J=8.8, 5.5 Hz, 1H), 7.25-7.20 (m, 1H), 6.99 (t, J=54.2 Hz, 1H), 6.33 (d, J=0.8 Hz, 1H), 5.99 (dd, J=12.5, 4.5 Hz, 1H), 2.69-2.60 (m, 1H), 2.23-2.14 (m, 1H), 2.04-1.90 (m, 2H), 1.53-1.36 (m, 2H), 0.95 (d, J=6.9 Hz, 3H), 0.75-0.59 (m, 1H). 19F NMR (471 MHz, CD3OD) δ −114.48 (s), −116.30 (s). Analytical HPLC (Method A): RT=8.64 min, purity=100%; Factor XIa Ki=0.24 nM, Plasma Kallikrein Ki=29 nM.

EXAMPLE 139

Preparation of (10R,14S)-14-{4-[5-chloro-2-(4-hydroxy-1H-1,2,3-triazol-1-yl)phenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate

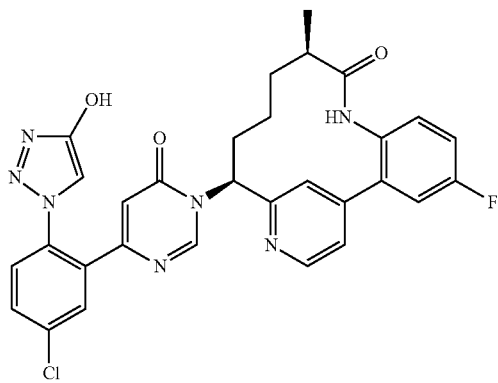 [SMILES: C[C@@H]1CCC[C@H](n2cnc(-c3cc(Cl)ccc3-n3cc(O)nn3)cc2=O)c2cc(ccn2)-c2cc(F)ccc2NC1=O]

To a solution of (10R,14S)-14-{4-[5-chloro-2-(4-ethoxy-1H-1,2,3-triazol-1-yl)phenyl]-6-oxo-1,6-dihydropyrimidin-1-yl}-4-fluoro-10-methyl-8,16-diazatricyclo [13.3.1.0$^{2,7}$]nonadeca-1(19),2(7),3,5,15,17-hexaen-9-one trifluoroacetate (7.5 mg, 10.30 µmol) in DCM (1 ml) was added AlCl$_3$ (0.014 g, 0.10 mmol). The reaction was microwaved at 100° C. for 10 min, and then the reaction was cooled to rt. Next, the reaction was cooled in a dry ice/acetone bath and then MeOH (1 ml) was added slowly. The reaction was allowed to warm to rt and the reaction was stirred until a solution formed. Then the reaction was concentrated to dryness. Purification by reverse phase chromatography afforded (10R,14S)-14-{4-[5-chloro-2-(4-hydroxy-1H-1,2,3-triazol-1-yl)phenyl]-6-oxo-1,6-dihydropyrimidin-1-yl}-4-fluoro-10-methyl-8,16-diazatricyclo [13.3.1.0$^{2,7}$]nonadeca-1(19),2(7),3,5,15,17-hexaen-9-one trifluoroacetate (5.6 mg, 77% yield) as a yellow solid. MS(ESI) m/z: 586.2 (M+H)$^+$. $^1$H NMR (500 MHz, CD$_3$OD) δ 8.97 (s, 1H), 8.68 (d, J=5.0 Hz, 1H), 7.86 (d, J=2.2 Hz, 1H), 7.75 (s, 1H), 7.69 (dd, J=8.4, 2.3 Hz, 1H), 7.59 (d, J=8.5 Hz, 1H), 7.46 (dd, J=5.1, 1.5 Hz, 1H), 7.43 (s, 1H), 7.39 (dd, J=9.1, 2.8 Hz, 1H), 7.31-7.21 (m, 2H), 6.21 (s, 1H), 5.98 (dd, J=12.7, 4.7 Hz, 1H), 2.70-2.61 (m, 1H), 2.29-2.20 (m, 1H), 2.08-1.89 (m, 2H), 1.55-1.37 (m, 2H), 0.96 (d, J=6.9 Hz, 3H), 0.76-0.58 (m, 1H). $^{19}$F NMR (471 MHz, CD$_3$OD) δ −77.66 (s), −116.24 (s). Analytical HPLC (Method A): RT=7.51 min, 99.5% purity; Factor XIa Ki=13 nM, Plasma Kallikrein Ki=510 nM.

EXAMPLE 140

Preparation of (10R,14S)-14-{4-[5-chloro-2-(4-chloro-1H-1,2,3-triazol-1-yl)phenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate

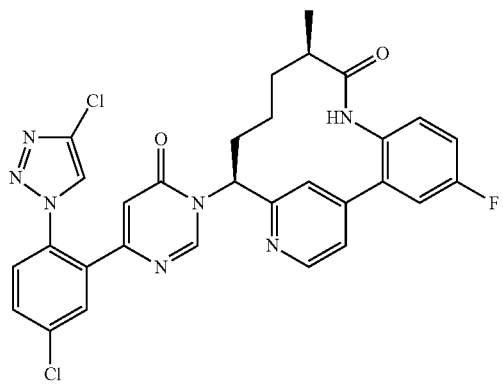 [SMILES: C[C@@H]1CCC[C@H](n2cnc(-c3cc(Cl)ccc3-n3cc(Cl)nn3)cc2=O)c2cc(ccn2)-c2cc(F)ccc2NC1=O]

(10R,14S)-14-{4-[5-Chloro-2-(4-chloro-1H-1,2,3-triazol-1-yl)phenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate (10.8 mg, 24.3% yield) was prepared in a similar manner as the procedure described in Example 129I, using 6-[5-chloro-2-(4-chloro-1H-1,2,3-triazol-1-yl)phenyl]pyrimidin-4-ol (19 mg, 0.062 mmol), prepared as described in Example 9 and (10R,14S)-14-amino-4-fluoro-10-methyl-8,16-diazatricyclo [13.3.1.0$^{2,7}$]nonadeca-1(19),2,4,6,15,17-hexaen-9-one (11.1 mg, 0.036 mmol), prepared as described in Example 28. MS(ESI) m/z: 604.2 (M+H)$^+$. $^1$H NMR (400 MHz, CD$_3$OD) δ 8.90 (s, 1H), 8.68 (d, J=5.1 Hz, 1H), 8.33 (s, 1H), 7.88 (d, J=2.2 Hz, 1H), 7.75 (s, 1H), 7.74-7.71 (m, 1H), 7.67-7.61 (m, 1H), 7.46 (dd, J=5.1, 1.5 Hz, 1H), 7.39 (dd, J=9.0, 2.6 Hz, 1H), 7.31-7.21 (m, 2H), 6.35 (s, 1H), 5.97 (dd, J=12.4, 4.7 Hz, 1H), 2.64 (d, J=6.4 Hz, 1H), 2.32-2.16 (m, 1H), 2.10-1.89 (m, 2H), 1.57-1.36 (m, 2H), 0.96 (d, J=6.8 Hz, 3H), 0.69 (m., 1H). $^{19}$F NMR (376 MHz, CD$_3$OD) δ −77.70 (s), −116.23 (s). Analytical HPLC (Method A): RT−9.45 min, purity−99.6%; Factor XIa Ki−0.1 nM, Plasma Kallikrein Ki−7 nM.

EXAMPLE 141

Preparation of (10R,14S)-14-{4-[5-chloro-2-(trifluoromethyl)phenyl]-6-oxo-1,6dihydropyrimidin-1-yl}-4-fluoro-10-methyl-8,16-diazatricyclo[13.3.1.0$^{2,7}$]nonadeca -1(19),2(7),3,5,15,17-hexaen-9-one trifluoroacetate

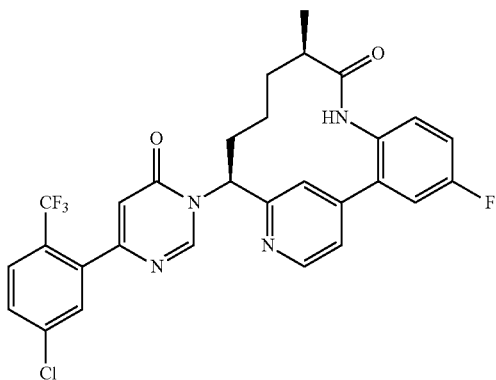 [SMILES: C[C@@H]1CCC[C@H](n2cnc(-c3cc(Cl)ccc3C(F)(F)F)cc2=O)c2cc(ccn2)-c2cc(F)ccc2NC1=O]

141A. Preparation of 4-[5-chloro-2-(trifluoromethyl)phenyl]-6-methoxypyrimidine

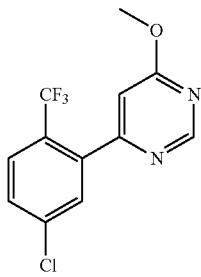 [SMILES: COc1cc(-c2cc(Cl)ccc2C(F)(F)F)ncn1]

A microwave vial containing 4-chloro-6-methoxypyrimidine (64 mg, 0.45 mmol), [5-chloro-2-(trifluoromethyl)phenyl]boronic acid (100 mg, 0.45 mmol) and Na$_2$CO$_3$ (47 mg, 0.446 mmol) in DME (2 ml ), EtOH (0.25 ml) and water (0.25 ml) was purged with N$_2$ for several min. Pd(dppf)Cl$_2$—CH$_2$Cl$_2$ adduct (36 mg, 0.05 mmol) was added and the vial was capped. The reaction was heated at 120° C. for 0.5 h. The reaction was diluted with water and extracted with EtOAc. The organic layer was washed with brine, concentrated and purified by normal phase chromatography to give 4-[5-chloro-2-(trifluoromethyl) phenyl]-6-methoxypyrimidine (88 mg, 34.2% yield) as a clear oil. MS(ESI) m/z: 288.95 (M+H)$^+$.

141B. Preparation of 6-[5-chloro-2-(trifluoromethyl)phenyl]pyrimidin-4-ol

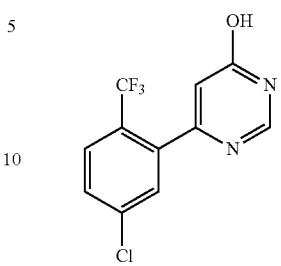

A solution of 4-[5-chloro-2-(trifluoromethyl)phenyl]-6-methoxypyrimidine (88 mg, 0.192 mmol) in 33% HBr in AcOH (0.3 ml, 5.52 mmol) was stirred at 60° C. for 1 h. The reaction was concentrated to dryness and partitioned between EtOAc, and sat NaHCO$_3$. The aqueous layer was separated and extracted with EtOAc (3×). The combined organic layers were washed with brine, dried over MgSO$_4$, filtered and concentrated to give 6-[5-chloro-2-(trifluoromethyl)phenyl]pyrimidin-4-ol (76 mg) as a white solid. MS(ESI) m/z: 274.95 (M+H)$^+$. $^1$H NMR (400 MHz, CD$_3$OD) δ 8.26 (d, J=0.7 Hz, 1H), 7.81 (d, J=8.6 Hz, 1H), 7.68 (dd, J=8.5, 1.2 Hz, 1H), 7.60 (d, J=2.0 Hz, 1H), 6.53 (d, J=0.4 Hz, 1H). $^{19}$F NMR (376 MHz, CD$_3$OD) δ −58.39 (s).

141C. Preparation of (10R,14S)-14-{4-[5-chloro-2-(trifluoromethyl)phenyl]6-oxo-1,6dihydropyrimidin-1-yl}-4-fluoro-10-methyl-8,16-diazatricyclo[13.3.1.0$^{2,7}$]nonadeca -1(19),2(7),3,5,15,17-hexaen-9-one trifluoroacetate

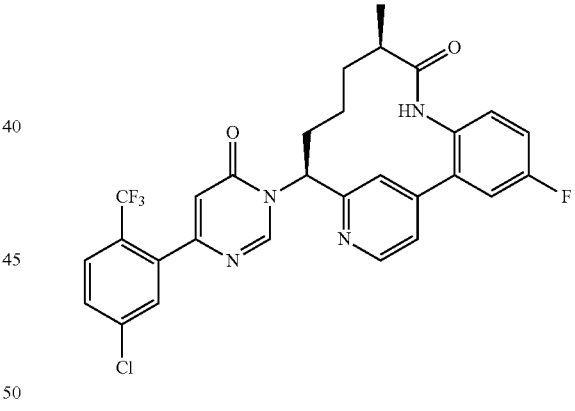

(10R,14S)-14-{4-[5-Chloro-2-(trifluoromethyl)phenyl]-6-oxo-1,6-dihydropyrimidin-1-yl}-4-fluoro-10-methyl-8,16-diazatricyclo[13.3.1.0$^{2,7}$]nonadeca -1(19),2(7),3,5,15,17-hexaen-9-one trifluoroacetate (13 mg, 52.4% yield) was prepared in a similar manner as the procedure described in Example 129I using 6-[5-chloro-2-(trifluoromethyl)phenyl]pyrimidin-4-ol (13 mg, 0.036 mmol) and (10R,14S)-14-amino-4-fluoro-10-methyl-8,16-diazatricyclo[13.3.1.0$^{2,7}$]nonadeca-1(19),2,4,6,15,17-hexaen-9-one (11.1 mg, 0.036 mmol), prepared as described in Example 28. MS(ESI) m/z: 571.3 (M+H)$^+$. $^1$H NMR (500 MHz, DMSO-d$_6$) δ 9.73 (s, 1H), 9.07 (br. s., 1H), 8.66 (d, J=4.9 Hz, 1H), 7.88 (d, J=8.5 Hz, 1H), 7.80-7.66 (m, 3H), 7.50-7.41 (m, 2H), 7.36-7.21 (m, 2H), 6.54 (s, 1H), 5.95 (d, J=10.1 Hz, 1H), 2.62 (m., 1H), 2.36-2.23 (m, 1H), 2.02-1.83 (m, 2H), 1.39 (m, 2H), 0.84 (d, J=6.7 Hz, 3H), 0.40 (m, 1H). Analytical HPLC

EXAMPLE 142

Preparation of (10R,14S)-14-{4-[3-Chloro-6-(4-chloro-1H-1,2,3-triazol-1-yl)-2-fluorophenyl]-6-oxo-1,6-dihydropyrimidin-1-yl}-4-fluoro-10-methyl-8,16-diazatricyclo [13.3.1.0$^{2,7}$]nonadeca-1(19),2(7),3,5,15,17-hexaen-9-one trifluoroacetate

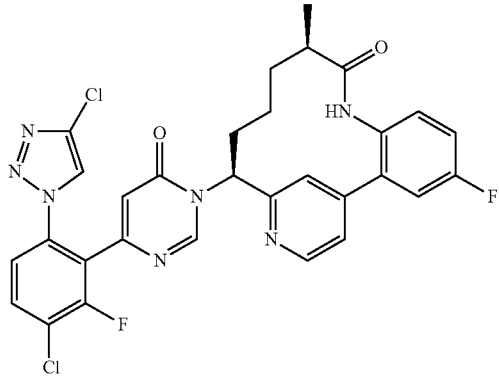 [SMILES: C[C@@H]1CCC[C@H](n2cnc(-c3c(-n4cc(Cl)nn4)ccc(Cl)c3F)cc2=O)c2cc(ccn2)-c2cc(F)ccc2NC1=O]

(10R,14S)-14-{4-[3-Chloro-6-(4-chloro-1H-1,2,3-triazol-1-yl)-2-fluorophenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate (5.9 mg, 51.2% yield) was prepared in a similar manner as the procedure described in Example 129I, by using 6-[3-chloro-6-(4-chloro-1H-1,2,3-triazol-1-yl)-2-fluorophenyl] pyrimidin-4-ol (10 mg, 0.015 mmol), prepared as described in Example 10, and (10R,14S)-14-amino-4-fluoro-10-methyl-8,16-diazatricyclo[13.3.1.0$^{2,7}$]nonadeca-1(19),2,4,6,15,17-hexaen-9-one (4.8 mg, 0.015 mmol), prepared as described in Example 28. MS(ESI) m/z: 622.15 (M+H)$^+$. $^1$H NMR (500 MHz, DMSO-d$_6$) δ 9.79 (s, 1H), 8.95 (m., 1H), 8.81-8.61 (m, 2H), 8.07 (t, J=8.1 Hz, 1H), 7.87-7.67 (m, 2H), 7.60-7.46 (m, 2H), 7.45-7.25 (m, 2H), 6.68 (s, 1H), 5.94 (m., 1H), 2.67 (m., 1H), 2.30 (m., 1H), 2.07-1.84 (m, 2H), 1.43 (m., 2H), 0.90 (d, J=6.7 Hz, 3H), 0.47 (m., 1H). Analytical HPLC (Method B): RT=1.77 min, purity=97%; Factor XIa Ki=1 nM, Plasma Kallikrein Ki=7 nM.

(Method B): RT=1.94 min, purity=96%; Factor XIa Ki=69 nM, Plasma Kallikrein Ki=580 nM.

EXAMPLE 143

Preparation of (10R,14S)-14-{4-[3-chloro-2-fluoro-6-(trifluoromethyl)phenyl]-6-oxo-1,6-dihydropyrimidin-1-yl}-4-fluoro-10-methyl-8,16-diazatricyclo [13.3.1.0$^{2,7}$]nonadeca -1(19),2(7),3,5,15,17-hexaen-9-one trifluoroacetate 143A. Preparation of 4-(3-chloro-2-fluoro-6-(trifluoromethyl)phenyl)-6-methoxypyrimidine A 1-dram vial containing AgF (0.088 g, 0.69 mmol) was purged with Ar (3x), then EtCN (2 ml) was added. The suspension was cooled to −78° C., and TMSCF$_3$ (0.10 mL, 0.69 mmol) was added. The mixture was allowed to warm to rt and the reaction was stirred for 15 min at rt to give a gray solution. In another vial was added 4-chloro-3-fluoro-2-(6-methoxypyrimidin-4-yl)aniline (0.05 g, 0.2 mmol) and EtCN (2 ml). The solution was cooled to 0° C., then concentrated HCl (0.033 ml, 0.39 mmol) was added. After 5 min, t-butyl nitrite (0.041 g, 0.39 mmol) was added, and the mixture was allowed to stir at 0° C. for 15 min. The resulting suspension was purged with Ar (3 ×) and then the reaction was warmed to rt. The reaction was then cooled to −78° C. Then the gray solution, prepared in the first vial, which was cooled to −78° C., was added dropwise via syringe. After the addition was complete, the reaction was stirred at −78° C. for 3 h, then the reaction was warmed to rt. After 1 h, the reaction was diluted with EtOAc, filtered, and the filtrate was concentrated. Purification by normal phase chromatography afforded 4-(3-chloro-2-fluoro-6-(trifluoromethyl)phenyl)-6-methoxypyrimidine (0.028 g, 46.3% yield) as a yellow oil. MS(ESI) m/z: 307.0 (M+H)$^+$. $^1$H NMR (400 MHz, CDCl$_3$) δ 8.88 (d, J=0.9 Hz, 1H), 7.65-7.59 (m, 1H), 7.55-7.50 (m, 1H), 6.83 (s, 1H), 4.07 (s, 3H).

143B. Preparation of 6-(3-chloro-2-fluoro-6-(trifluoromethyl) phenyl)pyrimidin-4-ol, hydrobromide A clear, yellow solution of 4-(3-chloro-2-fluoro-6-(trifluoromethyl)phenyl)-6-methoxypyrimidine (0.028 g, 0.091 mmol) in HOAc (0.91 ml) and 48% HBr in water (0.52 ml, 4.57 mmol) was warmed to 65° C. After 2 h, the reaction was cooled to rt. The reaction was concentrated. Et$_2$O (3 ml) was added and the mixture was sonicated to give a yellow suspension. The solid was collected by filtration and rinsed with Et$_2$O (2×1 ml), air-dried to give a yellow solid as 6-(3-chloro-2-fluoro-6-(trifluoromethyl)phenyl) pyrimidin-4-ol hydrobromide (0.03 g, 88% yield). MS(ESI) m/z: 293.0 (M+H)$^+$. $^1$H NMR (400 MHz, CD$_3$OD) δ 8.83 (d, J=0.9 Hz, 1H), 7.92 (t, J=7.9 Hz, 1H), 7.76-7.71 (m, 1H), 6.76 (s, 1H).

143C. Preparation of (10R,14S)-14-{4-[3-chloro-2-fluoro-6-(trifluoromethyl)phenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate (10R,14S)-14-{4-[3-Chloro-2-fluoro-6-(trifluoromethyl)phenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate (10 mg, 36.4% yield) was prepared in a similar manner as the procedure described in Example 147C, by replacing 6-(3,6-dichloro-2-fluorophenyl)pyrimidin-4-ol, hydrobromide (13.02 mg, 0.038 mmol) with 6-(3-chloro-2-fluoro-6-(trifluoromethyl)phenyl)pyrimidin-4-ol hydrobromide (14.30 mg, 0.038 mmol). MS(ESI) m/z: 589.1 (M+H)$^+$. $^1$H NMR (400 MHz, CD$_3$OD) δ 9.14 (s, 1H), 8.72 (d, J=4.8 Hz, 1H), 7.85-7.78 (m, 2H), 7.66 (dd, J=8.7, 0.8 Hz, 1H), 7.49 (dd, J=5.2, 1.7 Hz, 1H), 7.42 (dd, J=8.9, 2.8 Hz, 1H), 7.33-7.21 (m, 2H), 6.60 (s, 1H), 6.07 (dd, J=12.7, 4.7 Hz, 1H), 2.73-2.62 (m, 1H), 2.40-2.27 (m, 1H), 2.18-2.06 (m, 1H), 2.04-1.93 (m, 1H), 1.60-1.39 (m, 2H), 0.98 (d, J=7.0 Hz, 3H), 0.84-0.61 (m, 1H). $^{19}$F NMR (376 MHz, CD$_3$OD) δ −59.04 (s), −77.72 (s), −115.33 (s), −116.23 (s). Analytical HPLC (Method A): RT=10.09 min, 98.0% purity; Factor XIa Ki=17 nM, Plasma Kallikrein Ki=190 nM.

EXAMPLE 144

Preparation of (10R,14S)-14-{4-[5-chloro-2-(4-ethoxy-1H-1,2,3-triazol-1-yl)phenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate

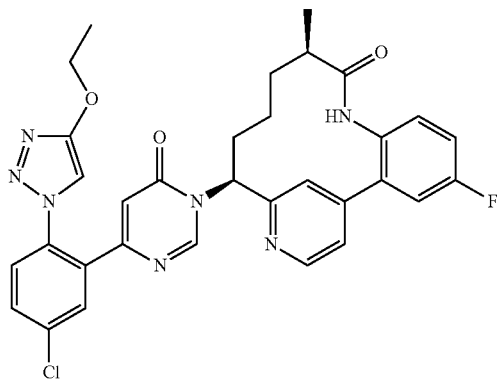 [SMILES: CCOc1cn(-c2ccc(Cl)cc2-c2cc(=O)n([C@H]3CCC[C@@H](C)C(=O)Nc4ccc(F)cc4-c4ccnc3c4)cn2)nn1]

144A. Preparation of 4-(5-chloro-2-(4-ethoxy-1H-1,2,3-triazol-1-yl)phenyl)-6methoxypyrimidine To a cooled (0° C.), clear yellow solution of 4-chloro-2-(6-methoxypyrimidin-4-yl)aniline (0.100 g, 0.42 mmol) in ACN (6.06 ml) was added isoamyl nitrite (0.086 ml, 0.64 mmol), followed by the dropwise addition of TMSN$_3$ (0.084 ml, 0.64 mmol). After 10 min, the cold bath was removed, and the reaction was allowed to warm to rt. After 1 h, 40% ethoxyacetylene in hexanes (0.31 ml, 1.27 mmol) and Cu$_2$O (6.07 mg, 0.042 mmol) were added. The flask was equipped with a reflux condenser and the reaction was heated to 50° C. for 1 h, then the reaction was cooled to rt. The reaction was diluted with DCM and washed with sat NH$_4$Cl, brine, dried over MgSO$_4$, filtered and concentrated to give a brown oil. Purification by normal phase chromatography afforded 4-(5-chloro-2-(4-ethoxy-1H-1,2,3-triazol-1-yl)phenyl)-6-methoxypyrimidine (0.115 g, 82% yield). MS(ESI) m/z: 332.0 (M+H)$^+$.

144B. Preparation of 6-(5-chloro-2-(4-ethoxy-1H-1,2,3-triazol-1-yl)phenyl)pyrimidin-4-ol, hydrobromide A clear, yellow solution of 4-(5-chloro-2-(4-ethoxy-1H-1,2,3-triazol-1-yl)phenyl)-6-methoxypyrimidine (0.06 g, 0.181 mmol) in HOAc (1.81 ml) and 48% HBr in water (1.02 ml, 9.04 mmol) was warmed to 65° C. for 2 h, then the reaction was cooled to rt and concentrated. Et$_2$O (3 ml) was added and the mixture was sonicated to give a yellow suspension. The solid was collected by filtration and rinsed with Et$_2$O (2×1 ml), air dried to give 6-(5-chloro-2-(4-ethoxy-1H-1,2,3-triazol-1-yl)phenyl)pyrimidin-4-ol hydrobromide (0.069 g, 96% yield) as a yellow solid. MS(ESI) m/z: 318.3 (M+H)$^+$.

144C. Preparation of (10R,14S)-14-{4-[5-chloro-2-(4-ethoxy-1H-1,2,3-triazol-1-yl)phenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate (10R,14S)-14-{4-[5-Chloro-2-(4-ethoxy-1H-1,2,3-triazol-1-yl)phenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate (9 mg, 32.3% yield) was prepared in a similar manner as the procedure described in Example 147C, by replacing 6-(3,6-dichloro-2-fluorophenyl)pyrimidin-4-ol, hydrobromide (13.02 mg, 0.038 mmol) with 6-(5-chloro-2-(4-ethoxy-1H-1,2,3-triazol-1-yl)phenyl)pyrimidin-4-ol hydrobromide (15.27 mg, 0.038 mmol). MS(ESI) m/z: 614.3 (M+H)$^+$. $^1$H NMR (400 MHz, CD$_3$OD) δ 8.98 (s, 1H), 8.66 (d, J=5.1 Hz, 1H), 7.88 (d, J=2.2 Hz, 1H), 7.74-7.69 (m, 3H), 7.64-7.60 (m, 1H), 7.44 (dd, J=5.1, 1.5 Hz, 1H), 7.38 (dd, J=9.0, 2.9 Hz, 1H), 7.31-7.20 (m, 2H), 6.22 (s, 1H), 5.99 (dd, J=12.5, 4.6 Hz, 1H), 4.15 (q, J=7.0 Hz, 2H), 2.71-2.61 (m, 1H), 2.28-2.17 (m, 1H), 2.07-1.90 (m, 2H), 1.56-1.32 (m, 5H), 0.95 (d, J=7.0 Hz, 3H), 0.75-0.55 (m, 1H). $^{19}$F NMR (376 MHz, CD$_3$OD) δ −77.46 (s), −116.24 (s). Analytical HPLC (Method A): RT=8.86 min, 100% purity; Factor XIa Ki=5 nM, Plasma Kallikrein Ki=210 nM.

EXAMPLE 145

Preparation of (10S,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,18-diazatricyclo[13.3.1.0$^{2,7}$]nonadeca-1(19),2,4,6,15,17-hexaen-9-one

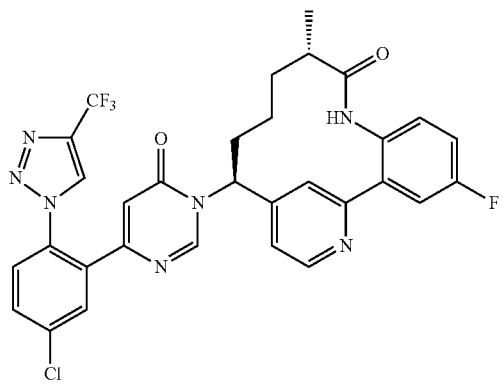 [SMILES: C[C@H]1CCC[C@H](n2cnc(-c3cc(Cl)ccc3-n3cc(C(F)(F)F)nn3)cc2=O)c2ccnc(c2)-c2cc(F)ccc2NC1=O]

(10S,14S)-14-(4-{5-Chloro-2-[4-(trifluoromethyl)-1H-1,2,3-triazol-1-yl]phenyl}6-oxo-1,6-dihydropyrimidin-1-yl)-4-fluoro-10-methyl-8,18-diazatricyclo[13.3.1.0$^{2,7}$]nonadeca-1(19),2,4,6,15,17-hexaen-9-one, (18 mg, 4.2%), a white solid, was isolated as the minor diastereomer from the preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-8,18-diazatricyclo[13.3.1.0$^{2,7}$]nonadeca-1(19),2(7),3,5,15,17-hexaen-9-one, Example 109, after chiral HPLC chromatography (Column: CHIRALPAK® IC, 30×250 mm, 5 μ; Mobile Phase: 30% MeOH/70% CO$_2$, Flow Conditions: 85 ml/min, 150 Bar, 40° C.). MS(ESI) m/z: 638.3 (M+H)$^+$. $^1$H NMR (400 MHz, CD$_3$OD) δ 8.88 (s, 1H), 8.64 (d, J=5.3 Hz, 1H), 8.52 (s, 1H), 7.93 (s, 1H), 7.84 (s, 1H), 7.82-7.76 (m, 1H), 7.76-7.71 (m, 1H), 7.63 (d, J=6.8 Hz, 1H), 7.42-7.24 (m, 2H), 7.04 (d, J=4.4 Hz, 1H), 6.55 (s, 1H), 5.72 (d, J=8.6 Hz, 1H), 2.50 (br. s., 1H), 2.31 (br. s., 1H), 2.12 (br. s., 1H), 1.86 (br. s., 1H), 1.51 (br. s., 2H), 1.32 (br. s., 1H), 1.29-1.21 (m, 3H). Analytical HPLC (Method A) RT=7.87 min, purity=97%; Factor XIa Ki=1.6 nM, Plasma Kallikrein Ki=100 nM.

EXAMPLE 146

Preparation of (10R,14S)-14-{4-[5-chloro-2-(trifluoromethoxy)phenyl]-6-oxo-1,6-dihydropyrimidin-1-yl}-4-fluoro-10-methyl-8,16-diazatricyclo[13.3.1.0$^{2,7}$]nonadeca -1(19),2(7),3,5,15,17-hexaen-9-one trifluoroacetate

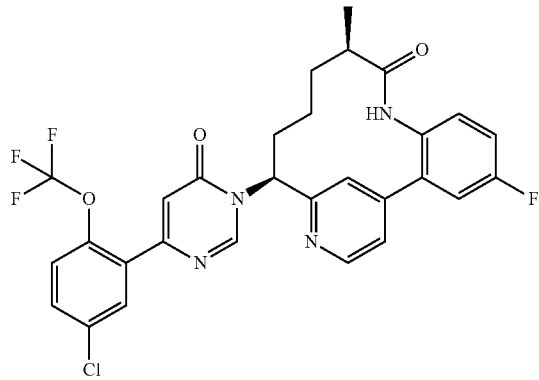 [SMILES: C[C@@H]1CCC[C@H](n2cnc(-c3cc(Cl)ccc3OC(F)(F)F)cc2=O)c2cc(ccn2)-c2cc(F)ccc2NC1=O]

146A. Preparation of 6-(5-chloro-2-(trifluoromethoxy)phenyl)pyrimidin-4-ol

A microwave vial containing 6-chloropyrimidin-4-ol (0.085 g, 0.65 mmol), (5-chloro-2-(trifluoromethoxy)phenyl)boronic acid (0.157 g, 0.65 mmol), and Pd(Ph$_3$P)$_4$ (0.075 g, 0.065 mmol) was purged with Ar for several min. Then degassed toluene (1.31 ml) and EtOH (1.31 ml) were added followed by DIEA (0.46 ml, 2.61 mmol). The vial was capped and the reaction was microwaved at 120° C. for 1 h, and then the reaction was cooled to rt and concentrated. Purification by normal phase chromatography afforded 6-(5-chloro-2-(trifluoromethoxy)phenyl)pyrimidin-4-ol (0.05 g, 26.3% yield) as a white solid. MS(ESI) m/z: 291.0 (M+H)$^+$. $^1$H NMR (400 MHz, CD$_3$OD) δ 8.29 (d, J=0.9 Hz, 1H), 7.88 (d, J=2.9 Hz, 1H), 7.59 (dd, J=8.9, 2.8 Hz, 1H), 7.47-7.43 (m, 1H), 6.77 (d, J=0.9 Hz, 1H).

146B. Preparation of (10R,14S)-14-{4-[5-chloro-2-(trifluoromethoxy)phenyl]-6-oxo-1,6-dihydropyrimidin-1-yl}-4-fluoro-10-methyl-8,16-diazatricyclo[13.3.1.0$^{2,7}$]nonadeca-1(19),2(7),3,5,15,17-hexaen-9-one trifluoroacetate (10R,14S)-14-{4-[5-Chloro-2-(trifluoromethoxy)phenyl]-6-oxo-1,6-dihydropyrimidin-1-yl}-4-fluoro-10-methyl-8,16-diazatricyclo[13.3.1.0$^{2,7}$]nonadeca -1(19),2(7),3,5,15,17-hexaen-9-one trifluoroacetate (10 mg, 37.1% yield) was prepared in a similar manner as the procedure described in Example 150B, by replacing 6-(5-chloro -2-methoxyphenyl)pyrimidin-4-ol with 6-(5-chloro-2-(trifluoromethoxy)phenyl) pyrimidin-4-ol (11.13 mg, 0.038 mmol). MS(ESI) m/z: 587.1 (M+H)$^3$ . $^1$H NMR (400 MHz, CD$_3$OD) δ 9.12 (s, 1H), 8.70 (d, J=5.1 Hz, 1H), 7.95 (d, J=2.6 Hz, 1H), 7.82 (d, J=0.9 Hz, 1H), 7.59 (dd, J=8.9, 2.8 Hz, 1H), 7.49 (dd, J=5.2, 1.7 Hz, 1H), 7.46-7.39 (m, 2H), 7.32-7.22 (m, 2H), 6.82 (d, J=0.7 Hz, 1H), 6.03 (dd, J=12.7, 4.7 Hz, 1H), 2.72-2.62 (m, 1H), 2.39-2.28 (m, 1H), 2.16-2.06 (m, 1H), 2.03-1.92 (m, 1H), 1.59-1.40 (m, 2H), 0.98 (d, J=7.0 Hz, 3H), 0.83-0.64 (m, 1H). $^{19}$F NMR (376 MHz, CD$_3$OD) δ 59.04 (s), -77.71 (s), -116.20 (s). Analytical HPLC (Method A): RT=11.05 min, 99.8% purity; Factor XIa Ki=138 nM, Plasma Kallikrein Ki=3,800 nM.

EXAMPLE 147

Preparation of (10R,14S)-14-[4-(3,6-dichloro-2-fluorophenyl)-6-oxo-1,6-dihydropyrimidin-1-yl]-4-fluoro-10-methyl-8,16-diazatricyclo[13.3.1.0$^{2,7}$] nonadeca -1(19),2(7),3,5,15,17-hexaen-9-one trifluoroacetate

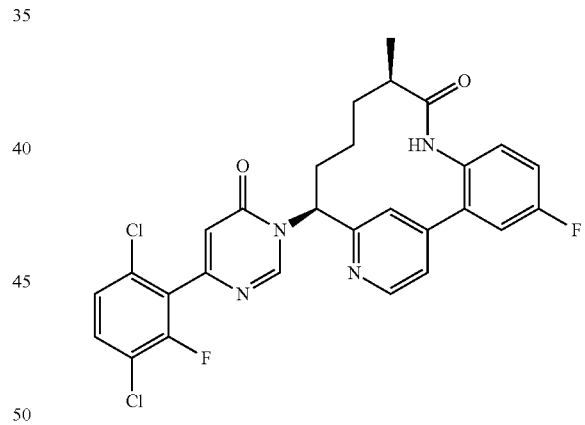

147A. Preparation of 4-(3,6-dichloro-2-fluorophenyl)-6-methoxypyrimidine

A 1-dram vial containing CuCl$_2$ (0.032 g, 0.24 mmol) was purged with Ar (3 ×), then ACN (2 ml) was added, followed by TBN (0.030 g, 0.3 mmol). To the resulting suspension was added 4-chloro-3-fluoro-2-(6-methoxypyrimidin-4-yl)aniline (0.05 g, 0.2 mmol) and the reaction was capped and heated at 65° C. for 10 min, then the reaction was cooled to rt. The reaction was diluted with EtOAc, washed with sat NaHCO$_3$, brine, dried over Na$_2$SO$_4$, filtered, and concentrated. Purification by normal phase chromatography afforded 4-(3,6-dichloro-2-fluorophenyl)-6-methoxypyrimidine (0.03 g, 55.7% yield) as a yellow oil. MS(ESI) m/z: 272.9 (M+H)$^+$. $^1$H NMR (400 MHz, CDCl$_3$) δ 8.94 (s, 1H), 7.48-7.41 (m, 1H), 7.31-7.25 (m, 1H), 6.87 (s, 1H), 4.09 (s, 3H).

147B. Preparation of 6-(3,6-dichloro-2-fluorophenyl)pyrimidin-4-ol, hydrobromide A clear, yellow solution of 4-(3,6-dichloro-2-fluorophenyl)-6-methoxypyrimidine (0.03 g, 0.11 mmol) in HOAc (1.1 ml) and 48% HBr in water (0.62 ml, 5.49 mmol) was warmed to 65° C. for 2 h, then the reaction was cooled to rt, and concentrated. Et$_2$O (3 ml) was added and sonicated to give a yellow suspension. The solid was collected by filtration and rinsed with Et$_2$O (2×1 ml), air-dried to give 6-(3,6-dichloro-2-fluorophenyl)pyrimidin-4-ol hydrobromide (0.027 g, 72.3% yield) as a yellow solid. MS(ESI) m/z: 259.0 (M+H)$^+$. $^1$H NMR (400 MHz, CD$_3$OD) δ 8.85 (d, J=0.7 Hz, 1H), 7.70 (dd, J=8.8, 7.9 Hz, 1H), 7.47 (dd, J=8.8, 1.5 Hz, 1H), 6.78 (d, J=0.7 Hz, 1H).

147C. Preparation of (10R,14S)-14-[4-(3,6-dichloro-2-fluorophenyl)-6-oxo-1,6-dihydropyrimidin-1-yl]-4-fluoro-10-methyl-8,16-diazatricyclo[13.3.1.0$^{2,7}$]nonadeca-1(19),2(7),3,5,15,17-hexaen-9-one trifluoroacetate To a scintillation vial containing 6-(3,6-dichloro-2-fluorophenyl)pyrimidin-4-ol, hydrobromide (13.02 mg, 0.038 mmol), HATU (18.93 mg, 0.050 mmol) in anhydrous ACN (0.5 ml) was added DBU (0.016 ml, 0.10 mmol). After 15 min, (10R,14S)-14-amino-4-fluoro-10-methyl-8,16-diazatricyclo[13.3.1.0$^{2,7}$]nonadeca-1(19),2,4,6,15,17-hexaen-9-one (12 mg, 0.038 mmol), prepared as described in Example 28, was added, followed by DMF (0.5 ml). The resulting solution was stirred at rt for 18 h then purified by reverse phase chromatography to give, after concentration and lyophilization, (10R,14S)-14-[4-(3,6-dichloro-2-fluorophenyl)-6-oxo-1,6-dihydropyrimidin-1-yl]-4-fluoro-10-methyl-8,16-diazatricyclo[13.3.1.0$^{2,7}$]nonadeca-1(19),2(7),3,5,15,17-hexaen-9-one trifluoroacetate (11 mg, 42.9% yield), as a white solid. MS(ESI) m/z: 555.1 (M+H)$^+$. $^1$H NMR (400 MHz, CD$_3$OD) δ 9.16 (s, 1H), 8.71 (d, J=5.1 Hz, 1H), 7.80 (s, 1H), 7.59 (dd, J=8.7, 7.8 Hz, 1H), 7.48 (dd, J=5.2, 1.7 Hz, 1H), 7.44-7.36 (m, 2H), 7.32-7.21 (m, 2H), 6.60 (s, 1H), 6.07 (dd, J=12.5, 4.8 Hz, 1H), 2.72-2.63 (m, 1H), 2.38-2.27 (m, 1H), 2.18-2.07 (m, 1H), 2.05-1.92 (m, 1H), 1.60-1.40 (m, 2H), 0.97 (d, J=7.0 Hz, 3H), 0.83-0.62 (m, 1H). $^{19}$F NMR (376 MHz, CD$_3$OD) δ −77.69 (s), −114.44 (s), −116.23 (s). Analytical HPLC (Method A): RT=9.81 min, 100% purity; Factor XIa Ki=19 nM, Plasma Kallikrein Ki=210 nM.

EXAMPLE 148

Preparation 1-(4-chloro-2-{1-[(10R,14S)-4-fluoro-10-methyl-9-oxo-8,16-diazatricyclo [13.3.1.0$^{2,7}$]nonadeca-1(19),2(7),3,5,15,17-hexaen-14-yl]-6-oxo-1,6-dihydropyrimidin-4-yl}phenyl)-1H-1,2,3-triazole-4-carbonitrile trifluoroacetate

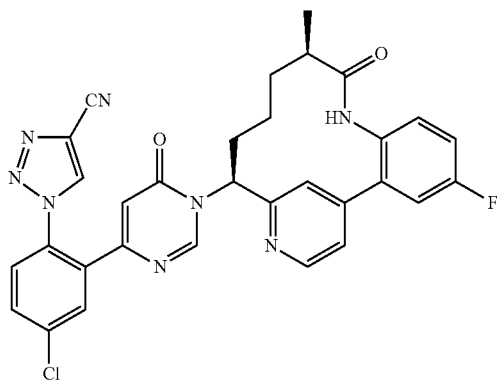

1-(4-Chloro-2-{1-[(10R,14S)-4-fluoro-10-methyl-9-oxo-8,16-diazatricyclo [13.3.1.0$^{2,7}$]nonadeca-1(19),2(7),3,5,15,17-hexaen-14-yl]-6-oxo-1,6-dihydropyrimidin-4-yl}phenyl)-1H-1,2,3-triazole-4-carbonitrile trifluoroacetate (22 mg, 54%) was prepared in a similar manner as the procedure described in Example 129I, using 1[4-chloro-2-(6-hydroxypyrimidin-4-yl)phenyl]-1H-1,2,3-triazole-4-carbonitrile (17.16 mg, 0.057 mmol), prepared as described in Example 18, and (10R,14S)-14-amino-4-fluoro-10-methyl-8,16-diazatricyclo[13.3.1.0$^{2,7}$]nonadeca-1(19),2,4,6,15,17-hexaen-9-one (11.1 mg, 0.036 mmol), prepared as described in Example 28. MS(ESI) m/z: 595.2 (M+H)$^+$. $^1$H NMR (400 MHz, CD$_3$OD) δ 8.94 (s, 1H), 8.82 (s, 1H), 8.69 (d, J=5.1 Hz, 1H), 7.89 (d, J=2.4 Hz, 1H), 7.78-7.73 (m, 2H), 7.71-7.65 (m, 1H), 7.47 (dd, J=5.1, 1.3 Hz, 1H), 7.40 (dd, J=9.0, 2.6 Hz, 1H), 7.32-7.19 (m, 2H), 6.46 (s, 1H), 5.96 (dd, J=12.5, 4.6 Hz, 1H), 2.64 (d, J=6.4 Hz, 1H), 2.29-2.16 (m, 1H), 2.09-1.87 (m, 2H), 1.57-1.35 (m, 2H), 0.96 (d, J=6.8 Hz, 3H), 0.72 (m., 1H). $^{19}$F NMR (376 MHz, CD$_3$OD) δ −76.88 (s), −116.22 (s). Analytical HPLC (Method A): RT=8.33 min, purity=100%; Factor XIa Ki=0.1 nM, Plasma Kallikrein Ki=9 nM.

EXAMPLE 149

Preparation 1-(4-chloro-2-{1-[(10R,14S)-4-fluoro-10-methyl-9-oxo-8,16-diazatricyclo [13.3.1.0$^{2,7}$]nonadeca-1(19),2(7),3,5,15,17-hexaen-14-yl]-6-oxo-1,6-dihydropyrimidin-4-yl}phenyl)-N-hydroxy-1H-1,2,3-triazole-4-carboximidamide bis-trifluoroacetate

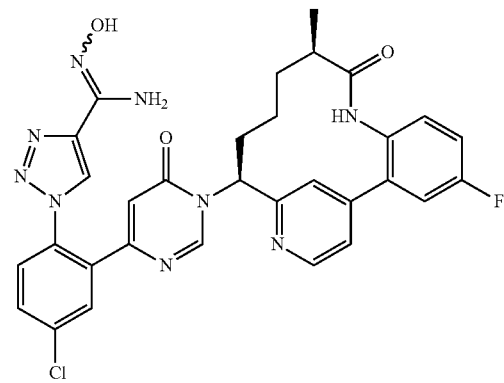 [SMILES: C[C@@H]1CCC[C@H](n2cnc(-c3cc(Cl)ccc3-n3cc(C(N)=NO)nn3)cc2=O)c2cc(ccn2)-c2cc(F)ccc2NC1=O]

To a 1 dram pressure vial containing 1-(4-chloro-2-{1-[(10R,14S)-4-fluoro-10-methyl-9-oxo-8,16-diazatricyclo [13.3.1.0$^{2,7}$]nonadeca-1(19),2(7),3,5,15,17-hexaen-14-yl]-6-oxo-1,6-dihydropyrimidin-4-yl}phenyl)-1H-1,2,3-triazole-4-carbonitrile trifluoroacetate (10 mg, 0.017 mmol), prepared as described in Example 148, NH$_2$OH.HCl (2.336 mg, 0.034 mmol) and NaHCO$_3$ (1.412 mg, 0.017 mmol) in MeOH (0.5 mL) was heated at 65° C. overnight. The reaction was cooled to rt and the solid were filtered and rinsed with MeOH. The filtrate was concentrate then purified by reverse phase chromatography to give 1-(4-chloro-2-{1-[(10R,14S)-4-fluoro-10-methyl-9-oxo -8,16-diazatricyclo [13.3.1.0$^{2,7}$]nonadeca-1(19),2(7),3,5,15,17-hexaen-14-yl]-6-oxo-1,6-dihydropyrimidin-4-yl}phenyl)-N-hydroxy-1H-1,2,3-triazole-4-carboximidamide bis -trifluoroacetate (6.1 mg, 42.4% yield) as a white solid. MS(ESI) m/z: 658.20 (M+H)$^+$. $^1$H NMR (500 MHz, DMSO-d$_6$) δ 9.85 -9.65 (m, 1H), 8.95 (s, 1H), 8.69 (d, J=4.9 Hz, 1H), 8.60 (s, 1H), 7.97 (d, J=2.4 Hz, 1H), 7.86 (dd, J=8.4, 2.3 Hz, 1H), 7.80-7.69 (m, 2H), 7.57-7.44 (m, 2H), 7.42-7.26 (m, 2H), 6.26 (s, 1H), 6.02-5.79 (m, 3H), 2.32-2.17 (m, 1H), 2.04-1.82 (m, 2H), 1.43 (m, 2H), 0.89 (d, J=6.7 Hz, 4H), 0.46 (m, 1H). Analytical HPLC (Method C): RT=1.32 min, purity=93.3%; Factor XIa Ki=0.59 nM, Plasma Kallikrein Ki=38 nM.

EXAMPLE 150

Preparation of (10R,14S)-14[4-(5-chloro-2-methoxyphenyl)-6-oxo-1,6-dihydropyrimidin-1-yl]-4-fluoro-10-methyl-8,16-diazatricyclo[13.3.1.0$^{2,7}$]nonadeca -1(19),2(7),3,5,15,17-hexaen-9-one trifluoroacetate

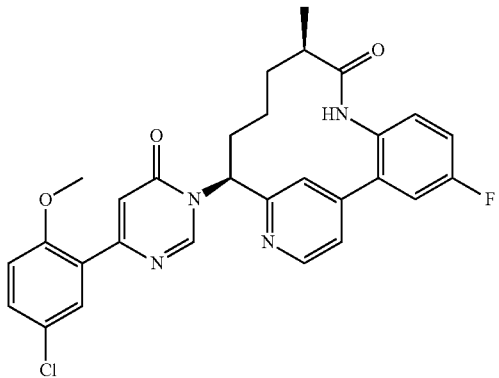 [SMILES: COc1ccc(Cl)cc1-c1cc(=O)n([C@H]2CCC[C@@H](C)C(=O)Nc3ccc(F)cc3-c3ccnc2c3)cn1]

150A. Preparation of 6-(5-chloro-2-methoxyphenyl)pyrimidin-4-ol

A microwave vial containing 6-chloropyrimidin-4-ol (0.112 g, 0.86 mmol), (5-chloro-2-methoxyphenyl)boronic acid (0.16 g, 0.86 mmol), and Pd(Ph$_3$P)$_4$ (0.099 g, 0.086 mmol) was purged with Ar for several min. Then degassed toluene (1.72 ml) and EtOH (1.72 ml) were added followed by DIEA (0.60 ml, 3.43 mmol). The vial was capped and the reaction was microwaved at 120° C. for 1 h. The clear yellow solution was allowed to cool to rt and concentrated. MeOH (2 ml) was added and the reaction was sonicated to afford a yellow suspension. The solid was collected by filtration, rinsing with a small amount of MeOH and air-dried to give a white solid. This white solid suspended in DCM (2 ml), sonicated, then filtered. The white solid was rinsed with a small amount of DCM, and air-dried to afford 6-(5-chloro-2-methoxyphenyl)pyrimidin-4-ol (0.024 g, 11.8% yield) as a white solid. MS(ESI) m/z: 237.1 (M+H)$^+$. $^1$H NMR (400 MHz, DMSO-d$_6$) δ 12.52 (br. s., 1H), 8.25 (d, J=0.9 Hz, 1H), 7.93 (d, J=2.9 Hz, 1H), 7.49 (dd, J=8.8, 2.9 Hz, 1H), 7.20 (d, J=8.8 Hz, 1H), 6.95 (s, 1H), 3.89 (s, 3H).

150B. Preparation of (10R,14S)-14-[4-(5-chloro-2-methoxyphenyl)-6-oxo-1,6-dihydropyrimidin-1-yl]-4-fluoro-10-methyl-8,16-diazatricyclo[13.3.1.0$^{2,7}$]nonadeca -1(19),2(7),3,5,15,17-hexaen-9-one trifluoroacetate To a scintillation vial containing 6-(5-chloro-2-methoxyphenyl)pyrimidin-4-ol (9.06 mg, 0.038 mmol), HATU (18.93 mg, 0.050 mmol) in ACN (0.5 ml) was added DBU (8.66 µl, 0.057 mmol). After 15 min, (10R,14S)-14-amino-4-fluoro-10-methyl -8,16-diazatricyclo[13.3.1.0$^{2,7}$]nonadeca-1(19),2,4,6,15,17-hexaen-9-one (12 mg, 0.038 mmol), prepared as described in Example 28, was added, followed by DMF (0.5 ml). The resulting solution was stirred at rt for 18 h then purified by reverse phase chromatography to give, after concentration and lyophilization, (10R,14S)-14-[4-(5-chloro-2-methoxyphenyl)-6-oxo-1,6-dihydropyrimidin-1-yl]-4-fluoro-10-methyl-8,16-diazatricyclo[13.3.1.0$^{2,7}$]nonadeca-1(19),2(7),3,5,15,17-hexaen-9-one trifluoroacetate (11 mg, 44.3% yield) as a white solid. MS(ESI) m/z: 533.1 (M+H)$^+$. $^1$H NMR (400 MHz, CD$_3$OD) δ 9.08 (s, 1H), 8.70 (d, J=5.3 Hz, 1H), 7.99 (d, J=2.9 Hz, 1H), 7.83 (s, 1H), 7.51 (dd, J=5.2, 1.7 Hz, 1H), 7.42 (td, J=9.0, 2.9 Hz, 2H), 7.33-7.22 (m, 2H), 7.16-7.10 (m, 2H), 6.01 (dd, J=12.5, 4.8 Hz, 1H), 3.90 (s, 3H), 2.72-2.62 (m, 1H), 2.39-2.28 (m, 1H), 2.16-1.91 (m, 2H), 1.59-1.40 (m, 2H), 0.98 (d, J=6.8 Hz, 3H), 0.82-0.64 (m, 1H). $^{19}$F NMR (376 MHz, CD$_3$OD) δ -77.69 (s), -116.17 (s). Analytical HPLC (Method A): RT=9.87 min, 99.7% purity; Factor XIa Ki=310 nM.

What is claimed is:

1. A compound of Formula (I):

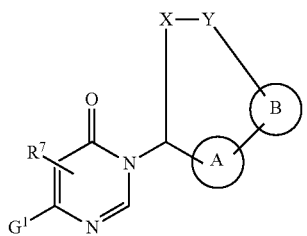

or a stereoisomer, a tautomer, a pharmaceutically acceptable salt thereof, wherein:

ring A is independently selected from 6-membered aryl and 5- to 6-membered heterocyclyl, wherein said aryl and heterocyclyl are optionally substituted with, where valence allows, one or more $R^4$;

ring B is 6-membered aryl optionally substituted with, where valence allows, one or more $R^3$;

$G^1$ is independently selected from $C_{1-10}$ carbocyclyl and 5- to 10-membered heterocyclyl, wherein said carbocyclyl and heterocyclyl are optionally substituted with, where valence allows, one or more $R^8$;

X is independently selected from $C_{4-8}$ alkylene and $C_{4-8}$ alkenylene, wherein said alkylene and alkenylene are substituted with $R^1$ and $R^2$; alternatively one or more of the carbon atoms of said alkylene and alkenylene may be replaced by O, C=O, S(=O)$_p$, S(=O)$_p$NH, and NR$^{15}$;

Y is independently selected from —CR$^{13}$NH—, —NHC(=O)—, —C(=O)NH—, —S(=O)$_p$NH—, —NHS(=O)$_p$—, and $C_{1-2}$ alkylene;

$R^1$ and $R^2$ are independently selected from H, halogen, haloalkyl, $C_{1-6}$ alkyl (optionally substituted with $R^6$), hydroxyl, and alkoxy (optionally substituted with $R^6$), and $C_{3-6}$ cycloalkyl optionally substituted with $R^6$; optionally, when $R^1$ and $R^2$ are attached to the same carbon atom, together they form an oxo group or $C_{3-6}$ cycloalkyl; optionally, when $R^1$ and $R^2$ are attached to carbon atoms adjacent to each other, together they form a bond or a carbocyclyl; optionally, $R^1$ and $R^{15}$ or $R^2$ and $R^{15}$ taken together form a ring;

$R^3$ is independently selected from H, NO$_2$, halogen, haloalkyl, $C_{1-4}$ alkyl (optionally substituted with $R^6$), $C_{2-4}$ alkenyl (optionally substituted with $R^6$), $C_{2-4}$ alkynyl (optionally substituted with $R^6$), CN, —(CH$_2$)$_n$—OR$^5$, —(CH$_2$)$_n$—NR$^5$R$^5$, —(CH$_2$)$_n$—C(=O)R$^5$, —(CH$_2$)$_n$—C(=O)OR$^5$, —(CH$_2$)$_n$—NR$^9$C(=O)OR$^5$, —(CH$_2$)$_n$—NR$^9$C(=O)R$^5$, —(CH$_2$)$_n$—NR$^9$C(N=CN)NHR$^5$, —(CH$_2$)$_n$—NR$^9$C(NH)NHR$^5$, —(CH$_2$)$_n$—N=CR$^9$NR$^5$R$^5$, —(CH$_2$)$_n$—NR$^9$C(=O)NR$^5$R$^5$, —(CH$_2$)$_n$—C(=O)NR$^5$R$^5$, —(CH$_2$)$_n$—NR$^9$C(=S)NR$^9$C(=O)R$^5$, —(CH$_2$)$_n$—S(=O)$_p$R$^5$, —(CH$_2$)$_n$—S(=O)$_p$NR$^5$R$^5$, —(CH$_2$)$_n$—NR$^9$S(=O)$_p$NR$^5$R$^5$, —(CH$_2$)$_n$—NR$^9$S(=O)$_p$R$^5$, —(CH$_2$)$_n$—C$_{3-10}$ carbocyclyl and —(CH$_2$)$_n$-4- to 10-membered heterocyclyl, wherein said carbocyclyl and heterocyclyl are optionally substituted with $R^6$; optionally, two adjacent $R^3$ groups on the carbocyclyl and heterocyclyl may form a ring optionally substituted with $R^6$;

$R^4$ is independently selected from H, OH, NH$_2$, halogen, CN, $C_{1-4}$ alkyl, $C_{1-4}$ haloalkyl, $C_{1-4}$ alkoxy, —CH$_2$OH, —C(=O)OH, —CH$_2$C(=O)OH, —CO$_2$($C_{1-4}$ alkyl), —C(=O)NH$_2$, —C(=O)NH($C_{1-4}$ alkyl), —C(=O)N($C_{1-4}$ alkyl)$_2$, —S(=O)$_2$$C_{1-4}$ alkyl, —S(=O)$_2$NH$_2$, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H, $C_{1-4}$ alkyl (optionally substituted with halogen, hydroxyl, alkoxy, carboxy, hydroxycarbonyl, alkoxycarbonyl, amino, substituted amino), —(CH$_2$)$_n$—$C_{3-10}$ carbocyclyl and —(CH$_2$)$_n$-4- to 10-membered heterocyclyl, wherein said carbocyclyl and heterocyclyl are optionally substituted with $R^6$; alternatively, $R^5$ and $R^5$ together with the nitrogen atom to which they are both attached form a heterocyclic ring optionally substituted with $R^6$;

$R^6$ is independently selected from H, —(CH$_2$)$_n$—OH, =O, —(CH$_2$)$_n$NH$_2$, —(CH$_2$)$_n$—CN, halogen, $C_{1-6}$ alkyl, —(CH$_2$)$_n$—C(=O)OH, —(CH$_2$)$_n$—C(=O)NH$_2$, —(CH$_2$)$_n$—C(=O)OC$_{1-4}$ alkyl, —(CH$_2$)$_n$—OC$_{1-4}$ alkyl, —(CH$_2$)$_n$—$C_{3-10}$ carbocyclyl, —(CH$_2$)$_n$-4- to 10-membered heterocyclyl, and —O-4- to 10-membered heterocyclyl, wherein said carbocyclyl and heterocyclyl are optionally substituted with $R^{10}$;

$R^7$ is independently selected from H, hydroxyl, alkoxy, halogen, amino, $C_{1-3}$ haloalkyl, and $C_{1-3}$ alkyl;

$R^8$ is independently selected from H, halogen, —(CH$_2$)$_n$CN, $C_{1-6}$ alkyl, amino, aminoalkyl, haloalkyl, hydroxyl, alkoxy, haloalkoxy, alkylcarbonyl, carboxyl, carboxyl ester, amide, haloalkylaminocarbonyl, arylalkylaminocarbonyl, haloalkylaminocarbonyl, alkoxycarbonylamino, haloalkylcarbonylamino, arylamino, heteroarylamino, arylalkylcarbonyl, aryloxy, heteroaryloxy, thio, thioalkyl, sulfonylalkyl, sulfonylaryl, sulfonylheteroaryl, sulfonamide, —(CH$_2$)$_n$-aryl, —(CH$_2$)$_n$—$C_{3-6}$ cycloalkyl, and —(CH$_2$)$_n$-4- to 12-membered heterocyclyl, wherein said aryl, cycloalkyl, and heterocyclyl are optionally substituted with $R^{10}$; alternatively, two adjacent $R^8$ groups form a heterocyclic ring optionally substituted with $R^{10}$;

$R^9$ is H or $C_{1-6}$ alkyl;

$R^{10}$ is independently selected from H, $C_{1-6}$ alkyl (optionally substituted with $R^{11}$), $C_{2-6}$ alkenyl, $C_{2-6}$ alkynyl, aryl (optionally substituted with $R^{11}$), —(CH$_2$)$_n$—$C_{3-6}$ cycloalkyl (optionally substituted with $R^{11}$), —(CH$_2$)$_n$—O-4- to 10-membered heterocyclyl (optionally substituted with $R^{11}$), halogen, —(CH$_2$)$_n$CN, NO$_2$, =O, C(=O)NR$^{12}$R$^{12}$, C(=O)OR$^{12}$, Si(C$_{1-4}$ alkyl)$_3$, —(CH$_2$)$_n$—OR$^{12}$, —(CH$_2$)$_n$—NR$^{12}$R$^{12}$, —S(=O)$_p$C$_{1-6}$ alkyl, NR$^{12}$S(=O)$_p$C$_{1-6}$ alkyl, S(=O)$_p$NR$^{12}$R$^{12}$, and C(=NOH)NH$_2$;

$R^{11}$, at each occurrence, is independently selected from H, halogen, $C_{1-5}$ alkyl, —(CH$_2$)n—OH, $C_{3-6}$ cycloalkyl, phenyl, and heterocyclyl;

$R^{12}$, at each occurrence, is independently selected from H, $C_{1-5}$ alkyl optionally substituted with $R^{11}$, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$ alkyl;

$R^{13}$ is, independently at each occurrence, selected from H, $C_{1-4}$ haloalkyl, $C_{1-4}$ alkyl, CO$_2$H, CO$_2$($C_{1-4}$ alkyl), CO$_2$(CH$_2$)$_2$O($C_{1-4}$ alkyl), CO$_2$($C_{1-4}$ haloalkyl), CH$_2$CO$_2$H, CH$_2$CO$_2$($C_{1-4}$ alkyl), CONH$_2$, CONH($C_{1-4}$ alkyl), CON($C_{1-4}$ alkyl)$_2$, and —CONH($C_{1-4}$ alkoxy);

$R^{15}$ is H or $C_{1-6}$ alkyl;

n, at each occurrence, is an integer independently selected from 0, 1, 2, 3, and 4; and p, at each occurrence, is an integer independently selected from 0, 1, and 2.

2. The compound of claim 1 having Formula (IIa):

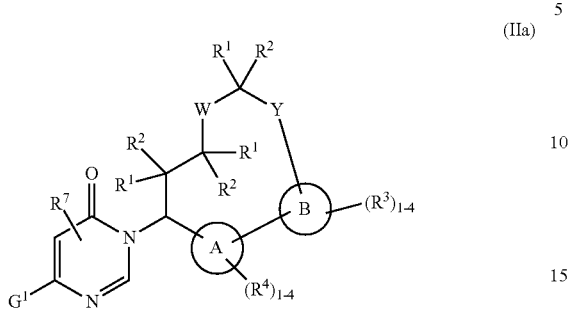

(IIa)

or a stereoisomer, a tautomer, a pharmaceutically acceptable salt thereof, wherein:
ring A is independently selected from 6-membered aryl and 5- to 6-membered heterocyclyl;
ring B is 6-membered aryl;
$G^1$ is independently selected from $C_{3-6}$ carbocyclyl and 5- to 10-membered heterocyclyl, wherein said carbocyclyl and heterocyclyl are substituted with 1-4 $R^8$;
W is independently selected from $(CR^1R^2)_{1-2}$, O, and $NR^{15}$;
Y is independently selected from —$CR^{13}NH$—, —NHC(=O)— and —C(=O)NH—;
$R^1$ and $R^2$ are independently selected from H, halogen, haloalkyl, $C_{1-4}$ alkyl (optionally substituted with $R^6$), hydroxyl, and alkoxy (optionally substituted with $R^6$), and $C_{3-5}$ cycloalkyl optionally substituted with $R^6$; optionally, $R^1$ and $R^{15}$ or $R^2$ and $R^{15}$ taken together form a ring;
$R^3$ is independently selected from H, halogen, haloalkyl, $C_{1-4}$ alkyl (optionally substituted with $R^6$), $C_{2-4}$ alkenyl (optionally substituted with $R^6$), $C_{2-4}$ alkynyl (optionally substituted with $R^6$), CN, $NO_2$, —$(CH_2)_n$—$OR^5$, —$(CH_2)_n$—$NR^5R^5$, —$(CH_2)_n$—$C(=O)R^5$, —$(CH_2)_n$—$C(=O)OR^5$, —$(CH_2)_n$—$NR^9C(=O)OR^5$, —$(CH_2)_n$—$NR^9C(=O)R^5$, —$(CH_2)_n$—$NR^9C(N=CN)NHR^5$, —$(CH_2)_n$—$NR^9C(NH)NHR^5$, —$(CH_2)_n$—$N=CR^9NR^5R^5$, —$(CH2)_n$—$NR^9C(=O)NR^5R^5$, —$(CH2)_n$—$C(=O)NR^5R^5$, —$(CH2)_n$—$NR^9C(S)NR^9C(=O)R^5$, —$(CH2)_n$—$S(=O)_pC_{1-6}$ alkyl optionally substituted with $R^{11}$, —$(CH_2)_n$—$S(=O)_pNR^5R^5$, —$(CH_2)_n$—$NR^9S(=O)_pNR^5R^5$, —$(CH_2)_n$—$NR^9S(=O)_pC_{1-6}$ alkyl optionally substituted with $R^{11}$, —$(CH_2)_n$—$C_{3-10}$ carbocyclyl and —$(CH_2)_n$-4- to 10-membered heterocyclyl, wherein said carbocyclyl and heterocyclyl are optionally substituted with $R^6$; optionally, two adjacent $R^3$ groups on the carbocyclyl and heterocyclyl may form a ring optionally substituted with $R^6$;
$R^4$ is independently selected from H, OH, halogen, CN, $C_{1-4}$ alkyl, $C_{1-4}$ haloalkyl, $C_{1-4}$ alkoxy, —$C(=O)NH_2$, —$C(=O)NH(C_{1-4}$ alkyl), —$C(=O)N(C_{1-4}$ alkyl$)_2$, $C_{3-6}$ cycloalkyl, aryl, and 5- to 6-membered heterocyclyl, wherein said cycloalkyl, aryl and heterocyclyl are optionally substituted with $R^6$;
$R^5$ is independently selected from H, $C_{1-4}$ alkyl (optionally substituted with halogen, hydroxyl, alkoxy, carboxy, alkoxycarbonyl, amino, substituted amino), $C_{3-10}$ carbocyclyl and 4- to 10-membered heterocyclyl, wherein said carbocyclyl and heterocyclyl are optionally substituted with $R^6$;

$R^6$ is independently selected from OH, =O, —$(CH_2)_n$$NH_2$, —$(CH_2)_n$CN, halogen, $C_{1-6}$ alkyl, —$(CH_2)_n$—$C(=O)OH$, —$(CH_2)_n$—$C(=O)OC_{1-4}$ alkyl, —$(CH_2)_n$—$OC_{1-4}$ alkyl, —$(CH_2)_n$—$C(=O)NH_2$, —$(CH_2)_n$—$C_{3-10}$ carbocyclyl, —$(CH_2)_n$-4- to 10-membered heterocyclyl, and —$(CH_2)_n$-4- to 10-membered heterocyclyl, wherein said carbocyclyl and heterocyclyl are optionally substituted with $R^{10}$;
$R^7$ is independently selected from H, hydroxyl, halogen, and methyl;
$R^8$ is independently selected from H, halogen, CN, $NH_2$, $C_{1-6}$ alkyl, haloalkyl, haloalkylcarbonylamino, arylamino, heteroarylamino, hydroxycarbonyl, haloalkylaminocarbonyl, arylalkylcarbonyl, alkylcarbonyl, alkoxy, haloalkoxy, —$(CH_2)_n$-aryl, —$(CH_2)_n$—$C_{3-6}$ cycloalkyl, and —$(CH_2)_n$-4- to 12-membered heterocyclyl, wherein said aryl, cycloalkyl, and heterocyclyl are optionally substituted with $R^{10}$; alternatively, two adjacent $R^8$ groups and $G_1$ form a fused

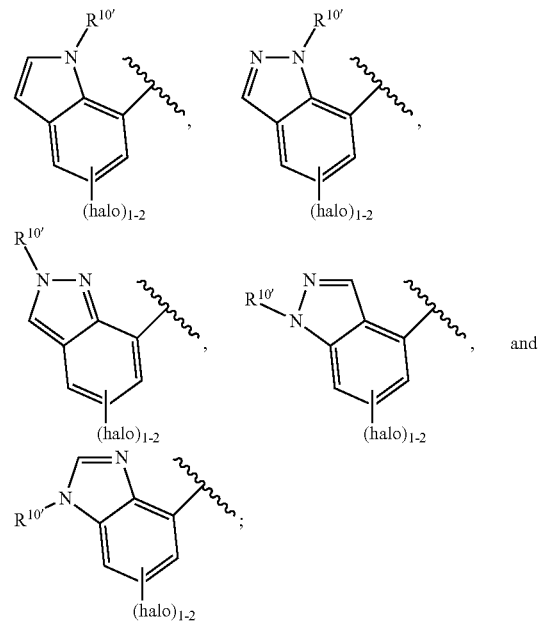

bi-heterocyclic group selected from
$R^9$ is H or $C_{1-6}$ alkyl;
$R^{10}$ is independently selected from H, $C_{1-6}$ alkyl (optionally substituted with $R^{11}$), $C_{2-6}$ alkenyl, $C_{2-6}$ alkynyl, aryl (optionally substituted with $R^{11}$), —$(CH_2)_n$—$C_{3-6}$ cycloalkyl (optionally substituted with $R^{11}$), —$(CH_2)_n$—$O$-4- to 10-membered heterocyclyl (optionally substituted with $R^{11}$), F, Cl, Br, —$(CH_2)_n$CN, $NO_2$, =O, $C(=O)NR^{12}R^{12}$, $C(=O)OR^{12}$, $Si(C_{1-4}$ alkyl$)_3$, —$(CH_2)_n$—$OR^{12}$, —$(CH_2)_n$—$NR^{12}R^{12}$, —$S(=O)_p$$C_{1-6}$ alkyl, $NR^{12}S(=O)_pC_{1-6}$ alkyl, $S(=O)_pNR^{12}R^{12}$, and $C(=NOH)NH_2$;
$R^{10'}$ is independently selected from H, $C_{1-6}$ alkyl (optionally substituted with $R^{11}$), aryl, —$(CH_2)_n$—$C_{3-6}$ cycloalkyl (optionally substituted with $R^{11}$), and —$(CH_2)_n$—O-4- to 10-membered heterocyclyl (optionally substituted with $R^{11}$);
$R^{11}$, at each occurrence, is independently selected from H, halogen, $C_{1-5}$ alkyl, —$(CH_2)_n$—OH, $C_{3-6}$ cycloalkyl, and phenyl;

$R^{12}$, at each occurrence, is independently selected from H, $C_{1-5}$ alkyl (optionally substituted with $R^{11}$), $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$alkyl;

$R^{13}$ is, independently at each occurrence, selected from H, $CF_3$, and $CH_3$;

$R^{15}$ is H or $C_{1-6}$ alkyl;

n, at each occurrence, is an integer independently selected from 0, 1, 2, 3, and 4; and p, at each occurrence, is an integer independently selected from 0, 1, and 2.

3. The compound of claim 2 having Formula (III):

(III)

or a stereoisomer, a tautomer, a pharmaceutically acceptable salt thereof, wherein:

ring A is independently selected from phenyl and 5- to 6-membered heterocyclyl;

$G^1$ is independently selected from aryl, $C_{3-6}$ cycloalkyl and 5- to 6-membered heterocyclyl, wherein said aryl, cycloalkyl and heterocyclyl are substituted with 1-4 $R^8$;

$R^1$ and $R^2$ are independently selected from H, halogen, $CF_3$, $C_{1-6}$ alkyl, and hydroxyl;

$R^3$ is independently selected from H, halogen, haloalkyl, $C_{1-4}$ alkyl (optionally substituted with $R^6$), $C_{2-4}$ alkenyl (optionally substituted with $R^6$), $C_{2-4}$ alkynyl (optionally substituted with $R^6$), CN, $NO_2$, —$(CH_2)_n$—$OR^5$, —$(CH_2)_n$—$NR^5R^5$, —$(CH_2)_n$—$C(=O)OR^5$, —$(CH_2)_n$—$NHC(=O)OR^5$, —$(CH_2)_n$—$NHC(=O)R^5$, —$(CH_2)_n$=$NHC(N=CN)NHR^5$, —$(CH_2)_n$—$NHC(NH)NHR^5$, —$(CH_2)_n$—$N=CHNR^5R^5$, —$(CH_2)_n$—$NHC(=O)$ $NR^5R^5$, —$(CH_2)_n$—$C(=O)$ $NR^5R^5$, —$(CH_2)_n$—$NHC(S)NR^9C(=O)R^5$, —$(CH_2)_n$—$S(=O)_pC_{1-6}$ alkyl optionally substituted with $R^{11}$, —$(CH_2)_n$—$S(=O)_pNR^5R^5$, —$(CH_2)_n$—$NHS(=O)_p$ $NR^5R^5$, —$(CH_2)_n$—$NHS(=O)_pC_{1-6}$ alkyl optionally substituted with $R^{11}$, —$(CH_2)_n$—$C_{3-10}$ carbocyclyl and —$(CH_2)_n$-4- to 10-membered heterocyclyl, wherein said carbocyclyl and heterocyclyl are optionally substituted with $R^6$; optionally, two adjacent $R^3$ groups on the carbocyclyl and heterocyclyl may form a ring optionally substituted with $R^6$;

$R^{3a}$ is independently selected from H and halogen;

$R^{3b}$ is independently selected from H, halogen, methyl, and CN;

$R^4$ is independently selected from H, OH, F, Cl, Br, $C_{1-4}$ alkyl, $C_{1-4}$ alkoxy, $CF_3$, CN, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), —$(CH_2)_n$—$C_{3-10}$ carbocyclyl and —$(CH_2)_n$-4- to 10-membered heterocyclyl, wherein said carbocyclyl and heterocyclyl are optionally substituted with $R^6$;

$R^6$ is independently selected from —$(CH_2)_n$—OH, =O, $NH_2$, —$(CH_2)_n$—CN, halogen, $C_{1-6}$ alkyl, —$(CH_2)_n$—$C(=O)OH$, —$(CH_2)_n$—$C(=O)OC_{1-4}$ alkyl, —$(CH_2)_n$—$C(=O)NH_2$, —$(CH_2)_n$—$OC_{1-4}$ alkyl, —$(CH_2)_n$—$C_{3-6}$ cycloalkyl, —$(CH_2)_n$-4- to 10-membered heterocyclyl, and —O—$(CH_2)_n$-4- to 10-membered heterocyclyl, wherein said cycloalkyl and heterocyclyl are optionally substituted with $R^{10}$;

$R^7$ is independently selected from H, F, Cl, and methyl;

$R^8$ is independently selected from H, halogen, CN, $NH_2$, $C_{1-6}$ alkyl, haloalkyl, haloalkylcarbonylamino, arylamino, heteroarylamino, hydroxycarbonyl, haloalkylaminocarbonyl, alkylcarbonyl, alkoxy, haloalkoxy, aryl, $C_{3-6}$ cycloalkyl, and 4- to 12-membered heterocyclyl, wherein said aryl, cycloalkyl, and heterocyclyl are optionally substituted with $R^{10}$;

$R^{10}$ is independently selected from H, $C_{1-6}$ alkyl (optionally substituted with $R^{11}$), $C_{1-6}$ alkenyl, $C_{2-6}$ alkynyl, aryl (optionally substituted with $R^{11}$), —$(CH_2)_n$—$C_{3-6}$ cycloalkyl (optionally substituted with $R^{11}$), —$(CH_2)_n$—O-4- to 10-membered heterocyclyl (optionally substituted with $R^{11}$), F, Cl, Br, CN, $NO_2$, =O, $C(=O)$ $NR^{12}R^{12}$; $C(=O)OR^{12}$, $Si(C_{1-4}$ alkyl$)_3$, —$(CH_2)_n$—$OR^{12}$, —$(CH_2)_n$—$NR^{12}R^{12}$, —$S(=O)_pC_{1-6}$ alkyl, $S(=O)_pNR^{12}R^{12}$, and $C(=NOH)NH_2$;

$R^{11}$, at each occurrence, is independently selected from H, halogen, $C_{1-5}$ alkyl, —$(CH_2)_n$—OH, $C_{3-6}$ cycloalkyl, and phenyl;

$R^{12}$, at each occurrence, is independently selected from H, $C_{1-5}$ alkyl (optionally substituted with $R^{11}$), $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$ alkyl;

n, at each occurrence, is an integer independently selected from 0, 1, and 2; and p, at each occurrence, is an integer independently selected from 0, 1, and 2.

4. The compound of claim 3, having Formula (IVa):

(IVa)

or a stereoisomer, a tautomer, a pharmaceutically acceptable salt thereof, wherein:

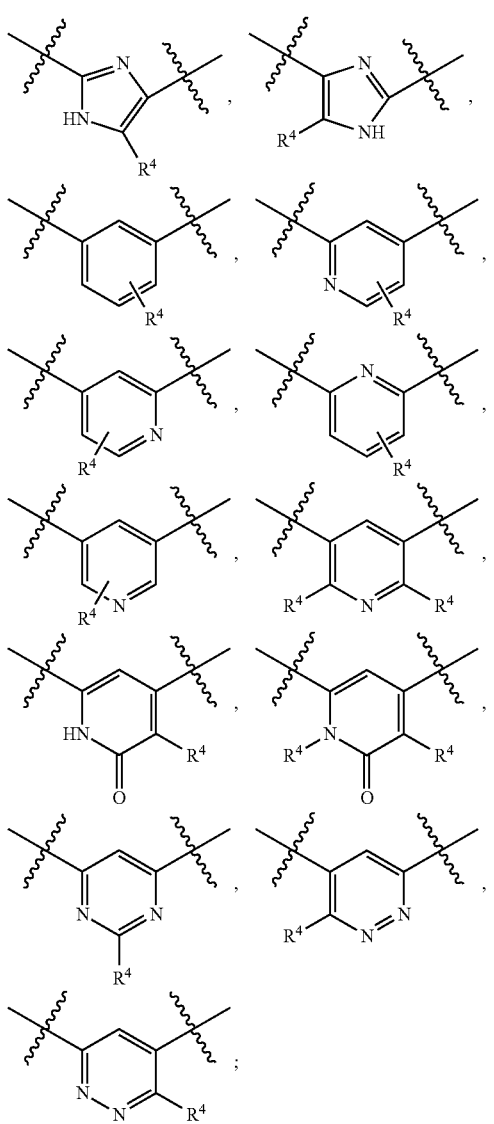

ring A is independently selected from

R$^1$ and R$^2$ are independently selected from H, F, C$_{1-4}$ alkyl, alkoxy, and hydroxyl;

R$^{1a}$, at each occurrence, is independently selected from H, F, CH$_3$ and hydroxyl;

R$^3$ is independently selected from H, F, Cl, Br, I, C$_{1-3}$ alkyl (optionally substituted with R$^6$), CN, —(CH$_2$)$_n$—OR$^5$, —(CH$_2$)$_n$—NHR$^5$, —(CH$_2$)$_n$—C(=O)OR$^5$, —NHC(=O)OR$^5$, —NHC(=O)R$^5$, —NHC(=O)NR$^5$R$^5$, —C(=O)NR$^5$R$^5$, and —S(=O)$_2$C$_{1-4}$alkyl;

R$^{3b}$ is independently selected from H, F, Cl, and methyl;

R$^4$ is independently selected from H, OH, F, OC$_{1-4}$ alkyl, C$_{1-4}$ alkyl, CN, C$_{3-6}$ cycloalkyl, aryl, and 5- to 6-membered heterocyclyl, wherein said cycloalkyl, aryl and heterocyclyl are optionally substituted with R$^6$;

R$^5$ is independently selected from H, C$_{1-4}$ alkyl (optionally substituted with halogen, hydroxyl, alkoxy, carboxy, alkoxycarbonyl), —(CH$_2$)$_n$—C$_{3-10}$ carbocyclyl and —(CH$_2$)$_n$4- to 10-membered heterocyclyl, wherein said carbocyclyl and heterocyclyl are optionally substituted with R$^6$;

R$^6$ is independently selected from OH, NH$_2$, halogen, C$_{1-6}$ alkyl, C$_{3-6}$ cycloalkyl, —(CH$_2$)$_n$—C(=O)OH, —(CH$_2$)$_n$—C(=O)OC$_{1-4}$ alkyl, —(CH$_2$)$_n$—C(=O)NH$_2$, —(CH$_2$)$_n$—OC$_{1-4}$ alkyl, =O, C$_{3-6}$ cycloalkyl, 4- to 10-membered heterocyclyl, and —O-4- to 10-membered heterocyclyl, wherein said cycloalkyl and heterocyclyl are optionally substituted with R$^{10}$;

R$^{8a}$ is independently selected from H, F, Cl, Br, I, —(CH$_2$)$_n$CN, —(CH$_2$)$_n$NH$_2$, CH$_3$CHF$_2$, CCH$_3$F$_2$, CF$_3$, OH, OCH$_3$, OCF$_3$, OCHF$_2$, C(=O)CH$_3$, C(=O)OH, C(=O)OCH$_3$, C(=O)NH$_2$, C(=O)NHCH$_2$CF$_3$, C(=O)NHCH$_2$Ph, NHC(=O)OCH$_3$, NHC(=O)CF$_3$,

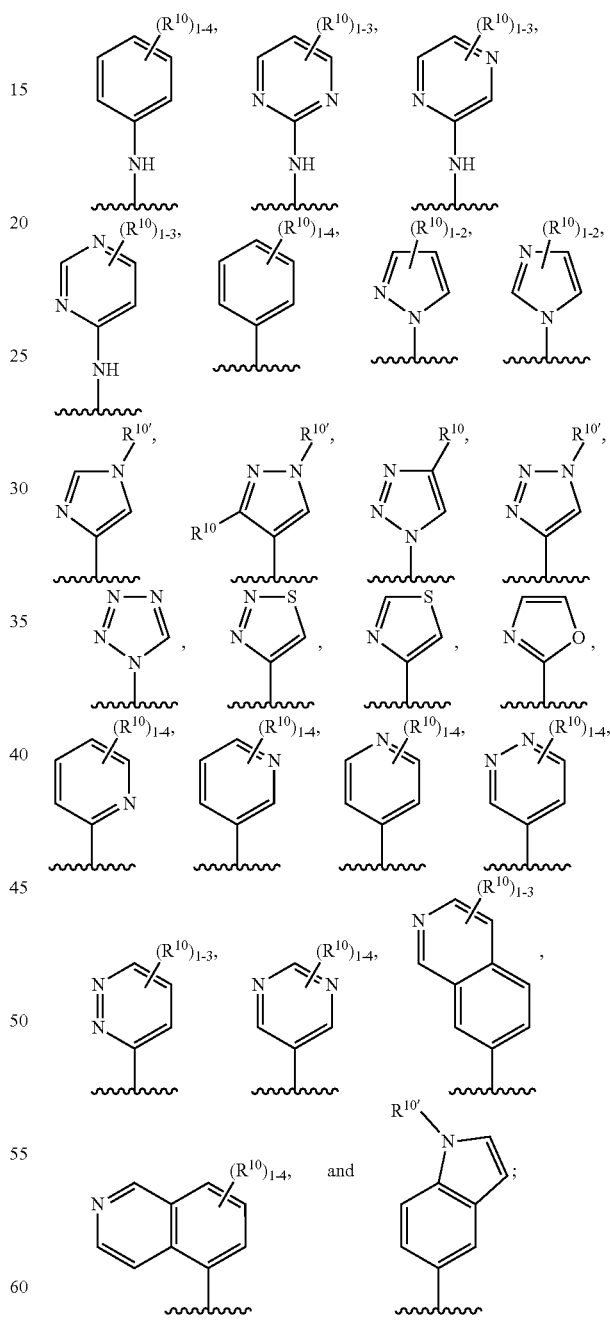

R$^{8b}$ is independently selected from H and F;

R$^{8c}$ is independently selected from H, F, Cl, CH$_3$, and OCH$_3$;

R$^{10}$ is independently selected from H, C$_{1-6}$ alkyl (optionally substituted with R$^{11}$), C$_{2-6}$ alkenyl, C$_{2-6}$ alkynyl, aryl, —(CH₂)ₙ—C₃₋₆ cycloalkyl (optionally substituted with R¹¹), —(CH₂)ₙ—O-4- to 10-membered heterocyclyl (optionally substituted with R¹¹), F, Cl, Br, CN, CONR¹²R¹², C(=O)OR¹², —(CH₂)ₙ—OR¹², —(CH₂)ₙNR¹²R¹², —S(=O)ₚC₁₋₆ alkyl, NR¹²S (=O)ₚ C₁₋₆ alkyl, S(=O)ₚNR¹²R¹² and C(=NOH)NH₂;

R¹⁰' is independently selected from H, C₁₋₆ alkyl (optionally substituted with R¹¹), aryl, —(CH₂)ₙ—C₃₋₆ cycloalkyl (optionally substituted with R¹¹), and —(CH₂)ₙ—O-4- to 10-membered heterocyclyl (optionally substituted with R¹¹);

R¹¹, at each occurrence, is independently selected from H, halogen, C₁₋₅ alkyl, —(CH₂)ₙ—OH, C₃₋₆ cycloalkyl, and phenyl;

R¹², at each occurrence, is independently selected from H, C₁₋₅ alkyl optionally substituted with R¹¹, C₃₋₆ cycloalkyl, phenyl, and heterocyclyl, or R¹² and R¹² together with the nitrogen atom to which they are both attached form a heterocyclic ring optionally substituted with C₁₋₄ alkyl;

n, at each occurrence, is an integer independently selected from 0, 1, and 2, and p, at each occurrence, is an integer independently selected from 0, 1, and 2.

5. The compound of claim 4, or a stereoisomer, a tautomer, a pharmaceutically acceptable salt thereof, wherein:
ring A is independently selected from

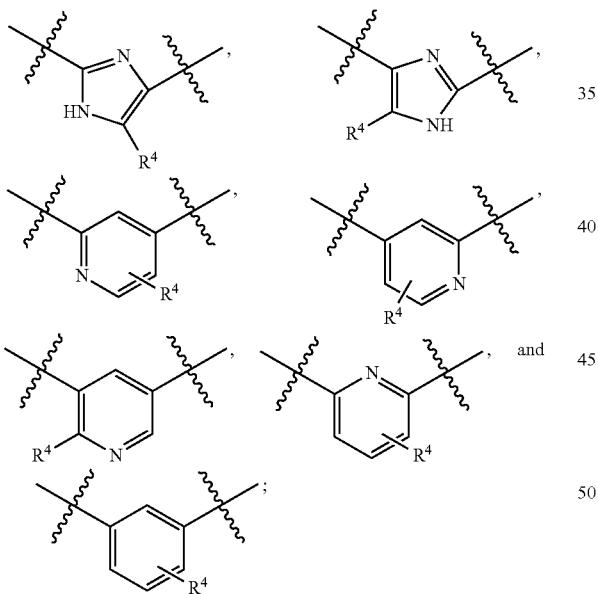

R¹ and R² are independently selected from H and C₁₋₄ alkyl;

R¹ᵃ, at each occurrence, is H;

R³ is independently selected from H, F, Cl, CH₃, CHF₂, C(CH₃)₂OH, CF₂CH₂OH, CF₂CONH₂, CH₂NHCOCF₃, CH₂NH₂, CN, —NHC(=O)OC₁₋₄ alkyl, —(CH₂)₀₋₁OH, OCHF₂, OCH₂COOCH₃, OCH₂COOH, —C(=O)OH, —C(=O)OC₁₋₄ alkyl, —C(=O)NH₂, and S(=O)₂C₁₋₄ alkyl;

R⁴ is independently selected from H and C₁₋₄ alkyl;

R⁸ᵃ is independently selected from H, F, Cl, Br, OCH₃, OCF₃, C(=O)OCH₃, C(=O)OH, CF₃,

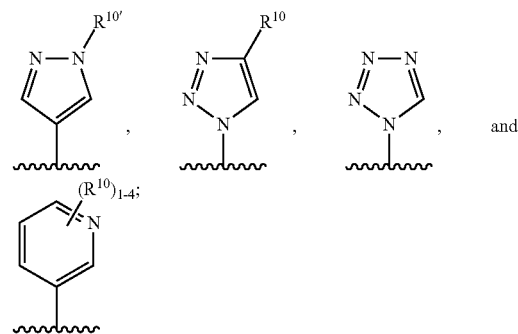

R⁸ᵇ is independently selected from H and F;

R⁸ᶜ is Cl and OCHF₂;

R¹⁰ is independently selected from H, CH₃, CF₃, CHF₂, F, Cl, Br, CN, C(=O)NR¹²R¹², C(=O)OR¹², —OC₁₋₄ alkyl, —OH, —S(=O)ₚC₁₋₆ alkyl, and C(=NOH)NH₂; and R¹⁰ is independently selected from H, CH₃, CF₃, and CHF₂.

6. The compound of claim 2, or a stereoisomer, a tautomer, a pharmaceutically acceptable salt thereof, wherein:
ring A is independently selected from

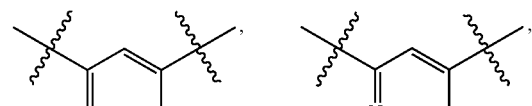

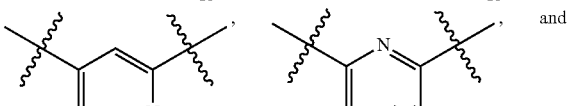

ring B is

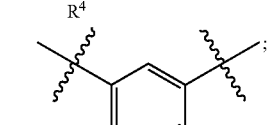

G¹ is independently selected from

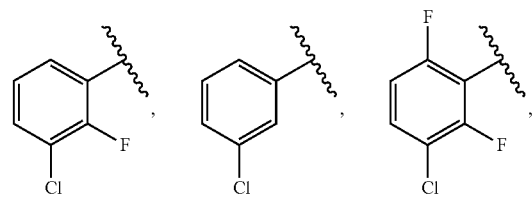

309
-continued
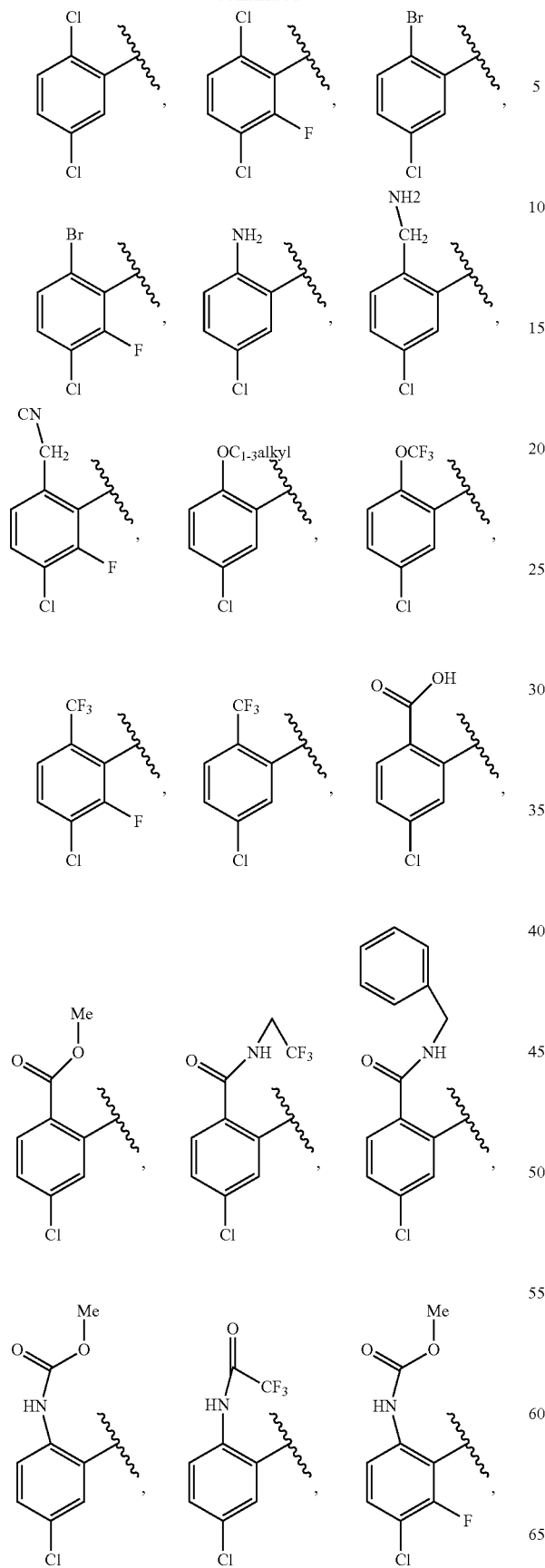
310
-continued
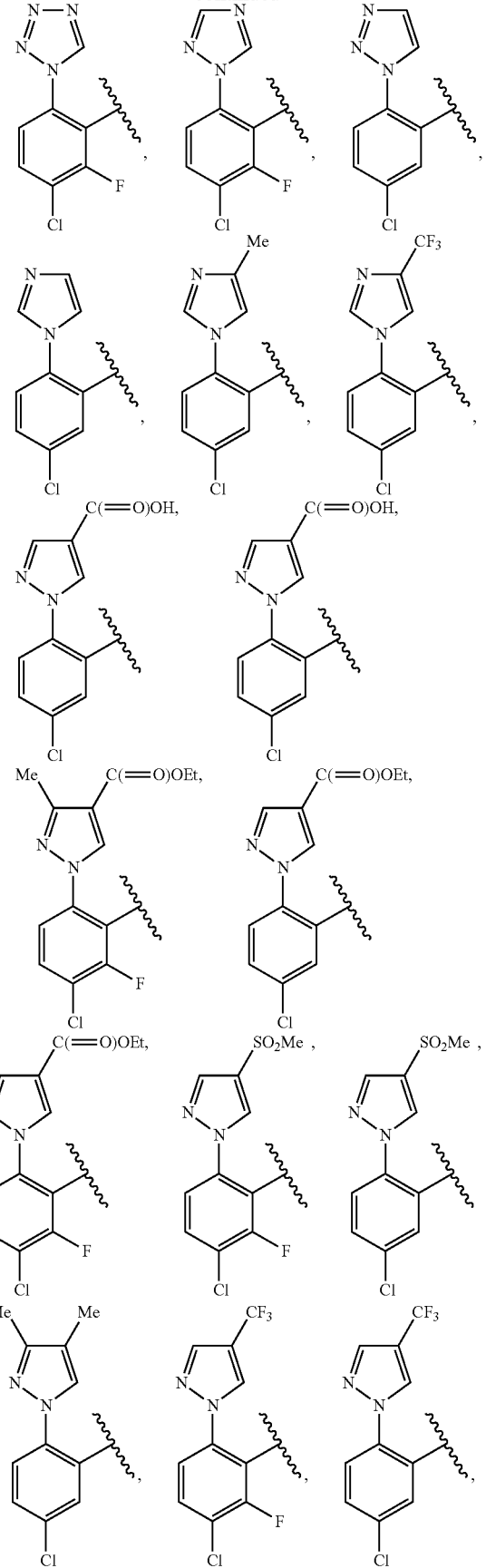

311
-continued
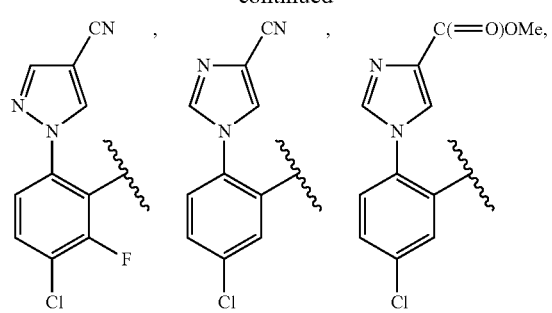
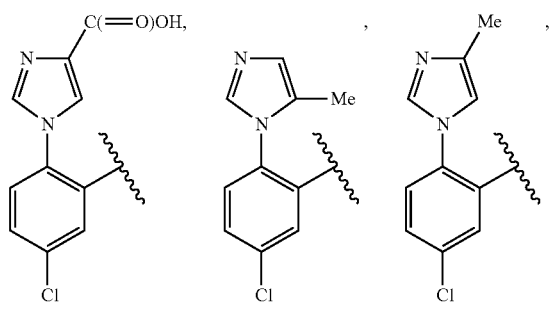
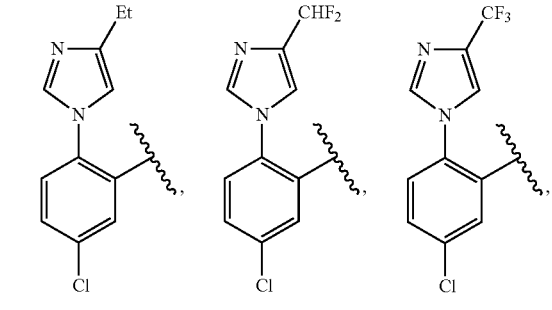
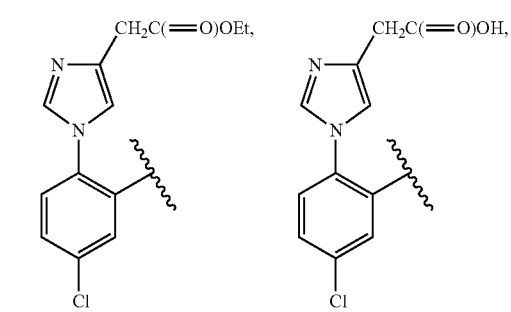
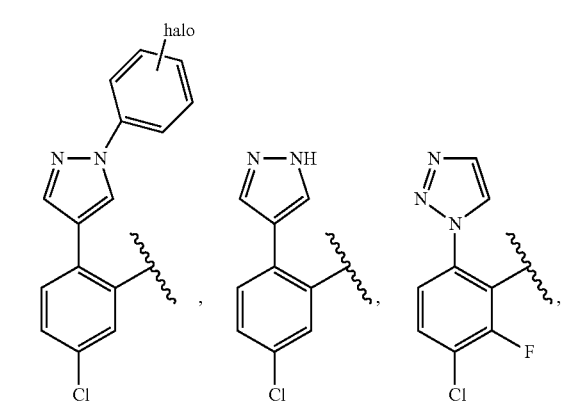
312
-continued
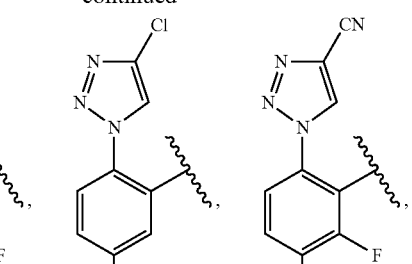
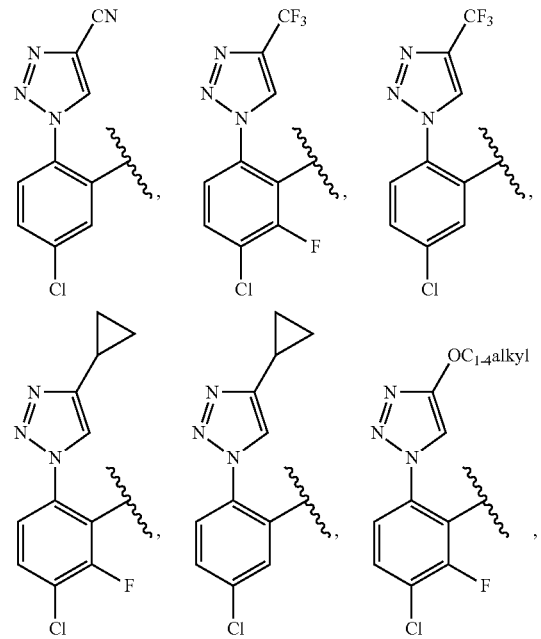
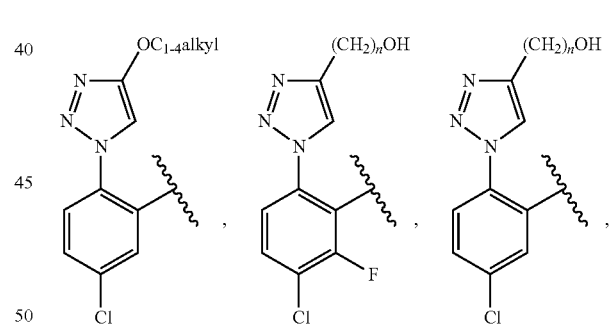
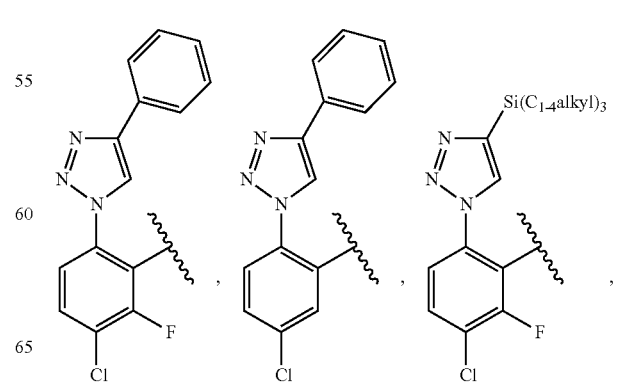

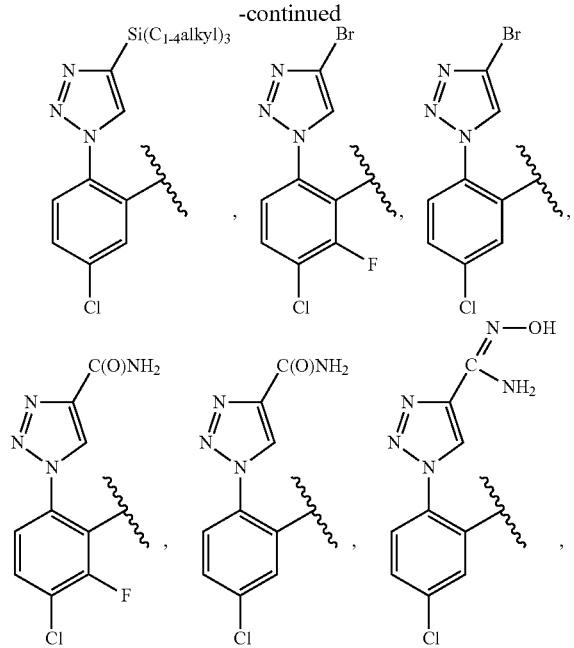
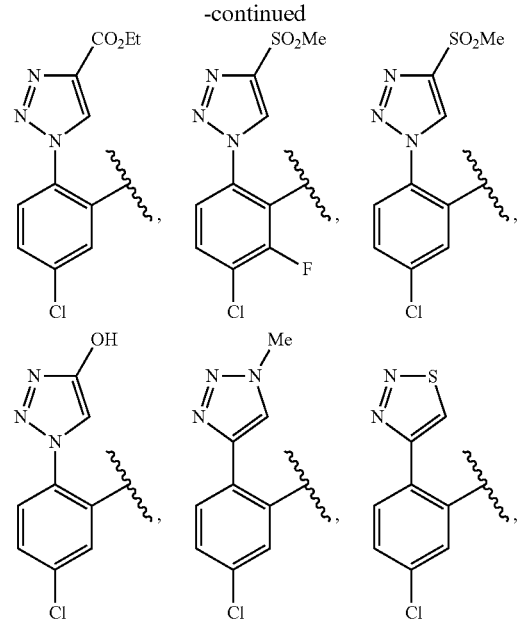
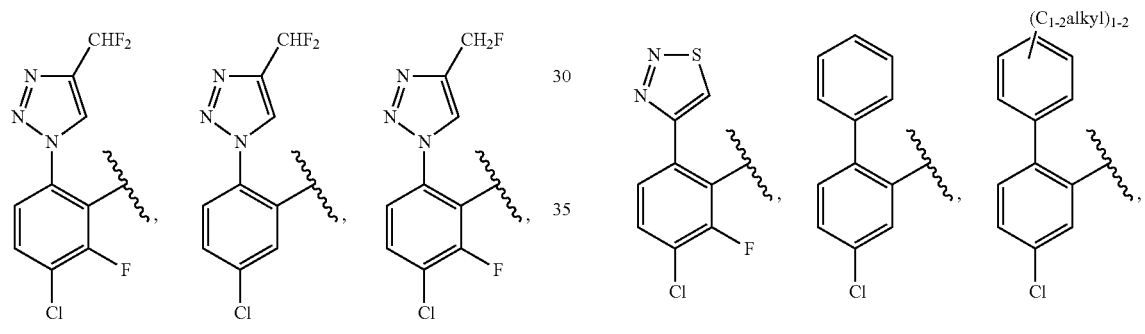
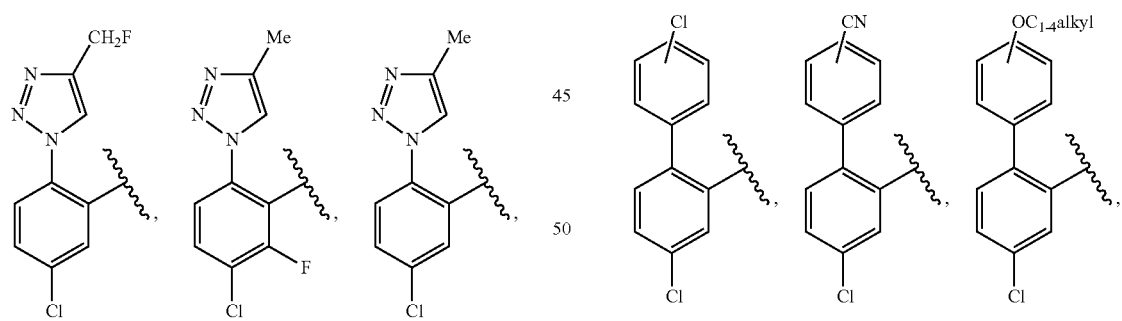
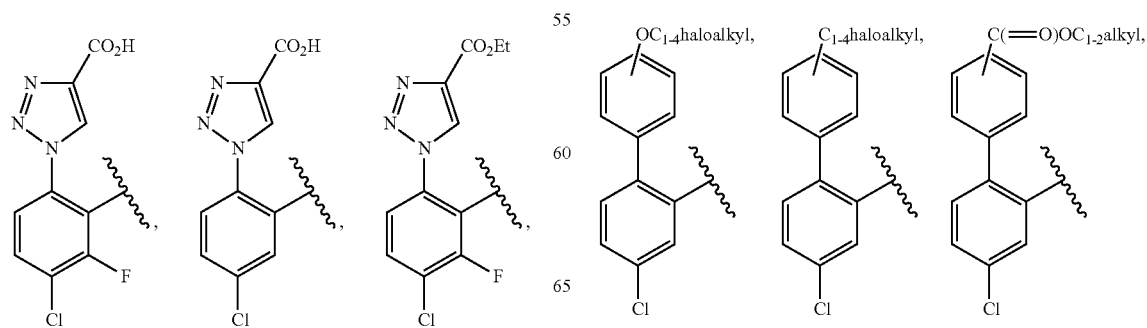

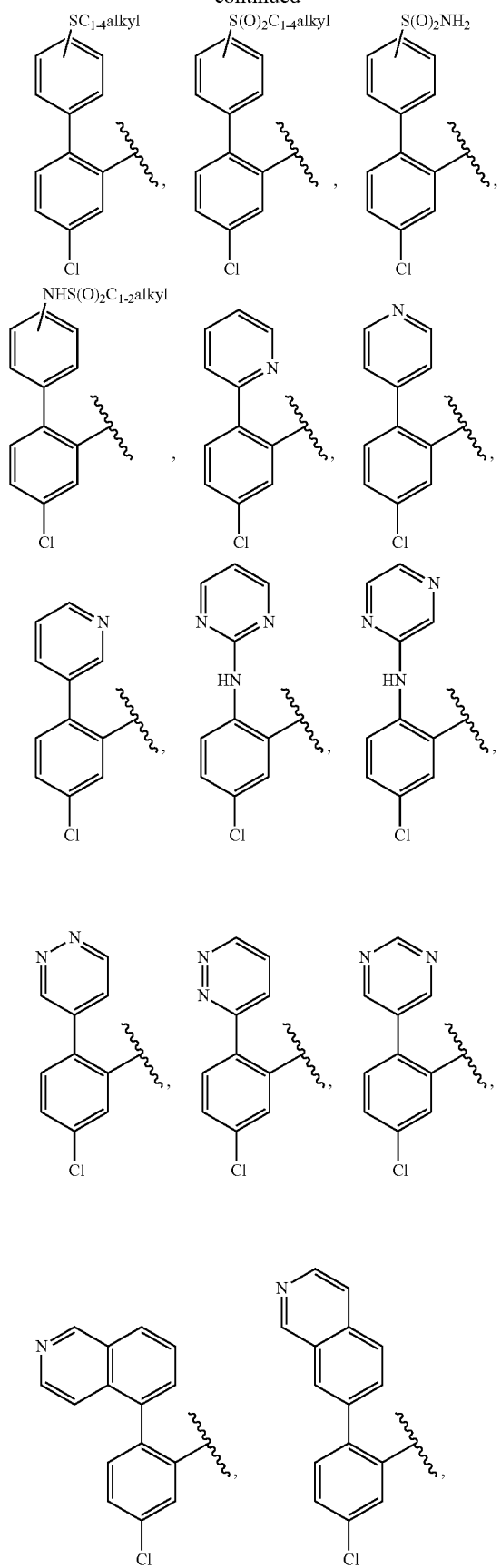
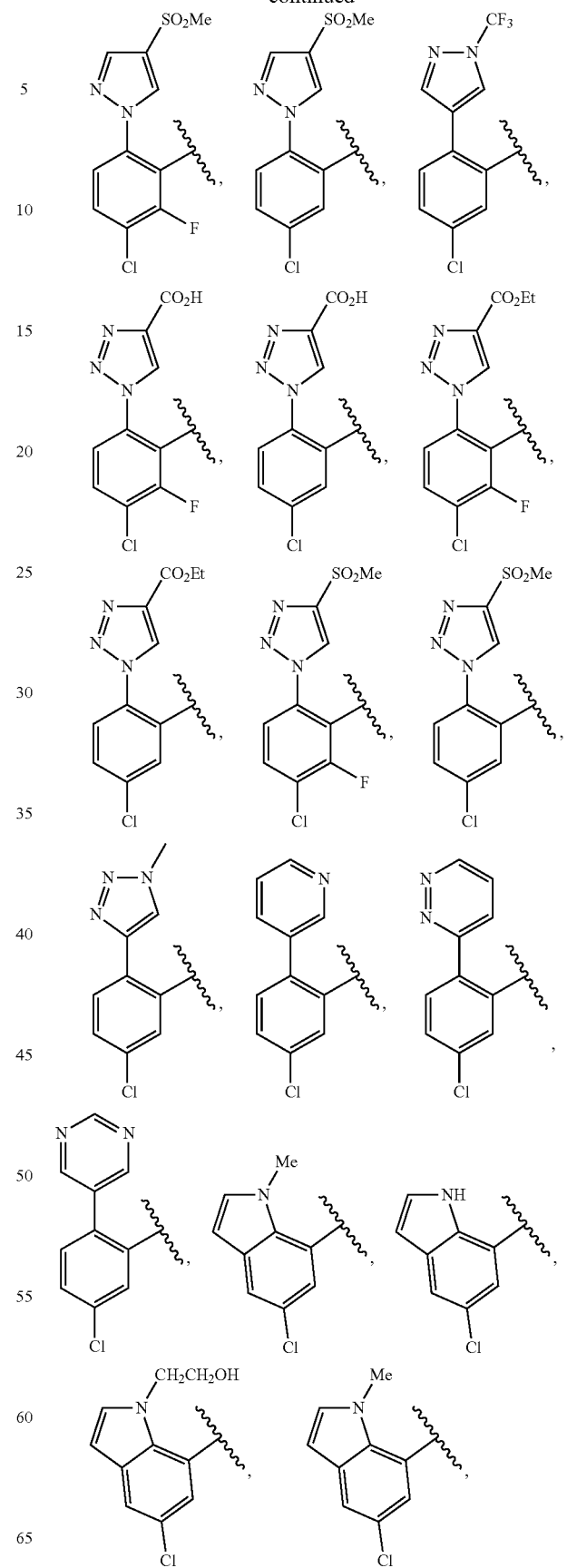

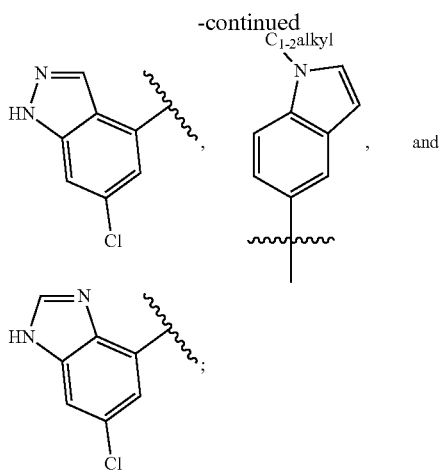

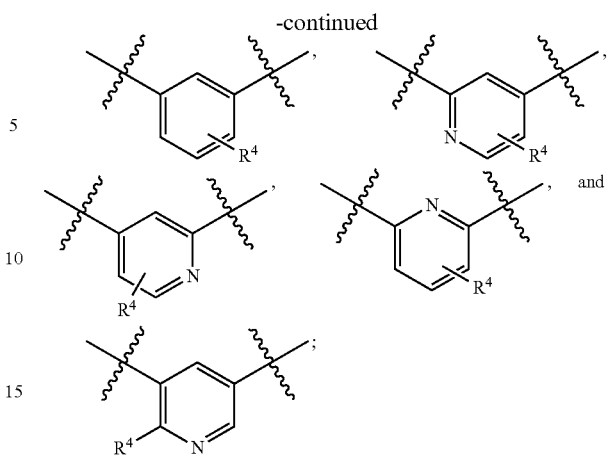

W is independently selected from CHR$^1$, O, NH, and N(C$_{1-4}$ alkyl);

Y is independently selected from —NH—, —NHC(=O)— and —C(=O)NH—;

R$^1$ and R$^2$ are independently selected from H, F, C$_{1-4}$ alkyl, and hydroxyl;

R$^3$ is independently selected from H, F, Cl, CHF$_2$, CF$_3$, OCF$_3$, OCHF$_2$, CH$_3$, CN, —(CH$_2$)$_{0-2}$—OH, OC$_{1-4}$ alkyl, C(=O)C$_{1-4}$ alkyl, —(CH$_2$)$_{0-1}$—C(=O)OH, —C(=O)OC$_{1-4}$ alkyl, —S(=O)$_2$C$_{1-4}$ alkyl, and —NHC(=O)OC$_{1-4}$ alkyl;

R$^4$ is independently selected from H, F, and C$_{1-4}$ alkyl; and

R$^7$ is H.

7. The compound of claim 4 having Formula (IVb):

(IVb)

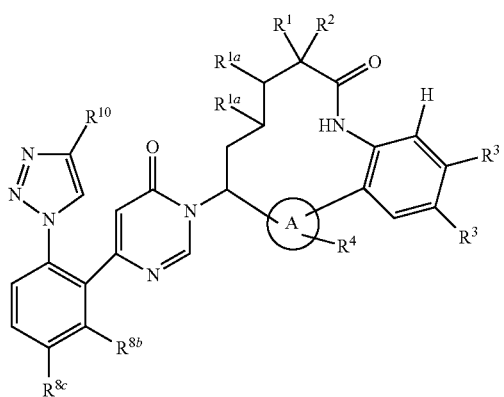

or stereoisomers, tautomers, pharmaceutically acceptable salts, solvates, or prodrugs thereof, wherein:

ring A is independently selected from

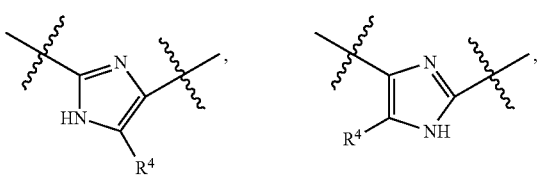

R$^1$ and R$^2$ are independently selected from H, F, C$_{1-4}$ alkyl, alkoxy, and hydroxyl;

R$^{1a}$, at each occurrence, is independently selected from H, F, CH$_3$, and hydroxyl;

R$^3$ is independently selected from H, F, Cl, Br, I, C$_{1-3}$ alkyl (optionally substituted with R$^6$), CN, —(CH$_2$)$_n$—OR$^5$, —(CH$_2$)$_n$—NHR$^5$, —(CH$_2$)$_n$—C(=O)OR$^5$, —NHC(=O)OR$^5$, —NHC(=O)R$^5$, —NHC(=O)NR$^5$R$^5$, —C(=O)NR$^5$R$^5$, and —S(=O)$_2$C$_{1-4}$alkyl;

R$^4$ is independently selected from H, OH, F, OC$_{1-4}$ alkyl, C$_{1-4}$ alkyl, CN, C$_{3-6}$ cycloalkyl, aryl, and 5- to 6-membered heterocyclyl, wherein said cycloalkyl, aryl and heterocyclyl are optionally substituted with R$^6$;

R$^5$ is independently selected from H, C$_{1-4}$ alkyl (optionally substituted with halogen, hydroxyl, alkoxy, carboxy, alkoxycarbonyl), —(CH$_2$)$_n$—C$_{3-10}$ carbocyclyl and —(CH$_2$)$_n$-4- to 10-membered heterocyclyl, wherein said carbocyclyl and heterocyclyl are optionally substituted with R$^6$;

R$^6$ is independently selected from OH, NH$_2$, halogen, C$_{1-6}$ alkyl, C$_{3-6}$ cycloalkyl, —(CH$_2$)$_n$—C(=O)OH, —(CH$_2$)$_n$—C(=O)OC$_{1-4}$ alkyl, —(CH$_2$)$_n$—C(=O)NH$_2$, —(CH$_2$)$_n$-OC$_{1-4}$ alkyl, =O, C$_{3-6}$ cycloalkyl, 4- to 10-membered heterocyclyl, and —O-4- to 10-membered heterocyclyl, wherein said cycloalkyl and heterocyclyl are optionally substituted with R$^{10}$;

R$^{8b}$ is independently selected from H and F;

R$^{8c}$ is independently selected from H, F, Cl, CH$_3$, and OCH$_3$;

R$^{10}$ is independently selected from H, C$_{1-6}$ alkyl (optionally substituted with R$^{11}$), C$_{2-6}$ alkenyl, C$_{2-6}$ alkynyl, aryl, —(CH$_2$)$_n$—C$_{3-6}$ cycloalkyl (optionally substituted with R$^{11}$), —(CH$_2$)$_n$-O-4- to 10-membered heterocyclyl (optionally substituted with R$^{11}$), F, Cl, Br, CN, CONR$^{12}$R$^{12}$, C(=O)OR$^{12}$, —(CH$_2$)$_n$—OR$^{12}$, —(CH$_2$)$_n$—NR$^{12}$R$^{12}$, —S(=O)$_p$C$_{1-6}$ alkyl, NR$^{12}$S(=O)$_p$C$_{1-6}$ alkyl, S(=O)$_p$NR$^{12}$R$^{12}$ and C(=NOH)NH$_2$;

R$^{11}$, at each occurrence, is independently selected from H, halogen, C$_{1-5}$ alkyl, —(CH$_2$)$_n$—OH, C$_{3-6}$ cycloalkyl, and phenyl;

R$^{12}$, at each occurrence, is independently selected from H, C$_{1-5}$ alkyl optionally substituted with R$^{11}$, C$_{3-6}$ cycloalkyl, phenyl, and heterocyclyl, or R$^{12}$ and R$^{12}$ together with the nitrogen atom to which they are both attached form a heterocyclic ring optionally substituted with C$_{1-4}$ alkyl;

n, at each occurrence, is an integer independently selected from 0, 1, and 2, and p, at each occurrence, is an integer independently selected from 0, 1, and 2.

8. A pharmaceutical composition comprising one or more compounds according to claim 1 and a pharmaceutically acceptable carrier or diluent.

9. A method for the treatment and/or prophylaxis of a thromboembolic disorder, comprising: administering to a patient in need thereof a therapeutically effective amount of a compound of claim 1 or a stereoisomer, a tautomer, or a pharmaceutically acceptable salt thereof, wherein the thromboembolic disorder is selected from arterial cardiovascular thromboembolic disorders, venous cardiovascular thromboembolic disorders, and thromboembolic disorders in the chambers of the heart or in the peripheral circulation.

10. A method according to claim 9, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

11. The compound of claim 1 selected from the group consisting of:

(10R,14S )-14-{4-[5-chloro-2-(4-chloro-1H-1,2,3-triazol-1-yl)phenyl]-6-oxo-1,6- dihydropyrimidin-1-yl}-10-methyl-9-oxo-8,16-diazatricyclo[13.3.1.0$^{2,7}$] nonadeca- 1(19),2(7),3,5,15,17-hexaene-4,5-dicarbonitrile;

(10R,14S)-14-{4-[5-chloro-2-(4-chloro-1H-1,2,3-triazol-1-yl)phenyl]-6-oxo-1,6- dihydropyrimidin-1-yl}-10-methyl-8,16-diazatricyclo[13.3.1.0$^{2,7}$]nonadeca-1(19),2,4,6,15,17- hexaen-9-one;

(10R,14S )-14-{4-[3-Chloro-6-(4-chloro-1H-1,2,3-triazol-1-yl)-2-fluorophenyl]-6-oxo-1,6- dihydropyrimidin-1-yl}-5-(hydroxymethyl)-10-methyl-8,16-diazatricyclo[13.3.1.0$^{2,7}$] nonadeca- 1(19),2(7),3,5,15,17-hexaen-9-one;

(10R,14S)-14-{4-[3-chloro-2-fluoro-6-(1H-1,2,3,4-tetrazol-1-yl)phenyl]-6-oxo-1,6- dihydropyrimidin-1-yl}-4-fluoro-10-methyl-8,16-diazatricyclo[13.3.1.0$^{2,7}$] nonadeca- 1(19),2(7),3,5,15,17-hexaen-9-one;

(10R,14S)-14-{4-[5-chloro-2-(1H-1,2,3,4-tetrazol-1-yl)phenyl]-6-oxo-1,6-dihydropyrimidin- 1-yl}-4-fluoro-10-methyl-8,16-diazatricyclo[13.3.1.0$^{2,7}$]nonadeca-1 (19),2(7),3,5,15,17-hexaen-9- one;

(10R,14S)-14-(4-{5-chloro-2-[4-(trifluoromethyl)-1H-1,2,3-triazol-1-yl]phenyl}-6-oxo-1,6- dihydropyrimidin-1-yl)-5-(hydroxymethyl)-10-methyl-8,16-diazatricyclo[13.3.1.0$^{2,7}$]nonadeca- 1(19),2(7),3,5,15,17-hexaen-9-one;

(10R,14S)-14-{4-[5-chloro-2-(4-cyano-1H-1,2,3-triazol-1-yl)phenyl]-6-oxo-1,6- dihydropyrimidin-1-yl}-10-methyl-9-oxo-8,16-diazatricyclo[13.3.1.0$^{2,7}$] nonadeca- 1(19),2(7),3,5,15,17-hexaene-5-carbonitrile;

(10R,14S)-14-{4-[5-chloro-2-(4-chloro-1H-1,2,3-triazol-1-yl)phenyl]-6-oxo-1,6- dihydropyrimidin-1-yl}-4-fluoro-12-hydroxy-10-methyl-8,16-diazatricyclo [13.3.1.0$^{2,7}$]nonadeca- 1(19),2(7),3,5,15,17-hexaen-9-one;

(10R,14S)-14- {4-[3 -chloro-6-(4-chloro-1H-1,2,3 -triazol-1-yl)-2-fluorophenyl]-6-oxo-1,6- dihydropyrimidin-1-yl }-4-fluoro-12-hydroxy-10-methyl-8,16-diazatricyclo[13.3.1.0$^{2,7}$]nonadeca- 1(19),2(7),3,5,15,17-hexaen-9-one;

methyl (10R,14S)-14- {4-[3-chloro-6-(4-chloro-1H-1,2,3-triazol-1-yl)-2-fluorophenyl]-6-oxo- 1,6-dihydropyrimidin-1-yl }-10-methyl-9-oxo-8,16-diazatricyclo [13.3.1.0$^{2,7}$9 nonadeca- 1(19),2(7),3,5,15,17-hexaene-5-carboxylate;

(10R,14S)-14- {4-[3 -chloro-6-(4-chloro-1H-1,2,3-triazol-1-yl)-2-fluorophenyl]-6-oxo-1,6- dihydropyrimidin-1-yl }-10-methyl-9-oxo-8,16-diazatricyclo [13.3.1.0$^{2,7}$]nonadeca- 1(19),2(7),3,5,15,17-hexaene-5-carbonitrile;

(10R,14S)-14-(4-{5-chloro-2[4-(trifluoromethyl)-1H-1,2,3-triazol-1-yl]phenyl}-6-oxo-1,6- dihydropyrimidin-1-yl)-10-methyl-9-oxo-8,16-diazatricyclo [13.3.1.0$^{2,7}$] nonadeca- 1(19),2(7),3,5,15,17-hexaene-5-carbonitrile;

(10R,14S)-14-(4-{5-chloro-2-[4-(difluoromethyl)-1H-1,2,3-triazol-1-yl]phenyl }-6-oxo-1,6- dihydropyrimidin-1-yl)-10-methyl-9-oxo-8,16-diazatricyclo [13.3.1.0$^{2,7}$] nonadeca- 1(19),2(7),3,5,15,17-hexaene-5-carbonitrile;

methyl N-[(10R,14S)-14-[4-(3-chloro-2-fluorophenyl)-6-oxo-1,6-dihydropyrimidin-1-yl]-10- methyl-9-oxo-8,16-diazatricyclo[13.3.1.0$^{2,7}$]nonadeca-1(18),2,4,6,15 (19),16-hexaen-5-yl]carbamate;

methyl N-[(10R,14S)-14-[4-(3-chloro-2,6-difluorophenyl)-6-oxo-1,6-dihydropyrimidin-1-yl]- 10-methyl-9-oxo-8,16-diazatricyclo[13.3.1.0$^{2,7}$]nonadeca-1(18),2,4, 6,15(19),16-hexaen-5- yl]carbamate;

methyl N-[(10R,14S)-14[4-(3-chloro-2-fluorophenyl)-6-oxo-1,6-dihydropyrimidin-1-yl]- 10,17-dimethyl-9-oxo-8,16,18-triazatricyclo[13.2.1.0$^{2,7}$]octadeca-1(17),2,4,6,15(18)- pentaen-5- yl]carbamate;

methyl N-[(10R,14S)-14[4-(3-chloro-2,6-difluorophenyl)-6-oxo-1,6-dihydropyrimidin-1-yl]- 10,17-dimethyl-9-oxo-8,16,18-triazatricyclo[13.2.1.0$^{2,7}$]octadeca-1(17),2,4,6,15(18)- pentaen-5- yl]carbamate;

methyl N-[(10R,14S)-14-[4-(5-chloro-2-fluorophenyl)-6-oxo-1,6-dihydropyrimidin-1-yl]-10- methyl-9-oxo-8,16-diazatricyclo[13.3.1.0$^{2,7}$]nonadeca-1(19),2(7),3,5, 15,17-hexaen-5-yl]carbamate;

(10R,14S)-14-[4-(5-chloro-2-fluorophenyl)-6-oxo-1,6-dihydropyrimidin-1-yl]-4-fluoro-10- methyl-8,16-diazatricyclo[13.3.1.0$^{2,7}$]nonadeca-1(19),2(7),3,5,15,17- hexaen-9-one;

(10R,14S)-14-{4-[5-chloro-2-(1H-1,2,3-triazol-1-yl)phenyl]-6-oxo-1,6-dihydropyrimidin-1- yl}4-fluoro-10-methyl-8,16-diazatricyclo[13.3.1.0$^{2,7}$]nonadeca-1(19), 2(7),3,5,15,17-hexaen-9-one;

(10R,14S)-14-{4-[3-chloro-2-fluoro-6-(1H-1,2,3-triazol-1-yl)phenyl]-6-oxo-1,6- dihydropyrimidin-1-yl}-4-fluoro-10-methyl-8,16-diazatricyclo[13.3.1.0$^{2,7}$]nonadeca- 1(19),2(7),3,5,15,17-hexaen-9-one;

(10R,14S)-14-[4-(2-bromo-5-chlorophenyl)-6-oxo-1,6-dihydropyrimidin-1-yl]-4-fluoro-10- methyl-8,16-diazatricyclo[13.3.1.0$^2$]nonadeca-1(19),2(7),3,5,15,17- hexaen-9-one;

(10R,14S)-14-{4-[3-chloro-2-fluoro-6-(1H-1,2,3-triazol-1-yl)phenyl]-6-oxo-1,6- dihydropyrimidin-1-yl}-3,4-difluoro-10-methyl-8,16-diazatricyclo[13.3.1.0$^{2,7}$] nonadeca- 1(19),2(7),3,5,15,17-hexaen-9-one;

(10R,12R,14S)-14-{4-[3-chloro-6-(4-chloro-1H-1,2,3-triazol-1-yl)-2-fluorophenyl]-6-oxo- 1,6-dihydropyrimidin-1-yl}-4,17-difluoro-12-hydroxy-10-methyl-8-zatricyclo[13.3.1.0$^{2,7}$]nonadeca- 1(19),2(7),3,5,15,17-hexaen-9-one;

(10R,12R,14S)-14-{4-[5-chloro-2-(4-chloro-1H-1,2,3-triazol-1-yl)phenyl]-6-oxo-1,6- dihydropyrimidin-1-yl}-4,17-difluoro-12-hydroxy-10-methyl-8-azatricyclo[13.3.1.0$^{2,7}$]nonadeca- 1(19),2(7),3,5,15,17-hexaen-9-one;

(10R,14S)-14-{4-[5chloro-2-(4-chloro-1H-1,2,3-triazol-1-yl)phenyl]-6-oxo-1,6- dihydropyrimidin-1-yl}-10-methyl-8,16-diazatricyclo[13.3.1.0$^{2,7}$]nonadeca-1(19),2,4,6,15,17- hexaen-9-one;

(10R,14S)-14-{4-[3-chloro-6-(4-chloro-1H-1,2,3-triazol-1-yl)-2-fluorophenyl]-6-oxo-1,6- dihydropyrimidin-1-yl}-10-methyl-8,16-diazatricyclo [13.31 0$^{2,7}$]nonadeca-1(19),2,4,6,15,17- hexaen-9-one;

(10S,14S)-14-{4-[5-chloro-2-(4-chloro-1H-1,2,3-triazol-1-yl)phenyl]-6-oxo-1,6- dihydropyrimidin-1-yl}-4-fluoro-10,11-dimethyl-8,11,16-triazatricyclo [13.31 0$^{2,7}$]nonadeca- 1(19),2(7),3,5,15,17-hexaen-9-one;

(10S,14S)-14-{4-[3-chloro-6-(4-chloro-1H-1,2,3-triazol-1-yl)-2-fluorophenyl]-6-oxo-1,6- dihydropyrimidin-1-yl}-4-fluoro-10,11-dimethyl-8,11,16-triazatricyclo[13.3.1.0$^{2,7}$]nonadeca- 1(19),2(7),3,5,15,17-hexaen-9-one;

6-[3-chloro-6-(4-chloro-1H-1,2,3-triazol-1-yl)-2-fluorophenyl]-3-[(10R,14S)-4-fluoro-10- methyl-8,16-diazatricyclo[13.3.1.0$^{2,7}$]nonadeca-1(19),2(7),3,5,15,17-hexaen-14-yl]-3,4- dihydropyrimidin-4-one;

(10R,14S)-14-{4-[3- chloro-6-(4-chloro-1H-1,2,3-triazol-1-yl)-2-fluorophenyl]-6-oxo-1,6- dihydropyrimidin-1-yl}-10-methyl-9-oxo-8,16-diazatricyclo[13.3.1.0$^{2,7}$]nonadeca- 1(19),2(7),3,5,15,17-hexaene-5-carbonitrile;

(10S,17S)-17-{4-[3-chloro-6-(4-chloro-1H-1,2,3 -triazol-1-yl)-2-fluorophenyl]-6-oxo-1,6- dihydropyrimidin-1-yl }-4-fluoro-8,14,19-triazatetracyclo [16.3.1.0$^{2,7}$.0$^{10,14}$]docosa- 1(22),2(7),3,5,18,20-hexaen-9-one;

(10R,14S)-14-(4-{2,3-difluoro-6-[4-(trifluoromethyl)-1H-1,2,3-triazol-1-yl]phenyl}-6-oxo- 1,6-dihydropyrimidin-1-yl)-4-fluoro-10-methyl-8,18-diazatricyclo[13.3.1.0$^{2,7}$]nonadeca- 1(19),2(7),3,5,15,17-hexaen-9-one;

(10R,14S)-14-{4-[5-chloro-2-(4-chloro-1H-1,2,3-triazol-1-yl)phenyl]-6-oxo-1,6- dihydropyrimidin-1-yl }-10-methyl-9-oxo-8,16-diazatricyclo[13.3.1.0$^{2,7}$]nonadeca- 1(19),2(7),3,5,15,17-hexaene-5-carboxamide, hydrochloride;

(10R,14S)-14-{4-[5-chloro-2-(1-methyl-1H-pyrazol-4-yl)phenyl]-6-oxo-1,6- dihydropyrimidin-1-yl}-4-fluoro-10-methyl-8,16-diazatricyclo[13.3.1.0$^{2,7}$]nonadeca- 1(19),2(7),3,5,15,17-hexaen-9-one;

(10R,14S)-14-{4-[5-chloro-2-(4-chloro-1H-1,2,3-triazol-1-yl)phenyl]-6-oxo-1,6- dihydropyrimidin-1-yl }-4-methanesulfonyl-10-methyl-8,16-diazatricyclo [13.3.1.0$^{2,7}$]nonadeca- 1(19),2(7),3,5,15,17-hexaen-9-one;

methyl 4-chloro-2-{1-[(10R,14S)-4-fluoro-10-methyl-9-oxo-8,16- diazatricyclo[13.3.1.0$^{2,7}$]nonadeca-1(19),2(7),3,5,15,17-hexaen-14-yl]-6-oxo-1,6-dihydropyrimidin- 4-yl}benzoate;

(10R,14S)-14-(4-{5-chloro-2-[4-(trifluoromethyl)-1H-1,2,3-triazol-1-yl]phenyl}-6-oxo-1,6- dihydropyrimidin-1-yl)-10-methyl-8,16-diazatricyclo [13.3.1.0$^{2,7}$]nonadeca-1(19),2(7),3,5,15,17- hexaen-9-one;

1-(4-chloro-2-{1-[(10R,14S)-5-(difluoromethyl)-10-methyl-9-oxo-8,16- diazatricyclo[13.3.1.0$^{2,7}$]nonadeca-1(19),2(7),3,5,15,17-hexaen-14-yl]-6-oxo-1,6-dihydropyrimidin- 4-yl}phenyl)-1H-1,2,3-triazole-4-carbonitrile;

(10R,14S)-14-[4-(5-chloro-1-methyl-1H-indazol-7-yl)-6-oxo-1,6-dihydropyrimidin-1-yl]-4-fluoro- 10-methyl-8,16-diazatricyclo[13.3.1.0$^{2,7}$]nonadeca-1(19),2(7),3, 5,15,17-hexaen-9-one;

(10R,14S)-14-(4-{5-chloro-2[4-(trifluoromethyl)-1H-1,2,3-triazol-1-yl]phenyl}-6-oxo-1,6- dihydropyrimidin-1-yl)-3,10-dimethyl-8,16-diazatricyclo [13.3.1.0$^{2,7}$]nonadeca-1(19),2(7),3,5,15,17- hexaen-9-one;

(10R,14S)-14-{4[5-chloro-2-(4-chloro-1H-1,2,3-triazol-1-yl)phenyl]-6-oxo-1,6- dihydropyrimidin-1-yl }-3,10-dimethyl-8,16-diazatricyclo[13.3.1.0$^{2,7}$]nonadeca-1(19),2(7),3,5,15,17- hexaen-9-one;

(10R,14S)-14-{4-[5-chloro-2-(4-chloro-1H-1,2,3-triazol-1-yl)phenyl]-6-oxo-1,6- dihydropyrimidin-1-yl}-5-(difluoromethyl)-10-methyl-8,16-diazatricyclo [13.3.1.0$^{2,7}$]nonadeca- 1(19),2(7),3,5,15,17-hexaen-9-one;

(10R,14S)-5-chloro-14-{4-[5-chloro-2-(4-chloro-1H-1,2,3-triazol-1-yl)phenyl]-6-oxo-1,6- dihydropyrimidin-1-yl}-10-methyl-8,16-diazatricyclo [13.3.1.0$^{2,7}$]nonadeca-1(19),2(7),3,5,15,17- hexaen-9-one;

(10R,14S)-14-(4-{5-chloro-2-[4-(trifluoromethyl)-1H-1,2,3-triazol-1-yl]phenyl}-6-oxo-1,6- dihydropyrimidin-1-yl)-10-methyl-9-oxo-8,16-diazatricyclo [13.3.1.0$^{2,7}$]nonadeca- 1(19),2(7),3,5,15,17-hexaene-5-carboxamide;

4-chloro-2-{1-[(10R,14S)-4-fluoro-10-methyl-9-oxo-8,16-diazatricyclo [13.3.1.0$^{2,7}$]nonadeca-1(19),2(7),3,5, 15,17-hexaen-14-yl]-6-oxo-1,6-dihydropyrimidin-4-yl}benzoic acid;

(10R,14S)-14-(4-{5-chloro-2-[4-(trifluoromethyl)-1H-1,2,3-triazol-1-yl]phenyl}-6-oxo-1,6- dihydropyrimidin-1-yl)-5,10-dimethyl-8,16-diazatricyclo [13.3.1.0$^{2,7}$]nonadeca-1(19),2(7),3,5,15,17- hexaen-9-one;

(10R,14S)-14-{4-[5-chloro-2-(4-chloro-1H-1,2,3-triazol-1-yl)phenyl]-6-oxo-1,6- dihydropyrimidin-1-yl}-5,10-dimethyl-8,16-diazatricyclo[13.3.1.0$^{2,7}$]nonadeca-1(19),2(7),3,5,15,17- hexaen-9-one;

methyl N-[(10R,14S)-14-[4-(3-chloro-2-methylphenyl)-6-oxo-1,6-dihydropyrimidin-1-yl]- 10-methyl-9-oxo-8,16-diazatricyclo[13.3.1.0$^{2,7}$]nonadeca-1(19),2(7),3,5, 15,17-hexaen-5- yl]carbamate;

(10R,14S)-10-methyl-14-(4-{5-methyl-2-[4-(trifluoromethyl)-1H-1,2,3-triazol-1-yl]phenyl}- 6-oxo-1,6-dihydropyrimidin-1-yl)-8,16-diazatricyclo [13.3.1.0$^{2,7}$]nonadeca-1(19),2(7),3,5,15,17- hexaen-9-one;

(10R,14S)-10-methyl-14-(4-{5-methyl-2-[54-(trifluoromethyl)-1H-1,2,3-triazol-1-yl]phenyl}- 6-oxo-1,6-dihydropyrimidin-1-yl)-9-oxo-8,16-diazatricyclo [13.3.1.0$^{2,7}$]nonadeca- 1(19),2(7),3,5,15,17-hexaene-5-carbonitrile;

(10R,14S)-14-{4-[3-chloro-2-fluoro-6-(1H-1,2,3-triazol-1-yl)phenyl]-6-oxo-1,6- dihydropyrimidin-1-yl}-10-methyl-9-oxo-8,16-diazatricyclo[13.3.1.0$^{2,7}$] nonadeca- 1(19),2(7),3,5,15,17-hexaene-5-carbonitrile;

(10R,14S)-14-{4-[5-chloro-2-(4-chloro-1H-1,2,3-triazol-1-yl)phenyl]-6-oxo-1,6- dihydropyrimidin-1-yl }-5-methoxy-10-methyl-8,16-diazatricyclo[13.3.1.0$^{2,7}$] nonadeca- 1(19),2(7),3,5,15,17-hexaen-9-one;

(10R,14S)-14-{4-[5-chloro-2-(4-chloro-1H-1,2,3-triazol-1-yl)phenyl]-6-oxo-1,6- dihydropyrimidin-1-yl }-5-hydroxy-10-methyl-8,16-diazatricyclo[13.3.1.0$^{2,7}$]nonadeca- 1(19),2(7),3,5,15,17-hexaen-9-one;

(10R,14S)-14-(4-{5-chloro-2-[4-(trifluoromethyl)-1H-1,2,3-triazol-1-yl]phenyl}-6-oxo-1,6- dihydropyrimidin- 1-yl)-5-(2-hydroxypropan-2-yl)-10-methyl-8,16-diazatricyclo[13.3.1.0²,⁷]nonadeca-1(19),2(7),3,5,15,17-hexaen-9-one;

(10R,14S)-14-{4[5-chloro-2-(5-fluoropyridin-3-yl)phenyl]-6-oxo-1,6-dihydropyrimidin-1- yl}-10-methyl-9-oxo-8,16-diazatricyclo[13.3.1.0²,⁷]nonadeca-1(19),2(7),3,5,15,17-hexaene-5- carbonitrile;

(10R,14S)-14-{4-[5-chloro-2-(4-chloro-1H-1,2,3-triazol-1-yl)phenyl]-6-oxo-1,6- dihydropyrimidin-1-yl}-5-(1,1-difluoro-2-hydroxyethyl)-10-methyl-8,16- diazatricyclo[13.3.1.0²,⁷]nonadeca-1(19),2(7),3,5,15,17-hexaen-9-one;

(10R,14S)-14-{4-[5-chloro-2-(4-chloro-1H-1,2,3-triazol-1-yl)phenyl]-6-oxo-1,6- dihydropyrimidin-1-yl -10-methyl-9-oxo-8,16-diazatricyclo[13.3.1.0²,⁷]nonadeca- 1(19),2(7),3,5,15,17-hexaene-5-carbonitrile;

2-[(10R,14S)-14-{4-[5-chloro-2-(4-chloro-1H-1,2,3-triazol-1-yl)phenyl]-6-oxo-1,6- dihydropyrimidin-1-yl }-10-methyl-9-oxo-8,16-diazatricyclo[13.3.1.0²,⁷]nonadeca- 1(19),2(7),3,5,15,17-hexaen-5-yl]-2,2-difluoroacetamide;

(10R,14S)-14-{4-[5-chloro-2-(4-chloro-1H-1,2,3-triazol-1-yl)phenyl]-6-oxo-1,6- dihydropyrimidin-1-yl}-5-ethynyl-10-methyl-8,16-diazatricyclo[13.3.1.0²,⁷]nonadeca- 1(19),2(7),3,5,15,17-hexaen-9-one;

(10R,14S)-14-(4-{5-chloro-2-[4(trifluoromethyl)-1H-1,2,3-triazol-1-yl]phenyl}-6-oxo-1,6- dihydropyrimidin-1-yl)-10-methyl-9-oxo-8,17-diazatricyclo [13.3.1.0²,⁷]nonadeca- 1(19),2(7),3,5,15,17-hexaene-5-carbonitrile;

(10R,14S)-14-{4-[5-chloro-2-(4-chloro-1H-1,2,3-triazol-1-yl)phenyl]-6-oxo-1,6- dihydropyrimidin-1-yl}-5-(difluoromethoxy)-10-methyl-8,16-diazatricyclo [13.3.1.0²,⁷]nonadeca- 1(19),2(7),3,5,15,17-hexaen-9-one;

(10R,14S)-14-(4-{5-chloro-2-[4-(difluoromethyl)-1H-1,2,3-triazol-1-yl]phenyl}-6-oxo-1,6- dihydropyrimidin-1-yl)-10-methyl-8,16-diazatricyclo[13.3.1.0²,⁷]nonadeca-1(19),2(7),3,5,15,17- hexaen-9-one;

(10R,14S)-14-(4-{3-chloro-6-[4-(difluoromethyl)-1H-1,2,3-triazol-1-yl]-2-fluorophenyl}-6- oxo-1,6-dihydropyrimidin-1-yl)-10-methyl-8,16-diazatricyclo [13.3.1.0²,⁷]nonadeca- 1(19),2(7),3,5,15,17-hexaen-9-one;

1-(4-chloro-2-{1-[(10R,14S)-10-methyl-9-oxo-8,16-diazatricyclo [13.3.1.0²,⁷]nonadeca- 1(19),2(7),3,5,15,17-hexaen-14-yl]-6-oxo-1,6-dihydropyrimidin-4-yl}phenyl)-1H-1,2,3-triazole-4- carbonitrile;

(10R,14S)-14-{5-chloro-4-[3-chloro-2-fluoro-6-(1H-1,2,3-triazol-1-yl)phenyl]-6-oxo-1,6-dihydropyrimidin-1-yl }-10-methyl-9-oxo-8,16-diazatricyclo [13.3.1.0²,⁷] nonadeca- 1(19),2(7),3,5,15,17-hexaene-5-carbonitrile;

(10R,14S)-14-{4-[3-chloro-6-(4-chloro-1H-1,2,3 -triazol-1-yl)-2-fluorophenyl]-6-oxo-1,6- dihydropyrimidin-1-yl}-10-methyl-9-oxo-8,16-diazatricyclo [13.3.1.0²,⁷]nonadeca- 1(19),2(7),3,5,15,17-hexaene-4-carbonitrile;

2-{[(10R,14S)-14-{4-[5-chloro-2-(4-chloro-1H-1,2,3-triazol-1-yl)phenyl]-6-oxo-1,6- dihydropyrimidin-1-yl}-10-methyl-9-oxo-8,16-diazatricyclo[13.3.1.0²,⁷]nonadeca- 1(19),2(7),3,5,15,17-hexaen-5-yl]oxy}acetic acid;

N-{[(10R,14S)-14-{4-[5-chloro-2-(4-chloro-1H-1,2,3-triazol-1-yl)phenyl]-6-oxo-1,6- dihydropyrimidin-1-yl} -10-methyl-9-oxo-8,17-diazatricyclo[13.3.1.0²,⁷] nonadeca- 1(19),2(7),3,5,15,17-hexaen-5-yl]methyl}-2,2,2-trifluoroacetamide;

(10R,14S)-5-(aminomethyl)-14-{4-[5-chloro-2-(4-chloro-1H-1,2,3-triazol-1-yl)phenyl]-6- oxo-1,6-dihydropyrimidin-1-yl }-10-methyl-8,17-diazatricyclo [13.3.1.0²,⁷]nonadeca- 1(19),2(7),3,5,15,17-hexaen-9-one;

(10R,14S)-14-(4-{5-chloro-2-[4(trifluoromethyl)-1H-1,2,3-triazol-1-yl]phenyl}-6-oxo-1,6- dihydropyrimidin-1-yl)-10-methyl-8,17-diazatricyclo [13.3.1.0²,⁷]nonadeca-1(19),2(7),3,5,15,17- hexaen-9-one;

(10R,14S)-14-(4-{5-chloro-2-[4-(trifluoromethyl)-1H-1,2,3-triazol-1-yl]phenyl}-6-oxo-1,6- dihydropyrimidin-1-yl)-4-fluoro-10-methyl-8,17-diazatricyclo[13.3.1.0²,⁷]nonadeca- 1(19),2(7),3,5,15,17-hexaen-9-one;

(10R,14S)-3-chloro-14-{4-[5-chloro-2-(4-chloro-1H-1,2,3-triazol-1-yl)phenyl]-6-oxo-1,6- dihydropyrimidin-1-yl}-10-methyl-8,16-diazatricyclo [13.3.1.0²,⁷]nonadeca-1(19),2(7),3,5,15,17- hexaen-9-one;

(10R,14S)-3-chloro-14-(4-{5-chloro-2-[4-(trifluoromethyl)-1H-1,2,3-triazol-1-yl]phenyl}-6- oxo-1,6-dihydropyrimidin-1-yl)-10-methyl-8,16-diazatricyclo [13.3.1.0²,⁷]nonadeca- 1(19),2(7),3,5,15,17-hexaen-9-one;

methyl N-[(10R,14S)-14-[4-(3-chloro-2,6-difluorophenyl)-6-oxo-1,6-dihydropyrimidin-1- yl]-10-methyl-9-oxo-8,18-diazatricyclo[13.3.1.0²,⁷]nonadeca-1(19),2(7),3,5,15,17-hexaen-5- yl]carbamate;

(10R,14S)-4-fluoro-14-(4-{5-methoxy-2-[4-(trifluoromethyl)-1H-1,2,3-triazol-1-yl]phenyl}- 6-oxo-1,6-dihydropyrimidin-1-yl)-10-methyl-8,17-diazatricyclo [13.3.1.0²,⁷]nonadeca- 1(19),2(7),3,5,15,17-hexaen-9-one;

(10R,14S)-14-{4-[5-chloro-2-(4-chloro-1H-1,2,3-triazol-1-yl)phenyl]-6-oxo-1,6- dihydropyrimidin-1-yl}-4-fluoro-10-methyl-8,18-diazatricyclo[13.3.1.0²,⁷]nonadeca- 1(19),2(7),3,5,15,17-hexaen-9-one;

Preparation of (10R,14S)-14-(4-{5-chloro-2-[4-(trifluoromethyl)-1H-1,2,3-triazol-1- yl]phenyl}-6-oxo-1,6-dihydropyrimidin-1-yl)-4-fluoro-10-methyl-8,18- diazatricyclo[13.3.1.0²,⁷]nonadeca-1(19),2(7),3,5,15,17-hexaen-9-one;

methyl N-[(10R,14S)-14-{4-[5-(difluoromethoxy)-2[4-(trifluoromethyl)-1H-1,2,3-triazol-1- yl]phenyl}-6-oxo-1,6-dihydropyrimidin-1-yl}-10-methyl-9-oxo-8,16- diazatricyclo[13.3.1.0²,⁷]nonadeca-1(19),2(7),3,5,15,17-hexaen-5-yl]carbamate;

(10R,14S)-14-(4-{5-chloro-2-[4-(trifluoromethyl)-1H-1,2,3-triazol-1-yl]phenyl}-6-oxo-1,6- dihydropyrimidin-1-yl)-3-fluoro-10-methyl-8,16-diazatricyclo [13.3.1.0²,⁷]nonadeca- 1(19),2(7),3,5,15,17-hexaen-9-one;

(10R,14S)-14-[4-{5-chloro-2-(4-chloro-1H-1,2,3-triazol-1-yl)phenyl]-6-oxo-1,6- dihydropyrimidin-1-yl}-10-methyl-9-oxo-8,18-diazatricyclo [13.3.1.0²,⁷]nonadeca- 1(19),2(7),3,5,15,17-hexaene-5-carbonitrile;

(10R,14S)-14-(4-{5-chloro-2-[4-(trifluoromethyl)-1H-1,2,3-triazol-1-yl]phenyl}-6-oxo-1,6- dihydropyrimidin-1-yl)-10-methyl-9-oxo-8,18-diazatricyclo [13.3.1.0²,⁷]nonadeca- 1(19),2(7),3,5,15,17-hexaene-5-carbonitrile;

(10R,14S)-14-{4-[5-chloro-2-(4-chloro-1H-1,2,3-triazol-1-yl)phenyl]-6-oxo-1,6- dihydropyrimidin-1-yl}-10-methyl-9-oxo-8,16-diazatricyclo[13.3.1.0²,⁷]nonadeca- 1(19),2(7),3,5,15,17-hexaene-4-carbonitrile;

methyl N-[(10R,14S)-14-(4-{5-methoxy-2-[4-(trifluoromethyl)-1H-1,2,3-triazol-1- yl]phenyl -6-oxo-1,6-dihydropyrimidin-1-yl)-10-methyl-9-oxo-8,16- diazatricyclo[13.3.1.0²,⁷ ]nonadeca-1(19),2(7),3,5,15,17-hexaen-5-yl]carbamate;

(10R,14S)-14-(4-{5-chloro-2-[4-(trifluoromethyl)-1H-1, 2,3-triazol-1-yl]phenyl }-6-oxo-1,6- dihydropyrimidin-1-yl)-4-fluoro-10-methyl-8,16,18-triazatricyclo [13.3.1.0²,⁷]nonadeca- 1(19),2(7),3,5,15,17-hexaen-9-one;

(10R,14S)-14-{4-[5-chloro-2-(1,2,3-thiadiazol-4-yl)phenyl]-6-oxo-1,6-dihydropyrimidin-1- yl}-4-fluoro-10-methyl-8,16-diazatricyclo[13.3.1.0²,⁷ ]nonadeca-1(19),2(7),3,5,15,17-hexaen-9-one;

(10R,14R)-14-(4-{5-chloro-2-[4-(trifluoromethyl)-1H-1, 2,3-triazol-1-yl]phenyl }-6-oxo-1,6- dihydropyrimidin-1-yl)-4-fluoro-10-methyl-8,16,18-triazatricyclo [13.3.1.0²,⁷]nonadeca- 1(19),2(7),3,5,15,17-hexaen-9-one;

(10R,14S)-14-[4-(5-chloro-1-methyl-1H-indazol-7-yl)-6-oxo-1,6-dihydropyrimidin-1-yl]-10- methyl-8,16-diazatricyclo[13.3.1.0²,⁷]nonadeca-1(19),2(7),3,5,15,17-hexaen-9-one;

N-[(10R,14S)-14-[4-(5-chloro-1-methyl-1H-indazol-7-yl)-6-oxo-1,6-dihydropyrimidin-1-yl]- 10-methyl-9-oxo-8,16-diazatricyclo[13.3.1.0²,⁷]nonadeca-1(19),2(7),3,5,15,17-hexaen-5- yl]carbamate;

(10S,14S)-14-{4[5-chloro-2-(4-chloro-1H-1,2,3-triazol-1-yl)phenyl]-6-oxo-1,6- dihydropyrimidin-1-yl}-4,11-difluoro-10-methyl-8,16-diazatricyclo[13.3.1.0²,⁷ ]nonadeca- 1(19),2(7),3,5,15,17-hexaen-9-one;

(10R,14S)-14-{4-[5-chloro-2-(4-chloro-1H-1,2,3-triazol-1-yl)phenyl]-6-oxo-1,6- dihydropyrimidin-1-yl }-N,10-dimethyl-9-oxo-8,16-diazatricyclo[13.3.1.0²,⁷ ]nonadeca- 1(19),2(7),3,5,15,17-hexaene-4-carboxamide;

(10R,14S)-14-[4-(5-chloro-1-methyl-1H-indazol-7-yl)-6-oxo-1,6-dihydropyrimidin-1-yl]-10- methyl-9-oxo-8,16-diazatricyclo[13.3.1.0²,⁷]nonadeca-1(19),2(7),3,5, 15,17-hexaene-5-carbonitrile;

(10R,14S)-14-(4-{5-chloro-2-[1-(difluoromethyl)-1H-pyrazol-4-yl]phenyl}-6-oxo-1,6- dihydropyrimidin-1-yl)-4-fluoro-10-methyl-8,16-diazatricyclo [13.3.1.0²,⁷] nonadeca- 1(19),2(7),3,5,15,17-hexaen-9-one;

(15S)-15-(4-{5-chloro-2[4-(difluoromethyl)-1H-1,2,3-triazol-1-yl]phenyl -6-oxo-1,6- dihydropyrimidin-1-yl)-4-fluoro-11-methyl-8,17-diazatricyclo [14.3.1.0²,⁷] icosa- 1(20),2(7),3,5,16,18-hexaen-9-one;

(10R,14S)-14-{4-[5-chloro-2-(4-chloro-1H-1,2,3-triazol-1-yl)phenyl]-6-oxo-1,6- dihydropyrimidin-1-yl}-10-methyl-9-oxo-8,16-diazatricyclo[13.3.1.0²,⁷]nonadeca- 1(19),2(7),3,5,15,17-hexaene-4-carboxylate;

(10R,14S)-14-{4[5-chloro-2-(4-chloro-1H-1,2,3-triazol-1-yl)phenyl]-6-oxo-1,6- dihydropyrimidin-1-yl}-10-methyl-9-oxo-8,16-diazatricyclo[13.3.1.0²,⁷]non-adeca- 1(19),2(7),3,5,15,17-hexaene-4-carboxylic acid;

(10R,14S)-14-[4-(3-chloro-2,6-difluorophenyl)-6-oxo-1, 6-dihydropyrimidin-1-yl]-4-fluoro- 10-methyl-8,16-diazatricyclo[13.3.1.0²,⁷]nonadeca-1(19),2(7),3,5, 15,17-hexaen-9-one;

(14S)-14-{4-[5-chloro-2-(4-chloro-1H-1,2,3-triazol-1-yl) phenyl]-6-oxo-1,6- dihydropyrimidin-1-yl}-4-fluoro-10-methyl-11-oxa-8,16-diazatricyclo[13.3.1.0²,⁷]nonadeca- 1(19),2(7),3,5,15,17-hexaen-9-one;

methyl N-[(14S)-14-{4-[5-chloro-2-(4-chloro-1H- 1,2,3-triazol-1-yl)phenyl]-6-oxo-1,6- dihydropyrimidin-1-yl}-16,18-diazatricyclo[13.2.1.0²,⁷]octadeca-1(17),2,4, 6,15(18)-pentaen-5- yl]carbamate;

methyl N-[(14S)-14-{4[5-chloro-2-(1H-1,2,3,4-tetrazol-1-yl)phenyl]-6-oxo-1,6- dihydropyrimidin-1-yl}-16, 18-diazatricyclo[13.2.1.0²,⁷octadeca-1(17),2,4,6,15 (18)-pentaen-5- yl]carbamate;

(15S)-15-(4-{5-chloro-2-[4-(difluoromethyl)-1H-1,2,3-triazol-1-yl]phenyl}-6-oxo-1,6- dihydropyrimidin-1-yl)-4-fluoro-11-methyl-8,17-diazatricyclo [14.3.1.0²,⁷] icosa- 1(20),2(7),3,5,16,18-hexaen-9-one;

(10R,14S)-14-(4-{3-chloro-6-[4-(difluoromethyl)-1H-1, 2,3-triazol-1-yl]-2-fluorophenyl}-6- oxo-1,6-dihydropyrimidin-1-yl)-4-fluoro-10-methyl-8,16-diazatricyclo [13.3.1.0²,⁷]nonadeca- 1(19),2(7),3,5,15,17-hexaen-9-one;

(10R,14S)-14-(4-{5-chloro-2[4-(trifluoromethyl)-1H-1,2, 3-triazol-1-yl]phenyl}-6-oxo-1,6- dihydropyrimidin-1-yl)-4-fluoro-10-methyl-8,16-diazatricyclo [13.3.1.0²,⁷] nonadeca- 1(19),2(7),3,5,15,17-hexaen-9-one;

(10R,14S)-14-{4-[3-chloro-6-(4-ethoxy-1H-1,2,3-triazol-1-yl)-2-fluorophenyl]-6-oxo-1,6- dihydropyrimidin-1-yl}-4-fluoro-10-methyl-8,16-diazatricyclo [13.3.1.0²,⁷] nonadeca- 1(19),2(7),3,5,15,17-hexaen-9-one;

(10R,14S)-14-{4[3-chloro-2-fluoro-6-(4-methyl-1H-1,2, 3-triazol-1-yl)phenyl]-6-oxo-1,6- dihydropyrimidin-1-yl}-4-fluoro-10-methyl-8,16-diazatricyclo [13.3.1.0²,⁷] nonadeca- 1(19),2(7),3,5,15,17-hexaen-9-one;

(10R,14S)-14-(4-{5-chloro-2-[4-(difluoromethyl)-1H-1, 2,3-triazol-1-yl]phenyl}-6-oxo-1,6- dihydropyrimidin-1-yl)-4-fluoro-10-methyl-8,16-diazatricyclo [13.3.1.0²,⁷]nonadeca- 1(19),2(7),3,5,15,17-hexaen-9-one;

(10R,14S)-14-{4[5-chloro-2-(4-hydroxy-1H-1,2,3-triazol-1-yl)phenyl]-6-oxo-1,6- dihydropyrimidin-1-yl}-4-fluoro-10-methyl-8,16-diazatricyclo[13.3.1.0²,⁷] nonadeca- 1(19),2(7),3,5,15,17-hexaen-9-one;

(10R,14S)-14-{4-[5-chloro-2-(4-chloro-1H-1,2,3-triazol-1-yl)phenyl]-6-oxo-1,6- dihydropyrimidin-1-yl}-4-fluoro-10-methyl-8,16-diazatricyclo[13.3.1.0²,⁷]nonadeca- 1(19),2(7),3,5,15,17-hexaen-9-one;

(10R,14S)-14-{4-[5-chloro-2-(trifluoromethyl)phenyl]-6-oxo-1,6-dihydropyrimidin-1-yl}-4- fluoro-10-methyl-8,16-diazatricyclo[13.3.1.0²,⁷]nonadeca-1(19),2(7),3, 5,15,17-hexaen-9-one;

(10R,14S)-14-{4-[3-chloro-6-(4-chloro-1H-1,2,3-triazol-1-yl)-2-fluorophenyl]-6-oxo-1,6- dihydropyrimidin-1-yl}-4-fluoro-10-methyl-8,16-diazatricyclo [13.3.1.0²,⁷] nonadeca- 1(19),2(7),3,5,15,17-hexaen-9-one;

(10R,14S)-14-{4-[3-chloro-2-fluoro-6-(trifluoromethyl) phenyl]-6-oxo-1,6-dihydropyrimidin- 1-yl}-4-fluoro-10-methyl-8,16-diazatricyclo[13.3.1.0²,⁷]nonadeca-1 (19),2(7),3,5,15,17-hexaen-9- one;

(10R,14S)-14-{4-[5-chloro-2-(4-ethoxy-1H-1,2,3-triazol-1-yl)phenyl}-6-oxo-1,6- dihydropyrimidin-1-yl -4-fluoro-10-methyl-8,16-diazatricyclo[13.3.1.0²,⁷] nonadeca- 1(19),2(7),3,5,15,17-hexaen-9-one;

(10S,14S)-14-(4-{5-chloro-2-[4-(trifluoromethyl)-1H-1, 2,3-triazol-1-yl]phenyl -6-oxo-1,6- dihydropyrimidin-1-yl)-4-fluoro-10-methyl-8,18-diazatricyclo[13.3.1.0²,⁷]nonadeca- 1(19),2,4,6,15,17-hexaen-9-one;

(10R,14S)-14-{4-[5-chloro-2-(trifluoromethoxy)phenyl]-6-oxo-1,6-dihydropyrimidin-1-yl}- 4-fluoro-10-methyl-8,16-diazatricyclo[13.3.1.0²,⁷]nonadeca-1(19), 2(7),3,5,15,17-hexaen-9-one;

(10R,14S)-14-[4-(3,6-dichloro-2-fluorophenyl)-6-oxo-1, 6-dihydropyrimidin-1-yl]-4-fluoro- 10-methyl-8,16-diazatricyclo[13.3.1.0²,⁷]nonadeca-1(19),2(7),3,5,15,17-hexaen-9-one;

1-(4-chloro-2- {1-[(10R,14S)-4-fluoro-10-methyl-9-oxo-8,16-diazatricyclo [13.3.1.0²,⁷nonadeca-1(19),2(7),3,5, 15,17-hexaen-14-yl]-6-oxo-1,6-dihydropyrimidin-4-yl}phenyl)- 1H-1,2,3-triazole-4-carbonitrile;

1-(4-chloro-2- {1-[(10R,14S)-4-fluoro-10-methyl-9-oxo-8,16-diazatricyclo [13.3.1.0$^{2,7}$]nonadeca-1(19),2(7),3,5,15,17-hexaen-14-yl]-6-oxo-1,6-dihydropyrimidin-4-yl}phenyl)- N'-hydroxy-1H-1,2,3-triazole-4-carboximidamide; and (10R,14S)-14-[4(5-chloro-2-methoxyphenyl)-6-oxo-1,6-dihydropyrimidin-1-yl]-4-fluoro-10- methyl-8,16-diazatricyclo[13.3.1.0$^{2,7}$]nonadeca-1(19),2(7),3,5,15,17-hexaen-9-one.

\* \* \* \* \*